United States Patent
Guerin et al.

(10) Patent No.: US 10,913,753 B2
(45) Date of Patent: Feb. 9, 2021

(54) THIENOPYRIDINE CARBOXAMIDES AS UBIQUITIN-SPECIFIC PROTEASE INHIBITORS

(71) Applicant: FORMA Therapeutics, Inc., Watertown, MA (US)

(72) Inventors: David Joseph Guerin, Natick, MA (US); Kenneth W. Bair, Wellesley, MA (US); Justin A. Caravella, Cambridge, MA (US); Stephanos Ioannidis, Jr., Natick, MA (US); David R. Lancia, Jr., Boston, MA (US); Hongbin Li, Madison, CT (US); Steven Mischke, Waltham, MA (US); Pui Yee Ng, Waltham, MA (US); David Richard, Littleton, MA (US); Shawn E. R. Schiller, Haverhill, MA (US); Tatiana Shelekhin, Ridgefield, CT (US); Zhongguo Wang, Lexington, MA (US)

(73) Assignee: VALO EARLY DISCOVERY, INC., Boston, MA (US)

( * ) Notice: Subject to any disclaimer, the term of this patent is extended or adjusted under 35 U.S.C. 154(b) by 270 days.

(21) Appl. No.: 16/077,407

(22) PCT Filed: Feb. 13, 2017

(86) PCT No.: PCT/US2017/017690
§ 371 (c)(1),
(2) Date: Aug. 10, 2018

(87) PCT Pub. No.: WO2017/139778
PCT Pub. Date: Aug. 17, 2017

(65) Prior Publication Data
US 2020/0017525 A1 Jan. 16, 2020

Related U.S. Application Data

(60) Provisional application No. 62/294,625, filed on Feb. 12, 2016.

(51) Int. Cl.
C07D 519/00 (2006.01)
C07D 495/04 (2006.01)

(52) U.S. Cl.
CPC ......... *C07D 519/00* (2013.01); *C07D 495/04* (2013.01)

(58) Field of Classification Search
CPC .............................. C07D 519/00; C07D 495/04
See application file for complete search history.

(56) References Cited

U.S. PATENT DOCUMENTS

2012/0022046 A1* 1/2012 Byrd .................. A61K 31/7056
514/215

FOREIGN PATENT DOCUMENTS

| WO | 2000078934 A2 | 12/2000 |
|---|---|---|
| WO | 2005037845 A1 | 4/2005 |
| WO | 2006068618 A1 | 6/2006 |
| WO | 2010092153 | 8/2010 |
| WO | 2010099166 A1 | 9/2010 |
| WO | 2012040527 A2 | 3/2012 |
| WO | 2014105952 A2 | 7/2014 |
| WO | 2014116859 A1 | 7/2014 |

OTHER PUBLICATIONS

Beroukhim et al., "The landscape of somatic copy-number alteration across human cancers," Nature vol. 463, doi.10.1038/nature08822, pp. 899-905, (2010).
Bradley et al., "Tumor necrosis factor receptor-associated factors (TRAFs)," Oncogene Nature 20, pp. 6482-6491, (2001).
Brockman et al., "Small Molecule Inhibitors of Aurora-A Induce Proteasomal Degradation of N-Myc in Childhood Neuroblastoma" Cancer Cell., 24(1), Doi:10.1016/.ccr.2013.05.005, pp. 75-89, (2013).
Colland et al., "Small-molecule inhibitor of USP7/HAUSP ubiquitin protease stabilizes and activates p53 in cells," Molecular Cancer Therapeutics, DOI: 10.1158-1535-7163.MCT-09-0097, pp. 2286-2295, (2009).
Colombo et al., "Synthesis and biological evaluation of 9-oxo-9H-indeno[1,2-b]pyrazine-2,3-dicarbonitrile Analogues as Potential Inhibitors of Deubiquitinating Enzymes," ChemMedChem DOI: 10.1002/cmdc.200900409, pp. 552-558, (2010).
Conacci-Sorrell et al., "An Overview of MYC and Its Interactome," Cold Spring Harb Perspect Med 2014;4: a014357, pp. 1-24 (2014).
Cui et al., "Mechanisms and pathways of innate immune activation and regulation in health and cancer," Human Vaccines & Immunotherapeutics 10:11, pp. 3270-3285, (2014).
D'Arcy et al., "Deubiquitinase inhibition as a cancer therapeutic strategy," Pharmacology & Therapeutics 147, http://dx.doi.org/10.1016/j.pharmthera.2014.11.002, pp. 32-54, (2015).
Diefenbacher et al., "The deubiquitinase USP28 controls intestinal homeostasis and promotes colorectal cancer," The Journal of Clinical Investigation, vol. 124, No. 8 doi:10.1172/JCI73733, pp. 3407-3418 (2014).
Flugel et al., "GSK-3B regulates cell growth, migration, and angiogenesis via Fbw7 and USP28-dependent degradation of HIF-1α," Vascular Biology, Blood, vol. 119, No. 5, pp. 1292-1301, (2012).

(Continued)

*Primary Examiner* — Timothy R Rozof
(74) *Attorney, Agent, or Firm* — Barnes & Thornburg LLP

(57) ABSTRACT

The disclosure relates to inhibitors of USP28 and/or USP25 useful in the treatment of cancers, inflammation, autoimmune diseases, and infectious diseases, having the Formula:

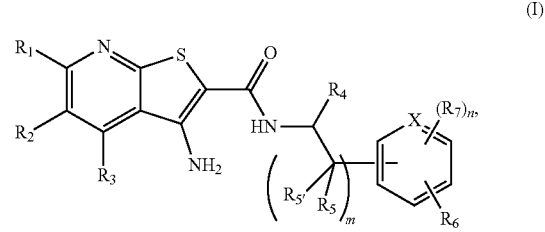

(I)

where $R_1$, $R_2$, $R_3$, $R_4$, $R_5$, $R_{5'}$, $R_6$, $R_7$, X, m, and n are described herein.

20 Claims, No Drawings

(56) References Cited

OTHER PUBLICATIONS

Gabay et al., "MYC Activation is a Hallmark of Cancer Initiation and Maintenance," Cold Spring Harb Perspect Med 2014;4:a014241, pp. 1-13 (2014).
Guo et al., "USP28 is a potential prognostic marker for bladder cancer," Tumor Biology DOI 10.1007/s13277-013-1525-1, pp. 4017-4022 (2013).
Huang et al., "Neuroblastoma and MYCN," Cold Spring Harb Perspect Med 2013;3:a014415; pp. 1-22, (2013).
International Search Report and Written Opinion for International Application No. PCT/US2017/017690, pp. 1-11, dated Apr. 19, 2017.
International Search Report and Written Opinion for International Application No. PCT/US2017/017691, pp. 1-6, dated Mar. 29, 2017.
Iwakura et al., "Functional Specialization of Interleukin-17 Family Members," Immunity 34, pp. 149-162 (2011).
Kapuria et al., "Deubiquitinase Inhibition by Small-Molecule WP1130 Triggers Aggresome Formation and Tumor Cell Apoptosis," Cancer Research Therapeutics, Targets, and Chemical Biology DOI: 10.1158/0008-5472.CAN-10-1530, pp. 9265-9276, (2010).
Knobel et al., "USP28 Is Recruited to Sites of DNA Damage by the Tandem BRCT Domains of 53BP1 but Plays a Minor Role in Double-Strand Break Metabolism," Molecular and Cellular Biology, vol. 34, No. 11, pp. 2062-2074 (2014).
Komander et al., "Breaking the chains: structure and function of the deubiquitinases," Nature, vol. 10, pp. 550-563 (2009).
Le et al., "Discovery of a selective M4 positive allosteric modulator based on the 3-amino-thieno[2,3-b]pyridine-2-carboxamide scaffold: development of ML253, a potent and brain penetrant compound that is active in a preclinical model of schizophrenia," Bioorg Med Chem Lett. doi:10.1016/j.bmcl.2012.10.073, pp. 346-350 (2013).
Lee et al., "Enhancement of proteasome activity by a small-molecule inhibitor of USP14," Nature 467 doi:10.1038/nature09299, pp. 179-184 (2010).
Li et al., "miRNA-200c inhibits invasion and metastasis of human non-small cell lung cancer by directly targeting ubiquitin specific peptidase 25," Molecular Cancer, vol. 13, pp. 1-14 (2014).
Liang et al., "A selective USP1-UAF1 inhibitor links deubiquitination to DNA damage responses," Nat. Chem. Biol. DOI: 10.1038/NCHEMBIO.1455, pp. 298-304 (2014).
Lorenzin et al., "Different promoter affinities account for specificity in MYC-dependent gene regulation," eLife 2016;5:e15161, pp. 1-35 (2016).
Meng et al., "γ-Secretase Inhibitors Abrogate Oxaliplatin-Induced Activation of the Notch-1 Signaling Pathway in Colon Cancer Cells Resulting in Enhanced Chemosensitivity," Cancer Research 69(2), pp. 573-582 (2009).
Metzger et al., "LSD1 demethylates repressive histone marks to promote androgen-receptor-dependent transcription," Nature doi:10.1038/nature04020, vol. 437, pp. 436-439 (2005).
Meyer et al. "Reflecting on 25 years with MYC," Nature Perspectives, vol. 8, pp. 976-990 (2008).
Nijman et al., "A Genomic and Functional Inventory of Deubiquitinating Enzymes," Cell 123, pp. 773-786 (2005).
Periz et al., "Regulation of Protein Quality Control by UBE4B and LSD1 through p53-Mediated Transcription," PLOS Biology DOI:10.1371/journal.pbio.1002114, pp. 1-29 (2015).
Popov et al., "The ubiquitin-specific protease USP28 is required for MYC stability," Nature Cell Biology, vol. 9, No. 7, pp. 765-774 (2007).
Reverdy et al., "Discovery of Specific Inhibitors of Human USP7/HAUSP Deubiquitinating Enzyme," Chemistry & Biology 19, pp. 467-477 + Supplemental Information, (2012).
Roussel et al., "Role of MYC in Medulloblastoma," Cold Spring Harb Perspect Med 2013;3:a014308; pp. 1-15, (2013).
Sankar et al., "Reversible LSD1 Inhibition Interferes with Global EWS/ETS Transcriptional Activity and Impedes Ewing Sarcoma Tumor Growth," Clinical Cancer Research, DOI: 10.1158/1078-0432.CCR-14-0072, pp. 4584-4597 (2014).
Schenk et al., "Inhibition of the LSD1 (KDM1A) demethylase reactivates the all-trans-retinoic acid differentiation pathway in acute myeloid leukemia," Nature Medicine, vol. 18, No. 4, pp. 605-611 (2012).
Schmitz et al., "Oncogenic Mechanisms in Burkitt Lymphoma," Cold Spring Harb Perspect Med 2014;4:a014282, pp. 1-13 (2014).
Sheridan, C., "Drug makers target ubiquitin proteasome pathway anew," Nature Biotechnology, vol. 33, No. 11, pp. 1115-1117 (2015); corrected version (2016).
Stoeck et al., "Discovery of Biomarkers Predictive of GSI Response in Triple-Negative Breast Cancer and Adenoid Cystic Carcinoma," American Association for Cancer Research, Cancer Discovery DOI: 10.1158/2159-8290. CD-13-0830, pp. 1155-1167 (2014).
Toffolo et al., "Phosphorylation of neuronal Lysine-Specific Demethylase 1LSD1/KDM1A impairs transcriptional repression by regulating interaction with CoREST and histone deacetylases HDAC1/2," Journal of Neurochemistry, vol. 128, doi: 10.1111/jnc.12457, pp. 603-616 (2014).
Walsh et al., "Tumor necrosis factor receptor-associated factor 6 (TRAF6) regulation of development, function, and homeostasis of the immune system," John Wiley & Sons Ltd, Immunological Reviews 0105-2896, vol. 266, pp. 72-92 (2015).
Walz et al., "Activation and repression by oncogenic MYC shape tumour-specific gene expression profiles," Nature, doi:10.1038/nature13473, pp. 1-17 (2014).
Wang et al., "Ubiquitin-specific protease 28 is overexpressed in human glioblastomas and contributes to glioma tumorigenicity by regulating MYC expression," Experimental Biology and Medicine, DOI: 10.1177/1535370215595468, pp. 255-264 (2015).
Weng et al., "Activating Mutations of NOTCH1 in Human T Cell Acute Lymphoblastic Leukemia," Science, vol. 306, pp. 269-271 (2004).
Wrigley et al., "Enzymatic characterisation of USP7 deubiquitinating activity and inhibition," Cell Biochem. Biophys., vol. 60, DOI 10.1007/s12013-011-9186-4, pp. 99-111 (2011).
Wrigley et al., "Identification and Characterization of Dual Inhibitors of the USP25/28 Deubiquitinating Enzyme Subfamily" ACS Chem. Biol. 12, pp. 3113-3125 (2017).
Wu et al., "The Deubiquitinase USP28 Stabilizes LSD1 and Confers Stem-Cell-like Traits to Breast Cancer Cells," Cell Press Reports, vol. 5, pp. 224-236 (2013).
Zhang et al., "A Role for the Deubiquitinating EnzymeUSP28 in Control of the DNA-Damage Response," Cell 126, pp. 529-542 (2006).
Zhang et al., "Overexpression of deubiquitinating enzyme USP28 promoted non-small cell lung cancer growth," J. Cell Mol. Med., pp. 1-7 , doi: 10.1111/jcmm.12426 (2015).
Zhong et al., "Negative regulation of IL-17-mediated signaling and inflammation by the ubiquitin-specific protease USP25," Nature Immunology, vol. 13, No. 11, pp. 1110-1117 (2012).
Zhong et al., "Ubiquitin-Specific Protease 25 Regulates TLR4-Dependent Innate Immune Responses Through Deubiquitination of the Adaptor Protein TRAF3," Science Signaling, vol. 6, Issue 275 ra35, pp. 1-10 (2013).
Zhong et al., "Ubiquitin-Specific Proteases 25 Negatively Regulates Virus-Induced Type I Interferon Signaling," PLOS One, vol. 8, Issue 11, pp. 1-14 (2013).
International Search Report issued in Application No. PCT/US2018/046061, dated Oct. 25, 2018.
International Search Report issued in Application No. PCT/US2019/045732, dated Oct. 23, 2019.
Examination Report issued in European Patent Application No. 17708031.4, dated Jun. 13, 2019.
Cremona et al., "Fbw7 and Its Counteracting Forces in Stem Cells and Cancer: Oncoproteins in the Balance," Semin Cancer Biol., 36:52-61, Feb. 2016.
Diefenbacher et al., "Usp28 Counteracts Fbw7 in Intestinal Homeostasis and Cancer," Cancer Res., 75(7):1181-6, Apr. 1, 2015. (Epub Feb. 25, 2015.).
Farshi et al., "Deubiquitinases (DUBs) and DUB inhibitors: a patent review," Expert Opin Ther Pat., 25(10)1191-1208, 2015.

(56) References Cited

OTHER PUBLICATIONS

Gersch et al., "Distinct USP25 and USP28 Oligomerization States Regulate Deubiquitinating Activity," Mol. Cell 74:436-451, May 2, 2019.

Popov et al., "Fbw7 and Usp28 Regulate Myc Protein Stability in Response to DNA Damage," Cell Cycle, 6:19, 2327-2331, Oct. 2, 2007.

Prieto-Garcia et al., "The USP28-ΔNp63 axis is a vulnerability of squamous tumours," bioRxiv preprint, Jun. 27, 2019.

Sacco et al., "Emerging Roles of Deubiquitinases in Cancer-Associated Pathways," Life 62(2):140-157, Feb. 2010.

Sauer et al., "Differential Oligomerization of the Deubiquitinases USP25 and USP28 Regulates Their Activities," Mol. Cell 74(3):421-435, May 2, 2019.

Schulein-Volk et al., "Dual Regulation of Fbw7 Function and Oncogenic Transformation b Usp28," Cell Reports 9, 1099-1109, Nov. 6, 2014.

Wrigley et al., "Identification and Characterization of Dual Inhibitors of the USP25/28 Deubiquitinating Enzyme Subfamily," Peer-reviewed (pre-print) version, published Nov. 13, 2017.

\* cited by examiner

THIENOPYRIDINE CARBOXAMIDES AS UBIQUITIN-SPECIFIC PROTEASE INHIBITORS

This application is a national phase entry pursuant to 35 U.S.C. § 371 of International Application No. PCT/US2017/017690, filed Feb. 13, 2017, which claims the benefit of and priority to U.S. provisional application No. 62/294,625, filed Feb. 12, 2016, the entire contents of which are incorporated herein by reference in its entirety.

RELATED APPLICATIONS

This application is a national phase entry pursuant to 35 U.S.C § 371 of International Application No. PCT/US2017/017690, filed Feb. 13, 2017, which claims the benefit of and priority to U.S. provisional application No. 62/294,625, filed Feb. 12, 2016, the entire contents of which are incorporated herein by reference in its entirety.

FIELD OF INVENTION

The present disclosure is directed to modulators of ubiquitin-specific protease 28 (USP28) and/or ubiquitin-specific protease 25 (USP25) useful in the treatment of diseases or disorders associated with USP28 and/or USP25 enzymes. Specifically, the disclosure is concerned with compounds and compositions inhibiting USP28 and/or USP25, methods of treating diseases or disorders associated with USP28 and/or USP25, and methods of synthesis of these compounds.

BACKGROUND OF THE INVENTION

USP28 and USP25 are cysteine isopeptidases of the USP sub-family of DUBs containing three distinct domains: an N-terminal UBA-like domain; a pair of ubiquitin-interacting motifs (UIM) and a USP domain that is predicted to have the conserved fold of the USP sub-family (Nijman et al., *Cell* 2005, 123, 773-786; Komander et al., *Mol. Cell Bio.* 2009, 10, 550-563). USP28 and USP25 exert their function through regulating the stability of a plethora of cellular proteins. USP28 has been characterized as a tumor-promoting factor and has been found to stabilize many oncoproteins. USP25 has been characterized as a tumor-promoting factor and as a regulator of cellular responses related to autoimmune disease, inflammation, and infectious diseases (such as viruses and bacteria).

Amplification, deletions and mutations of USP28 have been identified in multiple cancer types, including breast cancer, AML, ovarian cancer, and colorectal cancer. (cbioportal; http://www.cbioportal.org; Diefenbacher et al., *J. of Clin. Investi.* 2014, 124, 3407-3418; Popov et al., *Nat. Cell. Biol.* 2007, 9, 729-731). Furthermore, USP28 overexpression has been correlated with poor prognosis in patients with glioblastoma, non-small cell lung carcinoma and bladder cancers suggesting that USP28 plays an important role in tumorigenesis of these tumor types. (Wang et al., *Exp. Biol. Med.* 2016, 255-264; Zhang et al., *J. Cell. Mol. Med.* 2015, 19, 799-805; Guo et al., *Tumor Bio.* 2014, 35, 4017-4022).

A large-scale shRNA screen has also identified a role of USP28 in the control of the stability of MYC protein. (Popov, *Nat. Cell. Biol.*, 765-774). MYC is a master regulator of the transcription of genes involved in cell growth, proliferation and apoptosis and is essential for tumor initiation and maintenance in many tumor types. (Meyer et al., *Nat. Rev. Cancer* 2008, 8, 976-990; Conacci-Sorrell et al., *Cold Spring Harb. Perspect. Med.* 2014, 4, 1-24; Huang et al., *Cold Spring Harb. Perspect. Med.* 2013; Roussel et al., *Cold Spring Harb. Perspect. Med.* 2013; Gabay et al., *Cold Spring Harb. Perspect. Med.* 2014; Schmitz et al., *Cold Spring Harb. Perspect. Med.* 2014). In addition, MYC is the most frequently amplified oncogene in human cancer, with alterations in many tumor types including breast, lung and prostate. (Beroukhim et al. *Nature* 2010, 463, 899-905). Knockdown of the USP28 gene has been shown to lead to a decrease of MYC protein and an associated inhibition of growth in a panel of human cancer cell lines in vitro. (Popov, *Nat. Cell Biol.*, 765-774).

USP28 has also been reported to be required to impart stability on the LSD1 (lysine-specific demethylase 1) protein. (Wu et al., *Cell Rep.* 2013, 5, 224-236). LSD1 is a histone demethylase that complexes with many partner proteins to control cellular pluripotency and differentiation. (Metzger et al. *Nature* 2005, 437, 436-439; Toffolo et al, *J. Neurochem.* 2014 128, 603-616, 2014; Periz et al., *PloS Biology* 2015). Knockdown of USP28 in tumor cells has been shown to lead to the destabilization of LSD1 protein, the suppression of cancer stem cell (CSC)-like characteristics in vitro, and the inhibition of tumor growth in vivo. (Wu, *Cell Rep.*, 224-236). Small molecule inhibitors of LSD1 have shown antitumor activity in models of AML and Ewing sarcoma. (Sankar et al., *Clin Cancer Res.* 2014 4584-4597; Schenk et al., *Nat. Med.* 2012, 18, 605-611). Thus, USP28 inhibition represents an alternate approach to targeting LSD1 in these tumor types.

USP28 inhibition has also been shown to reduce NICD1-Levels and to lead to inhibition of the NOTCH pathway activity. (Diefenbacher et al.). NOTCH signaling controls diverse cellular differentiation decisions and drives tumorigenesis in certain tumor types. NOTCH1 is a potent T-cell oncogene, with >50% of T-cell acute lymphoblastic leukemia (T-ALL) cases carrying activating mutations in NOTCH1. (Weng et al. *Science* 2004, 306, 269-271). Increased NOTCH1 protein levels have also been associated with disease progression in colon cancer. (Meng et al., *Cancer Res.* 2009, 69, 573-582). NOTCH1 rearrangements lead to constitutive pathway activation and drive tumorigenesis in many cancer types, including triple-negative breast cancer. (Stoeck et al., *Cancer Discov.* 2014, 4, 1154-1167).

Other reported substrates of USP28 include c-Jun, Cyclin E, HIF-1α, Claspin, 53BP1, and Mdc1, many of which play important roles in tumorigenesis in humans. (Diefenbacher et al.; Flügel et al. *Blood* 2012, 119, 1292-1301; Zhang et al., *Cell* 2006, 126, 529-542). Interestingly, many USP28 substrates are recognized by FBW7, the substrate recognition subunit of SCF (FBW7) E3 ubiquitin ligase. (Diefenbacher et al.). FBW7 recognizes USP28 substrates in a phosphorylation-dependent manner and targets them for ubiquitination ultimately leading to their proteasomal degradation. The antagonizing roles of USP28 and FBW7 on their shared oncoprotein substrates indicate the intricate nature of protein stability control and may provide additional therapeutic opportunities for cancer treatment.

Mice with a germline knockout of USP28 have been shown to be viable and fertile, confirming that USP28 activity is not required for normal development and reproductive function. (Knobel et al., *Molecular and Cellular Biology* 2014, 34, 2062-2074). Conditional knockout of USP28 in mouse intestine led to the reduction of oncoproteins including c-Myc, active NOTCH (NICD1) and c-JUN which was associated with decreased intestinal cell proliferation and enhanced differentiation. More importantly, intestinal tumorigenesis induced by APC mutation was effectively blocked with acute USP28 depletion suggesting that USP28 could be an appealing target to reduce tumor burden and improve survival for intestinal cancers. (Diefenbacher et al.).

Mice with a germline knockout of USP25 have been shown to be viable and did not show any abnormalities in growth and survival (Zhong et al. *Nat. Immunol.* 2012, 13, 1110-1117). Deficiency of USP25 in these mice led to increased inflammation and autoimmune responses mediated by interleukin 17 (IL-17), a pro-inflammatory cytokine that is a known regulator of host defense to infection, autoimmunity, and tumorigenesis (Zhong et al. 2012; Iwakura et al., *Immunity* 2011, 34, 149-162). As such, USP25 was characterized as a negative regulator of IL-17 signaling through its deubiquitinase activity on the tumor necrosis factor receptor-associated 5 (TRAF5) and TRAF6 adapter proteins associated with the IL-17 receptor complex.

USP25 has also been shown to be a negative regulator of innate immune responses activated by pathogens such as viruses and bacteria. USP25 has been shown to regulate the type I interferon (IFN) signaling pathway via its deubiquitinase activity on RIG-I, TRAF2, and TRAF6 and Toll-like receptor 4 (TLR-4) signaling via its deubiquitinase activity on TRAF3 (Zhong et al., PLOS One 2013, 8, e80976; Zhong et al. *Sci. Signal.* 2013, 6, ra35). Since the TRAF-associated family of adapter proteins have wide specificities for other cell surface receptor complexes (e.g., IL-17 receptor, TNF receptor, T cell receptor, TGFβ receptor, the Toll like receptor family, etc.), USP25 is likely to be a pleiotropic regulator of immune and inflammatory signaling in multiple disease contexts, including cancers (Walsh et al., *Immunol. Rev.* 2015, 1, 72-92; Cui et al., Hum. Vaccin. Immunother.2014, 10, 3270-3285; Bradley and Pober, *Oncogene* 2001, 20, 6482-6491).

USP25 has been reported to promote tumor invasion and metastasis (Li et al., *Mol. Cell* 2014, 13, 166-170). Decreased expression of USP25 in lung cancer cell lines has been shown to decrease invasion and motility in in vitro experiments and to decrease tumor metastasis in in vivo experiments in mice. Studies have shown USP25 activity abrogated via expression of miRNA -200c which downregulates USP25 expression. Additionally, analysis of USP25 and miRNA-200c expression levels in tissue from lung cancer patients revealed expression profiles consistent with USP25-driven tumorigenesis (i.e., elevated levels of USP25 and decreased levels of miRNA-200c in tumor tissue versus healthy tissue increased metastatic lesions, and poor clinical prognosis in patients with elevated tumor levels of USP25).

In summary, USP28 and USP25 play important roles in promoting tumorigenesis in cells and modulating immune responses. Its major role being in the deubiquitination and stabilization of diverse oncoproteins and epigenetic drivers and immunomodulatory proteins among other cellular factors, which are necessary for immune responses and tumor initiation and growth in humans. Inhibition of USP28 and/or USP25 with small molecule inhibitors therefore has the potential to be a treatment for cancers, autoimmune diseases, inflammatory diseases, infectious diseases, and other disorders. For this reason, there remains a considerable need for novel and potent small molecule inhibitors of USP28 and/or USP25.

SUMMARY OF THE DISCLOSURE

A first aspect of the disclosure relates to compounds of Formula (I):

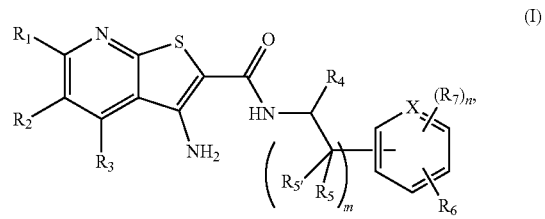

and pharmaceutically acceptable salts, hydrates, solvates, prodrugs, stereoisomers, and tautomers thereof,
wherein:
X is N or $CR_7$;
$R_1$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —CN, or —$NR_9R_{10}$;
$R_2$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{11}R_{12}$;
$R_3$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{13}R_{14}$;
wherein at least one of $R_1$, $R_2$, or $R_3$ is not H;
or $R_1$ and $R_2$ together form a $(C_4-C_8)$ cycloalkyl optionally substituted with one or more $R_{15}$;
or $R_2$ and $R_3$ together form a $(C_4-C_8)$ cycloalkyl optionally substituted with one or more $R_{15}$;
$R_4$ is H, $(C_1-C_6)$ alkyl, or $(C_1-C_6)$ haloalkyl;
$R_5$ is H, $(C_1-C_6)$ alkyl, halogen, or $(C_1-C_6)$ haloalkyl;
$R_{5'}$ is H, $(C_1-C_6)$ alkyl, halogen, or $(C_1-C_6)$ haloalkyl; or
$R_4$ and $R_5$ together with the carbon atoms to which they are attached form a $(C_3-C_8)$ cycloalkyl ring;
$R_6$ is —$(C_0-C_3)$ alkylene-C(O)OH, —$(C_0-C_3)$ alkylene-heterocycloalkyl, —O-heterocycloalkyl, —$(C_0-C_3)$ alkylene-aryl, —$(C_0-C_3)$ alkylene-heteroaryl or —$N(R_8)$-$(C_0-C_3)$ alkylene-heterocycloalkyl, wherein the heterocycloalkyl, aryl and heteroaryl are optionally substituted with one or more $R_{16}$;
each $R_7$ is independently at each occurrence H, $(C_1-C_6)$ alkyl, $(C_1-C_6)$ alkoxy, $(C_1-C_6)$ haloalkyl, $(C_1-C_6)$ haloalkoxy, halogen, —OH, —CN, $(C_3-C_8)$ cycloalkyl, heterocycloalkyl, aryl, or heteroaryl, wherein the alkyl is optionally substituted with one or more $(C_1-C_6)$ alkoxy or —OH, and wherein the cycloalkyl, heterocycloalkyl, aryl, and heteroaryl are optionally substituted with one or more $R_{17}$; or
$R_6$ and $R_7$ together when on adjacent atoms form a $(C_4-C_8)$ cycloalkyl ring optionally substituted with one or more $R_{18}$; or $R_6$ and $R_7$ together when on adjacent atoms form a heterocycloalkyl ring optionally substituted with one or more $R_{18}$; $R_6$ and $R_7$ together when on adjacent atoms form an aryl ring optionally substituted with one or more $R_{18}$; or $R_6$ and $R_7$ together when on adjacent atoms form a heteroaryl ring optionally substituted with one or more $R_{18}$; or
two $R_7$ together when on adjacent atoms form a $(C_4-C_8)$ cycloalkyl ring; or two $R_7$ together when on adjacent atoms form a heterocycloalkyl ring; two $R_7$ together when on adjacent atoms form an aryl ring; or two $R_7$ together when on adjacent atoms form a heteroaryl ring;

$R_8$ is H or $(C_1-C_6)$ alkyl;

each $R_9$, $R_{10}$, $R_{11}$, $R_{12}$, $R_{13}$, and $R_{14}$ is independently H, $(C_1-C_6)$ alkyl, or —C(O)$(C_1-C_6)$ alkyl;

each $R_{15}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or —OH;

each $R_{16}$ is independently at each occurrence $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —C(O)$NR_{21}R_{22}$, —S(O)$_2(C_1-C_6)$ alkyl, —OH, or —$NR_{19}R_{20}$, wherein the alkyl is optionally substituted with one or more substituents independently selected from $(C_1-C_6)$ alkoxy, OH, and heterocycloalkyl; or two $R_{16}$ together when attached to the same carbon can form —C=(O) when $R_6$ is —$(C_0-C_3)$ alkylene-heterocycloalkyl, —O-heterocycloalkyl, or —N($R_8$)-$(C_0-C_3)$ alkylene-heterocycloalkyl; or two $R_{16}$ together when attached to the same atom form a $(C_3-C_8)$ spirocycloalkyl optionally substituted with one or more $R_{23}$ when $R_6$ is —$(C_0-C_3)$ alkylene-heterocycloalkyl, —O-heterocycloalkyl, or —N($R_8$)-$(C_0-C_3)$ alkylene-heterocycloalkyl; or two $R_{16}$ together when attached to the same atom form a $(C_3-C_8)$ spiroheterocycloalkyl optionally substituted with one or more $R_{23}$ when $R_6$ is —$(C_0-C_3)$ alkylene-heterocycloalkyl, —O-heterocycloalkyl, or —N($R_8$)-$(C_0-C_3)$ alkylene-heterocycloalkyl; or two $R_{16}$ together when on adjacent atoms form a heterocycloalkyl ring optionally substituted with one or more $R_{23}$; or two $R_{16}$ together when on adjacent atoms form a heteroaryl ring optionally substituted with one or more $R_{23}$; or two $R_{16}$ together with the atoms to which they are attached can form a bridged heterocycloalkyl ring optionally substituted with one or more $R_{23}$ when $R_6$ is —$(C_0-C_3)$ alkylene-heterocycloalkyl, —O-heterocycloalkyl, or —N($R_8$)-$(C_0-C_3)$ alkylene-heterocycloalkyl;

each $R_{17}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, cycloalkyl, heterocycloalkyl, or —C(O)-heterocycloalkyl, wherein the alkyl is optionally substituted with one or more substituents independently selected from $(C_1-C_6)$ alkoxy and —OH;

each $R_{18}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, —CN, —C(O)OH, or —C(O)O$(C_1-C_6)$ alkyl;

each $R_{19}$ and $R_{20}$ is independently H, $(C_1-C_6)$ alkyl, $(C_3-C_8)$ cycloalkyl, —$CH_2C(O)NH_2$, —S(O)$_2(C_1-C_6)$ alkyl, —S(O)$_2(C_6-C_{10})$ aryl or —C(O)$(C_1-C_6)$ alkyl;

each $R_{21}$ and $R_{22}$ is independently H or $(C_1-C_6)$ alkyl;

each $R_{23}$ is independently at each occurrence $(C_1-C_6)$ alkyl, $(C_1-C_6)$ alkoxy, $(C_1-C_6)$ haloalkyl, $(C_1-C_6)$ haloalkoxy, or halogen; or two $R_{23}$ together when attached to the same carbon form —C=(O);

m is 1 or 2; and n is 0, 1, 2, or 3.

Another aspect of the disclosure relates to a method of treating a disease or disorder associated with inhibition of USP28. The method comprises administering to a patient in need of a treatment for diseases or disorders associated with inhibition of USP28 an effective amount of a compound of Formula (I), or a pharmaceutically acceptable salt, hydrate, solvate, prodrug, stereoisomer, or tautomer thereof.

Another aspect of the disclosure relates to a method of treating a disease or disorder associated with inhibition of USP25. The method comprises administering to a patient in need of a treatment for diseases or disorders associated with inhibition of USP28 an effective amount of a compound of Formula (I), or a pharmaceutically acceptable salt, hydrate, solvate, prodrug, stereoisomer, or tautomer thereof.

Another aspect of the disclosure relates to a method of treating a disease or disorder associated with inhibition of USP28 and USP25. The method comprises administering to a patient in need of a treatment for diseases or disorders associated with inhibition of USP28 an effective amount of a compound of Formula (I), or a pharmaceutically acceptable salt, hydrate, solvate, prodrug, stereoisomer, or tautomer thereof.

Another aspect of the disclosure is directed to a method of inhibiting USP28. The method involves administering to a patient in need thereof an effective amount of a compound of Formula (I), or a pharmaceutically acceptable salt, hydrate, solvate, prodrug, stereoisomer, or tautomer thereof.

Another aspect of the disclosure is directed to a method of inhibiting USP25. The method involves administering to a patient in need thereof an effective amount of a compound of Formula (I), or a pharmaceutically acceptable salt, hydrate, solvate, prodrug, stereoisomer, or tautomer thereof.

Another aspect of the disclosure is directed to a method of inhibiting USP28 and USP25. The method involves administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating inflammation. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating an autoimmune disease. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating an infectious disease. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating a viral infection. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure relates to a method of treating a bacterial infection. The method comprises administering to a patient in need thereof an effective amount of a compound of Formula (I), or a pharmaceutically acceptable salt, hydrate, solvate, prodrug, stereoisomer, or tautomer thereof.

Another aspect of the disclosure is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present disclosure relates to a compound of Formula (I), or a pharmaceutically acceptable salt, hydrate, solvate, prodrug, stereoisomer, or tautomer thereof, for use in the manufacture of a medicament for treating a disease associated with inhibiting USP28.

Another aspect of the present disclosure relates to the use of a compound of Formula (I), or a pharmaceutically acceptable salt, hydrate, solvate, prodrug, stereoisomer, or tautomer thereof, in the treatment of a disease associated with inhibiting USP28.

Another aspect of the present disclosure relates to the use of a compound of Formula (I), or a pharmaceutically acceptable salt, hydrate, solvate, prodrug, stereoisomer, or tautomer thereof, in the treatment of a disease associated with inhibiting USP25.

Another aspect of the present disclosure relates to the use of a compound of Formula (I), or a pharmaceutically acceptable salt, hydrate, solvate, prodrug, stereoisomer, or tautomer thereof, in the treatment of a disease associated with inhibiting USP28 and USP25.

The present disclosure further provides methods of treating a disease or disorder associated with modulation of USP28 and/or USP25 including, cancer, inflammation, an autoimmune disease, a viral infection, and a bacterial infection, comprising administering to a patient suffering from at least one of said diseases or disorder a compound of Formula (I), or a pharmaceutically acceptable salt, hydrate, solvate, prodrug, stereoisomer, or tautomer thereof.

The present disclosure provides inhibitors of USP28 and/or USP25 that are therapeutic agents in the treatment of diseases, such as cancer, inflammation, autoimmune diseases, viral infections, and bacterial infections. Ultimately the present disclosure provides the medical community with a novel pharmacological strategy for the treatment of diseases and disorders associated with USP28 and/or USP25 enzymes.

DETAILED DESCRIPTION OF THE DISCLOSURE

The present disclosure relates to compounds and compositions that are capable of inhibiting the activity USP28 and/or USP25. The disclosure features methods of treating, preventing or ameliorating a disease or disorder in which USP28 and/or USP25 plays a role by administering to a patient in need thereof a therapeutically effective amount of a compound of Formula (I), or a pharmaceutically acceptable salt, hydrate, solvate, prodrug, stereoisomer, or tautomer thereof. The methods of the present disclosure can be used in the treatment of a variety of USP28 and/or USP25 dependent diseases and disorders by inhibiting the activity of USP28 and/or USP25 enzymes. Inhibition of USP28 and/or USP25 provides a novel approach to the treatment, prevention, or amelioration of diseases including, but not limited to, cancer.

In a first aspect of the disclosure, the compounds of Formula (I) are described:

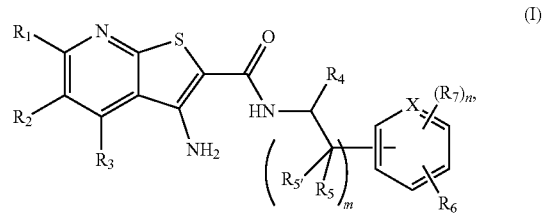

and pharmaceutically acceptable salts, hydrates, solvates, prodrugs, stereoisomers, and tautomers thereof, wherein $R_1$, $R_2$, $R_3$, $R_4$, $R_5$, $R_{5'}$, $R_6$, $R_7$, X, m, and n are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, —halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —C(O)($C_1$-$C_6$) alkyl, —C(O)O($C_1$-$C_6$) alkyl, —OC(O)O($C_1$-$C_6$) alkyl, —NH$_2$, NH(($C_1$-$C_6$) alkyl), N(($C_1$-$C_6$) alkyl)$_2$, —S(O)$_2$-($C_1$-$C_6$) alkyl, —S(O)NH($C_1$-$C_6$) alkyl, and —S(O)N(($C_1$-$C_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, and S, the remaining ring atoms being C. Heteroaryl as herein defined also means a bicyclic heteroaromatic group wherein the heteroatom is selected from N, O, and S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c] pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d] imidazol-2-one, 3,4-dihydro-2H-pyrazolo [1,5-b][1,2] oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, e.g., —O(alkyl). Examples of alkoxy groups include without limitation, methoxy, ethoxy, propoxy, butoxy, t-butoxy, or pentoxy groups.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_0$-$C_6$ alkylene. An alkylene may further be a $C_0$-$C_4$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Cycloalkyl" or "carbocyclyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $C_3$-$C_8$ cycloalkyl is a cycloalkyl group containing between 3 and 8 carbon atoms. A cycloalkyl group can be fused (e.g., decalin) or bridged (e.g., norbornane).

"Heterocyclyl" or "heterocycloalkyl" monocyclic or polycyclic rings containing carbon and heteroatoms taken from oxygen, nitrogen, or sulfur and wherein there is not delocalized π electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" means an alkyl group as defined above, where the alkyl group is substituted with one or more OH groups. Examples of hydroxyalkyl groups include HO—CH$_2$—, HO—CH$_2$—CH$_2$— and CH$_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, e.g., C≡N.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A ($C_3$-$C_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are tyl)ically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The term "cancer" includes, but is not limited to, the following cancers: bladder cancer, breast cancer (e.g., ductal carcinoma), cervical cancer (e.g.: squamous cell carcinoma), colorectal cancer (e.g., adenocarcinoma), esophageal cancer (e.g., squamous cell carcinoma), gastric cancer (e.g.: adenocarcinoma, medulloblastoma, colon cancer, choriocarcinoma, squamous cell carcinoma), head and neck cancer, hematologic cancer (e.g., acute lymphocytic anemia, acute myeloid leukemia, acute lymphoblastic B cell leukemia, anaplastic large cell lymphoma, B-cell lymphoma, Burkitt's lymphoma, chronic lymphocytic leukemia, chronic eosinophillic leukemia/hyl)ereosinophillic syndrome, chronic myeloid leukemia, Hodgkin's lymphoma, mantle cell lymphoma, multiple myeloma, T-cell acute lymphoblastic leukemia), lung cancer (e.g., bronchioloalveolar adenocarcinoma, mesothelioma, mucoepidermoid carcinoma, small-cell lung cancer, non-small cell lung cancer, adenocarcinoma, squamous cell carcinoma), liver cancer (e.g., hepatocellular carcinoma), lymphoma, neurological cancer (e.g., glioblastoma, neuroblastoma, neuroglioma), ovarian (e.g., adenocarcinoma), pancreatic cancer (e.g., ductal carcinoma), prostate cancer (e.g., adenocarcinoma), renal cancer (e.g., renal cell carcinoma, clear cell renal carcinoma), sarcoma (e.g., chondrosarcoma, Ewings sarcoma, fibrosarcoma, multipotential sarcoma, osteosarcoma, rhabdomyosarcoma, synovial sarcoma), skin cancer (e.g,. melanoma, epidermoid carcinoma, squamous cell carcinoma), thyroid cancer (e.g., medullary carcinoma), and uterine cancer.

As used herein, the terms "autoimmune disease" or "autoimmune disorder" refer to a condition that is immune-mediated due to an attack on self-tissues, such as when a subject's own antibodies react with host tissue, but can also involve an immune response to a microorganism. Examples of autoimmune diseases include, but are not limited to, multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, cutaneous lupus erythematosus including chilblain lupus erythematosus, lupus nephritis, discoid lupus, subacute cutaneous lupus erythematosus, dermatomyositis, polymyositis, idiopathic myxedema, Hashimoto's disease, Guillain-Barre' syndrome, Grave's disease, myasthenia gravis, Sjogren's syndrome, nodular panarteritis, autoimmune enteropathy, uveitis, autoimmune oophoritis, chronic immune thrombocytopenic purpura, colitis, diabetes, psoriasis, pemphigus vulgaris, proliferative glomerulonephritis, Wiskott-Aldrich syndrome, autoimmune lymphoproliferative syndrome, chronic arthritis, inflammatory chronic rhinosinusitis, colitis, celiac disease, inflammatory bowel disease, Barrett's esophagus, inflammatory gastritis, autoimmune nephritis, autoimmune vasculitis, autoimmune hepatitis, autoimmune carditis, autoimmune encephalitis, and autoimmune mediated hematological disease.

The present disclosure relates to compounds or pharmaceutically acceptable salts, hydrates, solvates, prodrugs, stereoisomers, or tautomers thereof, capable of inhibiting USP28 and/or USP25, which are useful for the treatment of diseases and disorders associated with modulation of a USP28 and/or USP25 enzyme. The disclosure further relates to compounds, or pharmaceutically acceptable salts, hydrates, solvates, prodrugs, stereoisomers, or tautomers thereof, which are useful for inhibiting USP28 and/or USP25.

In any of the embodiments of the invention, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

The present invention relates to compounds or pharmaceutically acceptable salts, hydrates, solvates, prodrugs, stereoisomers, or tautomers thereof, capable of inhibiting USP28 and/or USP25, which are useful for the treatment of diseases and disorders associated with modulation of a USP28 and/or USP25 enzyme. The invention further relates to compounds, or pharmaceutically acceptable salts, hydrates, solvates, prodrugs, stereoisomers, or tautomers thereof, which are useful for inhibiting USP28 and/or USP25.

In one embodiment, the compounds of Formula (I) have the structure of Formula (Ia):

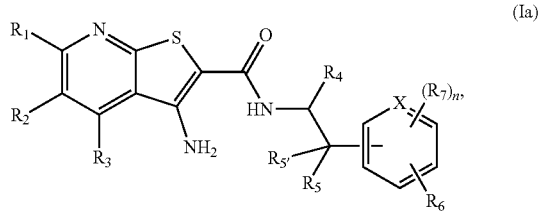

and pharmaceutically acceptable salts, hydrates, solvates, prodrugs, stereoisomers, and tautomers thereof, wherein:

X is N or $CR_7$;

$R_1$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —CN, or —$NR_9R_{10}$;

$R_2$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{11}R_{12}$;

$R_3$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{13}R_{14}$;

wherein at least one of $R_1$, $R_2$, or $R_3$ is not H;

or $R_1$ and $R_2$ together form a $(C_4-C_8)$ cycloalkyl optionally substituted with one or more $R_{15}$;

or $R_2$ and $R_3$ together form a $(C_4-C_8)$ cycloalkyl optionally substituted with one or more $R_{15}$;

$R_4$ is H, $(C_1-C_6)$ alkyl, or $(C_1-C_6)$ haloalkyl;

$R_5$ is H, $(C_1-C_6)$ alkyl, halogen, or $(C_1-C_6)$ haloalkyl;

$R_{5'}$ is H, $(C_1-C_6)$ alkyl, halogen, or $(C_1-C_6)$ haloalkyl;

$R_6$ is —$(C_0-C_3)$ alkylene-C(O)OH, —$(C_0-C_3)$ alkylene-heterocycloalkyl, —O-heterocycloalkyl, —$(C_0-C_3)$ alkylene-aryl, —$(C_0-C_3)$ alkylene-heteroaryl or —$N(R_8)$-$(C_0-C_3)$ alkylene-heterocycloalkyl, wherein the heterocycloalkyl, aryl and heteroaryl are optionally substituted with one or more $R_{16}$;

each $R_7$ is independently at each occurrence H, $(C_1-C_6)$ alkyl, $(C_1-C_6)$ alkoxy, $(C_1-C_6)$ haloalkyl, $(C_1-C_6)$ haloalkoxy, halogen, —OH, —CN, $(C_3-C_8)$ cycloalkyl, heterocycloalkyl, aryl, or heteroaryl, wherein the alkyl is optionally substituted with one or more $(C_1-C_6)$ alkoxy or —OH, and wherein the cycloalkyl, heterocycloalkyl, aryl, and heteroaryl are optionally substituted with one or more $R_{17}$; or $R_6$ and $R_7$ together when on adjacent atoms form a $(C_4-C_8)$ cycloalkyl ring optionally substituted with one or more $R_{18}$; or $R_6$ and $R_7$ together when on adjacent atoms form a heterocycloalkyl ring optionally substituted with one or more $R_{18}$; $R_6$ and $R_7$ together when on adjacent atoms form an aryl ring optionally substituted with one or more $R_{18}$; or $R_6$ and $R_7$ together when on adjacent atoms form a heteroaryl ring optionally substituted with one or more $R_{18}$; or two $R_7$ together when on adjacent atoms form a $(C_4-C_8)$ cycloalkyl ring; or two $R_7$ together when on adjacent atoms form a heterocycloalkyl ring; two $R_7$ together when on adjacent atoms form an aryl ring; or two $R_7$ together when on adjacent atoms form a heteroaryl ring;

$R_8$ is H or $(C_1-C_6)$ alkyl;

each $R_9$, $R_{10}$, $R_{11}$, $R_{12}$, $R_{13}$, and $R_{14}$ is independently H, $(C_1-C_6)$ alkyl, or —$C(O)(C_1-C_6)$ alkyl;

each $R_{15}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or —OH;

each $R_{16}$ is independently at each occurrence $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —$C(O)NR_{21}R_{22}$, —$S(O)_2(C_1-C_6)$ alkyl, —OH, or —$NR_{19}R_{20}$, wherein the alkyl is optionally substituted with one or more substituents independently selected from $(C_1-C_6)$ alkoxy, OH, and heterocycloalkyl; or two $R_{16}$ together when attached to the same carbon can form —C=(O) when $R_6$ is —$(C_0-C_3)$ alkylene-heterocycloalkyl, —O-heterocycloalkyl, or —$N(R_8)$-$(C_0-C_3)$ alkylene-heterocycloalkyl; or two $R_{16}$ together when attached to the same atom form a $(C_3-C_8)$ spirocycloalkyl optionally substituted with one or more $R_{23}$ when $R_6$ is —$(C_0-C_3)$ alkylene-heterocycloalkyl, —O-heterocycloalkyl, or —$N(R_8)$-$(C_0-C_3)$ alkylene-heterocycloalkyl; or two $R_{16}$ together when attached to the same atom form a $(C_3-C_8)$ spiroheterocycloalkyl optionally substituted with one or more $R_{23}$ when $R_6$ is —$(C_0-C_3)$ alkylene-heterocycloalkyl, —O-heterocycloalkyl, or —$N(R_8)$-$(C_0-C_3)$ alkylene-heterocycloalkyl; or two $R_{16}$ together when on adjacent atoms form a heterocycloalkyl ring optionally substituted with one or more $R_{23}$; or two $R_{16}$ together when on adjacent atoms form a heteroaryl ring optionally substituted with one or more $R_{23}$; or two $R_{16}$ together with the atoms to which they are attached can form a bridged heterocycloalkyl ring optionally substituted with one or more $R_{23}$ when $R_6$ is —$(C_0-C_3)$ alkylene-heterocycloalkyl, —O-heterocycloalkyl, or —$N(R_8)$-$(C_0-C_3)$ alkylene-heterocycloalkyl;

each $R_{17}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, cycloalkyl, heterocycloalkyl, or —C(O)-heterocycloalkyl, wherein the alkyl is optionally substituted with one or more substituents independently selected from $(C_1-C_6)$ alkoxy and —OH;

each $R_{18}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, —CN, —C(O)OH, or —C(O)O$(C_1-C_6)$ alkyl;

each $R_{19}$ and $R_{20}$ is independently H, $(C_1-C_6)$ alkyl, $(C_3-C_8)$ cycloalkyl, —CH$_2$C(O)NH$_2$, —S(O)$_2$$(C_1-C_6)$ alkyl, —S(O)$_2$$(C_6-C_{10})$ aryl or —C(O)$(C_1-C_6)$ alkyl;

each $R_{21}$ and $R_{22}$ is independently H or $(C_1-C_6)$ alkyl;

each $R_{23}$ is independently at each occurrence $(C_1-C_6)$ alkyl, $(C_1-C_6)$ alkoxy, $(C_1-C_6)$ haloalkyl, $(C_1-C_6)$ haloalkoxy, or halogen; or two $R_{23}$ together when attached to the same carbon form —C=(O); and n is 0, 1, 2, or 3.

In another embodiment, the compounds of Formula (I) have the structure of Formula (Ib):

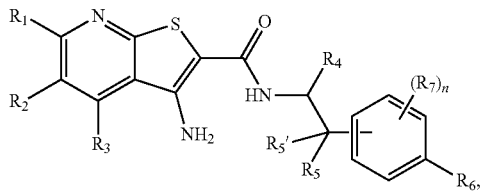

(Ib)

and pharmaceutically acceptable salts, hydrates, solvates, prodrugs, stereoisomers, and tautomers thereof.

In another embodiment, the compounds of Formula (I) have the structure of Formula (Ic):

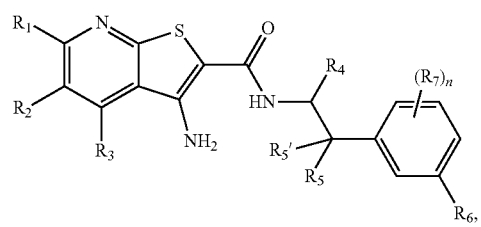

(Ic)

and pharmaceutically acceptable salts, hydrates, solvates, prodrugs, stereoisomers, and tautomers thereof.

In another embodiment, the compounds of Formula (I) have the structure of Formula (Id):

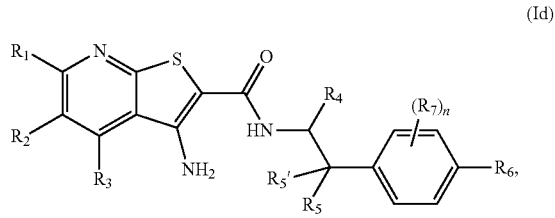

(Id)

and pharmaceutically acceptable salts, hydrates, solvates, prodrugs, stereoisomers, and tautomers thereof.

In another embodiment, the compounds of Formula (I) have the structure of Formula (Ie):

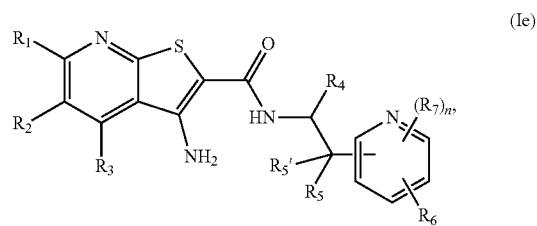

(Ie)

and pharmaceutically acceptable salts, hydrates, solvates, prodrugs, stereoisomers, and tautomers thereof.

In another embodiment, the compounds of Formula (I) have the structure of Formula (If):

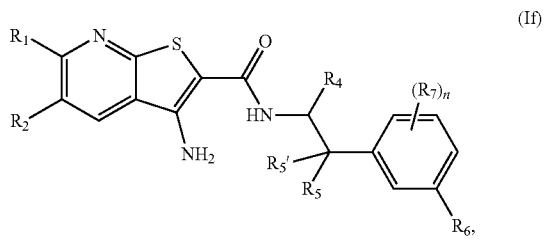

(If)

and pharmaceutically acceptable salts, hydrates, solvates, prodrugs, stereoisomers, and tautomers thereof.

In another embodiment, the compounds of Formula (I) have the structure of Formula (Ig):

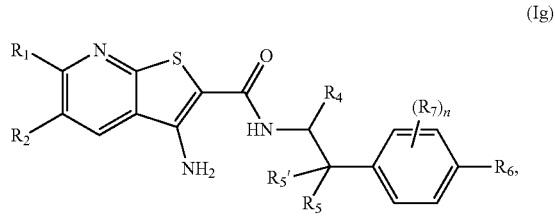

(Ig)

and pharmaceutically acceptable salts, hydrates, solvates, prodrugs, stereoisomers, and tautomers thereof.

In another embodiment, the compounds of Formula (I) have the structure of Formula (Ih):

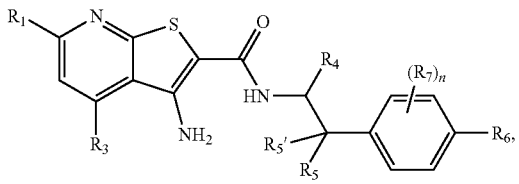

(Ih)

and pharmaceutically acceptable salts, hydrates, solvates, prodrugs, stereoisomers, and tautomers thereof.

In another embodiment, the compounds of Formula (I) have the structure of Formula (Ii):

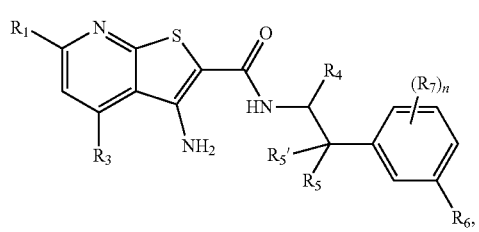

(Ii)

and pharmaceutically acceptable salts, hydrates, solvates, prodrugs, stereoisomers, and tautomers thereof.

In another embodiment, the compounds of Formula (I) have the structure of Formula (Ij):

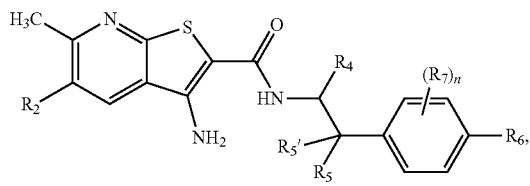

(Ij)

and pharmaceutically acceptable salts, hydrates, solvates, prodrugs, stereoisomers, and tautomers thereof.

In another embodiment, the compounds of Formula (I) have the structure of Formula (Ik):

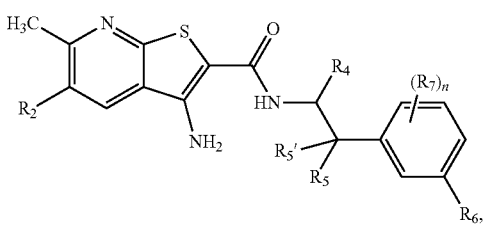

(Ik)

and pharmaceutically acceptable salts, hydrates, solvates, prodrugs, stereoisomers, and tautomers thereof.

In some embodiments of the Formulae above, $R_6$ is $-(C_0-C_3)$ alkylene-C(O)OH, $-(C_0-C_3)$ alkylene-heterocycloalkyl, $-(C_0-C_3)$ alkylene-aryl, $-(C_0-C_3)$ alkylene-heteroaryl or $-N(R_8)-(C_0-C_3)$ alkylene-heterocycloalkyl, wherein the heterocycloalkyl, aryl and heteroaryl are optionally substituted with one or more $R_{16}$; and each $R_{16}$ is independently at each occurrence $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, $-C(O)NR_{21}R_{22}$, $-S(O)_2(C_1-C_6)$ alkyl, $-OH$, or $-NR_{19}R_{20}$, wherein the alkyl is optionally substituted with one or more substituents independently selected from $(C_1-C_6)$ alkoxy, OH, and heterocycloalkyl; or two $R_{16}$ together when attached to the same carbon can form $-C=(O)$ when $R_6$ is $-(C_0-C_3)$ alkylene-heterocycloalkyl or $-N(R_8)-(C_0-C_3)$ alkylene-heterocycloalkyl; or two $R_{16}$ together when attached to the same atom form a $(C_3-C_8)$ spirocycloalkyl optionally substituted with one or more $R_{23}$ when $R_6$ is $-(C_0-C_3)$ alkylene-heterocycloalkyl, or $-N(R_8)-(C_0-C_3)$ alkylene-heterocycloalkyl; or two $R_{16}$ together when attached to the same atom form a $(C_3-C_8)$ spiroheterocycloalkyl optionally substituted with one or more $R_{23}$ when $R_6$ is $-(C_0-C_3)$ alkylene-heterocycloalkyl, or $-N(R_8)-(C_0-C_3)$ alkylene-heterocycloalkyl; or two $R_{16}$ together when on adjacent atoms form a heterocycloalkyl ring optionally substituted with one or more $R_{23}$; or two $R_{16}$ together when on adjacent atoms form a heteroaryl ring optionally substituted with one or more $R_{23}$; or two $R_{16}$ together with the atoms to which they are attached can form a bridged heterocycloalkyl ring optionally substituted with one or more $R_{23}$ when $R_6$ is $-(C_0-C_3)$ alkylene-heterocycloalkyl or $-N(R_8)-(C_0-C_3)$ alkylene-heterocycloalkyl.

In some embodiments of the Formulae above, X is $CR_7$. In another embodiment, X is N.

In some embodiments of the Formulae above, $R_1$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or $-NR_9R_{10}$. In another embodiment, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, $-CN$, or $-NR_9R_{10}$. In yet another embodiment, $R_1$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, $-CN$, or $-NR_9R_{10}$. In another embodiment, $R_1$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or $-NR_9R_{10}$. In yet another embodiment, $R_1$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, $-CN$, or $-NR_9R_{10}$. In another embodiment, $R_1$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or $-NR_9R_{10}$. In yet another embodiment, $R_1$ is H or $(C_1-C_4)$ alkyl. In another embodiment, $R_1$ is $(C_1-C_4)$ alkyl.

In some embodiments of the Formulae above, $R_2$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or $-NR_{11}R_{12}$. In another embodiment, $R_2$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or $-NR_{11}R_{12}$. In yet another embodiment, $R_2$ is H, $(C_1-C_4)$ alkyl, $(C_1-C_4)$ haloalkyl, halogen, $(C_3-C_6)$ cycloalkyl, or $-NR_{11}R_{12}$. In another embodiment, $R_2$ is H, $(C_1-C_3)$ alkyl, $(C_1-C_3)$ haloalkyl, halogen, $(C_3-C_6)$ cycloalkyl, or $-NR_{11}R_{12}$. In yet another embodiment, $R_2$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or $-NR_{11}R_{12}$. In another embodiment, $R_2$ is H or halogen.

In another embodiment, $R_1$ and $R_2$ together form a $(C_4-C_8)$ cycloalkyl optionally substituted with one to three $R_{15}$.

In yet another embodiment, $R_1$ and $R_2$ together form a $(C_4-C_6)$ cycloalkyl optionally substituted with one to three $R_{15}$.

In some embodiments of the Formulae above, $R_3$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or —$NR_{13}R_{14}$. In another embodiment, $R_3$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or —$NR_{13}R_{14}$. In yet another embodiment, $R_3$ is H, $(C_1-C_4)$ alkyl, $(C_1-C_4)$ alkoxy, or $(C_1-C_4)$ haloalkyl. In another embodiment, $R_3$ is H, $(C_1-C_3)$ alkyl, $(C_1-C_3)$ alkoxy, or $(C_1-C_3)$ haloalkyl. In another embodiment, $R_3$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or —$NR_{13}R_{14}$. In another embodiment, $R_3$ is H.

In some embodiments of the Formulae above, at least one of $R_1$, $R_2$, or $R_3$ is not H.

In some embodiments of the Formulae above, $R_1$ is $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —CN, or —$NR_9R_{10}$; and $R_2$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{11}R_{12}$.

In some embodiments of the Formulae above, $R_1$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —CN, or —$NR_9R_{10}$; and $R_2$ is $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{11}R_{12}$.

In some embodiments of the Formulae above, $R_1$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or —$NR_9R_{10}$; and $R_2$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or —$NR_{11}R_{12}$; and $R_3$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or —$NR_{13}R_{14}$.

In some embodiments of the Formulae above, $R_1$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —CN, or —$NR_9R_{10}$; $R_2$ is $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{11}R_{12}$; and $R_3$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{13}R_{14}$.

In some embodiments of the Formulae above, $R_1$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or —$NR_9R_{10}$; $R_2$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or —$NR_{11}R_{12}$; and $R_3$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or —$NR_{13}R_{14}$. and $R_3$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{13}R_{14}$.

In some embodiments of the Formulae above, $R_1$ is H, $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_6)$ cycloalkyl, or —$NR_9R_{10}$; $R_2$ is H, $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or —$NR_{11}R_{12}$; and $R_3$ is $(C_1-C_3)$ alkyl, $(C_1-C_3)$ alkoxy, $(C_1-C_3)$ haloalkyl, $(C_1-C_3)$ haloalkoxy, $(C_1-C_3)$ hydroxyalkyl, halogen, $(C_3-C_6)$ cycloalkyl, or —$NR_{13}R_{14}$. and $R_3$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{13}R_{14}$.

In another embodiment, $R_2$ and $R_3$ together form a $(C_4-C_8)$ cycloalkyl optionally substituted with one to three $R_{15}$. In yet another embodiment, $R_2$ and $R_3$ together form a $(C_4-C_6)$ cycloalkyl optionally substituted with one to three $R_{15}$.

In some embodiments of the Formulae above, $R_4$ is H, $(C_1-C_3)$ alkyl, or $(C_1-C_3)$ haloalkyl. In another embodiment, $R_4$ is H or $(C_1-C_3)$ alkyl. In yet another embodiment, $R_4$ is H. In another embodiment, $R_4$ is H, methyl, ethyl, n-propyl, or iso-propyl. In yet another embodiment, $R_4$ is H or methyl.

In some embodiments of the Formulae above, $R_5$ is H, $(C_1-C_3)$ alkyl, halogen, or $(C_1-C_3)$ haloalkyl. In another embodiment, $R_5$ is H, halogen, or $(C_1-C_3)$ alkyl. In yet another embodiment, $R_5$ is H or $(C_1-C_3)$ alkyl. In another embodiment, $R_5$ is H. In yet another embodiment, $R_5$ is H, F, Cl, methyl, ethyl, n-propyl, or iso-propyl. In another embodiment, $R_5$ is H, methyl, ethyl, n-propyl, or iso-propyl. In yet another embodiment, $R_5$ is H, F, or methyl. In another embodiment, $R_5$ is H or methyl.

In some embodiments of the Formulae above, $R_{5'}$ is H, $(C_1-C_3)$ alkyl, halogen, or $(C_1-C_3)$ haloalkyl. In another embodiment, $R_{5'}$ is H, halogen, or $(C_1-C_3)$ alkyl. In yet another embodiment, $R_{5'}$ is H or $(C_1-C_3)$ alkyl. In another embodiment, $R_{5'}$ is H. In yet another embodiment, $R_{5'}$ is H, F, Cl, methyl, ethyl, n-propyl, or iso-propyl. In another embodiment, $R_{5'}$ is H, methyl, ethyl, n-propyl, or iso-propyl. In yet another embodiment, $R_{5'}$ is H, F, or methyl. In another embodiment, $R_{5'}$ is H or methyl.

In some embodiments of the Formulae above, $R_4$ and $R_5$ together with the carbon atoms to which they are attached form a $(C_3-C_8)$ cycloalkyl ring. In another embodiment, $R_4$ and $R_5$ together with the carbon atoms to which they are attached form a $(C_4-C_6)$ cycloalkyl ring. In another embodiment, m is 2 and $R_4$ and $R_5$ together with the carbon atoms to which they are attached form a $(C_4-C_6)$ cycloalkyl ring.

In some embodiments of the Formulae above, $R_6$ is —$(C_0-C_2)$ alkylene-C(O)OH, —$(C_0-C_2)$ alkylene-heterocycloalkyl, —O-heterocycloalkyl, —$(C_0-C_2)$ alkylene-aryl, —$(C_0-C_2)$ alkylene-heteroaryl or —$N(R_8)$-$(C_0-C_3)$ alkylene-heterocycloalkyl, wherein the heterocycloalkyl, aryl and heteroaryl are optionally substituted with one or more $R_{16}$. In another embodiment, $R_6$ is —$(C_0-C_3)$ alkylene—C(O)OH, —$(C_0-C_3)$ alkylene-heterocycloalkyl, —$(C_0-C_3)$ alkylene-aryl, —$(C_0-C_3)$ alkylene-heteroaryl or —$N(R_8)$-$(C_0-C_3)$ alkylene-heterocycloalkyl, wherein the heterocycloalkyl, aryl and heteroaryl are optionally substituted with one to three $R_{16}$. In another embodiment, $R_6$ is —$(C_0-C_3)$ alkylene—C(O)OH, —$(C_0-C_3)$ alkylene-heterocycloalkyl, —$(C_0-C_3)$ alkylene-heteroaryl or —$N(R_8)$-$(C_0-C_3)$ alkylene-heterocycloalkyl, wherein the heterocycloalkyl and heteroaryl are optionally substituted with one to three $R_{16}$. In another embodiment, $R_6$ is —$(C_0-C_3)$ alkylene-heterocycloalkyl, —$(C_0-C_3)$ alkylene-heteroaryl or —$N(R_8)$-$(C_0-C_3)$ alkylene-heterocycloalkyl, wherein the heterocycloalkyl and heteroaryl are optionally substituted with one to three $R_{16}$. In another embodiment, $R_6$ is —$(C_0-C_3)$ alkylene-heterocycloalkyl, —O— heterocycloalkyl, —$(C_0-C_3)$ alkylene-heteroaryl or —$N(R_8)$-$(C_0-C_3)$ alkylene-heterocycloalkyl, wherein the heterocycloalkyl and heteroaryl are optionally substituted with one to three $R_{16}$.

In another embodiment, $R_6$ is —O— heterocycloalkyl optionally substituted with one to three $R_{16}$.

In some embodiments of the Formulae above, $R_7$ is H, $(C_1-C_4)$ alkyl, $(C_1-C_4)$ alkoxy, $(C_1-C_4)$ haloalkyl, $(C_1-C_4)$ haloalkoxy, halogen, —OH, —CN, $(C_3-C_8)$ cycloalkyl, heterocycloalkyl, aryl, or heteroaryl, wherein the alkyl is optionally substituted with one or more $(C_1-C_4)$ alkoxy or —OH, and wherein the cycloalkyl, heterocycloalkyl, aryl, and heteroaryl are optionally substituted with one to three $R_{17}$. In another embodiment, $R_7$ is H, $(C_1-C_4)$ alkyl, $(C_1-C_4)$ alkoxy, $(C_1-C_4)$ haloalkyl, $(C_1-C_4)$ haloalkoxy, halogen, —OH, —CN, $(C_3-C_8)$ cycloalkyl, aryl, or heteroaryl, wherein the alkyl is optionally substituted with one or more $(C_1-C_4)$ alkoxy or —OH, and wherein the cycloalkyl, aryl, and heteroaryl are optionally substituted with one to three $R_{17}$.

In another embodiment, $R_6$ and $R_7$ together when on adjacent atoms form a $(C_3-C_8)$ cycloalkyl ring optionally substituted with one to three $R_{18}$. In yet another embodiment, $R_6$ and $R_7$ together when on adjacent atoms form a heterocycloalkyl ring optionally substituted with one to three $R_{18}$. In another embodiment, $R_6$ and $R_7$ together when on adjacent atoms form an aryl ring optionally substituted with one to three $R_{18}$. In yet another embodiment, $R_6$ and $R_7$ together when on adjacent atoms form a heteroaryl ring optionally substituted with one to three $R_{18}$.

In another embodiment, two $R_7$ together when on adjacent atoms form a $(C_3-C_8)$ cycloalkyl ring. In yet another embodiment, two $R_7$ together when on adjacent atoms form a heterocycloalkyl ring. In another embodiment, two $R_7$ together when on adjacent atoms form an aryl ring. In yet another embodiment, two $R_7$ together when on adjacent atoms form a heteroaryl ring.

In some embodiments of the Formulae above, $R_8$ is H or $(C_1-C_3)$ alkyl. In another embodiment, $R_8$ is H. In yet another embodiment, $R_8$ is $(C_1-C_3)$ alkyl. In another embodiment, $R_8$ is H, methyl, ethyl, n-propyl, or iso-propyl. In another embodiment, $R_8$ is H, methyl, or ethyl.

In some embodiments of the Formulae above, $R_9$ is H, $(C_1-C_3)$ alkyl, or —C(O)$(C_1-C_3)$ alkyl. In another embodiment, $R_9$ is H, $(C_1-C_3)$ alkyl, or —C(O)$(C_1-C_2)$ alkyl. In yet another embodiment, $R_9$ is H, methyl, ethyl, n-propyl, iso-propyl, —C(O)CH$_3$, or —C(O)CH$_2$CH$_3$.

In some embodiments of the Formulae above, $R_{10}$ is H, $(C_1-C_3)$ alkyl, or —C(O)$(C_1-C_3)$ alkyl. In another embodiment, $R_{10}$ is H, $(C_1-C_3)$ alkyl, or —C(O)$(C_1-C_2)$ alkyl. In yet another embodiment, $R_{10}$ is H, methyl, ethyl, n-propyl, iso-propyl, —C(O)CH$_3$, or —C(O)CH$_2$CH$_3$.

In some embodiments of the Formulae above, $R_{11}$ is H, $(C_1-C_3)$ alkyl, or —C(O)$(C_1-C_3)$ alkyl. In another embodiment, $R_{11}$ is H, $(C_1-C_3)$ alkyl, or —C(O)$(C_1-C_2)$ alkyl. In yet another embodiment, $R_{11}$ is H, methyl, ethyl, n-propyl, iso-propyl, —C(O)CH$_3$, or —C(O)CH$_2$CH$_3$. In another embodiment, $R_{11}$ is H.

In some embodiments of the Formulae above, $R_{12}$ is H, $(C_1-C_3)$ alkyl, or —C(O)$(C_1-C_3)$ alkyl. In another embodiment, $R_{12}$ is H, $(C_1-C_3)$ alkyl, or —C(O)$(C_1-C_2)$ alkyl. In yet another embodiment, $R_{12}$ is H, methyl, ethyl, n-propyl, iso-propyl, —C(O)CH$_3$, or —C(O)CH$_2$CH$_3$. In another embodiment, $R_{12}$ is H.

In some embodiments of the Formulae above, $R_{13}$ is H, $(C_1-C_3)$ alkyl, or —C(O)$(C_1-C_3)$ alkyl. In another embodiment, $R_{13}$ is H, $(C_1-C_3)$ alkyl, or —C(O)$(C_1-C_2)$ alkyl. In yet another embodiment, $R_{13}$ is H, methyl, ethyl, n-propyl, iso-propyl, —C(O)CH$_3$, or —C(O)CH$_2$CH$_3$. In yet another embodiment, $R_{13}$ is H, methyl, ethyl, n-propyl, iso-propyl, —C(O)CH$_3$, or —C(O)CH$_2$CH$_3$. In another embodiment, $R_{13}$ is H.

In some embodiments of the Formulae above, $R_{14}$ is H, $(C_1-C_3)$ alkyl, or —C(O)$(C_1-C_3)$ alkyl. In another embodiment, $R_{14}$ is H, $(C_1-C_3)$ alkyl, or —C(O)$(C_1-C_2)$ alkyl. In yet another embodiment, $R_{14}$ is H, methyl, ethyl, n-propyl, iso-propyl, —C(O)CH$_3$, or —C(O)CH$_2$CH$_3$. In yet another embodiment, $R_{14}$ is H, methyl, ethyl, n-propyl, iso-propyl, —C(O)CH$_3$, or —C(O)CH$_2$CH$_3$. In another embodiment, $R_{14}$ is H.

In some embodiments of the Formulae above, $R_{15}$ is $(C_1-C_3)$ alkyl, $(C_1-C_3)$ alkoxy, $(C_1-C_3)$ haloalkyl, $(C_1-C_3)$ haloalkoxy, halogen, or —OH. In another embodiment, $R_{15}$ is $(C_1-C_3)$ alkyl, $(C_1-C_3)$ haloalkyl, halogen, or —OH. In yet another embodiment, $R_{15}$ is $(C_1-C_3)$ alkyl, halogen, or —OH. In another embodiment, $R_{15}$ is $(C_1-C_3)$ alkyl or —OH. In yet another embodiment, $R_{15}$ is —OH.

In some embodiments of the Formulae above, $R_{16}$ is $(C_1-C_4)$ alkyl, $(C_1-C_4)$ alkoxy, $(C_1-C_4)$ haloalkyl, $(C_1-C_4)$ haloalkoxy, $(C_1-C_4)$ hydroxyalkyl, halogen, $(C_3-C_8)$ cycloalkyl, —C(O)NR$_{21}$R$_{22}$, —S(O)$_2$$(C_1-C_6)$ alkyl, —OH, or —NR$_{19}$R$_{20}$, wherein the alkyl is optionally substituted with one to three substituents independently selected from $(C_1-C_6)$ alkoxy, OH, and heterocycloalkyl. In another embodiment, $R_{16}$ is $(C_1-C_4)$ alkyl, $(C_1-C_4)$ alkoxy, $(C_1-C_4)$ hydroxyalkyl, halogen, $(C_3-C_8)$ cycloalkyl, —C(O)NR$_{21}$R$_{22}$, —S(O)$_2$$(C_1-C_6)$ alkyl, —OH, or —NR$_{19}$R$_{20}$, wherein the alkyl is optionally substituted with one to three substituents independently selected from $(C_1-C_6)$ alkoxy, OH, and heterocycloalkyl. In yet another embodiment, $R_{16}$ is $(C_1-C_4)$ alkyl, $(C_1-C_4)$ alkoxy, $(C_1-C_4)$ hydroxyalkyl, halogen, $(C_3-C_8)$ cycloalkyl, or —NR19R$_{20}$, wherein the alkyl is optionally substituted with one to three substituents independently selected from $(C_1-C_6)$ alkoxy, OH, and heterocycloalkyl. In another embodiment, $R_{16}$ is $(C_1-C_4)$ alkyl, $(C_3-C_8)$ cycloalkyl, —C(O)NR$_{21}$R$_{22}$, —S(O)$_2$$(C_1-C_6)$ alkyl, —OH, or —NR$_{19}$R$_{20}$, wherein the alkyl is optionally substituted with one to three substituents independently selected from $(C_1-C_6)$ alkoxy, OH, and heterocycloalkyl. In yet another embodiment, $R_{16}$ is $(C_1-C_4)$ alkyl, $(C_3-C_8)$ cycloalkyl, or —NR$_{19}$R$_{20}$, wherein the alkyl is optionally substituted with one to three substituents independently selected from $(C_1-C_6)$ alkoxy, OH, and heterocycloalkyl.

In another embodiment, two $R_{16}$ together when attached to the same carbon can form —C=(O) when $R_6$ is —$(C_0-C_3)$ alkylene-heterocycloalkyl or —N(R$_8$)-$(C_0-C_3)$ alkylene-heterocycloalkyl. In yet another embodiment, two $R_{16}$ together when attached to the same atom form a $(C_3-C_8)$ spirocycloalkyl optionally substituted with one to three $R_{23}$ when $R_6$ is —$(C_0-C_3)$ alkylene-heterocycloalkyl or —N(R$_8$)-$(C_0-C_3)$ alkylene-heterocycloalkyl. In another embodiment, two $R_{16}$ together when attached to the same atom form a $(C_3-C_8)$ spiroheterocycloalkyl optionally substituted with one to three $R_{23}$ when $R_6$ is —$(C_0-C_3)$ alkylene-heterocycloalkyl or —N(R$_8$)-$(C_0-C_3)$ alkylene-heterocycloalkyl. In another embodiment, two $R_{16}$ together when on adjacent atoms form a heterocycloalkyl ring optionally substituted with one to three $R_{23}$. In another embodiment, two $R_{16}$ together when on adjacent atoms form a heteroaryl ring optionally substituted with one to three $R_{23}$. In another embodiment, two $R_{16}$ together with the atoms to which they are attached can form a bridged heterocycloalkyl ring optionally substituted with one or more $R_{23}$ when $R_6$ is —$(C_0-C_3)$ alkylene-heterocycloalkyl or —N(R$_8$)-$(C_0-C_3)$ alkylene-heterocycloalkyl.

In another embodiment, two $R_{16}$ together when attached to the same carbon can form —C=(O) when $R_6$ is —($C_0$-$C_3$) alkylene-heterocycloalkyl, —O-heterocycloalkyl, or —N($R_8$)-($C_0$-$C_3$) alkylene-heterocycloalkyl. In another embodiment, two $R_{16}$ together when attached to the same atom form a ($C_3$-$C_8$) spirocycloalkyl optionally substituted with one or more $R_{23}$ when $R_6$ is —($C_0$-$C_3$) alkylene-heterocycloalkyl, —O-heterocycloalkyl, or —N($R_8$)-($C_0$-$C_3$) alkylene-heterocycloalkyl. In another embodiment, two $R_{16}$ together when attached to the same atom form a ($C_3$-$C_8$) spiroheterocycloalkyl optionally substituted with one or more $R_{23}$ when $R_6$ is —($C_0$-$C_3$) alkylene-heterocycloalkyl, —O-heterocycloalkyl, or —N($R_8$)-($C_0$-$C_3$) alkylene-heterocycloalkyl. In another embodiment, two $R_{16}$ together when on adjacent atoms form a heterocycloalkyl ring optionally substituted with one or more $R_{23}$. In another embodiment, two $R_{16}$ together when on adjacent atoms form a heteroaryl ring optionally substituted with one or more $R_{23}$. In another embodiment, two $R_{16}$ together with the atoms to which they are attached can form a bridged heterocycloalkyl ring optionally substituted with one or more $R_{23}$ when $R_6$ is —($C_0$-$C_3$) alkylene-heterocycloalkyl, —O-heterocycloalkyl, or —N($R_8$)-($C_0$-$C_3$) alkylene-heterocycloalkyl.

In some embodiments of the Formulae above, $R_{17}$ is ($C_1$-$C_4$) alkyl, ($C_1$-$C_4$) alkoxy, ($C_1$-$C_4$) haloalkyl, ($C_1$-$C_4$) haloalkoxy, halogen, cycloalkyl, heterocycloalkyl, or -C(O)-heterocycloalkyl, wherein the alkyl is optionally substituted with one to three substituents independently selected from ($C_1$-$C_4$) alkoxy and —OH. In another embodiment, $R_{17}$ is ($C_1$-$C_4$) alkyl, ($C_1$-$C_4$) haloalkyl, halogen, heterocycloalkyl, or —C(O)-heterocycloalkyl, wherein the alkyl is optionally substituted with one to three substituents independently selected from ($C_1$-$C_4$) alkoxy and —OH.

In some embodiments of the Formulae above, $R_{18}$ is ($C_1$-$C_4$) alkyl, ($C_1$-$C_4$) alkoxy, ($C_1$-$C_4$) haloalkyl, ($C_1$-$C_4$) haloalkoxy, halogen, —OH, —CN, —C(O)OH, or —C(O)O($C_1$-$C_4$) alkyl. In another embodiment, $R_{18}$ is ($C_1$-$C_4$) alkyl, ($C_1$-$C_4$) haloalkyl, halogen, —OH, —CN, —C(O)OH, or —C(O)O($C_1$-$C_4$) alkyl. In yet another embodiment, $R_{18}$ is ($C_1$-$C_4$) alkyl, halogen, —OH, —CN, —C(O)OH, or —C(O)O($C_1$-$C_4$) alkyl. In another embodiment, $R_{18}$ is ($C_1$-$C_4$) alkyl, —OH, —C(O)OH, or —C(O)O($C_1$-$C_4$) alkyl. In another embodiment, $R_{18}$ is —C(O)OH, or —C(O)O($C_1$-$C_4$) alkyl.

In some embodiments of the Formulae above, $R_{19}$ is H, ($C_1$-$C_4$) alkyl, ($C_3$-$C_8$) cycloalkyl, —CH$_2$C(O)NH$_2$, —S(O)$_2$ ($C_1$-$C_4$) alkyl, —S(O)$_2$($C_6$-$C_{10}$) aryl or —C(O)($C_1$-$C_4$) alkyl. In another embodiment, $R_{19}$ is H, ($C_1$-$C_4$) alkyl, ($C_3$-$C_6$) cycloalkyl, —CH$_2$C(O)NH$_2$, —S(O)$_2$($C_1$-$C_4$) alkyl, —S(O)$_2$($C_6$-$C_{10}$) aryl, or —C(O)($C_1$-$C_4$) alkyl. In yet another embodiment, $R_{19}$ is H, ($C_1$-$C_4$) alkyl or ($C_3$-$C_6$) cycloalkyl. In another embodiment, $R_{19}$ is H, ($C_1$-$C_4$) alkyl —CH$_2$C(O)NH$_2$, —S(O)$_2$($C_1$-$C_4$) alkyl, —S(O)$_2$($C_6$-$C_{10}$) aryl, or —C(O)($C_1$-$C_4$) alkyl.

In some embodiments of the Formulae above, $R_{20}$ is H, ($C_1$-$C_4$) alkyl, ($C_3$-$C_8$) cycloalkyl, —CH$_2$C(O)NH$_2$, —S(O)$_2$ ($C_1$-$C_4$) alkyl, —S(O)$_2$($C_6$-$C_{10}$) aryl or —C(O)($C_1$-$C_4$) alkyl. In another embodiment, $R_{20}$ is H, ($C_1$-$C_4$) alkyl, ($C_3$-$C_6$) cycloalkyl, —CH$_2$C(O)NH$_2$, —S(O)$_2$($C_1$-$C_4$) alkyl, —S(O)$_2$($C_6$-$C_{10}$) aryl, or —C(O)($C_1$-$C_4$) alkyl. In yet another embodiment, $R_{20}$ is H, ($C_1$-$C_4$) alkyl or ($C_3$-$C_6$) cycloalkyl. In another embodiment, $R_{20}$ is H, ($C_1$-$C_4$) alkyl —CH$_2$C(O)NH$_2$, —S(O)$_2$($C_1$-$C_4$) alkyl, —S(O)$_2$($C_6$-$C_{10}$) aryl, or —C(O)($C_1$-$C_4$) alkyl.

In some embodiments of the Formulae above, $R_{21}$ is H or ($C_1$-$C_3$) alkyl. In another embodiment, $R_{21}$ is H, methyl, ethyl, n-propyl, or iso-propyl.

In some embodiments of the Formulae above, $R_{22}$ is H or ($C_1$-$C_3$) alkyl. In another embodiment, $R_{22}$ is H, methyl, ethyl, n-propyl, or iso-propyl.

In some embodiments of the Formulae above, $R_{23}$ is ($C_1$-$C_3$) alkyl, ($C_1$-$C_3$) alkoxy, ($C_1$-$C_3$) haloalkyl, ($C_1$-$C_3$) haloalkoxy, or halogen. In another embodiment, $R_{23}$ is ($C_1$-$C_2$) alkyl, ($C_1$-$C_2$) alkoxy, ($C_1$-$C_2$) haloalkyl, ($C_1$-$C_2$) haloalkoxy, or halogen. In yet another embodiment, $R_{23}$ is ($C_1$-$C_2$) alkyl, ($C_1$-$C_2$) haloalkyl, or halogen. In another embodiment, $R_{23}$ is ($C_1$-$C_2$) alkyl, or ($C_1$-$C_2$) haloalkyl. In another embodiment, $R_{23}$ is ($C_1$-$C_3$) alkyl. In another embodiment, $R_{23}$ is methyl, ethyl, n-propyl, or iso-propyl.

In another embodiment, two $R_{23}$ together when attached to the same carbon form —C=(O).

In some embodiments of the Formulae above, n is 0, 1, or 2. In another embodiment, n is 0 or 1. In yet another embodiment, n is 1, 2, or 3. In another embodiment, n is 1 or 2. In another embodiment, n is 2 or 3. In another embodiment, n is 0. In another embodiment, n is 1. In another embodiment, n is 2. In another embodiment, n is 3.

In some embodiments of the Formulae above, X is CH.

In some embodiments of the Formulae above, $R_4$ is H or CH$_3$ and Rs is H or CH$_3$.

In some embodiments of the Formulae above, $R_4$ is H or CH$_3$, Rs is H or CH$_3$, and $R_5$ is H, fluoro, or CH$_3$.

In some embodiments of the Formulae above, $R_2$ is H, ($C_1$-$C_6$) alkyl, ($C_1$-$C_6$) haloalkyl, halogen, ($C_3$-$C_8$) cycloalkyl, or —NH$_2$.

In some embodiments of the Formulae above, $R_1$ and $R_2$ together form a ($C_3$-$C_8$) cycloalkyl optionally substituted with one or more $R_1$.

In some embodiments of the Formulae above, $R_3$ is H, ($C_1$-$C_6$) alkyl, ($C_1$-$C_6$) alkoxy, or ($C_1$-$C_6$) haloalkyl.

In some embodiments of the Formulae above, $R_2$ and $R_3$ together form a ($C_3$-$C_8$) cycloalkyl optionally substituted with one or more $R_{15}$.

In another embodiment, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_6$) cycloalkyl, or —NR$_9$R$_{10}$; $R_2$ is ($C_1$-$C_3$) alkyl, ($C_1$-$C_3$) alkoxy, ($C_1$-$C_3$) haloalkyl, ($C_1$-$C_3$) haloalkoxy, ($C_1$-$C_3$) hydroxyalkyl, halogen, ($C_3$-$C_6$) cycloalkyl, or —NR$_{11}$R$_{12}$; and $R_3$ is H, ($C_1$-$C_3$) alkyl, ($C_1$-$C_3$) alkoxy, ($C_1$-$C_3$) haloalkyl, ($C_1$-$C_3$) haloalkoxy, ($C_1$-$C_3$) hydroxyalkyl, halogen, ($C_3$-$C_6$) cycloalkyl, or —NR$_{13}$R$_{14}$.

In some embodiments of the Formulae above, X is CR$_7$. In another embodiment, X is CR$_7$ and $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —NR$_9$R$_{10}$. In yet another embodiment, X is CR$_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —NR$_9$R$_{10}$ and $R_2$ is H, ($C_1$-$C_4$) alkyl, ($C_1$-$C_4$) haloalkyl, halogen, ($C_3$-$C_8$) cycloalkyl, or —NR$_{11}$R$_{12}$. In another embodiment, X is CR$_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —NR$_9$R$_{10}$, $R_2$ is H, ($C_1$-$C_4$) alkyl, ($C_1$-$C_4$) haloalkyl, halogen, ($C_3$-$C_8$) cycloalkyl, or —NR$_{11}$R$_{12}$, and $R_3$ is H, ($C_1$-$C_6$) alkyl, ($C_1$-$C_6$) alkoxy, ($C_1$-$C_6$) haloalkyl. In yet another embodiment, X is CR$_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —NR$_9$R$_{10}$, $R_2$ is H, ($C_1$-$C_4$) alkyl, ($C_1$-$C_4$) haloalkyl, halogen, ($C_3$-$C_8$) cycloalkyl, or —NR$_{11}$R$_{12}$, $R_3$ is H, ($C_1$-$C_6$) alkyl, ($C_1$-$C_6$) alkoxy, ($C_1$-$C_6$) haloalkyl, and $R_4$ is H or ($C_1$-$C_3$) alkyl. In another embodiment, X is CR$_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, and $R_5$ is H or ($C_1$-$C_3$) alkyl. In yet another embodiment, X is $CR_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, and $R_{5'}$ is H or ($C_1$-$C_3$) alkyl.

In another embodiment, X is $CR_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, $R_{5'}$ is H or ($C_1$-$C_3$) alkyl, and $R_6$ is —($C_0$-$C_3$) alkylene-heterocycloalkyl optionally substituted with one or more $R_{16}$.

In another embodiment, X is $CR_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, $R_{5'}$ is H or ($C_1$-$C_3$) alkyl, and $R_6$ is —O-heterocycloalkyl optionally substituted with one or more $R_{16}$.

In another embodiment, X is $CR_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, $R_{5'}$ is H or ($C_1$-$C_3$) alkyl, and $R_6$ is —($C_0$-$C_3$) alkylene —C(O)OH.

In another embodiment, X is $CR_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, $R_{5'}$ is H or ($C_1$-$C_3$) alkyl, and $R_6$ is —($C_0$-$C_3$) alkylene-heteroaryl optionally substituted with one or more $R_{16}$.

In another embodiment, X is $CR_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, $R_{5'}$ is H or ($C_1$-$C_3$) alkyl, and $R_6$ is —N($R_8$)-($C_0$-$C_3$) alkylene-heterocycloalkyl optionally substituted with one or more $R_{16}$.

In another embodiment, X is $CR_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, $R_{5'}$ is H or ($C_1$-$C_3$) alkyl, and $R_6$ is -($C_0$-$C_3$) alkylene-aryl optionally substituted with one or more $R_{16}$.

In another embodiment, X is $CR_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, $R_{5'}$ is H or ($C_1$-$C_3$) alkyl, and $R_6$ and $R_7$ together when on adjacent atoms form a ($C_4$-$C_8$) cycloalkyl ring optionally substituted with one or more $R_{18}$.

In another embodiment, X is $CR_7$, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, $R_{5'}$ is H or ($C_1$-$C_3$) alkyl, and $R_6$ and $R_7$ together when on adjacent atoms form a heterocycloalkyl ring optionally substituted with one or more $R_{18}$.

In some embodiments of the Formulae above, X is N. In another embodiment, X is N and $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$. In yet another embodiment, X is N, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, and $R_2$ is H, ($C_1$-$C_4$) alkyl, ($C_1$-$C_4$) haloalkyl, halogen, ($C_3$-$C_8$) cycloalkyl, or —$NR_{11}R_{12}$. In another embodiment, X is N, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, and $R_3$ is H, ($C_1$-$C_6$) alkyl, ($C_1$-$C_6$) alkoxy, ($C_1$-$C_6$) haloalkyl. In yet another embodiment, X is N, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, and $R_4$ is H or ($C_1$-$C_3$) alkyl. In another embodiment, X is N, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, and $R_5$ is H or ($C_1$-$C_3$) alkyl. In yet another embodiment, X is N, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, and $R_{5'}$ is H or ($C_1$-$C_3$) alkyl.

In another embodiment, X is N, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$) alkyl, ($C_1$-$C_6$) alkoxy, ($C_1$-$C_6$) haloalkyl, $R_4$ is H or ($C_1$-$C_3$) alkyl, $R_5$ is H or ($C_1$-$C_3$) alkyl, $R_{5'}$ is H or ($C_1$-$C_3$) alkyl, and $R_6$ is —($C_0$-$C_3$) alkylene-heterocycloalkyl optionally substituted with one or more $R_{16}$.

In another embodiment, X is N, $R_1$ is H, ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, halogen, ($C_3$-$C_8$) cycloalkyl, or —$NR_9R_{10}$, $R_2$ is H, ($C_1$-$C_4$) alkyl, ($C_1$-$C_4$) haloalkyl, halogen, ($C_3$-$C_8$) cycloalkyl, or —$NR_{11}R_{12}$, $R_3$ is H, ($C_1$-$C_6$)

alkyl, (C₁-C₆) alkoxy, (C₁-C₆) haloalkyl, R₄ is H or (C₁-C₃) alkyl, R₅ is H or (C₁-C₃) alkyl, R₅' is H or (C₁-C₃) alkyl, and R₆ is —O-heterocycloalkyl optionally substituted with one or more R₁₆.

In another embodiment, X is N, R₁ is H, (C₁-C₄) alkyl, (C₁-C₄) alkoxy, (C₁-C₄) haloalkyl, (C₁-C₄) haloalkoxy, (C₁-C₄) hydroxyalkyl, halogen, (C₃-C₈) cycloalkyl, or —NR₉R₁₀, R₂ is H, (C₁-C₄) alkyl, (C₁-C₄) haloalkyl, halogen, (C₃-C₈) cycloalkyl, or —NR₁₁R₁₂, R₃ is H, (C₁-C₆) alkyl, (C₁-C₆) alkoxy, (C₁-C₆) haloalkyl, R₄ is H or (C₁-C₃) alkyl, R₅ is H or (C₁-C₃) alkyl, R₅' is H or (C₁-C₃) alkyl, and R₆ is -(C₀-C₃) alkylene —C(O)OH.

In another embodiment, X is N, R₁ is H, (C₁-C₄) alkyl, (C₁-C₄) alkoxy, (C₁-C₄) haloalkyl, (C₁-C₄) haloalkoxy, (C₁-C₄) hydroxyalkyl, halogen, (C₃-C₈) cycloalkyl, or —NR₉R₁₀, R₂ is H, (C₁-C₄) alkyl, (C₁-C₄) haloalkyl, halogen, (C₃-C₈) cycloalkyl, or —NR₁₁R₁₂, R₃ is H, (C₁-C₆) alkyl, (C₁-C₆) alkoxy, (C₁-C₆) haloalkyl, R₄ is H or (C₁-C₃) alkyl, R₅ is H or (C₁-C₃) alkyl, R₅' is H or (C₁-C₃) alkyl, and R₆ is —(C₀-C₃) alkylene-heteroaryl optionally substituted with one or more R₁₆.

In another embodiment, X is N, R₁ is H, (C₁-C₄) alkyl, (C₁-C₄) alkoxy, (C₁-C₄) haloalkyl, (C₁-C₄) haloalkoxy, (C₁-C₄) hydroxyalkyl, halogen, (C₃-C₈) cycloalkyl, or —NR₉R₁₀, R₂ is H, (C₁-C₄) alkyl, (C₁-C₄) haloalkyl, halogen, (C₃-C₈) cycloalkyl, or —NR₁₁R₁₂, R₃ is H, (C₁-C₆) alkyl, (C₁-C₆) alkoxy, (C₁-C₆) haloalkyl, R₄ is H or (C₁-C₃) alkyl, R₅ is H or (C₁-C₃) alkyl, R₅' is H or (C₁-C₃) alkyl, and R₆ is —N(R₈)-(C₀-C₃) alkylene-heterocycloalkyl optionally substituted with one or more R₁₆.

In another embodiment, X is N, R₁ is H, (C₁-C₄) alkyl, (C₁-C₄) alkoxy, (C₁-C₄) haloalkyl, (C₁-C₄) haloalkoxy, (C₁-C₄) hydroxyalkyl, halogen, (C₃-C₈) cycloalkyl, or —NR₉R₁₀, R₂ is H, (C₁-C₄) alkyl, (C₁-C₄) haloalkyl, halogen, (C₃-C₈) cycloalkyl, or —NR₁₁R₁₂, R₃ is H, (C₁-C₆) alkyl, (C₁-C₆) alkoxy, (C₁-C₆) haloalkyl, R₄ is H or (C₁-C₃) alkyl, R₅ is H or (C₁-C₃) alkyl, R₅' is H or (C₁-C₃) alkyl, and R₆ is —(C₀-C₃) alkylene-aryl optionally substituted with one or more R₁₆.

In another embodiment, X is N, R₁ is H, (C₁-C₄) alkyl, (C₁-C₄) alkoxy, (C₁-C₄) haloalkyl, (C₁-C₄) haloalkoxy, (C₁-C₄) hydroxyalkyl, halogen, (C₃-C₈) cycloalkyl, or —NR₉R₁₀, R₂ is H, (C₁-C₄) alkyl, (C₁-C₄) haloalkyl, halogen, (C₃-C₈) cycloalkyl, or —NR₁₁R₁₂, R₃ is H, (C₁-C₆) alkyl, (C₁-C₆) alkoxy, (C₁-C₆) haloalkyl, R₄ is H or (C₁-C₃) alkyl, R₅ is H or (C₁-C₃) alkyl, R₅' is H or (C₁-C₃) alkyl, and R₆ and R₇ together when on adjacent atoms form a (C₄-C₈) cycloalkyl ring optionally substituted with one or more R₁₈.

In another embodiment, X is N, R₁ is H, (C₁-C₄) alkyl, (C₁-C₄) alkoxy, (C₁-C₄) haloalkyl, (C₁-C₄) haloalkoxy, (C₁-C₄) hydroxyalkyl, halogen, (C₃-C₈) cycloalkyl, or —NR₉R₁₀, R₂ is H, (C₁-C₄) alkyl, (C₁-C₄) haloalkyl, halogen, (C₃-C₈) cycloalkyl, or —NR₁₁R₁₂, R₃ is H, (C₁-C₆) alkyl, (C₁-C₆) alkoxy, (C₁-C₆) haloalkyl, R₄ is H or (C₁-C₃) alkyl, R₅ is H or (C₁-C₃) alkyl, R₅' is H or (C₁-C₃) alkyl, and R₆ and R₇ together when on adjacent atoms form a heterocycloalkyl ring optionally substituted with one or more R₁₈.

Non-limiting illustrative compounds of the disclosure include:

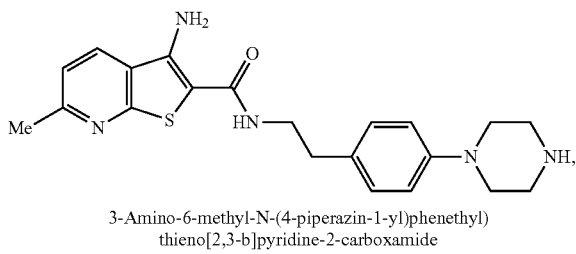

I-1

3-Amino-6-methyl-N-(4-piperazin-1-yl)phenethyl)thieno[2,3-b]pyridine-2-carboxamide

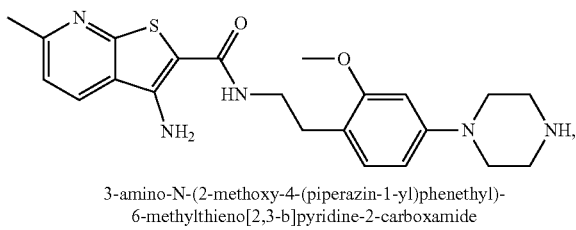

I-2

3-amino-N-(2-methoxy-4-(piperazin-1-yl)phenethyl)-6-methylthieno[2,3-b]pyridine-2-carboxamide

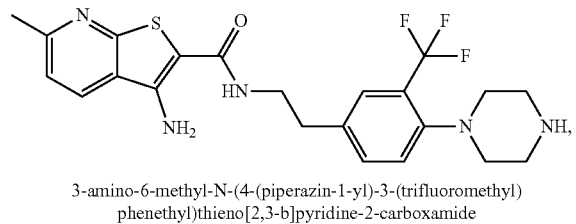

I-3

3-amino-6-methyl-N-(4-(piperazin-1-yl)-3-(trifluoromethyl)phenethyl)thieno[2,3-b]pyridine-2-carboxamide

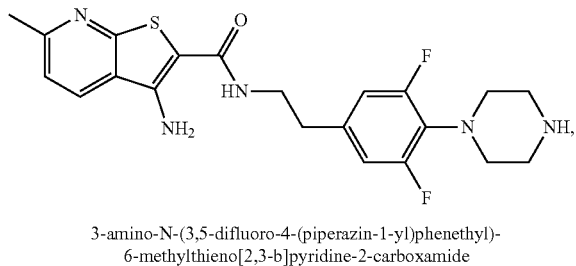

I-4

3-amino-N-(3,5-difluoro-4-(piperazin-1-yl)phenethyl)-6-methylthieno[2,3-b]pyridine-2-carboxamide

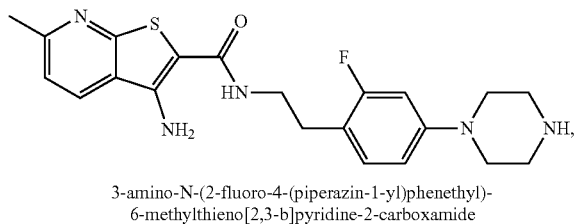

I-5

3-amino-N-(2-fluoro-4-(piperazin-1-yl)phenethyl)-6-methylthieno[2,3-b]pyridine-2-carboxamide

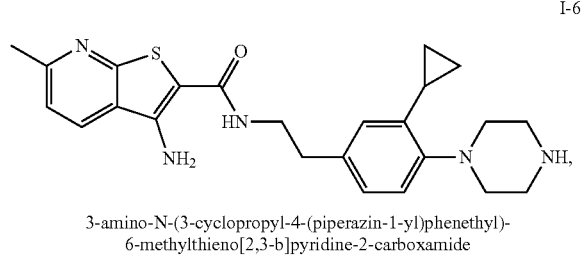

I-6

3-amino-N-(3-cyclopropyl-4-(piperazin-1-yl)phenethyl)-6-methylthieno[2,3-b]pyridine-2-carboxamide -continued

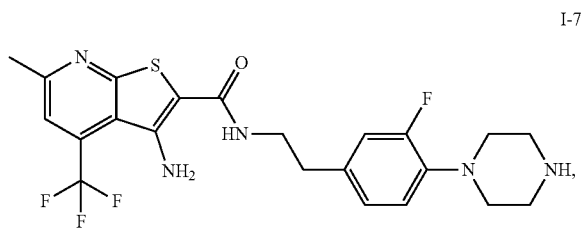

I-7

3-amino-N-(3-fluoro-4-(piperazin-1-yl)phenethyl)-
6-methyl-4-(trifluoromethyl)thieno[2,3-b]pyridine-2-carboxamide

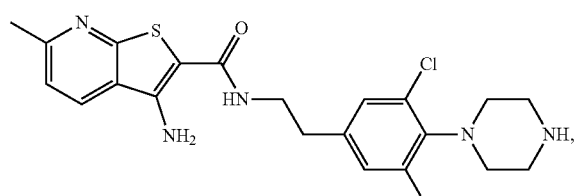

I-8

3-amino-N-(3-chloro-5-fluoro-4-(piperazin-1-yl)phenethyl)-
6-methylthieno[2,3-b]pyridine-2-carboxamide

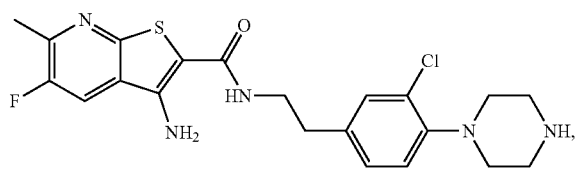

I-9

3-amino-N-(3-chloro-4-(piperazin-1-yl)phenethyl)-5-fluoro-
6-methylthieno[2,3-b]pyridine-2-carboxamide

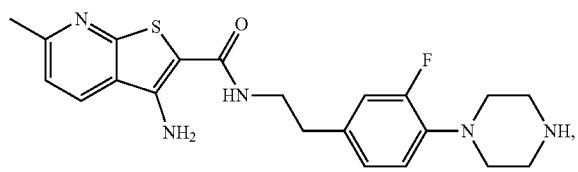

I-10

3-Amino-N-(3-fluoro-4-(piperazin-1-yl)phenethyl)-6-methylthieno
[2,3-b]pyridine-2-carboxamide

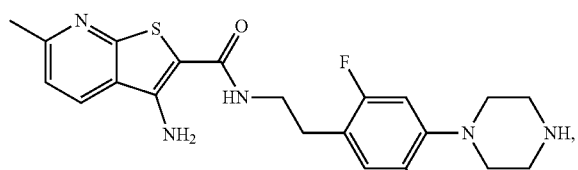

I-11

3-Amino-N-(2,5-difluoro-4-(piperazin-1-yl)phenethyl)-6-methylthieno
[2,3-b]pyridine-2-carboxamide -continued

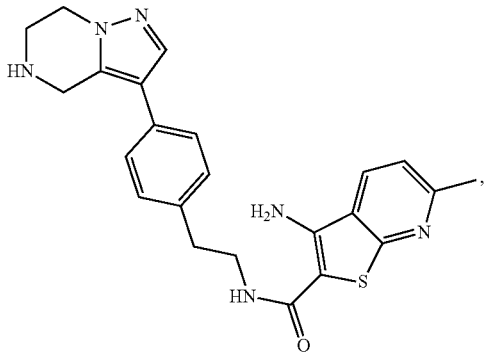

I-12

3-amino-6-methyl-N-(4-(4,5,6,7-tetrahydropyrazolo[1,5-a]
pyrazin-3-yl)phenethyl)thieno[2,3-b]pyridine-2-carboxamide

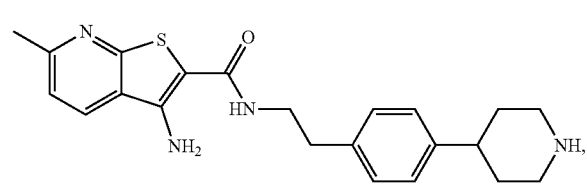

I-13

3-amino-6-methyl-N-(4-(piperidin-4-yl)phenethyl)thieno
[2,3-b]pyridine-2-carboxamide

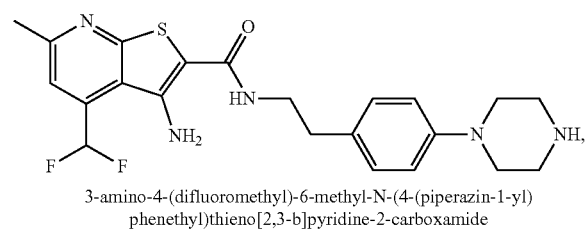

I-14

3-amino-4-(difluoromethyl)-6-methyl-N-(4-(piperazin-1-yl)
phenethyl)thieno[2,3-b]pyridine-2-carboxamide

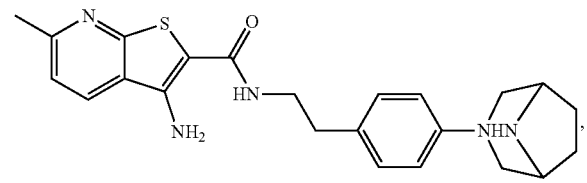

I-15

N-(4-(3,8-diazabicyclo[3.2.1]octan-3-yl)phenethyl)-3-
amino-6-methylthieno[2,3-b]pyridine-2-carboxamide

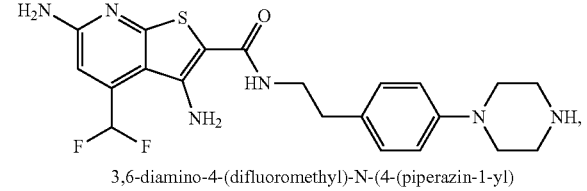

I-16

3,6-diamino-4-(difluoromethyl)-N-(4-(piperazin-1-yl)
phenethyl)thieno[2,3-b]pyridine-2-carboxamide

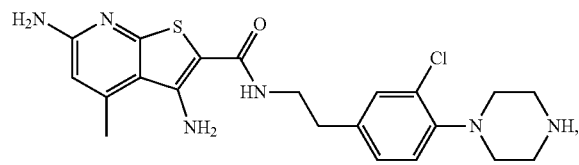

3,6-diamino-N-(3-chloro-4-(piperazin-1-yl)
phenethyl)-4-methylthieno[2,3-b]pyridine-2-carboxamide

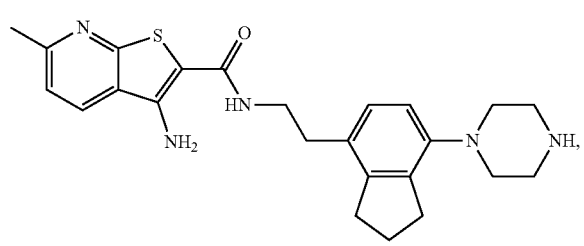

3-amino-6-methyl-N-(2-(7-(piperazin-1-yl)2,3-dihydro-1H-
inden-4-yl)ethyl)thieno[2,3-b]pyridine-2-carboxamide

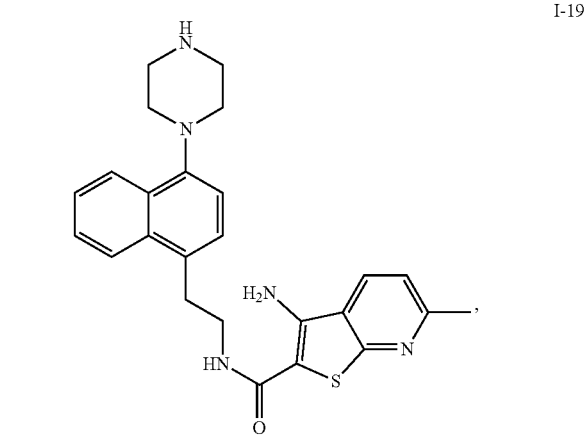

3-amino-6-methyl-N-(2-(4-(piperazin-1-yl)naphthalen-1-yl)
ethyl)thieno[2,3-b] pyridine-2-carboxide

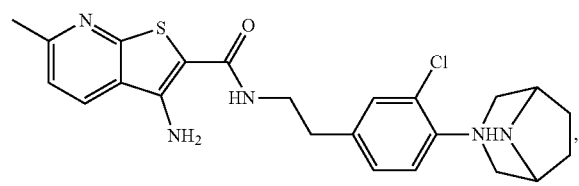

N-(4-(3,8-diazabicyclo[3.2.1]octan-3-yl)-3-chlorophenethyl)-
3-amino-6-methylthieno[2,3-b]pyridine-2-carboxamide

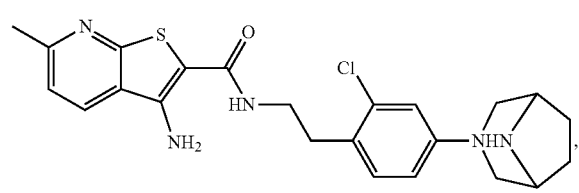

N-(4-(3,8-diazabicyclo[3.2.1]octan-3-yl)-2-chlorophenethyl)-
3-amino-6-methylthieno[2,3-b]pyridine-2-carboxamide

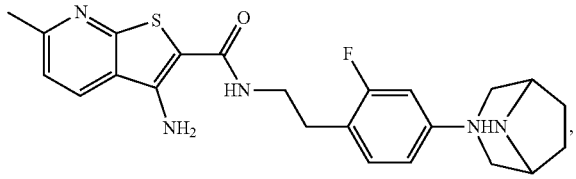

N-(4-(3,8-diazabicyclo[3.2.1]octan-3-yl)-2-fluorophenethyl)-
3-amino-6-methylthieno[2,3-b]pyridine-2-carboxamide

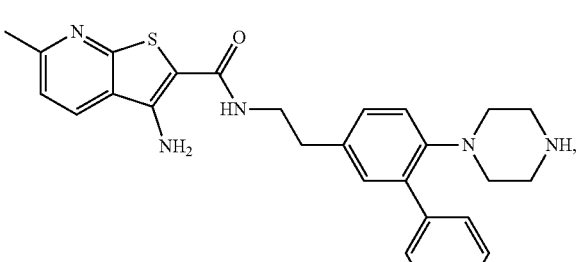

3-amino-6-methyl-N-(2-(6-(piperazin-1-yl)[1,1'-biphenyl]-
3-yl)ethyl)thieno[2,3-b]pyridine-2-carboxamide

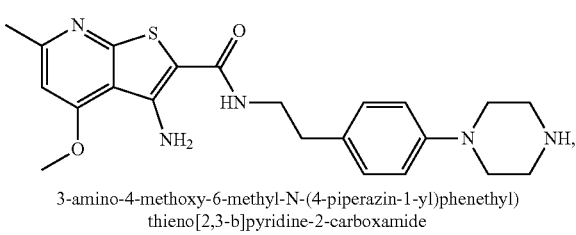

3-amino-4-methoxy-6-methyl-N-(4-piperazin-1-yl)phenethyl)
thieno[2,3-b]pyridine-2-carboxamide

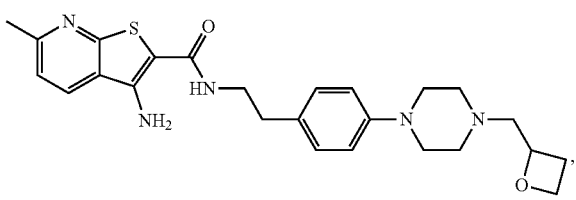

3-amino-6-methyl-N-(4-(4-(oxetan-2-ylmethyl)piperazin-1-yl)
phenethyl)thieno[2,3-b]pyridine-2-carboxamide

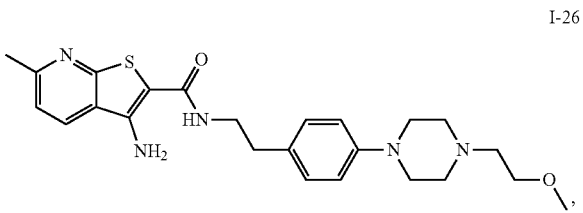

3-amino-N-(4-(4-(2-methoxyethyl)piperazin-1-yl)phenethyl)-
6-methylthieno[2,3-b]pyridine-2-carboxamide

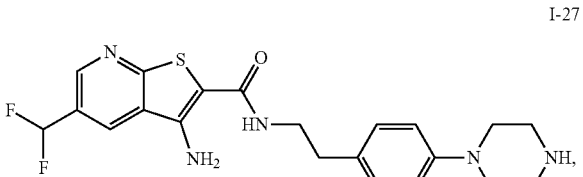

3-amino-5-(difluoromethyl)-N-(4-(piperazin-1-yl)phenethyl)
thieno[2,3-b]pyridine-2-carboxamide

I-28

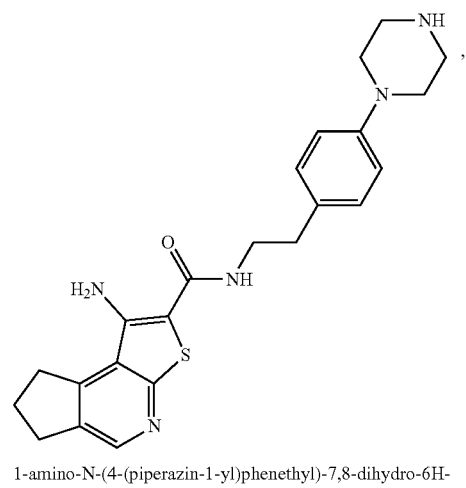

1-amino-N-(4-(piperazin-1-yl)phenethyl)-7,8-dihydro-6H-cyclopenta[d]thieno[2,3-b]pyridine-2-carboxamide

I-29

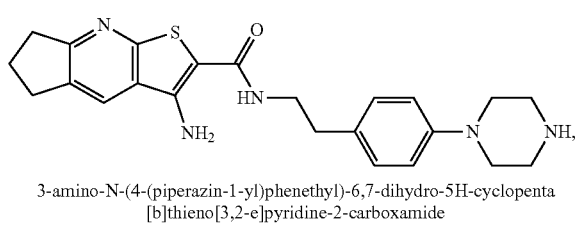

3-amino-N-(4-(piperazin-1-yl)phenethyl)-6,7-dihydro-5H-cyclopenta[b]thieno[3,2-e]pyridine-2-carboxamide

I-30

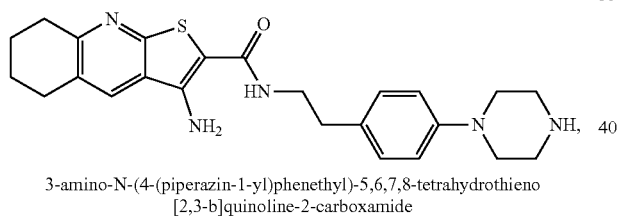

3-amino-N-(4-(piperazin-1-yl)phenethyl)-5,6,7,8-tetrahydrothieno[2,3-b]quinoline-2-carboxamide

I-31

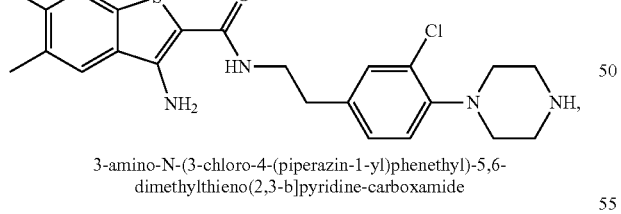

3-amino-N-(3-chloro-4-(piperazin-1-yl)phenethyl)-5,6-dimethylthieno(2,3-b)pyridine-carboxamide

I-32

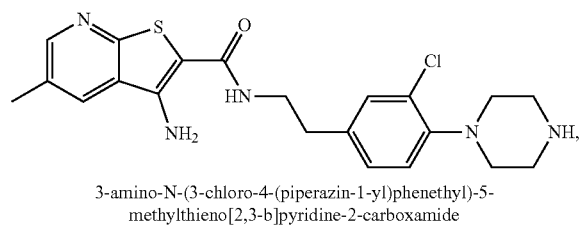

3-amino-N-(3-chloro-4-(piperazin-1-yl)phenethyl)-5-methylthieno[2,3-b]pyridine-2-carboxamide

I-33

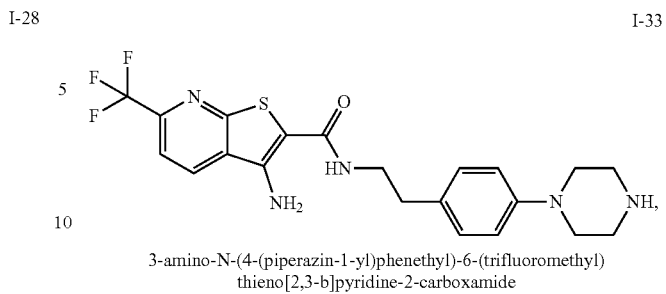

3-amino-N-(4-(piperazin-1-yl)phenethyl)-6-(trifluoromethyl)thieno[2,3-b]pyridine-2-carboxamide

I-34

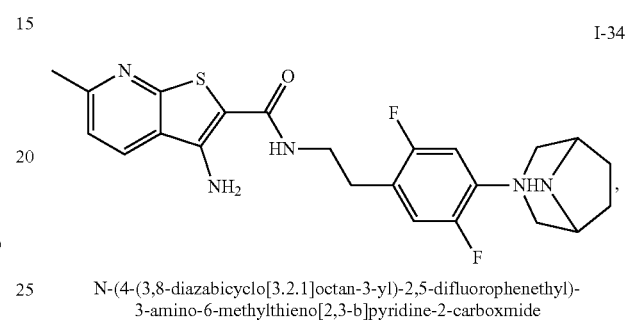

N-(4-(3,8-diazabicyclo[3.2.1]octan-3-yl)-2,5-difluorophenethyl)-3-amino-6-methylthieno[2,3-b]pyridine-2-carboxmide

I-35

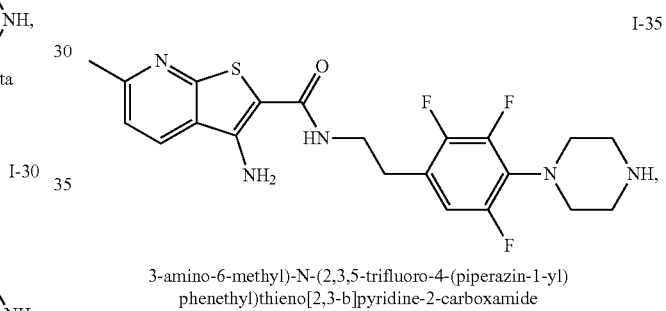

3-amino-6-methyl)-N-(2,3,5-trifluoro-4-(piperazin-1-yl)phenethyl)thieno[2,3-b]pyridine-2-carboxamide

I-36

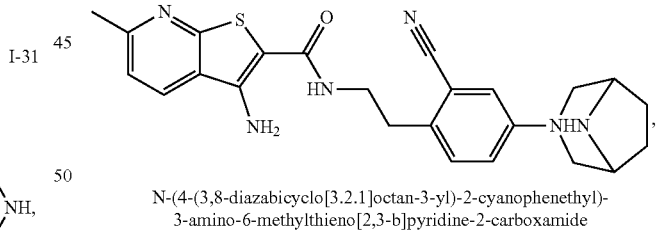

N-(4-(3,8-diazabicyclo[3.2.1]octan-3-yl)-2-cyanophenethyl)-3-amino-6-methylthieno[2,3-b]pyridine-2-carboxamide

I-37

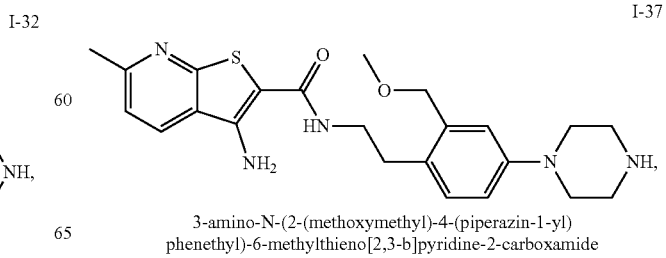

3-amino-N-(2-(methoxymethyl)-4-(piperazin-1-yl)phenethyl)-6-methylthieno[2,3-b]pyridine-2-carboxamide

I-38

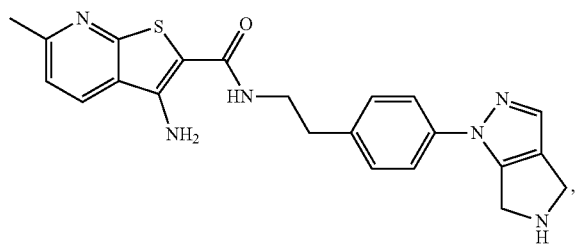

3-amino-N-(4-(5,6-dihydropyrrolo[3,4-c]pyrazol-1(4H)-yl)phenethyl)-6-methylthieno[2,3-b]pyridine-2-carboxamide

I-39

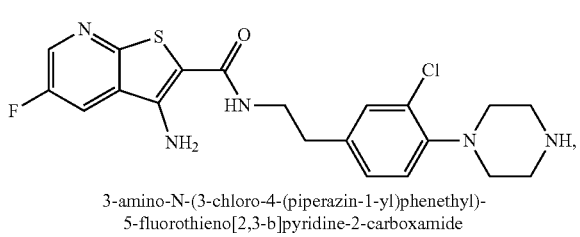

3-amino-N-(3-chloro-4-(piperazin-1-yl)phenethyl)-5-fluorothieno[2,3-b]pyridine-2-carboxamide

I-40

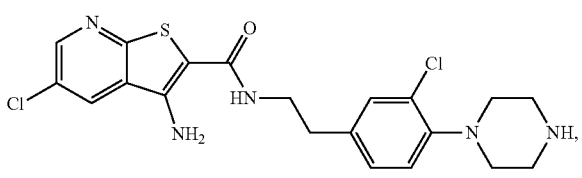

3-amino-5-chloro-N-(3-chloro-4-(piperazin-1-yl)phenethyl)thieno[2,3-b]pyridine-2-carboxamide

I-41

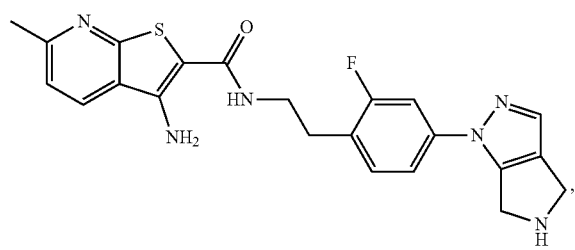

3-amino-N-(4-(5,6-dihydropyrrolo[3,4-c]pyrazol-1(4H)-yl)-2-fluorophenethyl)-6-methylthieno[2,3-b]pyridine-2-carboxamide

I-42

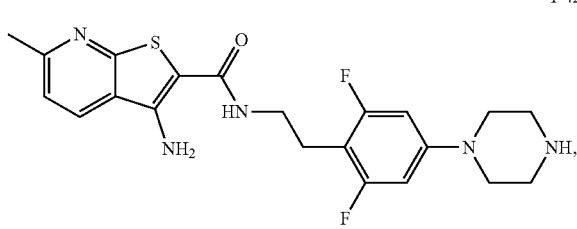

3-amino-N-(2,6-difluoro-4-(piperazin-1-yl)phenethyl)-6-methylthieno[2,3-b]pyridine-2-carboxamide

I-43

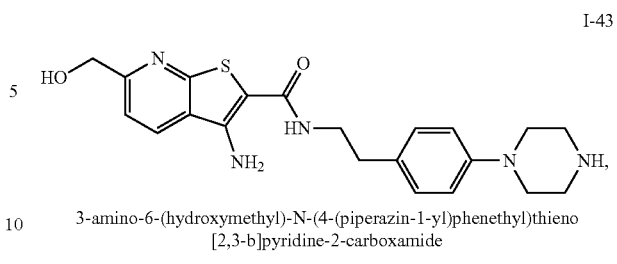

3-amino-6-(hydroxymethyl)-N-(4-(piperazin-1-yl)phenethyl)thieno[2,3-b]pyridine-2-carboxamide

I-44

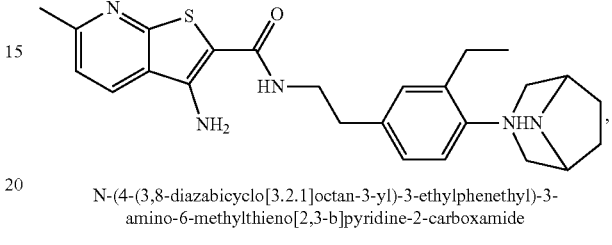

N-(4-(3,8-diazabicyclo[3.2.1]octan-3-yl)-3-ethylphenethyl)-3-amino-6-methylthieno[2,3-b]pyridine-2-carboxamide

I-45

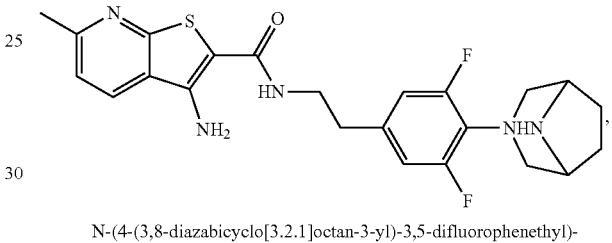

N-(4-(3,8-diazabicyclo[3.2.1]octan-3-yl)-3,5-difluorophenethyl)-3-amino-6-methylthieno[2,3-b]pyridine-2-carboxamide

I-46

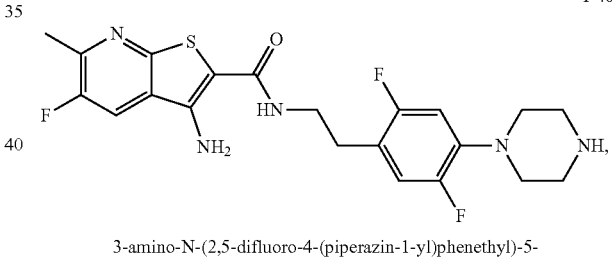

3-amino-N-(2,5-difluoro-4-(piperazin-1-yl)phenethyl)-5-fluoro-6-methylthieno[2,3-b]pyridine-2-carboxamide

I-47

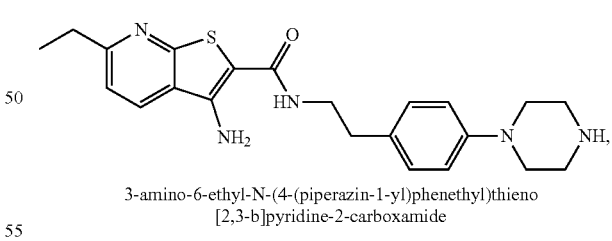

3-amino-6-ethyl-N-(4-(piperazin-1-yl)phenethyl)thieno[2,3-b]pyridine-2-carboxamide

I-48

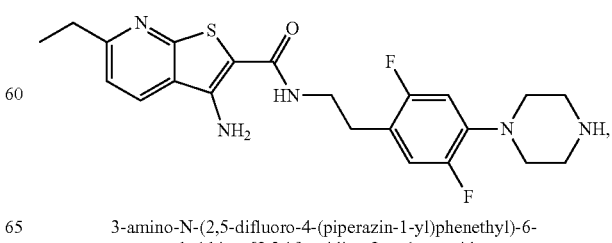

3-amino-N-(2,5-difluoro-4-(piperazin-1-yl)phenethyl)-6-ethylthieno[2,3-b]pyridine-2-carboxamide

I-49

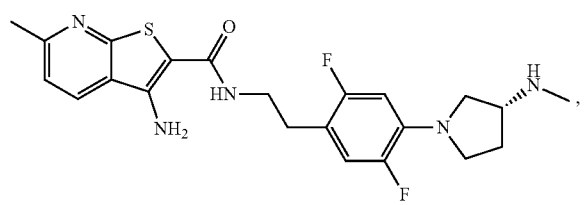

(R)-3-amino-N-(2,5-difluoro-4-(3-(methylamino)pyrrolidin-1-yl)
phenethyl)-6-methylthieno[2,3-b]pyridine-2-carboxamide

I-50

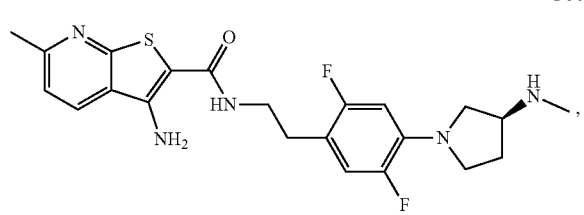

(S)-3-amino-N-(2,5-difluoro-4-(3-(methylamino)pyrrolidin-1-yl)
phenethyl)-6-methylthieno[2,3-b]pyridine-2-carboxamide

I-51

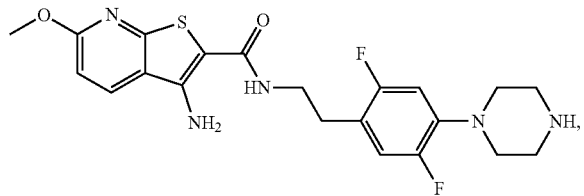

3-amino-N-(2,5-difluoro-4-(piperazin-1-yl)phenethyl)-
6-methoxythieno[2,3-b]pyridine-2-carboxamide

I-52

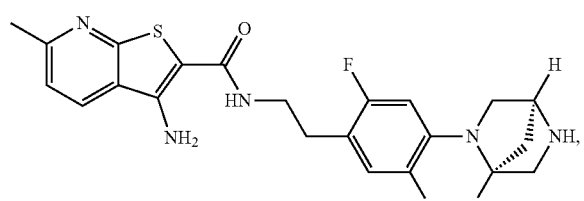

N-(4-((1S,4S)-2,5-diazabicyclo[2.2.1]heptan-2-yl)-2,5-difluorophenethyl)-
3-amino-6-methylthieno[2,3-b]pyridine-2-carboxamide

I-53

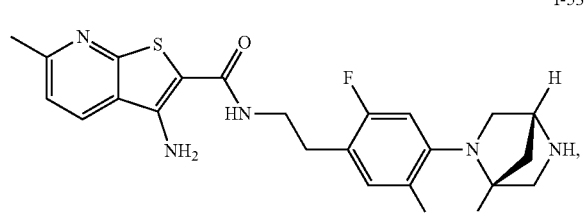

N-(4-((1R,4R)-2,5-diazabicyclo[2.2.1]heptan-2-yl)-2,5-difluorophenethyl)-
3-amino-6-methylthieno[2,3-b]pyridine-2-carboxamide

I-54

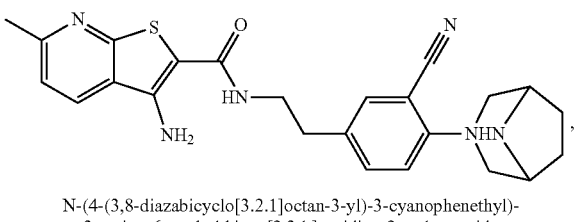

N-(4-(3,8-diazabicyclo[3.2.1]octan-3-yl)-3-cyanophenethyl)-
3-amino-6-methylthieno[2,3-b]pyridine-2-carboxamide

I-55

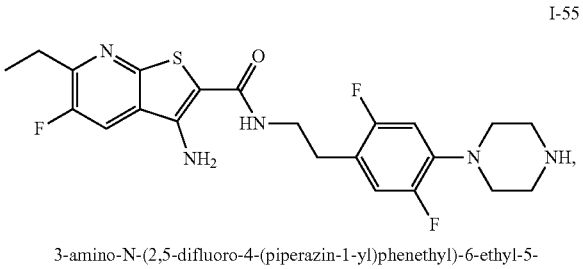

3-amino-N-(2,5-difluoro-4-(piperazin-1-yl)phenethyl)-6-ethyl-5-
fluorothieno[2,3-b]pyridine-2-carboxamide

I-56

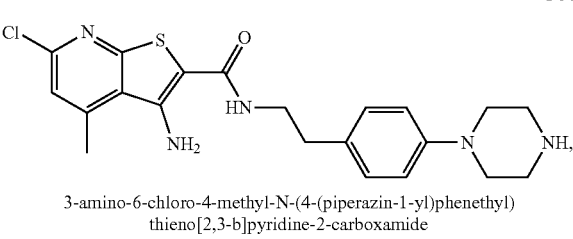

3-amino-6-chloro-4-methyl-N-(4-(piperazin-1-yl)phenethyl)
thieno[2,3-b]pyridine-2-carboxamide

I-57

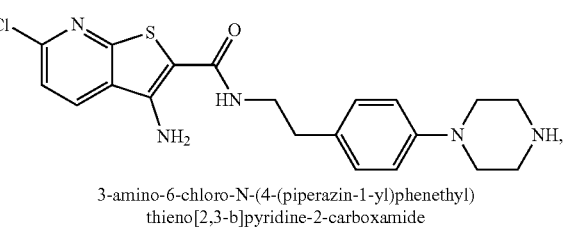

3-amino-6-chloro-N-(4-(piperazin-1-yl)phenethyl)
thieno[2,3-b]pyridine-2-carboxamide

I-58

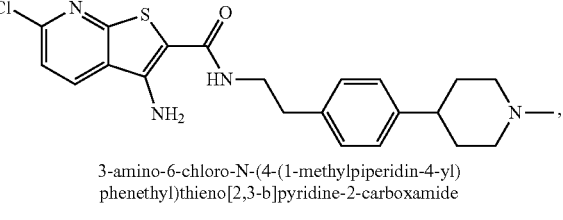

3-amino-6-chloro-N-(4-(1-methylpiperidin-4-yl)
phenethyl)thieno[2,3-b]pyridine-2-carboxamide

I-59

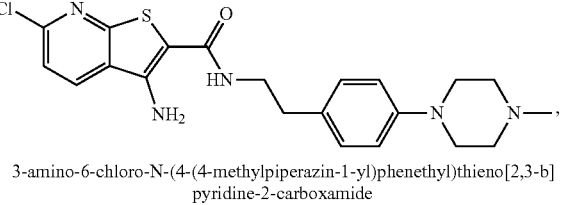

3-amino-6-chloro-N-(4-(4-methylpiperazin-1-yl)phenethyl)thieno[2,3-b]
pyridine-2-carboxamide

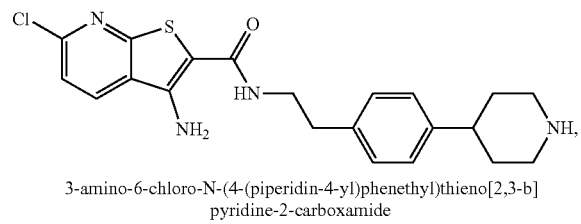

I-60

3-amino-6-chloro-N-(4-(piperidin-4-yl)phenethyl)thieno[2,3-b]
pyridine-2-carboxamide

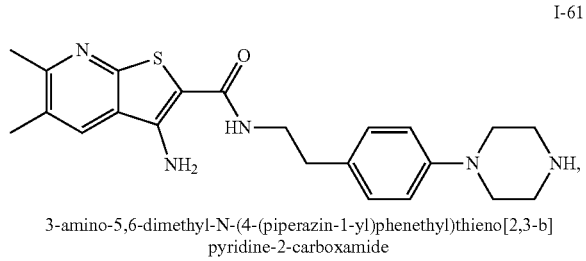

I-61

3-amino-5,6-dimethyl-N-(4-(piperazin-1-yl)phenethyl)thieno[2,3-b]
pyridine-2-carboxamide

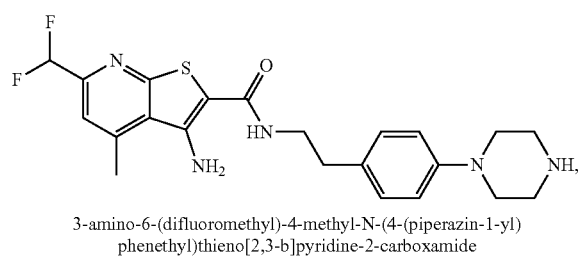

I-62

3-amino-6-(difluoromethyl)-4-methyl-N-(4-(piperazin-1-yl)
phenethyl)thieno[2,3-b]pyridine-2-carboxamide

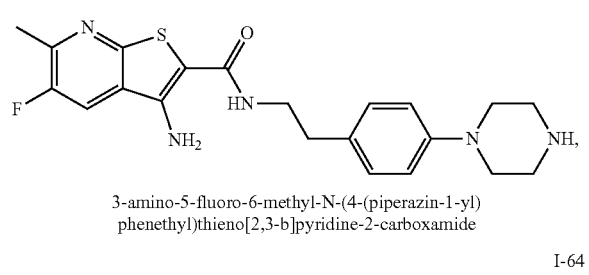

I-63

3-amino-5-fluoro-6-methyl-N-(4-(piperazin-1-yl)
phenethyl)thieno[2,3-b]pyridine-2-carboxamide

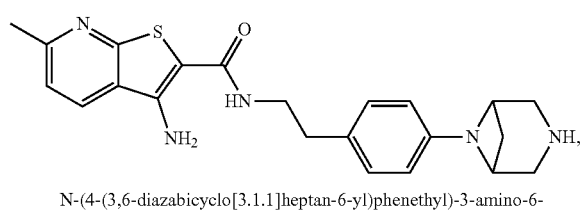

I-64

N-(4-(3,6-diazabicyclo[3.1.1]heptan-6-yl)phenethyl)-3-amino-6-
methylthieno[2,3-b]pyridine-2-carboxamide

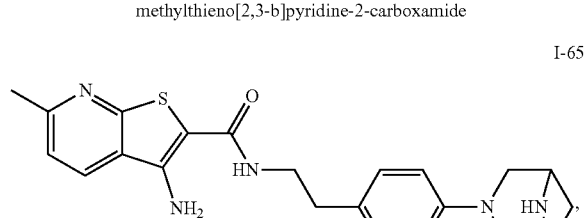

I-65

N-(4-(3,6-diazabicyclo[3.1.1]heptan-3-yl)phenethyl)-3-amino-6-
methylthieno[2,3-b]pyridine-2-carboxamide

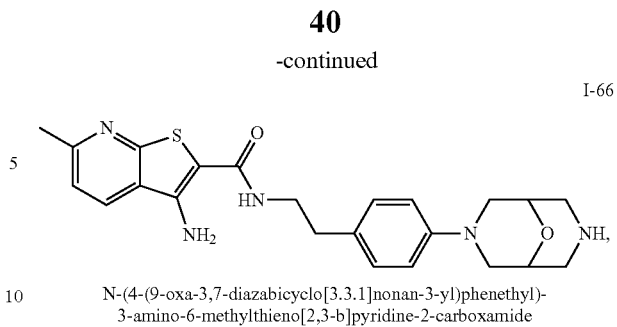

I-66

N-(4-(9-oxa-3,7-diazabicyclo[3.3.1]nonan-3-yl)phenethyl)-
3-amino-6-methylthieno[2,3-b]pyridine-2-carboxamide

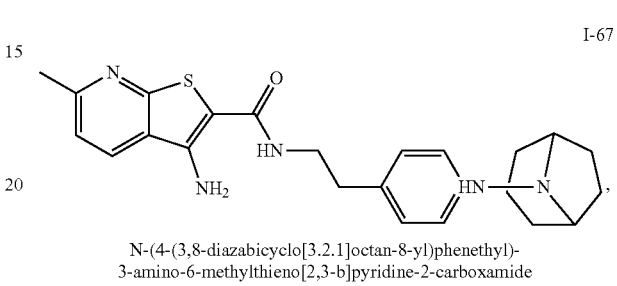

I-67

N-(4-(3,8-diazabicyclo[3.2.1]octan-8-yl)phenethyl)-
3-amino-6-methylthieno[2,3-b]pyridine-2-carboxamide

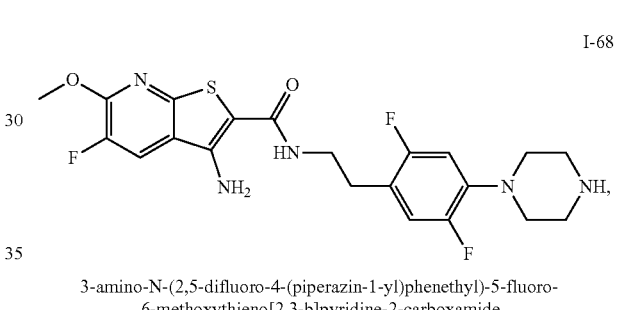

I-68

3-amino-N-(2,5-difluoro-4-(piperazin-1-yl)phenethyl)-5-fluoro-
6-methoxythieno[2,3-b]pyridine-2-carboxamide

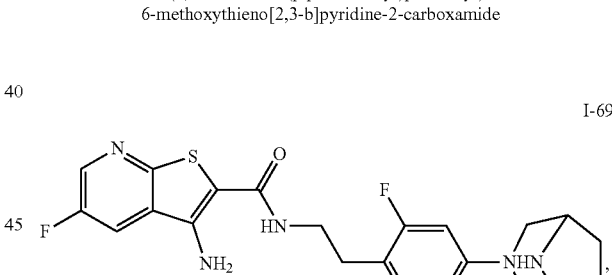

I-69

N-(4-(3,8-diazabicyclo[3.2.1]octan-3-yl)-2,5-difluorophenethyl)-3-
amino-5-fluorothieno[2,3-b]pyridine-2-carboxamide

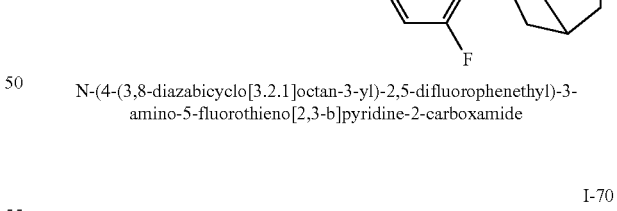

I-70

3-amino-N-(4-(azetidin-3-ylamino)-2,5-difluorophenethyl)-6-
methylthieno[2,3-b]pyridine-2-carboxamide

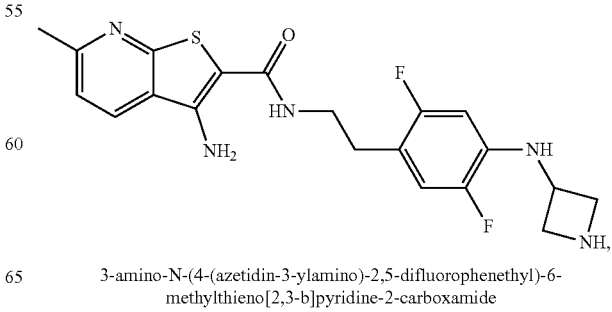

-continued

I-71

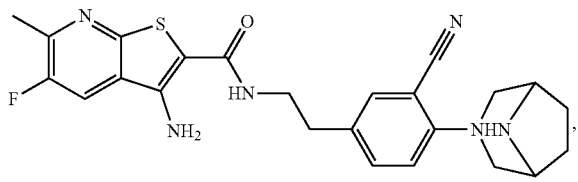

N-(4-(3,8-diazabicyclo[3.2.1]octan-3-yl)-3-cyanophenethyl)-3-amino-5-fluoro-6-methylthieno[2,3-b]pyridine-2-carboxamide

I-72

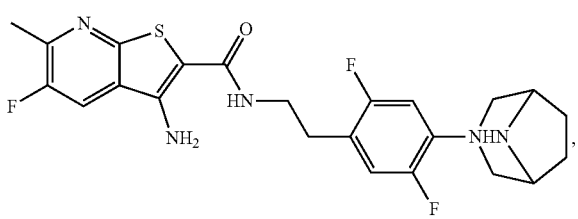

N-(4-(3,8-diazabicyclo[3.2.1]octan-3-yl)-2,5-difluorophenethyl)-3-amino-5-fluoro-6-methylthieno[2,3-b]pyridine-2-carboxamide

I-73

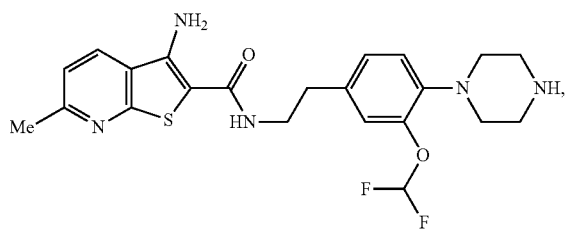

3-Amino-N-(3-(difluoromethoxy-4-(piperazin-1-yl)phenethyl)-6-methylthieno[2,3-b]pyridine-2-carboxamide

I-74

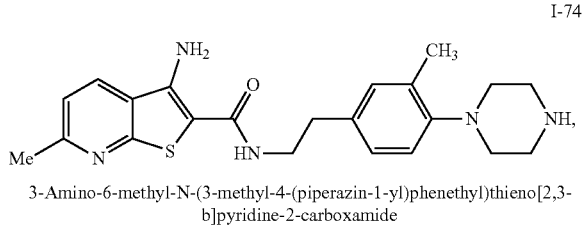

3-Amino-6-methyl-N-(3-methyl-4-(piperazin-1-yl)phenethyl)thieno[2,3-b]pyridine-2-carboxamide

I-75

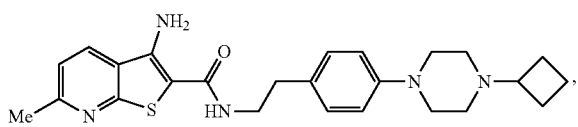

3-amino-N-(4-(4-cyclobutylpiperazin-1-yl)phenethyl)-6-methylthieno[2,3-b]pyridine-2-carboxamide

I-76

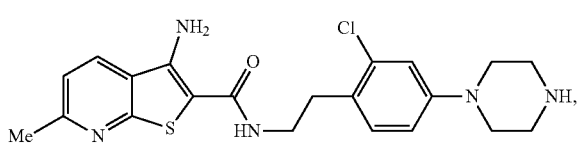

3-amino-N-(2-chloro-4-(piperazin-1-yl)phenethyl)-6-methylthieno[2,3-b]pyridine-carboxamide

I-77

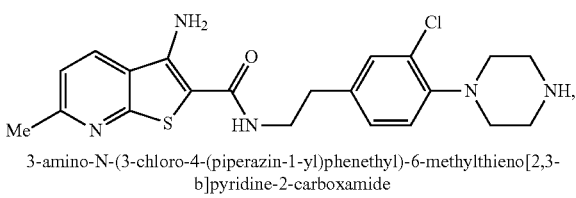

3-amino-N-(3-chloro-4-(piperazin-1-yl)phenethyl)-6-methylthieno[2,3-b]pyridine-2-carboxamide

I-78

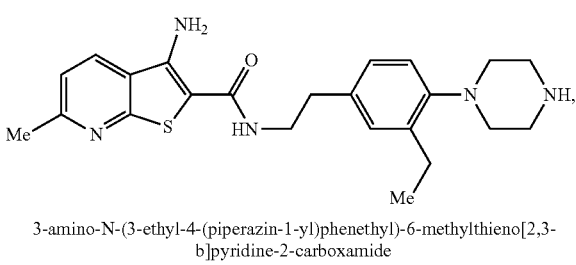

3-amino-N-(3-ethyl-4-(piperazin-1-yl)phenethyl)-6-methylthieno[2,3-b]pyridine-2-carboxamide

I-79

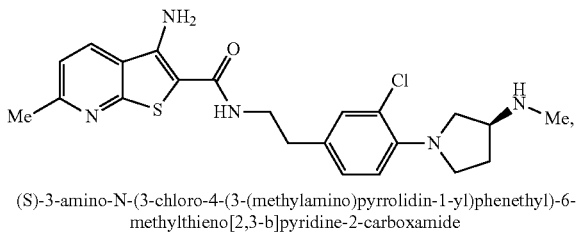

(S)-3-amino-N-(3-chloro-4-(3-(methylamino)pyrrolidin-1-yl)phenethyl)-6-methylthieno[2,3-b]pyridine-2-carboxamide

I-80

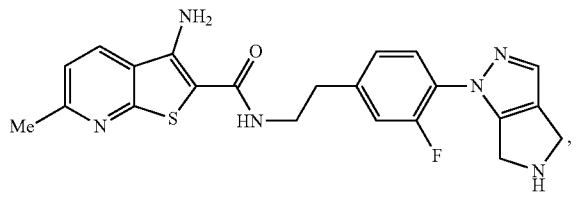

3-amino-N-(4-(5,6-dihydropryyolo[3,4-c]pyrazol-1(4H)-yl)-3-fluorophenethyl)-6-methylthieno[2,3-b]pyridine-2-carboxamide,

I-81

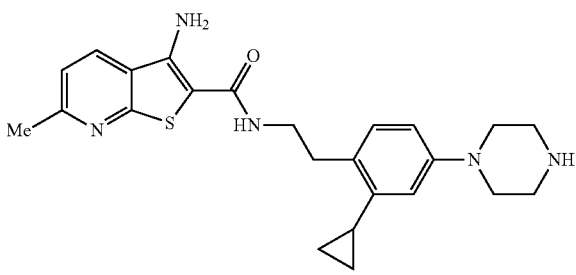

3-amino-N-(2-cyclopropyl-4-(piperazin-1-yl)phenethyl)-6-methylthieno[2,3-b]pyridine-2-carboxamide

I-82

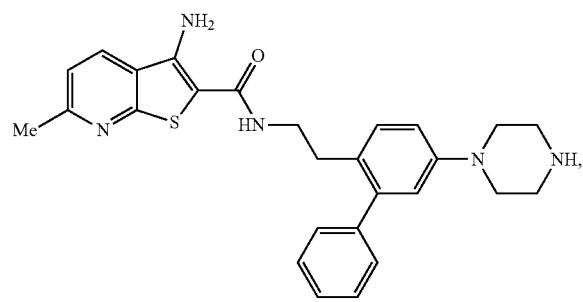

3-amino-6-methyl-N-(2-(5-(piperazin-1-yl)-[1,1'-biphenyl]-2-yl)ethyl)thieno[2,3-b]pyridine-2-carboxamide

I-83

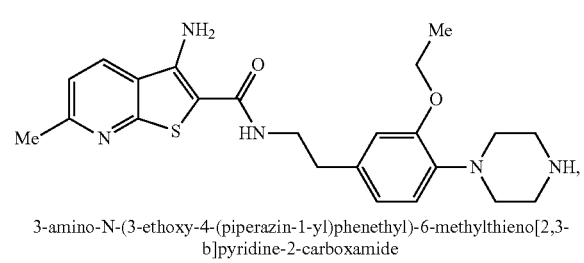

3-amino-N-(3-ethoxy-4-(piperazin-1-yl)phenethyl)-6-methylthieno[2,3-b]pyridine-2-carboxamide

I-84

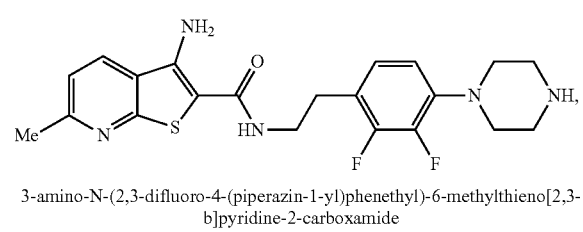

3-amino-N-(2,3-difluoro-4-(piperazin-1-yl)phenethyl)-6-methylthieno[2,3-b]pyridine-2-carboxamide

I-85

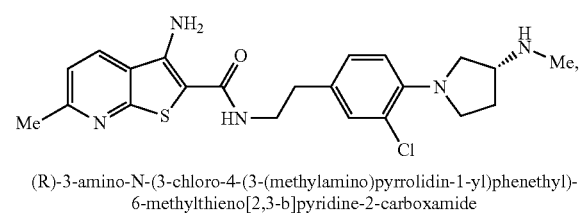

(R)-3-amino-N-(3-chloro-4-(3-(methylamino)pyrrolidin-1-yl)phenethyl)-6-methylthieno[2,3-b]pyridine-2-carboxamide

I-86

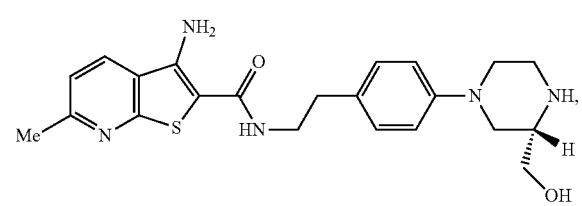

(S)-3-amino-N-(4-(3-(hydroxymethyl)piperazin-1-yl)phenethyl)-6-methylthieno[2,3-b]pyridine-2-carboxamide

I-87

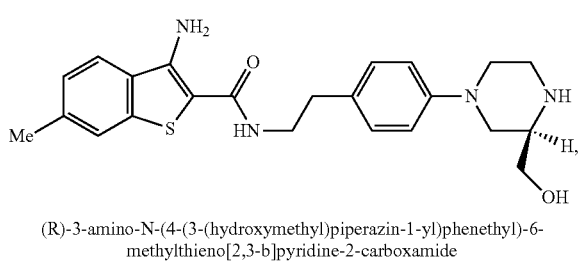

(R)-3-amino-N-(4-(3-(hydroxymethyl)piperazin-1-yl)phenethyl)-6-methylthieno[2,3-b]pyridine-2-carboxamide

I-88

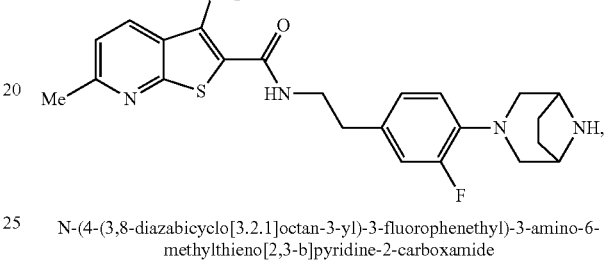

N-(4-(3,8-diazabicyclo[3.2.1]octan-3-yl)-3-fluorophenethyl)-3-amino-6-methylthieno[2,3-b]pyridine-2-carboxamide

I-89

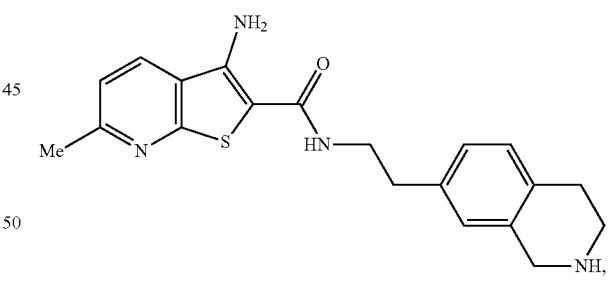

3-amino-6-methyl-N-(2-methyl-4-(piperazin-1-yl) phenethyl)thieno[2,3-b]pyridine-2-carboxamide

I-90

3-amino-6-methyl-N-(2-(1,2,3,4-tetrahydroisoquinolin-7-yl)ethyl)thieno[2,3-b]pyridine-2-carboxamide

I-91

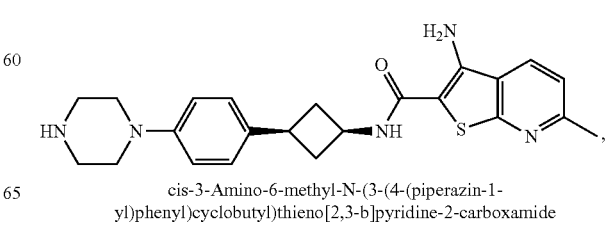

cis-3-Amino-6-methyl-N-(3-(4-(piperazin-1-yl)phenyl)cyclobutyl)thieno[2,3-b]pyridine-2-carboxamide

I-92

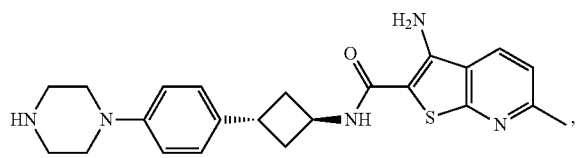

trans-3-amino-6-methyl-N-(3-(4-(piperazin-1-yl)phenyl)cyclobutyl)thieno[2,3-b]pyridine-2-carboxamide

I-93

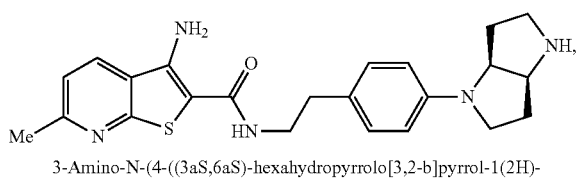

3-Amino-N-(4-((3aS,6aS)-hexahydropyrrolo[3,2-b]pyrrol-1(2H)-yl)phenethyl)-6-methylthieno[2,3-b]pyridine-2-carboxamide

I-94

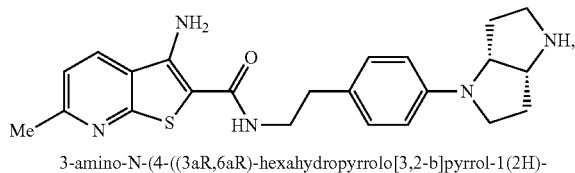

3-amino-N-(4-((3aR,6aR)-hexahydropyrrolo[3,2-b]pyrrol-1(2H)-yl)phenethyl)-6-methylthieno[2,3-b]pyridine-2-carboxamide

I-95

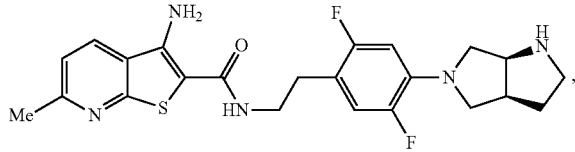

3-amino-N-(2,5-difluoro-4-((3aS,6aS)-hexahydropyrrolo[3,4-b]pyrrol-5(1H)-yl)phenethyl)-6-methylthieno[2,3-b]pyridine-2-carboxamide

I-96

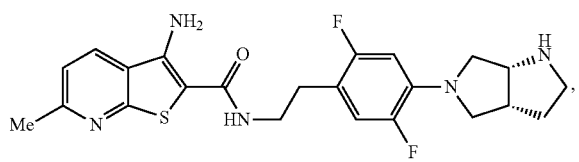

3-amino-N-(2,5-difluoro-4-((3aR,6aR)-hexahydropyrrolo[3,4-b]pyrrol-5(1H)-yl)phenethyl)-6-methylthieno[2,3-b]pyridine-2-carboxamide

I-97

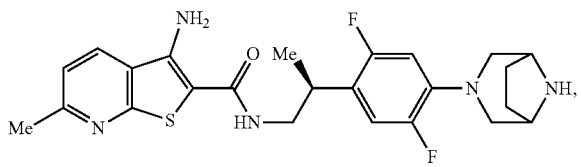

N-((2S)-2-(4-(3,8-diazabicyclo[3.2.1]octan-3-yl)-2,5-difluorophenyl)propyl)-3-amino-6-methylthieno[2,3-b]pyridine-2-carboxamide

I-98

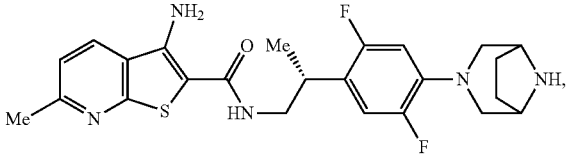

N-((2R)-2-(4-(3,8-diazabicyclo[3.2.1]octan-3-yl)-2,5-difluoropheneyl)propyl)-3-amino-6-methylthieno[2,3-b]pyridine-2-carboxamide

I-99

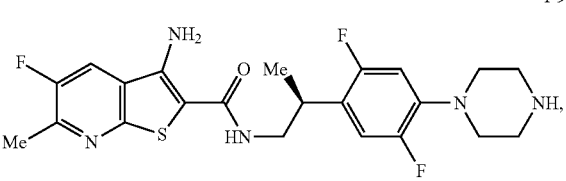

(S)-3-amino-N-(2-(2,5-difluoro-4-(piperazin-1-yl)phenyl)propyl)-5-fluoro-6-methylthieno[2,3-b]oyridine-2-carboxamide

I-100

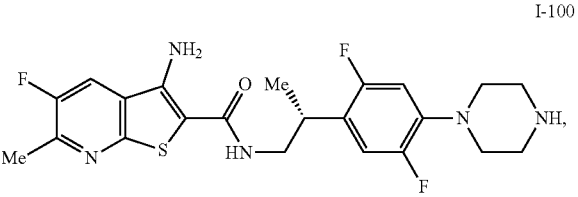

(R)-3-amino-N-(2-(2,5-difluoro-4-(piperazin-1-yl)phenyl)propyl)-5-fluoro-6-methylthieno[2,3-b]oyridine-2-carboxamide

I-101

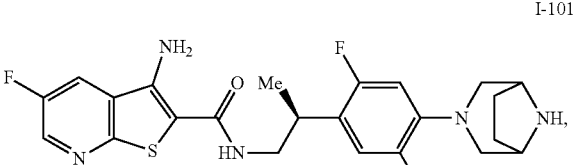

N-((2S)-2-(4-(3,8-diazabicyclo[3.2.1]octan-3-yl)-2,5-difluorophenyl)propyl)-3-amino-5-fluorothieno[2,3-b]pyridine-2-carboxamide

I-102

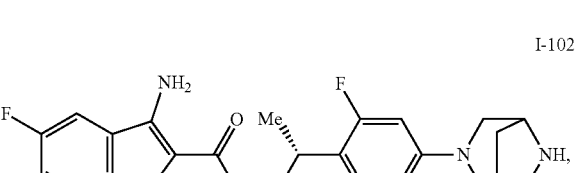

N-((2R)-2-(4-(3,8-diazabicyclo[3.2.1]octan-3-yl)-2,5-difluoropheneyl)propyl)-3-amino-5-fluorothieno[2,3-b]pyridine-2-carboxamide

I-103

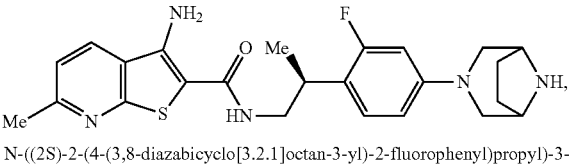

N-((2S)-2-(4-(3,8-diazabicyclo[3.2.1]octan-3-yl)-2-fluorophenyl)propyl)-3-amino-6-fluorothieno[2,3-b]pyridine-2-carboxamide -continued

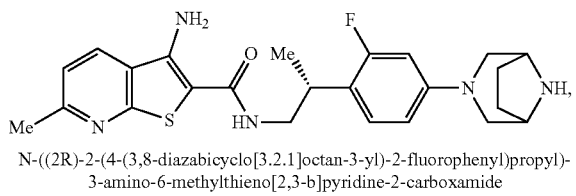

I-104

N-((2R)-2-(4-(3,8-diazabicyclo[3.2.1]octan-3-yl)-2-fluorophenyl)propyl)-3-amino-6-methylthieno[2,3-b]pyridine-2-carboxamide

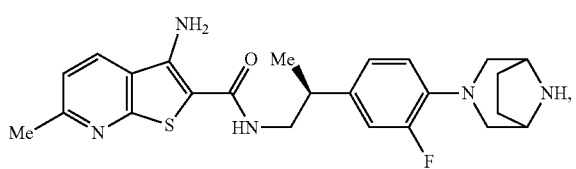

I-105

N-((2S)-2-(4-(3,8-diazabicyclo[3.2.1]octan-3-yl)-3-fluorophenyl)propyl)-3-amino-6-methylthieno[2,3-b]pyridine-2-carboxamide

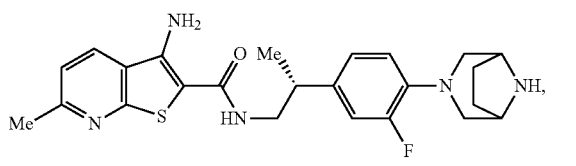

I-106

N-((2R)-2-(4-(3,8-diazabicyclo[3.2.1]octan-3-yl)-3-fluorophenyl)propyl)-3-amino-6-methylthieno[2,3-b]pyridine-2-carboxamide

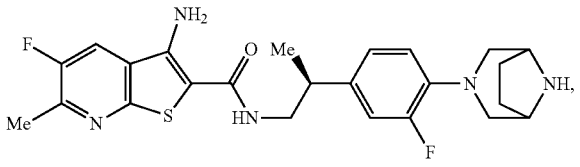

I-107

N-((2S)-2-(4-(3,8-diazabicyclo[3.2.1]octan-3-yl)-3-fluorophenyl)propyl)-3-amino-5-fluoro-6-methylthieno[2,3-b]pyridine-2-carboxamide

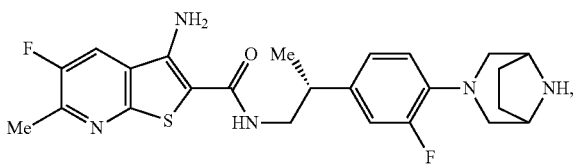

I-108

N-((2R)-2-(4-(3,8-diazabicyclo[3.2.1]octan-3-yl)-3-fluorophenyl)propyl)-3-amino-5-fluoro-6-methylthieno[2,3-b]pyridine-2-carboxamide

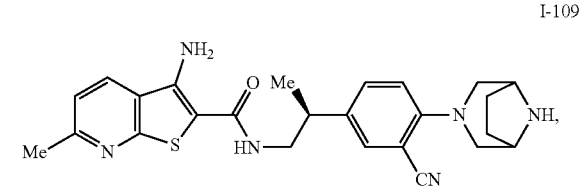

I-109

N-((2S)-2-(4-(3,8-diazabicyclo[3.2.1]octan-3-yl)-3-cyanophenyl)propyl)-3-amino-6-methylthieno[2,3-b]pyridine-2-carboxamide -continued

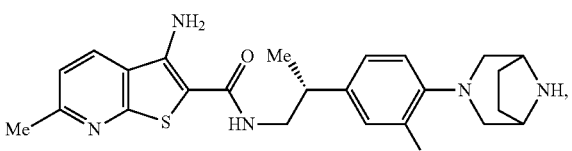

I-110

N-((2R)-2-(4-(3,8-diazabicyclo[3.2.1]octan-3-yl)-3-cyanophenyl)propyl)-3-amino-6-methylthieno[2,3-b]pyridine-2-carboxamide

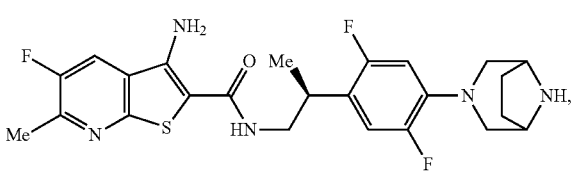

I-111

N-((2S)-2-(4-(3,8-diazabicyclo[3.2.1]octan-3-yl)-2,5-difluorophenyl)propyl)-3-amino-5-fluoro-6-methylthieno[2,3-b]pyridine-2-carboxamide

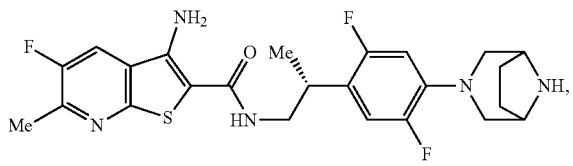

I-112

N-((2R)-2-(4-(3,8-diazabicyclo[3.2.1]octan-3-yl)-2,5-difluorophenyl)propyl)-3-amino-5-fluoro-6-methylthieno[2,3-b]pyridine-2-carboxamide

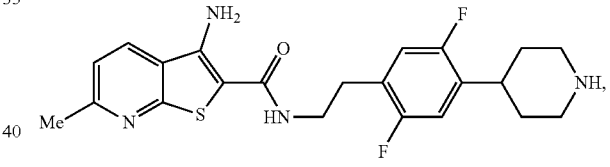

I-113

3-amino-N-(2,5-difluoro-4-(piperidin-4-yl)phenethyl)-6-methylthieno[2,3-b]pyridine-2-carboxamide

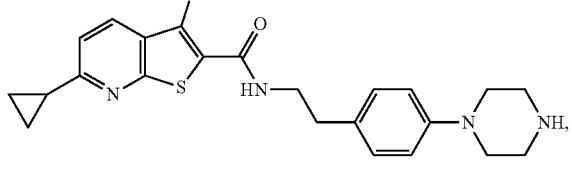

I-114

3-amino-6-cyclopropyl-N-(4-(piprazin-1-yl)phenethyl)thieno[2,3-b]pyridine-2-carboxamide

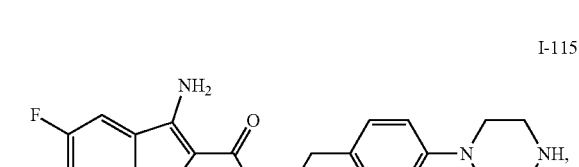

I-115

3,6-diamino-5-fluoro-N-(4-(piperazin-1-yl)phenethyl)thieno[2,3-b]pyridine-2-carboxamide

I-116

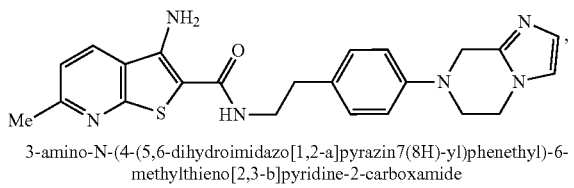

3-amino-N-(4-(5,6-dihydroimidazo[1,2-a]pyrazin7(8H)-yl)phenethyl)-6-methylthieno[2,3-b]pyridine-2-carboxamide

I-117

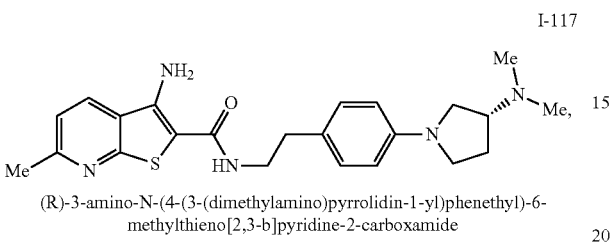

(R)-3-amino-N-(4-(3-(dimethylamino)pyrrolidin-1-yl)phenethyl)-6-methylthieno[2,3-b]pyridine-2-carboxamide

I-118

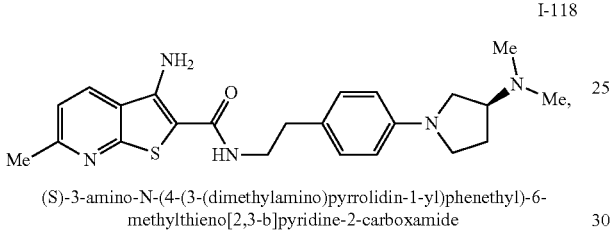

(S)-3-amino-N-(4-(3-(dimethylamino)pyrrolidin-1-yl)phenethyl)-6-methylthieno[2,3-b]pyridine-2-carboxamide

I-119

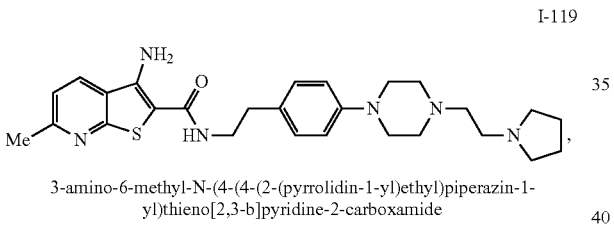

3-amino-6-methyl-N-(4-(4-(2-(pyrrolidin-1-yl)ethyl)piperazin-1-yl)thieno[2,3-b]pyridine-2-carboxamide

I-120

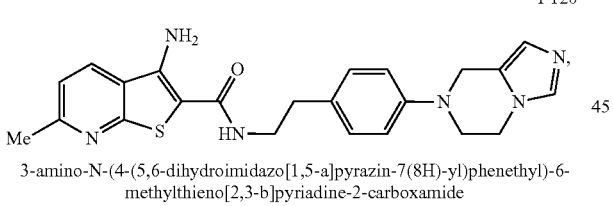

3-amino-N-(4-(5,6-dihydroimidazo[1,5-a]pyrazin-7(8H)-yl)phenethyl)-6-methylthieno[2,3-b]pyriadine-2-carboxamide

I-121

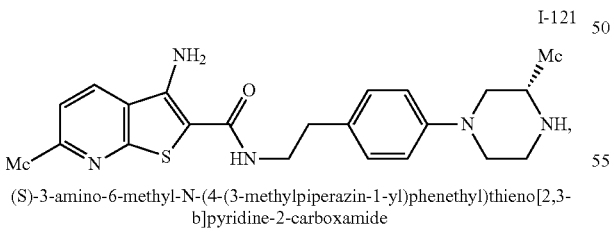

(S)-3-amino-6-methyl-N-(4-(3-methylpiperazin-1-yl)phenethyl)thieno[2,3-b]pyridine-2-carboxamide

I-122

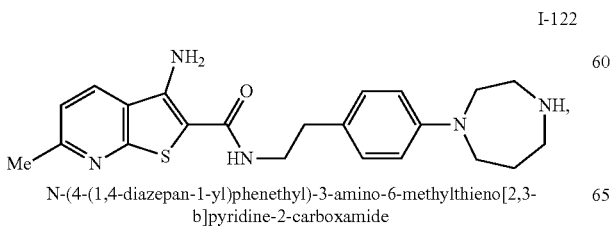

N-(4-(1,4-diazepan-1-yl)phenethyl)-3-amino-6-methylthieno[2,3-b]pyridine-2-carboxamide

I-123

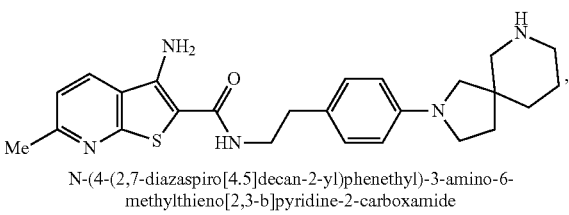

N-(4-(2,7-diazaspiro[4.5]decan-2-yl)phenethyl)-3-amino-6-methylthieno[2,3-b]pyridine-2-carboxamide

I-124

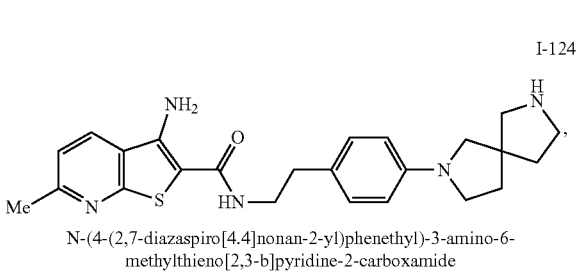

N-(4-(2,7-diazaspiro[4.4]nonan-2-yl)phenethyl)-3-amino-6-methylthieno[2,3-b]pyridine-2-carboxamide

I-125

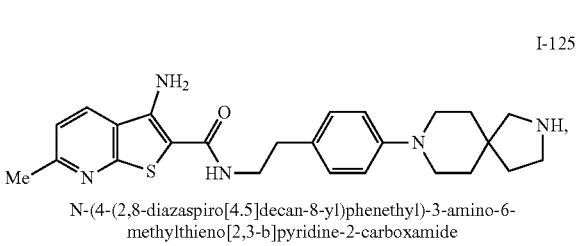

N-(4-(2,8-diazaspiro[4.5]decan-8-yl)phenethyl)-3-amino-6-methylthieno[2,3-b]pyridine-2-carboxamide

I-126

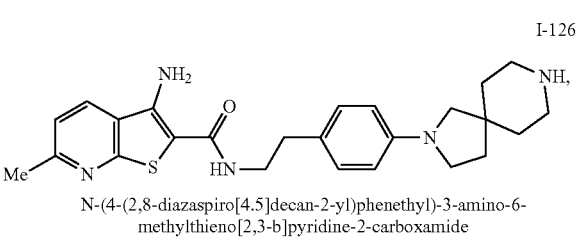

N-(4-(2,8-diazaspiro[4.5]decan-2-yl)phenethyl)-3-amino-6-methylthieno[2,3-b]pyridine-2-carboxamide

I-127

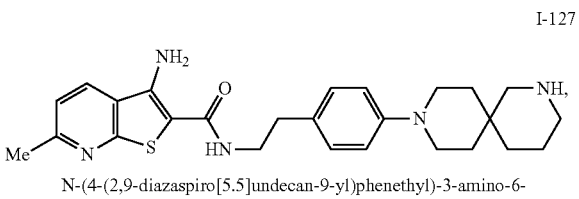

N-(4-(2,9-diazaspiro[5.5]undecan-9-yl)phenethyl)-3-amino-6-methythieno[2,3-b]pyridine-2-carboxamide

I-128

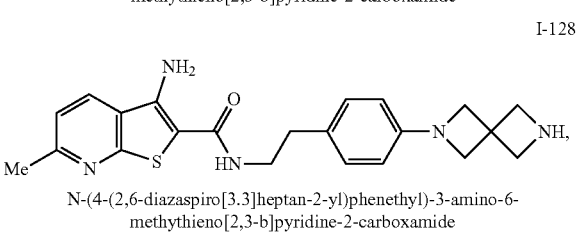

N-(4-(2,6-diazaspiro[3.3]heptan-2-yl)phenethyl)-3-amino-6-methythieno[2,3-b]pyridine-2-carboxamide

I-129

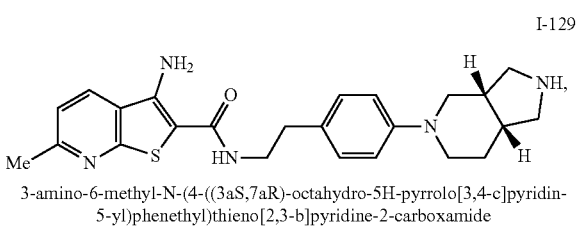

3-amino-6-methyl-N-(4-((3aS,7aR)-octahydro-5H-pyrrolo[3,4-c]pyridin-5-yl)phenethyl)thieno[2,3-b]pyridine-2-carboxamide

I-130

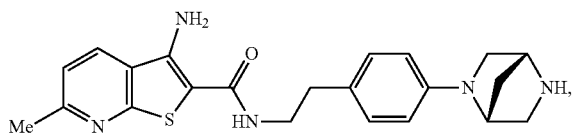

N-(4-((1S,4S)-2,5-diazabicyclo[2.2.1]heptan-2-yl)phenethyl)-3-amino-6-methylthieno[2,3-b]pyridine-2-carboxamide

I-131

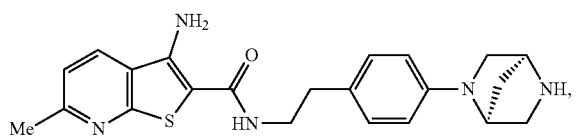

N-(4-((1R,4R)-2,5-diazabicyclo[2.2.1]heptan-2-yl)phenethyl)-3-amino-6-methylthieno[2,3-b]pyridine-2-carboxamide

I-132

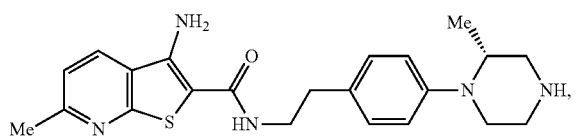

(R)-3-amino-6-methyl-N-(4-(2-methylpiperazin-1-yl)phenethyl)thieno[2,3-b]pyridine-2-carboxamide

I-133

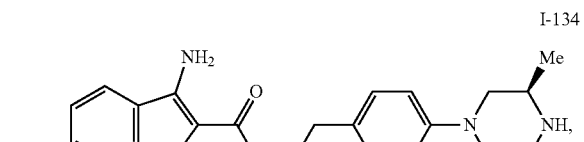

(S)-3-amino-6-methyl-N-(4-(2-methylpiperazin-1-yl)phenethyl)thieno[2,3-b]pyridine-2-carboxamide

I-134

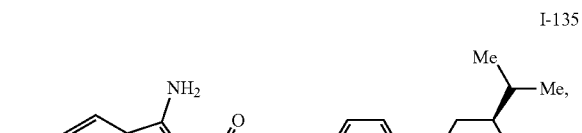

(R)-3-amino-6-methyl-N-(4-(3-methylpiperazin-1-yl)phenethyl)thieno[2,3-b]pyridine-2-carboxamide

I-135

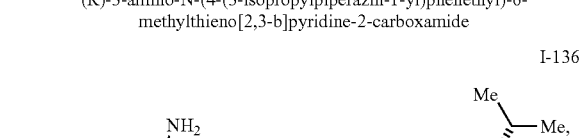

(R)-3-amino-N-(4-(3-isopropylpiperazin-1-yl)phenethyl)-6-methylthieno[2,3-b]pyridine-2-carboxamide

I-136

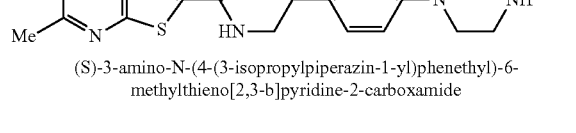

(S)-3-amino-N-(4-(3-isopropylpiperazin-1-yl)phenethyl)-6-methylthieno[2,3-b]pyridine-2-carboxamide

I-137

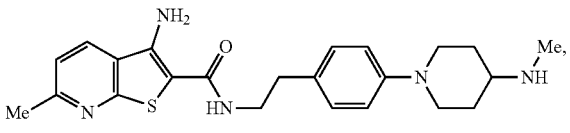

3-amino-6-methyl-N-(4-(4-(methylamino)piperidin-1-yl)phenethyl)thieno[2,3-b]pyridine-2-carboxamide

I-138

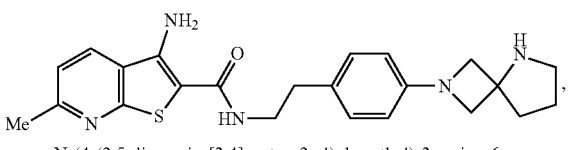

N-(4-(2,5-diazaspiro[3.4]octan-2-yl)phenethyl)-3-amino-6-methylthieno[2,3-b]pyridine-2-carboxamide

I-139

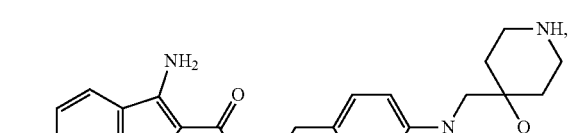

N-(4-(1-oxa-4,9-diazaspiro[5.5]undecan-4-yl)phenethyl)-3-amino-6-methylthieno[2,3-b]pyridine-2-carboxamide

I-140

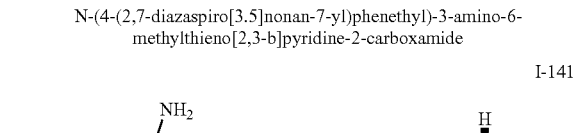

N-(4-(2,7-diazaspiro[3.5]nonan-7-yl)phenethyl)-3-amino-6-methylthieno[2,3-b]pyridine-2-carboxamide

I-141

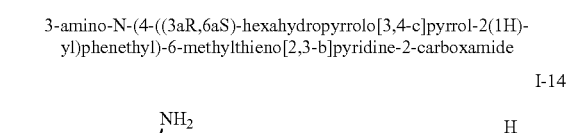

3-amino-N-(4-((3aR,6aS)-hexahydropyrrolo[3,4-c]pyrrol-2(1H)-yl)phenethyl)-6-methylthieno[2,3-b]pyridine-2-carboxamide

I-142

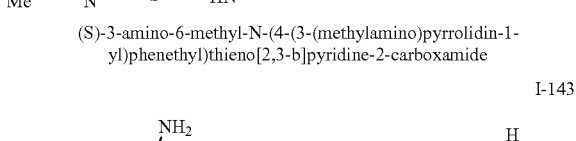

(S)-3-amino-6-methyl-N-(4-(3-(methylamino)pyrrolidin-1-yl)phenethyl)thieno[2,3-b]pyridine-2-carboxamide

I-143

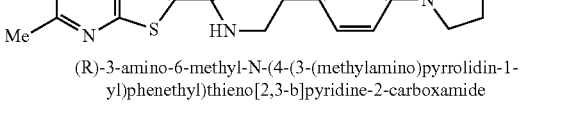

(R)-3-amino-6-methyl-N-(4-(3-(methylamino)pyrrolidin-1-yl)phenethyl)thieno[2,3-b]pyridine-2-carboxamide -continued

I-144

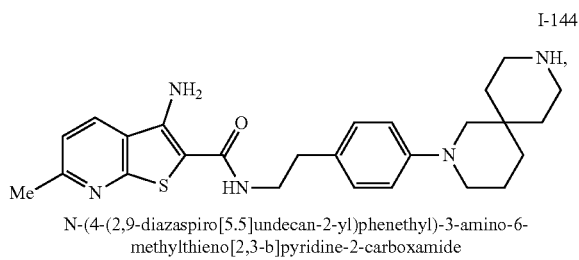

N-(4-(2,9-diazaspiro[5.5]undecan-2-yl)phenethyl)-3-amino-6-methylthieno[2,3-b]pyridine-2-carboxamide

I-145

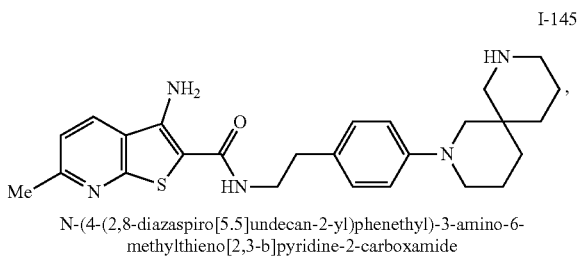

N-(4-(2,8-diazaspiro[5.5]undecan-2-yl)phenethyl)-3-amino-6-methylthieno[2,3-b]pyridine-2-carboxamide

I-146

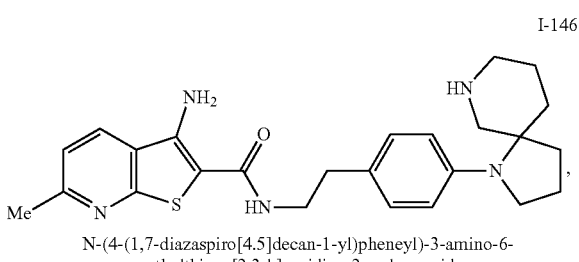

N-(4-(1,7-diazaspiro[4.5]decan-1-yl)pheneyl)-3-amino-6-methylthieno[2,3-b]pyridine-2-carboxamide

I-147

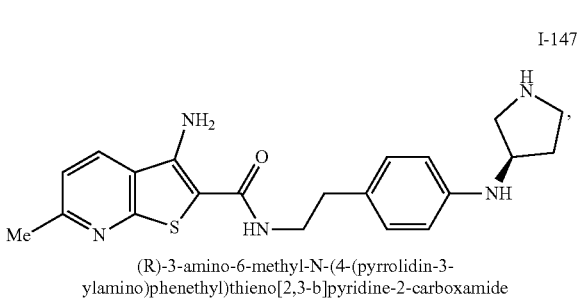

(R)-3-amino-6-methyl-N-(4-(pyrrolidin-3-ylamino)phenethyl)thieno[2,3-b]pyridine-2-carboxamide

I-148

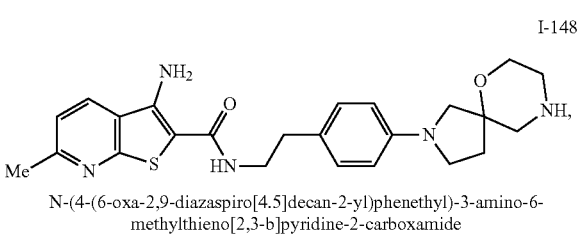

N-(4-(6-oxa-2,9-diazaspiro[4.5]decan-2-yl)phenethyl)-3-amino-6-methylthieno[2,3-b]pyridine-2-carboxamide

I-149

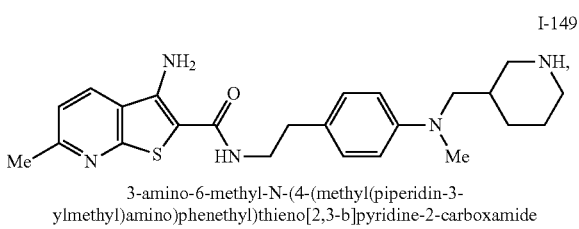

3-amino-6-methyl-N-(4-(methyl(piperidin-3-ylmethyl)amino)phenethyl)thieno[2,3-b]pyridine-2-carboxamide -continued

I-150

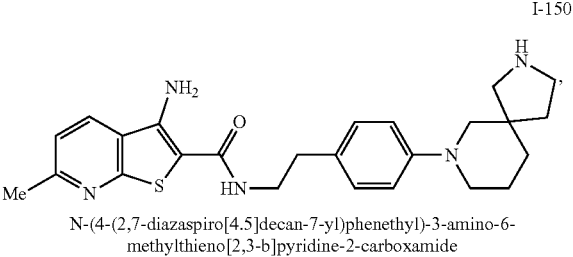

N-(4-(2,7-diazaspiro[4.5]decan-7-yl)phenethyl)-3-amino-6-methylthieno[2,3-b]pyridine-2-carboxamide

I-151

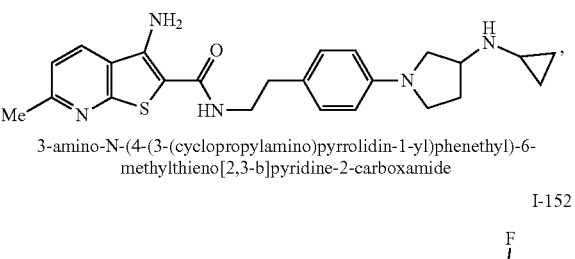

3-amino-N-(4-(3-(cyclopropylamino)pyrrolidin-1-yl)phenethyl)-6-methylthieno[2,3-b]pyridine-2-carboxamide

I-152

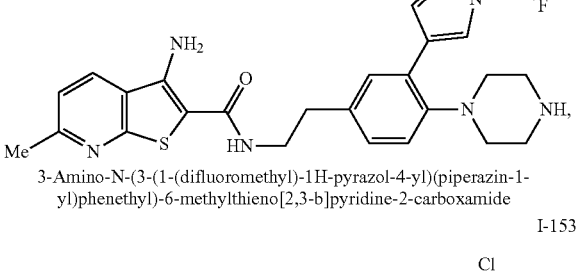

3-Amino-N-(3-(1-(difluoromethyl)-1H-pyrazol-4-yl)(piperazin-1-yl)phenethyl)-6-methylthieno[2,3-b]pyridine-2-carboxamide

I-153

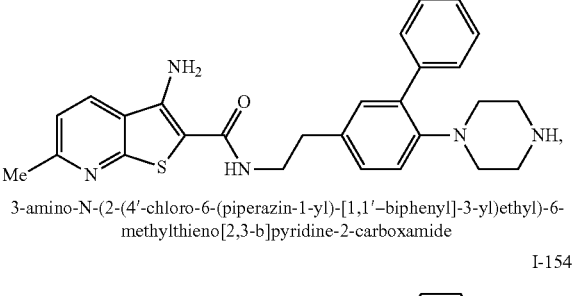

3-amino-N-(2-(4'-chloro-6-(piperazin-1-yl)-[1,1'–biphenyl]-3-yl)ethyl)-6-methylthieno[2,3-b]pyridine-2-carboxamide

I-154

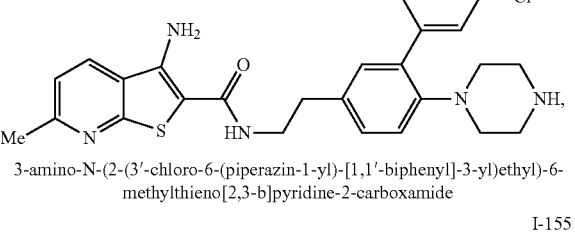

3-amino-N-(2-(3'-chloro-6-(piperazin-1-yl)-[1,1'-biphenyl]-3-yl)ethyl)-6-methylthieno[2,3-b]pyridine-2-carboxamide

I-155

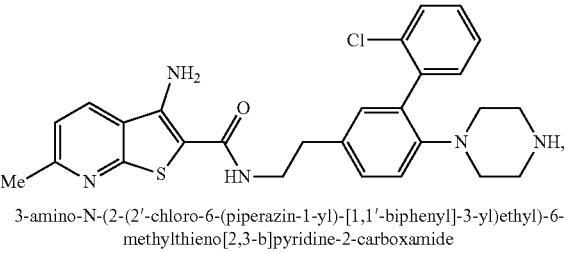

3-amino-N-(2-(2'-chloro-6-(piperazin-1-yl)-[1,1'-biphenyl]-3-yl)ethyl)-6-methylthieno[2,3-b]pyridine-2-carboxamide -continued

I-156

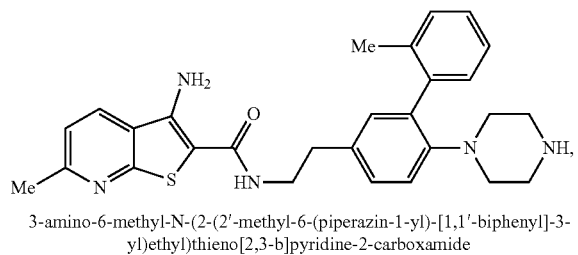

3-amino-6-methyl-N-(2-(2'-methyl-6-(piperazin-1-yl)-[1,1'-biphenyl]-3-yl)ethyl)thieno[2,3-b]pyridine-2-carboxamide

I-157

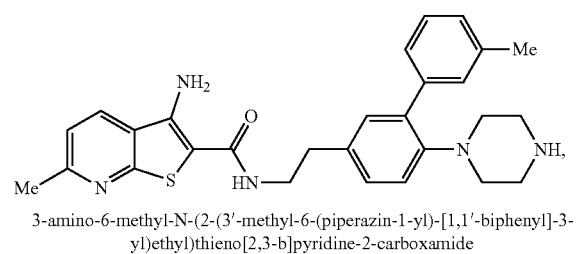

3-amino-6-methyl-N-(2-(3'-methyl-6-(piperazin-1-yl)-[1,1'-biphenyl]-3-yl)ethyl)thieno[2,3-b]pyridine-2-carboxamide

I-158

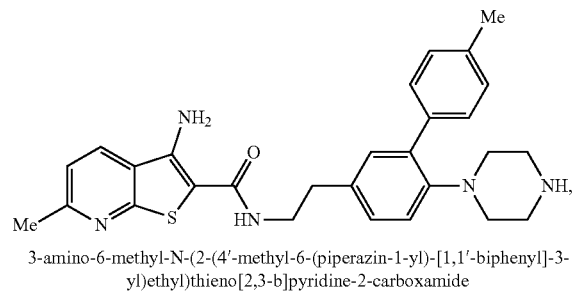

3-amino-6-methyl-N-(2-(4'-methyl-6-(piperazin-1-yl)-[1,1'-biphenyl]-3-yl)ethyl)thieno[2,3-b]pyridine-2-carboxamide

I-159

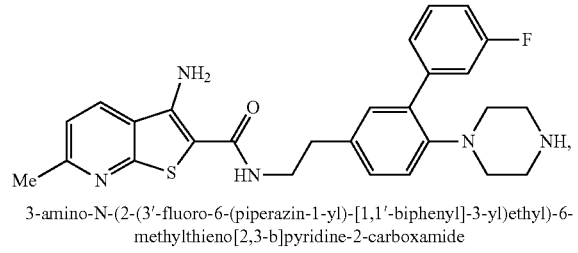

3-amino-N-(2-(3'-fluoro-6-(piperazin-1-yl)-[1,1'-biphenyl]-3-yl)ethyl)-6-methylthieno[2,3-b]pyridine-2-carboxamide

I-160

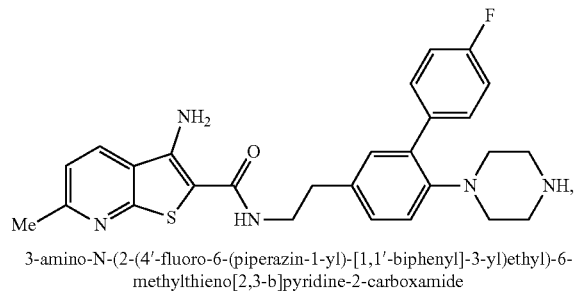

3-amino-N-(2-(4'-fluoro-6-(piperazin-1-yl)-[1,1'-biphenyl]-3-yl)ethyl)-6-methylthieno[2,3-b]pyridine-2-carboxamide -continued

I-161

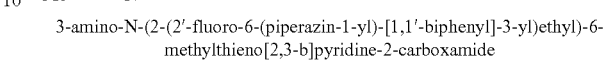

3-amino-N-(2-(2'-fluoro-6-(piperazin-1-yl)-[1,1'-biphenyl]-3-yl)ethyl)-6-methylthieno[2,3-b]pyridine-2-carboxamide

I-162

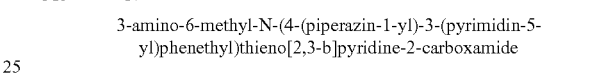

3-amino-6-methyl-N-(4-(piperazin-1-yl)-3-(pyrimidin-5-yl)phenethyl)thieno[2,3-b]pyridine-2-carboxamide

I-163

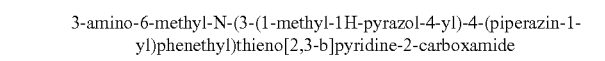

3-amino-6-methyl-N-(3-(1-methyl-1H-pyrazol-4-yl)-4-(piperazin-1-yl)phenethyl)thieno[2,3-b]pyridine-2-carboxamide

I-164

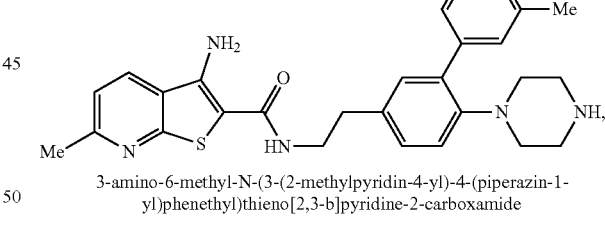

3-amino-6-methyl-N-(3-(2-methylpyridin-4-yl)-4-(piperazin-1-yl)phenethyl)thieno[2,3-b]pyridine-2-carboxamide

I-165

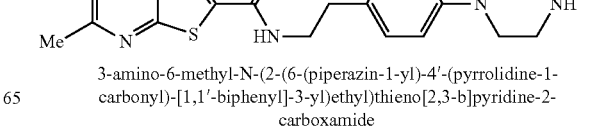

3-amino-6-methyl-N-(2-(6-(piperazin-1-yl)-4'-(pyrrolidine-1-carbonyl)-[1,1'-biphenyl]-3-yl)ethyl)thieno[2,3-b]pyridine-2-carboxamide

I-166

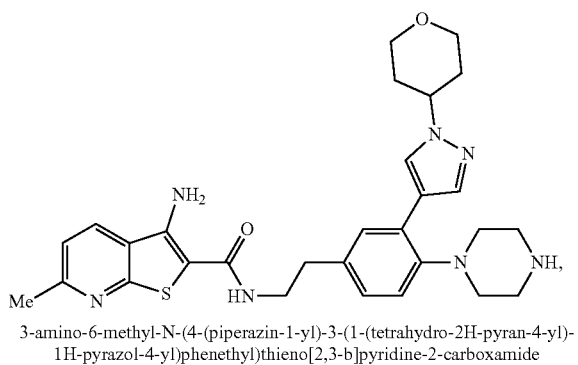

3-amino-6-methyl-N-(4-(piperazin-1-yl)-3-(1-(tetrahydro-2H-pyran-4-yl)-1H-pyrazol-4-yl)phenethyl)thieno[2,3-b]pyridine-2-carboxamide

I-167

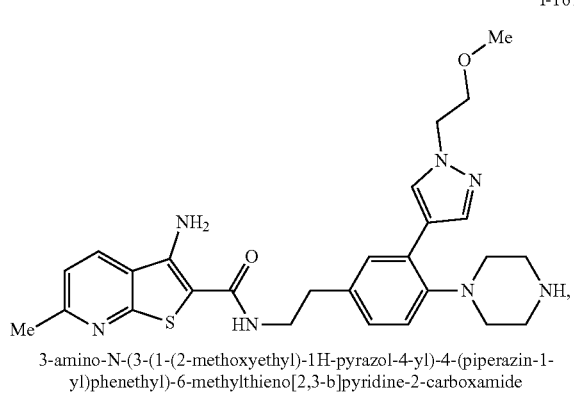

3-amino-N-(3-(1-(2-methoxyethyl)-1H-pyrazol-4-yl)-4-(piperazin-1-yl)phenethyl)-6-methylthieno[2,3-b]pyridine-2-carboxamide

I-168

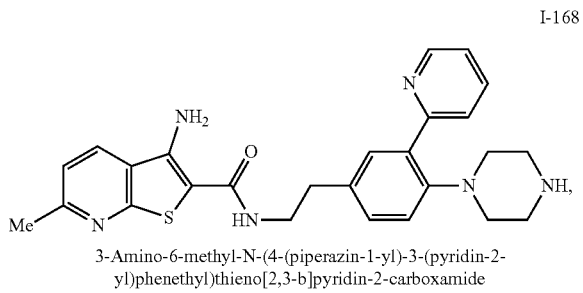

3-Amino-6-methyl-N-(4-(piperazin-1-yl)-3-(pyridin-2-yl)phenethyl)thieno[2,3-b]pyridin-2-carboxamide

I-169

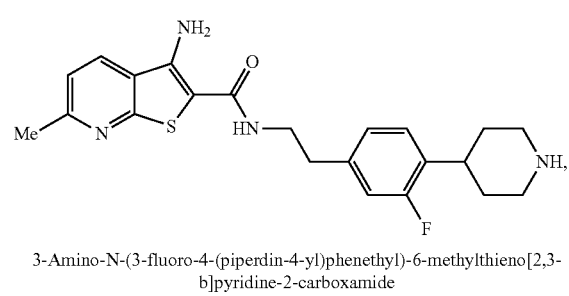

3-Amino-N-(3-fluoro-4-(piperdin-4-yl)phenethyl)-6-methylthieno[2,3-b]pyridine-2-carboxamide

I-170

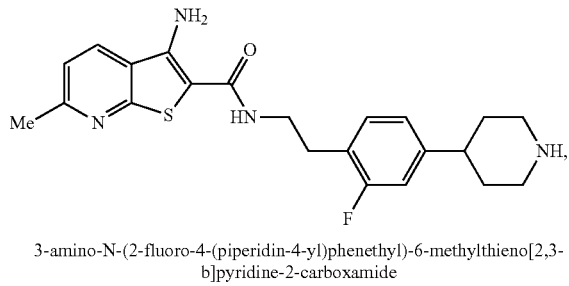

3-amino-N-(2-fluoro-4-(piperidin-4-yl)phenethyl)-6-methylthieno[2,3-b]pyridine-2-carboxamide

I-171

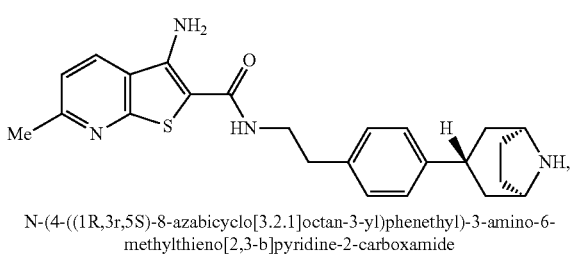

N-(4-((1R,3r,5S)-8-azabicyclo[3.2.1]octan-3-yl)phenethyl)-3-amino-6-methylthieno[2,3-b]pyridine-2-carboxamide

I-172

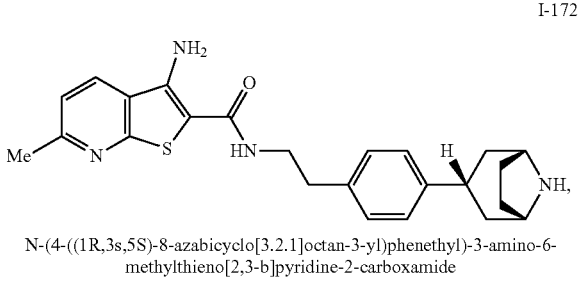

N-(4-((1R,3s,5S)-8-azabicyclo[3.2.1]octan-3-yl)phenethyl)-3-amino-6-methylthieno[2,3-b]pyridine-2-carboxamide

I-173

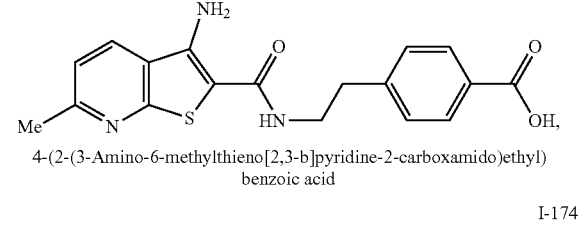

4-(2-(3-Amino-6-methylthieno[2,3-b]pyridine-2-carboxamido)ethyl)benzoic acid

I-174

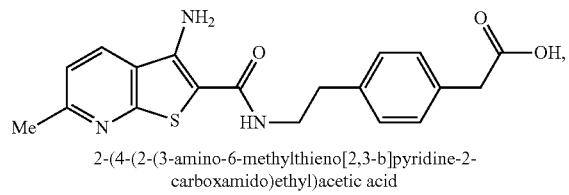

2-(4-(2-(3-amino-6-methylthieno[2,3-b]pyridine-2-carboxamido)ethyl)acetic acid

I-175

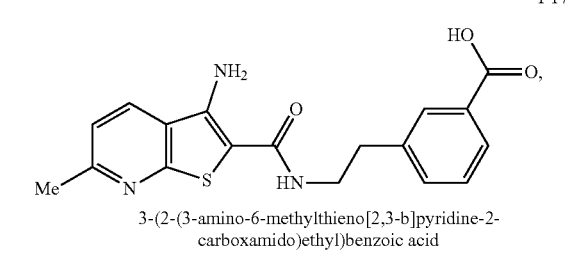

3-(2-(3-amino-6-methylthieno[2,3-b]pyridine-2-carboxamido)ethyl)benzoic acid

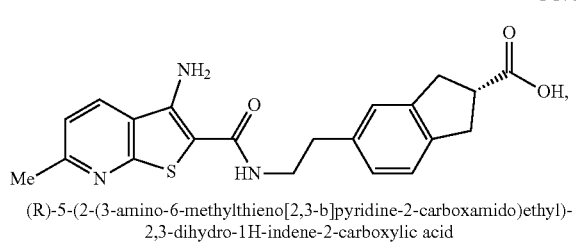

I-176

(R)-5-(2-(3-amino-6-methylthieno[2,3-b]pyridine-2-carboxamido)ethyl)-2,3-dihydro-1H-indene-2-carboxylic acid

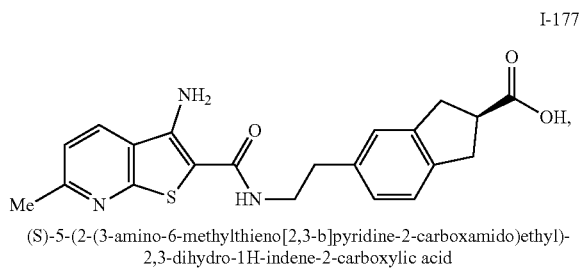

I-177

(S)-5-(2-(3-amino-6-methylthieno[2,3-b]pyridine-2-carboxamido)ethyl)-2,3-dihydro-1H-indene-2-carboxylic acid

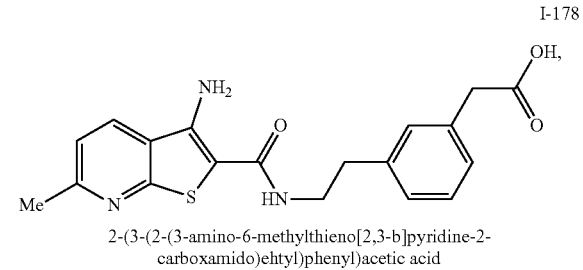

I-178

2-(3-(2-(3-amino-6-methylthieno[2,3-b]pyridine-2-carboxamido)ehtyl)phenyl)acetic acid

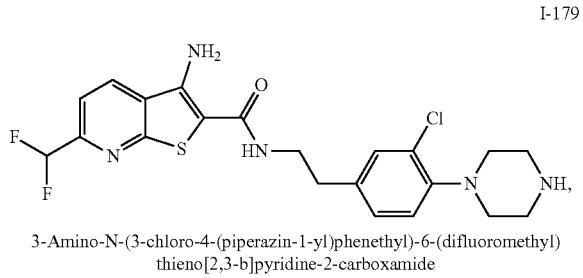

I-179

3-Amino-N-(3-chloro-4-(piperazin-1-yl)phenethyl)-6-(difluoromethyl)thieno[2,3-b]pyridine-2-carboxamide

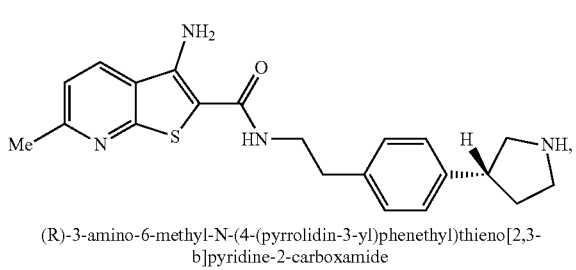

I-180

(R)-3-amino-6-methyl-N-(4-(pyrrolidin-3-yl)phenethyl)thieno[2,3-b]pyridine-2-carboxamide

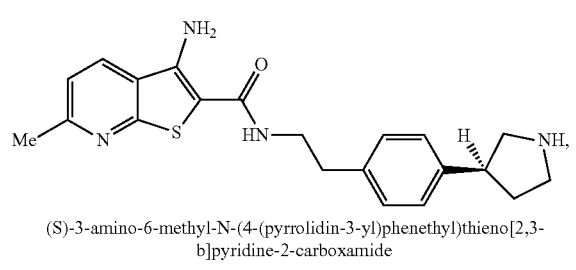

I-181

(S)-3-amino-6-methyl-N-(4-(pyrrolidin-3-yl)phenethyl)thieno[2,3-b]pyridine-2-carboxamide

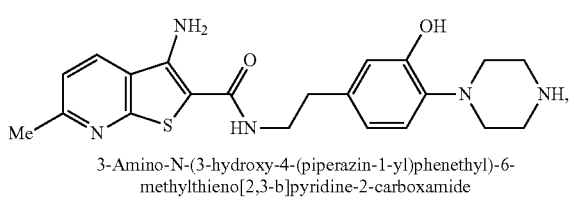

I-182

3-Amino-N-(3-hydroxy-4-(piperazin-1-yl)phenethyl)-6-methylthieno[2,3-b]pyridine-2-carboxamide

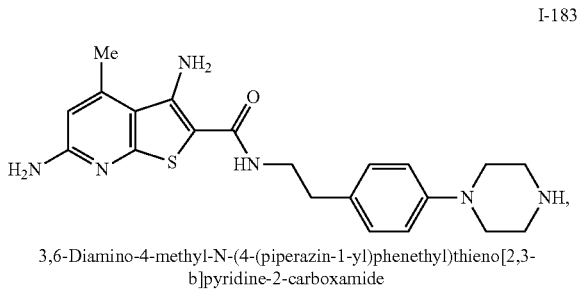

I-183

3,6-Diamino-4-methyl-N-(4-(piperazin-1-yl)phenethyl)thieno[2,3-b]pyridine-2-carboxamide

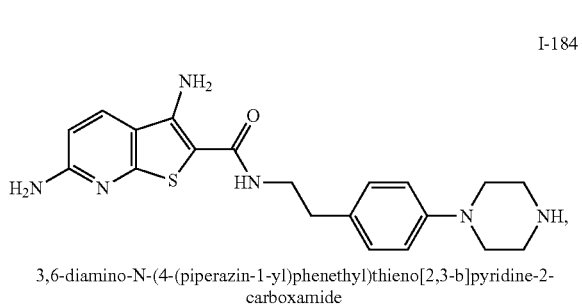

I-184

3,6-diamino-N-(4-(piperazin-1-yl)phenethyl)thieno[2,3-b]pyridine-2-carboxamide

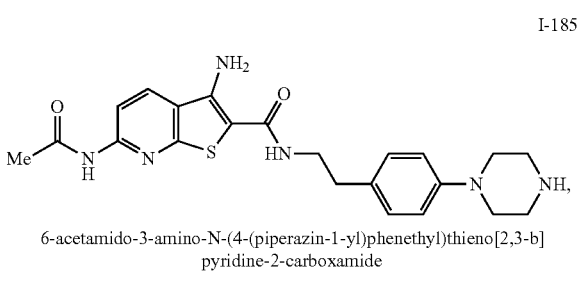

I-185

6-acetamido-3-amino-N-(4-(piperazin-1-yl)phenethyl)thieno[2,3-b]pyridine-2-carboxamide

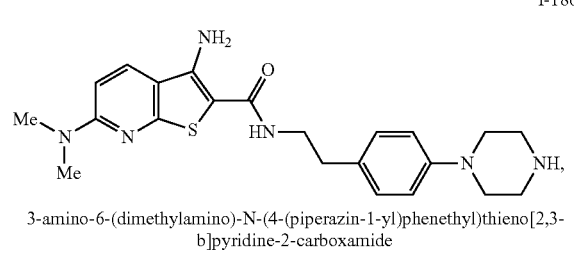

I-186

3-amino-6-(dimethylamino)-N-(4-(piperazin-1-yl)phenethyl)thieno[2,3-b]pyridine-2-carboxamide

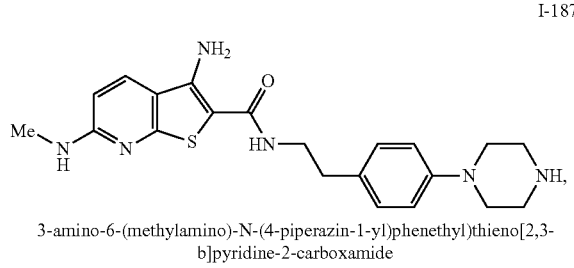

I-187

3-amino-6-(methylamino)-N-(4-piperazin-1-yl)phenethyl)thieno[2,3-b]pyridine-2-carboxamide -continued

I-188

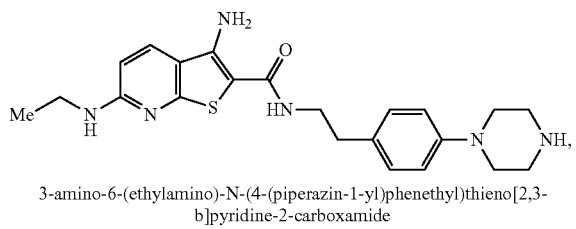

3-amino-6-(ethylamino)-N-(4-(piperazin-1-yl)phenethyl)thieno[2,3-b]pyridine-2-carboxamide

I-189

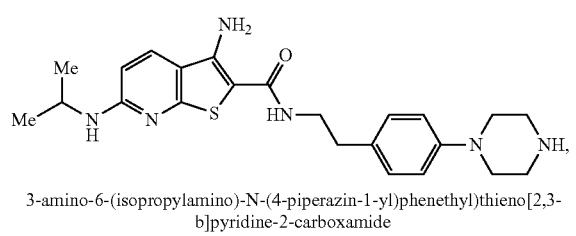

3-amino-6-(isopropylamino)-N-(4-piperazin-1-yl)phenethyl)thieno[2,3-b]pyridine-2-carboxamide

I-190

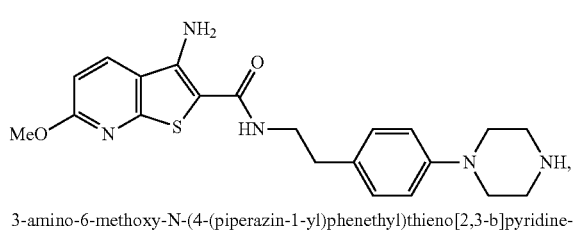

3-amino-6-methoxy-N-(4-(piperazin-1-yl)phenethyl)thieno[2,3-b]pyridine-2-carboxamide

I-191

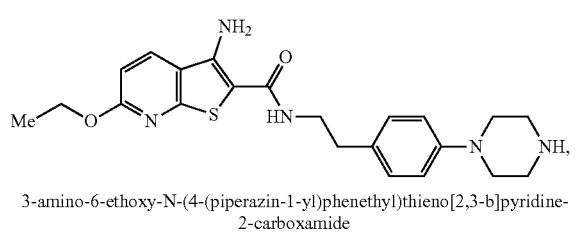

3-amino-6-ethoxy-N-(4-(piperazin-1-yl)phenethyl)thieno[2,3-b]pyridine-2-carboxamide

I-192

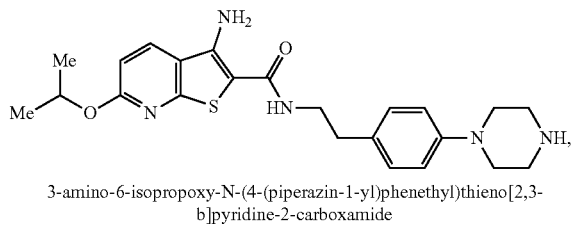

3-amino-6-isopropoxy-N-(4-(piperazin-1-yl)phenethyl)thieno[2,3-b]pyridine-2-carboxamide

I-193

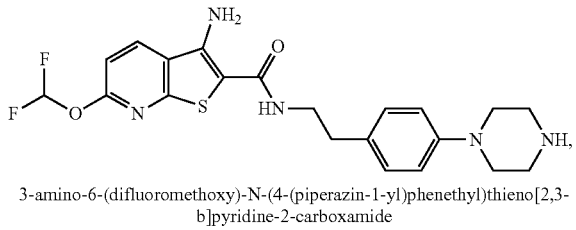

3-amino-6-(difluoromethoxy)-N-(4-(piperazin-1-yl)phenethyl)thieno[2,3-b]pyridine-2-carboxamide -continued

I-194

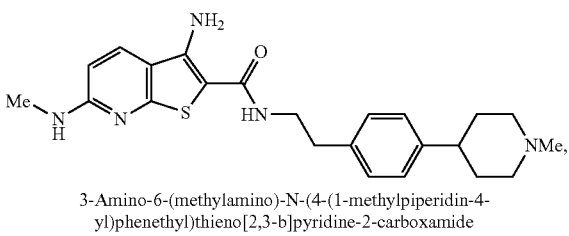

3-Amino-6-(methylamino)-N-(4-(1-methylpiperidin-4-yl)phenethyl)thieno[2,3-b]pyridine-2-carboxamide

I-195

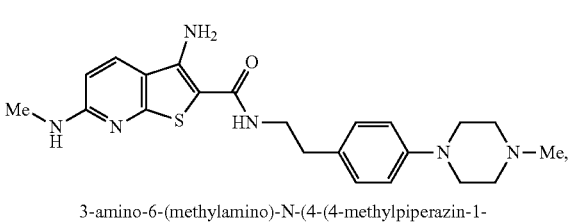

3-amino-6-(methylamino)-N-(4-(4-methylpiperazin-1-yl)phenethyl)thieno[2,3-b]pyridine-2-carboxamide

I-196

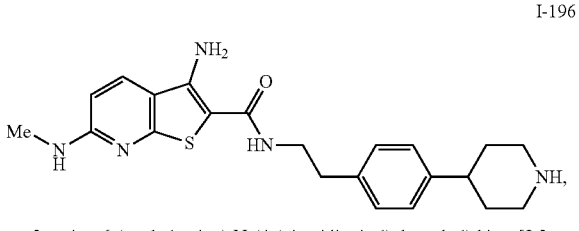

3-amino-6-(methylamino)-N-(4-(piperidin-4-yl)phenethyl)thieno[2,3-b]pyridine-2-carboxamide

I-197

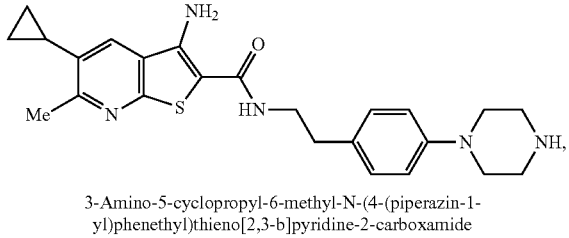

3-Amino-5-cyclopropyl-6-methyl-N-(4-(piperazin-1-yl)phenethyl)thieno[2,3-b]pyridine-2-carboxamide

I-198

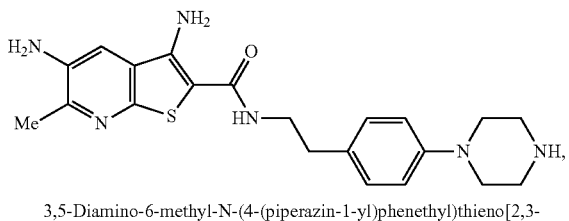

3,5-Diamino-6-methyl-N-(4-(piperazin-1-yl)phenethyl)thieno[2,3-b]pyridine-2-carboxamide

I-199

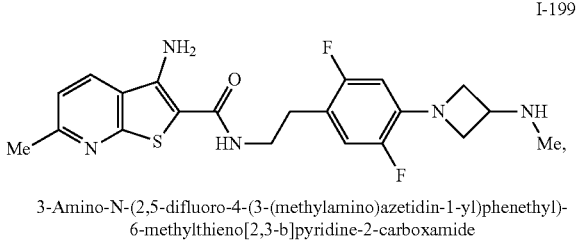

3-Amino-N-(2,5-difluoro-4-(3-(methylamino)azetidin-1-yl)phenethyl)-6-methylthieno[2,3-b]pyridine-2-carboxamide

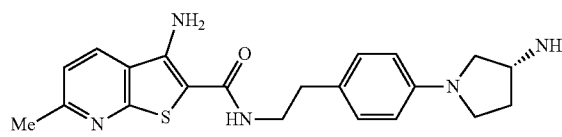

(R)-3-amino-N-(4-(3-(ethylamino)pyrrolidin-1-yl)phenethyl)-6-methylthieno[2,3-b]pyridine-2-carboxamide

I-200

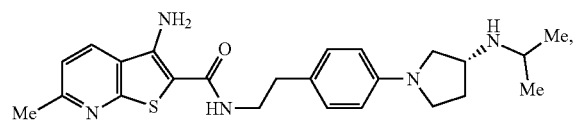

(R)-3-amino-N-(4-(3-(isopropylamino)pyrrolidin-1-yl)phenethyl)-6-methylthieno[2,3-b]pyridine-2-carboxamide

I-201

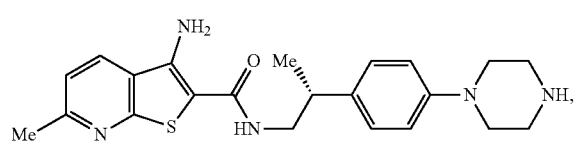

(R)-3-amino-6-methyl-N-(2-(4-(piperazin-1-yl)phenyl)propyl)thieno[2,3-b]pyridine-2-carboxamide

I-202

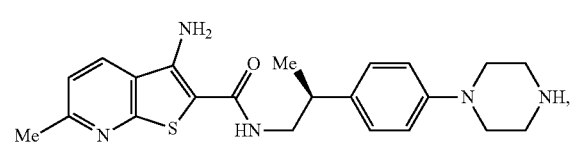

(S)-3-amino-6-methyl-N-(2-(4-(piperazin-1-yl)phenyl)propyl)thieno[2,3-b]pyridine-2-carboxamide

I-203

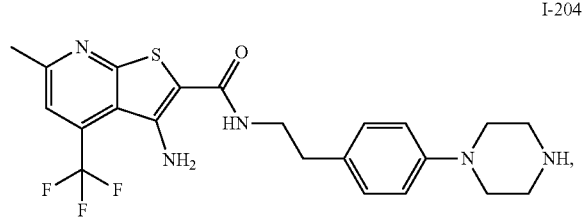

3-amino-6-methyl-N-(4-(piperazin-1-yl)phenethyl)-4-(trifluoromethyl)thieno[2,3-b]pyridine-2-carboxamide

I-204

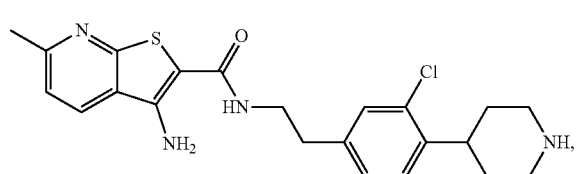

3-amino-N-(3-chloro-4-(piperidin-4-yl)phenethyl)-6-methylthieno[2,3-b]pyridine-2-carboxamide

I-205

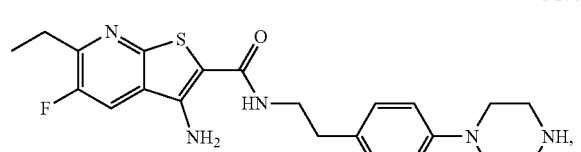

3-amino-6-ethyl-5-fluoro-N-(4-(piperazin-1-yl)phenethyl)thieno[2,3-b]pyridine-2-carboxamide

I-206

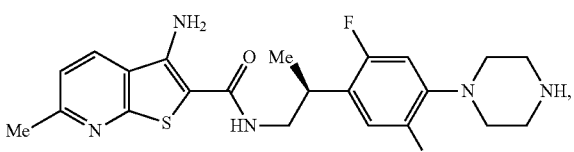

(S)-3-amino-N-(2-(2,5-difluoro-4-(piperazin-1-yl)phenyl)propyl)-6-methylthieno[2,3-b]pyridine-2-carboxamide

I-207

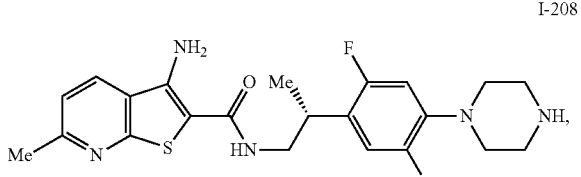

(R)-3-amino-N-(2-(2,5-difluoro-4-(piperazin-1-yl)phenyl)propyl)-6-methylthieno[2,3-b]pyridine-2-carboxamide

I-208

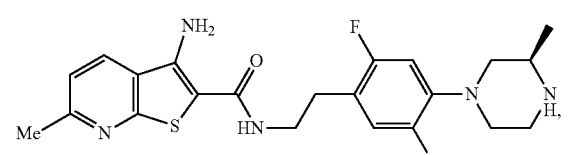

(R)-3-amino-N-(2,5-difluoro-4-(3-methylpiperazin-1-yl)phenethyl)-6-methylthieno[2,3-b]pyridine-2-carboxamide

I-209

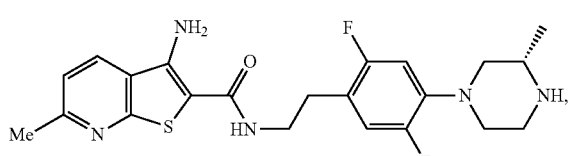

(S)-3-amino-N-(2,5-difluoro-4-(3-methylpiperazin-1-yl)phenethyl)-6-methylthieno[2,3-b]pyridine-2-carboxamide

I-210

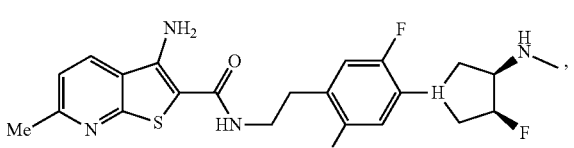

3-Amino-N-(2,5-difluoro-4-((3S,4R)-3-fluoro-4-(methylamino)pyrrolidin-1-yl)phenethyl)-6-methylthieno[2,3-b]pyridine-2-carboxamide

I-211

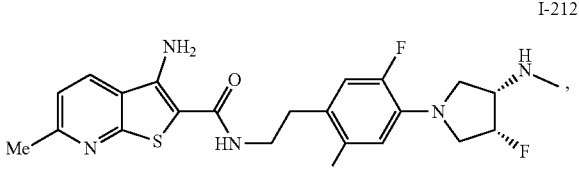

3-Amino-N-(2,5-difluoro-4-((3R,4S)-3-fluoro-4-(methylamino)pyrrolidin-1-yl)phenethyl)-6-methylthieno[2,3-b]pyridine-2-carboxamide

I-212

-continued

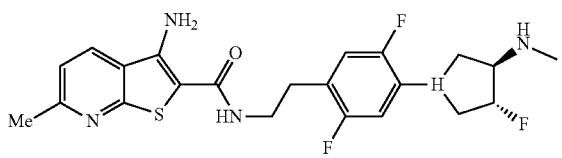

I-213

3-Amino-N-(2,5-difluoro-4-((3R,4R)-3-fluoro-4-(methylamino)
pyrrolidin-1-yl)phenethyl)-6-methylthieno[2,3-b]pyridine-2-carboxamide

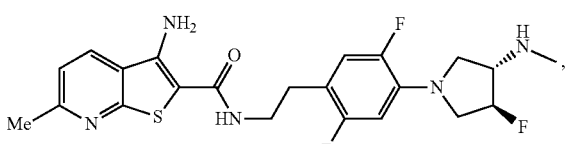

I-214

3-Amino-N-(2,5-difluoro-4-((3S,4S)-3-fluoro-4-(methylamino)pyrrolidin-
1-yl)phenethyl)-6-methylthieno[2,3-b]pyridine-2-carboxamide

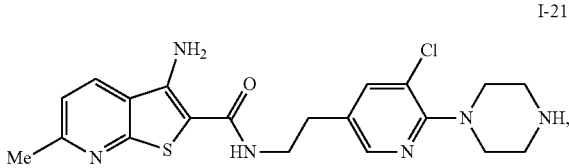

I-215

3-Amino-N-(2-(5-chloro-6-(piperazin-1-yl)pyridin-3-yl)ethyl)-6-
methylthieno[2,3-b]pyridine-2-carboxamide

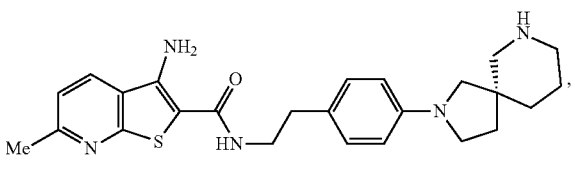

I-216

(S)-N-(4-(2,7-diazaspiro[4.5]decan-2-yl)phenethyl)-3-amino-6-
methylthieno[2,3-b]pyridine-2-carboxamide

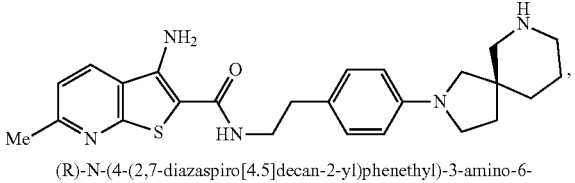

I-217

(R)-N-(4-(2,7-diazaspiro[4.5]decan-2-yl)phenethyl)-3-amino-6-
methylthieno[2,3-b]pyridine-2-carboxamide

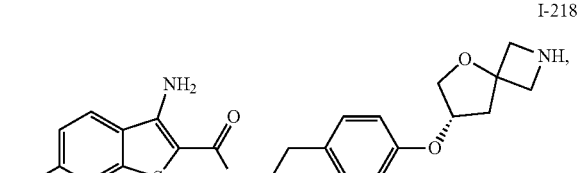

I-218

(S)-N-(4-((5-oxa-2-azaspiro[3.4]octan-7-yl)oxy)phenethyl)-3-amino-6-
methylthieno[2,3-b]pyridine-2-carboxamide -continued

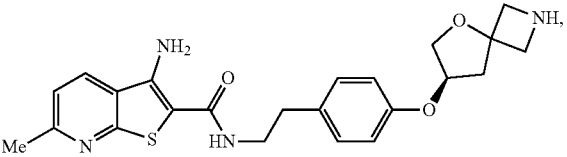

I-219

(R)-N-(4-((5-oxa-2-azaspiro[3.4]octan-7-yl)oxy)phenethyl)-3-amino-6-
methylthieno[2,3-b]pyridine-2-carboxamide

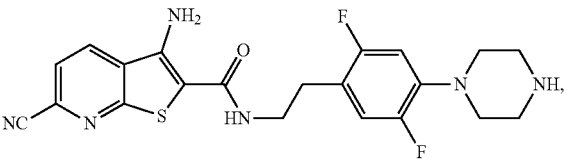

I-220

3-Amino-6-cyano-N-(2,5-difluoro-4-(piperazin-1-yl)phenethyl)thieno[2,3-
b]pyridine-2-carboxamide

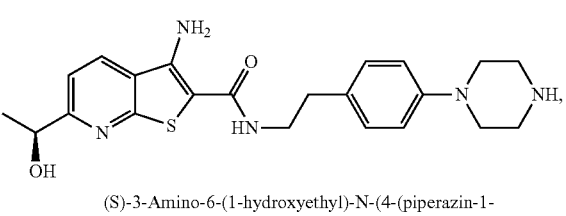

I-221

(S)-3-Amino-6-(1-hydroxyethyl)-N-(4-(piperazin-1-
yl)phenethyl)thieno[2,3-b]pyridine-2-carboxamide

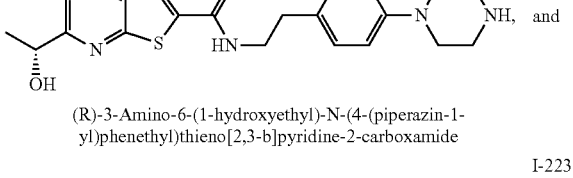

I-222

(R)-3-Amino-6-(1-hydroxyethyl)-N-(4-(piperazin-1-
yl)phenethyl)thieno[2,3-b]pyridine-2-carboxamide

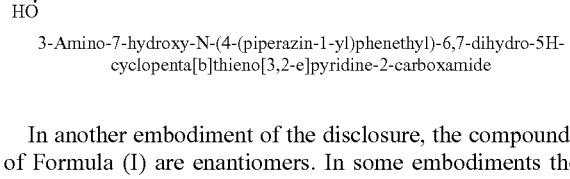

I-223

3-Amino-7-hydroxy-N-(4-(piperazin-1-yl)phenethyl)-6,7-dihydro-5H-
cyclopenta[b]thieno[3,2-e]pyridine-2-carboxamide In another embodiment of the disclosure, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, stereoisomers and prodrugs thereof may exist in their tautomeric form (for example, as an amide or imino ether). All such tautomeric forms are contemplated herein as part of the present disclosure.

The compounds of the disclosure may contain asymmetric or chiral centers, and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure. Also, for example, all keto-enol and imine-enamine forms of the compounds are included in the disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I)incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this disclosure. Reference to a compound of the Formula herein is understood to include reference to salts thereof, unless otherwise indicated.

The present disclosure relates to compounds which are modulators of USP28 and/or USP25. In one embodiment, the compounds of the present disclosure are inhibitors of USP28 and/or USP25.

The disclosure is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present disclosure may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley -Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereof as appreciated by those skilled in the art. Preferred methods include but are not limited to those methods described below. Compounds of the present invention can be synthesized by following the steps outlined in General Schemes 1 and 2 which comprise different sequences of assembling intermediates 2a, 2b, 2c, 2d, and 2e. Starting materials are either commercially available or made by known procedures in the reported literature or as illustrated.

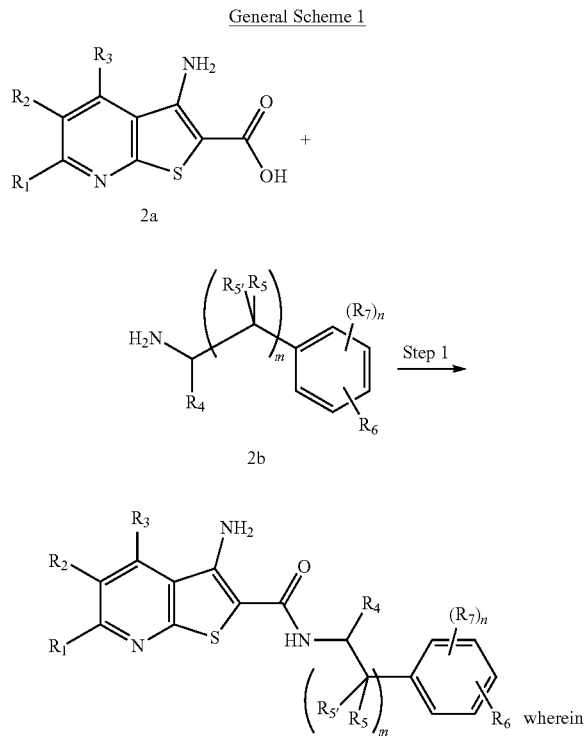

The general manner of preparing target compounds of Formula (I) by using intermediates 2a and 2b, is outlined above in General Scheme 1. Coupling of carboxylic acid 2a with amine 2b under standard amide forming conditions using a coupling agent, e.g., 1-Ethyl-3-(3-dimethylaminopropyl)carbodiimide with 1-hydroxybenzotriazole (EDCl/HOBt), (Benzotriazol-1-yloxy)tris(dimethylamino)phosphonium hexafluorophosphate (BOP), O-benzotriazole-N,N,N',N'-tetramethyl-uronium-hexafluoro-phosphate (HBTU) or [bis (dimethylamino)methylene]-1H-1,2,3 -triazolo[4,5-b]pyridinium-3-oxide hexafluorophosphate (HATU), and a base, e.g., triethylamine (TEA), N,N-diisopropylethylamine (DIEA), or 4-dimethylaminopyridine (DMAP), in a solvent (e.g. DCM or DMF, etc.) provides the desired product of Formula (I).

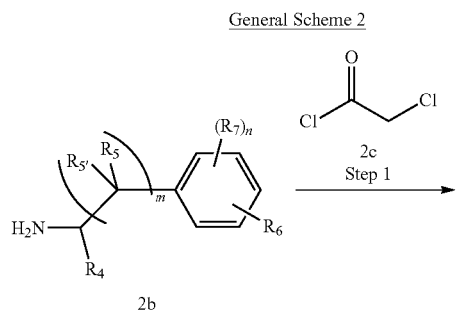

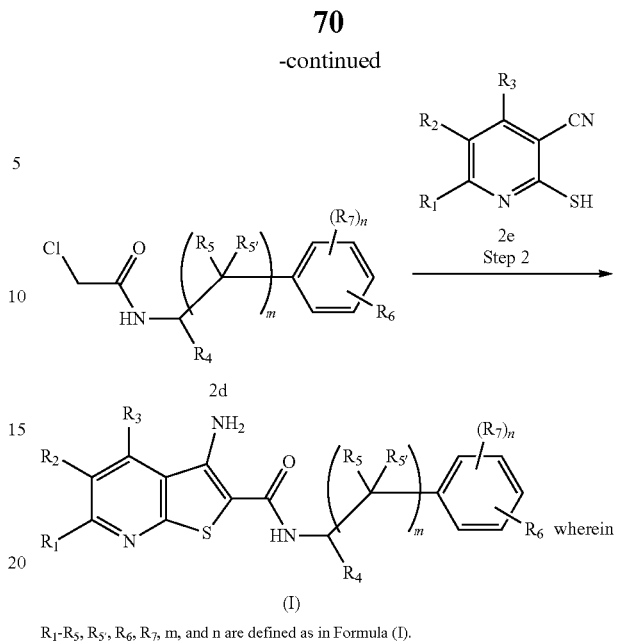

Alternatively, compounds of Formula (I) can also be prepared by using intermediates 2b, 2c, 2d, and 2e as depicted in General Scheme 2 above. Acylation of 2b with 2c in the presence of a base, e.g., triethylamine (TEA) or N,N-diisopropylethylamine (DIPEA), and in a solvent, e.g., DCM or THF, provides Intermediate 2d. Cyclization of 2d and 2e in the presence of a base, e.g., potassium carbonate ($K_2CO_3$) or sodium methoxide (NaOMe), and in a solvent, e.g., DMF or THF, optionally at elevated temperature provides the desired product of Formula (I).

Compounds of Formula (I) can exist as enantiomeric or diastereomeric stereoisomers. Enantiomerically pure compounds of Formula (I) can be prepared using enantiomerically pure chiral building blocks. Alternatively, racemic mixtures of the final compounds or a racemic mixture of an advanced intermediate can be subjected to chiral purification as described herein below to deliver the desired enantiomerically pure intermediates or final compounds. In the instances where an advanced intermediate is purified into its individual enantiomers, each individual enantiomer can be carried on separately to deliver the final enantiomerically pure compounds of Formula (I).

It should be understood that in the description and formula shown above, the various groups $R_1$-$R_5$, $R_{5'}$, $R_6$, $R_7$, m, n, and other variables are as defined above, except where otherwise indicated. Furthermore, for synthetic purposes, the compounds of General Schemes 1 and 2 are mere representative with elected radicals to illustrate the general synthetic methodology of the compounds of Formula (I) as defined herein.

Methods of Using the Disclosed Compounds

Another aspect of the disclosure relates to a method of treating, preventing, inhibiting, or eliminating a disease or disorder associated with modulation of USP28. The method comprises administering to a patient in need of a treatment for diseases or disorders associated with modulation of USP28 an effective amount the compositions and compounds of Formula (I). In one embodiment, the disease or disorder is cancer.

In another aspect, the present disclosure is directed to a method of treating, preventing, inhibiting, or eliminating a disease or disorder associated with inhibition of USP28. The method comprises administering to a patient in need of a treatment for diseases or disorders associated with modulation of USP28 an effective amount the compositions and compounds of Formula (I). In one embodiment, the disease or disorder is cancer.

In another aspect, the present disclosure is directed to a method of inhibiting USP28. The method involves administering to a patient in need thereof an effective amount of a compound of Formula (I).

Another aspect of the disclosure relates to a method of treating, preventing, inhibiting, or eliminating a disease or disorder associated with modulation of USP25. The method comprises administering to a patient in need of a treatment for diseases or disorders associated with modulation of USP25 an effective amount the compositions and compounds of Formula (I). In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present disclosure is directed to a method of treating, preventing, inhibiting, or eliminating a disease or disorder associated with inhibition of USP28. The method comprises administering to a patient in need of a treatment for diseases or disorders associated with modulation of USP25 an effective amount the compositions and compounds of Formula (I). In one embodiment, the disease or disorder is cancer. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present disclosure is directed to a method of inhibiting USP25. The method involves administering to a patient in need thereof an effective amount of a compound of Formula (I).

Another aspect of the disclosure relates to a method of treating, preventing, inhibiting, or eliminating a disease or disorder associated with modulation of USP25. The method comprises administering to a patient in need of a treatment for diseases or disorders associated with modulation of USP28 and USP25 an effective amount the compositions and compounds of Formula (I). In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present disclosure is directed to a method of treating, preventing, inhibiting, or eliminating a disease or disorder associated with inhibition of USP28. The method comprises administering to a patient in need of a treatment for diseases or disorders associated with modulation of USP28 and USP25 an effective amount the compositions and compounds of Formula (I). In one embodiment, the disease or disorder is cancer. In another embodiment, the disease or disorder is an autoimmune disease. In another embodiment, the disease or disorder is an infectious disease.

In another embodiment, the disease or disorder is a viral infection. In another embodiment, the disease or disorder is a bacterial infection.

In another aspect, the present disclosure is directed to a method of inhibiting USP28 and USP25. The method involves administering to a patient in need thereof an effective amount of a compound of Formula (I).

Another aspect of the present disclosure relates to a method of treating, preventing, inhibiting, or eliminating a disease or disorder in a patient associated with the inhibition of USP28, the method comprising administering to a patient in need thereof an effective amount of a compound of Formula (I). In one embodiment, the disease or disorder is cancer.

Another aspect of the present disclosure relates to a method of treating, preventing, inhibiting, or eliminating a disease or disorder in a patient associated with the inhibition of USP25, the method comprising administering to a patient in need thereof an effective amount of a compound of Formula (I). In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

Another aspect of the present disclosure relates to a method of treating, preventing, inhibiting, or eliminating a disease or disorder in a patient associated with the inhibition of USP28 and USP25, the method comprising administering to a patient in need thereof an effective amount of a compound of Formula (I). In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present invention relates to a method of treating, preventing, inhibiting, or eliminating cancer. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating inflammation. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an autoimmune disease. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an infectious disease. The method comprises administering to a patient in need of a treatment for cancer an effective amount of a compound of Formula (I), or a pharmaceutically acceptable salt, hydrate, solvate, prodrug, stereoisomer, or tautomer thereof. In one embodiment, the infectious disease is a viral infection. In another embodiment, the infectious disease is a bacterial infection.

In another aspect, the present invention relates to a method of treating, preventing, inhibiting, or eliminating a viral infection. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating a bacterial infection. The method comprises administering to a patient in need of a treatment for cancer an effective amount of a compound of Formula (I), or a pharmaceutically acceptable salt, hydrate, solvate, prodrug, stereoisomer, or tautomer thereof.

Another aspect of the present invention relates to a compound of Formula (I), or a pharmaceutically acceptable salt, hydrate, solvate, prodrug, stereoisomer, or tautomer thereof, for use in a method of treating, preventing, inhibiting, or eliminating a disease or disorder associated with inhibiting USP28. In one embodiment, the disease or disorder is cancer.

In another aspect, the present invention relates to a compound of Formula (I), or a pharmaceutically acceptable salt, hydrate, solvate, prodrug, stereoisomer, or tautomer thereof, for use in a method of treating, preventing, inhibiting, or eliminating a disease or disorder associated with inhibiting USP25. In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

Another aspect of the present invention relates to a compound of Formula (I), or a pharmaceutically acceptable salt, hydrate, solvate, prodrug, stereoisomer, or tautomer thereof, for use in a method of treating, preventing, inhibiting, or eliminating a disease or disorder associated with inhibiting USP28 and USP25. In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating cancer.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating inflammation.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating an autoimmune disease.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating an infectious disease.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating a viral infection.

In another aspect, the present invention relates to a compound of Formula (I), or a pharmaceutically acceptable salt, hydrate, solvate, prodrug, stereoisomer, or tautomer thereof, for use in a method for treating, preventing, inhibiting, or eliminating a bacterial infection.

Another aspect of the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a disease or disorder associated with inhibiting USP28. In one embodiment, the disease or disorder is cancer.

Another aspect of the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a disease or disorder associated with inhibiting USP25. In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

Another aspect of the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a disease or disorder associated with inhibiting USP28 and USP25. In one embodiment, the disease or disorder is cancer. In another embodiment, the disease or disorder is inflammation. In another embodiment, the disease or disorder is an autoimmune disease. In another embodiment, the disease or disorder is an infectious disease. In another embodiment, the disease or disorder is a viral infection. In another embodiment, the disease or disorder is a bacterial infection.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating cancer.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating inflammation.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating autoimmune disorder.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating an infection disease. In one embodiment, the infectious disease is a viral infection. In another embodiment, the infectious disease is a bacterial infection.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a viral infection.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a bacterial infection.

In other embodiments, the present invention relates to the use of an inhibitor of USP28 for the preparation of a medicament used in the treatment, prevention, inhibition or elimination of a disease or disorder associated with cancer.

In other embodiments, the present invention relates to the use of an inhibitor of USP28 for the preparation of a medicament used in the treatment, prevention, inhibition or elimination of a disease or disorder associated with inflammation.

In other embodiments, the present invention relates to the use of an inhibitor of USP28 for the preparation of a medicament used in the treatment, prevention, inhibition or elimination of a disease or disorder associated with an autoimmune disease.

In other embodiments, the present invention relates to the use of an inhibitor of USP28 for the preparation of a medicament used in the treatment, prevention, inhibition or elimination of a disease or disorder associated with an infectious disease. In one embodiment, the infectious disease is a viral infection. In another embodiment, the infectious disease is a bacterial infection.

In other embodiments, the present invention relates to the use of an inhibitor of USP28 for the preparation of a medicament used in the treatment, prevention, inhibition or elimination of a disease or disorder associated with a viral infection.

In other embodiments, the present invention relates to the use of an inhibitor of USP28 for the preparation of a medicament used in the treatment, prevention, inhibition or elimination of a disease or disorder associated with a bacterial infection.

The present disclosure also relates to the use of an inhibitor of USP28 for the preparation of a medicament used in the treatment, prevention, inhibition, or elimination of a disease or condition mediated by USP28, wherein the medicament comprises a compound of Formula (I).

The present disclosure also relates to the use of an inhibitor of USP25 for the preparation of a medicament used in the treatment, prevention, inhibition, or elimination of a disease or condition mediated by USP25, wherein the medicament comprises a compound of Formula (I).

The present disclosure also relates to the use of an inhibitor of USP28 and USP25 for the preparation of a medicament used in the treatment, prevention, inhibition, or elimination of a disease or condition mediated by USP28 and USP25, wherein the medicament comprises a compound of Formula (I).

In another aspect, the present disclosure relates to a method for the manufacture of a medicament for treating, preventing, inhibiting, or eliminating a disease or condition mediated by USP28, wherein the medicament comprises a compound of Formula (I).

Another aspect of the present disclosure relates to a method for the manufacture of a medicament for treating, preventing, inhibiting, or eliminating a disease or condition mediated by USP25, wherein the medicament comprises a compound of Formula (I).

In another aspect, the present disclosure relates to a method for the manufacture of a medicament for treating, preventing, inhibiting, or eliminating a disease or condition mediated by USP28 and USP25, wherein the medicament comprises a compound of Formula (I).

In some embodiments of the methods described herein, the cancer is selected from bladder cancer, breast cancer (e.g., ductal carcinoma), cervical cancer (e.g., squamous cell carcinoma), colorectal cancer (e.g., adenocarcinoma), colon cancer, esophageal cancer (e.g., squamous cell carcinoma), gastric cancer (e.g., adenocarcinoma, choriocarcinoma, squamous cell carcinoma), head and neck cancer, hematologic cancer (e.g., acute lymphocytic anemia, acute myeloid leukemia, acute lymphoblastic B cell leukemia, anaplastic large cell lymphoma, B-cell lymphoma, Burkitt's lymphoma, chronic lymphocytic leukemia, chronic eosinophillic leukemia/hyl)ereosinophillic syndrome, chronic myeloid leukemia, Hodgkin's lymphoma, mantle cell lymphoma, multiple myeloma, T-cell acute lymphoblastic leukemia, lung cancer (e.g., bronchioloalveolar adenocarcinoma, mesothelioma, mucoepidermoid carcinoma, small-cell lung cancer, non-small cell lung cancer, adenocarcinoma, squamous cell carcinoma), liver cancer (e.g., hepatocellular carcinoma), lymphoma, neurological cancer (e.g., glioblastoma, neuroblastoma, neuroglioma), ovarian cancer (e.g., adenocarcinoma), pancreatic cancer (e.g., ductal carcinoma), prostate cancer (e.g., adenocarcinoma), renal cancer (e.g., renal cell carcinoma, clear cell renal cancer carcinoma), sarcoma (e.g., chondrosarcoma, Ewings sarcoma, fibrosarcoma, multipotential sarcoma, osteosarcoma, rhabdomyosarcoma, synovial sarcoma), skin cancer (e.g., melanoma, epidermoid carcinoma, squamous cell carcinoma), thyroid cancer (e.g., medullary carcinoma), and uterine cancer. In some embodiments, the cancer is a cancer that is sensitive to USP28 inhibition. In other embodiments, the cancer is a cancer that is sensitive to USP25 inhibition. In other embodiments, the cancer is a cancer that is sensitive to USP28 and USP25 inhibition.

In any of the embodiments of the disclosure, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In other embodiments, the cancer is selected from acute myeloid leukemia, gastric, pancreatic, colorectal, glioblastoma, neuroblastoma, small-cell lung, non-small cell lung, and squamous cell carcinoma.

In another embodiment, the present disclosure relates to a compound of Formula (I) or a pharmaceutical composition comprising a compound of the present disclosure and a pharmaceutically acceptable carrier used for the treatment of cancers including, but not limited to, bladder cancer, breast cancer (e.g., ductal carcinoma), cervical cancer (e.g., squamous cell carcinoma), colorectal cancer (e.g., adenocarcinoma), esophageal cancer (e.g., squamous cell carcinoma), gastric cancer (e.g., adenocarcinoma, choriocarcinoma, squamous cell carcinoma), head and neck cancer, hematologic cancer (e.g., acute lymphocytic anemia, acute myeloid leukemia, acute lymphoblastic B cell leukemia, anaplastic large cell lymphoma, B-cell lymphoma, Burkitt's lymphoma, chronic lymphocytic leukemia, chronic eosinophillic leukemia/hyl)ereosinophillic syndrome, chronic myeloid leukemia, Hodgkin's lymphoma, mantle cell lymphoma, multiple myeloma, T-cell acute lymphoblastic leukemia), lung cancer (e.g., bronchioloalveolar adenocarcinoma, mesothelioma, mucoepidermoid carcinoma, small-cell lung cancer, non-small cell lung cancer, adenocarcinoma, squamous cell carcinoma), liver cancer (e.g., hepatocellular carcinoma), lymphoma, neurological cancer (e.g., glioblastoma, neuroblastoma, neuroglioma), ovarian cancer (e.g., adenocarcinoma), pancreatic cancer (e.g., ductal carcinoma), prostate cancer (e.g., adenocarcinoma), renal cancer (e.g., renal cell carcinoma, clear cell renal cancer carcinoma), sarcoma (e.g., chondrosarcoma, Ewings sarcoma, fibrosarcoma, multipotential sarcoma, osteosarcoma, rhabdomyosarcoma, synovial sarcoma), skin cancer (e.g., melanoma, epidermoid carcinoma, squamous cell carcinoma), thyroid cancer (e.g., medullary carcinoma), and uterine cancer. In other embodiments, the cancer is selected from acute myeloid leukemia, gastric cancer, pancreatic cancer, colorectal cancer, glioblastoma, neuroblastoma, small-cell lung cancer, non-small cell lung cancer, and squamous cell carcinoma.

In some embodiments, the patient is selected for treatment based on gene amplification and/or elevated tumor expression of USP28, MYC, LSD1, NICD1, and/or reduced expression of FBXW7 relative to tissue-matched expression.

In some embodiments, the patient is selected for treatment based on gene amplification and/or elevated tumor expression of USP28, USP25, MYC, LSD1, NICD1, and/or reduced expression of FBXW7 relative to tissue-matched expression.

In some embodiments, administration of a compound of Formula (I) or a pharmaceutical composition comprising a compound of the present disclosure and a pharmaceutically acceptable carrier induces a change in the cell cycle, cell viability, cell apoptosis, or differentiation.

For example, the change in the cell cycle or cell viability or differentiation may be indicated by decreased tumor levels of MYC, LSD1, NICD1, PIM1, CDK1, POLA2, HEY1, and/or CCND1, and/or increased levels of CD86, p21, LGALS4, and/or DLL1.

In another embodiment, the present disclosure relates to a compound of Formula (I) or a pharmaceutical composition comprising a compound of the present disclosure and a pharmaceutically acceptable carrier used for the treatment of autoimmune diseases including, but not limited to, multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, cutaneous lupus erythematosus including chilblain lupus erythematosus, lupus nephritis, discoid lupus, subacute cutaneous lupus erythematosus, dermatomyositis, polymyositis, idiopathic myxedema, Hashimoto's disease, Guillain-Barre' syndrome, Grave's disease, myasthenia gravis, Sjogren's syndrome, nodular panarteritis, autoimmune enteropathy, uveitis, autoimmune oophoritis, chronic immune thrombocytopenic purpura, colitis, diabetes, psoriasis, pemphigus vulgaris, proliferative glomerulonephritis, Wiskott-Aldrich syndrome, autoimmune lymphoproliferative syndrome, chronic arthritis, inflammatory chronic rhinosinusitis, colitis, celiac disease, inflammatory bowel disease, Barrett's esophagus, inflammatory gastritis, autoimmune nephritis, autoimmune vasculitis, autoimmune hepatitis, autoimmune carditis, autoimmune encephalitis, and autoimmune mediated hematological disease.

In any of the embodiments of the disclosure, the autoimmune disease can be, for example, an autoimmune disease selected from multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, cutaneous lupus erythematosus including chilblain lupus erythematosus, lupus nephritis, discoid lupus, subacute cutaneous lupus erythematosus, dermatomyositis, polymyositis, idiopathic myxedema, Hashimoto's disease, Guillain-Barre' syndrome, Grave's disease, myasthenia gravis, Sjogren's syndrome, nodular panarteritis, autoimmune enteropathy, uveitis, autoimmune oophoritis, chronic immune thrombocytopenic purpura, colitis, diabetes, psoriasis, pemphigus vulgaris, proliferative glomerulonephritis, Wiskott-Aldrich syndrome, autoimmune lymphoproliferative syndrome, chronic arthritis, inflammatory chronic rhinosinusitis, colitis, celiac disease, inflammatory bowel disease, Barrett's esophagus, inflammatory gastritis, autoimmune nephritis, autoimmune vasculitis, autoimmune hepatitis, autoimmune carditis, autoimmune encephalitis, and autoimmune mediated hematological disease.

Another aspect of the disclosure is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of USP28 including cancer comprising administering to a patient suffering from at least one of said diseases or disorder a compound of Formula (I).

In another embodiment, are provided methods of treating a disease or disorder associated with modulation of USP25 including cancer, inflammation, an autoimmune disease, a viral infection and a bacterial infection, comprising administering to a patient suffering from at least one of said diseases or disorder a compound of Formula (I).

In another embodiment, are provided methods of treating a disease or disorder associated with modulation of USP28 and USP25 including cancer, inflammation, an autoimmune disease, a viral infection and a bacterial infection, comprising administering to a patient suffering from at least one of said diseases or disorder a compound of Formula (I).

One therapeutic use of the compounds or compositions of the present disclosure which inhibit USP28 is to provide treatment to patients or subjects suffering from cancer.

Another therapeutic use of the compounds or compositions of the present disclosure which inhibit USP25 is to provide treatment to patients or subjects suffering from cancer.

Another therapeutic use of the compounds or compositions of the present disclosure which inhibit USP28 and USP25 is to provide treatment to patients or subjects suffering from cancer.

Another therapeutic use of the compounds or compositions of the present disclosure which inhibit USP25 is to provide treatment to patients or subjects suffering from inflammation.

Another therapeutic use of the compounds or compositions of the present disclosure which inhibit USP28 and USP25 is to provide treatment to patients or subjects suffering from inflammation.

Another therapeutic use of the compounds or compositions of the present disclosure which inhibit USP25 is to provide treatment to patients or subjects suffering from an autoimmune disease.

Another therapeutic use of the compounds or compositions of the present disclosure which inhibit USP28 and USP25 is to provide treatment to patients or subjects suffering from an autoimmune disease.

Another therapeutic use of the compounds or compositions of the present disclosure which inhibit USP25 is to provide treatment to patients or subjects suffering from an infectious disease.

Another therapeutic use of the compounds or compositions of the present disclosure which inhibit USP28 and USP25 is to provide treatment to patients or subjects suffering from an infectious disease.

Another therapeutic use of the compounds or compositions of the present disclosure which inhibit USP25 is to provide treatment to patients or subjects suffering from a viral infection.

Another therapeutic use of the compounds or compositions of the present disclosure which inhibit USP28 and USP25 is to provide treatment to patients or subjects suffering from a viral infection.

Another therapeutic use of the compounds or compositions of the present disclosure which inhibit USP25 is to provide treatment to patients or subjects suffering from a bacterial infection.

Another therapeutic use of the compounds or compositions of the present disclosure which inhibit USP28 and USP25 is to provide treatment to patients or subjects suffering from a bacterial infection.

The disclosed compounds of the disclosure can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxyl)ropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxyl)ropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 or 400 MHz. Spectra are given in ppm (δ) and coupling constants, J, are reported in Hertz. Mass spectra were collected using a Waters ZQ Single Quad Mass Spectrometer (ion trap electrospray ionization (ESI)). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 μm 2.1×50 mm; Flow rate 0.6mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 mins and 5% B at 2.21 mins. Preparatory HPLC purifications were conducted on a Waters SunFire C18 OBD Prep Column, 100 Å, 5 μm, 19 mm×50 mm, Waters XBridge BEH C18 OBD Prep Column, 130 Å, 5 μm, 19 mm×50 mm with UV detection (Waters 2489 UV/998 PDA), Waters SunFire C18 OBD Prep Column, 100 Å, 5 μm, 19 mm×150 mm, Waters XBridge BEH Shield RP18 OBD Prep Column, 130 Å, 5 μm, 19 mm×150 mm, or Waters XSelect CSH C18 OBD Prep Column, 130 Å, 5 μm, 19 mm×150 mm at 254 nm or 220 nm using a standard solvent gradient program (e.g., as designated below). The absolute configuration of the separated enantiomers of the compounds in the examples described herein were not determined. As such, the configuration of the resolved materials were arbitrarily assigned as R or S in each case.

Abbreviations used in the following examples and elsewhere herein are:
atm atmosphere
BAST bis(2-methoxyethyl)aminosulfur trifluoride
br broad
BINAP (2,2'-bis(diphenylphosphino)-1,1'-binaphthyl)
BOP ((1H-benzo[d][1,2,3]triazol-1-yl)oxy)tris(dimethylamino)phosphonium hexafluorophosphate(V)
Cbz carboxybenzyl
d doublet
DABCO 1,4-diazabicyclo[2.2.2]octane
DAST N,N-diethylaminosulfur trifluoride
DBU 2,3,4,6,7,8,9,10-octahydropyrimido[1,2-α]azepine
DCE 1,2-dichloroethane
DCM dichloromethane
DEA diethylamine
DIEA N,N-diisopropylethylamine
DMA N,N-dimethylacetamide
DME 1,2-dimethoxyethane
DMAP 4-dimethylaminopyridine
DMF N,N-dimethylformamide
DMF-DMA N,N-dimethylformamide dimethyl acetal
DMSO dimethyl sulfoxide
dppf 1,1'-bis(diphenylphosphino)ferrocene
EA ethyl acetate
EDCI N-(3-dimethylaminopropyl)-N'-ethylcarbodiimide hydrochloride
ESI electrospray ionization
FCC flash column chromatography
h hour(s)
HATU [bis(dimethylamino)methylene]-1H-1,2,3-triazolo[4,5-b]pyridinium 3-oxide hexafluorophosphate
HBTU 3-[bis(dimethylamino)methyliumyl]-3H-benzotriazol-1-oxide hexafluorophosphate
HMPA hexamethylphosphoramide
HOBt benzotriazol-1-ol
HPLC high-performance liquid chromatography
LCMS liquid chromatography—mass spectrometry
m multiplet
MHz megahertz
min minutes
MPLC Medium pressure liquid chromatography
MTBE 2-methoxy-2-methylpropane
μW microwave
NBS N-bromosuccinimide
NCS N-chlorosuccinimide
NMM 4-methylmorpholine
NMR nuclear magnetic resonance
$PCy_3$ tricyclohexylphosphine
PE petroleum ether
ppm parts per million
q quartet
RT room temperature
RuPhos 2-dicyclohexylphosphino-2',6'-diisopropoxybiphenyl RuPhos Pd 2nd Gen: Chloro(2-dicyclohexylphosphino-2',6'-diisopropoxy-1,1'-biphenyl)[2-(2'-amino-1,1'-biphenyl)]palladium(II)
s singlet
SCX strongly cationic exchange
SPhos 2-Dicyclohexylphosphino-2',6'-dimethoxybiphenyl
t triplet
TBDMS tert-butyldimethylsilyl
tBuBrettPhos di-tert-butyl(2',4',6'-triisopropyl-3,6-dimethoxy-[1,1'-biphenyl]-2-yl)phosphine
TEA triethylamine
TFA trifluoroacetic acid
THF tetrahydrofuran
TLC thin layer chromatography
TMSI trimethylsilyl iodide
TosMIC 1-(isocyanomethylsulfonyl)-4-methylbenzene
XantPhos 4,5-Bis(diphenylphosphino)-9,9-dimethylxanthene
XPhos 2-Dicyclohexylphosphino-2',4',6'-triisopropylbiphenyl
Xphos 2nd generation precatalyst: Chloro(2-dicyclohexylphosphino-2',4',6'-triisopropyl-1,1'-biphenyl)[2-(2'-amino-1,1'-biphenyl)]palladium(II)

Example 1

Intermediate 1: 3-Amino-6-methylthieno[2,3-b]pyridine-2-carboxylic acid

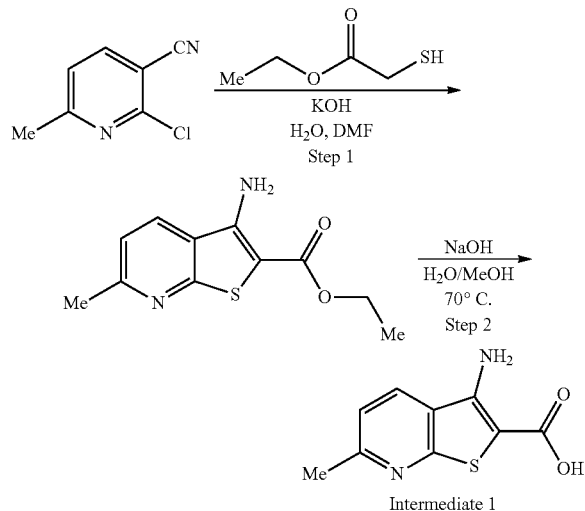

Step 1. Ethyl 3-amino-6-methylthieno[2,3-b]pyridine-2-carboxylate

To a solution of 2-chloro-6-methylnicotinonitrile (1.00 g, 6.55 mmol) in DMF (10 ml) was added ethyl 2-mercaptoacetate (0.72 ml, 6.6 mmol) followed by a solution of potassium hydroxide (powder) (1.47 g, 26.2 mmol) in 3.0 mL of water at 0° C. The reaction was stirred at 0° C. for 1 hour resulting in a precipitate. The precipitate was collected via filtration, washed with water (10 mL) followed by ether (10 mL) and then dried in vacuo to afford ethyl 3-amino-6-methylthieno[2,3-b]pyridine-2-carboxylate as a yellow powder (1.3 g, 85%). LCMS (ESI, m/z): 237 [M+H]+.

Step 2: 3-Amino-6-methylthieno[2,3-b]pyridine-2-carboxylic acid

To a solution of ethyl 3-amino-6-methylthieno[2,3-b]pyridine-2-carboxylate (2.30 g, 9.90 mmol) in methanol (15 mL) was added a solution of sodium hydroxide (2.00 g, 50.0 mmol) in water (15 mL). The resulting solution was stirred for 4 h at 70° C. The resulting mixture was concentrated in vacuo, and the pH of the solution was adjusted to 6 with aqueous hydrogen chloride (1M) resulting in a precipitate. The solids were collected by filtration and dried in vacuo to afford 3-amino-6-methylthieno[2,3-b]pyridine-2-carboxylic acid as a yellow solid (1.2 g, 58%). LCMS (ESI, m/z): 209 [M+H]+.

Example 2

Intermediate 2. 3-Amino-4-(difluoromethyl)-6-methylthieno[2,3-b]pyridine-2-carboxylic acid

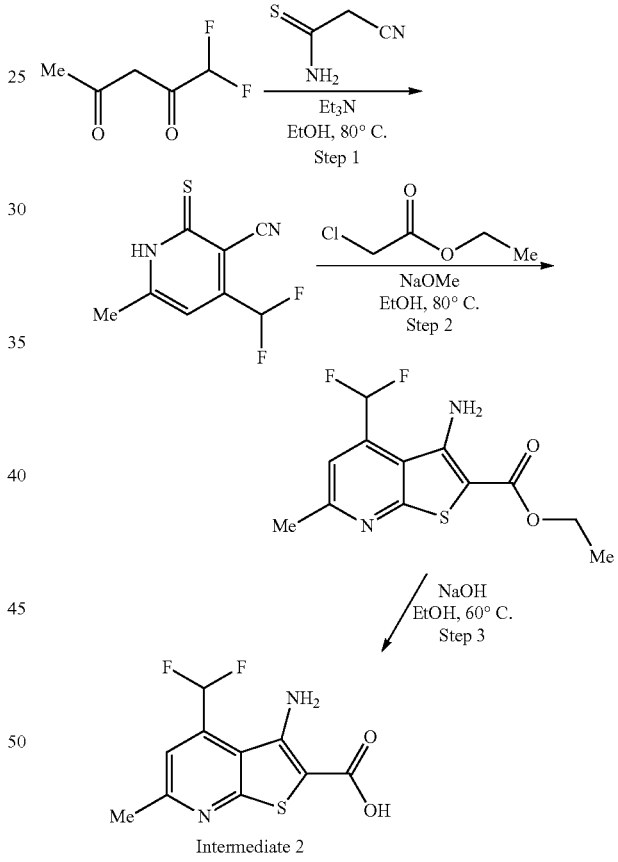

Step 1. 4-(Difluoromethyl)-6-methyl-2-thioxo-1,2-dihydropyridine-3-carbonitrile

Into a 100-mL round-bottom flask was added 1,1-difluoropentane-2,4-dione (2.00 g, 14.7 mmol), triethylamine (60 mg, 0.083 mL, 0.59 mmol), 2-cyanoethanethioamide (1.47 g, 14.7 mmol) and ethanol (30 mL). The reaction mixture was stirred for 2 h at 80° C., resulting in a precipitate that was collected by filtration and dried in vacuo to afford 4-(difluoromethyl)-6-methyl-2-thioxo-1,2-dihydropyridine-3-carbonitrile as an orange solid (1.72 g, 58%). LCMS (ESI, m/z): 201 [M+H]+.

Step 2. Ethyl 3-amino-4-(difluoromethyl)-6-methylthieno[2,3-b]pyridine-2-carboxylate Into a 100-mL round-bottom flask was added 4-(difluoromethyl)-6-methyl-2-thioxo-1,2-dihydropyridine-3-carbonitrile (1.00 g, 4.99 mmol), ethyl 2-chloroacetate (0.610 g, 4.98 mmol), sodium methoxide (0.810 g, 14.99 mmol), and ethanol (30 mL). The resulting solution was stirred for 2 h at 80° C. and then concentrated in vacuo. The resulting crude product was purified by FCC eluting with ethyl acetate/petroleum ether (2:3) to afford ethyl 3-amino-4-(difluoromethyl)-6-methylthieno[2,3-b]pyridine-2-carboxylate as a yellow solid (580 mg, 41%). LCMS (ESI, m/z): 287 [M+H]$^+$.

Step 3. 3-Amino-4-(difluoromethyl)-6-methylthieno[2,3-b]pyridine-2-carboxylic acid Into a 100-mL round-bottom flask was added ethyl 3-amino-4-(difluoromethyl)-6-methylthieno[2,3-b]pyridine-2-carboxylate (0.300 g, 1.05 mmol), sodium hydroxide (0.210 g, 5.25 mmol) and ethanol (20 mL). The resulting solution was stirred for 1 h at 60° C., concentrated in vacuo, and the pH was adjusted to 6 with hydrogen chloride (1 M). The solid product was collected by filtration and dried in vacuo to afford 3-amino-4-(difluoromethyl)-6-methylthieno[2,3-b]pyridine-2-carboxylic acid as a yellow solid (261 mg, 96%). LCMS (ESI, m/z): 259 [M+H]$^+$.

Example 3

Intermediate 3. 3-Amino-4-(difluoromethyl)-6-((2,4-dimethoxybenzyl)amino) thieno[2,3-b]pyridine-2-carboxylic acid

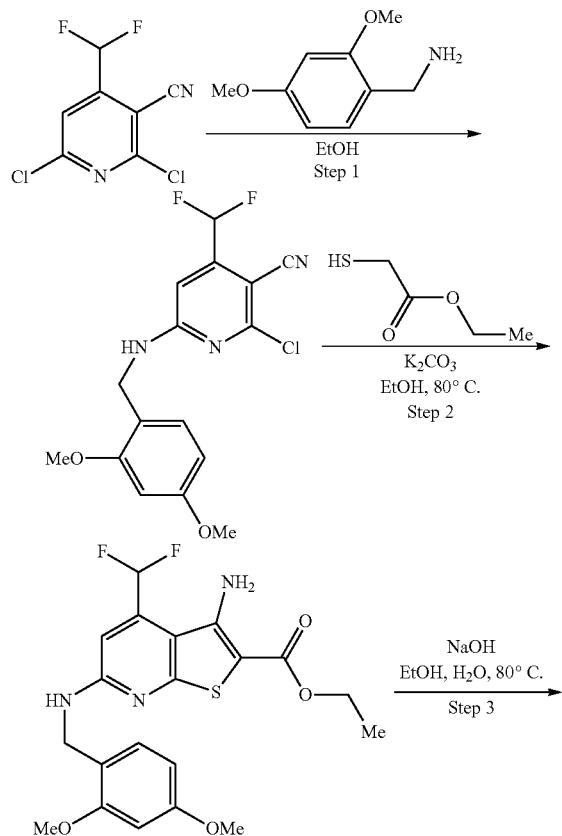

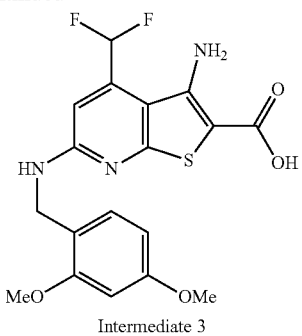

Intermediate 3

Step 1. 2-Chloro-4-(difluoromethyl)-6-((2,4-dimethoxybenzyl)amino)nicotinonitrile Into a 100-mL round-bottom flask was added 2,6-dichloro-4-(difluoromethyl) pyridine-3-carbonitrile (2.00 g, 8.97 mmol), (2,4-dimethoxyphenyl)methanamine (6.00 g, 35.9 mmol), and ethanol (30 mL). The resulting solution was stirred overnight at RT and then concentrated in vacuo. The resulting crude product was purified by FCC eluting with ethyl acetate/petroleum ether (1:1) to afford 2-chloro-4-(difluoromethyl)-6-((2,4-dimethoxybenzyl)pamino)nicotinonitrile as a white solid (560 mg, 18%). LCMS (ESI, m/z): 354 [M+H]$^+$.

Step 2. Ethyl 3-amino-4-(difluoromethyl)-6-((2,4-dimethoxybenzyl)amino)thieno[2,3-b]pyridine-2-carboxylate Into a 100-mL round-bottom flask was added 2-chloro-4-(difluoromethyl)-6-((2,4-dimethoxybenzyl)amino)nicotinonitrile (1.00 g, 2.83 mmol), potassium carbonate (1.17 g, 8.42 mmol), ethyl 2-mercaptoacetate (340 mg, 2.83 mmol), and ethanol (25 mL). The reaction mixture was stirred overnight at 80° C., concentrated in vacuo, and the resulting crude product purified by FCC eluting with ethyl acetate/petroleum ether (1:1) to afford ethyl 3-amino-4-(difluoromethyl) -6-((2,4-dimethoxybenzyl)amino)thieno[2,3-b]pyridine-2-carboxylate as a yellow solid (980 mg, 79%). LCMS (ESI, m/z): 438 [M+H]$^+$.

Step 3. 3-Amino-4-(difluoromethyl)-6-((2,4-dimethoxybenzyl)amino)thieno[2,3-b]pyridine -2-carboxylic acid Into a 100-mL round-bottom flask was added ethyl 3-amino-4-(difluoromethyl)-6-((2,4-dimethoxybenzyl) amino)thieno[2,3-b]pyridine-2-carboxylate (0.980 g, 2.24 mmol), sodium hydroxide (0.449 g, 11.2 mmol), ethanol (20 mL), and water (10 mL). The reaction mixture was stirred for 3 h at 80° C. and then cooled and concentrated in vacuo to remove the ethanol. The pH was adjusted to approximately 5 with 1 M aqueous HCl. The solid product was then collected by filtration to afford 3-amino-4-(difluoromethyl)-6-((2,4-dimethoxybenzyl) amino)thieno[2,3-b]pyridine-2-carboxylic acid as a yellow solid (500 mg, 55%). LCMS (ESI, m/z): 410 [M+H]$^+$.

Example 4

Intermediate 4. 3-Amino-6-((tert-butoxycarbonyl)amino)-4-methylthieno [2,3-b]pyridine-2-carboxylic acid

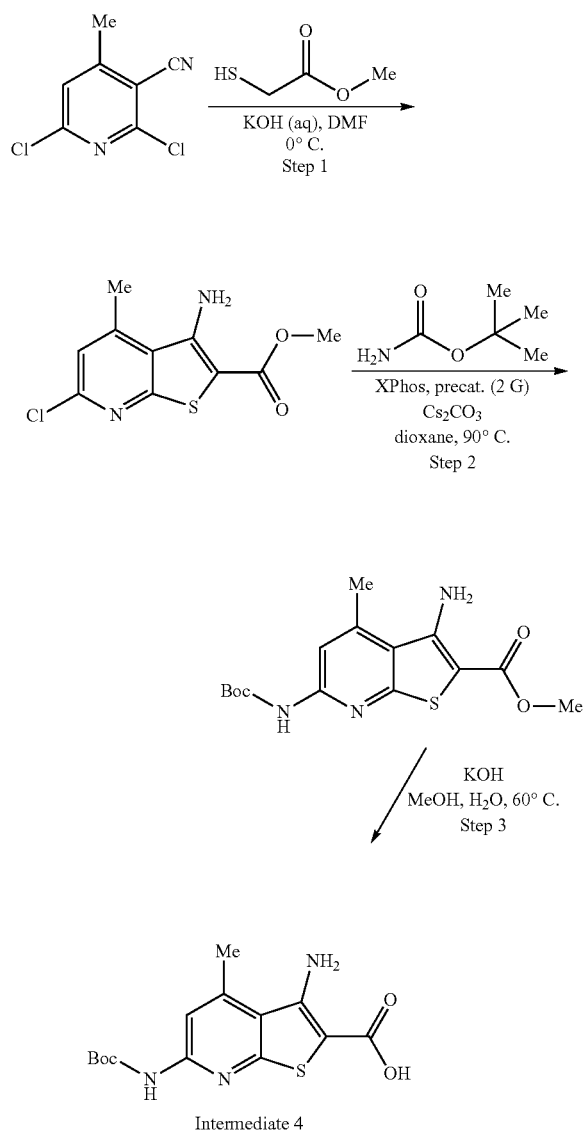

Intermediate 4

Step 1. Methyl 3-amino-6-chloro-4-methylthieno[2,3-b]pyridine-2-carboxylate

To a 250-mL round-bottom flask was added 2,6-dichloro-4-methylpyridine-3-carbonitrile (5.00 g, 26.7 mmol), methyl thioglycolate (2.93 mL, 32.1 mmol), and DMF (50 mL). A solution of potassium hydroxide (6.0 g, 106.9 mmol) in water (10 mL) was slowly added at 0 °C., and the resulting solution was stirred for 2 h at 0° C. The reaction was quenched with addition of water (50 mL). The solid product was isolated by filtration, washed with water (10 mL), and dried in vacuo to afford methyl 3-amino-6-chloro-4-methylthieno[2,3-b]pyridine-2-carboxylate as a yellow solid (2.6 g, 38%). LCMS (ESI, m/z): 257 [M+H]$^+$.

Step 2. Methyl 3-amino-6-((tert-butoxycarbonyl)amino)-4-methylthieno[2,3-b]pyridine-2-carboxylate Into a 100-mL round-bottom flask, purged and maintained under an inert atmosphere of nitrogen, was added methyl 3-amino-6-chloro-4-methylthieno[2,3-b]pyridine-2-carboxylate (1.00 g, 3.90 mmol), Cs$_2$CO$_3$ (6.34 g, 19.5 mmol), tert-butyl carbamate (2.29 g, 19.6 mmol), XPhos 2$^{nd}$ generation precatalyst (0.771 g, 0.98 mmol), and dioxane (15 mL). The reaction mixture was stirred overnight at 90° C. and then concentrated in vacuo to provide a crude product purified by FCC eluting with ethyl acetate/petroleum ether (1:10) to afford methyl 3-amino-6-((tert -butoxycarbonyl)amino)-4-methylthieno[2,3-b]pyridine-2-carboxylate as a yellow solid (1.2 g, 91%). LCMS (ESI, m/z): 338 [M+H]$^+$.

Step 3. 3-Amino-6-((tert-butoxycarbonyl)amino)-4-methylthieno[2,3-b]pyridine-2-carboxylic acid Into a 50-mL round-bottom flask was added methyl 3-amino-6-[[(tert -butoxy)carbonyl]amino]-4-methylthieno [2,3-b]pyridine-2-carboxylate (0.600 g, 1.78 mmol), potassium hydroxide (0.498 g, 8.88 mmol), methanol (10 mL), and water (2 mL). The resulting suspension was stirred for 3 h at 60° C. upon which dissolution occurred. The reaction was cooled to RT which resulted in the formation of a precipitate. The pH was adjusted to approximately 6 with aqueous hydrogen chloride (3 M) which resulted in a thick precipitate. The solid product was collected by filtration, washed with water (10 mL), and dried in vacuo to afford 3-amino-6-((tert -butoxycarbonyl)amino)-4-methylthieno[2,3-b]pyridine-2-carboxylic acid as a yellow solid (200 mg, 35%). LCMS (ESI, m/z): 324 [M+H]$^+$.

Example 5

Intermediate 5. 3-Amino-4-methoxy-6-methylthieno[2,3-b]pyridine-2-carboxylic acid

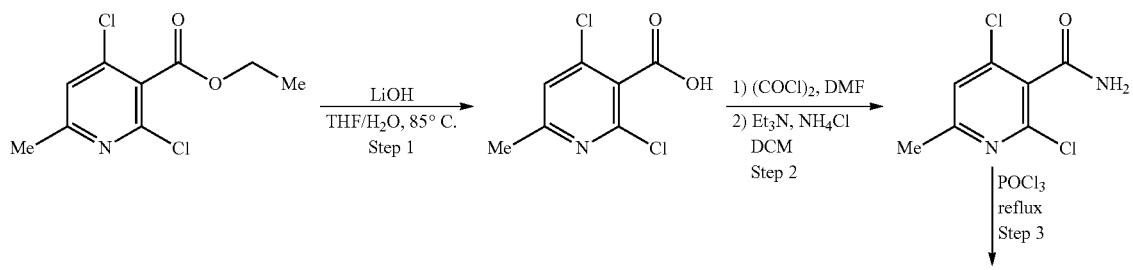

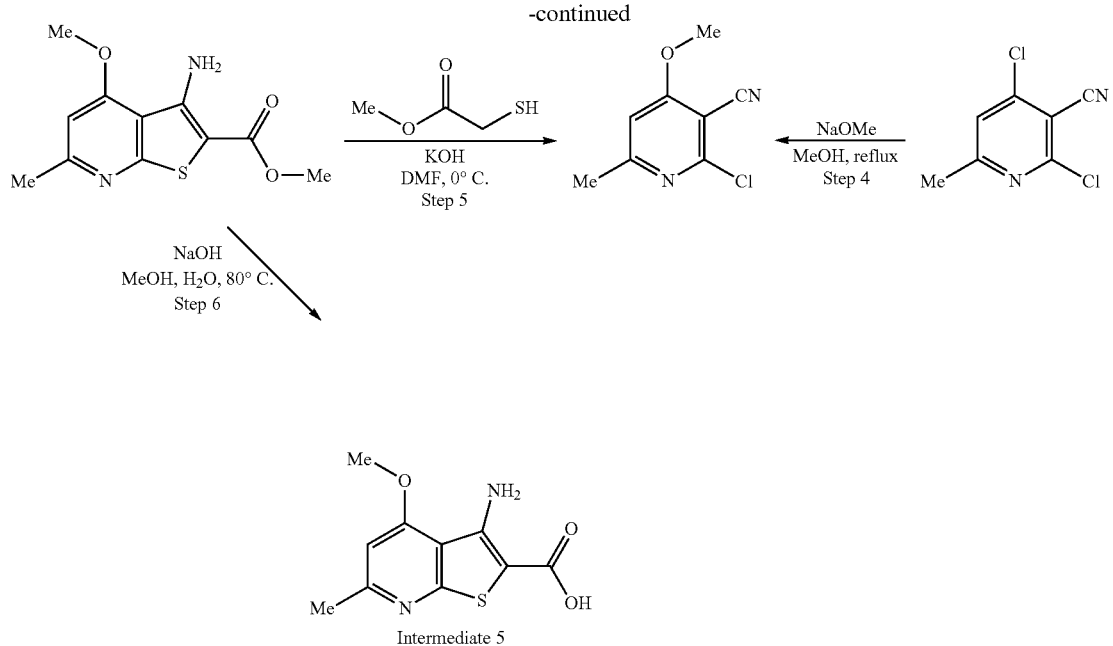

Step 1. 2,4-Dichloro-6-methylnicotinic acid

Into a 250-mL round-bottom flask was added ethyl 2,4-dichloro-6-methylpyridine-3-carboxylate (3.00 g, 12.8 mmol), THF (30 mL), and water (30 mL) followed by the portion-wise addition of LiOH (1.23 g, 51.3 mmol). The resulting solution was stirred for 3 days at 85° C. and then concentrated in vacuo. The pH was adjusted to 3 with 4 N HCl (aq) and the resulting precipitate was collected by filtration and dried in vacuo to afford 2,4-dichloro-6-methylnicotinic acid as a white solid (3.0 g). The material was used without further purification. LCMS (ESI, m/z): 206 [M+H]$^+$.

Step 2. 2,4-Dichloro-6-methylnicotinamide

Into a 250-mL round-bottom flask was added 2,4-dichloro-6-methylnicotinic acid (2.00 g, 9.71 mmol) and dichloromethane (50-mL) followed by the portion-wise addition of oxalyl chloride (6.35 g, 4.29 mL, 50.0 mmol). To this mixture was added DMF (50 mg, 0.053 mL) dropwise and with stirring. The resulting solution was stirred for 2 h at RT and then concentrated in vacuo to afford a crude product that was dissolved in dichloromethane (50-mL). To this solution was added NH$_4$Cl (2.12 g, 11.5 mmol) and triethylamine (10 g, 13.8 mL, 99.0 mmol) dropwise and with stirring. After stirring for 2 h at RT the reaction was quenched with 10 mL of water/ice and the resulting mixture was extracted with dichloromethane (3×30 mL). The organic layers were combined, washed with brine (30 mL), dried over anhydrous sodium sulfate, filtered, and concentrated in vacuo to afford 2,4-dichloro-6-methylnicotinamide as a white solid (2.1 g). The material was used without further purification. LCMS (ESI, m/z): 205 [M+H]$^+$.

Step 3. 2,4-Dichloro-6-methylnicotinonitrile

Into a 3-mL round-bottom flask was added 2,4-dichloro-6-methylnicotinamide (200 mg, 0.98 mmol) and POCl$_3$ (3 mL). The reaction mixture was stirred for 2 h at reflux and then cooled and quenched with 10 mL of water/ice. The resulting solution was extracted with dichloromethane (3×30 mL) and the combined organic layers were washed with brine (30 mL). The combined organic layers were dried over anhydrous sodium sulfate, filtered, and concentrated in vacuo to afford 2,4-dichloro-6-methylnicotinonitrile as a white solid (150 mg, 82%). LCMS (ESI, m/z): 187 [M+H]$^+$.

Step 4. 2-Chloro-4-methoxy-6-methylnicotinonitrile

Into a 250-mL round-bottom flask was added 2,4-dichloro-6-methylnicotinonitrile (1.00 g, 5.35 mmol) and methanol (100-mL) followed by the portion-wise addition of NaOMe (1.10 g, 20.4 mmol). The resulting solution was stirred for 4 h at reflux and then cooled and concentrated in vacuo. The resulting crude product was purified by FCC eluting with 0-30% ethyl acetate in petroleum ether to afford 2-chloro-4-methoxy-6-methylnicotinonitrile as a white solid (200 mg, 20%). LCMS (ESI, m/z): 183 [M+H]$^+$.

Step 5. Methyl 3-amino-4-methoxy-6-methylthieno[2,3-b]pyridine-2-carboxylate

Into a 25-mL round-bottom flask was added 2-chloro-4-methoxy-6-methylnicotinonitrile (0.260 g, 1.42 mmol), methyl thioglycolate (0.151 g, 1.42 mmol), and potassium hydroxide (0.320 g, 5.71 mmol), and DMF (5 mL) at 0° C. The resulting solution was stirred for 1 h at 0° C. and then quenched with water (30 mL). The resulting solids were collected by filtration to afford methyl 3-amino-4-methoxy-6-methylthieno[2,3-b]pyridine-2-carboxylate as a red solid (340 mg). The material was used without further purification. LCMS (ESI, m/z): 253 [M+H]$^+$.

Step 6. 3-Amino-4-methoxy-6-methylthieno [2,3-b]pyridine-2-carboxylic acid

Into a 50-mL round-bottom flask was added methyl 3-amino-4-methoxy-6-methylthieno[2,3-b]pyridine-2-carboxylate (0.110 g, 0.44 mmol), NaOH (0.035 g, 0.87 mmol), methanol (5 mL), and water (5 mL). The reaction mixture was stirred for 4 h at 80° C. and then concentrated in vacuo. The pH of the concentrated solution was adjusted to approximately 3 with aqueous HCl (3 M). The resulting precipitate was collected by filtration and dried in vacuo to afford 3-amino-4-methoxy-6-methylthieno[2,3-b]pyridine-2-carboxylic acid as a brown solid (130 mg). The material was used without further purification. LCMS (ESI, m/z): 239 [M+H]$^+$.

Example 6

Intermediate 6. 3-Amino-5-(difluoromethyl)thieno[2,3-b]pyridine-2-carboxylic acid

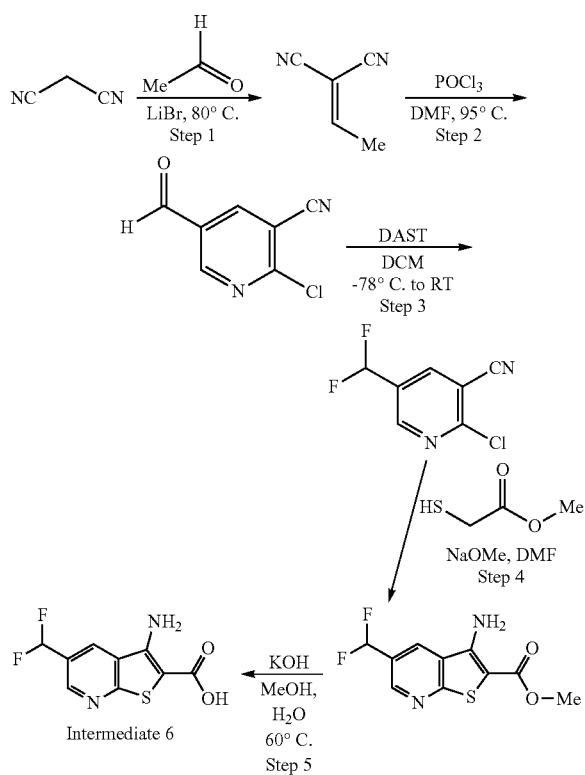

Step 1: 2-Ethylidenemalononitrile

Into a 250-mL round-bottom flask that was purged and maintained under an inert atmosphere of nitrogen was added lithium bromide (2.60 g, 29.9 mmol) and malononitrile (10.0 g, 151.37 mmol). The reaction mixture was stirred for 4 h at 80° C. and then acetaldehyde (13.0 g, 295 mmol) was added. The resulting solution was stirred for an additional 4 h at 80° C. and then cooled and diluted with aqueous saturated sodium bicarbonate (60 mL). The mixture was extracted with ethyl acetate (3×20 mL). The combined organic layers were dried over anhydrous sodium sulfate, filtered, and concentrated in vacuo to afford 2-ethylidenemalononitrile as a yellow oil (9 g, 65%). $^1$H-NMR (300 MHz, CDCl$_3$) δ ppm 7.46-7.39 (q, J=6 Hz, 1H), 2.30 (d, J=6 Hz, 3H).

Step 2: 2-Chloro-5-formylnicotinonitrile

Into a 500-mL round-bottom flask was added phosphoryl trichloride (67.0 g, 437 mmol), followed by the dropwise addition of DMF (32.0 g, 33.8 mL, 1.52 mol) with stirring at RT. To this mixture was added 2-ethylidenemalononitrile (10.0 g, 109 mmol) dropwise. The resulting solution was stirred for 40 min at RT and then for 3 h at 95° C. The reaction was cooled and then quenched with water/ice (500 mL). The pH of the solution was adjusted to approximately 7-8 with 60% aqueous sodium hydroxide. The resulting solution was extracted with ethyl acetate (3×100 mL). The combined organic layers were then washed with brine (2×500 mL), dried over anhydrous sodium sulfate, filtered, and concentrated in vacuo. The resulting crude product was purified by FCC eluting with ethyl acetate/petroleum ether (1:5) to afford 2-chloro-5-formylnicotinonitrile as a yellow oil (1.00 g, 6%). LCMS (ESI, m/z): 167 [M+H]$^+$.

Step 3: 2-Chloro-5-(difluoromethyl)nicotinonitrile

Into a 100-mL round-bottom flask, purged and maintained under an inert atmosphere of nitrogen, was added 2-chloro-5-formylnicotinonitrile (1.00 g, 6.00 mmol) and dichloromethane (20 mL). The resulting solution was cooled to −78° C. and DAST (1.90 g, 1.56 mL, 51.2 mmol) was then added dropwise and with stirring. The reaction mixture was warmed and stirred for 60 min at 0° C. The reaction was then warmed and stirred at RT overnight. The reaction mixture was quenched with water (100 mL) and was then extracted with dichloromethane (3×50 mL). The combined organic layers were dried over anhydrous sodium sulfate, filtered, and concentrated in vacuo. The resulting crude product was purified by FCC eluting with ethyl acetate/petroleum ether (1:5) to afford 2-chloro-5-(difluoromethyl) nicotinonitrile as a yellow solid (800 mg, 71%). LCMS (ESI, m/z): 189 [M+H]$^+$.

Step 4: Methyl 3-amino-5-(difluoromethyl)thieno[2,3-b]pyridine-2-carboxylate

Into a 50-mL round-bottom flask was added 2-chloro-5-(difluoromethyl) nicotinonitrile (0.500 g, 2.65 mmol) and DMF (5 mL). Methyl thioglycolate (0.562 g, 5.29 mmol) was then added followed by NaOMe (0.429 g, 7.94 mmol). The resulting solution was stirred overnight at 60° C. and then cooled and diluted with water (50 mL). The mixture was extracted with ethyl acetate (3×20 mL). The combined organic layers were washed with brine (2×50 mL), dried over anhydrous sodium sulfate, filtered, and concentrated in vacuo. The resulting crude product was purified by FCC eluting with ethyl acetate/petroleum ether (1:2) to afford methyl 3-amino-5-(difluoromethyl)thieno[2,3-b]pyridine-2-carboxylate as a yellow solid (300 mg, 44%). LCMS (ESI, m/z): 259 [M+H]$^+$.

Step 5: 3-Amino-5-(difluoromethyl)thieno [2,3-b]pyridine-2-carboxylic acid

Into a 100-mL round-bottom flask was added methyl 3-amino-5-(difluoromethyl) thieno[2,3-b]pyridine-2-carboxylate (0.500 g, 1.94 mmol) and methanol (20 mL). Water (2 mL) was then added, followed by potassium hydroxide (0.326 g, 5.81 mmol). The reaction mixture was stirred overnight at 60° C. and then cooled to RT. The pH of the solution was adjusted to approximately 6-7 with 1 M aqueous HCl. The resulting solid precipitate was collected by filtration and dried in vacuo to afford 3-amino-5-(difluoromethyl)thieno[2,3-b]pyridine-2-carboxylic acid as a yellow solid (300 mg, 63%). LCMS (ESI, m/z): 245 [M+H]$^+$.

Example 7

Intermediate 7. 1-Amino-7,8-dihydro-6H-cyclopenta[d]thieno[2,3-b]pyridine-2-carboxylic acid

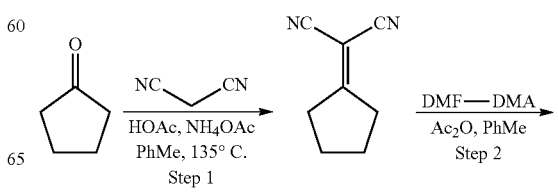

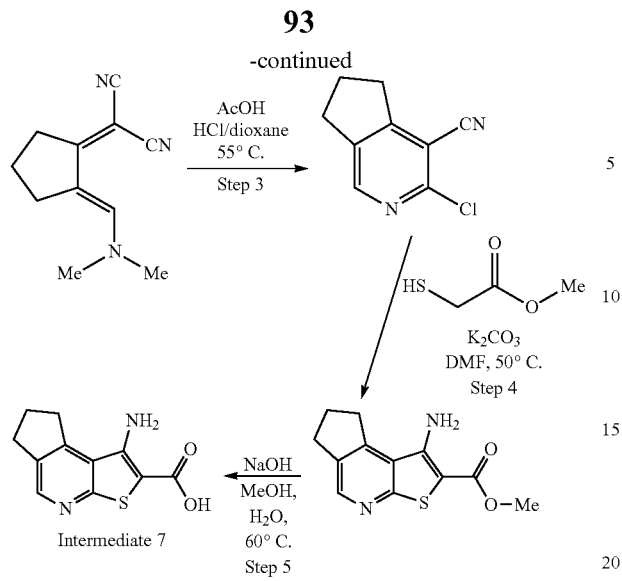

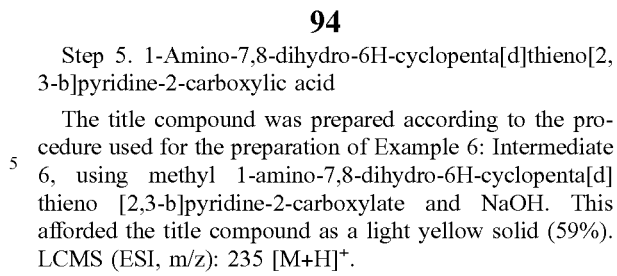

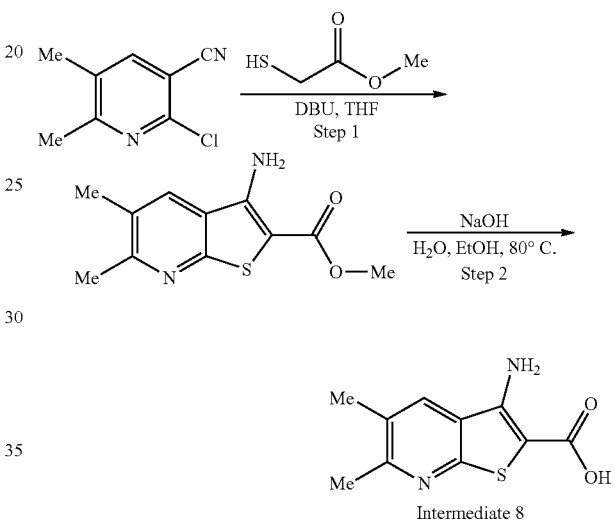

Step 5. 1-Amino-7,8-dihydro-6H-cyclopenta[d]thieno[2,3-b]pyridine-2-carboxylic acid The title compound was prepared according to the procedure used for the preparation of Example 6: Intermediate 6, using methyl 1-amino-7,8-dihydro-6H-cyclopenta[d]thieno [2,3-b]pyridine-2-carboxylate and NaOH. This afforded the title compound as a light yellow solid (59%). LCMS (ESI, m/z): 235 [M+H]⁺.

Example 8

Intermediate 8. 3-Amino-5,6-dimethylthieno[2,3-b]pyridine-2-carboxylic acid

Step 1. 2-Cyclopentylidenemalononitrile

Into a 250-mL round-bottom flask was added cyclopentanone (5.00 g, 59.4 mmol), malononitrile (5.90 g, 89.3 mmol), NH₄OAc (3.00 g, 39.0 mmol), HOAc (5 mL), and toluene (75 mL). The resulting solution was stirred overnight at 135° C. and then cooled and washed with H₂O (3×50 mL). The organic layer was separated and concentrated in vacuo to afford 2-cyclopentylidenemalononitrile as a light brown oil (7 g, 89%). LCMS (ESI, m/z): 133 [M+H]⁺.

Step 2. (E)-2-(2-((dimethylamino)methylene)cyclopentylidene)malononitrile

Into a 100-mL round-bottom flask was added 2-cyclopentylidenemalononitrile (3.00 g, 22.7 mmol) and toluene (23 mL). Acetic anhydride (0.45 mL) was then added, followed by DMF-DMA (3.6 mL). The resulting solution was stirred for 30 min at RT and then diluted with hexane (30 mL). The resulting solids were collected by filtration and dried in vacuo to afford (E)-2-(2-((dimethylamino)methylene)cyclopentylidene)malononitrile as a yellow solid (3.2 g, 75%). LCMS: (ESI, m/z): 188 [M+H]⁺.

Step 3. 3-Chloro-6,7-dihydro-5H-cyclopenta[c]pyridine-4-carbonitrile

Into a 50-mL sealed tube was added (E)-2-(2-((dimethylamino)methylene) cyclopentylidene)malononitrile (3.00 g, 16.0 mmol), HOAc (10 mL), and 4 N hydrogen chloride/dioxane (20 mL). The solution was stirred overnight at 55° C. and was then concentrated in vacuo. The resulting crude product was purified by FCC eluting with ethyl acetate/petroleum ether (1:3) to afford 3-chloro-6,7-dihydro-5H-cyclopenta[c]pyridine-4-carbonitrile as a white solid. (2.8 g, 98%). LCMS (ESI, m/z): 179 [M+H]⁺.

Step 4. Methyl 1-amino-7,8-dihydro-6H-cyclopenta[d]thieno[2,3-b]pyridine-2-carboxylate Into a 100-mL round-bottom flask was added 3-chloro-6,7-dihydro-5H-cyclopenta[c]pyridine-4-carbonitrile (1.00 g, 5.60 mmol), methyl thioglycolate (0.590 g, 0.500-mL, 5.60 mmol), potassium carbonate (2.31 g, 16.7 mmol), and DMF (20 mL). The reaction mixture was stirred overnight at 50° C. and then cooled and diluted with H₂O (30 mL). The resulting solids were collected by filtration and dried in vacuo to afford methyl 1-amino-7,8-dihydro-6H-cyclopenta[d]thieno[2,3-b]pyridine-2-carboxylate as an off-white solid (900 mg, 65%). LCMS (ESI, m/z): 249 [M+H]⁺.

Step 1. Methyl 3-amino-5,6-dimethylthieno[2,3-b]pyridine-2-carboxylate

Into a 50-mL round-bottom flask was added 2-chloro-5,6-dimethylpyridine-3-carbonitrile (0.332 g, 1.99 mmol) and tetrahydrofuran (10 mL). Methyl thioglycolate (0.254 g, 0.214 mL, 2.40 mmol) was then added, followed by DBU (0.456 g, 0.447 mL, 3.00 mmol). The resulting solution was stirred for 2 h at RT and then concentrated in vacuo. The resulting crude product was purified by FCC eluting with ethyl acetate/petroleum ether (1:1) to afford methyl 3-amino-5,6-dimethylthieno[2,3-b]pyridine-2-carboxylate as a light yellow solid (400 mg, 85%). LCMS: (ESI, m/z): 237 [M+H]⁺.

Step 2. 3-Amino-5,6-dimethylthieno[2,3-b]pyridine-2-carboxylic acid

Into a 50-mL round-bottom flask was added methyl 3-amino-5,6-dimethylthieno[2,3-b]pyridine-2-carboxylate (0.474 g, 2.01 mmol), a solution of sodium hydroxide (0.400 g, 10.00 mmol) in water (5 mL), and ethanol (5 mL). The solution was stirred for 2 h at 80° C., concentrated in vacuo, and the pH of the solution was then adjusted to approximately 7 with aqueous HCl (3 M). The resulting solid precipitate was collected by filtration and dried in vacuo to afford 3-amino-5,6-dimethylthieno[2,3-b]pyridine-2-carboxylic acid as a light yellow solid (400 mg, 90%). LCMS (ESI, m/z): 223 [M+H]⁺.

Example 9

Intermediate 9. 3-Amino-5-methylthieno[2,3-b]pyridine-2-carboxylic acid

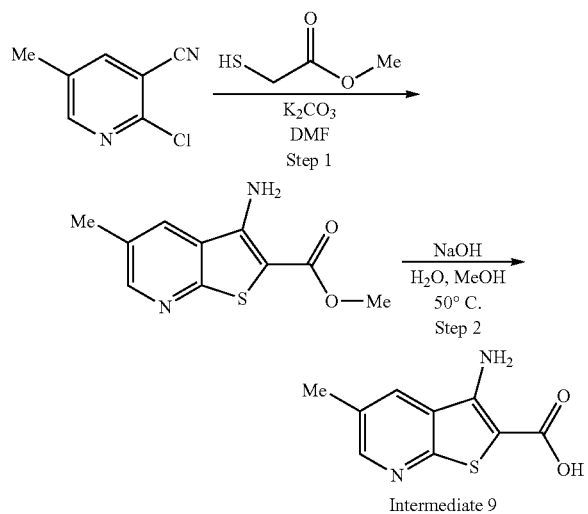

Intermediate 9

Step 1. Methyl 3-amino-5-methylthieno[2,3-b]pyridine-2-carboxylate

Into a 100-mL round-bottom flask was added 2-chloro-5-methylpyridine-3-carbonitrile (0.500 g, 3.28 mmol) and DMF (5 mL). Potassium carbonate (0.908 g, 6.57 mmol) was then added followed by methyl thioglycolate (0.349 g, 0.294 mL, 3.29 mmol) and the resulting solution was stirred for 2 h at RT. The reaction mixture was concentrated in vacuo. The resulting crude product was purified by FCC eluting with ethyl acetate/petroleum ether (1:1) to afford methyl 3-amino-5-methylthieno[2,3-b]pyridine-2-carboxylate as a yellow solid (700 mg, 96%). LCMS (ESI, m/z) 223 [M+H]$^+$.

Step 2. 3-Amino-5-methylthieno[2,3-b]pyridine-2-carboxylic acid

Into a 100-mL round-bottom flask was added methyl 3-amino-5-methylthieno[2,3-b]pyridine-2-carboxylate (0.650 g, 2.92 mmol), sodium hydroxide (1.17 g, 29.25 mmol), methanol (15 mL) and water (5 mL). The reaction mixture was stirred for 4 h at 50° C. and then concentrated in vacuo. The pH was adjusted to approximately 4 with aqueous HCl (2 M) and the resulting solid precipitate was collected by filtration and dried in vacuo to afford 3-amino-5-methylthieno[2,3-b]pyridine-2-carboxylic acid as a yellow solid (500 mg, 82%). LCMS (ESI, m/z) 209 [M+H]$^+$.

Example 10

Intermediate 10. 3-Amino-6-(trifluoromethyl)thieno[2,3-b]pyridine-2-carboxylic acid

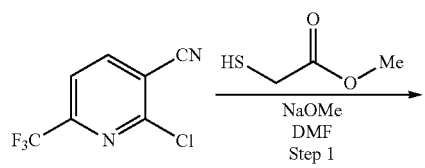

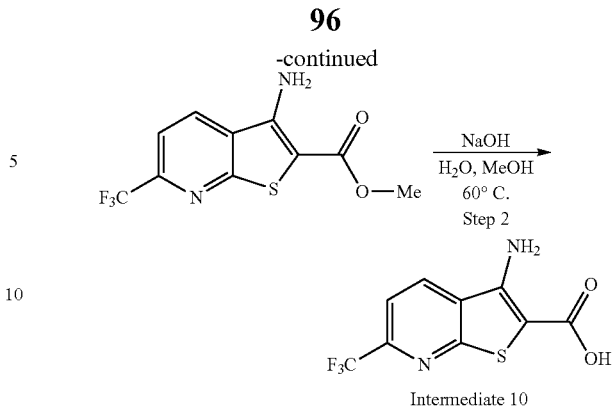

Intermediate 10

Step 1. Methyl 3-amino-6-(trifluoromethyl)thieno[2,3-b]pyridine-2-carboxylate

The title compound was prepared according to the procedure used for the preparation of Example 6: Intermediate 6, using 2-chloro-6-(trifluoromethyl)nicotinonitrile. This afforded the title compound as a yellow solid (67%). LCMS (ESI, m/z): 277 [M+H]$^+$.

Step 2. 3-Amino-6-(trifluoromethyl)thieno[2,3-b]pyridine-2-carboxylic acid

The title compound was prepared according to the procedure used for the preparation of Example 6: Intermediate 6, using methyl 3-amino-6-(trifluoromethyl)thieno[2,3-b]pyridine -2-carboxylate. This afforded the title compound as a yellow solid (93%). LCMS (ESI, m/z): 263 [M+H]$^+$.

Example 11

Intermediate 11. 3-Amino-6-methyl-4-(trifluoromethyl)thieno[2,3-b]pyridine -2-carboxylic acid

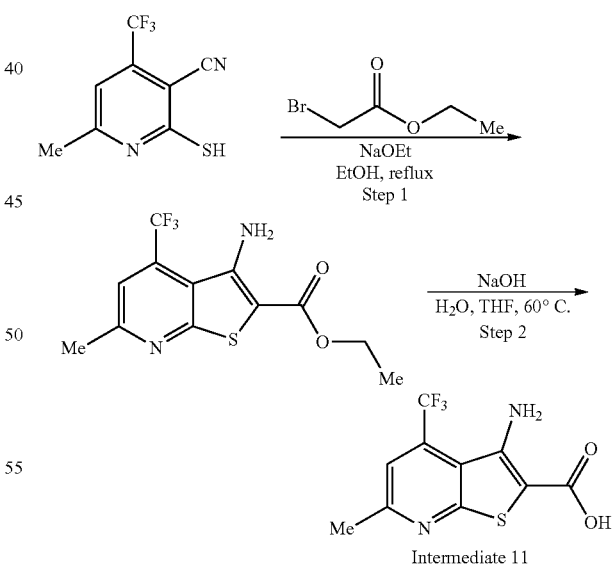

Intermediate 11

Step 1. Ethyl 3-amino-6-methyl-4-(trifluoromethyl)thieno[2,3-b]pyridine-2-carboxylate Into a 500-mL round-bottom flask was added 2-mercapto-6-methyl-4-(trifluoromethyl)nicotinonitrile (10.0 g, 45.8 mmol), ethyl 2-bromoacetate (7.66 g, 45.9 mmol) in EtOH (235 mL), and sodium ethoxide (4.67 g, 68.6 mmol) and the resulting solution was heated and stirred for 2 h at reflux.

The reaction was then cooled, quenched with water (100 mL), and the resulting mixture was extracted with DCM (3×100 mL). The combined organic layers were washed with brine (2×100 mL), dried over sodium sulfate, filtered, and concentrated in vacuo. The resulting crude product was purified by FCC eluting with DCM/MeOH (10:1) to afford ethyl 3-amino-6-methyl-4-(trifluoromethyl)thieno[2,3-b]pyridine-2-carboxylate as a yellow solid (12 g, 86%). LCMS (ES, m/z): 305 [M+H]$^+$.

Step 2. 3-Amino-6-methyl-4-(trifluoromethyl)thieno[2,3-b]pyridine-2-carboxylic acid Into a 500-mL round-bottom flask was added ethyl 3-amino-6-methyl-4-(trifluoromethyl)thieno[2,3-b]pyridine-2-carboxylate (12.0 g, 39.4 mmol) and THF (200 mL). Water (15 mL) was added, followed by sodium hydroxide (6.58 g, 165 mmol). The resulting solution was heated and stirred for 5 h at 60° C. and then cooled. The pH was adjusted to approximately 2-3 with concentrated aqueous HCl and the resulting solid precipitate was filtered, and dried in vacuo to afford 3-amino-6-methyl-4-(trifluoromethyl)thieno[2,3-b]pyridine-2-carboxylic acid as a yellow solid (9.4 g, 86%). LCMS (ESI, m/z): 277 [M+H]$^+$.

Example 12

Intermediate 12. 3-Amino-5-fluorothieno[2,3-b]pyridine-2-carboxylic acid

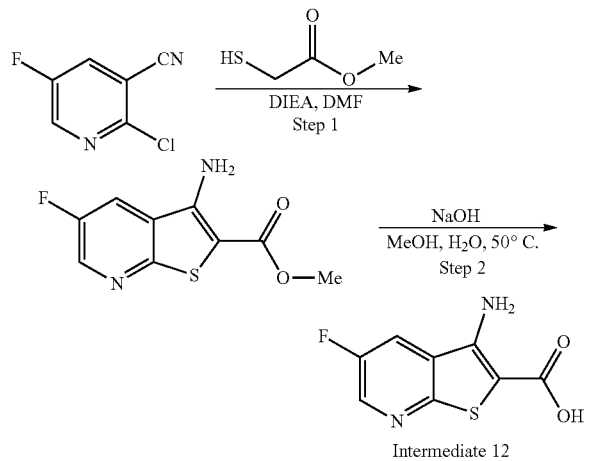

Intermediate 12

Step 1. Methyl 3-amino-5-fluorothieno[2,3-b]pyridine-2-carboxylate

Into a 50-mL round-bottom flask was added 2-chloro-5-fluoropyridine-3-carbonitrile (0.400 g, 2.56 mmol) and DMF (4 mL). DIEA (0.495 g, 0.667 mL, 3.83 mmol) was then added followed by methyl thioglycolate (0.136 g, 0.115 mL, 1.28 mmol). The resulting solution was stirred overnight at RT and then quenched with water (40 mL) and extracted with ethyl acetate (3 ×10 mL). The combined organic layers were then dried over anhydrous sodium sulfate, filtered, and concentrated in vacuo. The resulting crude product was purified by FCC eluting with ethyl acetate/petroleum ether (1:1) to afford methyl 3-amino-5-fluorothieno[2,3-b]pyridine-2-carboxylate as a yellow solid (110 mg, 19%). LCMS (ESI, m/z): 227 [M+H]$^+$.

Step 2. 3-Amino-5-fluorothieno[2,3-b]pyridine-2-carboxylic acid

The title compound was prepared according to the procedure used for the preparation of Example 6: Intermediate 6, using methyl 3-amino-5-fluorothieno[2,3-b]pyridine-2-carboxylate and NaOH at 50° C. This afforded the title compound as a yellow solid (66%). LCMS (ESI, m/z): 213 [M+H]$^+$.

Example 13

Intermediate 13. 3-Amino-5-chlorothieno[2,3-b]pyridine-2-carboxylic acid

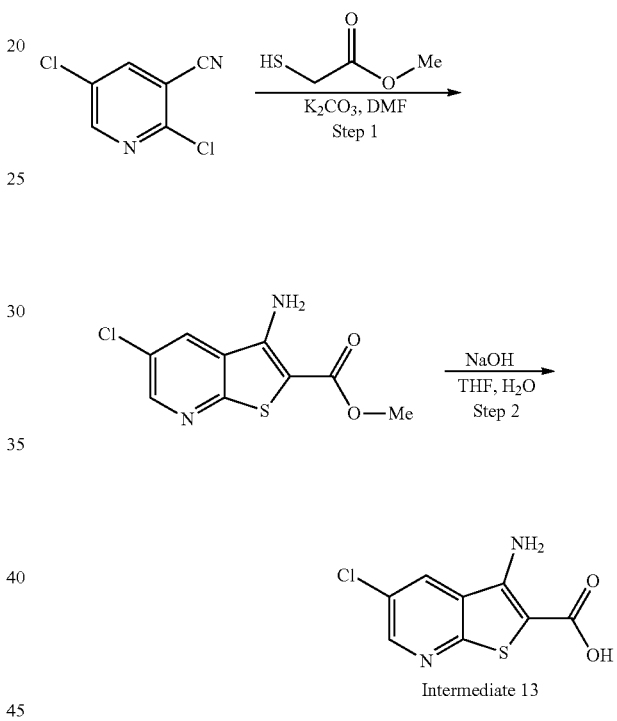

Intermediate 13

Step 1. Methyl 3-amino-5-chlorothieno[2,3-b]pyridine-2-carboxylate

The title compound was prepared according to the procedure used for the preparation of Example 12: Intermediate 12, using 2,5-dichloronicotinonitrile and potassium carbonate. This afforded the title compound as a yellow solid (84%). LCMS (ESI, m/z): 243 [M+H]$^+$.

Step 2. 3-Amino-5-chlorothieno[2,3-b]pyridine-2-carboxylic acid

Into a 100-mL round-bottom flask was added methyl 3-amino-5-chlorothieno[2,3-b]pyridine-2-carboxylate (1.40 g, 5.77 mmol) and tetrahydrofuran/H$_2$O (3/1; 15 mL). NaOH (1.20 g, 30.0 mmol) was then added and the resulting solution was stirred overnight at RT. The pH of the solution was adjusted to approximately 6 with aqueous HCl (2 M) and the resulting solid precipitate was collected by filtration and dried in vacuo to afford 3-amino-5-chlorothieno[2,3-b]pyridine-2-carboxylic acid as a yellow solid (1.1 g, 83%). LCMS (ESI, m/z) 229 [M+H]$^+$.

Example 14

Intermediate 14. 3-Amino-6-(hydroxymethyl)thieno[2,3-b]pyridine-2-carboxylic acid

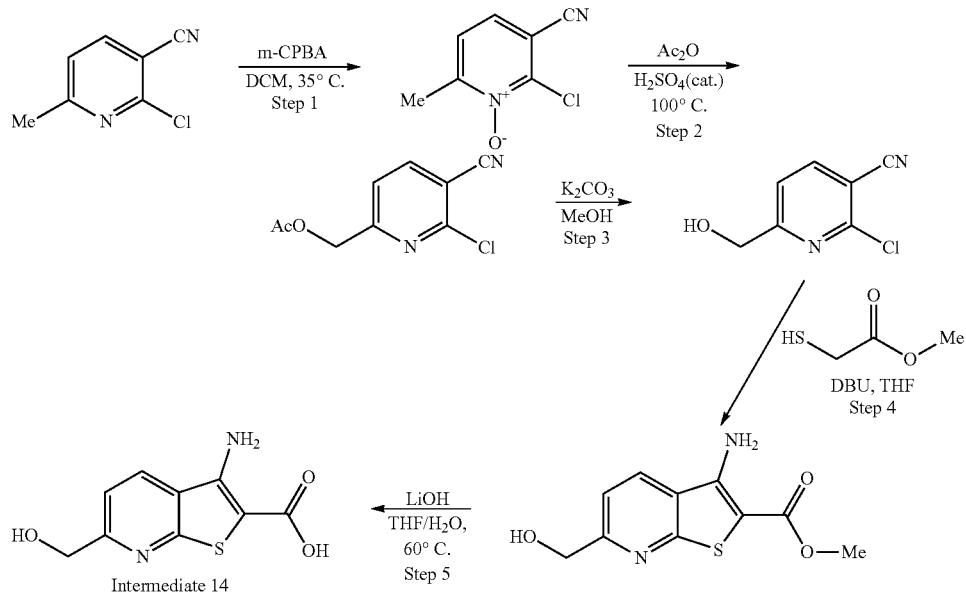

Step 1. 2-Chloro-3-cyano-6-methylpyridine 1-oxide

Into a 50-mL round-bottom flask that was purged and maintained under an inert atmosphere of nitrogen was added 2-chloro-6-methylpyridine-3-carbonitrile (0.200 g, 1.31 mmol), m-CPBA (0.339 g), and dichloromethane (6 mL). The solution was stirred overnight at 35° C. then concentrated in vacuo. The resulting crude product was purified by FCC eluting with petroleum ether : ethyl acetate (3:1) to afford 2-chloro-3-cyano-6-methylpyridine 1-oxide as a white solid (65 mg, 29%). LCMS (ESI, m/z): 169 [M+H]$^+$.

Step 2. (6-Chloro-5-cyanopyridin-2-yl)methyl acetate

Into a 100-mL round-bottom flask that was purged and maintained under an inert atmosphere of nitrogen was added a solution of 2-chloro-3-cyano-6-methylpyridine 1-oxide (0.250 g, 1.48 mmol), sulfuric acid (catalytic amount, approximately 1 drop), and acetic anhydride (6 mL). The solution was stirred for 3 h at 110° C., and then cooled and stirred overnight at RT. The reaction mixture was quenched with water (40 mL) and extracted with ethyl acetate (30 mL). The organic layer was washed with brine (10 mL), dried over anhydrous sodium sulfate, filtered, and concentrated in vacuo. The resulting crude product was purified by FCC eluting with ethyl acetate/petroleum ether (9:1) to afford (6-chloro-5-cyanopyridin-2-yl)methyl acetate as a yellow oil (190 mg, 61%). LCMS (ESI, m/z) 211 [M+H]$^+$.

Step 3. 2-Chloro-6-(hydroxymethyl)nicotinonitrile

Into a 50-mL round-bottom flask was added (6-chloro-5-cyanopyridin-2-yl)methyl acetate (0.190 g, 0.90 mmol), potassium carbonate (0.187 g, 1.35 mmol), and methanol (2 mL). The reaction mixture was stirred for 3 h at RT and then concentrated in vacuo. Water (10 ml) was added and the resulting solution was extracted with ethyl acetate (3×10 mL). The combined organic layers were washed with brine (10 mL), dried over anhydrous sodium sulfate, filtered, and concentrated in vacuo to afford 2-chloro-6-(hydroxymethyl) nicotinonitrile as a yellow oil (120 mg). The material was used without further purification. LCMS (ESI, m/z): 169 [M+H]$^+$.

Step 4. Methyl 3-amino-6-(hydroxymethyl)thieno[2,3-b]pyridine-2-carboxylate

The title compound was prepared according to the procedure used for the preparation of Example 8: Intermediate 8, using 2-chloro-6-(hydroxymethyl)nicotinonitrile. This afforded the title compound as a yellow solid (71%). LCMS (ESI, m/z): 239 [M+H]$^+$.

Step 5. 3-Amino-6-(hydroxymethyl)thieno[2,3-b]pyridine-2-carboxylic acid

The title compound was prepared according to the procedure used for the preparation of Example 6: Intermediate 6, using methyl 3-amino-6-(hydroxymethyl)thieno[2,3-b]pyridine -2-carboxylate and LiOH. This afforded the title compound as a yellow solid (49%). LCMS (ESI, m/z): 225 [M+H]$^+$.

Example 15

Intermediate 15. 3-Amino-5-fluoro-6-methylthieno[2,3-b]pyridine-2-carboxylic acid

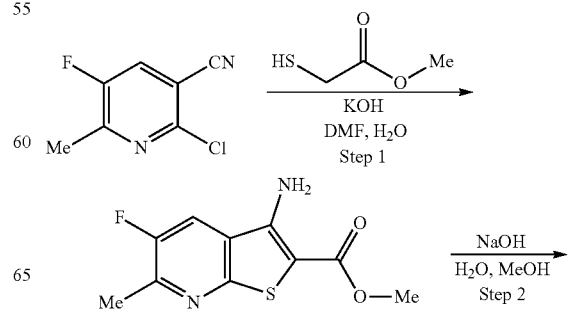

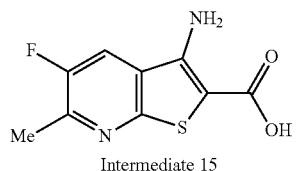

Intermediate 15

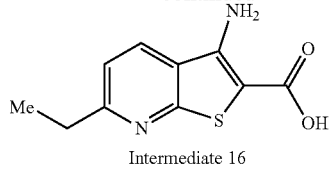

Intermediate 16

Step 1. Methyl 3-amino-5-fluoro-6-methylthieno[2,3-b]pyridine-2-carboxylate

Into a 50-mL round-bottom flask was added 2-chloro-5-fluoro-6-methylpyridine-3-carbonitrile (1.00 g, 5.86 mmol), DMF/H$_2$O (15 mL/15 mL), methyl 2-mercaptoacetate (1.25 g, 1.05 mL, 11.8 mmol), and KOH (0.990 g, 17.64 mmol). The resulting solution was stirred for 3 h at RT then extracted with ethyl acetate (3×200 mL). The combined organic layers were concentrated in vacuo. The crude product was purified via silica gel column chromatography and eluted with ethyl acetate/petroleum ether (1:4) to afford methyl 3-amino-5-fluoro-6-methylthieno[2,3-b]pyridine-2-carboxylate as a yellow solid (0.8 g, 57%). LCMS (ESI, m/z): 241 [M+H]$^+$.

Step 2. 3-Amino-5-fluoro-6-methylthieno[2,3-b]pyridine-2-carboxylic acid

The title compound was prepared according to the procedure used for the preparation of Example 12, Intermediate 12, using methyl 3-amino-5-fluoro-6-methylthieno[2,3-b]pyridine-2-carboxylate at RT. This afforded the title compound as a yellow oil (89%). LCMS (ESI, m/z): 227 [M+H]$^+$.

Example 16

Intermediate 16. 3-Amino-6-ethylthieno[2,3-b]pyridine-2-carboxylic acid

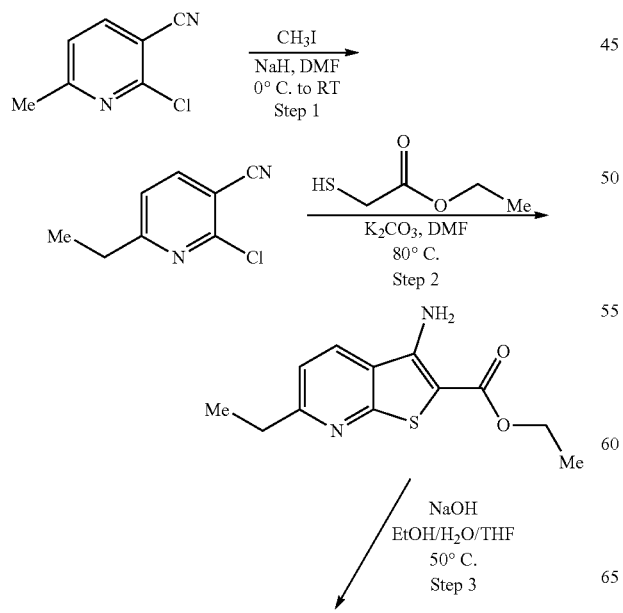

Step 1. 2-Chloro-6-ethylnicotinonitrile

Into a 500-mL round-bottom flask was added 2-chloro-6-methylpyridine-3-carbonitrile (8.00 g, 52.4 mmol) and DMF (200 mL). The resulting mixture was cooled to 0° C. and sodium hydride (60% dispersion in mineral oil; 3.00 g, 125 mmol) was added portion-wise. The reaction mixture was stirred for 10 min and then iodomethane (29.6 g, 13.0 mL, 209 mmol) was added dropwise with stirring. The resulting solution was stirred for 2 h at RT and then quenched with H$_2$O (500 mL). The reaction mixture was extracted with ethyl acetate (3×100mL), and the combined organic layers were washed with brine. The organic layer was dried over sodium sulfate, filtered, and concentrated in vacuo. The resulting crude product was purified by FCC eluting with ethyl acetate/petroleum ether (1:5) to afford 2-chloro-6-ethylnicotinonitrile as a yellow oil (4 g, 46%). LCMS (ESI, m/z): 168 [M+H]$^+$.

Step 2. Ethyl 3-amino-6-ethylthieno[2,3-b]pyridine-2-carboxylate

Into a 100-mL round-bottom flask was added 2-chloro-6-ethylnicotinonitrile (2.00 g, 12.0 mmol), DMF (50 mL), potassium carbonate (5.00 g, 35.9 mmol), ethyl 2-mercaptoacetate (1.35 g, 1.23 mL, 11.2 mmol). The resulting solution was stirred overnight at 80° C. and then cooled and extracted ethyl acetate (with 3×150 mL). The combined organic layers were washed with brine (3×100-mL), dried over anhydrous sodium sulfate, filtered, and concentrated in vacuo. The crude product was purified via silica gel column chromatography and eluted with ethyl acetate/petroleum ether (1:3) to afford ethyl 3-amino-6-ethylthieno[2,3-b]pyridine-2-carboxylate as a yellow solid (1.8 g, 63%). LCMS (ESI, m/z): 251 [M+H]$^+$.

Step 3. 3-Amino-6-ethylthieno[2,3-b]pyridine-2-carboxylic acid

Into a 100-mL round-bottom flask was added ethyl 3-amino-6-ethylthieno[2,3-b]pyridine-2-carboxylate (0.800 g, 3.20 mmol), ethanol (20 mL), and THF (20 mL). This was followed by the dropwise addition of a solution of sodium hydroxide (0.384 g, 9.60 mmol) in water (10 mL) with stirring. The resulting solution was stirred for 3 h at 50° C. The resulting mixture was concentrated in vacuo. The pH of the solution was adjusted to approximately 3-5 with aqueous HCl (3 M). The resulting precipitate was collected by filtration to afford 3-amino-6-ethylthieno[2,3-b]pyridine-2-carboxylic acid as a yellow solid (600 mg, 80%) that was carried on without further purification. LCMS (ESI, m/z): 223 [M+H]$^+$.

Example 17

Intermediate 17. 3-Amino-6-methoxythieno[2,3-b]pyridine-2-carboxylic acid

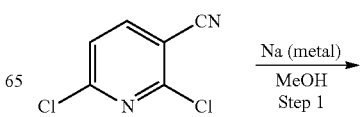

103
-continued

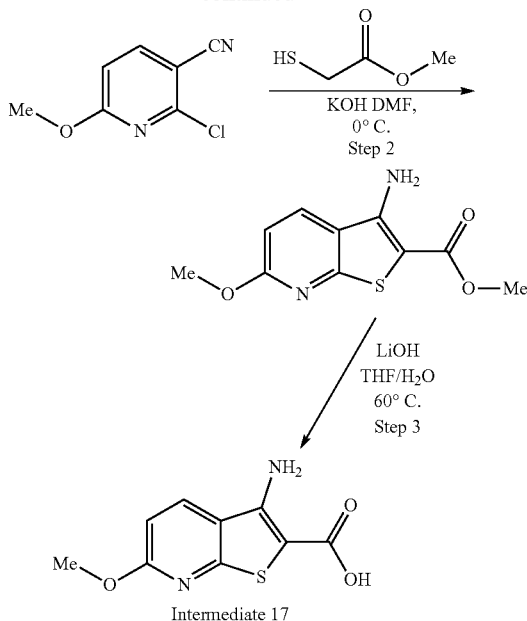

Intermediate 17

Step 1. 2-Chloro-6-methoxynicotinonitrile

Into an oven dried 250-mL round-bottom flask under a dry nitrogen atmosphere was added methanol (25 mL) followed by sodium metal (1.5 g, 65 mmol). After the metal had dissolved, 2,6-dichloropyridine-3-carbonitrile (5.00 g, 28.9 mmol) was then added over 5 min. The resulting solution was stirred overnight at RT. The solid precipitate was then removed by filtration, and the filtrate was concentrated in vacuo. The resulting crude product was purified by FCC eluting with ethyl acetate/hexane (1:3) to afford 2-chloro-6-methoxynicotinonitrile as a white solid (3.9 g, 80%). LCMS (ESI, m/z): 168 [M+H]$^+$.

Step 2. Methyl 3-amino-6-methoxythieno[2,3-b]pyridine-2-carboxylate

The title compound was prepared according to the procedure used for the preparation of Example 5: Intermediate 5, using 2-chloro-6-methoxynicotinonitrile. This afforded the title compound as a light yellow solid (51%). LCMS (ESI, m/z): 239 [M+H]$^+$; $^1$H-NMR (300 MHz, DMSO-$d_6$) δ ppm 8.40 (d, J=8.7 Hz, 1H), 7.24 (m, 2H), 6.89 (d, J=9.0 Hz, 1H), 3.93 (s, 3H), 3.77 (s, 3H).

Step 3. 3-Amino-6-methoxythieno[2,3-b]pyridine-2-carboxylic acid

Into a 50-mL round-bottom flask was placed methyl 3-amino-6-methoxythieno[2,3-b]pyridine-2-carboxylate (0.110 g, 0.46 mmol), tetrahydrofuran/H$_2$O (4 mL/1.5 mL), and LiOH (0.100 g, 4.18 mmol). The resulting solution was stirred for 2 h at 60° C. and then concentrated in vacuo to remove most of the THF. The resulting mixture was diluted with water (2 mL). The pH of the solution was adjusted to approximately 7 with aqueous HCl (1M). The solid product was isolated by filtration to afford 3-amino-6-methoxythieno[2,3-b]pyridine-2-carboxylic acid as a yellow solid (90 mg, 87%) that was carried on without further purification. LCMS (ESI, m/z): 225 [M+H]$^+$.

104
Example 18

Intermediate 18. 3-Amino-5-fluoro-6-methoxythieno[2,3-b]pyridine-2-carboxylic acid

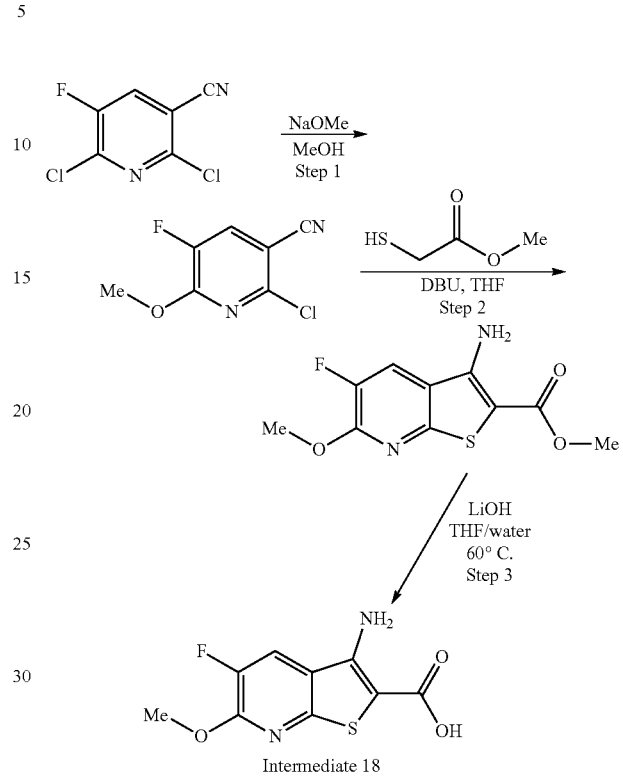

Intermediate 18

Step 1. 2-Chloro-5-fluoro-6-methoxynicotinonitrile

Into a 100-mL round-bottom flask that was purged and maintained under an inert atmosphere of nitrogen was added 2,6-dichloro-5-fluoropyridine-3-carbonitrile (3.00 g, 15.7 mmol), methanol (30 mL), and sodium methoxide (1.28 g, 23.7 mmol). The resulting solution was stirred for 5 h at RT and then concentrated in vacuo. The crude product was purified via silica gel column chromatography and eluted with ethyl acetate/petroleum ether (1:3) to afford 2-chloro-5-fluoro-6-methoxynicotinonitrile as a yellow solid (2.9 g) that was carried on without further purification. LCMS (ESI, m/z): 187 [M+H]$^+$.

Step 2. Methyl 3-amino-5-fluoro-6-methoxythieno [2,3-b]pyridine-2-carboxylate

Into a 100-mL round-bottom flask, purged and maintained under an inert atmosphere of nitrogen, was added 2-chloro-5-fluoro-6-methoxynicotinonitrile (2.94 g, 15.8 mmol), tetrahydrofuran (30 mL), methyl 2-mercaptoacetate (2.00 g, 1.68 mL, 18.8 mmol), and DBU (7.20 g, 7.07 mL, 47.3 mmol). The resulting solution was stirred overnight at RT and then concentrated in vacuo. The crude product was purified via silica gel column chromatography and eluted with ethyl acetate/petroleum ether (EA/PE=1/3) to afford methyl 3-amino-5-fluoro-6-methoxythieno[2,3-b]pyridine-2-carboxylate as a yellow solid (1.87 g, 46%). LCMS (ESI, m/z): 257 [M+H]$^+$.

Step 3. 3-Amino-5-fluoro-6-methoxythieno[2,3-b]pyridine-2-carboxylic acid

Into a 100-mL round-bottom flask was added methyl 3-amino-5-fluoro-6-methoxythieno[2,3-b]pyridine-2-carboxylate (0.500 g, 1.95 mmol), LiOH (0.236 g, 9.85 mmol), tetrahydrofuran (8 mL), and water (8 mL). The resulting solution was stirred overnight at 60° C. in an oil bath and then cooled to RT. The resulting mixture was concentrated in vacuo to remove the THF. The pH of the resulting mixture was adjusted to approximately 7 with aqueous HCl (4 M). The resulting solids were collected by vacuum filtration and dried in vacuo to afford 3-amino-5-fluoro-6-methoxythieno[2,3-b]pyridine-2-carboxylic acid as a yellow solid (260 mg, 55%). LCMS (ESI, m/z): 243 [M+H]+.

Example 19

Intermediate 19. 3-Amino-6-ethyl-5-fluorothieno[2,3-b]pyridine-2-carboxylic acid

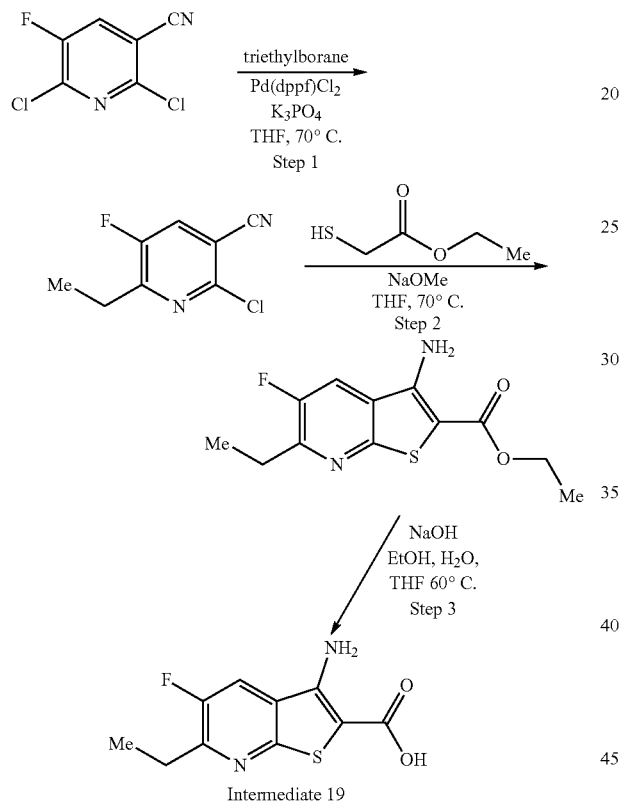

Intermediate 19

Step 1. 2-Chloro-6-ethyl-5-fluoronicotinonitrile

Into a 250-mL 3-necked round-bottom flask that was purged and maintained under an inert atmosphere of nitrogen was added 2,6-dichloro-5-fluoropyridine-3-carbonitrile (5.00 g, 26.2 mmol), potassium phosphate tribasic (5.60 g, 26.4 mmol), triethylborane (26.0 mL 28.80 mmol), Pd(dppf)Cl₂ (1.10 g, 1.50 mmol), and THF (100-mL). The reaction mixture was stirred overnight at 70° C. and then cooled to RT and concentrated in vacuo. The resulting crude product was purified by FCC eluting with ethyl acetate/petroleum ether (1:5) to afford 2-chloro-6-ethyl-5-fluoronicotinonitrile as a white solid (3.2 g, 66%). LCMS (ESI, m/z): 185 [M+H]+.

Step 2. Ethyl 3-amino-6-ethyl-5-fluorothieno[2,3-b]pyridine-2-carboxylate

Into a 100-mL round-bottom flask was added 2-chloro-6-ethyl-5-fluoronicotinonitrile (3.00 g, 16.3 mmol) and THF (40 mL). Sodium methoxide (2.63 g, 48.7 mmol) was added followed by ethyl thioglycolate (2.19 g, 2.00 mL, 18.2 mmol). The resulting solution was stirred overnight at 70° C. The reaction mixture was cooled to RT and concentrated in vacuo. The resulting crude product was purified by FCC eluting with ethyl acetate/petroleum ether (1:5) to afford ethyl 3-amino-6-ethyl-5-fluorothieno[2,3-b]pyridine-2-carboxylate as a yellow solid (2.3 g, 53%). LCMS (ESI, m/z): 269 [M+H]+.

Step 3. 3-Amino-6-ethyl-5-fluorothieno[2,3-b]pyridine-2-carboxylic acid

The title compound was prepared according to the procedure used for the preparation of example 11: Intermediate 11 using ethyl 3-amino-6-ethyl-5-fluorothieno[2,3-b]pyridine-2-carboxylate and EtOH which was added as a cosolvent. This afforded the title compound as a yellow solid (89%). LCMS (ESI, m/z): 241 [M+H]+.

Example 20

Intermediate 20. 3-Amino-6-chloro-4-methylthieno[2,3-b]pyridine-2-carboxylic acid

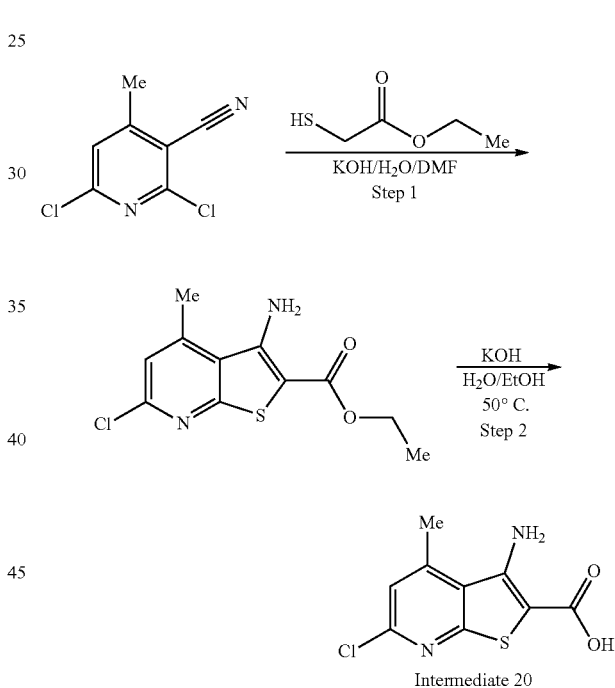

Intermediate 20

Step 1. Ethyl 3-amino-6-chloro-4-methylthieno[2,3-b]pyridine-2-carboxylate

Ethyl 2-mercaptoacetate (0.586 mL, 5.35 mmol) was added to a solution of 2,6-dichloro-4-methylnicotinonitrile (1.00 g, 5.35 mmol) in DMF (10 mL) at −5° C. This was followed by the slow addition of an aqueous solution of potassium hydroxide (powder; 1.20 g, 21.4 mmol) in water (2.5 mL). The reaction mixture was stirred at −5° C. for 1 hour (an orange precipitate forms). Water (5 mL) was added and the resulting precipitate was collected by vacuum filtration. The precipitate was washed with water (10 mL), collected, and dried in vacuo to afford ethyl 3-amino-6-chloro-4-methylthieno[2,3-b]pyridine-2-carboxylate as a pale orange powder (980 mg, 68%). LCMS (ESI, m/z): 271 [M+H]+.

Step 2. 3-Amino-6-chloro-4-methylthieno[2,3-b]pyridine-2-carboxylic acid

To a suspension of ethyl 3-amino-6-chloro-4-methylthieno[2,3-b]pyridine-2-carboxylate (0.970 g, 3.58 mmol) in ethanol (8 ml) was added water (4.00 ml) followed by potassium hydroxide (powder; 1.00 g, 17.9 mmol). The reaction mixture was stirred at 50° C. for 3 hours (white precipitate forms). The reaction was cooled to RT and acidified to approximately pH=5 with aqueous 1N HCl (the solution turns clear and then a white precipitate forms again). The precipitate was collected by filtration, washed with water (10 mL) and ether (10 mL), and dried in vacuo to afford 3-amino-6-chloro-4-methylthieno[2,3-b]pyridine-2-carboxylic acid as a white powder (560 mg, 64%). LCMS (ESI, m/z): 243 [M+H]+.

Example 21

Intermediate 21. 3-Amino-6-chlorothieno[2,3-b]pyridine-2-carboxylic acid

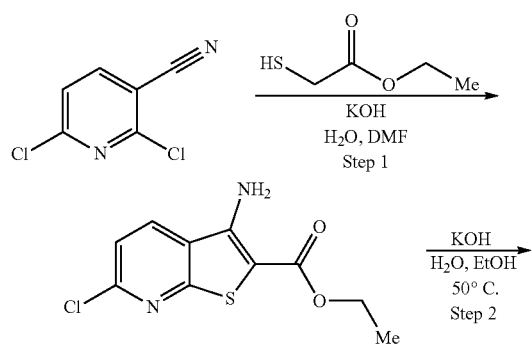

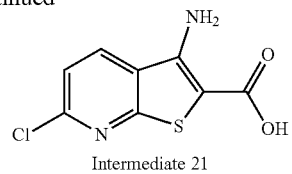

Intermediate 21

Step 1. Ethyl 3-amino-6-chlorothieno[2,3-b]pyridine-2-carboxylate

The title compound was prepared according to the procedure used for the preparation of Example 20: Intermediate 20, using 2,6-dichloronicotinonitrile. This afforded ethyl 3-amino-6-chlorothieno[2,3-b]pyridine-2-carboxylate as a light yellow solid (85%). LCMS (ESI, m/z): 257 [M+H]+.

Step 2. 3-Amino-6-chlorothieno[2,3-b]pyridine-2-carboxylic acid

The title compound was prepared according to the procedure used for the preparation of Example 20: Intermediate 20, using ethyl 3-amino-6-chlorothieno[2,3-b]pyridine-2-carboxylate. This afforded the title compound as a light yellow solid (98%). LCMS (ESI, m/z): 229 [M+H]+.

Example 22

Intermediate 22. 3-Amino-5-bromo-6-methylthieno[2,3-b]pyridine-2-carboxylic acid

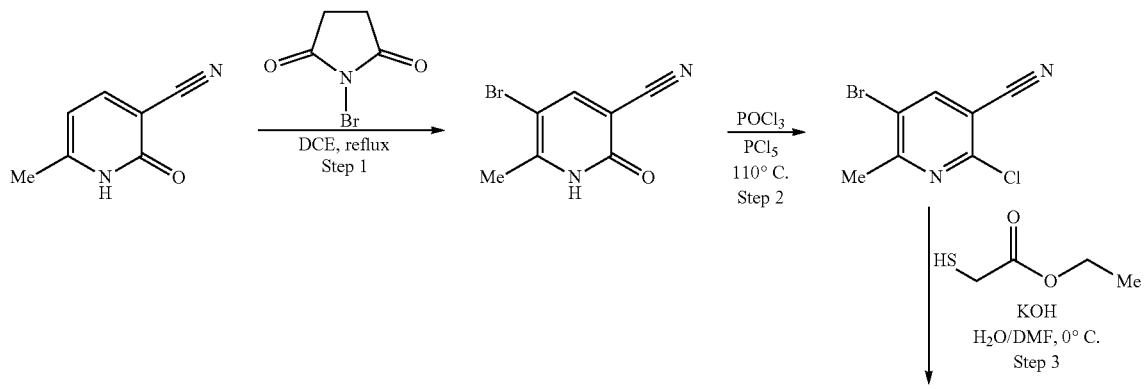

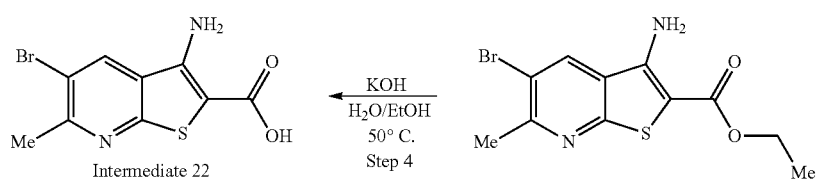

Step 1. 5-Bromo-6-methyl-2-oxo-1,2-dihydropyridine-3-carbonitrile

A mixture of 6-methyl-2-oxo-1,2-dihydropyridine-3-carbonitrile (4.00 g, 29.8 mmol) and NBS (11.2 g, 62.6 mmol) in DCE (150 mL) was heated to reflux overnight. The reaction was cooled to RT and the resulting precipitate was collected via vacuum filtration. The precipitate was suspended in water (330 mL), stirred for 2 hours, and then collected via vacuum filtration. The filter cake was washed with water (50 mL), collected, and dried in vacuo to afford 5-bromo-6-methyl-2-oxo-1,2-dihydropyridine-3-carbonitrile as a white powder (5.3 g, 84%). $^1$H NMR (300 MHz, DMSO-d$_6$) δ ppm 12.99 (br s, 1H), 8.36 (s, 1H), 2.35 (s, 3H).

Step 2. 5-Bromo-2-chloro-6-methylnicotinonitrile 5-bromo-6-methyl-2-oxo-1,2-dihydropyridine-3-carbonitrile (2.00 g, 9.39 mmol) was dissolved in phosphoryl trichloride (1.5 ml, 16.1 mmol) at RT. Phosphorous pentachloride (1.96 g, 9.39 mmol) was then added and the resulting mixture was heated to 110° C. overnight. The reaction mixture was cooled to RT and concentrated in vacuo. The crude product was purified by FCC eluting with 5-25% EtOAc in hexanes to afford 5-bromo-2-chloro-6-methylnicotinonitrile as a light yellow solid (2.1 g, 97%). $^1$H NMR (300 MHz, DMSO-d$_6$) δ ppm 8.80 (s, 1H), 2.63 (s, 3H).

Step 3. Ethyl 3-amino-5-bromo-6-methylthieno [2,3-b]pyridine-2-carboxylate

To a solution of 5-bromo-2-chloro-6-methylnicotinonitrile (0.81 g, 3.5 mmol) in DMF (10 mL) at 0° C. was added ethyl 2-mercaptoacetate (0.422 g, 0.384 mL, 3.50 mmol), followed by the slow addition of a solution of potassium hydroxide (powder; 0.785 g, 14.0 mmol) in water (2.5 mL). The reaction mixture was stirred at 0° C. for 1 hour (an orange precipitate forms). Water (5 mL) was then added and the resulting precipitate was collected by filtration, washed with water (10 mL), collected, and dried in vacuo to afford ethyl 3-amino-5-bromo-6-methylthieno[2,3-b]pyridine-2-carboxylate as a pale orange powder (1.0 g, 95%). LCMS (ESI, m/z): 316 [M+H]$^+$.

Step 4. 3-Amino-5-bromo-6-methylthieno[2,3-b]pyridine-2-carboxylic acid

The title compound was prepared according to the procedure used for the preparation of Example 21: Intermediate 21, using ethyl 3-amino-5-bromo-6-methylthieno[2,3-b]pyridine -2-carboxylate. This afforded the title compound as a white solid (93%). LCMS (ESI, m/z): 288 [M+H]$^+$.

Example 23

Intermediate 23: 3-Amino-6-(difluoromethyl)-4-methylthieno [2,3-b]pyridine-2-carboxylic acid

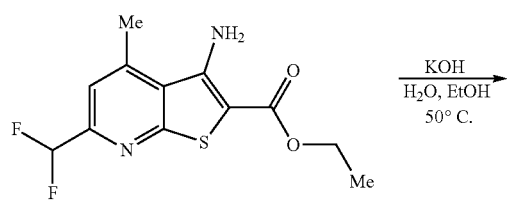

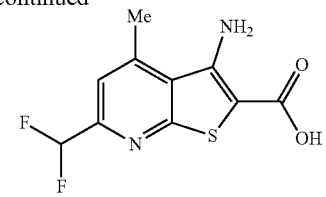

Intermediate 23

The title compound was prepared according to the procedure used for the preparation of Example 22: Intermediate 22, using ethyl 3-amino-6-(difluoromethyl)thieno[2,3-b] pyridine -2-carboxylate. This afforded the title compound as a white solid (99%). LCMS (ESI, m/z): 259 [M+H]$^+$.

Example 24

Intermediate 24: Ethyl 3-amino-6-((2,4-dimethoxybenzyl)amino)-5-fluorothieno [2,3-b]pyridine-2-carboxylate

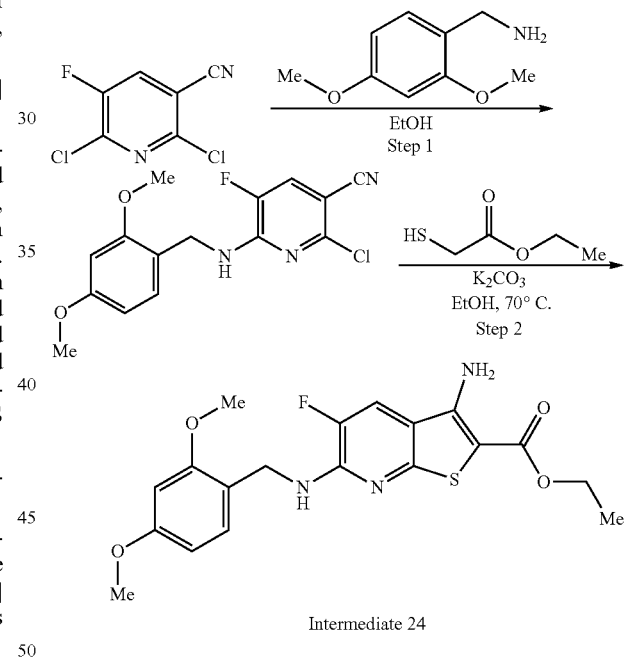

Intermediate 24

Step 1. 2-Chloro-6-((2,4-dimethoxybenzyl)amino)-5-fluoronicotinonitrile

Into a 250-mL round-bottom flask was added 2,6-dichloro-5-fluoropyridine-3-carbonitrile (5.00 g, 26.2 mmol), (2,5-dimethoxyphenyl)methanamine (13.0 g, 77.8 mmol), and ethanol (100 mL). The solution was stirred for 2 h at RT. The resulting solids were collected by filtration and dried in vacuo to afford the title compound as a white solid (6.6 g, 78%). LCMS (ESI, m/z): 322 [M+H]$^+$.

Step 2. Ethyl 3-amino-6-((2,4-dimethoxybenzyl)amino)-5-fluorothieno[2,3-b]pyridine-2-carboxylate Into a 100-mL round-bottom flask was added 2-chloro-6-((2,4-dimethoxybenzyl) amino)-5-fluoronicotinonitrile (2.00 g, 6.22 mmol), ethyl 2-mercaptoacetate (0.745 g, 0.680 mL, 6.20 mmol), potassium carbonate (2.57 g, 18.5 mmol), and ethanol (50 mL). The reaction mixture was stirred overnight at 70° C. and then cooled to RT and concentrated in vacuo. The resulting crude product was purified by FCC eluting with ethyl acetate/petroleum ether (1:3) to afford ethyl 3-amino-6-((2,4-dimethoxybenzyl) amino)-5-fluorothieno[2,3-b]pyridine-2-carboxylate as a light yellow solid (1.5 g, 60%). LCMS (ESI, m/z): 406 [M+H]+.

Example 25

Intermediate 25. Benzyl 4-(4-(2-aminoethyl)phenyl) piperazine-1-carboxylate (hydrochloride salt)

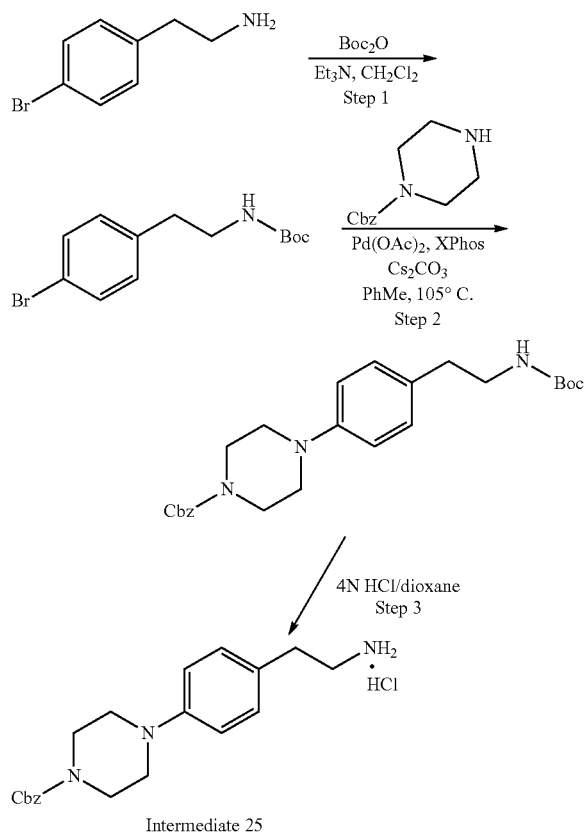

Intermediate 25

Step 1. tert-Butyl (4-bromophenethyl)carbamate

To a solution of 2-(4-bromophenyl)ethan-1-amine (5.00 g, 25.0 mmol) in anhydrous dichloromethane (50-mL) was added Boc$_2$O (6.57 g, 30.1 mmol) followed by Et$_3$N (10.4 mL, 74.9 mmol). The resulting solution was stirred overnight at 25° C. and then concentrated in vacuo. The resulting crude product was purified by FCC eluting with ethyl acetate/petroleum ether (PE/EA=3:1) to afford tert-butyl (4-bromophenethyl)carbamate as a white solid (7.1 g, 95%). LCMS (ESI, m/z): 300 [M+H]+.

Step 2. Benzyl 4-(4-(2-((tert-butoxycarbonyl)amino) ethyl)phenyl)piperazine-1-carboxylate Into a 100-mL round-bottom flask, purged and maintained under an inert atmosphere of nitrogen, was added tert-butyl (4-bromophenethyl)carbamate (4.00 g, 13.3 mmol) dissolved in anhydrous toluene (50-mL). To the resulting solution was added benzyl piperazine-1 -carboxylate (3.53 g, 16.0 mmol), Pd(OAc)$_2$ (0.300 g, 1.34 mmol), XPhos (1.28 g, 2.69 mmol), and Cs$_2$CO$_3$ (13.1 g, 40.0 mmol). The reaction mixture was stirred overnight at 105° C. in an oil bath and then cooled to RT and quenched with H$_2$O (200 mL). The resulting mixture was extracted with ethyl acetate (2×50 mL). The combined organic layers were washed with brine (1×200 mL), dried over anhydrous sodium sulfate, filtered, and concentrated in vacuo. The resulting crude product was purified by FCC eluting with ethyl acetate/ petroleum ether (PE/EA=3:1) to afford benzyl 4-(4-(2-((tert-butoxycarbonyl)amino)ethyl)phenyl) piperazine-1-carboxylate as a yellow solid (5 g, 85%). LCMS (ESI, m/z): 440 [M+H]+.

Step 3. Benzyl 4-(4-(2-aminoethyl)phenyl)piperazine-1-carboxylate (hydrochloride salt)

Into a 100-mL round-bottom flask was added benzyl 4-(4-(2-((tert -butoxycarbonyl)amino)ethyl)phenyl)piperazine-1-carboxylate, followed by 4 N hydrogen chloride/ dioxane (10 mL). The resulting solution was stirred for 1 h at RT and then concentrated in vacuo to afford benzyl 4-(4-(2-aminoethyl)phenyl)piperazine-1-carboxylate (hydrochloride salt) as a yellow solid (2.0 g, 86%). LCMS (ESI, m/z): 340 [M+H]+.

Example 26

Intermediate 26. 2-(4-(4-Cyclobutylpiperazin-1-yl) phenyl)ethan-1-amine (hydrochloride salt)

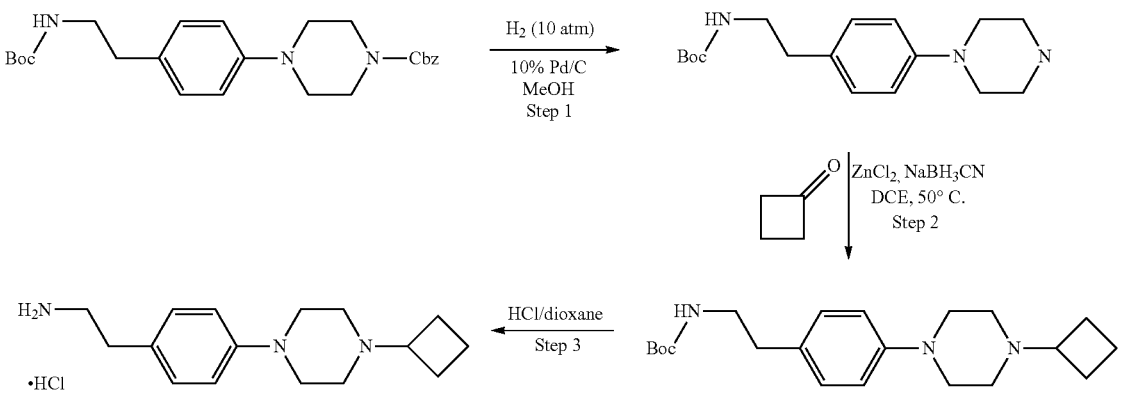

Intermediate 26

Step 1. tert-Butyl (4-(piperazin-1-yl)phenethyl)carbamate

Into a 50-mL high pressure reactor under an inert atmosphere of nitrogen was added benzyl 4-[4-(2-[[(tert-butoxy)carbonyl]amino]ethyl)phenyl] piperazine-1-carboxylate (1.00 g, 2.28 mmol) and 10% palladium on carbon (0.1 g), followed by methanol (15 mL). The reactor was then pressurized with hydrogen (10 atm), and the resulting mixture was stirred for 16 h at RT. The reaction mixture was vented to nitrogen and the solids were removed by filtration through Celite. The resulting filtrate was concentrated in vacuo to provide tert-butyl (4-(piperazin-1-yl)phenethyl)carbamate as a yellow oil (0.67 g, 96%). LCMS (ESI, m/z): 306 $[M+H]^+$.

Step 2. tert-Butyl (4-(4-cyclobutylpiperazin-1-yl)phenethyl)carbamate

Into a 100-mL round-bottom flask was added tert-butyl (4-(piperazin-1-yl)phenethyl)carbamate (0.700 g, 2.29 mmol), cyclobutanone (0.320 g, 4.57 mmol), and $ZnCl_2$ (0.610 g, 4.47 mmol), followed by DCE (15 mL). $NaBH_3CN$ (0.290 g, 4.61 mmol) was then added and the resulting mixture was stirred for 16 h at 50° C. The reaction mixture was concentrated in vacuo and the crude product was purified by FCC eluting with DCM:MeOH (3:1) to afford tert-butyl (4-(4-cyclobutylpiperazin-1-yl)phenethyl)carbamate as a yellow oil (0.5 g, 61%). LCMS (ESI, m/z): 360 $[M+H]^+$.

Step 3. 2-(4-(4-Cyclobutylpiperazin-1-yl)phenyl)ethan-1-amine hydrochloride

Into a 25-mL round-bottom flask was added tert-butyl (4-(4-cyclobutylpiperazin-1-yl)phenethyl)carbamate (0.500 g, 1.39 mmol) followed by HCl/dioxane (4 N, 10 ml). The resulting solution was stirred for 6 h at RT and the solid product formed was collected by filtration to afford 2-(4-(4-cyclobutylpiperazin-1-yl)phenyl)ethan-1-amine (hydrochloride salt) as a light yellow solid (0.3 g, 73%). LCMS (ESI, m/z): 260 $[M+H]^+$.

Example 27

Intermediate 27. Benzyl 4-(4-(2-aminoethyl)-3-methoxyphenyl)piperazine-1-carboxylate (hydrochloride salt)

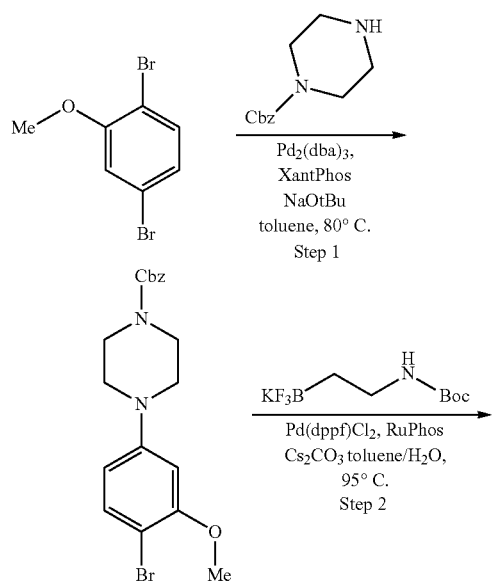

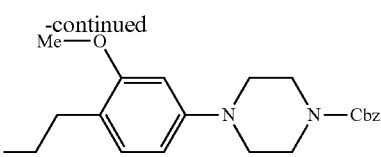

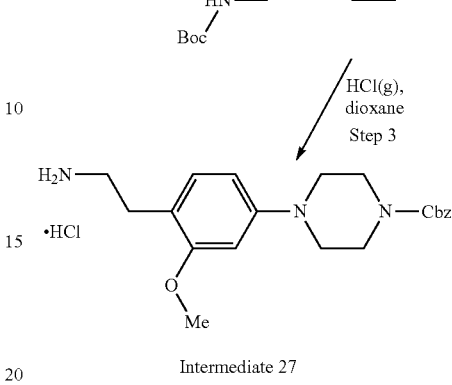

Intermediate 27

Step 1. Benzyl 4-(4-bromo-3-methoxyphenyl)piperazine-1-carboxylate

Into a 100-mL round-bottom flask, purged and maintained under an inert atmosphere of nitrogen, was added 1,4-dibromo-2-methoxybenzene (2.60 g, 9.78 mmol), benzyl piperazine-1-carboxylate (2.37 g, 10.8 mmol), $Pd_2(dba)_3$ $CHCl_3$ (0.508 g, 0.490 mmol), XantPhos (0.583 g, 0.980 mmol), and NaOtBu (2.82 g, 29.3 mmol) followed by toluene (40 mL). The reaction mixture was stirred for 3 h at 80° C. and then concentrated in vacuo. The resulting crude product was purified by FCC eluting with ethyl acetate/petroleum ether (1:10) to afford benzyl 4-(4-bromo-3-methoxyphenyl)piperazine-1-carboxylate as a brown solid (2 g, 50%). LCMS (ESI, m/z): 405, 407 $[M+H]^+$.

Step 2. Benzyl 4-(4-(2-((tert-butoxycarbonyl)amino)ethyl)-3-methoxyphenyl)piperazine-1-carboxylate.

Into a 100-mL round-bottom flask, purged and maintained under an inert atmosphere of nitrogen, was added benzyl 4-(4-bromo-3-methoxyphenyl)piperazine-1-carboxylate (0.500 g, 1.23 mmol), potassium (2-((tert-butoxycarbonyl)amino)ethyl) trifluoroborate (0.308 g, 1.22 mmol), Pd(dppf)$Cl_2$ (0.050 g, 0.07 mmol), RuPhos (0.057 g, 0.12 mmol), $Cs_2CO_3$ (1.19 g, 3.65 mmol), toluene (10 mL), and water (3 mL). The resulting solution was stirred for 5 h at 95° C. in an oil bath and then concentrated in vacuo. The crude product was purified via silica gel chromatography and eluted with ethyl acetate/petroleum ether (1:10) to afford benzyl 4-[4-(2-[[benzyloxy)carbonyl]amino]ethyl)-3-methoxyphenyl]piperazine-1-carboxylate as a brown solid (540 mg, 87%). LCMS (ESI, m/z): 470 $[M+H]^+$.

Step 3. Benzyl 4-(4-(2-aminoethyl)-3-methoxyphenyl)piperazine-1-carboxylate (hydrochloride salt)

Into a 100-mL round-bottom flask was added benzyl 4-[4-(2-[[(tert-butoxy)carbonyl]amino]ethyl)-3-methoxyphenyl]piperazine-1-carboxylate (0.470 g, 1.00 mmol), and dioxane (5 mL). HCl gas was bubbled into the reaction mixture and the resulting solution was stirred for 2 h at RT. The reaction mixture was concentrated in vacuo to afford benzyl 4-[4-(2-aminoethyl)-3-methoxyphenyl]piperazine-1-carboxylate (hydrochloride salt) as a white solid (400 mg, 98%) that was carried on without further purification. LCMS (ESI, m/z): 370 $[M+H]^+$.

Example 28

Intermediate 28. Benzyl 4-(4-(2-aminoethyl)-2-(trifluoromethyl)phenyl) piperazine-1-carboxylate (hydrochloride salt)

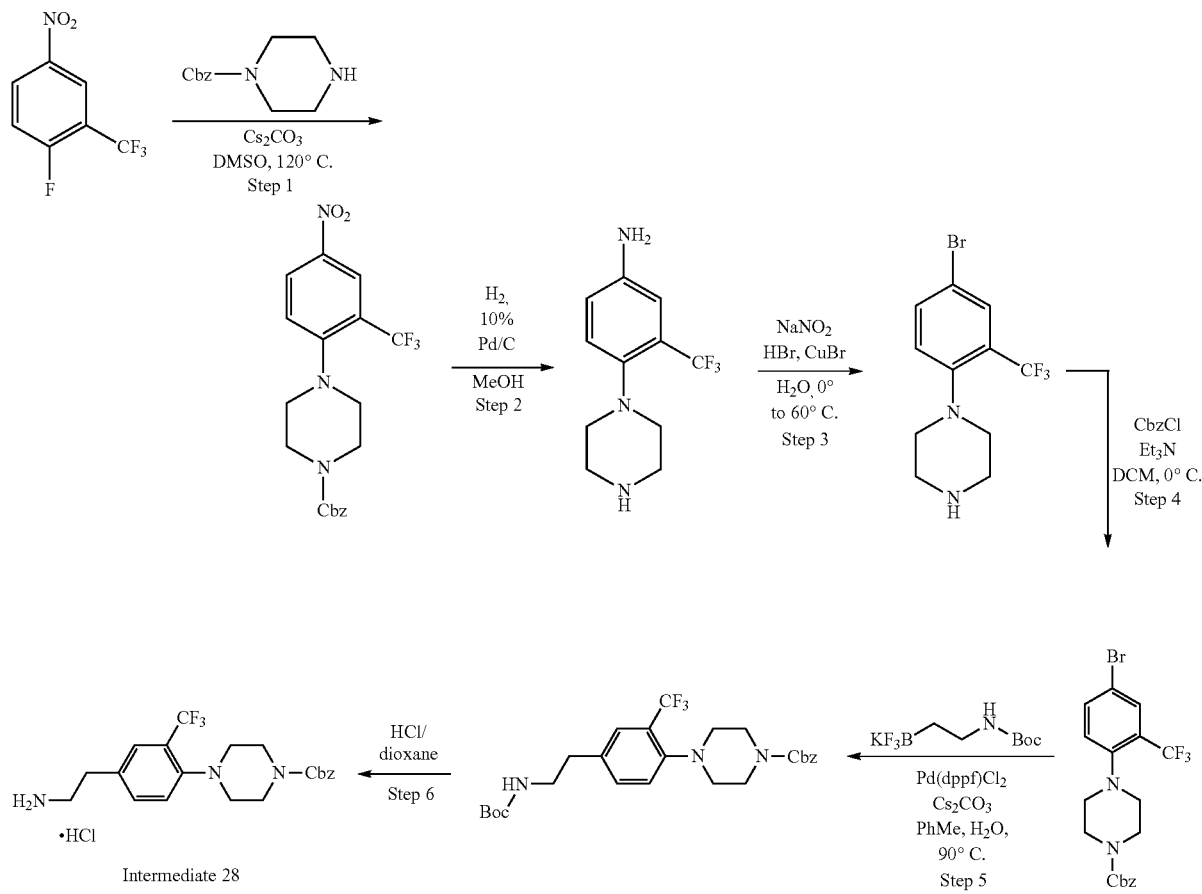

Step 1. Benzyl 4-(4-nitro-2-(trifluoromethyl)phenyl)piperazine-1-carboxylate

Into a 100-mL round-bottom flask was added 1-fluoro-4-nitro-2-(trifluoromethyl)benzene (3.20 g, 15.3 mmol) followed by DMSO (20 mL). Benzyl piperazine-1-carboxylate (3.30 g, 15.0 mmol) and $Cs_2CO_3$ (15.0 g, 46.0 mmol) were then added and the reaction mixture was stirred overnight at 120° C. The reaction mixture was cooled to RT, quenched with water (100 mL), and extracted with ethyl acetate (3×15 mL). The combined organic layers were concentrated in vacuo to afford a crude product that purified by FCC eluting with ethyl acetate/petroleum ether (1:10) to afford benzyl 4-(4-nitro-2-(trifluoromethyl)phenyl)piperazine-1-carboxylate as an orange oil (3.2 g, 51%). LCMS (ESI, m/z): 410 $[M+H]^+$.

Step 2. 4-(Piperazin-1-yl)-3-(trifluoromethyl)aniline

Into a 50-mL round-bottom flask purged with nitrogen was added benzyl 4-(4-nitro-2-(trifluoromethyl)phenyl)piperazine-1-carboxylate (2.00 g, 4.89 mmol) followed by methanol (20 mL). 10% Palladium on carbon (200 mg) was added and the reaction was purged with hydrogen using a hydrogen filled balloon (subsurface bubbling). The reaction mixture was stirred for 2 h under a hydrogen atmosphere, vented to nitrogen, and the solids were removed by filtration over Celite. The filtrate was then concentrated in vacuo to afford 4-(piperazin-1-yl)-3-(trifluoromethyl)aniline as a black oil (1.0 g, 83%). LCMS (ESI, m/z): 246 $[M+H]^+$.

Step 3. 1-(4-Bromo-2-(trifluoromethyl)phenyl)piperazine

Into a 50-mL round-bottom flask was added 4-(piperazin-1-yl)-3-(trifluoromethyl)aniline (1.30 g, 5.30 mmol), CuBr (0.400 g, 2.79 mmol), aqueous HBr (48% by weight; 4.2 mL), and water (15 mL). A solution of $NaNO_2$ in water $H_2O$ (1.6 g, 23.2 mmol in 2 mL) was then added dropwise at 0° C. and the resulting reaction mixture was stirred for 2 h at 60° C. The pH of the solution was adjusted to approximately 8 with aqueous sodium hydroxide (2 M) and then extracted with ethyl acetate (3×15 mL). The combined organic layers were dried over anhydrous sodium sulfate, filtered, and concentrated in vacuo to afford a crude product that purified by FCC eluting with ethyl acetate/petroleum ether (1:1) to afford 1-(4-bromo-2-(trifluoromethyl)phenyl)piperazine as a yellow oil (613 mg, 37%). LCMS (ESI, m/z): 309 $[M+H]^+$.

Step 4. Benzyl 4-(4-bromo-2-(trifluoromethyl)phenyl) piperazine-1-carboxylate

Into a 50-mL round-bottom flask was added 1-[4-bromo-2-(trifluoromethyl)phenyl] piperazine (0.520 g, 1.68 mmol) followed by dichloromethane (10 mL). The resulting mixture was cooled to 0° C. and benzyl chloroformate (0.347 g, 0.290 mL, 2.03 mmol) was then added followed by triethylamine (0.515 g. 0.709 mL, 5.09 mmol). The resulting solution was stirred for 3 h at 0° C. and then concentrated in vacuo. The crude product was purified by FCC eluting with ethyl acetate/petroleum ether (1:3) to afford benzyl 4-(4-bromo-2-(trifluoromethyl)phenyl) piperazine-1-carboxylate as a colorless oil (410 mg, 55%). LCMS (ESI, m/z): 443 [M+H]$^+$.

Step 5. Benzyl 4-(4-(2-((tert-butoxycarbonyl)amino)ethyl)-2-(trifluoromethyl)phenyl) piperazine-1-carboxylate Into a 50-mL round-bottom flask was added benzyl 4-(4-bromo-2-(trifluoromethyl)phenyl)piperazine-1-carboxylate (0.410 g, 0.92 mmol) followed by a mixture of toluene and H$_2$O (8 mL/ 2 mL). Potassium (2-((tert-butoxycarbonyl)amino)ethyl) trifluoroborate (0.251 g, 1.00 mmol) was then added followed by Cs$_2$CO$_3$ (0.912 g, 2.80 mmol) and Pd(dppf)Cl$_2$ (70 mg, 0.10 mmol). The reaction mixture was purged with nitrogen (subsurface bubbling for 5 minutes) and then stirred for 3 h at 90° C. The resulting mixture was concentrated in vacuo and the crude product was purified by FCC eluting with ethyl acetate/petroleum ether (1:3) to afford benzyl 4-(4-(2-((tert-butoxycarbonyl)amino)ethyl)-2-(trifluoromethyl)phenyl)piperazine-1-carboxylate as a yellow oil (363 mg, 77%). LCMS (ESI, m/z): 508 [M+H]$^+$.

Step 6. Benzyl 4-(4-(2-aminoethyl)-2-(trifluoromethyl)phenyl)piperazine-1-carboxylate hydrochloride Into a 50-mL round-bottom flask was added benzyl 4-(4-(2-((tert-butoxycarbonyl) amino)ethyl)-2-(trifluoromethyl)phenyl)piperazine-1-carboxylate (0.400 g, 0.79 mmol). 4 N HCl in dioxane (10 mL) was then added and the resulting solution was stirred for 2 h at RT. The reaction mixture was concentrated in vacuo to afford the title compound as a light yellow solid (302 mg, 94%). LCMS (ESI, m/z): 408 [M+H]$^+$.

Example 29

Intermediate 29. Benzyl 4-(4-bromo-2-methylphenyl)piperazine-1-carboxylate

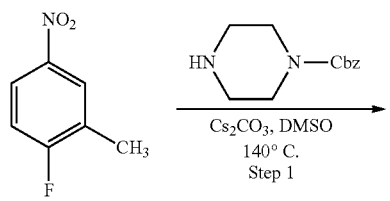

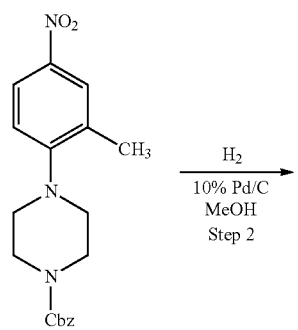

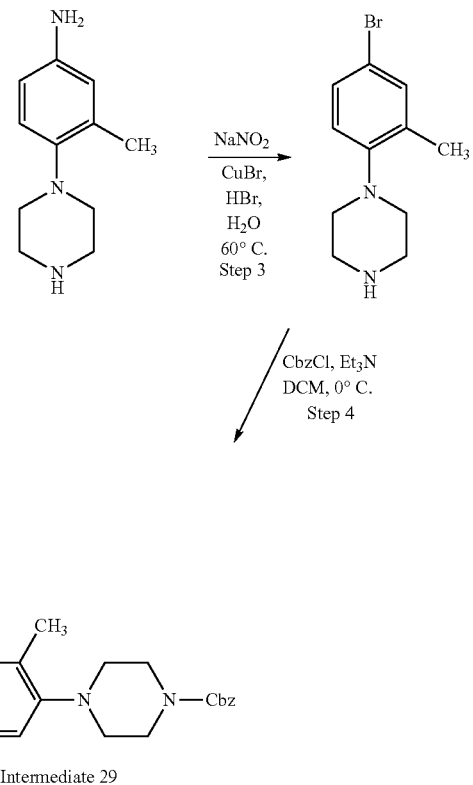

Intermediate 29

Step 1. Benzyl 4-(2-methyl-4-nitrophenyl)piperazine-1-carboxylate

Into a 100-mL round-bottom flask was added 1-fluoro-2-methyl-4-nitrobenzene (1.55 g, 9.99 mmol), benzyl piperazine-1-carboxylate (2.20 g, 9.99 mmol) and Cs$_2$CO$_3$ (9.78 g, 30.0 mmol) followed by DMSO (15 mL). The resulting suspension was stirred for 2 h at 140° C. and then quenched with water (50 mL) and extracted with ethyl acetate (3×100-mL). The combined organic layers were dried over anhydrous sodium sulfate, filtered, and concentrated in vacuo. The crude product was purified by FCC eluting with ethyl acetate/petroleum ether (1:10) to afford benzyl 4-(2-methyl-4-nitrophenyl)piperazine-1-carboxylate as an orange solid (2.1 g, 59%). LCMS (ESI, m/z): 356 [M+H]$^+$.

Step 2. 3-Methyl-4-(piperazin-1-yl)aniline

Into a 250-mL round-bottom flask was added benzyl 4-(2-methyl-4-nitrophenyl)piperazine-1-carboxylate (4.16 g, 11.7 mmol), 10% palladium on carbon (400 mg), and methanol (120 mL) under an atmosphere of nitrogen. The reaction mixture was purged with a hydrogen-filled balloon (subsurface bubbling) and then stirred overnight at RT. The reaction was vented to nitrogen and the solids were removed by filtration through Celite. The filtrate was concentrated in vacuo to afford 3-methyl-4-(piperazin-1-yl)aniline as an orange solid (2.22 g, 99%). LCMS (ESI, m/z): 192 [M+H]$^+$ Step 3. 1-(4-Bromo-2-methylphenyl)piperazine Into a 50-mL round-bottom flask was added 3-methyl-4-(piperazin-1-yl)aniline (1.12 g, 5.86 mmol), aqueous HBr (48% by weight, 5.23 g), and NaNO$_2$ (647 mg, 9.38 mmol) in water (9 mL). To another 50-mL round-bottom flask charged with CuBr (1.53 g, 10.7 mmol) in water (7 mL) and aqueous HBr (48% by weight, 4.75 g), was added the former solution dropwise. The resulting solution was stirred for 2 h at 60° C., quenched with water (20 mL), and extracted with ethyl acetate (3×100-mL). The combined organic layers were then dried over anhydrous sodium sulfate, filtered, and concentrated in vacuo. The crude product was purified by FCC eluting with ethyl acetate/petroleum ether (1:3) to afford 1-(4-bromo-2-methylphenyl)piperazine as a purple solid (630 mg, 42%). LCMS (ESI, m/z): 255 [M+H]$^+$.

Step 4. Benzyl 4-(4-bromo-2-methylphenyl)piperazine-1-carboxylate

Into a 250-mL round-bottom flask was added 1-(4-bromo-2-methylphenyl)piperazine (0.630 g, 2.47 mmol), Et$_3$N (0.758 g, 1.04 mL, 7.49 mmol), and dichloromethane (80 mL). This was followed by the dropwise addition of benzyl chloroformate (0.468 g, 0.390 mL, 2.74 mmol) with stirring. The resulting solution was stirred for 1 h at 0° C. in a water/ice bath and then concentrated in vacuo. The crude product was purified by FCC eluting with ethyl acetate/petroleum ether (1:10) to afford benzyl 4-(4-bromo-2-methylphenyl)piperazine-1-carboxylate as a brown oil (680 mg, 71%). LCMS (ESI, m/z): 389 [M+H]$^+$.

Example 30

Intermediate 30. tert-Butyl 4-(4-bromo-2-(difluoromethoxy)phenyl) piperazine-1-carboxylate

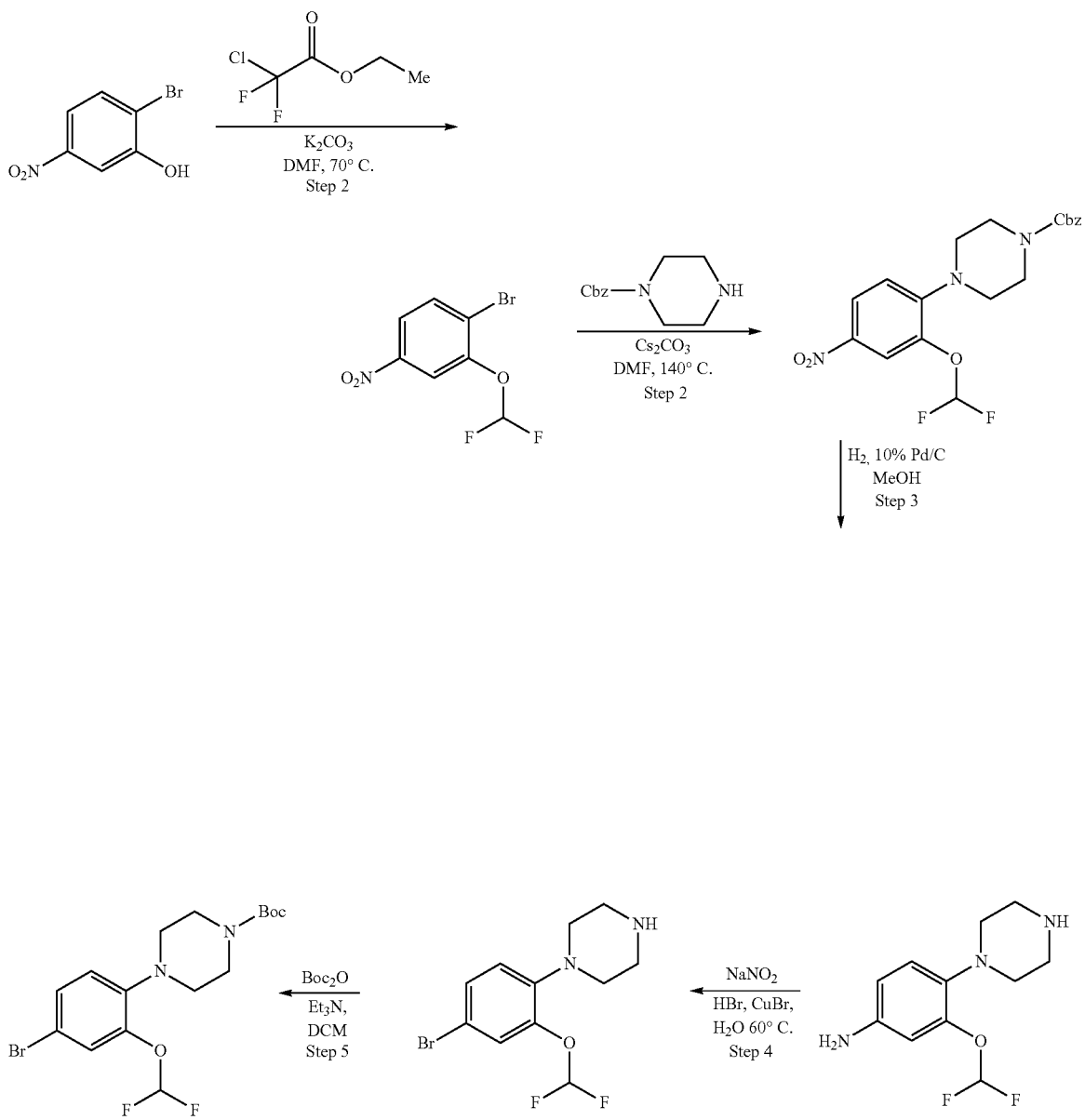

Intermediate 30

Step 1. 1-Bromo-2-(difluoromethoxy)-4-nitrobenzene

Into a 250-mL round-bottom flask, purged and maintained under an inert atmosphere of nitrogen, was added 2-bromo-5-nitrophenol (4.65 g, 21.3 mmol), ethyl 2-chloro-2,2-difluoroacetate (4.50 g, 28.4 mmol), and potassium carbonate (2.9 g, 21 mmol) followed by DMF (30 mL). The reaction mixture was stirred overnight at 70° C. in an oil bath and then quenched with water (50 mL). The resulting solution was extracted with ethyl acetate (3×100mL), the organic layers combined, dried over anhydrous sodium sulfate filtered, and concentrated in vacuo to afford 1-bromo-2-(difluoromethoxy)-4-nitrobenzene as a red oil (5.68 g, 99%). LCMS (ESI, m/z): 268 [M+H]$^+$.

Step 2. Benzyl 4-(2-(difluoromethoxy)-4-nitrophenyl)piperazine-1-carboxylate

Into a 250-mL round-bottom flask was added 1-bromo-2-(difluoromethoxy)-4-nitrobenzene (5.68 g, 21.2 mmol), benzyl piperazine-1-carboxylate (5.61 g, 25.5 mmol), and cesium carbonate (8.80 g, 26.9 mmol) followed by DMF (20 mL). The reaction mixture was heated and stirred for 3 h at 140° C. and then quenched with water (50 mL). The reaction mixture was extracted with ethyl acetate (2×100 mL), the combined organic layers were then dried over anhydrous sodium sulfate, filtered, and concentrated in vacuo. The resulting crude product was purified by FCC eluting with ethyl acetate/petroleum ether (1:3) to afford benzyl 4-(2-(difluoromethoxy)-4-nitrophenyl)piperazine-1-carboxylate as a red solid (4.8 g, 56%). LCMS (ESI, m/z): 408 [M+H]$^+$.

Step 3. 3-(Difluoromethoxy)-4-(piperazin-1-yl)aniline

Into a 250-mL round-bottom flask that was purged with nitrogen was added benzyl 4-(2-(difluoromethoxy)-4-nitrophenyl)piperazine-1-carboxylate (4.80 g, 11.8 mmol), 10% palladium on carbon (500 mg) and methanol (100 mL). The reaction mixture was sparged with hydrogen gas (subsurface bubbling) and was then stirred overnight under hydrogen (balloon) at RT. The reaction mixture was filtered over Celite, and the filtrate was concentrated in vacuo to afford 3-(difluoromethoxy)-4-(piperazin-1-yl)aniline as an orange solid (2.8 g, 98%). LCMS (ESI, m/z): 244 [M+H]$^+$.

Step 4. 1-(4-Bromo-2-(difluoromethoxy)phenyl)piperazine

Into a 250-mL round-bottom flask was added 3-(difluoromethoxy)-4-(piperazin-1-yl)aniline (2.80 g, 11.5 mmol), aqueous HBr (48% by weight, 10 g), NaNO$_2$ (1.27 g, 18.4 mmol) and water (12 mL). The resulting solution was carefully added to a solution of CuBr (2.99 g) in aqueous HBr (48% by weight, 9.6 g). The reaction mixture was stirred for 2 h at 60° C. and then quenched with water (50 mL). The pH of the solution was adjusted to approximately 7 with sodium hydroxide (1 M). The resulting solution was extracted with dichloromethane (3×100mL). The combined organic layers were then dried over anhydrous sodium sulfate, filtered, and concentrated in vacuo to afford 1-(4-bromo-2-(difluoromethoxy)phenyl)piperazine as a brown oil (2 g, 57%). LCMS (ESI, m/z): 307 [M+H]$^+$.

Step 5. tert-Butyl-4-(4-bromo-2-(difluoromethoxy)phenyl)piperazine-1-carboxylate Into a 250-mL round-bottom flask was added 1-(4-bromo-2-(difluoromethoxy)phenyl)piperazine (2.00 g, 6.51 mmol), Boc$_2$O (1.70 g, 7.79 mmol) and dichloromethane (50 mL). Triethylamine (1.98 g, 19.6 mmol) was added and the resulting solution was stirred for 2 h at RT and then concentrated in vacuo. The resulting crude product was purified by FCC eluting with ethyl acetate/petroleum ether (1:5) to afford tert-butyl 4-(4-bromo-2-(difluoromethoxy)phenyl)piperazine-1-carboxylate as a white solid (2.5 g, 94%). LCMS (ESI, m/z): 407 [M+H]$^+$.

Example 31-1

Intermediate 31-1. Benzyl 4-(4-bromo-2-chlorophenyl)piperazine-1-carboxylate

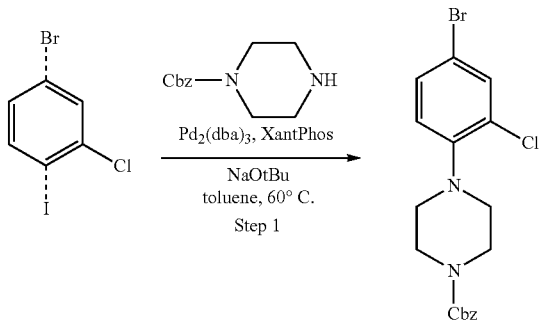

Intermediate 31-1

Into a 100-mL round-bottom flask that purged and maintained under an inert atmosphere of nitrogen was added 4-bromo-2-chloro-1-iodobenzene (1.20 g, 3.78 mmol), benzyl piperazine-1-carboxylate (0.924 g, 4.19 mmol), NaOtBu (1.10 g, 11.4 mmol), XantPhos (0.695 g, 1.20 mmol), Pd$_2$(dba)$_3$ (0.393 g, 0.430 mmol), and toluene (10 mL). The reaction mixture was stirred for 4 h at 60° C. and then concentrated in vacuo to provide a crude product that was purified by FCC eluting with ethyl acetate/petroleum ether (1:10) to afford benzyl 4-(4-bromo-2-chlorophenyl)piperazine-1-carboxylate as a colorless oil (713 mg, 46%). LCMS (ESI, m/z) 409, 411 [M+H]$^+$.

The Intermediates in Table 1 below were synthesized according to the procedures (palladium catalyzed C-N coupling) outlined above for Example 31-1, Intermediate 31-1, using the appropriate synthetic precursors.

TABLE 1

| Intermediate No.: | Precursors Used (Notes) | MS (ESI, m/z) [M + H] |
|---|---|---|
| Intermediate 31-2. Benzyl 4-(4-bromo-3-chlorophenyl)piperazine-1-carboxylate | 1-Bromo-2-chloro-4-iodobenzene and benzyl piperazine-1-carboxylate | 409 |
| Intermediate 31-3. Benzyl 4-(4-bromo-2-fluorophenyl)piperazine-1-carboxylate | 4-Bromo-2-fluoro-1-iodobenzene and benzyl piperazine-1-carboxylate | 393 |
| Intermediate 31-4. Benzyl 4-(4-bromo-3-fluorophenyl)piperazine-1-carboxylate | 1-Bromo-2-fluoro-4-iodobenzene and benzyl piperazine-1-carboxylate (Step 1 was conducted at 80° C.) | 393 |

TABLE 1-continued

| Intermediate No.: | Precursors Used (Notes) | MS (ESI, m/z) [M + H] |
|---|---|---|
| Intermediate 31-5. tert-Butyl 3-(4-bromo-2,5-difluorophenyl)-3,8-diazabicyclo[3.2.1]octane-8-carboxylate | 1,4-Dibromo-2,5-difluorobenzene and tert-butyl 3,8-diazabicyclo[3.2.1]octane-8-carboxylate (Step 1 was conducted at 70° C.) | 403 |
| Intermediate 31-6. tert-Butyl 3-(4-bromo-3-cyanophenyl)-3,8-diazabicyclo[3.2.1]octane-8-carboxylate | 2,5-Dibromobenzonitrile and tert-butyl 3,8-diazabicyclo[3.2.1]octane-8-carboxytate (Step 1 was conducted at 100° C. and BINAP was used as the phosphine ligand) | 392 |
| Intermediate 31-7. tert-Butyl 4-(4-bromonaphthalen-1-yl)piperazine-1-carboxylate | 1,4-Dibromonaphthalene and tert-butyl piperazine-1-carboxylate (Step 1 was conducted at 80° C.) | 391 |
| Intermediate 31-8. tert-Butyl 3-(4-bromo-2-ethylphenyl)-3,8-diazabicyclo[3.2.1]octane-8-carboxylate | 4-Bromo-2-ethyl-1-iodobenzene and tert-butyl 3,8-diazabicyclo[3.2.1]octane-8-carboxylate | 395 |
| Intermediate 31-9. tert-Butyl (R)-(1-(4-bromo-2,5-difluorophenyl)pyrrolidin-3-yl)(methyl)carbamate | 1,4-Dibromo-2,5-difluorobenzene and tert-butyl N-methyl-N-[(3R)-pyrrolidin-3-yl]carbamate (BINAP was used as the ligand, $Cs_2CO_3$ as the base, and 80° C. as the reaction temp) | 335 |
| Intermediate 31-10. Racemic-tert-butyl (1-(4-bromo-2,5-difluorophenyl)pyrrolidin-3-yl)(methyl)carbamate | 1,4-Dibromo-2,5-difluorobenzene and racemic tert-butyl N-methyl(pyrrolidin-3-yl)carbamate (BINAP was used as the ligand, $Cs_2CO_3$ as the base, and 80° C. as the reaction temp) | 335 |
| Intermediate 31-11. tert-Butyl (1S,4S)-5-(4-bromo-2,5-difluorophenyl)-2,5-diazabicyclo[2.2.1]heptane-2-carboxylate | 1,4-Dibromo-2,5-difluorobenzene and tert-butyl (1S,4S)-2,5-diazabicyclo[2.2.1]heptane-2-carboxylate (reaction temp: 70° C.) | 389 |
| Intermediate 31-12. tert-Butyl (1R,4R)-5-(4-bromo-2,5-difluorophenyl)-2,5-diazabicyclo[2.2.1]heptane-2-carboxylate | 1,4-Dibromo-2,5-difluorobenzene and tert-butyl (1R,4R)-2,5-diazabicyclo[2.2.1]heptane-2-carboxylate (reaction temp: 70° C.) | 389 |
| Intermediate 31-13. tert-Butyl 5-(4-bromo-2,5-difluorophenyl)hexahydropyrrolo[3,4-b]pyrrole-1(2H)-carboxylate | 1,4-Dibromo-2,5-difluorobenzene and tert-butyl octahydropyrrolo[3,4-b]pyrrole-1-carboxylate (reaction temp: 80° C.) | 403 |
| Intermediate 31-14. tert-Butyl (1-(4-bromo-2,5-difluorophenyl)azetidin-3-yl)carbamate | 1,4-Dibromo-2,5-difluorobenzene and tert-butyl N-(azetidin-3-yl)carbamate | 363, 365 |
| Intermediate 31-15: tert-Butyl 3-((4-bromo-2,5-difluorophenyl)amino)azetidine-1-carboxylate | 1,4-Dibromo-2,5-difluorobenzene and tert-butyl 3-aminoazetidine-1-carboxylate (reaction temp: 70° C.) | 363, 365 |

Example 32

Intermediate 32. Benzyl 4-(4-bromo-2,6-difluorophenyl)piperazine-1-carboxylate

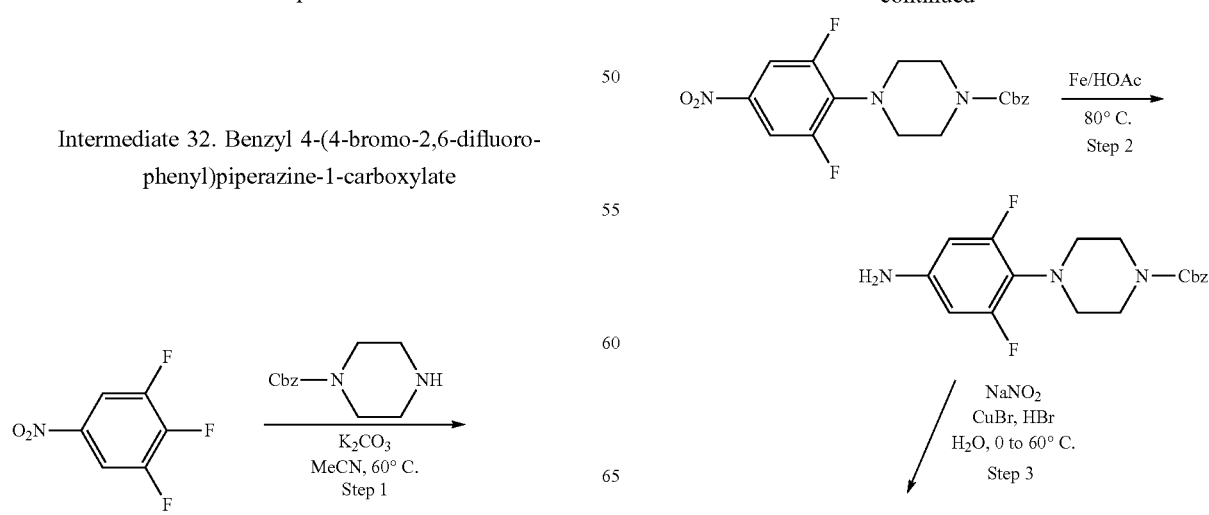

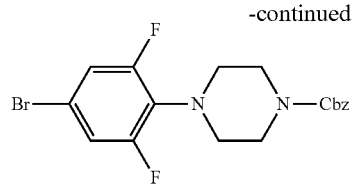

Intermediate 32

Step 1. Benzyl 4-(2,6-difluoro-4-nitrophenyl)piperazine-1-carboxylate

Into a 500-mL round-bottom flask was added 1,2,3-trifluoro-5-nitrobenzene (3.00 g, 16.9 mmol), benzyl piperazine-1-carboxylate (3.70 g, 16.8 mmol), potassium carbonate (5.85 g, 42.3 mmol), and MeCN (200 mL). The reaction mixture was stirred overnight at 60° C. and then concentrated in vacuo. The resulting crude product was purified by FCC eluting with PE/EA (1/1) to afford benzyl 4-(2,6-difluoro-4-nitrophenyl)piperazine-1-carboxylate as a yellow solid. LCMS (ESI, m/z): 378 [M+H]$^+$.

Step 2. Benzyl 4-(4-amino-2,6-difluorophenyl)piperazine-1-carboxylate

Into a 250-mL round-bottom flask was added benzyl 4-(2,6-difluoro-4-nitrophenyl)piperazine-1-carboxylate (1.60 g, 4.24 mmol), iron dust (1.6 g), and acetic acid (25 mL). The reaction mixture was stirred for 3 h at 80° C. and then cooled to RT. The solids were removed by filtration over Celite and the filtrate was diluted with EtOAc (250-mL). The organic solution was then washed with 10% aqueous sodium bicarbonate solution (1×300 mL), followed by brine (100-mL). The organic layer was dried over sodium sulfate, filtered, and concentrated in vacuo to afford benzyl 4-(4-amino-2,6-difluorophenyl)piperazine-1-carboxylate as a yellow solid (1.2 g, 81%). LCMS (ESI, m/z): 348 [M+H]$^+$.

Step 3. Benzyl 4-(4-bromo-2,6-difluorophenyl)piperazine-1-carboxylate

The title compound was prepared according to the procedure used for the preparation of Example 28: Intermediate 28, except benzyl 4-(4-amino-2,6-difluorophenyl)piperazine-1-carboxylate was used in place of 4-(piperazin-1-yl)-3-(trifluoromethyl)aniline. The title compound was obtained as a yellow solid (57%). LCMS (ESI, m/z): 411 [M+H]$^+$.

Example 33

Intermediate 33. Benzyl 4-(4-(2-((tert-butoxycarbonyl)amino)ethyl)-2-chloro-6-fluorophenyl)piperazine-1-carboxylate

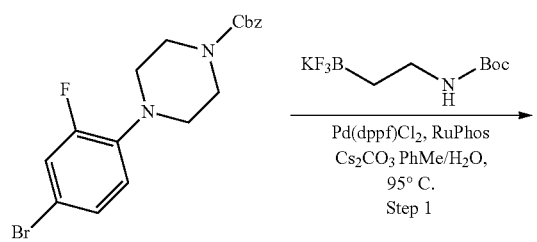

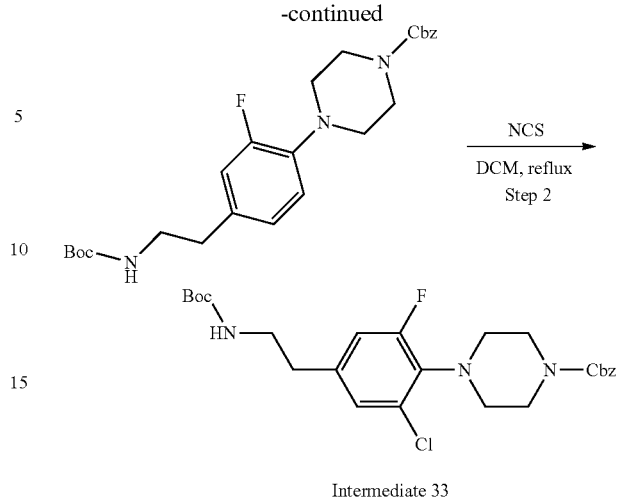

Intermediate 33

Step 1. Benzyl 4-(4-(2-((tert-butoxycarbonyl)amino)ethyl)-2-fluorophenyl)piperazine-1-carboxylate Into a 250-mL 3-necked round-bottom flask that was purged and maintained under an inert atmosphere of nitrogen was added benzyl 4-(4-bromo-2-fluorophenyl)piperazine-1-carboxylate (Intermediate 31-3, 3.20 g, 8.14 mmol), potassium (2-((tert -butoxycarbonyl)amino)ethyl) trifluoroborate (2.45 g, 9.76 mmol), Pd(dppf)Cl$_2$ (0.670 g, 0.92 mmol), cesium carbonate (7.94 g, 24.3 mmol), RuPhos (0.760 g, 1.63 mmol), toluene (90 mL) and water (30 mL). The reaction mixture was stirred for 4 h at 95° C. and then cooled and concentrated in vacuo. The resulting crude product was purified by FCC eluting with ethyl acetate/petroleum ether (1:5) to afford benzyl 4-(4-(2-((tert-butoxycarbonyl)amino)ethyl)-2-fluorophenyl) piperazine-1-carboxylate as a light yellow solid (2.2 g, 59%). LCMS (ESI, m/z): 458 [M+H]$^+$.

Step 2. Benzyl 4-(4-(2-((tert-butoxycarbonyl)amino)ethyl)-2-chloro-6-fluorophenyl) piperazine-1-carboxylate Into a 100-mL round-bottom flask was added benzyl 4-(4-(2-((tert-butoxycarbonyl) amino)ethyl)-2-fluorophenyl)piperazine-1-carboxylate (1.00 g, 2.19 mmol), dichloromethane (40 mL), and NCS (0.293 g, 2.19 mmol). The resulting solution was stirred overnight at reflux and then concentrated in vacuo to afford the crude product. The crude product was purified via silica gel chromatography and eluted with ethyl acetate/petroleum ether (1:10) to afford benzyl 4-(4-(2- ((tert-butoxycarbonyl)amino)ethyl)-2-chloro-6-fluorophenyl)piperazine-1-carboxylate as yellow oil (350 mg, 33%). LCMS (ESI, m/z): 492 [M+H]$^+$.

Example 34

Intermediate 34. Benzyl 4-(4-(2-((tert-butoxycarbonyl)amino)ethyl)-2-chlorophenyl)piperazine-1-carboxylate

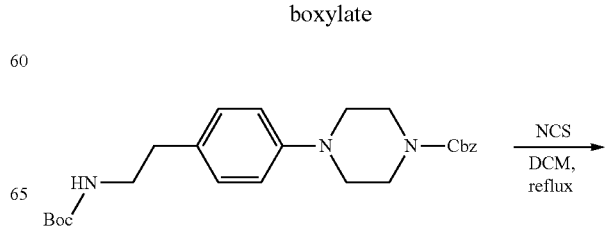

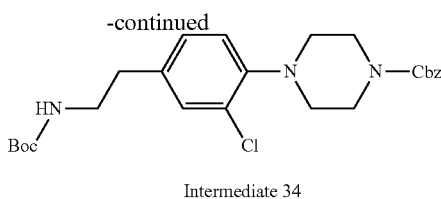

Intermediate 34

The title compound was prepared according to the procedure used for the preparation of Example 33: Intermediate 33, except benzyl 4-(4-(2-((tert-butoxycarbonyl)amino)ethyl) phenyl)piperazine-1-carboxylate was used in place of benzyl 4-[4-(2-[[(tert-butoxy)carbonyl]amino]ethyl)-2-fluorophenyl]piperazine-1-carboxylate. This afforded the title compound as a yellow solid (57%). LCMS (ESI, m/z): 474 [M+H]$^+$.

Example 35

Intermediate 35. Benzyl 7-bromo-3,4-dihydroisoquinoline-2(1H)-carboxylate

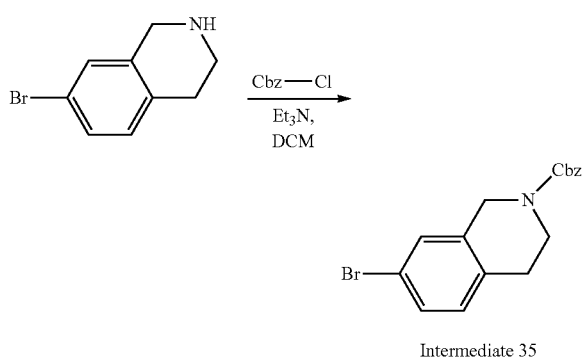

Intermediate 35

Into a 250-mL round-bottom flask was added a 7-bromo-1,2,3,4-tetrahydroisoquinoline (2.00 g, 9.43 mmol) and dichloromethane (30 mL). Triethylamine (4.80 g, 6.61 mL, 47.4 mmol) was added followed by benzyl chloroformate (1.61 g, 1.34 mL, 9.44 mmol) and the resulting solution was stirred for 1 h at RT. The reaction mixture was concentrated in vacuo and the crude product was purified by FCC eluting with ethyl acetate/petroleum ether (1:1) to afford benzyl 7-bromo-3,4-dihydroisoquinoline-2(1H)-carboxylate as a colorless oil (2.7 g, 83%). LCMS (ESI, m/z): 346 [M+H]$^+$.

Example 36

Intermediate 36. Benzyl 4-(4-bromo-2-cyclopropylphenyl)piperazine-1-carboxylate

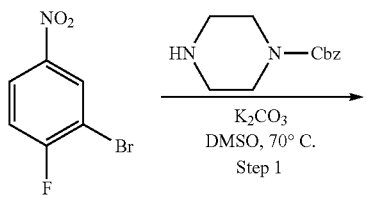

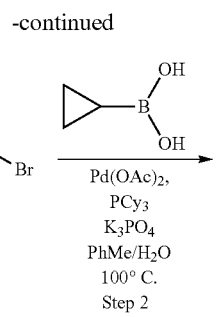

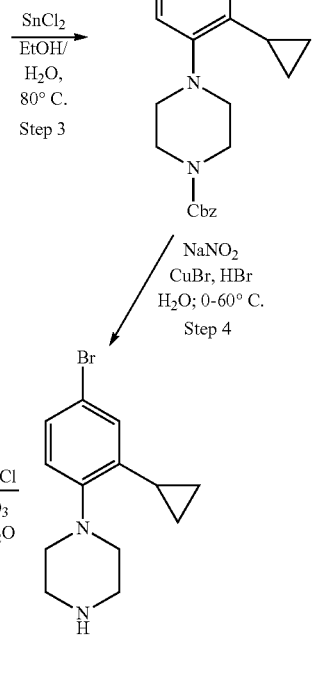

Intermediate 36

Step 1. Benzyl 4-(2-bromo-4-nitrophenyl)piperazine-1-carboxylate

Into a 250-mL round-bottom flask was added 2-bromo-1-fluoro-4-nitrobenzene (10.0 g, 45.5 mmol), benzyl piperazine-1-carboxylate (20.0 g, 90.8 mmol), potassium carbonate (12.6 g, 90.5 mmol) and DMSO (100 mL). The resulting mixture was stirred for 2 h at 70° C. and then cooled, diluted with H$_2$O (100 mL), and extracted with ethyl acetate (3×150 mL). The combined organic layers were dried over anhydrous sodium sulfate, filtered, and concentrated in vacuo to afford benzyl 4-(2-bromo-4-nitrophenyl)piperazine-1-carboxylate as yellow oil that was carried on without further purification (20 g crude; 54%). LCMS (ES, m/z): 420, 422 [M+H]$^+$.

Step 2. Benzyl 4-(2-cyclopropyl-4-nitrophenyl)piperazine-1-carboxylate

Into a 500-mL 3-necked round-bottom flask that was purged and maintained under an inert atmosphere of nitrogen was added benzyl 4-(2-bromo-4-nitrophenyl)piperazine-1-carboxylate (8.00 g, 19.0 mmol), cyclopropylboronic acid (6.55 g, 76.3 mmol), Pd(OAc)$_2$ (0.21 g, 0.95 mmol), PCy3 (0.536 g, 1.90 mmol), potassium phosphate tribasic (14.1 g, 66.43 mmol), toluene (200 mL), and water (10 mL). The reaction mixture was stirred for 2 h at 100° C. and then cooled and concentrated in vacuo. The resulting crude product was purified by FCC eluting with ethyl acetate/petroleum ether (1:3) to afford benzyl 4-(2-cyclopropyl-4-nitrophenyl)piperazine-1-carboxylate as a yellow solid (6.6 g, 91%). LCMS (ESI, m/z): 382 [M+H]$^+$.

Step 3. Benzyl 4-(4-amino-2-cyclopropylphenyl)piperazine-1-carboxylate

Into a 250-mL round-bottom flask was added a benzyl 4-(2-cyclopropyl-4-nitrophenyl)piperazine-1-carboxylate (3.60 g, 9.44 mmol), anhydrous tin (II) chloride (8.54 g, 45.0 mmol), ethanol (100-mL), and water (10 mL). The reaction mixture was stirred for 3 h at 80° C. and then cooled and concentrated in vacuo. The resulting crude product was purified by FCC eluting with ethyl acetate to afford benzyl 4-(4-amino-2-cyclopropylphenyl)piperazine-1-carboxylate as a yellow solid (3 g, 90%). LCMS (ESI, m/z): 352 [M+H]$^+$.

Step 4. 1-(4-Bromo-2-cyclopropylphenyl)piperazine.

Into a 100-mL 3-necked round-bottom flask was added benzyl 4-(4-amino-2-cyclopropylphenyl)piperazine-1-carboxylate (2.00 g, 5.69 mmol) and aqueous HBr (48%, 20 mL). This was followed by the addition of a solution of sodium nitrite (0.430 g, 6.23 mmol) in water (5 mL) dropwise with stirring at 0° C. The resulting solution was stirred for 30 min at 0° C. and then a solution of cuprous bromide (1.7 g, 11.85 mmol) in aqueous HBr (48%, 20 mL) was added dropwise with stirring at 0° C. The resulting solution was stirred for 1 h at 60° C. The pH of the solution was adjusted to approximately 8-9 with aqueous sodium hydroxide (2 M) and then the solution was extracted with ethyl acetate (3×100 mL). The combined organic layers were then dried over anhydrous sodium sulfate, filtered, and concentrated in vacuo to provide a crude product that was purified by FCC eluting with ethyl acetate/petroleum ether (1:1) to afford 1-(4-bromo-2-cyclopropylphenyl)piperazine as a yellow solid (1 g, 62%). LCMS (ES, m/z): 281, 283 [M+H]$^+$.

Step 5. Benzyl 4-(4-bromo-2-cyclopropylphenyl)piperazine-1-carboxylate

Into a 50-mL round-bottom flask was added 1-(4-bromo-2-cyclopropylphenyl)piperazine (1.00 g, 3.56 mmol) and tetrahydrofuran (15 mL). This was followed by the addition of a solution of sodium carbonate (1.13 g, 13.4 mmol) in water (5 mL) dropwise with stirring. To the reaction mixture was added benzyl chloroformate (0.730 g, 0.608 mL, 4.28 mmol) dropwise with stirring at 0° C. The resulting solution was warmed and stirred for 1 h at RT and then washed with H$_2$O (2×10 mL). The organic layer was dried over sodium sulfate, filtered, and concentrated in vacuo. The resulting crude product was purified by FCC eluting with ethyl acetate/petroleum ether (1:10) to afford benzyl 4-(4-bromo-2-cyclopropylphenyl)piperazine -1-carboxylate as a yellow solid (1.1 g, 74%). LCMS (ESI, m/z): 414, 416 [M+H]$^+$.

Example 37

Intermediate 37. Benzyl 4-(4-(2-((tert-butoxycarbonyl)amino)ethyl)-3-cyclopropylphenyl)piperazine-1-carboxylate

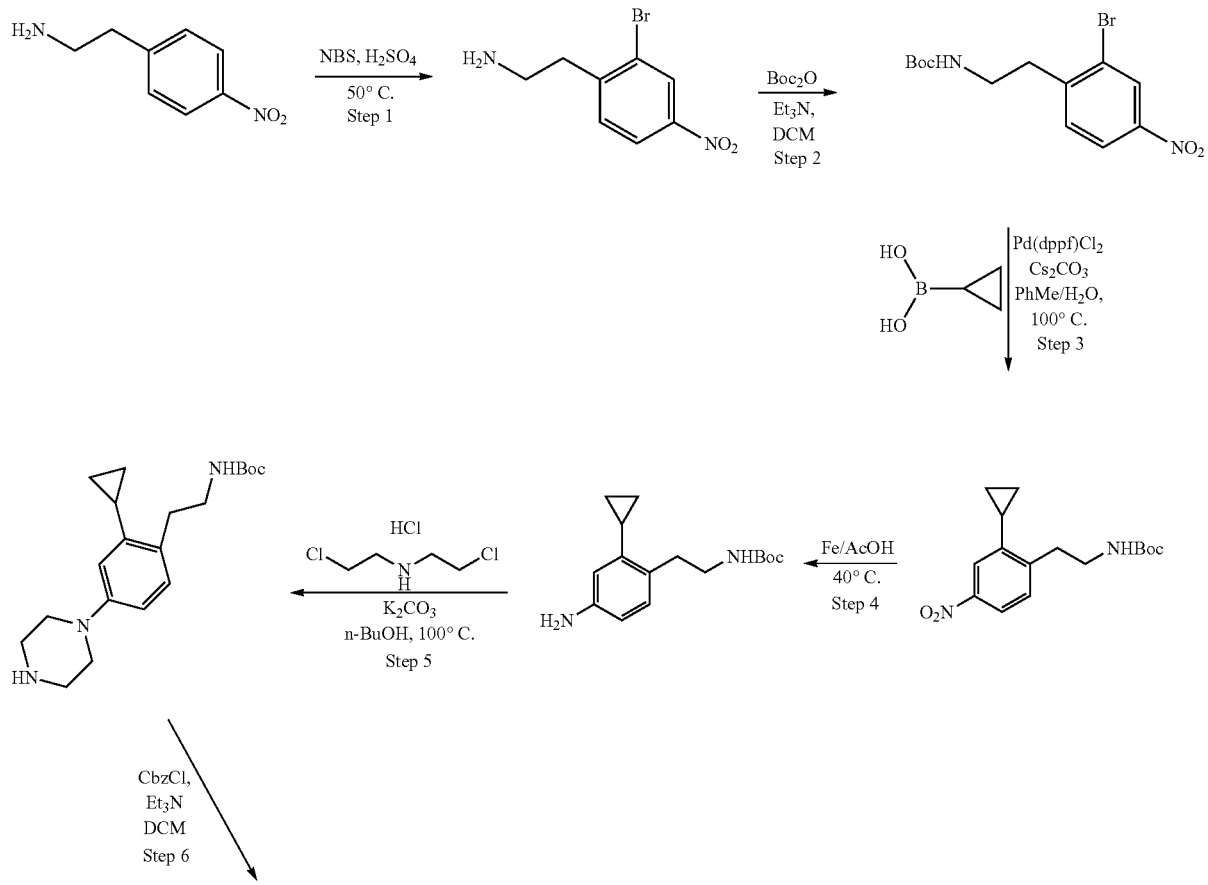

-continued

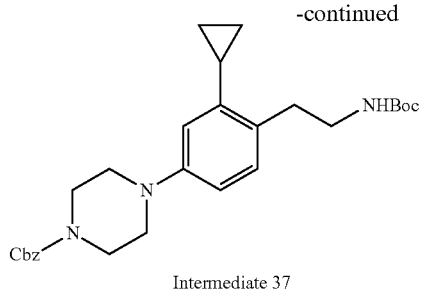

Intermediate 37

Step 1. 2-(2-Bromo-4-nitrophenyl)ethan-1-amine

Into a 500-mL round-bottom flask was added 2-(4-nitrophenyl)ethan-1-amine (8.30 g, 50.0 mmol), NBS (9.79 g, 55.0 mmol), and sulfuric acid (conc., 200 mL). The resulting solution was stirred for 2 h at 50° C. and then cooled to RT, and quenched with water (200 mL). The pH of the solution was adjusted to approximately 7 with aqueous sodium hydroxide (1 M). The resulting solution was extracted with dichloromethane (3×300 mL). The combined organic layers were dried over anhydrous sodium sulfate, filtered, and concentrated in vacuo to afford 2-(2-bromo-4-nitrophenyl)ethan-1-amine as an off-white oil (12 g, 98%). LCMS (ESI, m/z): 245 [M+H]$^+$.

Step 2. tert-Butyl (2-bromo-4-nitrophenethyl)carbamate

Into a 500-mL round-bottom flask was added 2-(2-bromo-4-nitrophenyl)ethan-1-amine (12.0 g, 49.0 mmol) and dichloromethane (250-mL). Boc$_2$O (11.0 g, 50.40 mmol) was added followed by triethylamine (15.0 g, 20.7 mL, 149 mmol), and the resulting solution was stirred for 2 h at RT. The reaction mixture was concentrated in vacuo. The resulting crude product was purified by FCC eluting with ethyl acetate/petroleum ether (1:5) to afford tert-butyl (2-bromo-4-nitrophenethyl)carbamate as a yellow solid (13 g, 77%). LCMS (ESI, m/z): 345 [M+H]$^+$.

Step 3. tert-Butyl (2-cyclopropyl-4-nitrophenethyl)carbamate

Into a 100-mL round-bottom flask, purged and maintained under an inert atmosphere of nitrogen, was added tert-butyl (2-bromo-4-nitrophenethyl)carbamate (3.44 g, 9.97 mmol), cyclopropylboronic acid (1.72 g, 20.0 mmol), Pd(dppf)Cl$_2$ (0.732 g, 1.00 mmol), Cs$_2$CO$_3$ (9.78 g, 30.0 mmol), toluene (20 mL), and water (2 mL). The reaction mixture was stirred overnight at 100° C. then cooled and concentrated in vacuo. The resulting crude product was purified by FCC eluting with ethyl acetate/petroleum ether (1:5) to afford tert-butyl (2-cyclopropyl-4-nitrophenethyl)carbamate as an orange solid (2.8 g, 91%). LCMS: (ESI, m/z): 307 [M+H]$^+$.

Step 4. tert-Butyl (4-amino-2-cyclopropylphenethyl)carbamate

Into a 250-mL round-bottom flask was added tert-butyl (2-cyclopropyl-4-nitrophenethyl)carbamate (1.40 g, 4.57 mmol), iron powder (2.8 g, 50.1 mmol), and AcOH (20 mL). The reaction mixture was stirred for 2 h at 40° C. and then quenched with water (100-mL). The pH of the solution was adjusted to approximately 7 with aqueous sodium bicarbonate. The mixture was extracted with dichloromethane (3×300 mL). The combined organic layers were then dried over sodium sulfate, filtered, and concentrated in vacuo to afford tert-butyl (4-amino -2-cyclopropylphenethyl)carbamate as a brown oil (1.1 g, 87%). LCMS (ESI, m/z): 277 [M+H]$^+$.

Step 5. tert-Butyl (2-cyclopropyl-4-(piperazin-1-yl)phenethyl)carbamate

Into a 250-mL round-bottom flask, purged and maintained under an inert atmosphere of nitrogen, was added tert-butyl (4-amino-2-cyclopropylphenethyl)carbamate (1.10 g, 3.98 mmol), bis(2-chloroethyl)amine hydrochloride (1.10 g, 6.16 mmol; Caution: toxic), potassium carbonate (1.70 g, 12.3 mmol), and n-BuOH (20 mL). The reaction mixture was stirred overnight at 100° C. in an oil bath and then cooled and concentrated in vacuo to afford tert-butyl (2-cyclopropyl-4-(piperazin-1-yl)phenethyl)carbamate as a brown solid (1.2 g, 87%). LCMS (ESI, m/z): 346 [M+H]$^+$.

Step 6. Benzyl 4-(4-(2-((tert-butoxycarbonyl)amino)ethyl)-3-cyclopropylphenyl)piperazine -1-carboxylate Into a 250-mL round-bottom flask was added tert-butyl (2-cyclopropyl-4-(piperazin-1-yl)phenethyl)carbamate (1.20 g, 3.47 mmol), triethylamine (1.10 g, 1.51 mL, 10.87 mmol), and dichloromethane (40 mL) followed by the dropwise addition of Cbz-Cl (0.663 g, 0.552 mL, 3.89 mmol) with stirring. The resulting solution was stirred overnight at RT and then concentrated in vacuo. The resulting crude product was purified by FCC eluting with ethyl acetate/petroleum ether (1:1) to afford benzyl 4-(4-(2-((tert-butoxycarbonyl)amino)ethyl)-3-cyclopropylphenyl)piperazine-1-carboxylate as a colorless oil (1 g, 60%). LCMS (ESI, m/z): 480 [M+H]$^+$.

Example 38

Intermediate 38. Benzyl 4-(6-(2-((tert-butoxycarbonyl)amino)ethyl)-[1,1'-biphenyl]-3-yl)piperazine-1-carboxylate

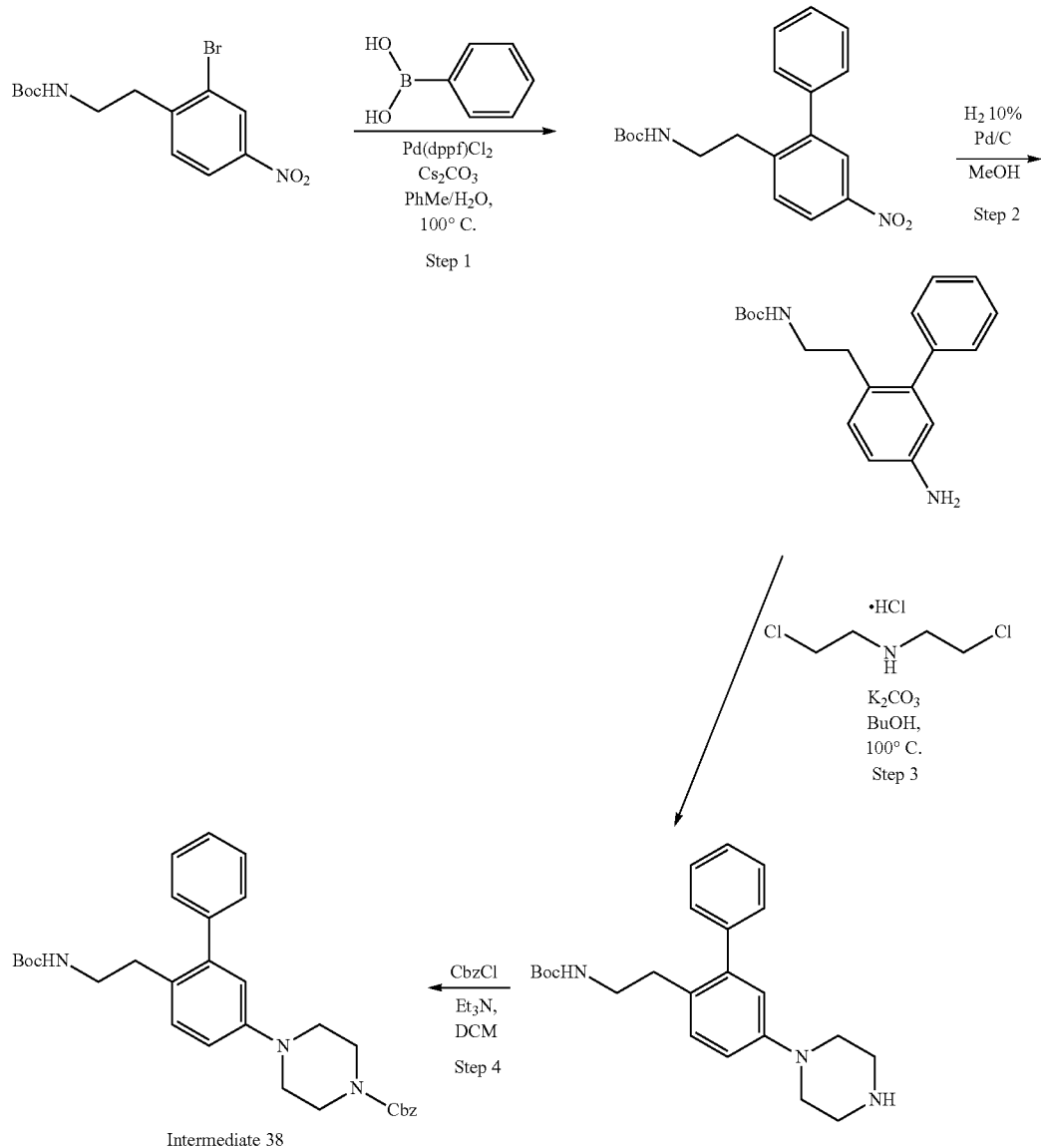

Intermediate 38

Step 1. tert-Butyl (2-(5-nitro-[1,1'-biphenyl]-2-yl)ethyl)carbamate

Into a 100-mL round-bottom flask, purged and maintained under an inert atmosphere of nitrogen, was added tert-butyl N-[2-(2-bromo-4-nitrophenyl)ethyl]carbamate (3.44 g, 9.97 mmol), phenylboronic acid (2.44 g, 20.0 mmol), Pd(dppf)Cl$_2$ (0.732 g, 1.00 mmol), Cs$_2$CO$_3$ (9.78 g, 30.0 mmol), toluene (20 mL), and water (2 mL). The reaction mixture was stirred overnight at 100° C. and then cooled and concentrated in vacuo. The resulting crude product was purified by FCC eluting with ethyl acetate/petroleum ether (1:5) to afford tert-butyl (2-(5-nitro-[1,1'-biphenyl]-2-yl)ethyl)carbamate as an orange oil (3.3 g, 97%). LCMS (ESI, m/z): 343 [M+H]$^+$ Step 2. tert-Butyl (2-(5-amino-[1,1'-biphenyl]-2-yl)ethyl)carbamate Into a 250-mL round-bottom flask, purged and maintained with nitrogen, was added tert-butyl (2-(5-nitro-[1,1'-biphenyl]-2-yl)ethyl)carbamate (1.73 g, 5.05 mmol), 10% palladium on carbon (173 mg), and methanol (80 mL). The resulting mixture was sparged with hydrogen and the reaction mixture was stirred for 2 h at RT under a hydrogen atmosphere using a hydrogen balloon. The reaction was vented to nitrogen and the solids were removed by filtration over Celite. The filtrate was concentrated in vacuo to afford tert-butyl (2-(5-amino-[1,1'-biphenyl]-2-yl)ethyl)carbamate as a brown oil (1.5 g, 95%). LCMS (ESI, m/z): 313 [M+H]$^+$.

Step 3. tert-Butyl (2-(5-(piperazin-1-yl)-[1,1'-biphenyl]-2-yl)ethyl)carbamate

Into a 250-mL round-bottom flask, purged and maintained under an inert atmosphere of nitrogen, was added tert-butyl (2-(5-amino-[1,1'-biphenyl]-2-yl)ethyl)carbamate (1.50 g, 4.80 mmol), bis(2-chloroethyl)amine hydrochloride (1.30 g, 7.28 mmol), potassium carbonate (2.00 g, 14.5 mmol), and BuOH (30 mL). The resulting solution was stirred overnight at 100° C. in an oil bath and then the resulting mixture was concentrated in vacuo to afford crude tert-butyl (2-(5-(piperazin-1-yl)-[1,1'-biphenyl]-2-yl)ethyl)carbamate as a brown solid (1.7 g) that was carried on without further purification. LCMS (ESI, m/z): 382 [M+H]$^+$.

Step 4. Benzyl 4-(6-(2-((tert-butoxycarbonyl)amino)ethyl)-[1,1'-biphenyl]-3-yl)piperazine-1-carboxylate Into a 250-mL round-bottom flask was added tert-butyl (2-(5-(piperazin-1-yl)-[1,1'-biphenyl]-2-yl)ethyl)carbamate (1.70 g, 4.46 mmol), dichloromethane (100 mL), and TEA (1.40 g, 13.8 mmol). This was followed by the dropwise addition of Cbz-Cl (1.20 g, 1.00 mL, 7.03 mmol) with stirring. The resulting solution was stirred for 2 h at RT and then was concentrated in vacuo to afford the crude product that was purified via silica gel chromatography and eluted with ethyl acetate/petroleum ether (1:5) to afford benzyl 4-(6-(2-((tert-butoxycarbonyl)amino) ethyl)-[1,1'-biphenyl]-3-yl)piperazine-1-carboxylate as a brown solid (800 mg, 35%). LCMS (ESI, m/z): 516 [M+H]$^+$.

Example 39

Intermediate 39. Benzyl 4-(4-bromo-2-ethoxyphenyl)piperazine-1-carboxylate

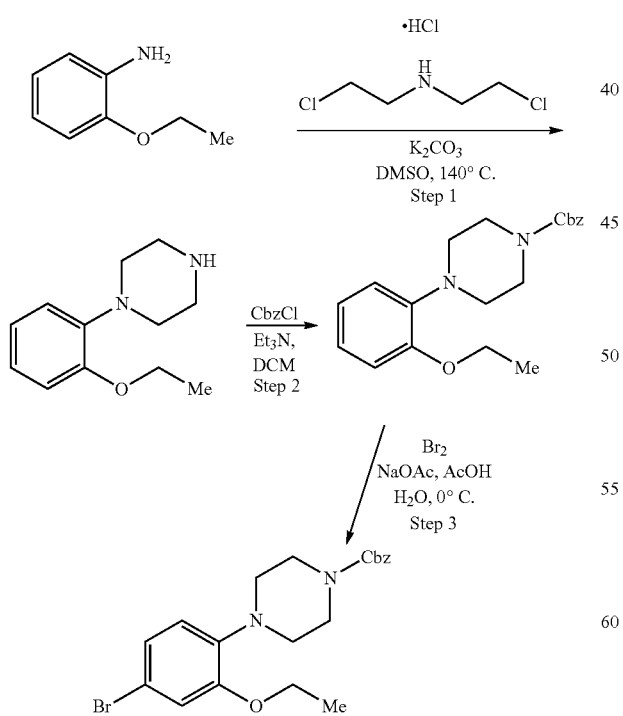

Intermediate 39

Step 1. 1-(2-Ethoxyphenyl)piperazine

Into a 250-mL round-bottom flask was added 2-ethoxyaniline (4.11 g, 30.0 mmol), bis(2-chloroethyl)amine hydrochloride (6.40 g, 35.9 mmol), potassium carbonate (12.4 g, 89.9 mmol), and DMSO (30 mL). The reaction mixture was stirred overnight at 140° C. and then concentrated in vacuo. The resulting crude product was purified by FCC eluting with dichloromethane/methanol (5:1) to afford 1-(2-ethoxyphenyl)piperazine as a brown oil (5.1 g, 83%). LCMS (ESI, m/z): 207 [M+H]$^+$.

Step 2. Benzyl 4-(2-ethoxyphenyl)piperazine-1-carboxylate

Into a 500-mL round-bottom flask was added 1-(2-ethoxyphenyl)piperazine (9.20 g, 44.6 mmol), triethylamine (14.2 g, 140 mmol), and dichloromethane (250 mL). Benzyl chloroformate (9.60 g, 8.00 mL, 56.3 mmol) was added and the resulting solution was stirred for 1 h at RT. The reaction was then concentrated in vacuo and the crude product was purified by FCC eluting with ethyl acetate/petroleum ether (1:5) to afford benzyl 4-(2-ethoxyphenyl)piperazine-1-carboxylate as a purple solid (3.1 g, 20%). LCMS (ESI, m/z): 341 [M+H]$^+$.

Step 3. Benzyl 4-(4-bromo-2-ethoxyphenyl)piperazine-1-carboxylate

Into a 50-mL round-bottom flask was added benzyl 4-(2-ethoxyphenyl)piperazine-1-carboxylate (0.680 g, 2.00 mmol), NaOAc (0.164 g, 2.00 mmol), AcOH (14 mL), and water (3 mL). To the resulting solution Br$_2$ (0.316 g, 0.102 mL, 1.98 mmol) was added dropwise at 0° C., The reaction mixture was stirred for 2 h at 0° C. and then concentrated in vacuo and diluted with water (20 mL). The pH of the solution was adjusted to approximately 7 with aqueous sodium hydroxide (1 M). The resulting solution was extracted with ethyl acetate (3×50-mL). The combined organic layers were then dried over anhydrous sodium sulfate, filtered, and concentrated in vacuo to afford benzyl 4-(4-bromo-2-ethoxyphenyl)piperazine-1-carboxylate as a purple oil (280 mg, 33%). LCMS (ESI, m/z): 419 [M+H]$^+$.

Example 40

Intermediate 40. Methyl 5-bromo-2,3-dihydro-1H-indene-2-carboxylate

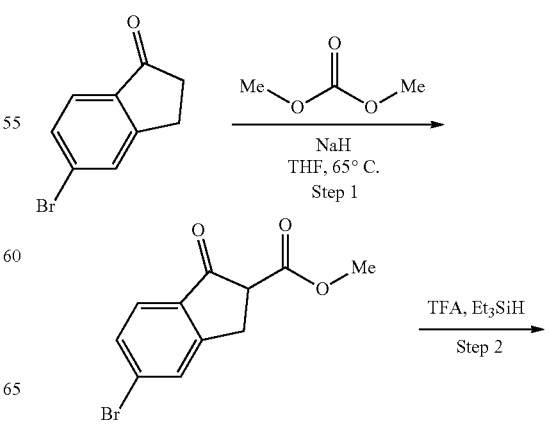

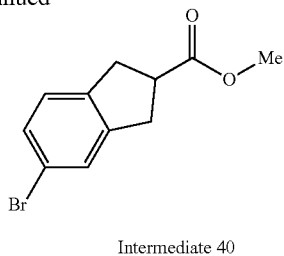

Intermediate 40

Step 1. Methyl 5-bromo-1-oxo-2,3-dihydro-1H-indene-2-carboxylate

Into a 250-mL round-bottom flask was added 5-bromo-2,3-dihydro-1H-inden-1-one (6.93 g, 32.8 mmol) and THF (30 mL). To the resulting solution was added sodium hydride (60% dispersion in mineral oil; 2.64 g, 110 mmol), followed by dimethyl carbonate (4.49 g, 4.2 mL, 49.9 mmol). The reaction mixture was stirred for 30 min at 65° C. The reaction was cooled to RT, and was quenched with HCl (3 M) to a final pH of approximately 6. The resulting solution was extracted with ethyl acetate (3×100 mL). The combined organic layers were then dried over anhydrous magnesium sulfate, filtered and concentrated in vacuo to afford methyl 5-bromo-1-oxo-2,3-dihydro-1H-indene-2-carboxylate as a yellow solid (8.5 g, 96%). LCMS (ESI, m/z): 269 [M+H]$^+$.

Step 2. Methyl 5-bromo-2,3-dihydro-1H-indene-2-carboxylate

Into a 250-mL round-bottom flask was added methyl 5-bromo-1-oxo-2,3-dihydro-1H-indene-2-carboxylate (7.80 g, 29.0 mmol) and trifluoroacetic acid (132 mL). Triethylsilane (20.4 g, 28 mL, 175 mmol) was added and the resulting solution was stirred for 2 h at RT. The reaction mixture was concentrated in vacuo and diluted with water (100 mL). The solution was then extracted with ethyl acetate (3×600 mL). The combined organic layers were then dried over anhydrous magnesium sulfate, filtered, and concentrated in vacuo to afford methyl 5-bromo-2,3-dihydro-1H-indene-2-carboxylate as a yellow solid (6.21 g, 84%). LCMS (ESI, m/z): 255 [M+H]$^+$.

Example 41

Intermediate 41. Methyl 4-(2-((tert-butoxycarbonyl)amino)ethyl)benzoate

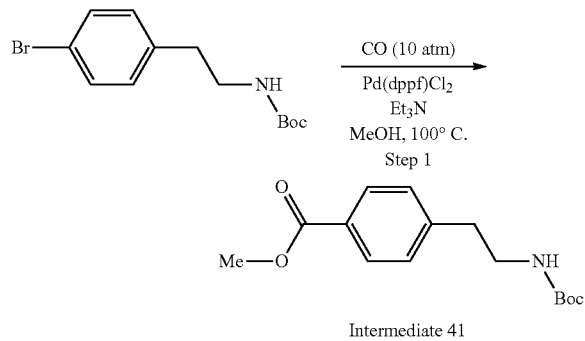

Intermediate 41

Into a 100-mL pressure tank reactor was added tert-butyl N-[2-(4-bromophenyl)ethyl]carbamate (1.50 g, 5.00 mmol), Pd(dppf)Cl$_2$ (0.367 g, 0.500 mmol), triethylamine (1.01g, 1.39 mL, 9.98 mmol), and methanol (20 mL). The reaction vessel was pressurized with CO (10 atm) and the reaction mixture was stirred overnight at 100° C. under carbon monoxide atmosphere (10 atm). The reaction was vented to nitrogen and the solids were removed by filtration over Celite. The filtrate was concentrated in vacuo to provide a crude product that was purified by FCC eluting with ethyl acetate/petroleum ether (1:1) to afford methyl 4-(2-((tert-butoxycarbonyl)amino)ethyl)benzoate as a white solid (1.1 g, 79%). LCMS (ESI, m/z): 280 [M+H]$^+$.

Example 42

Intermediate 42. Methyl 3-(2-aminoethyl)benzoate

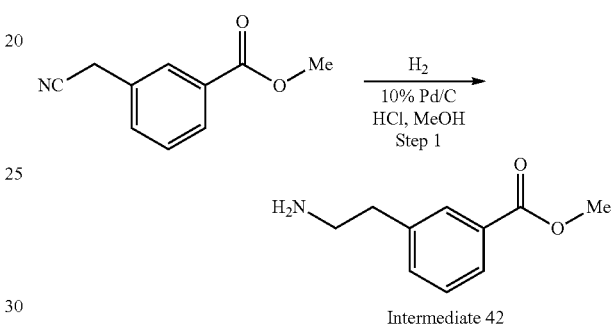

Intermediate 42

Into a 250-mL round-bottom flask purged and maintained with nitrogen was added methyl 3-(cyanomethyl)benzoate (1.00 g, 5.71 mmol), methanol (60 mL), and aqueous HCl (1 M; 0.66 mL). This was followed by the addition of 10% palladium on carbon (0.48 g). The resulting mixture was sparged with hydrogen and then stirred for 2 h at RT under a hydrogen atmosphere using a hydrogen balloon. The reaction was vented to nitrogen and the solids were removed by filtration over Celite. The filtrate was concentrated in vacuo to afford methyl 3-(2-aminoethyl)benzoate as a yellow solid (0.8 g, 78%). LCMS (ESI, m/z): 180 [M+H]$^+$.

The Intermediates in Table 2 below were synthesized according to Steps 5 and 6 of the procedure outlined above for Example 28: Intermediate 28, using the appropriate synthetic precursors. Either Method A (Steps 1 and 2 below) or Method B (Step 2 only) was used to obtain the title compounds below.

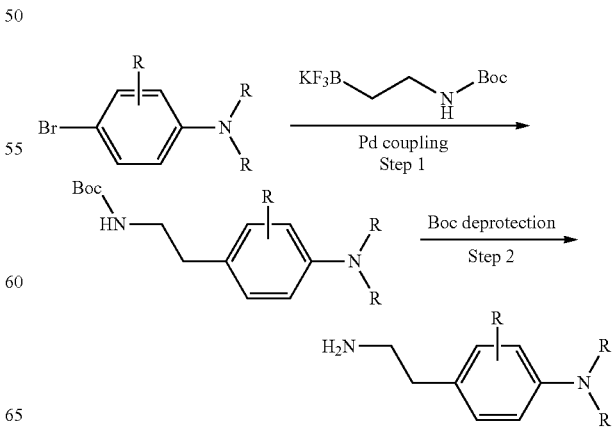

TABLE 2

| Intermediate No.: | Precursors Used (Notes) | MS (ESI, m/z) [M + H] |
|---|---|---|
| Intermediate 43-1. Benzyl 4-(4-(2-aminoethyl)-2-methylphenyl)piperazine-1-carboxylate (hydrochloride salt) | Benzyl 4-(4-bromo-2-methylphenyl)piperazine-1-carboxylate (Method A) | 354 |
| Intermediate 43-2. Benzyl 4-(4-(2-aminoethyl)-2-chlorophenyl)piperazine-1-carboxylate (hydrochloride salt) | Benzyl 4-(4-bromo-2-chlorophenyl)piperazine-1-carboxylate (Method A) | 374 |
| Intermediate 43-3. Benzyl 4-(4-(2-aminoethyl)-2-fluorophenyl)piperazine-1-carboxylate (hydrochloride salt) | Benzyl 4-(4-bromo-2-fluorophenyl)piperazine-1-carboxylate (Method A) | 358 |
| Intermediate 43-4. Benzyl 4-(4-(2-aminoethyl)-3-fluorophenyl)piperazine-1-carboxylate (hydrochloride salt) | Benzyl 4-(4-bromo-3-fluorophenyl)piperazine-1-carboxylate (Method A; no phosphine ligand was used in the Pd coupling) | 358 |
| Intermediate 43-5. Methyl 2-(3-(2-aminoethyl)phenyl)acetate (hydrochloride salt) | Methyl 2-(3-bromophenyl)acetate (Method A; no phosphine ligand was used in the Pd coupling) | 194 |
| Intermediate 43-6. Benzyl 4-(4-(2-aminoethyl)-2-chloro-6-fluorophenyl)piperazine-1-carboxylate (hydrochloride salt) | Benzyl 4-(4-(2-((tert-butoxycarbonyl)amino)ethyl)-2-chloro-6-fluorophenyl)piperazine-1-carboxylate (Method B; MeOH solvent used in Boc deprotection) | 392 |
| Intermediate 43-7. Benzyl 7-(2-aminoethyl)-3,4-dihydroisoquinoline-2(1H)-carboxylate (hydrochloride salt) | Benzyl 7-bromo-3,4-dihydroisoquinoline-2(1H)-carboxylate (Method A; no phosphine ligand was used in the Pd coupling) | 311 |
| Intermediate 43-8. Benzyl 4-(4-(2-aminoethyl)-2-cyclopropylphenyl)piperazine-1-carboxylate (hydrochloride salt) | Benzyl 4-(4-bromo-2-cyclopropylphenyl)piperazine-1-carboxylate (Method A) | 380 |
| Intermediate 43-9. Benzyl 4-(4-(2-aminoethyl)-3-cyclopropylphenyl)piperazine-1-carboxylate (hydrochloride salt) | Benzyl 4-[4-(2-[[(tert-butoxy)carbonyl]amino]ethyl)-3-cyclopropylphenyl]piperazine-1-carboxylate (Method B) | 380 |
| Intermediate 43-10. Benzyl 4-(6-(2-aminoethyl)-[1,1'-biphenyl]-3-yl)piperazine-1-carboxylate (hydrochloride salt) | Benzyl 4-(6-(2-((tert-butoxycarbonyl)amino)ethyl)-[1,1'-biphenyl]-3-yl)piperazine-1-carboxylate (Method B) | 416 |
| Intermediate 43-11. Benzyl 4-(4-(2-aminoethyl)-2-ethoxyphenyl)piperazine-1-carboxylate (hydrochloride salt) | Benzyl 4-(4-bromo-2-ethoxyphenyl)piperazine-1-carboxylate (Method A; no phosphine ligand was used in the Pd coupling) | 384 |
| Intermediate 43-12. Methyl 5-(2-aminoethyl)-2,3-dihydro-1H-indene-2-carboxylate | Methyl 5-bromo-2,3-dihydro-1H-indene-2-carboxylate (Method A; no phosphine ligand was used in the Pd coupling) | 220 |
| Intermediate 43-13. Benzyl 1-(4-(2-aminoethyl)-2-fluorophenyl)-4,6-dihydropyrrolo[3,4-c]pyrazole-5(1H)-carboxylate (hydrochloride salt) | Benzyl 1-(4-bromo-2-fluorophenyl)-1H,4H,5H,6H-pyrrolo[3,4-c]pyrazole-5-carboxylate (Method A; no phosphine ligand was used in the Pd coupling) | 381 |
| Intermediate 43-14. Methyl 4-(2-aminoethyl)benzoate | Methyl 4-(2-((tert-butoxycarbonyl)amino)ethyl)benzoate (Method B; the product was isolated as the free base following aqueous workup with DCM/saturated NaHCO$_3$) | 180 |
| Intermediate 43-15. Benzyl 4-(4-(2-aminoethyl)-3-chlorophenyl)piperazine-1-carboxylate (hydrochloride salt) | Benzyl 4-(4-bromo-3-chlorophenyl)piperazine-1-carboxylate (Method A; no phosphine ligand was used in the Pd coupling) | 374 |
| Intermediate 43-16. Benzyl 4-(4-(2-aminoethyl)-2,6-difluorophenyl)piperazine-1-carboxylate (hydrochloride salt) | Benzyl 4-(4-bromo-2,6-difluorophenyl)piperazine-1-carboxylate (Method A) | 376 |

Example 44

Intermediate 44. tert-Butyl 4-(4-(2-aminoethyl)-2-fluorophenyl)piperazine-1-carboxylate

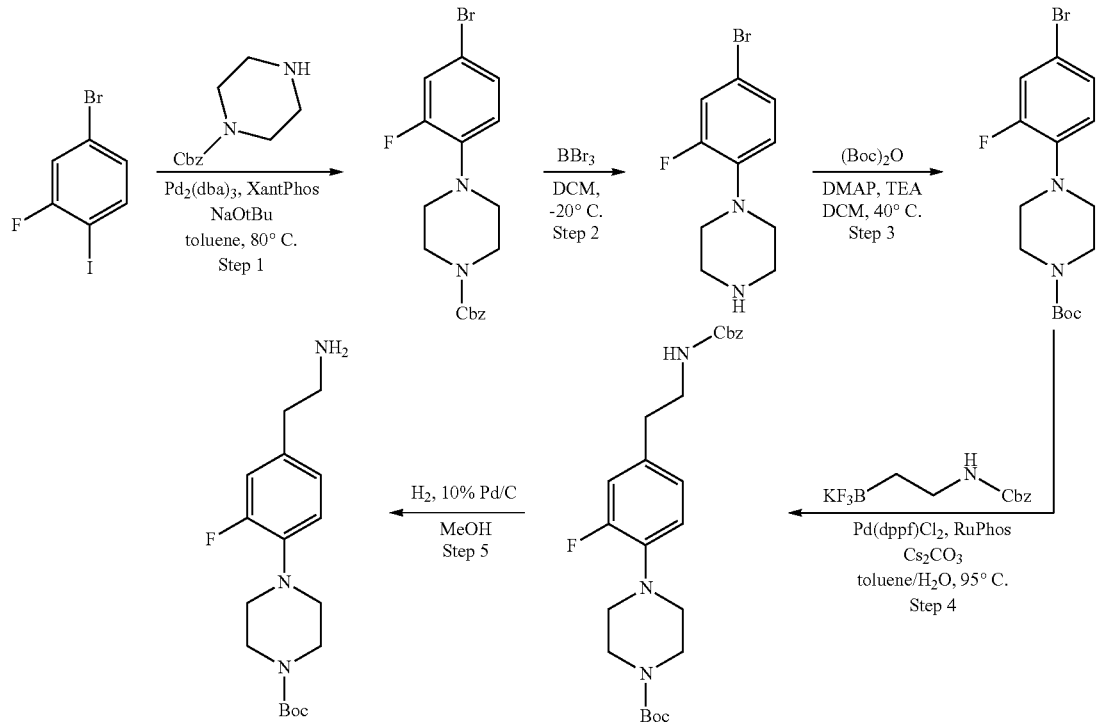

Intermediate 44

Step 1. Benzyl 4-(4-bromo-2-fluorophenyl)piperazine-1-carboxylate

Into a 100-mL round-bottom flask, purged and maintained under an inert atmosphere of nitrogen, was added 4-bromo-2-fluoro-1-iodobenzene (3.00 g, 10.0 mmol), benzyl piperazine-1-carboxylate (2.60 g, 11.8 mmol), Pd$_2$(dba)$_3$ (0.458 g, 0.500 mmol), XantPhos (0.595 g, 1.00 mmol), and NaOtBu (2.88 g, 30.0 mmol). Toluene (30 mL) was added and the reaction mixture was stirred for 2 h at 80° C. then concentrated in vacuo to a crude material that was purified by FCC eluting with ethyl acetate/petroleum ether (1:10) to afford benzyl 4-(4-bromo-2-fluorophenyl)piperazine-1-carboxylate as a brown oil (2.5 g, 64%). LCMS (ESI, m/z): 393 [M+H]$^+$.

Step 2. 1-(4-Bromo-2-fluorophenyl)piperazine

Into a 100-mL round-bottom flask was added a solution of benzyl 4-(4-bromo-2-fluorophenyl)piperazine-1-carboxylate (3.00 g, 7.63 mmol) in dichloromethane (20 mL) followed by boron tribromide (3.00 mL, 22.8 mmol) dropwise at −20° C. The resulting solution was stirred for 1 h at −20° C. and then quenched with methanol (10 mL). The reaction mixture was concentrated in vacuo to afford a crude product that was purified by FCC eluting with ethyl acetate/petroleum ether (1:3) to afford 1-(4-bromo-2-fluorophenyl)piperazine as a yellow solid (1.6 g, 81%). LCMS (ESI, m/z): 259 [M+H]$^+$.

Step 3. tert-Butyl 4-(4-bromo-2-fluorophenyl)piperazine-1-carboxylate

Into a 50-mL round-bottom flask was added 1-(4-bromo-2-fluorophenyl)piperazine (1.5 g, 6.0 mmol), 4-dimethylaminopyridine (0.150 g, 1.0 mmol), triethylamine (1.76 g, 2.42 mL, 17.5 mmol), di-tert-butyl dicarbonate (1.52 g, 7.50 mmol), and dichloromethane (20 mL). The resulting solution was stirred for 2 h at 40° C. in an oil bath and then concentrated in vacuo. The resulting crude product was purified by FCC eluting with ethyl acetate/petroleum ether (1:10) to afford tert-butyl 4-(4-bromo-2-fluorophenyl)piperazine-1-carboxylate as a white solid (2.02 g, 98%). LCMS (ESI, m/z): 359 [M+H]$^+$.

Step 4. tert-Butyl 4-(4-(2-(((benzyloxy)carbonyl)amino)ethyl)-2-fluorophenyl)piperazine-1-carboxylate Into a 100-mL round-bottom flask, purged and maintained under an inert atmosphere of nitrogen, was added tert-butyl 4-(4-bromo-2-fluorophenyl)piperazine-1-carboxylate (0.500 g, 1.39 mmol), potassium (2-(benzyloxycarbonylamino)ethyl) trifluoroborate (0.398 g, 1.40 mmol; either purchased commercially or prepared according to the procedure of Molander, G. A. et al; *J. Org. Chem.* 2007, 72, 8422.), Pd(dppf)Cl$_2$ (0.114 g, 0.160 mmol), Cs$_2$CO$_3$ (1.36 g, 4.18 mmol), RuPhos (0.130 g, 0.280 mmol), and toluene/water (10 mL/ 3 mL). The resulting mixture was stirred for 5 h at 95° C. in an oil bath and then cooled to RT, and concentrated in vacuo. The resulting crude product was purified by FCC eluting with ethyl acetate/petroleum ether (1:5) to afford tert-butyl 4-(4-(2-(((benzyloxy)carbonyl)amino)ethyl)-2-fluorophenyl) piperazine-1-carboxylate as a brown oil (400 mg, 62.8%). LCMS (ESI, m/z): 458 [M+H]$^+$.

Step 5. tert-Butyl 4-(4-(2-aminoethyl)-2-fluorophenyl) piperazine-1-carboxylate

Into a 50-mL round-bottom flask purged with nitrogen was added tert-butyl 4-(4-(2-(((benzyloxy)carbonyl)amino)

ethyl)-2-fluorophenyl)piperazine-1-carboxylate (0.30 g, 0.66 mmol) and 10% palladium on carbon (30 mg). Methanol (10 mL) was added under an atmosphere of nitrogen and the solution was then purged with a hydrogen filled balloon. The resulting suspension was stirred for 1 h under an atmosphere of hydrogen. The reaction was vented to nitrogen and the solids were then removed by filtration over Celite. The filtrate was concentrated in vacuo to afford tert-butyl 4-(4-(2-aminoethyl)-2-fluorophenyl)piperazine-1-carboxylate as a white solid (200 mg, 94%). LCMS (ESI, m/z): 324 [M+H]$^+$.

Example 45

Intermediate 45. tert-Butyl 4-(4-(2-aminoethyl)phenyl)piperidine-1-carboxylate

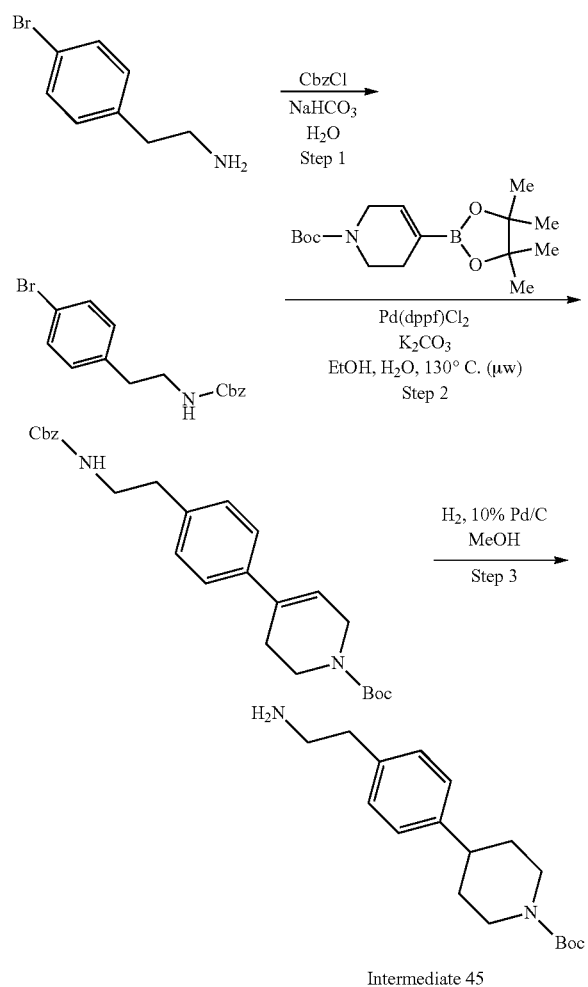

Intermediate 45

Step 1. Benzyl (4-bromophenethyl)carbamate

To a mixture of 2-(4-bromophenyl)ethanamine (10.0 g, 50.0 mmol) and saturated aqueous sodium bicarbonate (375 ml) was slowly added Cbz-Cl (10.3 g, 8.56 ml, 60.0 mmol). The reaction mixture was allowed to stir at RT for 1 hour (a white precipitate forms) and then extracted with EtOAc (2×200 mL). The organic layers were combined, washed with water (100 mL) and brine (100 mL), dried over sodium sulfate, filtered, and concentrated in vacuo. The resulting crude product was purified by FCC eluting with 5-20% EtOAc in hexanes to afford benzyl (4-bromophenethyl)carbamate as a white solid (16.7 g, 100%). LCMS (ESI, m/z): 334, 336 [M+H]$^+$.

Step 2. tert-Butyl 4-(4-(2-(((benzyloxy)carbonyl)amino)ethyl)phenyl)-3,6-dihydropyridine-1(2H)-carboxylate Into a 50-mL microwave tube was added benzyl (4-bromophenethyl)carbamate (1.45 g, 4.34 mmol), tert-butyl 4-(tetramethyl-1,3,2-dioxaborolan-2-yl)-1,2,3,6-tetrahydropyridine-1-carboxylate (2.69 g, 8.70 mmol), Pd(dppf)Cl$_2$ (0.32 g, 0.44 mmol), potassium carbonate (1.20 g, 8.68 mmol), ethanol (10 mL) and water (2 mL). The mixture was heated under microwave irradiation for 1 h at 130° C. The solids were removed by filtration and the filtrate was concentrated in vacuo. The resulting crude product was purified by FCC eluting with ethyl acetate/petroleum ether (1:10) to afford tert-butyl 4-(4-(2-(((benzyloxy)carbonyl)amino)ethyl)phenyl)-3,6-dihydropyridine-1(2H)-carboxylate as a yellow solid (218 mg, 12%). LCMS (ESI, m/z): 437 [M+H]$^+$.

Step 3. tert-Butyl 4-(4-(2-aminoethyl)phenyl)piperidine-1-carboxylate

Into a 100-mL round-bottom flask purged with nitrogen was added tert-butyl 4-(4-(2-(((benzyloxy)carbonyl)amino)ethyl)phenyl)-3,6-dihydropyridine-1(2H)-carboxylate (0.200 g, 0.46 mmol), 10% palladium on carbon (100 mg), and methanol (10 mL). The resulting mixture was sparged with hydrogen and stirred overnight at RT under a hydrogen atmosphere. The reaction was vented to nitrogen and the solids were removed by filtration over Celite. The filtrate was concentrated in vacuo. The resulting crude product was purified by FCC eluting with dichloromethane/methanol (3:1) to afford tert-butyl 4-(4-(2-aminoethyl)phenyl)piperidine-1-carboxylate as a brown oil (400 mg). LCMS (ESI, m/z): 305 [M+H]$^+$.

Example 46

Intermediate 46. tert-Butyl 4-(4-(2-aminoethyl)phenyl)piperazine-1-carboxylate

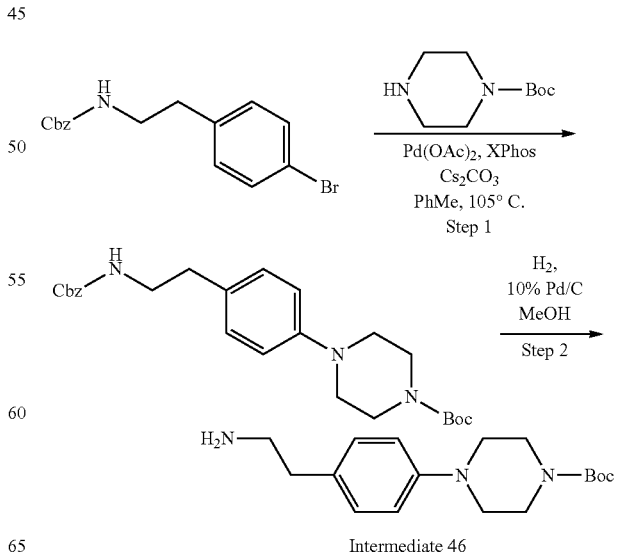

Intermediate 46

Step 1. tert-Butyl 4-(4-(2-(((benzyloxy)carbonyl)amino)ethyl)phenyl)piperazine-1-carboxylate Into a 1-L round-bottom flask, purged and maintained under an inert atmosphere of nitrogen, was added benzyl (4-bromophenethyl)carbamate (50.0 g, 150 mmol) and anhydrous toluene (500 mL). To the resulting solution was added tert-butyl piperazine-1-carboxylate (34.0 g, 183 mmol), Pd(OAc)$_2$ (3.40 g, 15.1 mmol), XPhos (14.3 g, 30.0 mmol), and Cs$_2$CO$_3$ (98.0 g, 301 mmol). The reaction mixture was stirred overnight at 105° C. in an oil bath and then cooled to RT, and quenched with H$_2$O (500 mL). The mixture was extracted with ethyl acetate (2×500-mL), the combined organic layers were washed with brine (1×500 mL). The organic layer was dried over anhydrous sodium sulfate, filtered, and concentrated in vacuo. The resulting crude product was purified by FCC eluting with ethyl acetate/petroleum ether (1:1) to afford tert-butyl 4-(4-(2-(((benzyloxy)carbonyl)amino)ethyl)phenyl)piperazine-1-carboxylate as a yellow solid (26 g, 40%). LCMS (ESI, m/z): 440 [M+H]$^+$.

Step 2. tert-Butyl 4-(4-(2-aminoethyl)phenyl)piperazine-1-carboxylate

Into a 500-mL round-bottom flask that was purged and maintained under an atmosphere of nitrogen was added tert-butyl4-(4-(2-(((benzyloxy)carbonyl)amino)ethyl)phenyl)piperazine-1-carboxylate (26.0 g, 59.2 mmol), 10% palladium on carbon (13.0 g), and methanol (300 mL). The resulting mixture was sparged with a hydrogen filled balloon and the reaction was stirred at RT under hydrogen for 1 h. The reaction was vented to nitrogen, the solids were removed by filtration over Celite and the filtrate was concentrated in vacuo to afford tert-butyl 4-(4-(2-aminoethyl)phenyl)piperazine-1-carboxylate as a yellow solid (18.0 g, 100%). LCMS (ESI, m/z): 306 [M+H]$^+$.

Example 47

Intermediate 47. tert-Butyl 4-(4-(2-aminoethyl)-2-chlorophenyl)piperazine-1-carboxylate

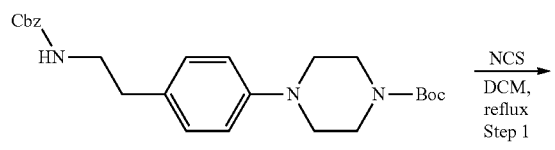

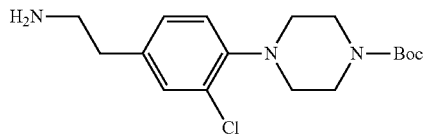

Intermediate 47

Step 1. tert-Butyl 4-(4-(2-(((benzyloxy)carbonyl)amino)ethyl)-2-chlorophenyl)piperazine-1-carboxylate Into a 500-mL round-bottom flask, purged and maintained under an inert atmosphere of nitrogen, was added tert-butyl 4-[4-(2-[[(benzyloxy)carbonyl]amino]ethyl)phenyl]piperazine-1-carboxylate (7.00 g, 15.9 mmol), NCS (2.13 g, 16.0 mmol), and dichloromethane (120 mL). The reaction mixture was stirred overnight at reflux and then cooled and concentrated in vacuo. The resulting crude product was purified by FCC eluting with ethyl acetate/petroleum ether (2:3) to afford tert-butyl 4-(4-(2-(((benzyloxy)carbonyl)amino)ethyl)-2-chlorophenyl)piperazine-1-carboxylate as a yellow oil (8.0 g). The material was used without further purification. LCMS (ESI, m/z): 374 [M+H]$^+$.

Step 2. tert-Butyl 4-(4-(2-aminoethyl)-2-chlorophenyl)piperazine-1-carboxylate

Into a 250-mL round-bottom flask, purged and maintained with nitrogen, was added tert-butyl 4-(4-(2-(((benzyloxy)carbonyl)amino)ethyl)-2-chlorophenyl)piperazine-1-carboxylate (4.00 g, 8.44 mmol), Raney Nickel (1.0 g), and methanol (150 mL). The reaction mixture was sparged with a hydrogen filled balloon and stirred for 3 days at RT under hydrogen. The reaction was vented to nitrogen and the solids were removed by filtration over Celite. The filtrate was concentrated in vacuo to afford tert-butyl 4-(4-(2-aminoethyl)-2-chlorophenyl)piperazine-1-carboxylate as a gray solid (3.0 g). The material was used without further purification. LCMS (ESI, m/z): 340 [M+H]$^+$.

Example 48-1

Intermediate 48-1. tert-Butyl (R)-(1-(4-(2-aminoethyl)-2-chlorophenyl) pyrrolidin-3-yl)(methyl)carbamate

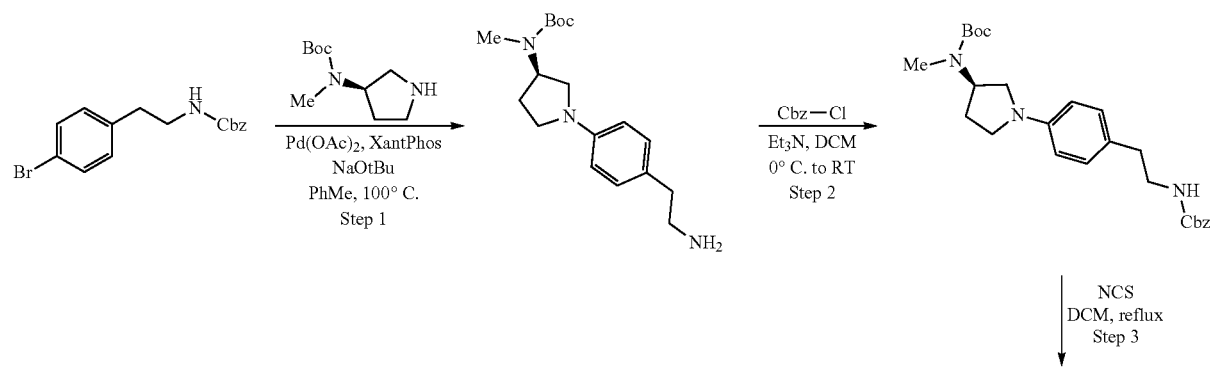

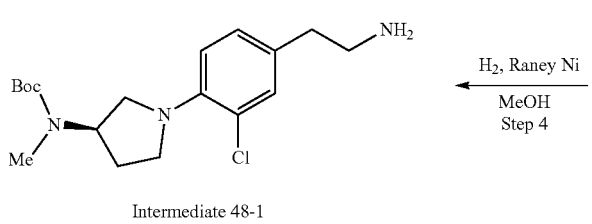

Intermediate 48-1

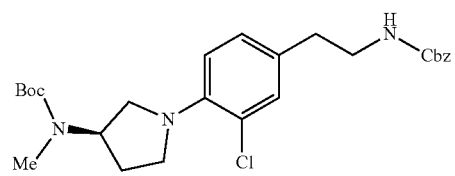

Step 1. tert-Butyl (R)-(1-(4-(2-aminoethyl)phenyl)pyrrolidin-3-yl)(methyl)carbamate Into a 250-mL round-bottom flask, purged and maintained under an inert atmosphere of nitrogen, was added benzyl N-[2-(4-bromophenyl)ethyl]carbamate (2.00 g, 5.98 mmol), tert -butyl N-methyl-N-[(3R)-pyrrolidin-3-yl]carbamate (1.30 g, 6.49 mmol), toluene (20 mL), Pd(OAc)$_2$ (0.135 g, 0.600 mmol), XantPhos (0.347 g, 0.600 mmol), and NaOtBu (1.70 g, 17.69 mmol). The reaction mixture was stirred overnight at 100° C. in an oil bath and then cooled and concentrated in vacuo to provide a crude product that was purified via silica gel chromatography and eluted with dichloromethane/methanol (10:1) to afford tert-butyl (R)-(1-(4-(2-aminoethyl)phenyl)pyrrolidin-3-yl)(methyl)carbamate as yellow oil (1.0 g, 52%). LCMS (ESI, m/z): 320 [M+H]$^+$.

Step 2. tert-Butyl (R)-(1-(4-(2-(((benzyloxy)carbonyl)amino)ethyl)phenyl)pyrrolidin-3-yl)(methyl)carbamate Into a 250-mL round-bottom flask was added tert-butyl (R)-(1-(4-(2-aminoethyl)phenyl)pyrrolidin-3-yl)(methyl) carbamate (1.50 g, 4.70 mmol), dichloromethane (20 mL), and triethylamine (1.50 g, 2.07 mL, 14.8 mmol). The reaction mixture was cooled to 0° C. and then benzyl chloroformate (0.941 g, 0.784 mL, 5.52 mmol) was added dropwise. The resulting solution was stirred for 1 h at RT and then quenched with water (50-mL). The resulting solution was extracted with dichloromethane (3×20 mL), and the organic layers were combined. The combined organic layers were washed with brine (2×80 mL), dried over anhydrous sodium sulfate, filtered, and concentrated in vacuo to afford tert-butyl (R)-(1-(4-(2-(((benzyloxy)carbonyl)amino)ethyl) phenyl)pyrrolidin-3-yl)(methyl)carbamate as a yellow oil (1.5 g, 70%). LCMS (ESI, m/z): 454 [M+H]$^+$.

Step 3. tert-Butyl (R)-(1-(4-(2-(((benzyloxy)carbonyl) amino)ethyl)-2-chlorophenyl) pyrrolidin-3-yl)(methyl)carbamate Into a 100-mL round-bottom flask was added tert-butyl (R)-(1-(4-(2-(((benzyloxy)carbonyl)amino)ethyl)phenyl) pyrmlidin-3-yl)(methyl)carbamate (0.600 g, 1.32 mmol), NCS (0.177 g, 1.33 mmol), and dichloromethane (10 mL).

The resulting solution was stirred for 2 h at 50° C. in an oil bath and then cooled and concentrated in vacuo to provide a crude product that was purified via silica gel chromatography and eluted with ethyl acetate/petroleum ether (1:5) to afford tert-butyl (R)-(1-(4-(2-(((benzyloxy)carbonyl)amino) ethyl)-2-chlorophenyl)pyrrolidin-3-yl)(methyl)carbamate as yellow oil (300 mg, 46%). LCMS (ES, m/z): 488 [M+H]$^+$.

Step 4. tert-Butyl (R)-(1-(4-(2-aminoethyl)-2-chlorophenyl)pyrrolidin-3-yl)(methyl)carbamate Into a 100-mL round-bottom flask, purged and maintained under an inert atmosphere of nitrogen, was added tert-butyl (R)-(1-(4-(2-(((benzyloxy)carbonyl)amino)ethyl)-2-chlorophenyl) pyrrolidin-3-yl)(methyl)carbamate (0.300 g, 0.610 mmol), methanol (20 mL), and Raney Nickel (50 mg). The reaction mixture was stirred overnight under hydrogen (balloon pressure) at RT and then the solids were removed by filtration over Celite. The filtrate was concentrated in vacuo to afford tert-butyl (R)-(1-(4-(2-aminoethyl)-2-chlorophenyl)pyrrolidin-3-yl)(methyl)carbamate as yellow oil (170 mg, 78%). LCMS (ESI, m/z): 354 [M+H]$^+$.

The Intermediates in Table 3 below were synthesized according to the procedures outlined above for Example 48-1, Intermediate 48-1, using the appropriate synthetic precursors.

TABLE 3

| Intermediate No.: | Precursors Used (Notes) | MS (ESI, m/z) [M + H] |
|---|---|---|
| Intermediate 48-2. tert-Butyl (S)-(1-(4-(2-aminoethyl)-2-chlorophenyl)pyrrolidin-3-yl)(methyl)carbamate | Benzyl N-[2-(4-bromophenyl)ethyl]carbamate and tert-butyl N-methyl-N-[(3S)-pyrrolidin-3-yl]carbamate | 354 |
| Intermediate 43-2. (alternative synthesis) tert-Butyl 4-(4-(2-aminoethyl)-2-chlorophenyl)piperazine-1-carboxylate | tert-Butyl 4-(4-(2-(((benzyloxy)carbonyl)amino)ethyl)phenyl)piperazine-1-carboxylate (Step 3 and 4 only) | 340 |

Example 49

Intermediate 49. tert-Butyl 4-(4-(2-aminoethyl)-2,5-difluorophenyl) piperazine -1-carboxylate

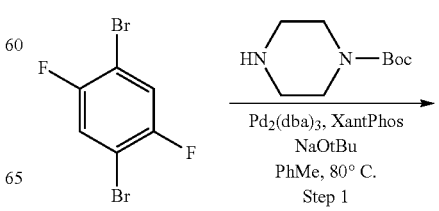

Step 1

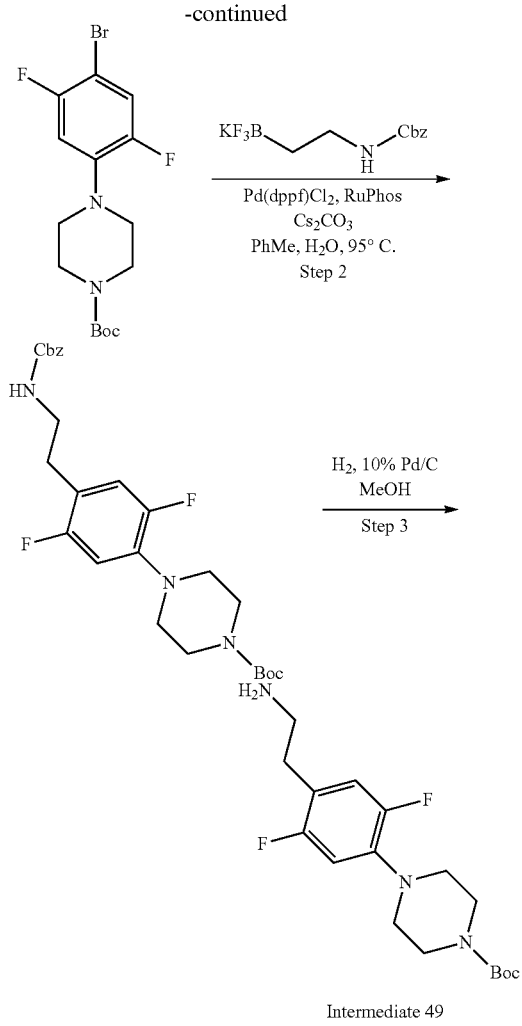

Intermediate 49

Step 1. tert-Butyl 4-(4-bromo-2,5-difluorophenyl)piperazine-1-carboxylate

Into a 500-ml round-bottom flask was added 1,4-dibromo-2,5-difluorobenzene (10.0 g, 36.0 mmol), tert-butyl piperazine-1-carboxylate (7.27 g, 37.8 mmol), XantPhos (2.09 g, 3.60 mmol), and Pd$_2$(dba)$_3$ (1.65 g, 1.80 mmol). Toluene (100 mL) was added, and the resulting mixture was sparged with nitrogen for 10 min. NaOtBu (10.4 g, 108 mmol) was added and the nitrogen sparging was continued for an additional 5 min. The reaction mixture was heated under an atmophere of nitrogen at 80° C. in an oil bath for 15 min. The reaction was cooled to RT, and filtered over Celite. The filtrate was washed with water (2×100 mL) and brine (1×100 mL). The aqueous layers were combined and extracted with EtOAc (200 mL). The combined organic layers were dried over MgSO4, filtered, and concentrated in vacuo. The resulting crude product was purified by FCC eluting with ethyl acetate/hexanes (1:5) to afford tert-butyl 4-(4-bromo-2,5-difluorophenyl)piperazine-1-carboxylate as a green solid (8.12 g). LCMS (ESI, m/z): 378 [M+H]$^+$.

Step 2. tert-Butyl 4-(4-(2-(((benzyloxy)carbonyl)amino)ethyl)-2,5-difluorophenyl) piperazine-1-carboxylate Into a 500-mL round-bottom flask was added tert-butyl 4-(4-bromo-2,5-difluorophenyl) piperazine-1-carboxylate (8.13 g, 19.4 mmol), potassium (2-(benzyloxycarbonylamino)ethyl) trifluoroborate (8.30 g, 29.1 mmol), Pd(dppf)Cl$_2$ (3.48 g, 4.27 mmol), RuPhos (3.81 g, 7.76 mmol), cesium carbonate (19.0 g, 58.2 mmol), toluene (120 mL), and water (40 mL). The resulting mixture was sparged with nitrogen for 20 min. The reaction mixture heated at 95° C. in an oil bath for 3 hours. The reaction was cooled to RT and then extracted with EtOAc (3×200 mL). The combined organic layers were washed with water (200 mL) and brine (200 mL), dried over anhydrous sodium sulfate, filtered, and concentrated in vacuo to provide a crude product that was purified by FCC eluting with EtOAc/Hexanes (1:4) to afford tert -butyl 4-(4-(2-(((benzyloxy)carbonyl)amino)ethyl-2,5-difluorophenyl)piperazine-1-carboxylate as a beige solid (5.39 g, 58%). LCMS (ESI, m/z): 476 [M+H]$^+$.

Step 3. tert-Butyl 4-(4-(2-aminoethyl)-2,5-difluorophenyl)piperazine-1-carboxylate Into a 500-mL round-bottom flask that was purged and maintained under an atmosphere of nitrogen was added tert-butyl 4-(4-(2-(((benzyloxy)carbonyl)amino)ethyl)-2,5-difluorophenyl)piperazine-1-carboxylate (5.47 g, 11.5 mmol), 10% palladium on carbon (1.22 g) and MeOH (110 mL). The reaction flask was flushed with nitrogen, followed by hydrogen from a balloon (3x). The reaction mixture was stirred under hydrogen for 1.5 h and then vented with nitrogen and filtered over Celite. The resulting filtrate was concentrated in vacuo by co-evaporating with DCM and EtOAc to afford tert-butyl 4-(4-(2-aminoethyl)-2,5-difluorophenyl)piperazine-1-carboxylate as a light yellow gum (3.9 g, 99%) that was used without further purification. LCMS (ESI, m/z): 342 [M+H]$^+$.

The Intermediates in Table 4 below were synthesized according to Steps 2 and 3 of the procedure outlined above for Example 49, Intermediate 49, using the appropriate synthetic precursors.

TABLE 4

| Intermediate No.: | Precursor Used (Notes) | MS (ESI, m/z) [M + H] |
|---|---|---|
| Intermediate 50-1. tert-Butyl 4-(4-(2-aminoethyl)naphthalen-1-yl)piperazine-1-carboxylate | tert-Butyl 4-(4-bromonaphthalen-1-yl)piperazine-1-carboxylate | 356 |
| Intermediate 50-2. tert-Butyl 3-(4-(2-aminoethyl)-3-cyanophenyl)-3,8-diazabicyclo[3.2.1]octane-8-carboxylate | tert-Butyl 3-(4-bromo-3-cyanophenyl)-3,8-diazabicyclo[3.2.1]octane-8-carboxylate | 357 |
| Intermediate 50-3. tert-Butyl 3-(4-(2-aminoethyl)-2-ethylphenyl)-3,8-diazabicyclo[3.2.1]octane-8-carboxylate | tert-Butyl 3-(4-bromo-2-ethylphenyl)-3,8-diazabicyclo[3.2.1]octane-8-carboxylate | 360 |

TABLE 4-continued

| Intermediate No.: | Precursor Used (Notes) | MS (ESI, m/z) [M + H] |
| --- | --- | --- |
| Intermediate 50-4. tert-Butyl (R)-(1-(4-(2-aminoethyl)-2,5-difluorophenyl)pyrrolidin-3-yl)(methyl)carbamate | tert-Butyl (R)-(1-(4-bromo-2,5-difluorophenyl)pyrrolidin-3-yl)(methyl)carbamate | 356 |
| Intermediate 50-5. Racemic-tert-Butyl (1-(4-(2-aminoethyl)-2,5-difluorophenyl)pyrrolidin-3-yl)(methyl)carbamate | Racemic tert-Butyl (1-(4-bromo-2,5-difluorophenyl)pyrrolidin-3-yl)(methyl)carbamate | 356 |
| Intermediate 50-6. tert-Butyl (1S,4S)-5-(4-(2-aminoethyl)-2,5-difluorophenyl)-2,5-diazabicyclo[2.2.1]heptane-2-carboxylate | tert-Butyl (1S,4S)-5-(4-bromo-2,5-difluorophenyl)-2,5-diazabicyclo[2.2.1]heptane-2-carboxylate | 354 |
| Intermediate 50-7. tert-Butyl (1R,4R)-5-(4-(2-aminoethyl)-2,5-difluorophenyl)-2,5-diazabicyclo[2.2.1]heptane-2-carboxylate | tert-Butyl (1R,4R)-5-(4-bromo-2,5-difluorophenyl)-2,5-diazabicyclo[2.2.1]heptane-2-carboxylate | 354 |
| Intermediate 50-8. tert-Butyl 5-(4-(2-aminoethyl)-2,5-difluorophenyl)hexahydropyrrolo[3,4-b]pyrrole-1(2H)-carboxylate | tert-Butyl 5-(4-bromo-2,5-difluorophenyl)hexahydropyrrolo[3,4-b]pyrrole-1(2H)-carboxylate | 368 |
| Intermediate 50-9. tert-Butyl 3-(4-(2-aminoethyl)-2,5-difluorophenyl)-3,8-diazabicyclo[3.2.1]octane-8-carboxylate | tert-Butyl 3-(4-bromo-2,5-difluorophenyl)-3,8-diazabicyclo[3.2.1]octane-8-carboxylate | 368 |
| Intermediate 50-10. tert-Butyl 4-(4-(2-aminoethyl)-2-(difluoromethoxy)phenyl)piperazine-1-carboxylate | tert-Butyl 4-(4-bromo-2-(difluoromethoxy)phenyl)piperazine-1-carboxylate | 372 |
| Intermediate 50-11. tert-Butyl 3-((4-(2-aminoethyl)-2,5-difluorophenyl)amino)azetidine-1-carboxylate | tert-Butyl 3-((4-bromo-2,5-difluorophenyl)amino)azetidine-1-carboxylate | 328 |

Example 51

Intermediate 51. tert-Butyl (1-(4-(2-aminoethyl)-2,5-difluorophenyl)azetidin-3-yl)(methyl)carbamate

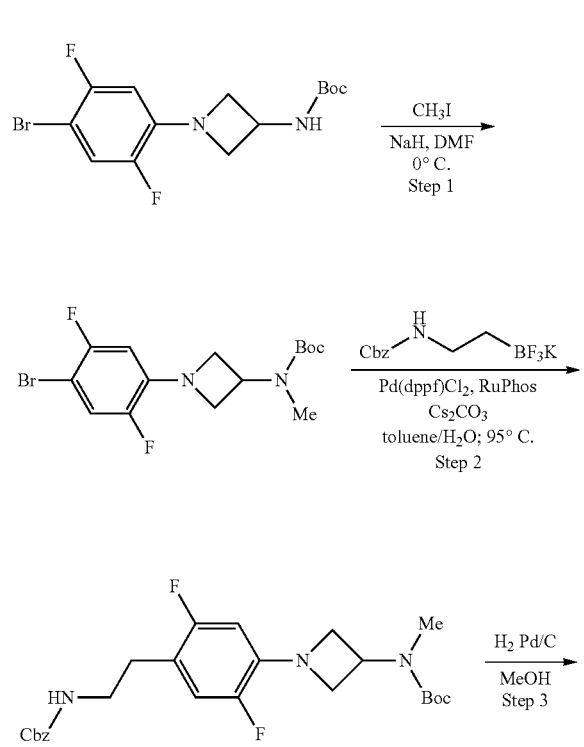

Intermediate 51

Step 1. tert-Butyl (1-(4-bromo-2,5-difluorophenyl)azetidin-3-yl)(methyl)carbamate Into a 100-mL round-bottom flask was added tert-butyl N-[1-(4-bromo-2,5-difluorophenyl)azetidin-3-yl]carbamate (2.00 g, 5.51 mmol), and DMF (50 mL). This was followed by the addition of sodium hydride in mineral oil (60%, 0.330 g, 8.25 mmol) in portions at 0° C. The resulting solution was stirred for 30 min at 0° C. and then iodomethane (0.860 g, 0.377 mL, 6.06 mmol) was added dropwise with stirring. The resulting solution was stirred for another 1 h at 0° C. and then quenched with water (100 mL). The resulting solution was extracted with ethyl acetate (3×100 mL) and the combined organic layers were then dried over anhydrous sodium sulfate, filtered, and concentrated in vacuo to afford tert-butyl (1-(4-bromo-2,5-difluorophenyl)azetidin-3-yl)(methyl)carbamate as a light yellow solid (1.8 g, 87%). LCMS (ESI, m/z): 377, 379 [M+H]+.

Step 2. tert-Butyl (1-(4-(2-(((benzyloxy)carbonyl)amino)ethyl)-2,5-difluorophenyl)azetidin-3-yl)(methyl)carbamate Into a 100-mL 3-necked round-bottom flask, purged and maintained under an inert atmosphere of nitrogen, was added tert-butyl (1-(4-bromo-2,5-difluorophenyl)azetidin-3-yl)(methyl)carbamate (1.00 g, 2.65 mmol), Cs2CO3 (2.59 g, 7.95 mmol), potassium (2-(benzyloxycarbonylamino)ethyl)

trifluoroborate (0.907 g, 3.18 mmol), Pd(dppf)Cl₂ (0.194 g, 0.270 mmol), RuPhos (0.25 g, 0.53 mmol), toluene (30 mL), and water (10 mL). The resulting solution was stirred for 3 h at 95° C. and then cooled to RT. The resulting mixture was poured into water (20 mL) and extracted with ethyl acetate (3×50 mL). The combined organic layers were dried over anhydrous sodium sulfate, filtered, and concentrated in vacuo to provide a crude product that was purified via silica gel chromatography and eluted with ethyl acetate/petroleum ether (PE/EA=100:1 to 5:1) to afford tert-butyl (1-(4-(2-(((benzyloxy)carbonyl)amino)ethyl)-2,5-difluorophenyl)azetidin-3-yl)(methyl)carbamate as a yellow oil (650 mg, 52%). LCMS (ESI, m/z): 476 [M+H]⁺.

Step 3. tert-Butyl (1-(4-(2-aminoethyl)-2,5-difluorophenyl)azetidin-3-yl)(methyl)carbamate Into a 50-mL 3-necked round-bottom flask, purged and maintained with nitrogen, was added tert-butyl (1-(4-(2-(((benzyloxy)carbonylamino)ethyl)-2,5-difluorophenyl)azetidin-3-yl)(methyl)carbamate (0.30 g, 0.63 mmol) and methanol (15 mL). This was followed by the addition of 10% palladium on carbon (300 mg). The reaction mixture was sparged with hydrogen and then stirred for 2 h at 25° C. under a hydrogen atmosphere. The solids were removed by filtration over Celite, and the filtrate was concentrated in vacuo to afford tert-butyl (1-(4-(2-aminoethyl)-2,5-difluorophenyl)azetidin-3-yl)(methyl)carbamate as light yellow oil (180 mg, 84%). LCMS (ESI, m/z): 342 [M+H]⁺.

Example 52

Intermediate 52. tert-Butyl 4-(7-bromo-2,3-dihydro-1H-inden-4-yl)piperazine-1-carboxylate

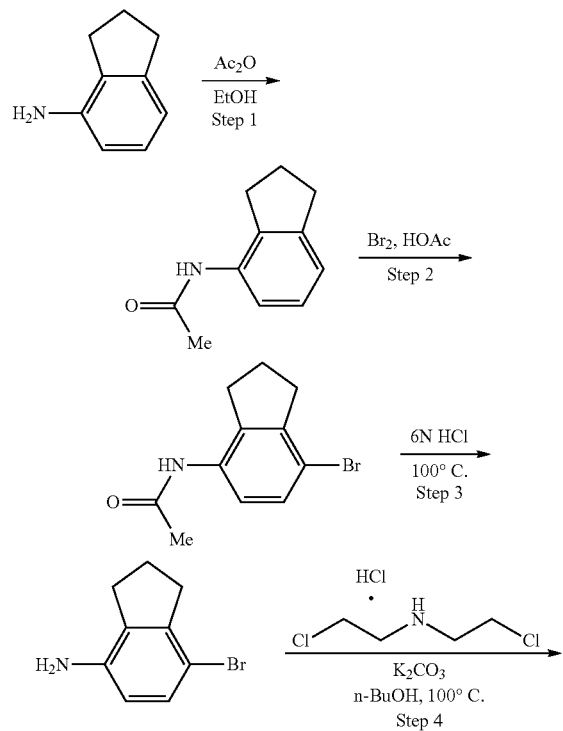

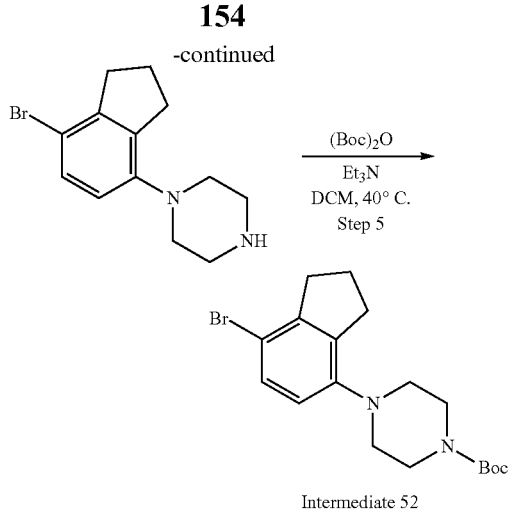

Intermediate 52

Step 1. N-(2,3-dihydro-1H-inden-4-yl)acetamide

Into a 250-mL round-bottom flask was added 2,3-dihydro-1H-inden-4-amine (5.00 g, 37.5 mmol) and ethanol (100 mL). Acetic anhydride (7.67 g, 7.10 mL, 75.1 mmol) was added and the resulting solution was stirred for 1 h at RT. The reaction mixture was concentrated in vacuo and then diluted with ether (20 mL). The solid product was collected by filtration and dried in vacuo to afford N-(2,3-dihydro-1H-inden-4-yl)acetamide as an off-white solid (6.0 g, 91%). LCMS (ESI, m/z): 176 [M+H]⁺.

Step 2. N-(7-bromo-2,3-dihydro-1H-inden-4-yl)acetamide

Into a 250-mL round-bottom flask was added N-(2,3-dihydro-1H-inden-4-yl)acetamide (5.00 g, 28.5 mmol) and acetic acid (80 mL). The resulting solution was cooled to 0° C. and then a solution of bromine (9.03 g, 56.5 mmol) in acetic acid (20 mL) was added dropwise with stirring over 10 min. The cooling bath was removed and the reaction mixture was stirred for 1 h at RT. Water was added and the resulting solid product precipitate was collected by filtration and dried in vacuo to afford N-(7-bromo-2,3-dihydro-1H-inden-4-yl)acetamide as a white solid (7.1 g, 98%). LCMS (ESI, m/z): 254 [M+H]⁺.

Step 3. 7-Bromo-2,3-dihydro-1H-inden-4-amine

Into a 250-mL round-bottom flask was added N-(7-bromo-2,3-dihydro-1H-inden-4-yl)acetamide (7.00 g, 27.6 mmol) and 6 N HCl (100 mL). The resulting solution was stirred for 4 h at 100° C. and then cooled to RT and the pH was adjusted to approximately 7 with saturated aqueous sodium bicarbonate (caution: gas evolution). The resulting solid product was collected by filtration and dried in vacuo to afford 7-bromo-2,3-dihydro-1H-inden-4-amine as an off-white solid (5.7 g, 98%). LCMS (ESI, m/z): 212 [M+H]⁺.

Step 4. 1-(7-Bromo-2,3-dihydro-1H-inden-4-yl)piperazine

Into a 250-mL round-bottom flask that was purged and maintained under an inert atmosphere of nitrogen was added 7-bromo-2,3-dihydro-1H-inden-4-amine (5.70 g, 26.9 mmol), potassium carbonate (15.0 g, 109 mmol), bis(2-chloroethyl)amine hydrochloride (5.74 g, 32.2 mmol), and n-BuOH (80 mL). The reaction mixture was stirred overnight at 100° C. and then concentrated in vacuo. The resulting crude product was purified by FCC eluting with dichloromethane/methanol (20:1) to afford 1-(7-bromo-2,3-dihydro-1H-inden-4-yl)piperazine as a yellow solid (3.2 g, 42%). LCMS (ESI, m/z): 281 [M+H]⁺.

Step 5. tert-Butyl 4-(7-bromo-2,3-dihydro-1H-inden-4-yl)piperazine-1-carboxylate Into a 100-mL round-bottom flask was added 1-(7-bromo-2,3-dihydro-1H-inden-4-yl)piperazine (1.00 g, 3.56 mmol), triethylamine (1.08 g, 10.7 mmol), and dichloromethane (15 mL). Di-tert-butyl dicarbonate (1.17 g, 5.36 mmol) was added and the resulting solution was stirred for 1 h at 40° C. The reaction mixture was concentrated in vacuo. The resulting crude product was purified by FCC eluting with ethyl acetate/petroleum ether (1:20) to afford tert-butyl 4-(7-bromo-2,3-dihydro-1H-inden-4-yl)piperazine-1-carboxylate as a yellow solid (1.05 g, 77%). LCMS (ESI, m/z): 381 [M+H]+.

Example 53

Intermediate 53. tert-Butyl 3-(4-(2-(((benzyloxy)carbonyl)amino)ethyl) phenyl)-3,8-diazabicyclo[3.2.1]octane-8-carboxylate

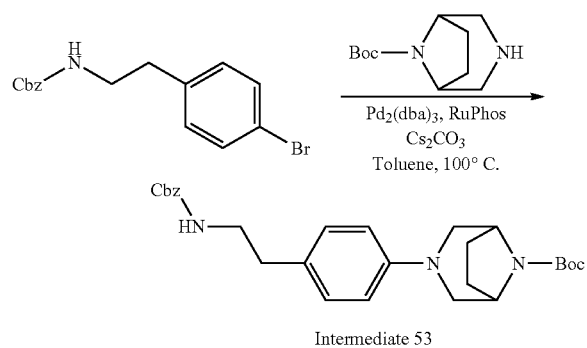

Intermediate 53

Into a 50-mL round-bottom flask, purged and maintained under an inert atmosphere of nitrogen, was added benzyl N-[2-(4-bromophenyl)ethyl]carbamate (3.15 g, 9.43 mmol), tert-butyl 3,8-diazabicyclo[3.2.1]octane-8-carboxylate (2.00 g, 9.43 mmol), Pd$_2$(dba)$_3$(0.800 g, 1.09 mmol), RuPhos (0.800 g, 1.71 mmol), Cs$_2$CO$_3$ (9.00 g, 27.6 mmol) and toluene (50 mL). The reaction mixture was stirred at 100° C. overnight in an oil bath. The resulting mixture was concentrated in vacuo to remove most of the solvent and then diluted with DCM (50 mL). The solids were removed by filtration, the filtrate was concentrated in vacuo, and the crude product that was purified via silica gel chromatography and eluted with petroleum ether/ethyl acetate (3:1) to afford tert-Butyl 3-(4-(2-(((benzyloxy)carbonyl)amino) ethyl) phenyl)-3,8-diazabicyclo[3.2.1]octane-8-carboxylate as a yellow oil (1.2 g, 27%). LCMS (ESI, m/z): 466 [M+H]+.

Example 54-1

Intermediate 54-1. tert-Butyl 3-(4-(2-(((benzyloxy)carbonyl)amino)ethyl)-3-fluorophenyl)-3,8-diazabicyclo[3.2.1]octane-8-carboxylate

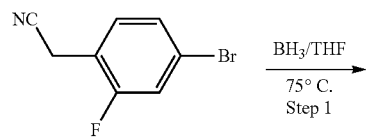

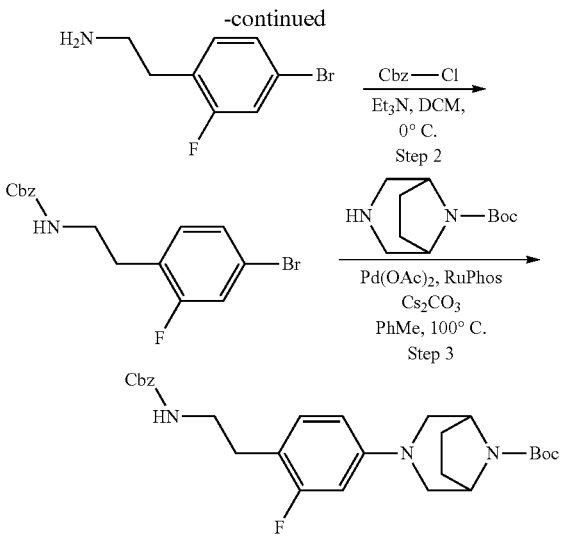

Intermediate 54-1

Step 1. 2-(4-Bromo-2-fluorophenyl)ethan-1-amine

Into a 100-mL round-bottom flask was added 2-(4-bromo-2-fluorophenyl)acetonitrile (2.00 g, 9.34 mmol) and tetrahydrofuran (20 mL). BH$_3$ in THF (1M, 5 mL) was added and the resulting solution was heated and stirred for 6 h at 75° C. and then cooled to RT and quenched with water (50 mL). The resulting solution was extracted with dichloromethane (3×30 mL). The combined organic layers were then dried over anhydrous sodium sulfate, filtered, and concentrated in vacuo to afford the title compound as a colorless oil (1.4 g, crude). LCMS (ESI, m/z) 218 [M+H]+.

Step 2. Benzyl (4-bromo-2-fluorophenethyl)carbamate

Into a 50-mL round-bottom flask was added 2-(4-bromo-2-fluorophenyl)ethan-1-amine (2.00 g, 9.17 mmol), triethylamine (2.33 g, 3.21 mL, 23.0 mmol), and dichloromethane (15 mL). The resulting solution was cooled to 0° C. and benzyl chloroformate (1.60 g, 1.33 mL, 9.38 mmol) was slowly added. The mixture was stirred at this temperature for 17 h. The reaction was quenched with water (30 mL) and then extracted with dichloromethane (3×30 mL). The combined organic layers were dried over anhydrous sodium sulfate, filtered, and concentrated in vacuo to provide a crude product that was purified by FCC eluting with petroleum ether : ethyl acetate (1:1) to afford benzyl (4-bromo-2-fluorophenethyl)carbamate as a colorless oil (1.1 g, 34%). LCMS (ESI, m/z) 352 [M+H]+.

Step 3. tert-Butyl 3-(4-(2-(((benzyloxy)carbonyl)amino)ethyl)-3-fluorophenyl)-3,8-diazabicyclo[3.2.1]octane-8-carboxylate Into a 100-mL round-bottom flask was placed benzyl (4-bromo-2-fluorophenethyl)carbamate (0.825 g, 2.34 mmol), tert-butyl 3,8-diazabicyclo[3.2.1]octane-8-carboxylate (0.500 g, 2.36 mmol), Pd(OAc)$_2$ (0.050 g, 0.22 mmol), RuPhos (0.050 g), Cs$_2$CO$_3$ (2.23 g, 6.84 mmol), and toluene (10 mL). The resulting solution was stirred for 17 h at 100° C. in an oil bath and then concentrated in vacuo to afford the crude product. To the crude product was added DCM (50-mL) and then the inorganic solids were removed by filtration. The filtrate was concentrated in vacuo to afford the crude product that was purified by FCC eluting with petroleum ether : ethyl acetate (1:1) to afford tert-butyl 3-(4-(2-(((benzyloxy)carbonyl)amino) ethyl)-3-fluorophenyl)-3,8- diazabicyclo[3.2.1]octane-8-carboxylate as a yellow oil (15%). LCMS (ESI, m/z): 484 [M+H]+.

The Intermediates in Table 5 below were synthesized according to the procedures outlined above for Example 54-1, Intermediate 54-1, using the appropriate synthetic precursors.

TABLE 5

| Intermediate No.: | Precursors Used (Notes) | MS (ESI, m/z) [M + H] |
|---|---|---|
| Intermediate 54-2. tert-Butyl 3-(4-(2-(((benzyloxy)carbonyl)amino)ethyl)-2-fluorophenyl)-3,8-diazabicyclo[3.2.1]octane-8-carboxylate | 2-(4-Bromo-3-fluorophenyl)acetonitrile and tert-butyl 3,8-diazabicyclo[3.2.1]octane-8-carboxylate (Pd$_2$(dba)$_3$•CHCl$_3$ was used as the palladium source in step 3) | 484 |
| Intermediate 54-3. tert-Butyl 4-(4-(2-(((benzyloxy)carbonyl)amino)ethyl)-3,5-difluorophenyl)piperazine-1-carboxylate | 2-(4-Bromo-2,6-difluorophenyl)acetonitrile and tert-butyl piperazine-1-carboxylate (BH$_3$ reduction conducted at 80° C.) | 476 |

Example 55

Intermediate 55. Benzyl (4-(4-(2-methoxyethyl)piperazin-1-yl)phenethyl)carbamate

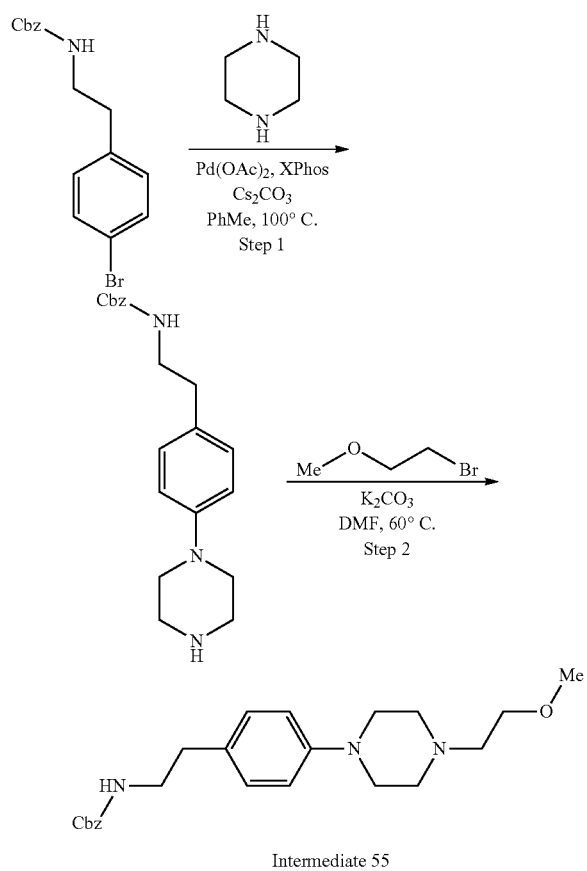

Intermediate 55

Step 1. Benzyl (4-(piperazin-1-yl)phenethyl)carbamate

Into a 250-mL 3-necked round-bottom flask, purged and maintained with nitrogen, was added benzyl (4-bromophenethyl)carbamate (4.00 g, 12.0 mmol), piperazine (1.26 g, 14.6 mmol), cesium carbonate (11.7 g, 35.8 mmol), toluene (80 mL), XPhos (1.14 g, 2.39 mmol), and Pd(OAc)$_2$ (0.270 g, 1.20 mmol). The resulting solution was stirred overnight at 100° C. and then cooled to RT. The resulting mixture was concentrated in vacuo to provide a crude product that was purified via silica gel chromatography and eluted with ethyl acetate/petroleum ether (2:1) to afford benzyl (4-(piperazin-1-yl)phenethyl)carbamate as light yellow oil (1.6 g, 39%). LCMS (ESI, m/z): 340 [M+H]+.

Step 2. Benzyl (4-(4-(2-methoxyethyl)piperazin-1-yl)phenethyl)carbamate

Into a 100-mL round-bottom flask was added benzyl (4-(piperazin-1-yl)phenethyl)carbamate (0.600 g, 1.77 mmol), 1-bromo-2-methoxyethane (0.369 g, 2.65 mmol), potassium carbonate (0.733 g, 5.27 mmol), and DMF (20 mL). The reaction was stirred overnight at 60° C. and then cooled and extracted with ethyl acetate (3×100 mL). The combined organic layers were washed with brine (2×100 mL), dried over anhydrous sodium sulfate, filtered, and concentrated in vacuo. The resulting crude product was purified by FCC eluting with ethyl acetate/petroleum ether (1:1) to afford benzyl (4-(4-(2-methoxyethyl)piperazin-1-yl)phenethyl)carbamate as a gray oil (280 mg, 40%). LCMS (ESI, m/z): 398 [M+H]+.

Example 56

Intermediate 56. Benzyl (4-(4-(oxetan-2-ylmethyl)piperazin-1-yl)phenethyl)carbamate

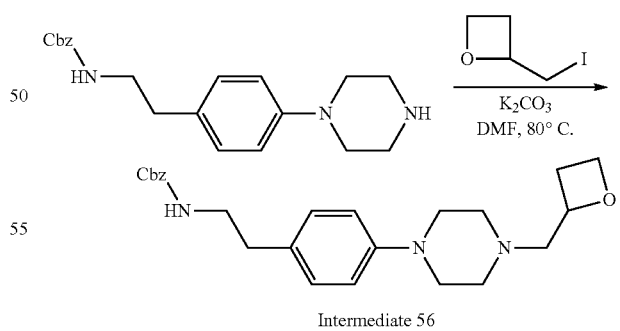

Intermediate 56

Into a 100-mL round-bottom flask was added benzyl (4-(piperazin-1-yl)phenethyl)carbamate (0.570 g, 1.68 mmol) and DMF (20 mL). 2-(Iodomethyl)oxetane (0.500 g, 2.53 mmol) was added followed by potassium carbonate (0.930 g, 6.74 mmol). The resulting suspension was stirred for 4 h at 80° C. and then cooled, and quenched with water (20 mL). The resulting solution was extracted with ethyl acetate (3×15 mL). The combined organic layers were washed with water (3×20 mL) and brine (3×20 mL). The organic layer was dried over anhydrous sodium sulfate, filtered, and concentrated in vacuo. The resulting crude product was purified by FCC eluting with dichloromethane/methanol (10:1) to afford benzyl (4-(4-(oxetan-2-ylmethyl)piperazin-1-yl)phenethyl)carbamate as a gray solid (280 mg, 41%). LCMS (ESI, m/z): 410 [M+H]+.

Example 57

Intermediate 57. tert-Butyl 4-(4-(2-(((benzyloxy)carbonyl)amino) ethyl)phenyl)-2-(((tert-butyldimethylsilyl)oxy)methyl)piperazine-1-carboxylate

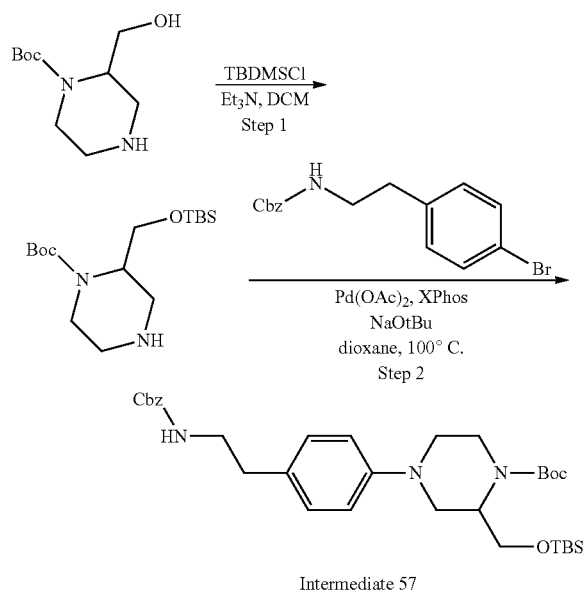

Intermediate 57

Step 1. tert-Butyl 2-(((tert-butyldimethylsilyl)oxy)methyl)piperazine-1-carboxylate Into a 250-mL round-bottom flask was added tert-butyl 2-(hydroxymethyl)piperazine -1-carboxylate (2.00 g, 9.25 mmol) and dichloromethane (30 mL). Triethylamine (2.30 g, 3.17 mL, 22.7 mmol) was added followed by tert-butyl (chloro)dimethylsilane (1.40 g, 9.29 mmol). The resulting solution was stirred overnight at RT and then concentrated in vacuo to provide a crude product that was purified by FCC eluting with dichloromethane/methanol (40:1) to afford tert-butyl 2-(((tert-butyldimethylsilyl)oxy)methyl) piperazine-1-carboxylate as a yellow oil (2.0 g, 65%). LCMS (ESI, m/z): 331 [M+H]+.

Step 2. tert-Butyl 4-(4-(2-(((benzyloxy)carbonyl)amino) ethyl)phenyl)-2-(((tert -butyldimethylsilyl)oxy)methyl)piperazine-1-carboxylate Into a 250-mL round-bottom flask that was purged and maintained under an inert atmosphere of nitrogen was added benzyl N-[2-(4-bromophenyl)ethyl]carbamate (2.00 g, 5.98 mmol), tert-butyl 2-(((tert-butyldimethylsilyl)oxy)methyl) piperazine-1-carboxylate (2.00 g, 6.05 mmol), XPhos (0.286 g), NaOtBu (1.20 g, 12.5 mmol), Pd(OAc)$_2$ (0.135 g, 0.60 mmol), and dioxane (25 mL). The reaction mixture was stirred overnight at 100° C. and then diluted with water (80 mL) and extracted with ethyl acetate (3×20 mL). The combined organic layers were washed with brine (2×80 mL). The organic layer was then dried over anhydrous sodium sulfate, filtered, and concentrated in vacuo. The resulting crude product was purified by FCC eluting with ethyl acetate/petroleum ether (1:3) to afford tert-butyl 4-(4-(2-(((benzyloxy)carbonyl)amino)ethyl)phenyl)-2-(((tert-butyldimethylsilyl)oxy)methyl)piperazine -1-carboxylate as a yellow oil (1.2 g, 34%). LCMS (ESI, m/z): 584 [M+H]+.

Example 58-1

Intermediate 58-1. tert-Butyl 4-(4-bromo-2,3,6-trifluorophenyl)piperazine-1-carboxylate

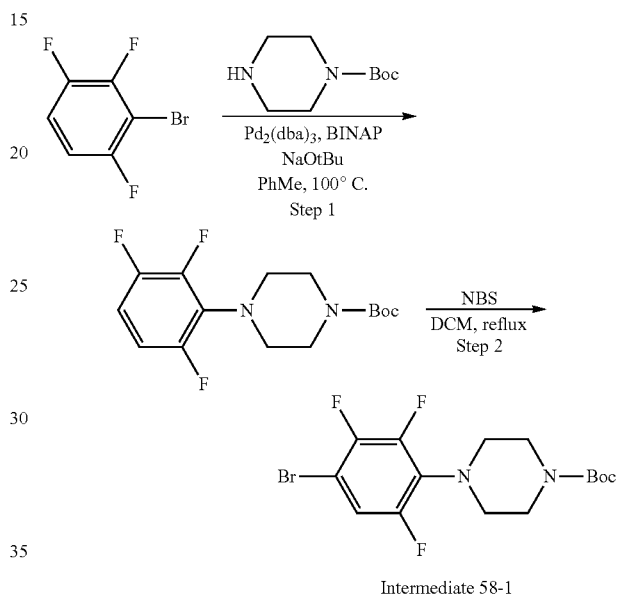

Intermediate 58-1

Step 1. tert-Butyl 4-(2,3,6-trifluorophenyl)piperazine-1-carboxylate

Into a 250-mL round-bottom flask that was purged and maintained under an inert atmosphere of nitrogen was added 2-bromo-1,3,4-trifluorobenzene (5.00 g, 23.7 mmol), tert-butyl piperazine-1-carboxylate (4.43 g, 23.8 mmol), Pd$_2$(dba)$_3$ (1.10 g, 1.20 mmol), BINAP (1.50 g, 2.41 mmol), NaOtBu (6.91 g, 71.9 mmol), and toluene (50 mL). The reaction mixture was stirred for 3 h at 100° C. and then cooled and concentrated in vacuo. The resulting crude product was purified by FCC eluting with ethyl acetate/petroleum ether (1:3) to afford tert-butyl 4-(2,3,6-trifluorophenyl)piperazine-1-carboxylate as a yellow solid (5.3 g, 71%). LCMS (ESI, m/z) 317 [M+H]+.

Step 2. tert-Butyl 4-(4-bromo-2,3,6-trifluorophenyl)piperazine-1-carboxylate

Into a 100-mL round-bottom flask was added tert-butyl 4-(2,3,6-trifluorophenyl)piperazine-1-carboxylate (3.00 g, 9.48 mmol), NBS (1.68 g, 9.44 mmol), and dichloromethane (30 mL). The reaction mixture was stirred overnight at reflux and then concentrated in vacuo to provide a crude product that was subject to purification by FCC eluting with ethyl acetate/petroleum ether (1:3) to afford tert-butyl 4-(4-bromo-2,3,6-trifluorophenyl)piperazine-1-carboxylate as a yellow oil (1.0 g, 27%). LCMS (ESI, m/z) 395, 397 [M+H]+.

The Intermediate in Table 6 below was synthesized according to the procedures outlined above for Example 58-1, Intermediate 58-1, using the appropriate synthetic precursors.

TABLE 6

| Intermediate No.: | Precursor Used (Notes) | MS (ESI, m/z) [M + H] |
|---|---|---|
| Intermediate 58-2. tert-Butyl 3-(4-bromo-2,6-difluorophenyl)-3,8-diazabicyclo[3.2.1]octane-8-carboxylate | tert-Butyl 3,8-diazabicyclo[3.2.1]octane-8-carboxylate | 403, 405 |

Example 59

Intermediate 59. tert-Butyl 4-(4-bromo-3-(methoxymethyl)phenyl)piperazine -1-carboxylate

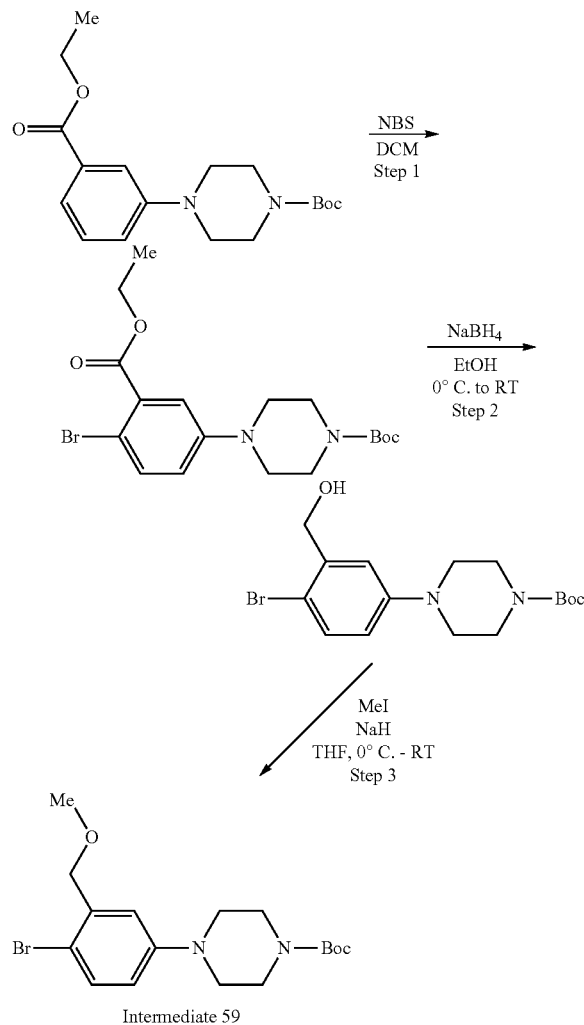

Intermediate 59

Step 1. tert-Butyl 4-(4-bromo-3-(ethoxycarbonyl)phenyl)piperazine-1-carboxylate

Into a 100-mL round-bottom flask was added tert-butyl 4-[3-(ethoxycarbonyl)phenyl]piperazine-1-carboxylate (5.00 g, 15.0 mmol) and dichloromethane (50-mL). NBS (3.18 g, 17.9 mmol) was added and the resulting solution was stirred for 0.5 h at RT. The reaction mixture was concentrated in vacuo and the crude product was purified by FCC eluting with ethyl acetate/petroleum ether (1:3) to afford tert-butyl 4-(4-bromo-3-(ethoxycarbonyl)phenyl)piperazine-1-carboxylate as a light yellow oil (5.8 g, 94%). LCMS (ESI, m/z) 413, 415 [M+H]$^+$.

Step 2. tert-Butyl 4-(4-bromo-3-(hydroxymethyl)phenyl)piperazine-1-carboxylate

Into a 100-mL round-bottom flask was added tert-butyl 4-(4-bromo-3-(ethoxycarbonyl)phenyl)piperazine-1-carboxylate (3.00 g, 7.26 mmol) and ethanol (30 mL). This was followed by the portion-wise addition of NaBH$_4$ (1.66 g, 43.9 mmol) at 0° C. The resulting solution was warmed and stirred overnight at RT and then poured into ice water (200 mL) and extracted with ethyl acetate (3×50 mL). The combined organic layers were washed with brine (1 ×200 mL) and then dried over anhydrous sodium sulfate, filtered, and concentrated in vacuo. The resulting crude product was purified by FCC eluting with ethyl acetate/petroleum ether (1:3) to afford tert-butyl 4-(4-bromo-3-(hydroxymethyl)phenyl)piperazine-1-carboxylate as a light yellow oil (1.77 g, 66%). LCMS (ESI, m/z) 371, 373 [M+H]$^+$.

Step 3. tert-Butyl 4-(4-bromo-3-(methoxymethyl)phenyl)piperazine-1-carboxylate

Into a 100-mL round-bottom flask, purged and maintained under an inert atmosphere of nitrogen, was added a solution of tert-butyl 4-(4-bromo-3-(hydroxymethyl)phenyl)piperazine -1-carboxylate (0.650 g, 1.75 mmol) and tetrahydrofuran (10 mL). This was followed by the portion-wise addition of sodium hydride (60% dispersion in mineral oil; 0.141 g, 5.88 mmol) at 0 ° C. The resulting solution was warmed and stirred at RT for 1 h. To this was added MeI (0.499 g, 0.218 mL, 3.52 mmol) and the resulting solution was stirred overnight at RT. The reaction was quenched with aqueous saturated NH$_4$Cl (100 mL). The resulting solution was extracted with ethyl acetate (3×30 mL) and the organic layers were combined. The combined organic layers were washed with brine (200 mL), dried over anhydrous sodium sulfate, filtered, and concentrated in vacuo to afford tert-butyl 4-(4-bromo-3-(methoxymethyl)phenyl)piperazine-1-carboxylate as a yellow oil (650 mg (crude)). LCMS (ESI, m/z) 385,387 [M+H]$^+$.

Example 60-1

Intermediate 60-1. tert-Butyl 1-(4-bromophenyl)-4,6-dihydropyrrolo[3,4-c]pyrazole-5(1H)-carboxylate

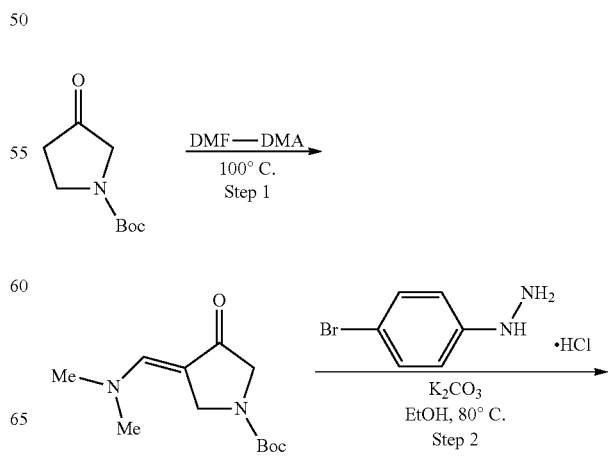

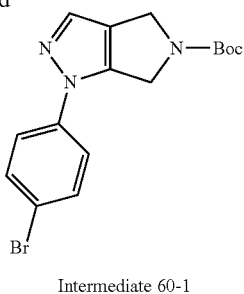

Intermediate 60-1

Step 1. tert-Butyl (E)-3-(((dimethylamino)methylene)-4-oxopyrrolidine-1-carboxylate Into a 100-mL round-bottom flask was added tert-butyl 3-oxopyrrolidine-1-carboxylate (10.0 g, 54.0 mmol) and DMF-DMA (50 mL). The resulting solution was stirred for 1 h at 100° C. and then cooled to RT, concentrated in vacuo, and then diluted with ethyl ether (10 mL). The resulting solids were collected by filtration and dried in vacuo to afford tert-butyl (E) -3-(((dimethylamino)methylene)-4-oxopyrrolidine-1-carboxylate as a yellow solid (7.6 g, 59%). LCMS (ESI, m/z): 241 [M+H]$^+$.

Step 2. tert-Butyl 1-(4-bromophenyl)-4,6-dihydropyrrolo[3,4-c]pyrazole-5(1H)-carboxylate Into a 50-mL round-bottom flask, was placed tert-butyl (E)-3-((dimethylamino)methylene)-4-oxopyrrolidine-1-carboxylate (1.0 g, 4.16 mmol), (4-bromophenyl)hydrazine hydrochloride (1.03 g, 5.51 mmol), potassium carbonate (1.15 g, 8.32 mmol), and ethanol (10 mL). The resulting solution was stirred for 1 h at 80° C. in an oil bath and then cooled and concentrated in vacuo to provide a crude product that was purified via silica gel chromatography and eluted with petroleum ether/EtOAc (5:1) to afford tert-butyl 1-(4-bromophenyl)-4,6-dihydropyrrolo[3,4-c]pyrazole-5(1H)-carboxylate as a red oil (0.5 g, 33%). LCMS (ESI, m/z) 364,366 [M+H]$^+$.

The Intermediate in Table 7 below was synthesized according to the procedures outlined above for Example 60-1, Intermediate 60-1, using the appropriate synthetic precursors.

TABLE 7

| Intermediate No.: | Precursor Used (Notes) | MS (ESI, m/z) [M + H] |
|---|---|---|
| Intermediate 60-2. Benzyl 1-(4-bromo-2-fluorophenyl)-1H,4H,5H,6H-pyrrolo[3,4-c]pyrazole-5-carboxylate | tert-Butyl 3-oxopyrrolidine-1-carboxylate and 4-bromo-2-fluorophenylhydrazine (hydrochloride salt) | 416 |

Example 61

Intermediate 61. tert-Butyl 1-(4-(2-(((benzyloxy)carbonyl)amino)ethyl)-3-fluorophenyl)-4,6-dihydropyrrolo[3,4-c]pyrazole-5(1H)-carboxylate

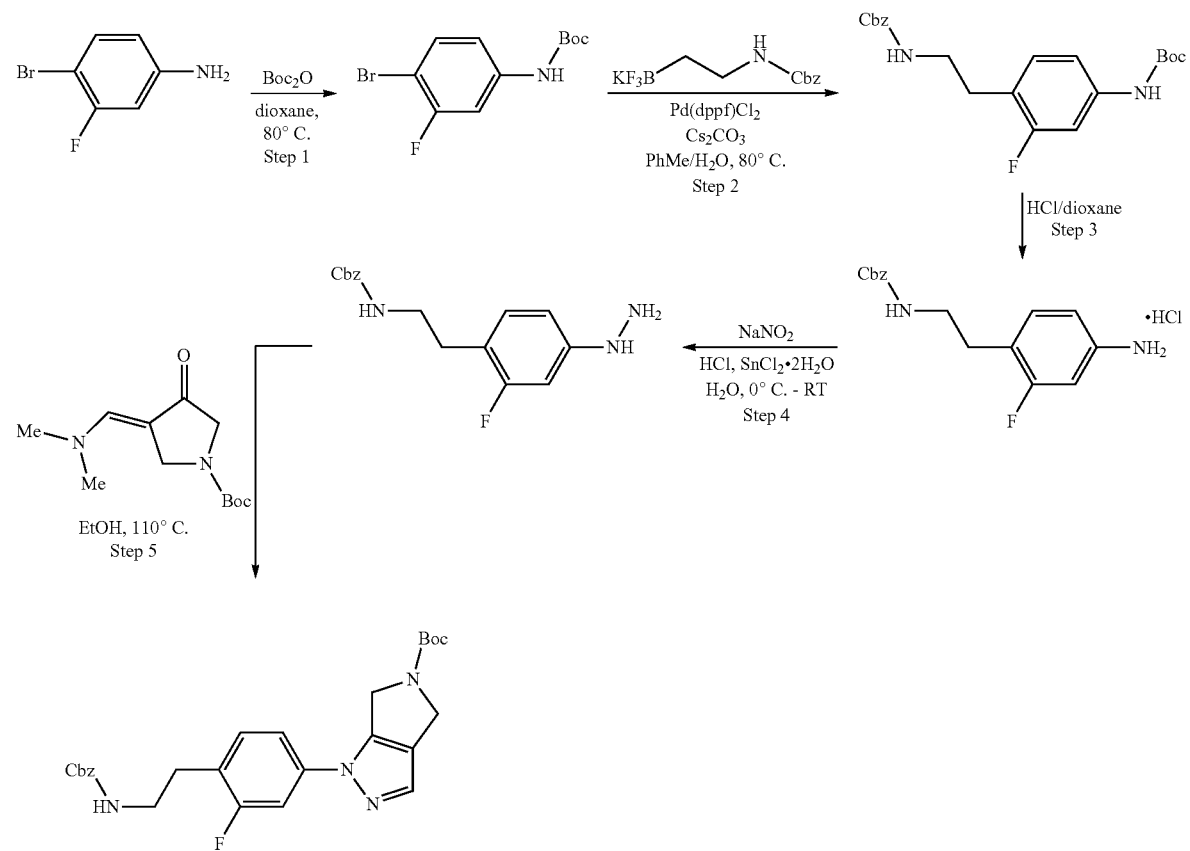

Intermediate 61

Step 1. tert-Butyl (4-bromo-3-fluorophenyl)carbamate

Into a 100-mL round-bottom flask was added 4-bromo-3-fluoroaniline (10.0 g, 52.6 mmol) and dioxane (300 mL). Boc$_2$O (23.1 g, 106 mmol) was added and the resulting solution was stirred overnight at 80° C. The reaction mixture was cooled and concentrated in vacuo. The resulting crude product was purified by FCC eluting with petroleum ether/ethyl acetate (5:1) to afford tert-butyl (4-bromo-3-fluorophenyl)carbamate as a white solid (16 g, 100%). $^1$H-NMR (300 MHz, DMSO-d$_6$) δ ppm 9.47 (s, 1H), 7.64-7.44 (m, 2H), 7.28-7.10 (m, 2H), 1.47 (s, 9H).

Step 2. tert-Butyl (4-(2-(((benzyloxy)carbonyl)amino)ethyl)-3-fluorophenyl)carbamate Into a 500-mL round-bottom flask, purged and maintained under an inert atmosphere of nitrogen, was added tert-butyl (4-bromo-3-fluorophenyl)carbamate (8.00 g, 27.6 mmol), potassium (2-(benzyloxycarbonylamino)ethyl) trifluoroborate (9.47 g, 33.2 mmol), Cs$_2$CO$_3$ (27.1 g, 83.2 mmol), Pd(dppf)Cl$_2$·CH$_2$Cl$_2$ (4.52 g, 5.53 mmol), and PhMe/H$_2$O (30 mL/10 mL). The reaction mixture was stirred overnight at 80° C. and then cooled and concentrated in vacuo. The resulting crude product was purified by FCC eluting with ethyl acetate/hexane (1:5) to afford tert-butyl (4-(2-(((benzyloxy)carbonyl)amino)ethyl)-3-fluorophenyl)carbamate as a white solid (5 g, 47%). LCMS (ESI, m/z): 411 [M+Na]$^+$.

Step 3. Benzyl (4-amino-2-fluorophenethyl)carbamate (hydrochloride salt)

Into a 100-mL round-bottom flask was added tert-butyl (4-(2-(((benzyloxy)carbonyl) amino)ethyl)-3-fluorophenyl)carbamate (5 g, 12.9 mmol) and 4 M HCl/dioxane (20 mL). The resulting solution was stirred for 2 h at RT and then concentrated in vacuo to afford benzyl (4-amino-2-fluorophenethyl)carbamate (hydrochloride salt) as a yellow solid (1.4 g, 33%). $^1$H-NMR (300 MHz, DMSO-d$_6$) δ ppm 7.50-7.41 (m, 1H), 7.40-7.28 (m, 5H), 7.21-7.09 (m, 2H), 5.04 (s, 2H), 3.38 (t, J=6.9 Hz, 2H) 2.90 (t, J=6.9 Hz, 2H).

Step 4. Benzyl (2-fluoro-4-hydrazinylphenethyl)carbamate

Into a 250-mL 3-necked round-bottom flask was added benzyl (4-amino-2-fluorophenethyl)carbamate (HCl salt; 2.70 g, 8.31 mmol) and aqueous HCl (12 M, 30 mL). This was followed by the addition of a solution of NaNO$_2$ in H$_2$O (0.860 g in 2 mL) at 0° C. over 1.5 h. A solution of SnCl$_2$·2H$_2$O in H$_2$O (7.5 g in 10 mL) was added at 0° C. over 3 h and then the resulting solution was warmed and stirred overnight at RT. The reaction was diluted by the addition of water (50 mL). The pH of the solution was adjusted to approximately 7 with ammonium hydroxide and then extracted with ethyl acetate (3×80 mL). The combined organic layers were washed with water (50 mL) and brine (50 mL). The organic layer was dried over anhydrous sodium sulfate, filtered, and concentrated in vacuo to afford benzyl (2-fluoro-4-hydrazinylphenethyl)carbamate as a yellow oil (0.5 g, 20%). LCMS (ESI, m/z): 304 [M+H]$^+$.

Step 5. tert-Butyl 1-(4-(2-(((benzyloxy)carbonyl)amino)ethyl)-3-fluorophenyl)-4,6-dihydropyrrolo[3,4-c]pyrazole-5(1H)-carboxylate Into a 50-mL round-bottom flask was added benzyl (2-fluoro-4-hydrazinylphenethyl)carbamate (0.30 g, 0.99 mmol), tert-butyl (3E)-3-[(dimethylamino)methylidene]-4-oxopyrrolidine-1-carboxylate (0.243 g, 1.01 mmol) and ethanol (10 mL). The resulting solution was stirred overnight at 110° C. The reaction mixture was concentrated in vacuo to provide a crude product that was purified via silica gel chromatography and eluted with ethyl acetate/petroleum ether (1:1) to afford tert-butyl 1-(4-(2-(((benzyloxy)carbonyl) amino)ethyl)-3-fluorophenyl)-4,6-dihydropyrrolo[3,4-c-]pyrazole-5(1H) -carboxylate as yellow oil (0.215 g, 45%). LCMS (ESI, m/z): 481 [M+H]$^+$.

Example 62

Intermediate 62. tert-Butyl 4-(4-(2-(((benzyloxy)carbonyl)amino) ethyl)phenyl)hexahydropyrrolo[3,2-b]pyrrole-1(2H)-carboxylate

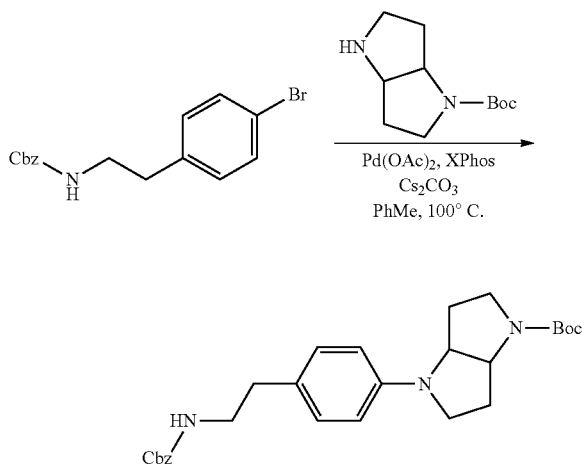

Intermediate 62

Into a 100-mL round-bottom flask, purged and maintained under an inert atmosphere of nitrogen, was added benzyl N[2-(4-bromophenyl)ethyl]carbamate (0.788 g, 2.36 mmol), toluene (50 mL), XPhos (0.225 g, 0.470 mmol), Pd(OAc)$_2$ (0.053 g, 0.24 mmol), cesium carbonate (2.30 g, 7.04 mmol), and tert-butyl octahydropyrrolo[3,2-b]pyrrole-1-carboxylate (0.500 g, 2.36 mmol). The reaction mixture was stirred for 2 h at 100° C. and then cooled and concentrated in vacuo to provide a crude product that was purified via silica gel chromatography and eluted with ethyl acetate/petroleum ether (1:5) to afford tert-butyl 4-(4-(2-(((benzyloxy) carbonyl)amino)ethyl)phenyl)hexahydropyrrolo[3,2-b]pyrrole-1(2H)-carboxylate as a yellow oil (0.700 g , 64). LCMS (ESI, m/z): 466 [M+H]$^+$.

Example 63

Intermediate 63. tert-butyl 3-(4-bromo-2-cyanophenyl)-3,8-diazabicyclo [3.2.1]octane-8-carboxylate

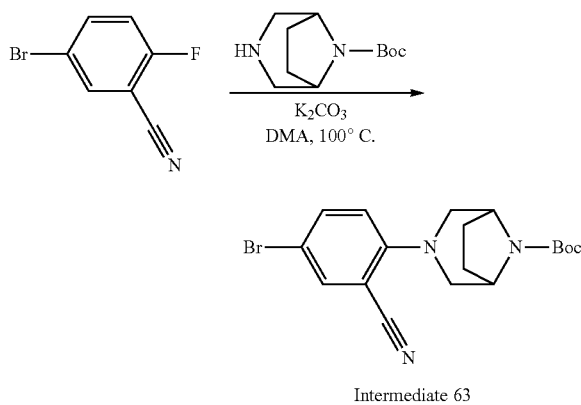

Intermediate 63

Into a 50-mL round-bottom flask was added 5-bromo-2-fluorobenzonitrile (1.03 g, 5.17 mmol), tert-butyl 3,8-diazabicyclo[3.2.1]octane-8-carboxylate (1.00 g, 4.71 mmol), potassium carbonate (1.30 g, 9.43 mmol), and DMA (10 mL). The reaction mixture was stirred for 3 h at 100° C. and then cooled and extracted with ethyl acetate (3×15 mL). The combined organic layers were then dried over anhydrous sodium sulfate, filtered, and concentrated in vacuo. The resulting crude product was purified by FCC eluting with ethyl acetate/petroleum ether (1:3) to afford tert -butyl 3-(4-bromo-2-cyanophenyl)-3,8-diazabicyclo[3.2.1]octane-8-carboxylate as a light yellow oil (196 mg, 11%). LCMS (ESI, m/z) 392, 394 [M+H]$^+$.

Example 64

Intermediate 64. tert-Butyl 3-(4-(2-(((benzyloxy)carbonyl)amino)ethyl) phenyl)-6,7-dihydropyrazolo[1,5-a]pyrazine-5(4H)-carboxylate

Step 1. Benzyl (4-(4,4,5,5-tetramethyl-1,3,2-dioxaborolan-2-yl)phenethyl)carbamate Into a 100-mL round-bottom flask was added benzyl (4-bromophenethyl)carbamate (2.00 g, 6.00 mmol), bis(pinacolato)diboron (2.30 g, 9.10 mmol), Pd(dppf)Cl$_2$ (0.440 g, 0.60 mmol), and KOAc (1.50 g, 15.0 mmol). The flask was evacuated and flushed with nitrogen (3 times). Toluene (30 mL; degassed with nitrogen) was added and the resulting mixture was stirred overnight at 100° C. The reaction was cooled then concentrated in vacuo. The resulting crude product was purified by FCC eluting with ethyl acetate/petroleum ether (1:5) to afford benzyl (4-(4,4,5,5-tetramethyl-1,3,2-dioxaborolan-2-yl)phenethyl)carbamate as a yellow oil (2.16 g, 95%). LCMS (ESI, m/z): 382 [M+H]$^+$.

Step 2. tert-Butyl 3-(4-(2-(((benzyloxy)carbonyl)amino)ethyl)phenyl)-6,7-dihydropyrazolo [1,5-a]pyrazine-5(4H)-carboxylate Into a 50-mL round-bottom flask was added tert-butyl 3-bromo-4H,5H,6H,7H -pyrazolo[1,5-a]pyrazine-5-carboxylate (0.300 g, 0.99 mmol), benzyl (4-(4,4,5,5-tetramethyl -1,3,2-dioxaborolan-2-yl)phenethyl)carbamate (0.380 g, 1.00 mmol), Pd (dppf)Cl$_2$.CH$_2$Cl$_2$ (0.073 g, 0.10 mmol), Cs$_2$CO$_3$ (0.972 g, 2.98 mmol), dioxane (5 mL), and water (0.5 mL). The reaction mixture was sparged with nitrogen and stirred overnight at 100° C., and then cooled and concentrated in vacuo. The resulting crude product was purified by FCC eluting with ethyl acetate/petroleum ether (1:1) to afford tert-butyl 3-(4-(2-(((benzyloxy)carbonyl)amino)ethyl) phenyl)-6,7-dihydropyrazolo[1,5-a]pyrazine-5 (4H)-carboxylate as a yellow oil (300 mg, 63%). LCMS (ESI, m/z): 477 [M+H]$^+$.

The Intermediates in Table 8 below were synthesized according to the procedures outlined above for Example 49, Intermediate 49, using the appropriate synthetic precursors. For some examples below, both the palladium-catalyzed BF$_3$ salt coupling and hydrogenolysis were performed (Method A), and for others only hydrogenolysis (Method B).

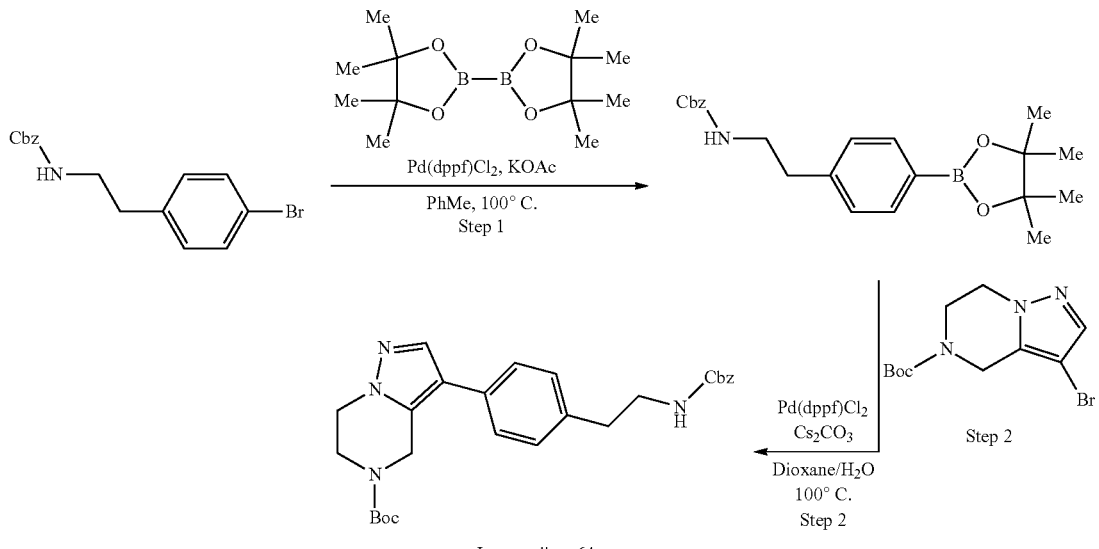

Intermediate 64

TABLE 8

| Intermediate No.: | Precursor Used (Notes) | MS (ESI, m/z) [M + H] |
|---|---|---|
| Intermediate 65-1. tert-Butyl 4-(7-(2-aminoethyl)-2,3-dihydro-1H-inden-4-yl)piperazine-1-carboxylate | tert-Butyl 4-(7-bromo-2,3-dihydro-1H-inden-4-yl)piperazine-1-carboxylate (Method A) | 346 |
| Intermediate 65-2. tert-Butyl 3-[4-(2-aminoethyl)phenyl]-3,8-diazabicyclo[3.2.1]octane-8-carboxylate | tert-Butyl 3-(4-(2-(((benzyloxy)carbonyl)amino)ethyl)phenyl)-3,8-diazabicyclo[3.2.1]octane-8-carboxylate (Method B: 10 atm of hydrogen pressure used; 40° C. reaction temp) | 332 |
| Intermediate 65-3. tert-Butyl 3-(4-(2-aminoethyl)-3-fluorophenyl)-3,8-diazabicyclo[3.2.1]octane-8-carboxylate | tert-Butyl 3-(4-(2-(((benzyloxy)carbonyl)amino)ethyl)-3-fluorophenyl)-3,8-diazabicyclo[3.2.1]octane-8-carboxylate (Method B) | 350 |
| Intermediate 65-4. tert-Butyl 3-(4-(2-aminoethyl)-2-fluorophenyl)-3,8-diazabicyclo[3.2.1]octane-8-carboxylate | tert-Butyl 3-(4-(2-(((benzyloxy)carbonyl)amino)ethyl)-2-fluorophenyl)-3,8-diazabicyclo[3.2.1]octane-8-carboxylate (Method B) | 350 |
| Intermediate 65-5. 2-(4-(4-(2-Methoxyethyl)piperazin-1-yl)phenyl)ethan-1-amine | Benzyl (4-(4-(2-methoxyethyl)piperazin-1-yl)phenethyl)carbamate (Method B) | 264 |
| Intermediate 65-6. 2-(4-(4-(Oxetan-2-ylmethyl)piperazin-1-yl)phenyl)ethan-1-amine | Benzyl (4-(4-(oxetan-2-ylmethyl)piperazin-1-yl)phenethyl)carbamate (Method B) | 276 |
| Intermediate 65-7. tert-Butyl 4-(4-(2-aminoethyl)phenyl)-2-(((tert-butyldimethylsilyl)oxy)methyl)piperazine-1-carboxylate | tert-Butyl 4-(4-(2-(((benzyloxy)carbonyl)amino)ethyl)phenyl)-2-(((tert-butyldimethylsilyl)oxy)methyl)piperazine-1-carboxylate (Method B) | 450 |
| Intermediate 65-8. tert-Butyl 4-(4-(2-aminoethyl)-2,3,6-trifluorophenyl)piperazine-1-carboxylate | tert-Butyl 4-(4-bromo-2,3,6-trifluorophenyl)piperazine-1-carboxylate (Method A) | 360 |
| Intermediate 65-9. tert-Butyl 3-(4-(2-aminoethyl)-2,6-difluorophenyl)-3,8-diazabicyclo[3.2.1]octane-8-carboxylate | tert-Butyl 3-(4-bromo-2,6-difluorophenyl)-3,8-diazabicyclo[3.2.1]octane-8-carboxylate (Method A) | 368 |
| Intermediate 65-10. tert-Butyl 4-(4-(2-aminoethyl)-3-(methoxymethyl)phenyl)piperazine-1-carboxylate | tert-Butyl 4-(4-bromo-3-(methoxymethyl)phenyl)piperazine-1-carboxylate (Method A) | 350 |
| Intermediate 65-11. tert-butyl 1-(4-(2-aminoethyl)phenyl)-4,6-dihydropyrrolo[3,4-c]pyrazole-5(1H)-carboxylate | tert-butyl 1-(4-bromophenyl)-4,6-dihydropyrrolo[3,4-c]pyrazole-5(1H)-carboxylate (Method A: no phosphine ligand was used in the BF$_3$ salt Pd coupling) | 329 |
| Intermediate 65-12. tert-Butyl 1-(4-(2-aminoethyl)-3-fluorophenyl)-4,6-dihydropyrrolo[3,4-c]pyrazole-5(1H)-carboxylate | tert-butyl 1-(4-(2-(((benzyloxy)carbonyl)amino)ethyl)-3-fluorophenyl)-4,6-dihydropyrrolo[3,4-c]pyrazole-5(1H)-carboxylate (Method B) | 347 |
| Intermediate 65-13. tert-Butyl 4-(4-(2-aminoethyl)-3,5-difluorophenyl)piperazine-1-carboxylate | tert-Butyl 4-(4-(2-(((benzyloxy)carbonyl)amino)ethyl)-3,5-difluorophenyl)piperazine-1-carboxylate (Method B) | 342 |
| Intermediate 65-14. tert-Butyl 4-(4-(2-aminoethyl)phenyl)hexahydropyrrolo[3,2-b]pyrrole-1(2H)-carboxylate | tert-Butyl 4-(4-(2-(((benzyloxy)carbonyl)amino)ethyl)phenyl)hexahydropyrrolo[3,2-b]pyrrole-1(2H)-carboxylate (Method B) | 332 |
| Intermediate 65-15. tert-Butyl 3-(4-(2-aminoethyl)-2-cyanophenyl)-3,8-diazabicyclo[3.2.1]octane-8-carboxylate | tert-Butyl 3-(4-bromo-2-cyanophenyl)-3,8-diazabicyclo[3.2.1]octane-8-carboxylate (Method A) | 357 |
| Intermediate 65-16. tert-Butyl 3-(4-(2-aminoethyl)phenyl)-6,7-dihydropyrazolo[1,5-a]pyrazine-5(4H)-carboxylate | tert-Butyl 3-(4-(2-(((benzyloxy)carbonyl)amino)ethyl)phenyl)-6,7-dihydropyrazolo[1,5-a]pyrazine-5(4H)-carboxylate (Method B) | 343 |
| Intermediate 65-17: tert-butyl 3-(4-(2-aminoethyl)phenyl)-3,8-diazabicyclo[3.2.1]octane-8-carboxylate | tert-butyl 3-(4-(2-(((benzyloxy)carbonyl)amino)ethyl)phenyl)-3,8-diazabicyclo[3.2.1]octane-8-carboxylate (Method B; H$_2$ pressure: 10 atm) | 332 |

TABLE 8-continued

| Intermediate No.: | Precursor Used (Notes) | MS (ESI, m/z) [M + H] |
|---|---|---|
| Intermediate 65-18: tert-butyl 8-(4-(2-aminoethyl)phenyl)-3,8-diazabicyclo[3.2.1]octane-3-carboxylate | tert-butyl 8-(4-(2-(((benzyloxy)carbonyl)amino)ethyl)phenyl)-3,8-diazabicyclo[3.2.1]octane-3-carboxylate (Method B; H₂ pressure: 10 atm) | 332 |

Example 66

Intermediate 66: tert-Butyl 4-(4-(2-aminoethyl)-2,5-difluorophenyl)-3,6-dihydropyridine-1(2H)-carboxylate

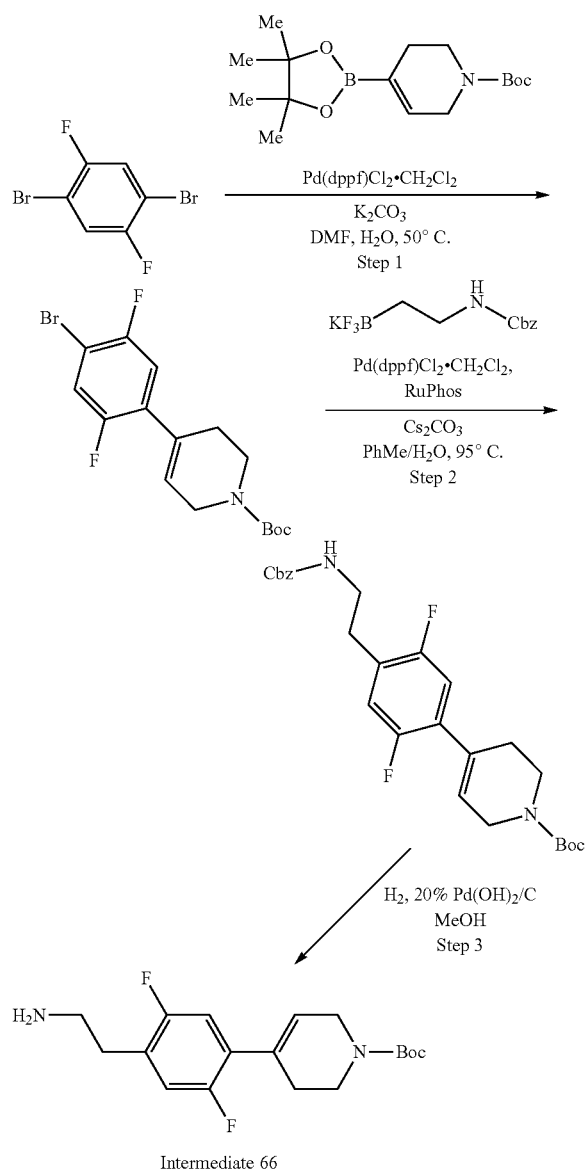

Intermediate 66

Step 1. tert-Butyl 4-(4-bromo-2,5-difluorophenyl)-3,6-dihydropyridine-1(2H)-carboxylate Into a 50-mL round-bottom flask that was purged and maintained under an inert atmosphere of nitrogen was added 1,4-dibromo-2,5-difluorobenzene (1.50 g, 5.52 mmol), tert-butyl 4-(tetramethyl-1,3,2-dioxaborolan-2-yl)-1,2,3,6-tetrahydropyridine-1-carboxylate (1.88 g, 6.06 mmol), potassium carbonate (2.28 g, 16.5 mmol), Pd(dppf)Cl$_2$·CH$_2$Cl$_2$ (400 mg, 0.49 mmol), DMF (20 mL) and H$_2$O (2 mL). The reaction mixture was stirred for 2 h at 50° C. and then cooled and quenched with water (20 mL). The resulting solution was extracted with ethyl acetate (3×50 mL). The combined organic layers were washed with water (50 mL) and brine (50 mL). The organic layer was then concentrated in vacuo. The resulting crude product was purified by FCC eluting with petroleum ether/ethyl acetate (5:1) to afford tert-butyl 4-(4-bromo-2,5-difluorophenyl)-3,6-dihydropyridine-1(2H)-carboxylate (1.5 g, 73%). $^1$H-NMR (300 MHz, CDCl$_3$) δ ppm 7.21-7.29 (m, 1H), 6.93-7.08 (m, 1H), 5.81-5.61 (m, 1H), 4.01-4.14 (m, 2H), 3.62 (t, J=5.7 Hz, 2H), 2.48-2.51 (m, 2H), 1.50 (s, 9H).

Step 2. tert-Butyl 4-(4-(2-(((benzyloxy)carbonyl)amino)ethyl)-2,5-difluorophenyl)-3,6-dihydropyridine-1(2H)-carboxylate Into a 100-mL round-bottom flask purged and maintained under an atmosphere of nitrogen was added tert-butyl 4-(4-bromo-2,5-difluorophenyl)-3,6-dihydropyridine-1(2H)-carboxylate (0.440 g, 1.18 mmol), potassium (2-(benzyloxycarbonylamino)ethyl) trifluoroborate (0.504 g, 1.77 mmol), toluene/H$_2$O (24/8 mL), Cs$_2$CO$_3$ (1.15 g, 3.53 mmol), Pd(dppf)Cl$_2$·CH$_2$Cl$_2$ (0.193 g, 0.236 mmol), and RuPhos (0.220 g, 0.471 mmol). The resulting solution was stirred for 3 h at 95° C. and then concentrated in vacuo to afford the crude product that was purified by FCC eluting with petroleum ether/EtOAc to afford tert-butyl 4-(4-(2-(((benzyloxy)carbonyl)amino)ethyl)-2,5-difluorophenyl)-3,6-dihydropyridine-1(2H)-carboxylate as a yellow oil (45%). $^1$H-NMR (300 MHz, CD$_3$OD) δ ppm 7.20-7.46 (m, 5H), 6.81-7.18 (m, 2H), 5.85-6.10 (m, 1H), 5.06 (s, 2H), 4.71-4.98 (m, 4H), 3.90-4.20 (m, 2H), 3.61 (t, J=5.4 Hz, 2H), 3.30-3.45 (m, 2H), 2.82 (t, J=6.9 Hz, 2H), 1.51 (s, 9H).

Step 3. tert-Butyl 4-(4-(2-aminoethyl)-2,5-difluorophenyl)-3,6-dihydropyridine-1(2H)-carboxylate Into a 50-mL round-bottom flask purged and maintained with nitrogen was added tert-butyl 4-(4-(2-(((benzyloxy)carbonyl)amino)ethyl)-2,5-difluorophenyl)-3,6-dihydropyridine-1(2H)-carboxylate (0.200 g, 0.42 mmol), 20% Pd(OH)$_2$/C (0.050 g), and methanol (8 mL). The resulting mixture was sparged with hydrogen gas and then stirred for 3 h at RT under hydrogen atmosphere. The reaction was vented to nitrogen and the solids were removed by filtration over Celite. The filtrate was concentrated in vacuo to afford tert-butyl 4-(4-(2-aminoethyl)-2,5-difluorophenyl)-3,6-dihydropyridine-1(2H)-carboxylate as a yellow oil (200 mg). The material was used without further purification. LCMS (ESI, m/z): 339 [M+H]$^+$.

Example 67

Intermediate 67. 2-(4-(1-Methylpiperidin-4-yl)phenyl)ethan-1-amine

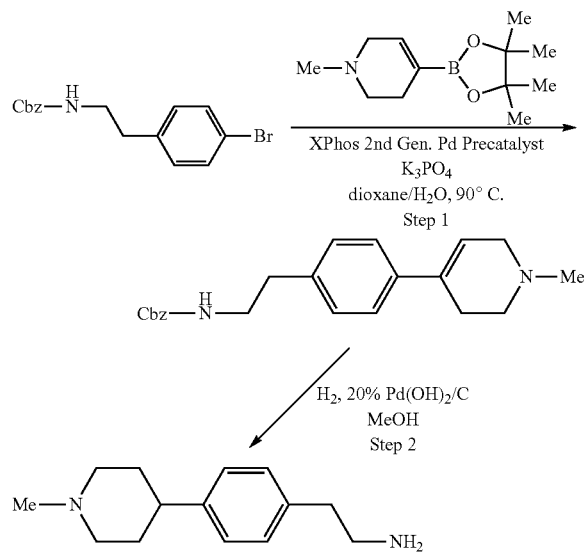

Intermediate 67

Example 68-1

Intermediate 68-1: tert-Butyl 6-(4-(2-aminoethyl)phenyl)-3,6-diazabicyclo[3.1.1]heptane-3-carboxylate

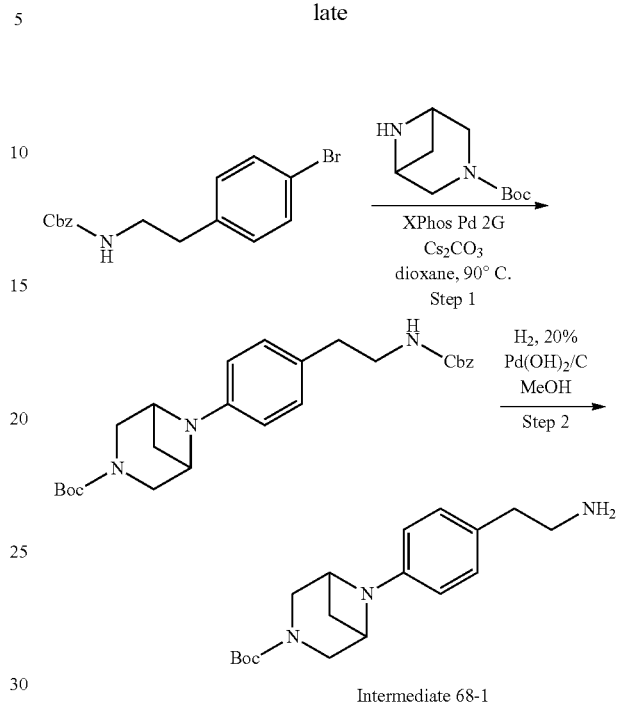

Intermediate 68-1

Step 1. Benzyl (4-(1-methyl-1,2,3,6-tetrahydropyridin-4-yl)phenethyl)carbamate

To a one dram vial was added benzyl 4-bromophenethylcarbamate (1.50 g, 4.49 mmol), 1-methyl-4-(4,4,5,5-tetramethyl-1,3,2-dioxaborolan-2-yl)-1,2,3,6-tetrahydropyridine (1.00 g, 4.49 mmol), potassium phosphate tribasic (3.81 g, 18.0 mmol), and XPhos $2^{nd}$ generation Pd precatalyst (0.353 g, 0.449 mmol). The flask was backfilled with dry nitrogen 3 times and degassed dioxane (9.8 ml) and water (2.80 ml) were added. The reaction mixture was heated to 90° C. overnight and then cooled to RT, filtered through a bed of Celite, and concentrated in vacuo. The resulting crude product was purified by FCC eluting with 20-30% EtOAc in hexanes to afford benzyl (4-(1-methyl-1,2,3,6-tetrahydropyridin-4-yl)phenethyl)carbamate as a white solid (1.2 g, 77%). LCMS (ESI, m/z): 351 [M+H]$^+$.

Step 2. 2-(4-(1-Methylpiperidin-4-yl)phenyl)ethan-1-amine

To a suspension of benzyl 4-(1-methyl-1,2,3,6-tetrahydropyridin-4-yl) phenethylcarbamate (1.2 g, 3.42 mmol) in MeOH (25 ml) under an atmosphere of nitrogen was added 20% palladium hydroxide/carbon (0.200 g, 1.42 mmol). The reaction was placed under a hydrogen atmosphere and stirred for 3 hours. The reaction was vented to nitrogen and filtered through Celite, washing the filter cake with EtOAc (~200 mL). The filtrate was concentrated in vacuo to afford 2-(4-(1-methylpiperidin-4-yl)phenyl)ethan-1-amine as a white solid (724 mg, 97%). LCMS (ESI, m/z): 219 [M+H]$^+$.

Step 1. tert-Butyl 6-(4-(2-(((benzyloxy)carbonyl)amino)ethyl)phenyl)-3,6-diazabicyclo[3.1.1]heptane-3-carboxylate To a vial was added benzyl 4-bromophenethylcarbamate (0.337 g, 1.01 mmol), tert -butyl 3,6-diazabicyclo[3.1.1]heptane-3-carboxylate (0.200 g, 1.01 mmol), Cs$_2$CO$_3$ (0.822 g, 2.52 mmol), and XPhos Pd $2^{nd}$ generation precatalyst (0.079 g, 0.10 mmol). The vial was backfilled with dry nitrogen 3 times. Dioxane (2 ml) was added to the solid mixture and a stream of dry nitrogen was bubbled through the reaction for 2 minutes. The reaction mixture was heated to 90 ° C. overnight and then cooled to RT, filtered through Celite and concentrated in vacuo. The resulting crude product was purified by FCC eluting with 20-30% EtOAc in hexanes to afford tert-butyl 6-(4-(2-(((benzyloxy)carbonyl)amino)ethyl)phenyl)-3,6-diazabicyclo[3.1.1]heptane-3-carboxylate as a white solid (322 mg, 71%). LCMS (ESI, m/z): 452 [M+H]$^+$.

Step 2. tert-Butyl 6-(4-(2-aminoethyl)phenyl)-3,6-diazabicyclo[3.1.1]heptane-3-carboxylate To a solution of tert-butyl 6-(4-(2-(((benzyloxy)carbonyl)amino)ethyl)phenyl)-3,6-diazabicyclo[3.1.1]heptane-3-carboxylate (0.322 g, 0.714 mmol) in methanol (20 ml) under an atmosphere of nitrogen was added 20% palladium hydroxide on carbon (100 mg, 0.714 mmol). The reaction was placed under a hydrogen atmosphere (balloon) and stirred for 3 h. The reaction was vented to nitrogen and filtered through Celite. The filter cake was washed with EtOAc (~80 mL) and the filtrate was concentrated in vacuo to afford tert-butyl 6-(4-(2-aminoethyl)phenyl) -3,6-diazabicyclo[3.1.1]heptane-3-carboxylate as a light yellow oil (99%) that was carried on without further purification. LCMS (ESI, m/z): 318 [M+H]$^+$.

The Intermediates in Table 9 below were synthesized according to the procedures outlined above for Example 68-1, Intermediate 68-1, using the appropriate synthetic precursors.

TABLE 9

| Intermediate No.: | Precursors Used (Notes) | MS (ESI, m/z) [M + H] |
|---|---|---|
| Intermediate 68-2. tert-Butyl 3-(4-(2-aminoethyl)phenyl)-3,6-diazabicyclo[3.1.1]heptane-6-carboxylate | Benzyl (4-bromophenethyl)carbamate and tert-Butyl 3,6-diazabicyclo[3.1.1]heptane-6-carboxylate | 318 |
| Intermediate 68-3. tert-Butyl (1R,5S)-7-(4-(2-aminoethyl)phenyl)-9-oxa-3,7-diazabicyclo[3.3.1]nonane-3-carboxylate | tert-Butyl (1R,5S)-9-oxa-3,7-diazabicyclo[3.3.1]nonane-3-carboxylate | — |

Example 69

Intermediate 69. tert-Butyl 3-(4-(2-aminoethyl)-2-chlorophenyl)-3,8-diazabicyclo[3.2.1]octane-8-carboxylate

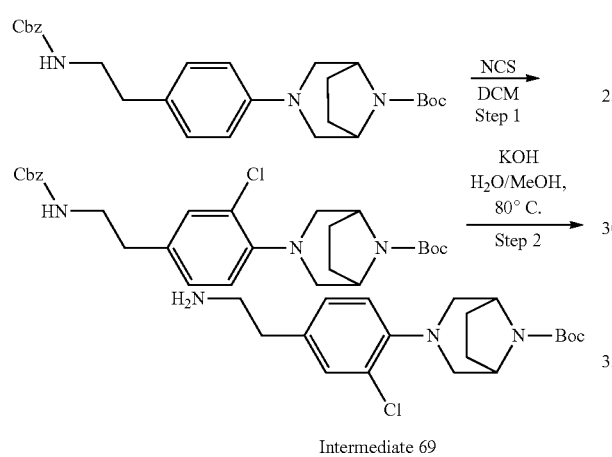

Intermediate 69

Step 1. tert-Butyl 3-(4-(2-(((benzyloxy)carbonyl)amino)ethyl)-2-chlorophenyl)-3,8-diazabicyclo[3.2.1]octane-8-carboxylate Into a 50-mL round-bottom flask was added tert-butyl 3-[4-(2-[[(benzyloxy)carbonyl]amino]ethyl)phenyl]-3,8-diazabicyclo[3.2.1]octane-8-carboxylate (0.500 g, 1.07 mmol), NCS (0.140 g, 1.05 mmol), and dichloromethane (5 mL). The reaction mixture was stirred for 27 h at RT and then concentrated in vacuo. The resulting crude product was purified by FCC eluting with petroleum ether/ethyl acetate (3:1) to afford tert-butyl 3-(4-(2-(((benzyloxy)carbonyl)amino)ethyl)-2-chlorophenyl)-3,8-diazabicyclo[3.2.1]octane-8-carboxylate as a yellow oil (380 mg, 71%). LCMS (ESI, m/z) 500 [M+H]+.

Step 2. tert-Butyl 3-(4-(2-aminoethyl)-2-chlorophenyl)-3,8-diazabicyclo[3.2.1]octane-8-carboxylate Into a 50-mL round-bottom flask was added tert-butyl 3-(4-(2-(((benzyloxy)carbonyl) amino)ethyl)-2-chlorophenyl)-3,8-diazabicyclo[3.2.1]octane-8-carboxylate (0.38 g, 0.76 mmol), potassium hydroxide solution (40% aqueous, 5 mL), and MeOH (10 mL). The resulting solution was stirred for 4 h at 80° C. and then cooled and concentrated in vacuo to afford tert-butyl 3-(4-(2-aminoethyl)-2-chlorophenyl)-3,8-diazabicyclo[3.2.1]octane-8-carboxylate as a brown oil (300 mg). The material was used without further purification. LCMS (ESI, m/z) 366 [M+H]+.

Example 70

Intermediate 70. tert-Butyl 4-(4-(2-aminoethyl)-3-methylphenyl)piperazine-1-carboxylate

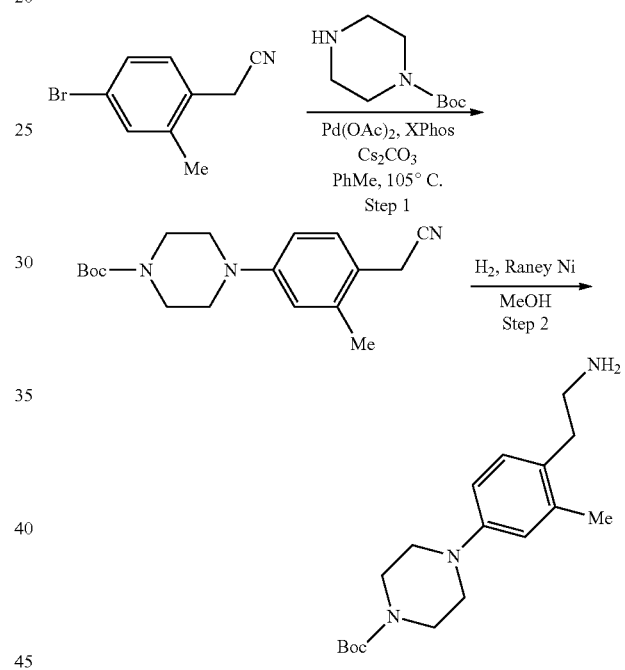

Intermediate 70

Step 1. tert-Butyl 4-(4-(cyanomethyl)-3-methylphenyl)piperazine-1-carboxylate

Into a 100-mL round-bottom flask, purged and maintained under an inert atmosphere of nitrogen, was added 2-(4-bromo-2-methylphenyl)acetonitrile (2.65 g, 12.6 mmol), tert-butyl piperazine-1-carboxylate (2.83 g, 15.2 mmol), Pd(OAc)$_2$ (0.568 g, 2.54 mmol), XPhos (2.42 g, 5.07 mmol), Cs$_2$CO$_3$ (8.45 g, 25.9 mmol), and toluene (30 mL). The reaction mixture was stirred overnight at 105° C. in an oil bath and then cooled and concentrated in vacuo to provide a crude product that was purified via silica gel chromatography and eluted with ethyl acetate/petroleum ether (1:3) to afford tert-butyl 4-(4-(cyanomethyl)-3-methylphenyl)piperazine-1-carboxylate as a yellow solid (1.3 g, 33%). LCMS (ESI, m/z): 316 [M+H]+.

Step 2. tert-Butyl 4-(4-(2-aminoethyl)-3-methylphenyl)piperazine-1-carboxylate

Into a 100-mL round-bottom flask, purged and maintained with nitrogen, was added tert-butyl 4-(4-(cyanomethyl)-3- methylphenyl)piperazine-1-carboxylate (1.30 g, 4.12 mmol), Raney Ni (500 mg), and methanol (20 mL). The resulting mixture was sparged with hydrogen and was stirred overnight at RT under hydrogen (balloon). The reaction was vented to nitrogen and the solids were removed by filtration. The filtrate was concentrated in vacuo to afford tert-butyl 4-(4-(2-aminoethyl)-3-methylphenyl)piperazine-1-carboxylate as a yellow oil (400 mg, 30%). LCMS (ESI, m/z) 320 [M+H]$^+$.

Example 71-1

Intermediate 71-1. tert-Butyl 4-(4-(2-aminoethyl)-2-fluorophenyl)-3,6-dihydropyridine-1(2H)-carboxylate

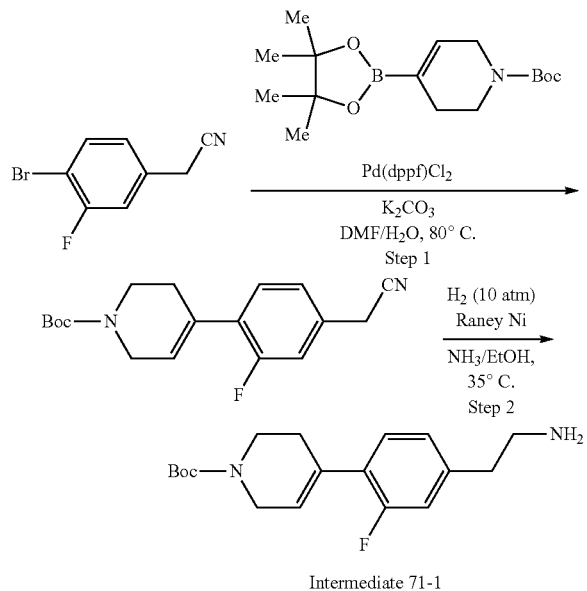

Intermediate 71-1

Step 1. tert-Butyl 4-(4-(cyanomethyl)-2-fluorophenyl)-3,6-dihydropyridine-1(2H)-carboxylate Into a 100-mL round-bottom flask that was purged and maintained under an inert atmosphere of nitrogen was added 2-(4-bromo-3-fluorophenyl)acetonitrile (0.500 g, 2.34 mmol), tert-butyl 4-(tetramethyl-1,3,2-dioxaborolan-2-yl)-1,2,3,6-tetrahydropyridine-1-carboxylate (1.09 g, 3.53 mmol), potassium carbonate (0.972 g, 7.03 mmol), Pd(dppf)Cl$_2$.CH$_2$Cl$_2$ (0.384 g, 0.47 mmol), DMF (20 mL) and H$_2$O (2 mL). The reaction mixture was stirred at 80° C. for 3 h and then cooled and concentrated in vacuo. The resulting crude product was purified by FCC eluting with ethyl acetate/petroleum ether (1:5) to afford tert-butyl 4-(4-(cyanomethyl)-2-fluorophenyl)-3,6-dihydropyridine-1(2H)-carboxylate as a yellow solid (0.7 g, 95%). $^1$H-NMR (300 MHz, CDCl$_3$) δ ppm 7.33-7.23 (m, 1H), 7.18-7.00 (m, 2H), 5.97 (s, 1H), 4.17-4.06 (m, 2H), 3.81-3.70 (m, 2H), 3.64 (t, J=5.5 Hz, 2H), 2.51-2.46 (m, 2H), 1.5 (s, 9H).

Step 2. tert-Butyl 4-(4-(2-aminoethyl)-2-fluorophenyl)-3,6-dihydropyridine-1(2H)-carboxylate Into a 50-mL high pressure reactor that was purged and maintained under an inert atmosphere of nitrogen was added tert-butyl 4-(4-(cyanomethyl)-2-fluorophenyl)-3,6-dihydropyridine-1(2H)-carboxylate (0.300 g, 0.95 mmol), Raney Ni (0.2 g), and NH$_3$/EtOH (4 N; 25 mL). The reaction vessel was pressurized with hydrogen (10 atm) and the mixture was stirred overnight at 35° C. The reaction was vented to nitrogen and the solids were removed by filtration over Celite. The filtrate was concentrated in vacuo to afford tert-butyl 4-(4-(2-aminoethyl)-2-fluorophenyl)-3,6-dihydropyridine-1(2H)-carboxylate as a light yellow oil (440 mg). The material was carried on without further purification. LCMS (ESI, m/z): 321 [M+H]$^+$.

The Intermediate in Table 10 below was synthesized according to the procedures outlined above for Example 71-1, Intermediate 71-1, using the appropriate synthetic precursors.

TABLE 10

| Intermediate No.: | Precursors Used (Notes) | MS (ESI, m/z) [M + H] |
|---|---|---|
| Intermediate 71-2. tert-Butyl 4-(4-(2-aminoethyl)-3-fluorophenyl)-3,6-dihydropyridine-1(2H)-carboxylate | 2-(4-Bromo-2-fluorophenyl)acetonitrile and tert-butyl 4-(4,4,5,5-tetramethyl-1,3,2-dioxaborolan-2-yl)-3,6-dihydropyridine-1(2H)-carboxylate | 321 |

Example 72

Intermediate 72. tert-Butyl 3-(4-(2-aminoethyl)-3-chlorophenyl)-3,8-diazabicyclo[3.2.1]octane-8-carboxylate

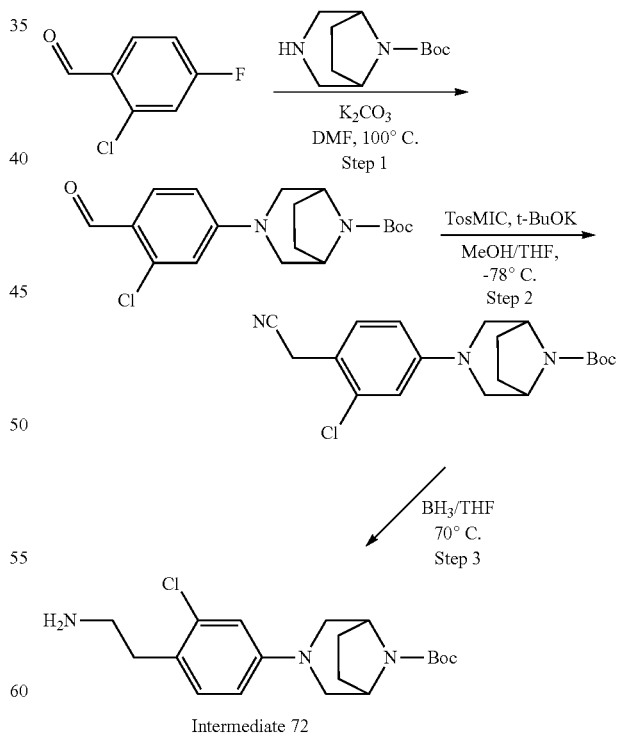

Intermediate 72

Step 1. tert-Butyl 3-(3-chloro-4-formylphenyl)-3,8-diazabicyclo[3.2.1]octane-8-carboxylate Into a 100-mL round-bottom flask was added 2-chloro-4-fluorobenzaldehyde (0.743 g, 4.69 mmol), tert-butyl 3,8- diazabicyclo[3.2.1]octane-8-carboxylate (1.00 g, 4.71 mmol), potassium carbonate (1.30 g, 9.41 mmol), and DMF (15 mL). The reaction mixture was stirred for 3 h at 100° C. and then cooled to RT and quenched with water (50 mL). The resulting solution was extracted with ethyl acetate (3×20 mL) and the combined organic layers were dried over anhydrous sodium sulfate. The solids were removed by filtration over Celite and the filtrate was concentrated in vacuo. The resulting crude product was purified by FCC eluting with ethyl acetate/petroleum ether (1:3) to afford tert-butyl 3-(3-chloro-4-formylphenyl)-3,8-diazabicyclo[3.2.1]octane-8-carboxylate as a white solid (640 mg, 39%). LCMS (ESI, m/z): 351 [M+H]+.

Step 2. tert-Butyl 3-(3-chloro-4-(cyanomethyl)phenyl)-3,8-diazabicyclo[3.2.1]octane-8-carboxylate Into a 250-mL 3-necked round-bottom flask purged and maintained with nitrogen atmosphere was added KOt-Bu (0.820 g, 7.32 mmol) and tetrahydrofuran (60 mL). The resulting solution was cooled to −78° C. and treated with a solution of p-toluenesulfonyl isocyanide (0.713 g, 3.94 mmol) in THF (2 mL). The resulting solution was stirred for 15 min. This was followed by the addition of a solution of tert-butyl 3-(3-chloro-4-formylphenyl)-3,8-diazabicyclo[3.2.1]octane-8-carboxylate (640 mg, 1.82 mmol) in THF (2 mL). The resulting mixture was stirred for 2 h at −78° C. and then methanol (5 mL) was added. The resulting solution was heated to 80° C. for 30 min and then cooled and concentrated in vacuo. The crude product was purified by FCC eluting with ethyl acetate/petroleum ether (1:3) to afford the title compound as a yellow solid (240 mg, 36%). LCMS (ESI, m/z): 362 [M+H]+.

Step 3. tert-Butyl 3-(4-(2-aminoethyl)-3-chlorophenyl)-3,8-diazabicyclo[3.2.1]octane-8-carboxylate Into a 50-mL round-bottom flask that was purged and maintained with nitrogen was added tert-butyl 3-(3-chloro-4-(cyanomethyl)phenyl)-3,8-diazabicyclo[3.2.1]octane-8-carboxylate (0.22 g, 0.61 mmol) followed by BH$_3$/THF (1.0 M, 10 mL). The resulting solution was stirred for 3 h at 70° C. and then cooled to RT and quenched with methanol (1 mL). The resulting mixture was concentrated in vacuo to afford tert-butyl 3-(4-(2-aminoethyl)-3-chlorophenyl)-3,8-diazabicyclo[3.2.1]octane-8-carboxylate as a white solid (223 mg) that was used without further purification. LCMS (ESI, m/z): 366 [M+H]+.

Example 73

Intermediate 73. tert-Butyl 4-(4-(2-aminoethyl)-2,3-difluorophenyl) piperazine -1-carboxylate

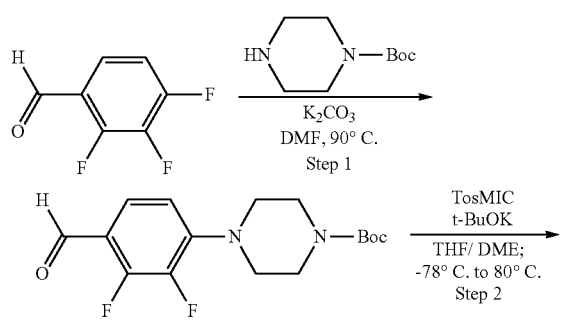

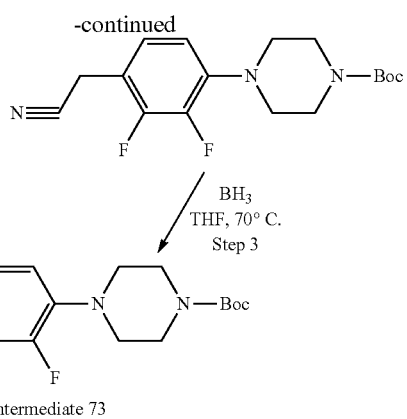

Intermediate 73

Step 1. tert-Butyl 4-(2,3-difluoro-4-formylphenyl)piperazine-1-carboxylate

The title compound was prepared according to the procedure used for Step 1 of the preparation of Example 72: Intermediate 72 at 90° C. using 2,3,4-trifluorobenzaldehyde. This afforded the title compound as a white solid (46%). LCMS (ESI, m/z): 327 [M+H]+.

Step 2. tert-Butyl 4-(4-(cyanomethyl)-2,3-difluorophenyl)piperazine-1-carboxylate Into a 100-mL round-bottom flask that was purged and maintained under an inert atmosphere of nitrogen was added a solution of t-BuOK (1.03 g, 9.18 mmol) in tetrahydrofuran (10 mL). The solution was cooled to −78° C. and 4-methylbenzene-1-sulfonyl isocyanide (1.00 g, 5.46 mmol) in ethylene glycol dimethyl ether (10 mL) and a solution of tert-butyl 4-(2,3-difluoro-4-formylphenyl)piperazine-1-carboxylate (1.50 g, 4.60 mmol) in ethylene glycol dimethyl ether (15 mL) was added at −78° C. The reaction mixture was stirred for 4 h at −78° C. and then methanol (15 mL) was added. The resulting solution was heated and stirred overnight at 80° C. and then cooled and concentrated in vacuo. The resulting crude product was purified by FCC eluting with ethyl acetate/petroleum ether (1:3) to afford tert-butyl 4-(4-(cyanomethyl)-2,3-difluorophenyl)piperazine-1-carboxylate as a white solid (900 mg, 58%). LCMS (ESI, m/z): 338 [M+H]+.

Step 3. tert-Butyl 4-(4-(2-aminoethyl)-2,3-difluorophenyl)piperazine-1-carboxylate Into a 50-mL round-bottom flask that was purged and maintained with nitrogen was added tert-butyl 4-(4-(cyanomethyl)-2,3-difluorophenyl)piperazine-1-carboxylate (0.200 g, 0.590 mmol) and tetrahydrofuran (5 mL). To the solution was added BH3 (1 M in THF; 2 mL, 2 mmol). The resulting solution was stirred overnight at 70° C. and then cooled to RT and quenched with methanol (10 mL). The resulting mixture was concentrated in vacuo to afford tert-butyl 4-(4-(2-aminoethyl)-2,3-difluorophenyl) piperazine-1-carboxylate as a colorless oil (120 mg). The material was used without further purification. LCMS (ESI, m/z): 342 [M+H]+.

Example 74

Intermediate 74. tert-Butyl 4-(5-(2-aminoethyl)-[1,1'-biphenyl]-2-yl)piperazine-1-carboxylate

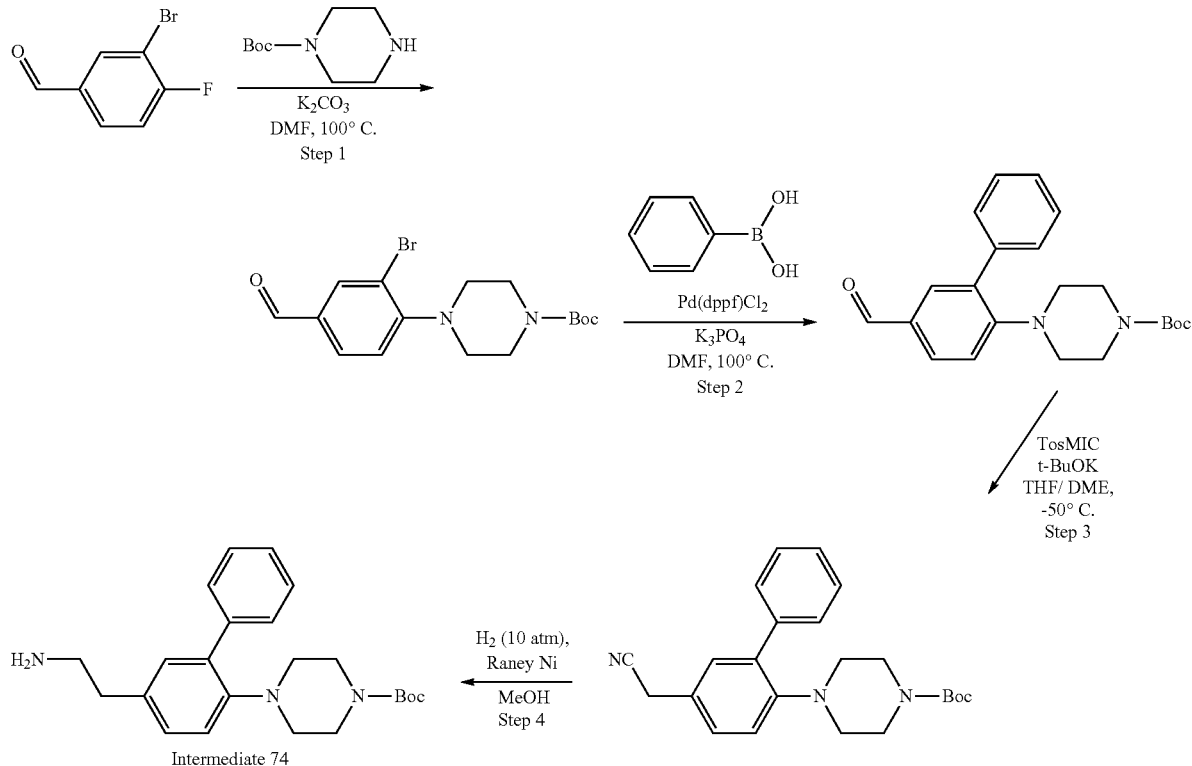

Step 1. tert-Butyl 4-(2-bromo-4-formylphenyl)piperazine-1-carboxylate

The title compound was prepared according to the procedure used for Step 1 of the preparation of Example 72: Intermediate 72, using 3-bromo-4-fluorobenzaldehyde as the starting material. This afforded the title compound as a light yellow solid (52%). LCMS (ESI, m/z): 369, 371 [M+H]$^+$.

Step 2. tert-Butyl 4-(5-formyl-[1,1'-biphenyl]-2-yl)piperazine-1-carboxylate

Into a 50-mL round-bottom flask, purged and maintained under an inert atmosphere of nitrogen, was added tert-butyl 4-(2-bromo-4-formylphenyl)piperazine-1-carboxylate (2.14 g, 5.80 mmol), phenylboronic acid (0.848 g, 6.95 mmol), $K_3PO_4$ (4.15 g, 15.8 mmol), Pd(dppf)Cl$_2$ (0.42 g, 0.57 mmol), and DMF (25 mL). The reaction mixture was stirred for 12 h at 100° C. and then cooled to RT. The resulting mixture was quenched with H$_2$O (50-mL) and extracted with dichloromethane (2×25 mL). The combined organic layers were washed with brine (10 mL), concentrated in vacuo, and the crude product was purified by FCC eluting with ethyl acetate/petroleum ether (1:6) to afford tert-butyl 4-(5-formyl [1,1'-biphenyl]-2-yl)piperazine-1-carboxylate as a brown solid (1.8 g, 85%). LCMS (ESI, m/z): 367 [M+H]$^+$.

Step 3. tert-Butyl 4-(5-(cyanomethyl)-[1,1'-biphenyl]-2-yl)piperazine-1-carboxylate Into a 50-mL 3-necked round-bottom flask was added a solution of KOt-Bu (0.610 g, 5.44 mmol) in tetrahydrofuran (3 mL). This was followed by the addition of a solution of TosMIC (0.590 g, 2.99 mmol) in ethylene glycol dimethyl ether (4 mL) at −50° C. To this was added a solution of tert-butyl 4-(5-formyl-[1,1'-biphenyl]-2-yl)piperazine-1-carboxylate (1.00 g, 2.73 mmol) in ethylene glycol dimethyl ether (4 mL) dropwise with stirring at −50° C. over 15 min. The resulting solution was stirred for 2 h at 0° C. and then heated to 80° C. and stirred for 30 minutes. The reaction mixture was cooled and concentrated in vacuo to provide a crude product that was dissolved in DCM (30 mL) and washed with brine (3×10 mL). The organic layer was then concentrated in vacuo and the crude product was purified by FCC eluting with ethyl acetate/petroleum ether (2:3) to afford tert-butyl 4-(5-(cyanomethyl)[1,1'-biphenyl]-2-yl)piperazine-1-carboxylate as a yellow solid (220 mg, 21%). LCMS (ESI, m/z): 378 [M+H]$^+$.

Step 4. tert-Butyl 4-(5-(2-aminoethyl)[1,1'-biphenyl]-2-yl)piperazine-1-carboxylate Into a 50-mL high pressure tank reactor that was purged and maintained with nitrogen was added tert-butyl 4-(5-(cyanomethyl)[1,1'-biphenyl]-2-yl)piperazine-1-carboxylate (0.230 g, 0.61 mmol), Raney Ni (3.5 mg), and 4 M NH$_3$/methanol (20 mL). The reaction vessel was pressurized with hydrogen (10 atm), stirred for 12 h at RT, and then vented with nitrogen. The solids were removed by filtration over Celite and the filtrate was concentrated in vacuo to afford tert-butyl 4-(5-(2-aminoethyl)-[1,1'-biphenyl]-2-yl) piperazine-1-carboxylate as a white solid (180 mg, 77%). LCMS (ESI, m/z): 382 [M+H]$^+$.

Example 75

Intermediate 75. tert-Butyl 3-(4-(2-aminoethyl)phenyl)-3-hydroxypyrrolidine-1-carboxylate

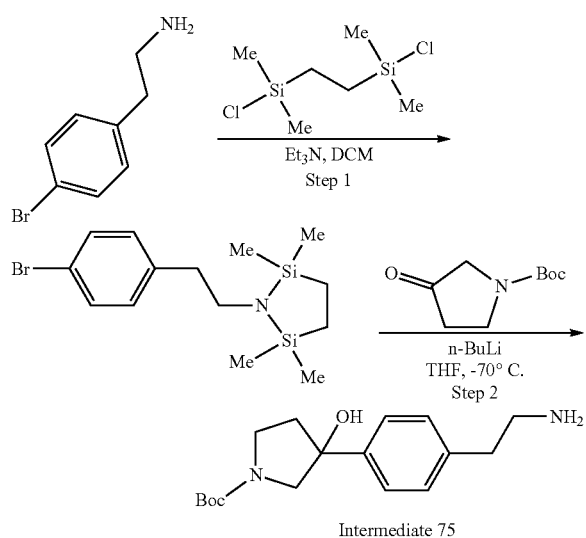

Intermediate 75

Step 1. 1-(4-Bromophenethyl)-2,2,5,5-tetramethyl-1,2,5-azadisilolidine

Into a 50-mL round-bottom flask was added 2-(4-bromophenyl)ethan-1-amine (0.500 g, 2.50 mmol) and dichloromethane (15 mL). This was followed by the addition of triethylamine (0.505 g, 0.696 mL, 5.00 mmol) dropwise with stirring. Chloro [2-(chlorodimethylsilyl)ethyl]dimethylsilane (0.538 g, 2.50 mmol) was then added portion-wise. The resulting solution was stirred for 2 h at RT and then extracted with ethyl acetate (3×20 mL). The combined organic layers were washed with brine (20 mL), dried over anhydrous sodium sulfate, filtered, and concentrated in vacuo to afford 1-(4-bromophenethyl)-2,2,5,5-tetramethyl-1,2,5-azadisilolidine as a white solid (600 mg). The material was used without further purification.

Step 2. tert-Butyl 3-(4-(2-aminoethyl)phenyl)-3-hydroxypyrrolidine-1-carboxylate Into a 250-mL 3-necked round-bottom flask, purged and maintained under an inert atmosphere of nitrogen, was added 1-(4-bromophenethyl)-2,2,5,5-tetramethyl-1,2,5-azadisilolidine (2.06 g, 6.02 mmol) and tetrahydrofuran (30 mL). The resulting solution was cooled −70° C. and then n-BuLi (2.5 M, 2.6 mL) was added dropwise with stirring. The resulting solution was stirred for 0.5 h and then tert-butyl 3-oxopyrrolidine-1-carboxylate (1.10 g, 5.94 mmol), was added portion-wise. The resulting solution was stirred for 2 h at −70° C. and then quenched with saturated aqueous $NH_4Cl$ solution (50-mL). The mixture was extracted with dichloromethane (3×50-mL) and the combined organic layers were washed with brine (1×50-mL), dried over anhydrous sodium sulfate, filtered, and concentrated in vacuo to afford tert-butyl 3-(4-(2-aminoethyl)phenyl)-3-hydroxyl)yrrolidine-1-carboxylate as a brown solid (1.0 g, 55%). The material was used without further purification. LCMS (ESI, m/z): 307 $[M+H]^+$.

Example 76-1

Intermediate 76-1. tert-Butyl 3-[4-(1-aminopropan-2-yl)-2,5-difluorophenyl]-3,8-diazabicyclo[3.2.1]octane-8-carboxylate

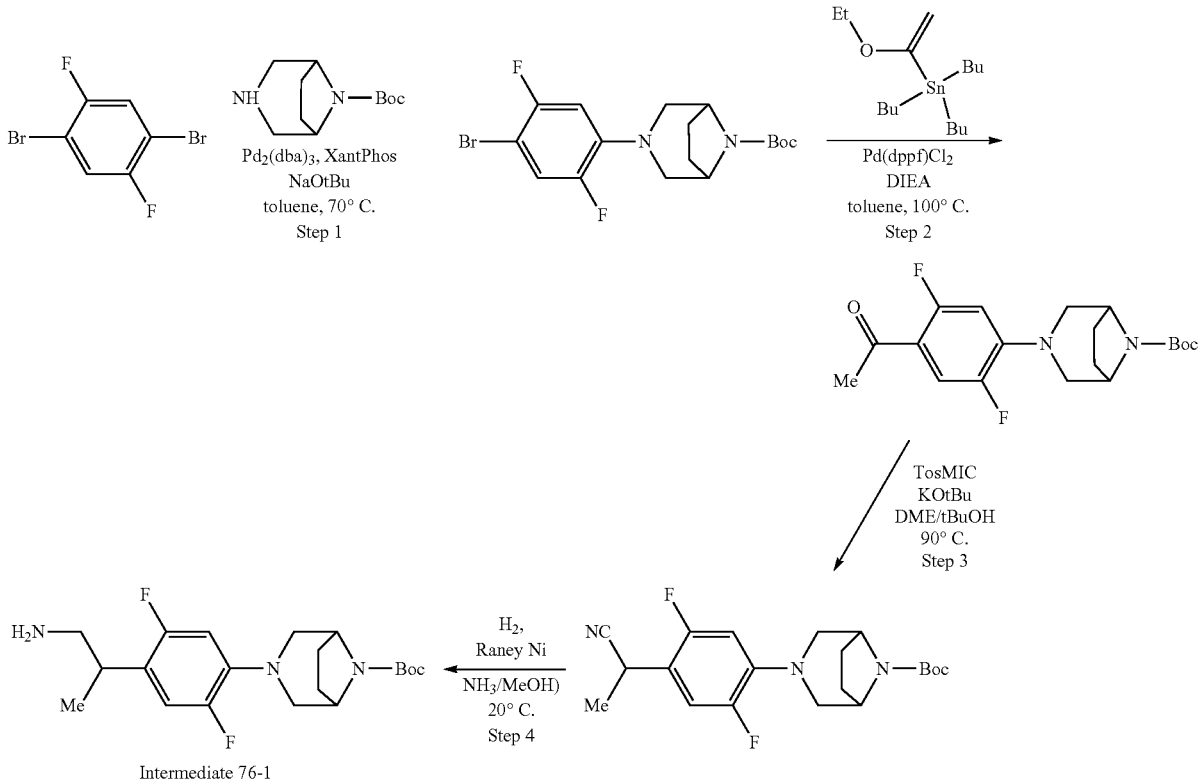

Intermediate 76-1

Step 1. tert-Butyl 3-(4-bromo-2,5-difluorophenyl)-3,8-diazabicyclo[3.2.1]octane-8-carboxylate Into a 250-mL round-bottom flask that was purged and maintained under an inert atmosphere of nitrogen was added 1,4-dibromo-2,5-difluorobenzene (2.97 g, 10.9 mmol), tert-butyl 3,8-diazabicyclo[3.2.1]octane-8-carboxylate (2.12 g, 9.99 mmol), Pd$_2$(dba)$_3$·CHCl$_3$ (0.52 g, 0.50 mmol), XantPhos (0.578 g, 1.00 mmol), sodium t-butoxide (1.92 g, 20.0 mmol), and toluene (100 mL). The resulting mixture was stirred for 45 min at 70° C. and then cooled to RT and quenched with water (20 mL). The resulting solution was extracted with ethyl acetate (3×20 mL). The combined organic layers were then dried over anhydrous sodium sulfate, filtered, and concentrated in vacuo to provide a crude product that was purified via silica gel chromatography and eluted with ethyl acetate/petroleum ether (EA/PE=1:100 to 1:5) to afford tert-butyl 3-(4-bromo-2,5-difluorophenyl)-3,8-diazabicyclo[3.2.1]octane-8-carboxylate as a light yellow solid (2.6 g, 58%). LCMS (ESI, m/z): 403, 405 [M+H]$^+$.

Step 2. tert-Butyl 3-(4-acetyl-2,5-difluorophenyl)-3,8-diazabicyclo[3.2.1]octane-8-carboxylate Into a 250-mL round-bottom flask, purged and maintained under an inert atmosphere of nitrogen, was added tert-butyl 3-(4-bromo-2,5-difluorophenyl)-3,8-diazabicyclo[3.2.1]octane-8-carboxylate (1.30 g, 3.22 mmol), tributyl(1-ethoxyethenyl)stannane (1.75 g, 1.64 mL, 4.85 mmol), Pd(dppf)Cl$_2$·CH$_2$Cl$_2$ (0.53 g, 0.64 mmol), DIEA (1.25 g, 1.68 mL, 9.67 mmol), and toluene (100 mL). The resulting solution was stirred for 18 h at 100° C. and then cooled to RT and quenched with saturated aqueous ammonium chloride solution (30 mL). The resulting mixture was extracted with ethyl acetate (3×100 mL) and the combined organic layers were dried over sodium sulfate, filtered, and concentrated in vacuo to provide a crude product that was purified via silica gel chromatography and eluted with ethyl acetate/petroleum ether (EA/PE=1:100 to 1:10) to afford tert-butyl 3-(4-acetyl-2,5-difluorophenyl)-3,8-diazabicyclo[3.2.1]octane-8-carboxylate as light yellow oil (460 mg, 35%). LCMS (ESI, m/z): 367 [M+H]$^+$.

Step 3. tert-Butyl 3-[4-(1-cyanoethyl)-2,5-difluorophenyl]-3,8-diazabicyclo[3.2.1]octane-8-carboxylate Into a 100-mL round-bottom flask was added tert-butyl 3-(4-acetyl-2,5-difluorophenyl)-3,8-diazabicyclo[3.2.1]octane-8-carboxylate (0.420 g, 1.15 mmol), TosMIC (0.336 g, 1.71 mmol), potassium t-butoxide (0.321 g, 2.86 mmol), t-butanol (10 mL), and ethylene glycol dimethyl ether (10 mL). The resulting solution was stirred for 18 h at 90° C. and then cooled to RT and quenched with water (50 mL). The resulting mixture was extracted with ethyl acetate (3×20 mL). The combined organic layers were then dried over sodium sulfate, filtered, and concentrated in vacuo to provide a crude product that was purified via silica gel chromatography and eluted with ethyl acetate/petroleum ether (EA/PE=1:100 to 1:10) to afford tert-butyl 3-[4-(1-cyanoethyl)-2,5-difluorophenyl]-3,8-diazabicyclo[3.2.1]octane-8-carboxylate as a light yellow solid (350 mg, 73%). LCMS (ESI, m/z): 378 [M+H]$^+$.

Step 4. tert-Butyl 3-4-(1-aminopropan-2-yl)-2,5-difluorophenyl]-3,8-diazabicyclo[3.2.1]octane-8-carboxylate Into a 50-mL round-bottom flask purged and maintained with nitrogen was added tert-butyl 3-[4-(1-cyanoethyl)-2,5-difluorophenyl]-3,8-diazabicyclo[3.2.1]octane-8-carboxylate (0.35 g, 0.93 mmol), Raney Ni (0.35 g), and a solution of ammonia in methanol (7 M, 20 mL). The resulting mixture was sparged with hydrogen and then stirred for 2 h at 20° C. under a hydrogen atmosphere. The solids were removed by filtration through Celite and the filtrate was concentrated in vacuo to afford tert-butyl 3-[4-(1-aminopropan-2-yl)-2,5-difluorophenyl]-3,8-diazabicyclo[3.2.1] octane-8-carboxylate as a light yellow solid (200 mg, 51%). LCMS (ESI, m/z): 382 [M+H]$^+$.

The Intermediate in Table 11 below was synthesized according to the procedures outlined above for Example 76-1, Intermediate 76-1, using the appropriate synthetic precursors.

TABLE 11

| Intermediate No.: | Precursors Used (Notes) | MS (ESI, m/z) [M + H] |
|---|---|---|
| Intermediate 76-2. tert-Butyl 4-[4-(1-aminopropan-2-yl)-2,5-difluorophenyl]piperazine-1-1-carboxylate | 1,4-Dibromo-2,5-difluorobenzene and tert-butyl piperazine-carboxylate | 356 |

Example 77-1

Intermediate 77-1. tert-Butyl 3-[4-(1-aminopropan-2-yl)-3-fluorophenyl]-3,8-diazabicyclo[3.2.1]octane-8-carboxylate

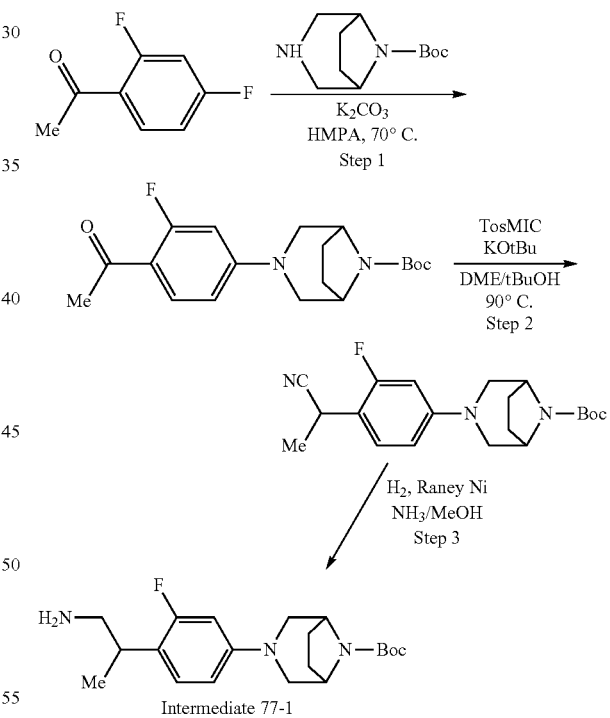

Intermediate 77-1

Step 1. tert-Butyl 3-(4-acetyl-3-fluorophenyl)-3,8-diazabicyclo[3.2.1]octane-8-carboxylate Into a 100-mL round-bottom flask was added 1-(2,4-difluorophenyl)ethan-1-one (2.65 g, 17.0 mmol), tert-butyl 3,8-diazabicyclo[3.2.1]octane-8-carboxylate (3.00 g, 14.1 mmol), potassium carbonate (5.86 g, 42.4 mmol), and HMPA (30 mL). The resulting solution was stirred overnight at 70° C. in an oil bath and then cooled to RT and quenched with water (30 mL). The resulting solution was extracted with ethyl acetate (3×30 mL). The combined organic layers were concentrated in vacuo to provide a crude product that was purified via silica gel chromatography and eluted with ethyl acetate/petroleum ether (1:5) to afford tert-butyl 3-(4-acetyl-3-fluorophenyl)-3,8-diazabicyclo[3.2.1]octane-8-carboxylate as brown oil (1.8 g, 30%). LCMS (ESI, m/z): 349 [M+H]⁺.

Step 2. tert-Butyl 3-[4-(1-cyanoethyl)-3-fluorophenyl]-3,8-diazabicyclo[3.2.1]octane-8-carboxylate Into a 100-mL round-bottom flask was added tert-butyl 3-(4-acetyl-3-fluorophenyl) -3,8-diazabicyclo[3.2.1]octane-8-carboxylate (1.80 g, 5.17 mmol), KOt-Bu (1.45 g, 13.0 mmol), p -toluenesulfonyl isocyanide (1.51 g, 7.74 mmol), tert-butanol (20 mL), and ethylene glycol dimethyl ether (20 mL). The resulting solution was stirred overnight at 90° C. in an oil bath and then cooled and quenched by the addition water (20 mL). The resulting solution was extracted with ethyl acetate (3×20 mL). The combined organic layers were then dried over anhydrous sodium sulfate, filtered, and concentrated in vacuo to provide a crude product that was purified via silica gel chromatography and eluted with ethyl acetate/petroleum ether (1:5) to afford tert-butyl 3-[4-(1-cyanoethyl)-3-fluorophenyl]-3,8-diazabicyclo[3.2.1]octane-8-carboxylate as a brown oil (1.2 g, 65%). LCMS (ESI, m/z): 360 [M+H]⁺.

Step 3. tert-Butyl 3-[4-(1-aminopropan-2-yl)-3-fluorophenyl]-3,8-diazabicyclo[3.2.1]octane -8-carboxylate Into a 100-mL round-bottom flask, purged and maintained with nitrogen, was added tert-butyl 3-[4-(1-cyanoethyl)-3-fluorophenyl]-3,8-diazabicyclo[3.2.1]octane-8-carboxylate (1.00 g, 2.78 mmol), NH₃/MeOH (7 M, 20 mL), and Raney Ni (500 mg). The reaction mixture was sparged with hydrogen and was stirred for 2 h at RT under an atmosphere of hydrogen. The solids were removed by filtration over Celite and the filtrate was concentrated in vacuo to provide a crude product that was purified via silica gel chromatography and eluted with dichloromethane/methanol (10:1) to afford tert-butyl 3- [4-(1 -aminopropan-2-yl)-3-fluorophenyl]-3,8-diazabicyclo[3.2.1]octane-8-carboxylate as yellow oil (800 mg, 79%). LCMS (ESI, m/z): 364 [M+H]⁺.

The Intermediate in Table 12 below was synthesized according to the procedures outlined above for Example 77-1, Intermediate 77-1, using the appropriate synthetic precursors.

TABLE 12

| Intermediate No.: | Precursors Used (Notes) | MS (ESI, m/z) [M + H] |
|---|---|---|
| Intermediate 77-2. tert-Butyl 3-[4-(1-aminopropan-2-yl)-2-fluorophenyl]-3,8-8-diazabicyclo[3.2.1]octane-carboxylate | 1-(3,4-Difluorophenyl)ethan-1-one and tert-butyl 3,8-diazabicyclo[3.2.1]octane-8-carboxylate | 364 |

Example 78

Intermediate 78. tert-Butyl 3-(4-(1-aminopropan-2-yl)-2-cyanophenyl)-3,8-diazabicyclo[3.2.1]octane-8-carboxylate

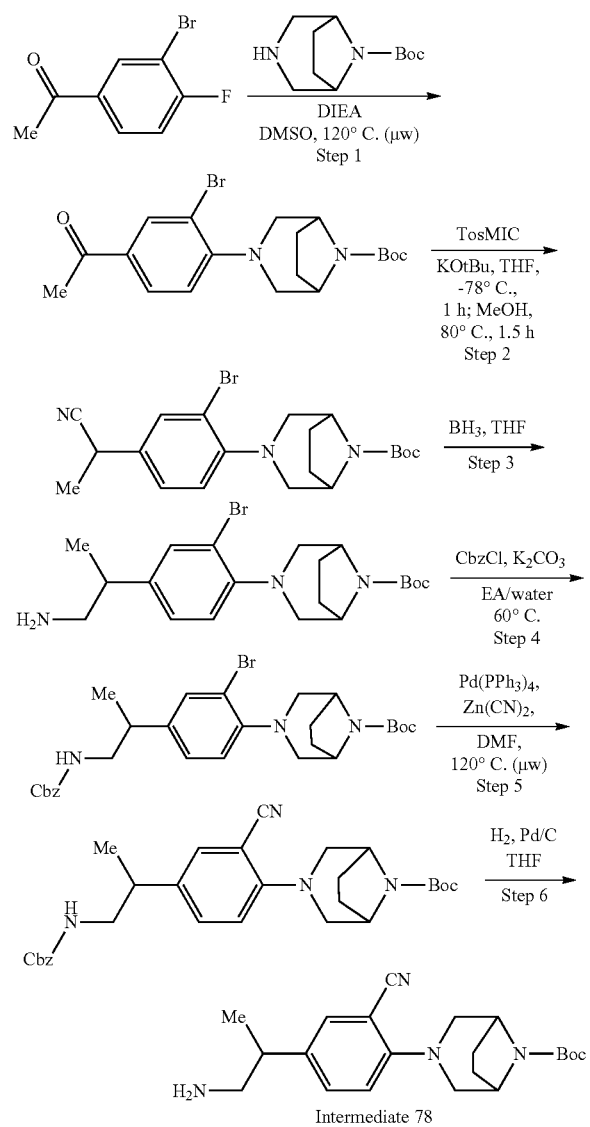

Intermediate 78

Step 1. tert-Butyl 3-(4-acetyl-2-bromophenyl)-3,8-diazabicyclo[3.2.1]octane-8-carboxylate Into a 20-mL microwave tube was added 1-(3-bromo-4-fluorophenyl)ethan-1-one (3.00 g, 13.8 mmol), tert-butyl 3,8-diazabicyclo[3.2.1]octane-8-carboxylate (3.67 g, 17.3 mmol), DIEA (5.48 g, 7.39 mL, 42.4 mmol), and DMSO (8 mL). The resulting solution was heated to 120° C. for 4 h under microwave irradiation. The reaction mixture was cooled to RT and then quenched with water (30 mL). The resulting mixture was extracted with ethyl acetate (3×30 mL), and the combined organic layers were then dried over anhydrous sodium sulfate, filtered, and concentrated in vacuo to provide a crude product that was purified via silica gel chromatography and eluted with ethyl acetate/petroleum ether (1:5) to afford tert-butyl 3-(4-acetyl-2-bromophenyl)-

3,8-diazabicyclo[3.2.1]octane-8-carboxylate as a yellow oil (1.5 g, 27%). LCMS (ESI, m/z) 409, 411 [M+H]⁺.

Step 2. tert-Butyl 3-[2-bromo-4-(1-cyanoethyl)phenyl]-3,8-diazabicyclo[3.2.1]octane-8-carboxylate Into a 100-mL 3-necked round-bottom flask, purged and maintained under an inert atmosphere of nitrogen, was added potassium t-butoxide (0.480 g, 4.28 mmol) and tetrahydrofuran (15 mL) followed by the dropwise addition of a solution ofp-toluenesulfonyl isocyanide (0.500 g, 2.56 mmol) in tetrahydrofuran (3 mL) with stirring at −78° C. The resulting solution was stirred for 15 minutes at −78° C. and then a solution of tert-butyl 3-(4-acetyl-2-bromophenyl)-3,8-diazabicyclo[3.2.1]octane-8-carboxylate (0.700 g, 1.71 mmol) in tetrahydrofuran (5 mL) was added dropwise with stirring at −78° C. The resulting mixture was stirred for an additional 1.5 h at this temperature. Methanol (10 mL) was added, and the resulting solution was heated to 80° C. and stirred for an additional 30 minutes. The reaction was cooled to RT and concentrated in vacuo to provide a crude product that was purified via silica gel chromatography and eluted with ethyl acetate/petroleum ether (1:5) to afford tert-butyl 3-[2-bromo-4-(1-cyanoethyl)phenyl]-3,8-diazabicyclo[3.2.1]octane-8-carboxylate as a yellow oil (500 mg, 70%). LCMS (ESI, m/z) 420, 422 [M+H]⁺.

Step 3. tert-Butyl 3-[4-(1-aminopropan-2-yl)-2-bromophenyl]-3,8-diazabicyclo[3.2.1]octane -8-carboxylate Into a 250-mL round-bottom flask that was purged and maintained with nitrogen was added tert-butyl 3-[2-bromo-4-(1-cyanoethyl)phenyl]-3,8-diazabicyclo[3.2.1]octane-8-carboxylate (1.50 g, 3.57 mmol) and borane tetrahydrofuran complex (1 M, 20 mL, 20 mmol). The resulting solution was stirred for 2 h at 25° C. and then quenched with methanol (30 mL). The resulting mixture was concentrated in vacuo to provide a crude product that was purified via silica gel chromatography and eluted with dichloromethane/methanol (10:1) to afford tert-butyl 3-[4-(1-aminopropan-2-yl)-2-bromophenyl]-3,8-diazabicyclo[3.2.1]octane-8-carboxylate as a white solid (1.3 g, 86%). LCMS (ESI, m/z) 424, 426[M+H]⁺.

Step 4. tert-Butyl 3-[4-(1-[[(benzyloxy)carbonyl]amino]propan-2-yl)-2-bromophenyl]-3,8-diazabicyclo[3.2.1]octane-8-carboxylate Into a 100-mL round-bottom flask was added tert-butyl 3-[4-(1-aminopropan-2-yl)-2-bromophenyl]-3,8-diazabicyclo[3.2.1]octane-8-carboxylate (1.40 g, 3.30 mmol), potassium carbonate (1.37 g, 9.91 mmol), ethyl acetate (20 mL), water (20 mL) and CbzCl (0.619 g, 0.516 mL, 3.63 mmol). The resulting mixture was stirred for 3 h at 60° C. in an oil bath and then cooled to RT. The resulting solution was diluted with water (100 mL) and extracted with ethyl acetate (3×20 mL). The combined organic layers were then dried over anhydrous sodium sulfate, filtered, and concentrated in vacuo to provide a crude product that was purified via silica gel chromatography and eluted with ethyl acetate/petroleum ether (1:1) to afford tert-butyl 3-[4-(1-[[(benzyloxy)carbonyl]amino]propan-2-yl)-2-bromophenyl]-3,8-diazabicyclo[3.2.1]octane-8-carboxylate as a light yellow oil (1.0 g, 54%). LCMS (ESI, m/z) 558, 560[M+H]⁺.

Step 5. tert-Butyl 3-[4-(1-[[(benzyloxy)carbonyl]amino]propan-2-yl)-2-cyanophenyl]-3,8-diazabicyclo[3.2.1]octane-8-carboxylate Into a 10-mL microwave tube purged and maintained under an inert atmosphere of nitrogen was placed tert-butyl 3-[4-(1-[[(benzyloxy)carbonyl]amino]propan-2-yl)-2-bromophenyl]-3,8-diazabicyclo[3.2.1]octane-8-carboxylate (0.800 mg, 1.43 mmol), Zn(CN)₂ (0.167 g, 1.42 mmol), Pd(PPh3)₄ (0.166 g, 0.14 mmol), and DMF (3 mL). The resulting mixture heated at 120° C. for 1 h under microwave irradiation. The reaction mixture was cooled to RT, quenched with water (50-mL), and extracted with ethyl acetate (3×10 mL). The combined organic layers were concentrated in vacuo to provide a crude product that was purified via Prep-TLC and eluted with ethyl acetate/petroleum ether (1:3) to afford tert-butyl 3-[4-(1-[[(benzyloxy)carbonyl]amino]propan-2-yl)-2-cyanophenyl]-3,8-diazabicyclo[3.2.1]octane-8-carboxylate as colorless oil (400 mg, 55%). LCMS (ESI, m/z) 505[M+H]⁺.

Step 6. tert-Butyl 3-(4-(1-aminopropan-2-yl)-2-cyanophenyl)-3,8-diazabicyclo[3.2.1]octane -8-carboxylate Into a 100-mL round-bottom flask purged and maintained with nitrogen was added tert -butyl 3-[4-(1-[[(benzyloxy)carbonyl]amino]propan-2-yl)-2-cyanophenyl]-3,8-diazabicyclo [3.2.1]octane-8-carboxylate (0.35 g, 0.69 mmol), tetrahydrofuran (15 mL), and 10% palladium on carbon (350 mg). The reaction mixture was sparged with hydrogen and then stirred for 1 h at RT under an atmosphere of hydrogen. The solids were removed by filtration over Celite, and the filtrate was concentrated in vacuo to provide a crude product that was purified via prep-TLC and eluted with dichloromethane/methanol (10:1) to afford tert-Butyl 3-(4-(1-aminopropan-2-yl)-2-cyanophenyl)-3,8-diazabicyclo[3.2.1]octane-8-carboxylate as a brown oil (180 mg, 70%). LCMS (ESI, m/z) 371[M+H]⁺.

Example 109

Intermediate 79: tert-Butyl 4-(4-(1-aminopropan-2-yl)phenyl)piperazine-1-carboxylate

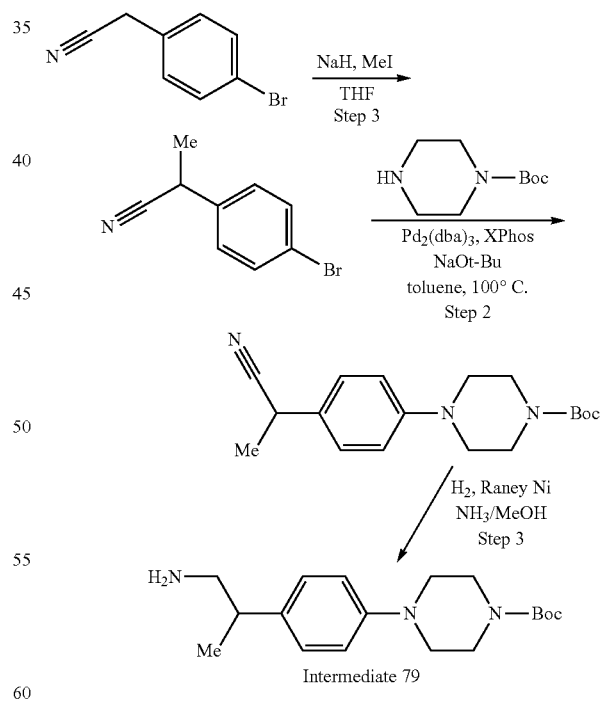

Intermediate 79

Step 1. 2-(4-Bromophenyl)propanenitrile

Into a 100-mL round-bottom flask was added 2-(4-bromophenyl)acetonitrile (3.00 g, 15.3 mmol), tetrahydrofuran (30 mL), and sodium hydride (60% by weight; 2.60 g, 65.0 mmol). The reaction mixture was stirred for 1 h at RT. The reaction mixture was cooled to 0° C. then iodomethane (0.551 g, 0.242 mL, 3.88 mmol) was added and the reaction mixture was stirred at RT for an additional 2 h. The reaction was then quenched by the addition of H₂O (10 mL), and then was extracted with dichloromethane (3×30 mL). The organic layers were combined, dried over anhydrous sodium sulfate, filtered, and concentrated in vacuo to afford 2-(4-bromophenyl)propanenitrile (2 g, 62%) as a yellow solid. LCMS (ESI, m/z) 210 [M+H]⁺.

Step 2. tert-Butyl 4-(4-(1-cyanoethyl)phenyl)piperazine-1-carboxylate

Into a 100-mL round-bottom flask that was purged and maintained with an inert atmosphere of nitrogen was added 2-(4-bromophenyl)propanenitrile (1.05 g, 5.00 mmol), tert -butyl piperazine-1-carboxylate (1.02 g, 5.49 mmol), Pd(OAc)₂ (0.056 g, 0.25 mmol), XPhos (0.239 g, 0.501 mmol), NaOt-Bu (0.096 g, 1.00 mmol), and toluene (20 mL). The resulting solution was stirred for 2 h at 100° C. then was cooled and concentrated under vacuum. The crude product was purified via silica gel column chromatography and eluted with ethyl acetate/petroleum ether (1:5) to afford tert-butyl 4-(4-(1-cyanoethyl)phenyl)piperazine-1-carboxylate (600 mg, 38%) as brown oil. LCMS (ESI, m/z) 316 [M+H]⁺.

Step 3. tert-Butyl 4-(4-(1-aminopropan-2-yl)phenyl)piperazine-1-carboxylate

Into a 50-mL round-bottom flask purged and maintained with nitrogen was added tert -butyl 4-(4-(1-cyanoethyl) phenyl)piperazine-1-carboxylate (0.630 g, 2.00 mmol), Raney Ni (20 mg), and NH₃/MeOH (7 M; 20 mL). The reaction mixture was sparged with hydrogen, and then was stirred overnight at RT under hydrogen (balloon pressure). The solids were removed by filtration over Celite, and the filtrate was concentrated in vacuo to afford tert-butyl 4-(4-(1-aminopropan-2-yl)phenyl)piperazine-1-carboxylate (450 mg, 71%) as light yellow oil. LCMS (ESI, m/z) 320[M+H]⁺.

Example 110

Intermediate 80: tert-Butyl 4-(4-(2-aminoethyl)-2-chlorophenyl)piperidine-1-carboxylate

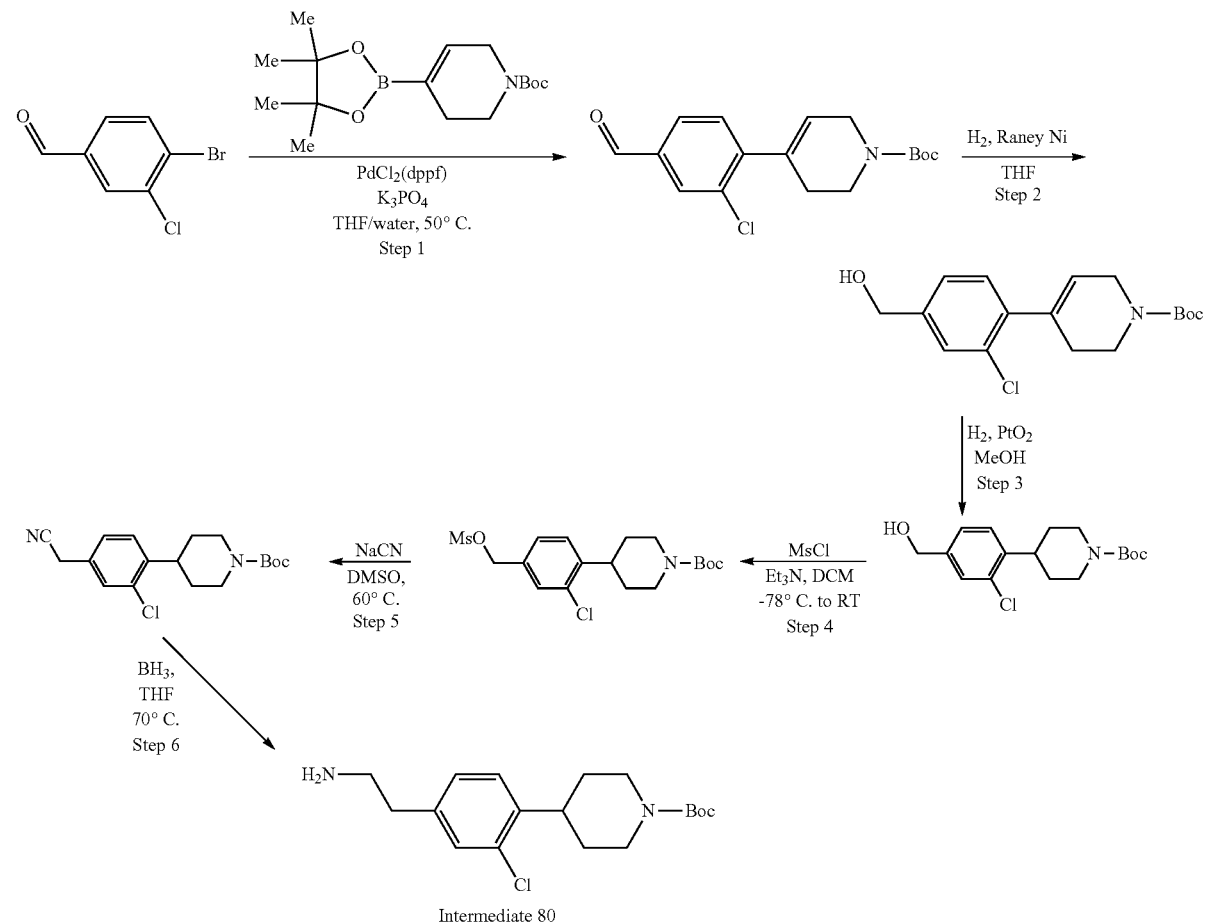

Intermediate 80

Step 1. tert-Butyl 4-(2-chloro-4-formylphenyl)-3,6-dihydropyridine-1(2H)-carboxylate Into a 50-mL 3-necked round-bottom flask purged and maintained with nitrogen was added 4-bromo-3-chlorobenzaldehyde (1.10 g, 5.01 mmol), tert-butyl 4-(tetramethyl-1,3,2-dioxaborolan-2-yl)-1,2,3,6-tetrahydropyridine-1-carboxylate (2.00 g, 6.47 mmol), Pd(dppf)Cl₂ (0.47 g, 0.64 mmol), K₃PO₄·7H₂O (0.600 g, 2.83 mmol), tetrahydrofuran (20 mL), and water (2 mL). The reaction mixture was stirred for 1 h at 50° C., and then was cooled to RT and concentrated in vacuo. The crude product was purified via silica gel column chromatography and eluted with ethyl acetate/petroleum ether (1:3) to afford tert-butyl 4-(2-chloro-4-formylphenyl)-3,6-dihydropyridine-1(2H)-carboxylate (1.5 g, 90%) as a yellow solid. LCMS (ESI, m/z) 322 [M+H]⁺.

Step 2. tert-Butyl 4-(2-chloro-4-(hydroxymethyl)phenyl)-3,6-dihydropyridine-1(2H)-carboxylate Into a 50-mL round-bottom flask purged and maintained with nitrogen was added tert-butyl 4-(2-chloro-4-formylphenyl)-3,6-dihydropyridine-1(2H)-carboxylate (1.50 g, 4.66 mmol), Raney Ni (0.8 g), and tetrahydrofuran (15 mL). The reaction mixture was sparged with hydrogen then was stirred overnight at RT under hydrogen (balloon). The solids were removed by filtration over Celite and the filtrate was concentrated in vacuo to afford tert-butyl 4-(2-chloro-4-(hydroxymethyl)phenyl)-3,6-dihydropyridine-1(2H)-carboxylate (1.4 g, 93%) as a colorless oil that was carried on without further purification. LCMS (ESI, m/z) 324 [M+H]$^+$.

Step 3. tert-Butyl 4-(2-chloro-4-(hydroxymethyl)phenyl)piperidine-1-carboxylate

Into a 100-mL round-bottom flask purged and maintained with nitrogen was added tert-butyl 4-(2-chloro-4-(hydroxymethyl)phenyl)-3,6-dihydropyridine-1(2H)-carboxylate (0.800 g, 2.47 mmol), methanol (10 mL), and PtO$_2$ (0.100 g). The reaction mixture was sparged with hydrogen then was stirred overnight at RT. The solids were removed by filtration and the filtrate was concentrated in vacuo. The crude product was purified via silica gel column chromatography and eluted with ethyl acetate/petroleum ether (1:3) to afford tert-butyl 4-(2-chloro-4-(hydroxymethyl)phenyl)piperidine-1-carboxylate (470 mg, 58%) as a yellow oil. LCMS (ESI, m/z): 326 [M+H]$^+$.

Step 4. tert-Butyl 4-(2-chloro-4-(((methylsulfonyl)oxy)methyl)phenyl)piperidine-1-carboxylate Into a 50-mL round-bottom flask was added tert-butyl 4-(2-chloro-4-(hydroxymethyl)phenyl)piperidine-1-carboxylate (0.460 g, 1.41 mmol), dichloromethane (5 mL), and triethylamine (0.429 g, 0.591 mL, 4.24 mmol). The resulting mixture was cooled to −78° C. then MsCl (0.37 g, 0.25 mL 3.22 mmol) was added dropwise over 5 min. The resulting solution was allowed to warm to RT gradually and stirred for 3 h at RT. The reaction was quenched by the addition of water (30 mL) then was extracted with dichloromethane (3×30 mL). The organic layers were combined, washed with water (30 mL) and brine (30 mL), dried over anhydrous sodium sulfate, filtered, and concentrated in vacuo to afford tert-butyl 4-(2-chloro-4-(((methylsulfonyl)oxy)methyl)phenyl)piperidine-1-carboxylate (800 mg) as a light yellow oil that was carried on without further purification. LCMS (ESI, m/z): 404 [M+H]$^+$.

Step 5. tert-Butyl 4-(2-chloro-4-(cyanomethyl)phenyl)piperidine-1-carboxylate

Into a 50-mL round-bottom flask was added tert-butyl 4-(2-chloro-4-(((methylsulfonyl)oxy)methyl)phenyl)piperidine-1-carboxylate (0.800 g, 1.98 mmol), DMSO (4 mL), and NaCN (0.500 g, 10.2 mmol). The resulting mixture was stirred for 2 h at 60° C. then was quenched by the addition of water (30 mL). The resulting solution was extracted with ethyl acetate (3×30 mL). The organic layers were combined, washed with water (30 mL) and brine (30 mL), dried over anhydrous sodium sulfate, filtered, and concentrated in vacuo to afford tert-butyl 4-(2-chloro-4-(cyanomethyl)phenyl)piperidine-1-carboxylate (290 mg, 44%) as a yellow oil that was carried on without further purification. LCMS (ESI, m/z): 335 [M+H]$^+$. Caution: The aqueous layers containing NaCN were carefully treated with excess aqueous FeSO$_4$ solution prior to disposal.

Step 6. tert-Butyl 4-(4-(2-aminoethyl)-2-chlorophenyl)piperidine-1-carboxylate

Into a 50-mL round-bottom flask purged and maintained with nitrogen was added tert-butyl 4-(2-chloro-4-(cyanomethyl)phenyl)piperidine-1-carboxylate (0.30 g, 0.90 mmol) and a solution of borane in THF (1 M, 5 mL). The resulting solution was stirred for 2 h at 70° C. then was cooled to RT and quenched by the addition of methanol (10 mL). After stirring for 30 min at RT, the resulting mixture was concentrated in vacuo to afford tert-butyl 4-(4-(2-aminoethyl)-2-chlorophenyl)piperidine-1-carboxylate (0.4 g) as a yellow oil that was carried on without further purification. LCMS (ESI, m/z): 339 [M+H]$^+$.

Methods for the Synthesis of Compounds of Formula (I)

Example 79-1

3-Amino-6-methyl-N-(4-(piperazin-1-yl)phenethyl)thieno[2,3-b]pyridine-2-carboxamide (I-1)

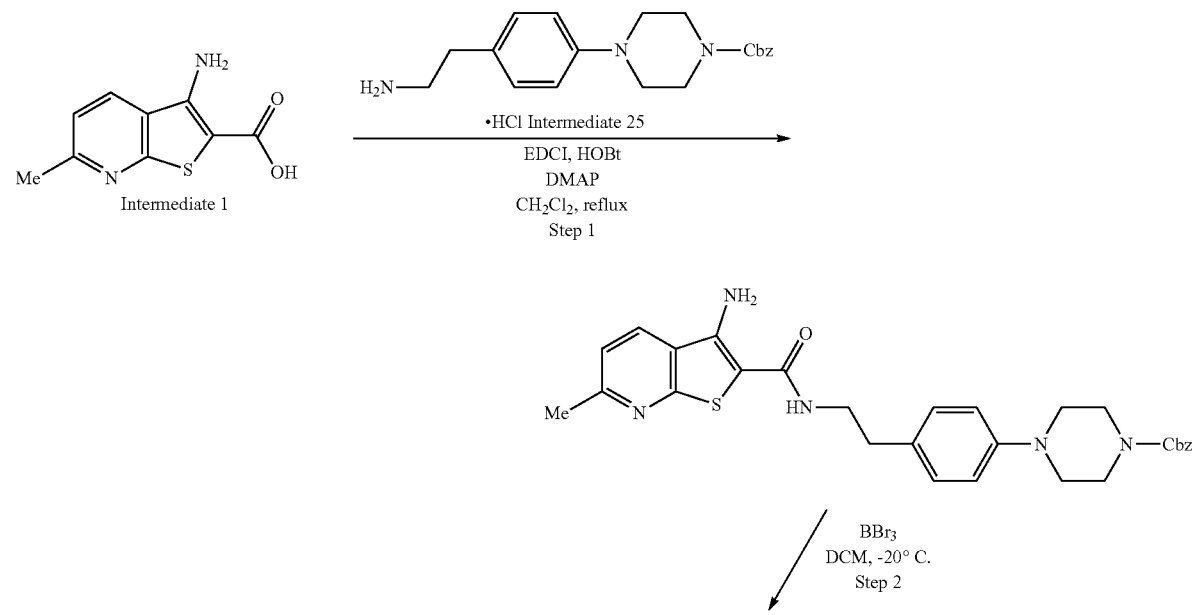

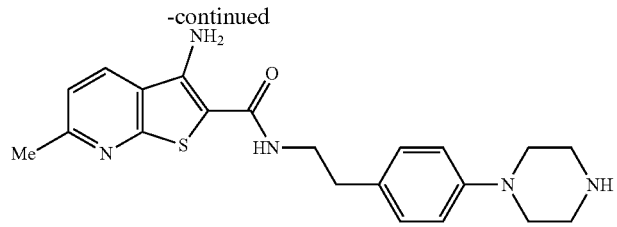

Example 79-1 (I-1)

Step 1. Benzyl 4-(4-(2-(3-amino-6-methylthieno[2,3-b]pyridine-2-carboxamido)ethyl)phenyl)piperazine-1-carboxylate Into a 40 mL vial that was purged and maintained under an inert atmosphere of nitrogen was added benzyl 4-(4-(2-aminoethyl)phenyl)piperazine-1-carboxylate (hydrochloride salt, Intermediate 25; 0.570 g, 1.68 mmol) followed by anhydrous dichloromethane (10 mL). 3-Amino-6-methylthieno[2,3-b]pyridine-2-carboxylic acid (Example 1: Intermediate 1, 0.350 g, 1.68 mmol) was then added, followed by EDCI (0.646 g, 3.37 mmol), HOBt (0.448 g, 3.32 mmol), and 4-dimethylaminopyridine (0.308 g, 2.52 mmol). The resulting reaction mixture was stirred overnight at reflux and then concentrated in vacuo. The resulting crude product was purified by FCC eluting with dichloromethane/methanol (10:1) to afford benzyl 4-(4-(2-(3-amino-6-methylthieno[2,3-b]pyridine-2-carboxamido)ethyl)phenyl)piperazine-1-carboxylate as a white solid (200 mg, 22%). LCMS (ESI, m/z): 530 [M+H]+.

Step 2. 3-Amino-6-methyl-N-(4-(piperazin-1-yl)phenethyl)thieno[2,3-b]pyridine-2-carboxamide Into a 50 mL 3-necked round-bottom flask that was purged and maintained under an inert atmosphere of nitrogen was added benzyl 4-(4-(2-(3-amino-6-methylthieno[2,3-b]pyridine-2-carboxamido)ethyl)phenyl)piperazine-1-carboxylate (0.100 g, 0.19 mmol). This was followed by the addition of BBr$_3$/DCM (1.0 M in DCM, 3 mL) dropwise with stirring at −20° C. The resulting solution was warmed, stirred for 1 h at 25° C., and then quenched with 5 mL of methanol. The resulting mixture was concentrated in vacuo to afford a crude product that was purified by Prep-HPLC using the following conditions (Water-2767): Column, XBridge RP18 19*150 mm, 5 μm; mobile phase, A: water (contains 10 mM NH$_4$HCO$_3$+5% NH$_4$OH) B: CH$_3$CN (25% to 65% over 6 min); Flow rate: 20 mL/min; UV Detector 220 nm. This afforded 3-amino-6-methyl-N-(4-(piperazin-1-yl)phenethyl)thieno[2,3-b]pyridine-2-carboxamide as an off-white solid (13.9 mg, 19%). LCMS (ESI, m/z): 396 [M+H]+; $^1$H NMR (300 MHz, DMSO-d$_6$) δ ppm 8.29 (d, J=8.2 Hz, 1H), 7.68 (t, J=5.5 Hz, 1H), 7.30 (d, J=8.4 Hz, 1H), 7.14-7.02 (m, 4H), 6.85 (d, J=8.6 Hz, 2H), 3.39-3.34 (m, 2H), 2.99 (dd, J=6.1, 3.7 Hz, 4H), 2.82 (dd, J=6.2, 3.7 Hz, 4H), 2.78-2.69 (m, 2H), 2.58 (s, 3H).

The Examples in Table 13 below were synthesized according to the procedures outlined above for Example 79-1(I-1), using the appropriate synthetic precursors. Additional detail around the synthetic methods as well as HPLC purification conditions appear below the examples.

TABLE 13

| Example (Cmpd no.) | MS (ESI, m/z) [M + H] | $^1$H NMR |
|---|---|---|
| 79-2[1] (I-2) | 426 | (300 MHz, CD$_3$OD) δ ppm 8.52 (br s, 1H), 8.19 (d, J = 8.1 Hz, 1H), 7.30 (d, J = 8.4 Hz, 1H), 7.11 (d, J = 8.4 Hz, 1H), 6.63 (s, 1H), 6.54 (d, J = 6.3 Hz, 1H), 3.87 (s, 3H), 3.51-3.47 (m, 2H), 3.37-3.31 (m, 8H), 2.87-2.83 (m, 2H), 2.64 (s, 3H) |
| 79-3[2] (I-3) | 464 | (300 MHz, DMSO-d$_6$) δ ppm 8.30 (d, J = 8.3 Hz, 1H), 7.75-7.72 (m, 1H), 7.54-7.39 (m, 3H), 7.30 (d, J = 8.3 Hz, 1H), 7.12 (br s, 2H), 3.45-3.41 (m, 2H), 3.01-2.75 (m, 10H), 2.56 (s, 3H) |
| 79-4[3] (I-4) | 432 | (300 MHz, DMSO-d$_6$) δ ppm 8.29 (d, J = 8.1 Hz, 1H), 7.73 (t, J = 4.8 Hz, 1H), 7.30 (d, J = 8.4 Hz, 1H), 7.12 (br s, 2H), 6.89 (d, J = 10.2 Hz, 2H), 3.47-3.30 (m, 2H), 3.05-2.90 (m, 4H), 2.79-2.69 (m, 6H), 2.57 (s, 3H) |
| 79-5[4] (I-5) | 414 | (300 MHz, CD$_3$OD) δ ppm 8.20 (d, J = 8.1 Hz, 1H), 7.31 (d, J = 8.1 Hz, 1H), 7.08-7.00 (m, 3H), 3.54-3.42 (m, 2H) 3.42-3.27 (m, 8H), 2.89-2.86 (m, 2H), 2.65 (s, 3H) |
| 79-6[5] (I-6) | 436 | (300 MHz, DMSO-d$_6$) δ ppm 8.30 (d, J = 8.2 Hz, 1H), 7.70-7.64 (m, 1H), 7.30 (d, J = 8.2 Hz, 1H), 7.12 (br s, 2H), 7.01-6.85 (m, 2H), 6.58 (s, 1H), 3.33 (br s, 2H), 2.83 (br s, 8H), 2.75-2.66 (m, 2H), 2.56 (s, 3H), 2.28-2.14 (m, 1H), 0.94-0.91 (m, 2H), 0.69-0.60 (m, 2H) |
| 79-7[6] (I-7) | 482 | (300 MHz, DMSO-d$_6$) δ ppm 8.13-8.10 (m, 1H), 7.75 (s, 1H), 7.12-7.06 (m, 1H), 6.70-6.60 (m, 4H), 3.42-3.35 (m, 3H), 3.02 (br s, 4H), 2.82-2.73 (m, 5H), 2.69 (s, 3H) |
| 79-8[7] (I-8) | 433 | (300 MHz, DMSO-d$_6$) δ ppm 9.11 (br s, 2H), 8.34 (d, J = 8.3 Hz, 1H), 7.82-7.65 (m, 1H), 7.37-7.31 (m, 1H), 7.22 (s, 1H), 7.16-7.07 (m, 1H), 3.51-3.36 (m, 2H), 3.37-3.01 (m, 8H), 2.87-2.72 (m, 2H), 2.59 (s, 3H) |
| 79-9[8] (I-9) | 450 | (300 MHz, CDCl$_3$) δ ppm 8.28 (d, J = 10.8 Hz, 1H), 7.83-7.77 (m, 1H), 7.26 (s, 1H), 7.18-7.02 (m, 4H), 3.45-3.35 (m, 2H), 2.83 (s, 8H), 2.79-2.70 (m, 2H), 2.56 (s, 3H) |

TABLE 13-continued

| Example (Cmpd no.) | MS (ESI, m/z) [M + H] | $^1$H NMR |
|---|---|---|
| 79-10[9] (I-204) | 464 | (300 MHz, DMSO) δ 8.08 (t, J = 5.6 Hz, 1H), 7.75 (s, 1H), 7.08 (d, J = 8.6 Hz, 1H), 6.85 (d, J = 8.7 Hz, 1H), 6.60 (s, 1H), 3.46-3.36 (m, 1H), 3.06-2.90 (m, 2H), 2.89-2.77 (m, 2H), 2.73 (t, J = 6.9 Hz, 1H), 2.69 (s, 1H) |

[1]Note:
Et$_3$N was used as the base in Step 1. Prep HPLC Purification Method: (Waters 2767): Column, SunFire ™ prep C18, 19 × 100 mm; mobile phase, A: water (containing 0.1% FA) and B: CH$_3$CN (30% to 65% over 8 min); UV Detector: 254 nm.

[2]Note:
The amide coupling was performed using HATU and DIEA in DMF at RT. The Cbz deprotection was carried out at −30° C. Prep HPLC Purification Method: (waters-2767): Column, SunFire ™ C18, 19 × 150 mm, 5 μm; mobile phase, A: water (containing 0.05% ammonium hydroxide) and B: CH$_3$CN (18% to 40% over 6 min); UV Detector: 254 nm.

[3]Note:
Et$_3$N was used as the base in Step 1, and the temperature for Step 2 was −78° C. Prep HPLC Purification Method: Column, X-Bridge C18, 19 * 150 mm, 5 um; mobile phase, A: water (containing 10 mm NH$_4$HCO$_3$ + 0.05% ammonium hydroxide) and CH$_3$CN (60% to 80% over 8 min); UV Detector: 254 nm.

[4]Note:
DIEA was used as the base in Step 1. Prep HPLC Purification Method: (Waters2767): Column, X-bridge RP18, 5 μm, 19 × 100 mm; mobile phase, A: water (containing 10 mm NH$_4$HCO$_3$ + 0.05% ammonium hydroxide) and B: CH$_3$CN (54% to 60% over 8 min); UV Detector: 254 nm.

[5]Note:
DIEA was used as the base in Step 1. Prep HPLC Purification Method: (Waters I): Column, SunFire Prep C18 OBD column, 5 μm, 19 * 150 mm; mobile phase: A: water (containing 0.05% FA) and B: CH$_3$CN (30% to 40% over 8 min); UV Detector: 220 & 254 nm.

[6]Note:
DIEA was used as the base in Step 1. Step 2 was conducted at 0° C. to RT. Prep HPLC Purification Method: (Waters-2767): Column, X-bridge RP18, 5 μm, 19 * 100 mm; mobile phase, A: water (containing 0.03% ammonium hydroxide) and B: CH$_3$CN (45% to 60% over 5 min); UV Detector: 254 nm.

[7]HPLC Purification Method: (Waters I): Column, SunFire Prep C18 OBD column, 5 μm, 19 * 150 mm mobile phase, A: water (0.1% FA) and B: CH$_3$CN (15% to 25% over 4 min, and then 25% to 60% over 6 min); UV Detector: 254 nm. The purified product was then stirred with 4N HCl/dioxane (5 mL) for 30 min and concentrated in vacuo to afford a slurry. The solid product (as the HCl salt) was collected by filtration washing the filter cake with diethyl ether.

[8]Notes:
Step 1 was conducted at RT with DIEA as the base. Step 2 was conducted at RT. HPLC Purification Method: conditions (XSelect CSH Prep C18): Column, 19 * 150 nm 5 μm; mobile phase, A: water (containing 10um NH$_4$HCO$_3$ + 0.05% ammonium hydroxide) and B: CH$_3$CN (15% to 45% over 5 min, and then 45% to 75% over 5 min); UV Detector: 254 nm.

[9]Notes:
Step 1 was conducted with HATU and DIEA in DMF solvent. Step 2 was conducted at 0° C. HPLC Purification Method: (Waters-I): Column: X-Bridge C18, 19 * 150 nm, 5um; mobile phase, water (NH$_4$HCO$_3$ + 0.05% NH$_3$•H$_2$O) and ACN(35% CH$_3$CN up to 42% in 9 min); Detector, 254 nm.

Example 80

3-Amino-N-(3-fluoro-4-(piperazin-1-yl)phenethyl)-6-methylthieno[2,3-b]pyridine-2-carboxamide (HCl salt) (I-10)

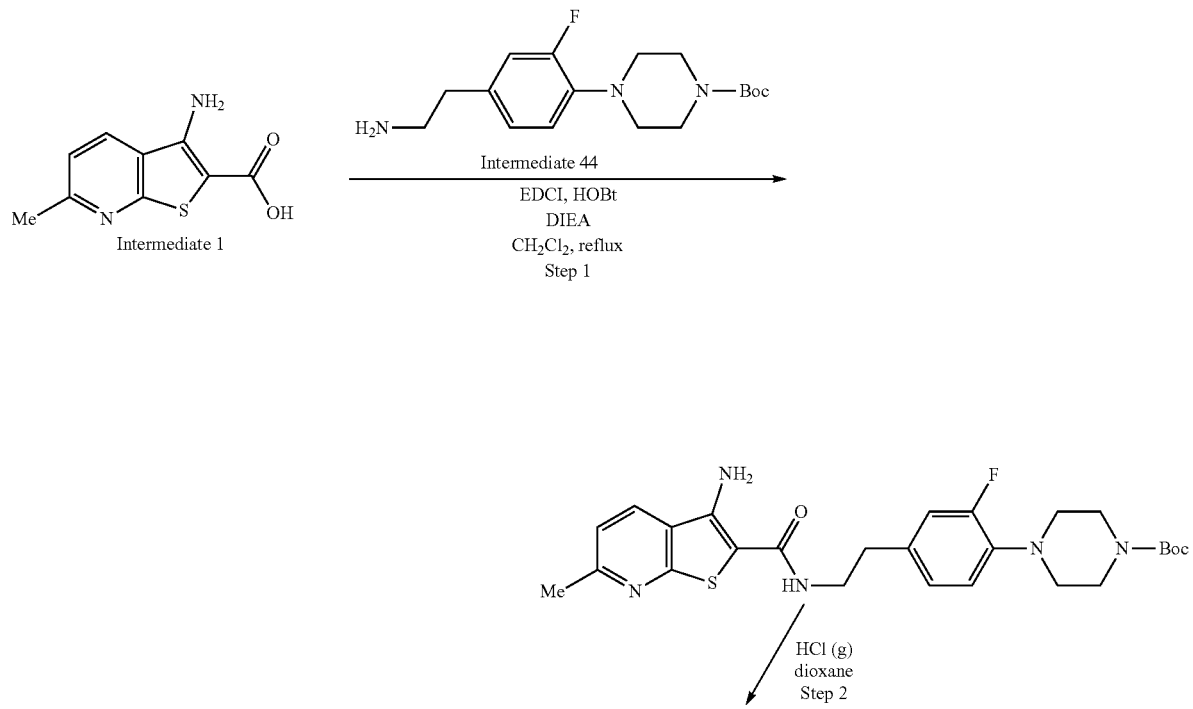

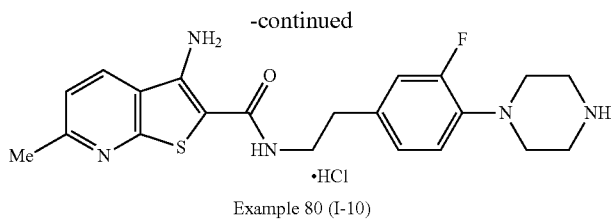

Example 80 (I-10)

Step 1. tert-Butyl 4-(4-(2-(3-amino-6-methylthieno[2,3-b]pyridine-2-carboxamido)ethyl)-2-fluorophenyl)piperazine-1-carboxylate Into a 50-mL round-bottom flask, was placed tert-butyl 4-[4-(2-aminoethyl)-2-fluorophenyl]piperazine-1-carboxylate (Example 44: Intermediate 44. 0.150 g, 0.46 mmol), HOBT (0.075 g, 0.56 mmol), EDCI (0.107 g, 0.56 mmol), 3-amino-6-methylthieno[2,3-b]pyridine-2-carboxylic acid (Example 1: Intermediate 1, 0.106 g, 0.51 mmol), dichloromethane (10 mL), and DIEA (0.179 g, 0.247 mL, 1.39 mmol). The resulting solution was refluxed for 3 h in an oil bath and then cooled and concentrated in vacuo to afford a crude product that was purified by Prep-HPLC (Column, XBridge Prep RP18, 5 μm, 19*150 mm; Mobile phase, A: water (contains 0.05% NH₄OH) and B: CH₃CN (60% to 70% over 6 min); UV Detector, 254 nm) to afford tert-butyl 4-(4-(2-(3-amino-6-methylthieno[2,3-b]pyridine-2-carboxamido)ethyl)-2-fluorophenyl)piperazine-1-carboxylate as a yellow solid (42%). LCMS (ESI, m/z): 514 [M+H]⁺.

Step 2. 3-Amino-N-(3-fluoro-4-(piperazin-1-yl)phenethyl)-6-methylthieno[2,3-b]pyridine-2-carboxamide (hydrochloride salt)

Into a 50-mL round-bottom flask, was added tert-butyl 4-(4-(2-(3-amino-6-methylthieno[2,3-b]pyridine-2-carboxamido)ethyl)-2-fluorophenyl)piperazine-1-carboxylate (0.090 g, 0.17 mmol) followed by dioxane (5 mL). Hydrogen chloride (gas) was bubbled through the solution for 30 seconds and the reaction was stirred for 2 h at RT. The resulting mixture was concentrated in vacuo to afford a solid that was collected by filtration, washed with ether and dried in vacuo to afford 3-amino-N-(3-fluoro-4-(piperazin-1-yl)phenethyl)-6-methylthieno[2,3-b]pyridine-2-carboxamide (hydrochloride salt) as a yellow solid (22.6 mg, 29%). LCMS (ESI, m/z): 414 [M+H]⁺; ¹NMR (300 MHz, DMSO-d₆) δ ppm 8.32 (d, J=8.1 Hz, 1H), 7.32 (d, J=8.4 Hz, 1H), 7.15 (t, J=8.7 Hz, 1H), 6.77-6.73 (m, 2H), 3.36-3.33 (m, 6H), 3.19-3.16 (m, 4H), 2.77-2.75 (m, 2H), 2.50 (s, 3H).

Example 81-1

3-Amino-N-(2,5-difluoro-4-(piperazin-1-yl)phenethyl)-6-methylthieno[2,3-b]pyridine-2-carboxamide (I-11)

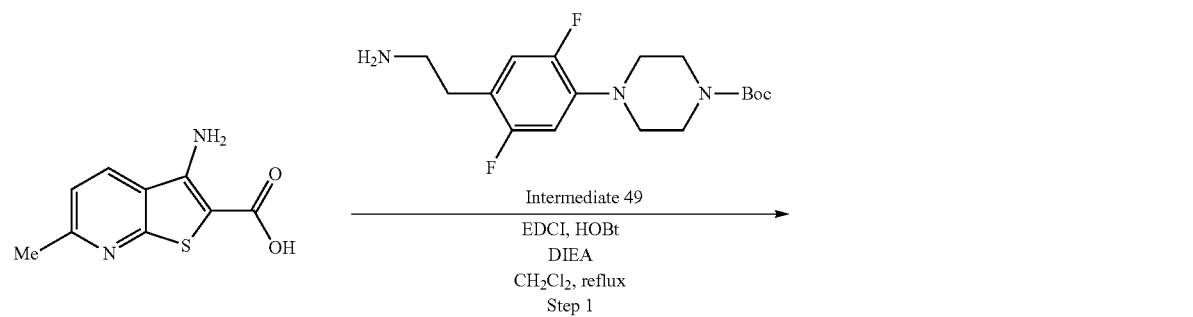

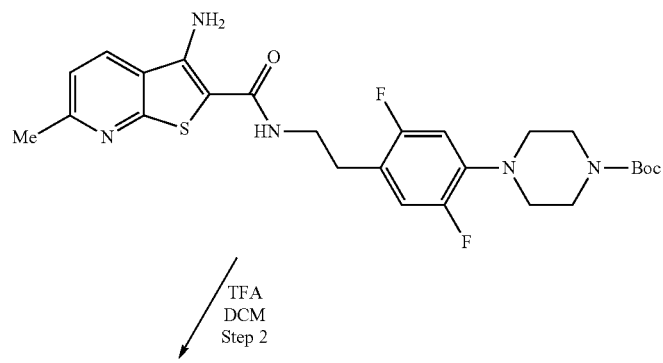

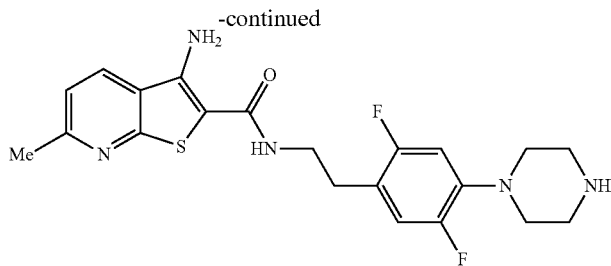

Example 81-1 (I-11)

Step 1. tert-Butyl 4-(4-(2-(3-amino-6-methylthieno[2,3-b]pyridine-2-carboxamido)ethyl)-2,5-difluorophenyl)piperazine-1-carboxylate Into a 500-mL round-bottom flask was added tert-butyl 4-(4-(2-aminoethyl)-2,5-difluorophenyl)piperazine-1-carboxylate (3.93 g, 11.5 mmol), 3-amino-6-methylthieno[2,3-b]pyridine-2-carboxylic acid (2.63 g, 12.7 mmol), HOBt (2.11 g, 13.8 mmol), EDCI (2.65 g, 13.8 mmol) and dichloromethane (115 mL). DIEA (6.03 mL, 34.5 mmol) added, and the resulting mixture was stirred for 2 h at 40° C. in an oil bath. The reaction was cooled to RT and water (60 mL) was added. The layers were separated, and the aqueous layer was extracted with DCM (3×80 mL). The combined organic layers were concentrated in vacuo to provide a crude product that was dissolved in EtOAc (250 mL) and washed sequentially with aqueous NaHCO$_3$ (10 mL of saturated solution was diluted with 10 mL of water), water, and then aqueous saturated sodium chloride. The organic layer was dried over anhydrous sodium sulfate, filtered, and concentrated in vacuo to afford the crude product. The material was dissolved in DCM (~60 mL; with heat) and purified by FCC eluting with DCM/EtOAc (5:2) to afford tert-butyl 4-(4-(2-(3-amino-6-methylthieno[2,3-b]pyridine-2-carboxamido)ethyl)-2,5-difluorophenyl) piperazine-1-carboxylate as a solid (4.3 g, 71%). LCMS (ESI, m/z): 532 [M+H]$^+$.

Step 2. 3-Amino-N-(2,5-difluoro-4-(piperazin-1-yl)phenethyl)-6-methylthieno[2,3-b]pyridine-2-carboxamide Into a 50-mL round-bottom flask was added tert-butyl 4-(4-(2-(3-amino-6-methylthieno[2,3-b]pyridine-2-carboxamido)ethyl)-2,5-difluorophenyl)piperazine-1-carboxylate (0.300 g, 0.56 mmol), dichloromethane (30 mL) and trifluoroacetic acid (2 mL) and the resulting solution was stirred for 1 h at RT. The reaction mixture was cooled with a water/ice bath and the pH of the solution was adjusted to approximately 8 with aqueous saturated sodium carbonate. The resulting solution was extracted with dichloromethane (2×20 mL) and then the combined organic layers were then dried over anhydrous sodium sulfate, filtered, and concentrated in vacuo to afford 3-amino-N-(2,5-difluoro-4-(piperazin-1-yl)phenethyl)-6-methylthieno[2,3-b]pyridine-2-carboxamide as a white solid (213 mg, 67%). LCMS (ESI, m/z) 432 [M+H]$^+$; $^1$H NMR (300 MHz, DMSO-d$_6$) δ ppm 8.29 (d, J=8.1 Hz ,1H), 7.74 (s, 1H), 7.29 (d, J=8.1 Hz, 1H), 7.08-7.19 (m, 3H), 6.76-6.82 (m, 1H), 3.39-3.62 (m, 2H), 2.76-2.89 (m, 10H), 2.63 (s, 3H), 2.34-2.50 (m,1H).

The Examples in Table 14 below were synthesized according to the procedures outlined above for Example 81-1 (I-11), using the appropriate synthetic precursors. Additional detail around the synthetic methods as well as HPLC purification conditions appear below the examples.

TABLE 14

| Example (Cmpd No.) | MS (ESI, m/z) [M + H] | $^1$H NMR |
|---|---|---|
| 81-2[1] (I-12) | 432 | (300 MHz, DMSO-d$_6$) δ ppm 9.98 (br s, 2H), 8.32-8.35 (d, J = 8.4 Hz, 1H), 7.88 (s, 1H), 7.76-7.79 (m, 1H), 7.28-7.39 (m, 5H), 4.59 (br s, 2H), 4.37-4.40 (m, 2H), 3.67 (m, 2H), 3.40-3.47 (m, 2H), 2.80-2.87, (m, 2H), 2.59 (s, 3H) |
| 81-3[2] (I-13) | 395 | (300 MHz, DMSO-d$_6$) δ ppm 8.21 (d, J = 8.1 Hz, 1H), 7.29 (d, J = 8.4 Hz, 1H), 7.09-7.21 (m, 4H), 3.43-3.32 (m, 2H), 3.20-3.18 (m, 2H), 2.86-2.66 (m, 5H), 2.54 (s, 3H), 1.89-1.75 (m, 2H), 1.72-1.61 (m, 2H) |
| 81-4[3] (I-14) | 446 | (300 MHz, DMSO-d$_6$) δ ppm 8.00-7.98 (m, 1H), 7.63 (t, J = 9.0 Hz, 1H), 7.59 (s, 1H), 7.12-7.07 (m, 2H), 6.86-6.83 (m, 2H), 6.68 (br s, 2H), 3.37-3.31 (m, 2H), 3.12-3.06 (m, 4H), 2.83-2.79 (m, 4H), 2.78-2.71 (m, 2H), 2.65 (s, 3H) |
| 81-5[4] (I-15) | 422 | (300 MHz, DMSO-d$_6$) δ ppm 9.33 (br s, 1H), 9.00 (br s, 1H), 8.32 (d, J = 8.1 Hz, 1H), 7.72-7.69 (m, 1H), 7.32 (d, J = 8.1 Hz, 1H), 7.12 (d, J = 8.1 Hz, 2H), 6.85 (d, J = 8.1 Hz, 2H), 4.35 (br s, 2H), 3.42-3.35 (m, 2H), 3.07-2.93 (m, 4H), 2.75-2.58 (m, 2H), 2.57 (s, 3H), 2.06-1.99 (m, 4H) |
| 81-6[5] (I-16) | 447 | (300 MHz, DMSO-d$_6$) δ ppm 7.60-7.52 (m, 1H), 7.51 (t, J = 5.7 Hz, 1H), 6.94-6.89 (m, 2H), 6.89-6.84 (br s, 2H), 6.82-6.73 (br s, 1H), 6.55-6.48 (br s, 2H), 3.32-3.27 (m, 2H), 2.99-2.95 (m, 4H), 2.82-2.78 (m, 4H), 2.72-2.66 (m, 2H) |
| 81-7[6] (I-17) | 445 | (300 MHz, CD$_3$OD) δ ppm 7.37 (s, 1H), 7.26-7.20 (m, 1H), 7.17-7.11 (m, 1H), 6.63 (br s, 1H), 3.53-3.45 (m, 2H), 3.42-3.36 (m, 4H), 3.28-3.19 (m, 4H), 2.87-2.81 (m, 2H), 2.78 (s, 3H) |

TABLE 14-continued

| Example (Cmpd No.) | MS (ESI, m/z) [M + H] | 1H NMR |
|---|---|---|
| 81-8[7] (I-18) | 436 | (300 MHz, DMSO-d6) δ ppm 8.30 (d, J = 8.3 Hz, 1H), 7.77-7.69 (m, 1H), 7.30 (d, J = 8.2 Hz, 1H), 7.14 (br s, 2H), 6.91 (d, J = 7.8 Hz, 1H), 6.65 (d, J = 8.2 Hz, 1H), 3.33 (br s, 2H), 2.89-2.63 (m, 14H), 2.57 (s, 3H) 2.01-1.89 (m, 2H) |
| 81-9[8] (I-19) | 446 | (300 MHz, CD3OD) δ ppm 8.62 (d, J = 8.4 Hz, 1H), 8.37-8.22 (m, 2H), 7.72-7.49 (m, 3H), 7.40 (d, J = 7.7 Hz, 1H), 7.19 (d, J = 7.6 Hz, 1H), 3.74-3.60 (m, 2H), 3.59-3.45 (m, 4H), 3.44-3.33 (m, 6H), 2.81 (s, 3H) |
| 81-10[9] (I-20) | 456 | (300 MHz, DMSO-d6) δ ppm 8.29 (d, J = 8.1 Hz, 1H), 7.73-7.69 (m, 1H), 7.30 (d, J = 8.1 Hz, 1H), 7.24 (s, 1H), 7.12-7.11 (m, 3H), 7.05-6.98 (m, 1H), 3.39-3.33 (m, 4H), 2.99-2.95 (m, 2H), 2.79-2.73 (m, 4H), 2.58 (s, 3H), 2.36-2.29 (m, 1H), 1.96-1.94 (m, 2H), 1.67-1.60 (m, 2H) |
| 81-11[10] (I-21) | 456 | (300 MHz, DMSO-d6) δ ppm 8.29 (d, J = 8.4 Hz, 1H), 7.74-7.70 (m, 1H) 7.30 (d, J = 8.4 Hz, 1H), 7.12-7.09 (m, 1H), 6.76-6.69 (m, 7H) 3.47 (m, 2H), 3.39-3.35 (m, 4H), 2.84-2.79 (m, 2H), 2.72-2.69 (m, 2H), 2.58 (s, 3H), 2.39-2.30 (m, 1H), 1.65 (br s, 4H) |
| 81-12[11] (I-22) | 440 | (300 MHz, DMSO-d6) δ ppm 8.29 (d, J = 8.4 Hz, 1H), 7.72-7.68 (m, 1H), 7.30 (d, J = 8.4 Hz, 1H), 7.10-7.02 (m, 3H), 6.55-6.51 (m, 2H), 3.47 (br s, 2H), 3.37-3.31 (m, 4H), 2.74-2.68 (m, 4H), 2.57 (s, 3H), 1.65 (br s, 4H) |
| 81-13[12] (I-23) | 472 | (300 MHz, CD3OD) δ ppm 8.41 (d, J = 8.4 Hz, 1H), 7.58-7.5 (m, 2H), 7.45 (d, J = 8.4 Hz, 1H), 7.37-7.32 (m, 2H), 7.29-7.25 (m, 2H), 7.24-7.19 (m, 1H), 7.12-7.08 (m, 1H), 3.75-3.72 (m, 2H), 3.11-3.02 (m, 8H), 2.95-2.83 (m, 2H), 2.73 (s, 3H) |
| 81-14[13] (I-24) | 426 | (300 MHz, DMSO-d6) δ ppm 7.60-7.56 (m, 1H), 7.11-7.02 (m, 2H), 7.70-6.78 (m, 5H), 3.98 (s, 3H), 3.39-3.22 (br s, 5H), 3.08-2.96 (br s, 4H), 2.90-2.79 (br s, 4H), 2.77-2.62 (m, 2H) |
| 81-15[14] (I-25) | 466 | (300 MHz, DMSO-d6) δ ppm 8.29 (d, J = 8.2 Hz, 1H), 7.70-7.67 (m, 1H), 7.30 (d, J = 8.3 Hz, 1H), 7.22-6.93 (m, 4H), 6.85 (d, J = 8.7 Hz, 2H), 4.90-4.93 (m, 1H), 4.54-4.46 (m, 1H), 4.43-4.30 (m, 1H), 3.14-2.98 (m, 4H), 2.73-2.71 (m, 2H), 2.69-2.61 (m, 2H), 2.57 (s, 3H), 2.54-2.50 (m, 6H), 2.45-2.24 (m, 2H) |
| 81-16[15] (I-26) | 454 | (300 MHz, DMSO-d6) δ ppm 8.29 (d, J = 8.3 Hz, 1H), 7.71-7.67 (m, 1H), 7.30 (d, J = 8.3 Hz, 1H), 7.21-6.93 (m, 4H), 6.86 (d, J = 8.6 Hz, 2H), 3.46 (t, J = 5.8 Hz, 2H), 3.41-3.34 (m, 2H), 3.25 (s, 3H), 3.12-3.01 (m, 4H), 2.76-2.67 (m, 2H), 2.58 (s, 3H), 2.57-2.53 (m, 6H) |
| 81-17[16] (I-27) | 432 | (300 MHz, DMSO-d6) δ ppm 8.82 (s, 1H), 8.75 (s, 1H), 7.91-7.88 (m, 1H), 7.28 (s, 2H), 7.28-7.06 (m, 2H), 6.86-6.71 (m, 2H), 3.46-3.33 (m, 2H), 3.00-2.97 (m, 4H), 2.98-2.70 (m, 6H) |
| 81-18[17] (I-28) | 422 | (300 MHz, D2O) δ ppm 8.11 (s, 1H), 7.20 (d, J = 8.2 Hz, 2H), 6.98 (d, J = 8.3 Hz, 2H), 3.45-3.40 (m, 2H), 3.32 (br s, 8H), 3.19-3.15 (m, 2H), 2.86-2.61 (m, 4H), 2.17-1.98 (m, 2H) |
| 81-19[18] (I-29) | 422 | (300 MHz, DMSO-d6) δ ppm 9.18 (br s, 2 H), 8.21 (s, 1 H), 7.67 (br s, 1 H), 7.11 (br d, J = 8.21 Hz, 2 H), 6.92 (br d, J = 8.50 Hz, 2 H), 3.61-3.80 (m, 1 H), 3.25-3.39 (m, 6H), 3.12-3.17 (m, 4 H), 2.96 (q, J = 6.64 Hz, 3 H), 2.71 (t, J = 7.33 Hz, 2 H), 2.02-2.26 (m, 2 H) |
| 81-20[19] (I-30) | 436 | (300 MHz, DMSO-d6) δ 8.04 (s, 1H), 7.61 (m, 1H), 7.04 (m, 3H), 6.78-6.93 (m, 2H), 5.76 (s, 1H), 3.20-3.57 (m, 6H), 2.93-3.05 (m, 4H), 2.73-2.87 (m, 4H), 2.64-2.74 (m, 2H), 1.76-1.94 (m, 4H) |
| 81-21[20] (I-31) | 444 | (300 MHz, DMSO-d6) δ ppm 8.14 (s, 1H), 7.75-7.61 (m, 1H), 7.34 (s, 1H), 7.21-6.98 (m, 4H), 3.46-3.35 (m, 2H), 2.89 (s, 8H), 2.81-2.71, (m, 2H), 2.56-2.51 (m, 3H), 2.27 (s, 3H) |
| 81-22[21] (I-32) | 430 | (300 MHz, DMSO-d6) δ ppm 8.49 (s, 1H), 8.25 (s, 1H), 7.78-7.74 (m, 1H), 7.26 (s, 1H), 7.17-7.02 (m, 4H), 3.43-3.38 (m, 2H), 2.83-2.79 (br s, 8H), 2.79-2.74 (m, 2H), 2.42 (s, 3H) |
| 81-23[22] (I-33) | 450 | (300 MHz, DMSO-d6) δ ppm 8.72 (d, J = 8.4 Hz, H), 8.03-7.56 (m, 2H), 7.31 (br s, 2H), 7.09 (d, J = 8.4 Hz, 2H), 6.87 (d, J = 8.7 Hz, 2H), 3.42-3.34 (m, 2H), 3.06-3.03 (m, 4H), 2.91-2.87 (m, 4H), 2.76-2.71 (m, 2H) |
| 81-24[23] (I-34) | 458 | (300 MHz, DMSO-d6) δ ppm 8.29 (d, J = 8.1 Hz, 1H), 7.72 (t, J = 5.4 Hz, 1H), 7.30 (d, J = 8.1 Hz, 1H), 7.11 (s, 2H), 7.01 (dd, J = 13.6, 7.1 Hz, 1H), 6.68 (dd, J = 11.8, 7.5 Hz, 1H), 3.44-3.34 (m, 4H), 3.13-3.04 (m, 2H), 2.84-2.70 (m, 4H), 2.58 (s, 3H), 2.37 (s, 1H), 1.83-1.57 (m, 4H) |
| 81-25[24] (I-35) | 450 | 1H NMR (300 MHz, DMSO-d6) δ 8.30 (d, J = 8.1 Hz, 1H), 7.76 (t, J = 5.8 Hz, 1H), 7.30 (d, J = 8.4 Hz, 1H), 7.12 (br s, 2H), 7.01-6.92 (m, 1H), 3.45-3.38 (m, 2H), 3.10-2.95 (m, 4H), 2.87-2.74 (m, 6H), 2.58 (s, 3H) |
| 81-26[25] (I-36) | 447 | (300 MHz, CD3OD) δ ppm 8.20 (d, J = 8.4 Hz, 1H), 7.30-7.33 (m, 2H), 7.11 (br s, 2H), 3.66 (s, 2H), 3.59 (t, J = 7.1 Hz, 2H), 3.51 (d, J = 11.4 Hz, 2H), 3.03-3.10 (m, 2H), 2.90 (d, J = 9.6 Hz, 2H), 2.65 (s, 3H), 1.88 (br s, 4H) |

TABLE 14-continued

| Example (Cmpd No.) | MS (ESI, m/z) [M + H] | $^1$H NMR |
|---|---|---|
| 81-27[26] (I-37) | 440 | (300 MHz, DMSO-d$_6$) δ ppm 8.30 (d, J = 8.4 Hz, 1H), 7.72 (t, J = 5.4 Hz, 1H), 7.30 (d, J = 8.1 Hz, 1H), 7.13 (br s, 2H), 7.06 (d, J = 8.4 Hz, 1H), 6.88 (s, 1H), 6.81 (d, J = 8.1 Hz, 1H), 4.44 (s, 2H), 3.41-3.35 (m, 5H) 3.09-2.95 (m, 4H), 2.90-2.70 (m, 6H), 2.58 (s, 3H) |
| 81-28[27] (I-38) | 419 | (300 MHz, CD$_3$OD): δ 8.56 (d, J = 8.4 Hz, 1H), 7.60-7.55 (m, 4H), 7.46 (d, J = 8.4 Hz, 2H), 4.79 (s, 2H), 4.48 (s, 2H), 3.63-3.58 (m, 2H), 3.01-2.96 (m, 2H), 2.79 (s, 3H) |
| 81-29[28] (I-39) | 434 | (300 MHz, DMSO-d$_6$) δ ppm 8.69 (d, J = 1.5 Hz, 1H), 8.39 (dd, J = 9.6, 2.7 Hz, 1H), 7.91-7.87 (m, 1H), 7.27 (s, 1H), 7.16-7.06 (m, 4H), 3.36-3.32 (m, 2H), 2.89-2.83 (br s, 8H), 2.79-2.75 (m, 2H) |
| 81-30[29] (I-40) | 450 | (300 MHz, DMSO-d$_6$) δ ppm 8.66 (d, J = 9.0 Hz, 2H), 7.92-7.89 (m, 1H), 7.29 (s, 1H), 7.17-7.12 (m, 3H), 7.10-7.07 (m, 1H), 3.44-3.37 (m, 2H), 2.94 (br s, 8H), 2.84-2.73 (m, 2H) |
| 81-31[30] (I-41) | 437 | (300 MHz, CD$_3$OD) δ ppm 8.20 (d, J = 8.4 Hz, 1H), 7.58-7.20 (m, 5H), 4.52-4.23 (m, 2H), 4.17-4.00 (m, 2H), 3.69-3.51 (m, 2H), 3.11-2.92 (m, 2H), 2.65 (s, 3H) |
| 81-32[31] (I-42) | 432 | (300 MHz, CD$_3$OD) δ ppm 8.19 (d, J = 8.1 Hz, 1H), 7.30 (d, J = 8.4 Hz, 1H), 6.55 (s, 1H), 6.48 (s, 1H), 3.51-3.49 (m, 2H), 3.16-3.13 (m, 4H), 2.97-2.87 (m, 6H), 2.65 (s, 3H) |
| 81-33[32] (I-43) | 412 | (300 MHz, CD$_3$OD) δ ppm 8.30 (d, J = 8.4 Hz, 1H), 7.56 (d, J = 6.9 Hz, 1H), 7.18 (d, J = 8.4 Hz, 2H), 6.93 (d, J = 8.4 Hz, 2H), 4.88 (s, 2H), 3.54-3.49 (m, 2H), 3.14-3.11 (m, 4H), 3.02-3.00 (m, 4H), 2.85-2.74 (m, 2H) |
| 81-34[33] (I-44) | 450 | (300 MHz, DMSO-d$_6$) δ ppm 9.32-9.17 (m, 2H), 8.32 (d, J = 8.4 Hz, 1H), 7.73-7.71 (m, 1H), 7.34 (d, J = 7.5 Hz, 1H), 7.11-7.09 (m, 3H), 4.03 (s, 2H), 3.39-3.35 (m, 2H), 3.28-3.19 (m, 2H), 2.82-2.77 (m, 4H), 2.67-2.64 (m, 2H), 2.50 (s, 3H), 2.10-1.97 (m, 4H), 1.17 (t, J = 7.2 Hz, 3H) |
| 81-35[34] (I-45) | 458 | (300 MHz, DMSO-d$_6$) δ ppm 8.29 (d, J = 8.4 Hz, 1H), 7.71-7.68 (m, 1H), 7.30 (d, J = 8.4 Hz, 1H), 7.12 (br s, 2H), 6.88-6.77 (m, 2H), 3.82 (br s, 2H), 3.42-3.36 (m, 2H), 2.90 (d, J = 11.7 Hz, 2H), 2.78-2.68 (m, 2H), 2.61 (s, 3H), 2.57-2.53 (m, 2H), 1.87-1.79 (m, 4H) |
| 81-36[35] (I-46) | 450 | (300 MHz, DMSO-d$_6$) δ ppm 8.28 (d, J = 10.5 Hz, 1H), 7.82 (t, J = 5.1 Hz, 1H), 7.02-7.08 (m, 3H), 6.79 (dd, J = 7.5 Hz, 1H), 3.39-3.42 (m, 2H) 2.87-2.89 (m, 4H), 2.74-2.82 (m, 6H), 2.55 (s, 3H) |
| 81-37[36] (I-47) | 410 | (300 MHz, DMSO-d$_6$) δ ppm 9.28 (br s, 2H), 8.39 (d, J = 8.3 Hz, 1H), 7.83-7.65 (m, 1H), 7.36 (d, J = 8.3 Hz, 1H), 7.22-7.09 (m, 2H), 7.02-6.86 (m, 2H), 3.54-3.21 (m, 6H), 3.20 (br s, 4H), 3.00-2.66 (m, 4H), 1.27 (t, J = 7.6 Hz, 3H) |
| 81-38[37] (I-48) | 446 | $^1$H-NMR (300 MHz, DMSO-d$_6$) δ ppm 9.07 (br s, 2H), 8.34 (d, J = 8.3 Hz, 1H), 7.83-7.65 (m, 1H), 7.33 (d, J = 8.3 Hz, 1H), 7.14 (dd, J = 13.0, 6.9 Hz, 1H), 6.95 (dd, J = 11.4, 7.4 Hz, 1H), 3.52-3.32 (m, 2H), 3.19 (br s, 8H), 2.93-2.69 (m, 4H), 1.26 (t, J = 7.6 Hz, 3H) |
| 81-39[38] (I-49) | 446 | (300 MHz, CD$_3$OD) δ ppm 8.20 (d, J = 8.4 Hz, 1H), 7.31 (d, J = 8.1 Hz, 1H), 6.93 (dd, J = 13.8, 7.2 Hz, 1H), 6.45 (dd, J = 12.9, 7.5 Hz, 1H), 3.62-3.44 (m, 4H), 3.31-3.17 (m, 3H), 2.88-2.76 (m, 2H), 2.42 (s, 3H), 2.65 (s, 3H), 2.30-2.11 (m, 1H), 1.92-1.77 (m, 1H) |
| 81-40[39] (I-50) | 446 | (300 MHz, CD$_3$OD) δ ppm 8.21 (d, J = 8.4 Hz, 1H), 7.32 (d, J = 8.4 Hz, 1H), 6.94 (dd, J = 13.8, 6.9 Hz, 1H), 6.46 (dd, J = 12.0, 7.8 Hz, 1H), 3.60-3.41 (m, 4H), 3.41-3.38 (m, 1H), 3.31-3.20 (m, 2H) 2.91-2.73 (m, 2H), 2.44 (s, 3H), 2.66 (s, 3H), 2.29-2.11 (m, 1H). 1.96-1.78 (m, 1H) |
| 81-41[40] (I-51) | 448 | (300 MHz, DMSO-d$_6$) δ ppm 8.12 (d, J = 8.7 Hz, 1H), 7.03 (dd, J = 12.9, 6.9 Hz, 1H), 6.71-6.87 (m, 2H), 4.00 (s, 3H), 3.58-3.45 (m, 2H), 2.98-3.10 (m, 8H), 2.90-2.82 (m, 2H) |
| 81-42[41] (I-52) | 444 | (300 MHz, DMSO-d$_6$) δ ppm 8.29 (d, J = 8.4 Hz, 1H), 7.74-7.71 (m, 1H), 7.30 (d, J = 8.4 Hz, 1H), 7.12 (br s, 2H), 7.00-6.93 (m, 1H), 6.54-6.47 (m, 1H), 4.27 (s, 1H), 3.58-3.53 (m, 2H), 3.39-3.36 (m, 2H), 3.01-2.98 (m, 1H), 2.92-2.80 (m, 2H), 2.78-2.68 (m, 2H), 2.59 (s, 3H), 1.77-1.72 (m, 1H), 1.63-1.58 (m, 1H) |
| 81-43[42] (I-53) | 444 | (300 MHz, DMSO-d$_6$) δ ppm 8.29 (d, J = 8.4 Hz, 1H), 7.75-7.71 (m, 1H), 7.30 (d, J = 8.1 Hz, 1H), 7.12 (br s, 2H), 7.00-6.93 (m, 1H), 6.54-6.47 (m, 1H), 4.27 (s, 1H), 3.59-3.53 (m, 2H), 3.39-3.36 (m, 2H), 3.01-2.98 (m, 1H), 2.92-2.80 (m, 2H), 2.80-2.68 (m, 2H), 2.59 (s, 3H), 1.74-1.71 (m, 1H), 1.61-1.58 (m, 1H) |
| 81-44[43] (I-54) | 447 | (300 MHz, CD$_3$OD) δ ppm 8.20 (d, J = 8.4 Hz, 1H), 7.53 (s, 1H), 7.48 (d, J = 8.4 Hz, 1H), 7.31 (d, J = 8.4 Hz, 1H), 7.08 (d, J = 8.4 Hz, 1H), 3.64 (br s, 2H), 3.58-3.52 (m, 2H), 3.40-3.36 (m, 2H), 3.04 (d, J = 10.5 Hz, 2H), 2.94-2.85 (m, 2H), 2.65 (s, 3H), 2.23-2.18 (m, 2H), 1.93-1.86 (m, 2H) |
| 81-45[44] (I-55) | 464 | (300 MHz, CD$_3$OD) δ ppm 8.08 (d, J = 10.1 Hz, 1H), 7.10 (dd, J = 12.6, 6.8 Hz, 1H), 6.87 (dd, J = 11.0, 7.3 Hz, 1H), 3.56 (t, J = 7.2 Hz, 2H), 3.44-3.34 (m, 6H), 3.32-3.30 (m, 2H), 3.05-2.94 (m, 2H), 2.90-2.87 (m, 2H), 1.36 (t, J = 7.6 Hz, 3H) |

TABLE 14-continued

| Example (Cmpd No.) | MS (ESI, m/z) [M + H] | $^1$H NMR |
|---|---|---|
| 81-46[45] (I-56) | 431 | (300 MHz, DMSO-d$_6$) δ ppm 8.48 (d, J = 8.5 Hz, 1H), 7.88 (m, 1H), 7.56 (d, J = 8.5 Hz, 1H), 7.23 (s, 2H), 7.06 (d, J = 8.5 Hz, 2H), 6.84 (d, J = 8.5 Hz, 2H), 3.37 (m, 2H), 2.98 (m, 4H), 2.81 (m, 4H), 2.71 (m, 2H), 2.55 (s, 3H) |
| 81-47[46] (I-57) | 417 | (300 MHz, DMSO-d$_6$) δ ppm 8.48 (d, J = 8.5 Hz, 1H), 7.88 (m, 1H), 7.56 (d, J = 8.5 Hz, 1H), 7.23 (s, 2H), 7.06 (d, J = 8.5 Hz, 2H), 6.84 (d, J = 8.5 Hz, 2H), 3.37 (m, 2H), 2.98 (m, 4H), 2.81 (m, 4H), 2.71 (m, 2H) |
| 81-48[47] (I-58) | 429 | (300 MHz, DMSO-d$_6$) δ ppm 8.48 (d, J = 8.5 Hz, 1H). 7.91 (m, 1H), 7.55 (d, J = 8.5 Hz, 1H), 7.26 (s, 2H), 7.16 (m, 4H), 3.39 (m, 2H), 2.82 (m, 4H), 2.40 (m, 1H), 2.18 (s, 3H), 1.94 (m, 2H), 1.67 (m, 4H) |
| 81-49[48] (I-59) | 431 | (300 MHz, DMSO-d$_6$) δ ppm 8.47 (d, J = 8.5 Hz, 1H), 7.87 (m, 1H), 7.56 (d, J = 8.5 Hz, 1H), 7.22 (s, 2H), 7.06 (d, J = 8.5 Hz, 2H), 6.86 (d, J = 8.5 Hz, 2H), 3.35 (m, 2H), 3.08 (m, 4H), 2.73 (m, 2H), 2.44 (m, 4H), 2.21 (s, 3H) |
| 81-50[49] (I-60) | 416 | (300 MHz, CD$_3$OD) δ ppm 8.27 (d, J = 8.5 Hz, 1H), 7.44 (d, J = 8.5 Hz, 1H), 7.20 (m, 4H), 3.50 (m, 2H), 3.25 (m, 2H), 2.85 (m, 4H), 2.72 (m, 1H), 1.87 (m, 2H), 1.70 (m, 2H) |
| 81-51[50] (I-61) | 410 | (300 MHz, DMSO-d$_6$) δ ppm 8.14 (s, 1H), 7.66 (m, 1H), 7.06 (m, 4H), 6.84 (d, J = 8.8 Hz, 2H), 3.34 (m, 2H), 2.98 (m, 4H), 2.82 (m, 4H), 2.70 (m, 2H), 2.52 (s, 3H), 2.34 (s, 3H) |
| 81-52[51] (I-62) | 446 | (300 MHz, DMSO-d$_6$) δ ppm 8.00 (m, 1H), 7.65 (s, 1H), 7.52 (s, 1H), 7.05 (d, J = 8.5 Hz, 2H), 6.83 (d, J = 8.5 Hz, 2H), 6.67 (s, 2H), 3.28 (m, 2H), 2.97 (m, 4H), 2.79 (m, 4H), 2.70 (m, 2H), 2.63 (s, 3H) |
| 81-53[52] (I-63) | 414 | (300 MHz, CD$_3$OD) δ ppm 8.02 (d, J = 10.0 Hz, 1H), 7.15 (d, J = 8.5 Hz, 2H), 6.92 (d, J = 8.5 Hz, 2H), 3.51 (m, 2H), 3.11 (m, 4H), 2.99 (m, 4H), 2.80 (m, 2H), 2.60 (s, 3H) |
| 81-54[53] (I-64) | 408 | (300 MHz, CD$_3$OD) δ ppm 8.18 (d, J = 8.5 Hz, 1H), 7.31 (d, J = 8.5 Hz, 1H), 7.09 (d, J = 8.5 Hz, 2H), 6.57 (d, J = 8.5 Hz, 2H), 4.40 (m, 1H), 3.90 (m, 1H), 3.60 (m, 1H), 3.46 (m, 2H), 3.03 (m, 3H), 2.76 (m, 2H), 2.63 (s, 3H), 2.02 (m, 1 H), 1.82 (m, 1H) |
| 81-55[54] (I-65) | 408 | (300 MHz, CD$_3$OD) δ ppm 8.18 (d, J = 8.2 Hz, 1H), 7.30 (d, J = 8.2 Hz, 1H), 7.08 (d, J = 8.5 Hz, 2H), 6.55 (d, J = 8.5 Hz, 2H), 4.34 (m, 1H), 3.74 (m, 1H), 3.58 (m, 1H), 3.46 (m, 2H), 3.00 (m, 3H), 2.76 (m, 2H), 2.63 (s, 3H), 1.94 (m, 1 H), 1.76 (m, 1H) |
| 81-56[55] (I-66) | 438 | (300 MHz, DMSO-d$_6$) δ ppm 8.29 (d, J = 8.2 Hz, 1H), 7.70 (m, 1H), 7.30 (d, J = 8.2 Hz, 1H), 7.11 (m, 4H), 6.91 (d, J = 8.5 Hz, 2H), 3.71 (m, 3H), 3.33 (m, 2H), 3.00 (m, 6H), 2.73 (m, 3H), 2.58 (s, 3H) |
| 81-57[56] (I-67) | 422 | (300 MHz, DMSO-d$_6$) δ ppm 9.33 (br s, 1H), 9.00 (br s, 1H), 8.32 (d, J = 8.1 Hz, 1H), 7.72-7.69 (m, 1H), 7.32 (d, J = 8.1 Hz, 1H), 7.12 (d, J = 8.1 Hz, 2H), 6.85 (d, J = 8.1 Hz, 2H), 4.35 (br s, 2H), 3.42-3.35 (m, 2H), 3.07-2.93 (m, 4H), 2.75-2.58 (m, 2H), 2.57 (s, 3H), 2.06-1.99 (m, 4H) |
| 81-58[57] (I-68) | 466 | (300 MHz, CD$_3$OD) δ 7.93 (d, J = 10.6 Hz, 1H), 6.84-7.05 (m, 1H), 6.69-6.78 (m, 1H), 4.04 (s, 3H), 3.47 (t, J = 7.2 Hz, 2H), 2.89-3.02 (m, 8H), 2.78-2.91 (m, 2H) |
| 81-59[58] (I-69) | 462 | (300 MHz, CDCl3) δ 8.56 (s, 1H), 7.63 (d, J = 5.7 Hz, 1H), 6.83-6.93 (m, 1H), 6.53-6.60 (m, 1H), 5.97 (br s, 2H), 5.65-5.72 (m, 1H), 3.57-3.67 (m, 4H), 3.23-3.33 (m, 2H), 2.85-2.96 (m, 4H), 1.94-2.03 (m, 2H), 1.79-1.83 (m, 2H) |
| 81-60[59] (I-70) | 418 | (300 MHz, CD$_3$OD) δ 8.19 (d, J = 8.1 Hz, 1H), 7.31 (d, J = 8.4 Hz, 1H), 6.88-6.96 (m, 1H), 6.28-6.37 (m, 1H), 4.30-4.38 (m, 1H), 3.92-4.07 (m, 2H), 3.64-3.76 (m, 2H), 3.44-3.55 (m, 2H), 2.78-2.84 (m, 2H), 2.65 (s, 3H) |
| 81-61[60] (I-71) | 465 | (300 MHz, CD$_3$OD) δ 7.99 (d, J = 9.9 Hz, 1H), 7.37-7.51 (m, 2H), 7.02 (d, J = 8.4 Hz, 1H), 3.45-3.52 (m, 4H), 3.32-3.35 (m, 2H), 2.97 (d, J = 11.1 Hz, 2H), 2.71-2.91 (m, 2H), 2.57 (s, 3H), 2.05-2.12 (m, 2H), 1.69-1.80 (m, 2H) |
| 81-62[61] (I-72) | 476 | (300 MHz, CD$_3$OD) δ 7.99 (d, J = 9.9 Hz, 1H), 6.90-6.93 (m, 1H), 6.58-6.64 (m, 1H), 3.38-3.52 (m, 4H), 3.11-3.28 (m, 2H), 2.74-2.91 (m, 4H), 2.57 (d, J = 3.0 Hz, 3H), 1.85-2.04 (m, 2H), 1.71-1.79 (m, 2H) |
| 81-63 (I-205)[62] | 429 | (300 Hz, CD$_3$OD) δ 8.19-8.26 (m, 1H), 7.18-7.39 (m, 4H), 3.51-3.58 (m, 2H), 3.16-3.29 (m, 3H), 2.82-2.97 (m, 4H), 2.66 (s, 3H), 1.81-1.95 (m, 2H), 1.61-1.78 (m, 2H) |

TABLE 14-continued

| Example (Cmpd No.) | MS (ESI, m/z) [M + H] | $^1$H NMR |
|---|---|---|
| 81-64 (I-206)[63] | 428 | (300 MHz, DMSO-$d_6$) 8.82 (br s, 2H), 8.30 (d, J = 10.8 Hz, 1H), 7.74-7.78 (m, 1H), 7.04-7.15 (m, 2H), 6.84-6.94 (m, 2H), 3.34-3.59 (m, 6H), 3.10-3.21 (m, 4H), 2.83-2.89 (m, 2H), 2.72-2.77 (m, 2H), 1.36 (t, J = 8.4 Hz, 3H) |

[1]Notes:

HATU was used instead of EDCI/HOBt, and DMF was used as the solvent in Step 1. 4N HCl in dioxane was used in Step 2. Prep HPLC Purification Method: (waters 2767): Column: SunFire Prep C18 5 μm 19 × 150 mm; mobile phase: mobile phase, A: water (containing 0.05% TFA) and B: CH$_3$CN (20% to 30% over 6 min); Flow rate: 20 mL/min; UV Detector: 220 nm.

[2]Notes:

HATU was used instead of EDCI/HOBt, and DMF was used as the solvent in Step 1. 4N HCl in dioxane was used in Step 2. Prep HPLC Purification Method: Column: Sunfire prep C18, 5 μm, 19 × 150 mm; mobile phase, A: water (containing 0.05% TFA) and B: CH$_3$CN (35% to 48% over 8 min); UV Detector: 254 nm. After the fractions containing product were combined and lyophilized the resulting solid was dissolved in MeOH (2 mL) and free-based using a resin-bound HCO$_3$ cartridge (PL-HCO$_3$ MP SPE, 500 mg per 6 mL tube).

[3]Notes:

4N HCl in dioxane was used in Step 2. Prep HPLC Purification Method: (Water I): Column: Xbridge C18, 5 μm, 19 * 150 mm; mobile phase: A: water (containing 10 mM NH$_4$HCO$_3$ + 0.05% ammonium hydroxide) and B: CH$_3$CN (15% to 40% over 8 min and then 45% to 80% over 8 min); UV Detector: 254 nm.

[4]Notes:

HATU was used instead of EDCI/HOBt, and DMF was used as the solvent in Step 1. TFA/DCM was used in Step 2. Prep HPLC Purification Method: Column: X Bridge C18, 19 * 150 mm, 5 μm; mobile phase: A: water (containing 10 mM NH$_4$HCO$_3$ + 0.05% ammonium hydroxide) and B: CH$_3$CN (15% to 30% over 8 min); Flow rate: 20 mL/min; UV Detector: 254 nm.

[5]Notes:

Step 1 was conducted at RT. TFA/DCM was used in Step 2. Prep HPLC Purification Method: ((Waters-2767)): Column: XBridge RP18, 5 μm, 19 * 100 mm; mobile phase: A: water (containing 0.03% ammonium hydroxide) and B: CH$_3$CN (45% to 60% over 5 min); UV Detector: 254 nm.

[6]Notes:

Step 1 was conducted at RT. 4N HCl in dioxane was used in Step 2 and MeOH was used as a cosolvent. The product was isolated as the HCl salt by filtration.

[7]Notes:

4N HCl in dioxane was used in Step 2 and MeOH was used as a cosolvent. Prep HPLC Purification Method: Column: X Bridge C18, 19 * 150 mm, 5 μm; mobile phase: A: water (containing 10 mM NH$_4$HCO$_3$ + 0.05% ammonium hydroxide) and B: CH$_3$CN (15% to 45% over 8 min); UV Detector: 254 nm.

[8]Notes:

4N HCl in dioxane was used in Step 2. The product was isolated as the HCl salt by concentration in vacuo, trituration of the resulting solid with ether, and filtration to isolate the solid product.

[9]Notes:

HATU was used instead of EDCI/HOBt, and DMF was used as the solvent in Step 1. TFA/DCM was used in Step 2. Prep HPLC Purification Method: Column: X Bridge C18, 19 * 150 mm, 5 um; mobile phase: A: water (contains 0.05% ammonium hydroxide) and B: CH$_3$CN (30% to 70% over 10 min); Flow rate: 20 mL/mm; UV Detector: 254 nm.

[10]Notes:

HATU was used instead of EDCI/HOBt, and DMF was used as the solvent in Step 1. TFA/DCM was used in Step 2. Prep HPLC Purification Method: (Waters I): Column: XBridge C 18, 5 μm; mobile phase: A: water (containing 0.05% ammonium hydroxide) and B: CH$_3$CN (20% to 76% over 6 min); Flow rate: 15 mL/min; UV Detector: 254 nm.

[11]Notes:

HATU was used instead of EDCI/HOBt, and DMF was used as the solvent in Step 1. TFA/DCM was used in Step 2. Prep HPLC Purification Method: Column: X Bridge C18, 19 * 150 mm, 5 μm; mobile phase: A: water (containing 0.05% ammonium hydroxide) and B: CH$_3$CN (20% to 84% over 6 min); Flow rate: 15 mL/min; UV Detector: 254 nm.

[12]Notes:

HATU was used instead of EDCI/HOBt, and DMF was used as the solvent in Step 1 (at RT). 4N HCl in dioxane was used in Step 2. Prep HPLC Purification Method: (waters 2767): Column: Waters XBridge C18 19 * 150 mm, 5 μm; mobile phase: A: water (containing 0.05% Formic Acid) and B: CH$_3$CN; UV Detector: 254 nm.

[13]Notes:

HATU was used instead of EDCI/HOBt, and DMF was used as the solvent in Step 1 (at RT). TFA/DCM was used in Step 2. Prep HPLC Purification Method: (waters 2767): Column: X Bridge C18, 19 * 150 mm, 5 μm; mobile phase: A: water (containing 10 mM NH$_4$HCO$_3$ + 0.05% ammonium hydroxide) and B: CH$_3$CN (30% to 75% over 8 min); UV Detector: 254 nm.

[14]Notes:

Step 1 was conducted at RT. Only Step 1 was conducted since deprotection step was unnecessary. Prep HPLC Purification Method: (Waters 2767): Column: X Bridge C18, 19 * 150 mm, 5 μm; mobile phase, A: Water (containing 10 mM NH$_4$HCO$_3$ + 0.05% ammonium hydroxide) and B: MeCN (35% to 40% over 8 min); UV Detector: 254 nm.

[15]Notes:

Step 1 was conducted at RT. Only Step 1 was conducted since deprotection was unnecessary. Prep HPLC Purification Method: (Waters 2767): Column: XBridge RP18, 5 um, 19 × 100 mm; mobile phase: A: water(10 mM NH$_4$HCO$_3$ + 0.05% ammonium hydroxide) and B: CH$_3$CN (35% to 40% over 8 min); UV Detector: 254 nm.

[16]Notes:

HATU was used instead of EDCI/HOBt, and DMF was used as the solvent in Step 1 (at RT). 4N HCl in dioxane was used in Step 2. Prep HPLC Purification Method: (Waters I): Column: Xbridge Prep C18 OBD column, 5 μm, 19 * 150 mm; mobile phase: A: water (containing 0.03% NH$_4$OH) and B: CH$_3$CN (16% to 34% over 10 min); UV Detector: 220 & 254 nm.

[17]Notes:

4N HCl in dioxane was used in Step 2 and MeOH was used as a cosolvent. The product was isolated as the HCl salt by concentration of the reaction mixture to a slurry in vacuo, and filtration (washing the filter cake with diethyl ether) to isolate the solid product.

[18]Notes:

4N HCl in dioxane was used in Step 2 and MeOH was used as a cosolvent. The product was isolated as the HCl salt by concentration of the reaction mixture to a slurry in vacuo, and filtration (washing the filter cake with diethyl ether) to isolate the solid product.

[19]Notes:

4N HCl in dioxane was used in Step 2 and MeOH was used as a cosolvent. The product was isolated as the HCl salt by concentration of the reaction mixture to a slurry in vacuo and then filtered (washing the filter cake with diethyl ether) and purified further by mass-triggered reverse phase HPLC.

[20]Notes:

4N HCl in dioxane was used in Step 2. Prep HPLC Purification Method: (waters-2767): Column: X Bridge C18, 19 * 150 mm, 5 um; mobile phase: A: water (containing 10 mM NH$_4$HCO$_3$ + 0.05% ammonium hydroxide) and B: MeCN (35% to 55% over 8 min); UV Detector: 254 nm.

[21]Notes:

HATU was used instead of EDCI/HOBt, and DMF was used as the solvent in Step 1 (at RT). 4N HCl in dioxane was used in Step 2. Prep HPLC Purification Method: Column: X Bridge C18, 5 μm, 19 × 100 mm; Mobile phase: A: water (containing 10 mM NH$_4$HCO$_3$ + 0.05% ammonium, hydroxide) and B: CH$_3$CN (40% to 45% over 5 min); Flow rate: 15 mL/min; UV Detector: 254 nm.

TABLE 14-continued

| Example (Cmpd No.) | MS (ESI, m/z) [M + H] | ¹H NMR |
| --- | --- | --- |

[22]Notes:
Step 1 was conducted at RT. 4N HCl in dioxane was used in Step 2 and MeOH was used as a cosolvent. Purification conditions: The final product was isolated as the free base following aqueous workup with EA and saturated aqueous NaHCO₃.

[23]Notes:
Step 2 was conducted with TFA/DCM. Prep HPLC Purification Method: Column: X Bridge C18, 19 * 150 mm, 5 μm; mobile phase: water (containing 10 mM NH₄HCO₃ + 0.05% ammonia) and CH₃CN; Gradient: 35% to 45% in 8 min; Flow rate: 15 mL/min; Detector, 254 nm.

[24]Notes:
Step 2 was conducted with TFA/DCM. Prep HPLC Purification Method: Column: X Bridge C18, 19 * 150 mm, 5 μm; mobile phase: A: water (containing 10 mM NH₄HCO₃ + 0.05% ammonium) and B: CH₃CN (15% to 45% over 4 min and then 45% to 75% over 6 min); Flow rate: 15 mL/min; UV Detector: 254 nm.

[25]Notes:
Step 2 was conducted with TFA/DCM. Prep HPLC Purification Method: Column: SunFire Prep C18, 19 * 150 mm, 5 μm; mobile phase: A: water (containing 0.05% formic acid) and B: CH₃CN (35% to 40% over 9 min); Flow rate: 15 mL/min; UV Detector: 254 nm; The purified product was dissolved in small amount of MeOH and passed through a pre-packed cartridge (agilent, PL-HCO₃ MP SPE 100 mg/6 mL) to remove formic acid.

[26]Notes:
Step 2 was conducted with TFA/DCM. Prep HPLC Purification Method: Column: SunFire Prep Phenyl, 19 * 150 mm, 5 μm: mobile phase: A: water (containing 0.05% ammonium hydroxide) and B: CH₃CN (20% to 55% over 6 min); Flow rate: 15 mL/min; UV Detector: 254 nm.

[27]Notes:
HATU was used instead of EDCI/HOBt, and DMF was used as the solvent in Step 1 (at RT). Step 2 was conducted with TFA/DCM. Prep HPLC Purification Method: Column: X Bridge C18, 19 * 150 mm, 5 μm; mobile phase: A: water (containing 10 mM NH₄HCO₃ + 0.05% ammonium hydroxide)and B: CH₃CN (20% to 45% over 8 min); Flow rate: 20 mL/min; UV Detector: 254 nm.

[28]Notes:
HATU was used instead of EDCI/HOBt, and DMF was used as the solvent in Step 1 (at RT), Step 2 was conducted with 4N HCl/dioxane, Prep HPLC Purification Method: (Waters I): Column: X Bridge C 18, 19 * 150 mm, 5 μm; mobile phase: A: water (containing 10 mM NH₄HCO₃ + 0.05% ammonium hydroxide) and B: CH₃CN (30% to 60% over 8 min); Flow rate: 15 mL/min; UV Detector: 254 nm.

[29]Notes:
HATU was used instead of EDCI/HOBt, and DMF was used as the solvent in Step 1 (at RT). Step 2 was conducted with 4N HCl/dioxane. Prep HPLC Purification Method: (Waters-2767): Column: X Bridge C 18, 19 * 150 nm, 5 μm; mobile phase: A: Water (containing 10 mM NH₄HCO₃ + 0.05% ammonium hydroxide) and B: CH₃CN (40% to 75% over 5 min); Flow rate: 15 mL/min; UV Detector: 254 nm.

[30]Notes:
Step 2 was conducted with TFA/DCM. Prep HPLC Purification Method: Column: X Bridge C18, 19 * 150 mm, 5 μm; mobile phase: A: water (containing 10 mM NH₄HCO₃ and 0.05% ammonium hydroxide) and B: CH₃CN (48% to 58% over 6 min); UV Detector: 254 nm.

[31]Notes:
HATU was used instead of EDCI/HOBt, and DMF was used as the solvent in Step 1 (at RT). Step 2 was conducted with TFA/DCM. Prep HPLC Purification Method: Column: X Bridge C18, 19 * 150 mm, 5 μm; mobile phase: A: water (containing 10 mM NH₄HCO₃ + 0.05% ammonium hydroxide) and B: CH₃CN (15% to 45% over 5 min, and then 45% to 75% over 5 min); Flow rate: 15 mL/min; UV Detector: 254 nm.

[32]Notes:
HATU was used instead of EDCI/HOBt, and THF was used as the solvent in Step 1 (at RT). Step 2 was conducted with 4N HCl/dioxane. Prep HPLC Purification Method: Column, X Bridge C18, 19 * 150 mm, 5 μm; mobile phase. A: water (containing 10 mM NH₄HCO₃ and 0.05% ammonium hydroxide) and B: CH₃CN (15% to 45% over 8 min, and then 45% to 85% over 8 min); Flow rate: 15 ml/min; UV Detector: 254 nm.

[33]Notes:
Step 2 was conducted with 4N HCl/dioxane. The product was isolated by direct isolation of the HCl salt by filtration and washing the filter cake with diethyl ether.

[34]Notes:
Step 2 was conducted with TFA/DCM. Prep HPLC Purification Method: Column, X Bridge C18, 19 * 150 mm, 5 μm; mobile phase, A: water (containing 0.05% ammonium hydroxide) and B: CH₃CN (15% to 45% over 4 min, and then 45% to 75% over 6 min); Flow rate: 15 mL/min; UV Detector: 254 nm.

[35]Notes:
Step 2 was conducted with 4N HCl/dioxane. Prep HPLC Purification Method: Column: X Bridge C18, 19 * 150 mm, 5 um; mobile phase, A: water (containing 10 mM NH₄HCO₃ + 0.05% ammonium hydroxide) and B: CH₃CN (15% to 45% over 5 min, and then 45% to 75% over 5 min); Flow rate: 15 mL/min; UV Detector: 254 nm.

[36]Notes:
Step 2 was conducted with 4N HCl/dioxane with MeOH as a cosolvent. The product was isolated as the HCl salt after direct filtration and washing the filter cake with diethyl ether.

[37]Notes:
Step 2 was conducted with 4N HCl/dioxane with MeOH as a cosolvent. The product was isolated as the HCl salt after direct filtration and washing the filter cake with diethyl ether.

[38]Notes:
Step 2 was conducted with TFA/DCM. Prep HPLC Purification Method: Column, X Bridge C18, 19 * 150 mm, 5 μm; mobile phase, A: water (containing 10 mM NH₄HCO₃ and 0.05% ammonium hydroxide) and B: CH₃CN (28% to 38% over 3 min, and then 38% to 75% over 6 min); UV Detector: 254 nm.

[39]Notes:
The individual enantiomers were separated after Step 1 using the following Chiral HPLC Method: (SHIMADZU LC-20AD): Column, DAICEL CHIRALPAK AD-3; mobile phase, Phase A: n-Hexane (containing 0.1% DEA) Phase B: Ethanol; UV Detector: 190 nm-500 nm; Step 2 was conducted with TFA/DCM. HPLC Prep Purification Method: Column, X Bridge C18, 19 * 150 mm, 5 μm; mobile phase, A: water (containing 10 mM NH₄HCO₃ and 0.05% ammonium hydroxide) and B: CH₃CN (28% to 38% over 3 min; and then 38% to 75% over 6 min); UV Detector: 254 nm.

[40]Notes:
Step 2 was conducted with TFA/DCM. HPLC Prep Purification Method: Column, X Bridge C18, 19 * 150 mm, 5 μm; mobile phase, A: water (containing 10 mM NH₄HCO₃ and 0.05% ammonium hydroxide) and B: CH₃CN (15% to 45% over 5 min); UV Detector: 254 nm.

[41]Notes:
Step 2 was conducted with TFA/DCM. HPLC Prep Purification Method: (Waters-2767): Column, X Bridge C 18, 19 * 150 mm, 5 μm; mobile phase, A: water (containing 10 mM NH₄HCO₃ and 0.05% ammonium hydroxide) and B: CH₃CN (15% to 45% over 5 min, and then 45% to 75% over 5 min); Flow rate: 20 mL/min); UV Detector: 254 nm.

[42]Notes:
Step 2 was conducted with TFA/DCM. HPLC Prep Purification Method: (Waters-2767): Column, X Bridge C 18, 19 * 150 mm, 5 μm; mobile phase, A: water (containing 10 mM NH₄HCO₃ and 0.05% ammonium hydroxide) and B: CH₃CN (15% to 45% over 5 min, and then 45% to 75% over 5 min); Flow rate: 20 mL/min); UV Detector: 254 nm.

[43]Notes:
Step 2 was conducted with TFA/DCM. HPLC Prep Purification Method: (Water I): Column, X Bridge C 18, 19 * 150 nm, 5 μm; mobile phase, A: water(containing 10 mM NH₄HCO₃ and 0.05% ammonium hydroxide) and B: CH₃CN (20% to 30% over 5 min); Flow rate: 20 mL/min; UV Detector: 254 nm.

TABLE 14-continued

|  | MS |  |
|---|---|---|
| Example | (ESI, | |
| (Cmpd | m/z) | |
| No.) | [M + H] | $^1$H NMR |

$^{44}$Notes:

Step 2 was conducted with 4N HCl/dioxane and MeOH as a cosolvent. The product was isolated directly as the HCl salt by filtration and washing with diethyl ether.

$^{45}$Notes:

Step 1 was conducted using HBTU as the coupling reagent. DIEA and DMAP as bases in DMF solvent at 80° C. Step 2 was conducted with TFA/DCM. HPLC Prep Purification Method: (C18 column; gradient: 0-90% MeCN in water containing 0.1% ammonium hydroxide over 15 minutes); the product was isolated by lyophilization.

$^{46}$Notes:

Step 1 was conducted using HBTU as the coupling reagent, DIEA and DMAP as bases in DMF solvent at 80° C. Step 2 was conducted with TFA/DCM. HPLC Prep Purification Method: (C18 column; gradient: 0-90% MeCN in water containing 0.1% ammonium hydroxide over 15 minutes); the product was isolated by lyophilization.

$^{47}$Notes:

Step 1 was conducted using HBTU as the coupling reagent, DIEA and DMAP as bases, and DMF as the solvent at 80° C. Step 2 was unnecessary. Purification Method: FCC eluting with 40-60% EtOAc in hexanes.

$^{48}$Notes:

Step 1 was conducted using HBTU as the coupling reagent, DIEA and DMAP as bases, and DMF as the solvent at 80° C. Step 2 was unnecessary. Purification Method: FCC eluting with 40-60% EtOAc in hexanes.

$^{49}$Notes:

Step 1 was conducted using HBTU as the coupling reagent, DIEA and DMAP as bases, and DMF as the solvent at 80° C. Step 2 was conducted with TFA/DCM. HPLC Prep Purification Method: (C18 column; gradient: 0-90% MeCN in water containing 0.1% ammonium hydroxide over 15 minutes); the product was isolated by lyophilization.

$^{50}$Notes:

Step 1 was conducted using HBTU as the coupling reagent, DIEA and DMAP as bases, and DMF as the solvent at 80° C. Step 2 was conducted with TFA/DCM. HPLC Prep Purification Method: (C18 column; gradient: 0-90% MeCN in water containing 0.1% ammonium hydroxide over 15 minutes); the product was isolated by lyophilization.

$^{51}$Notes:

Step 1 was conducted using HBTU as the coupling reagent, DIEA and DMAP as bases, and DMF as the solvent at 80° C. Step 2 was conducted with TFA/DCM. HPLC Prep Purification Method: (C18 column; gradient: 0-90% MeCN in water containing 0.1% ammonium hydroxide over 15 minutes); the product was isolated by lyophilization.

$^{52}$Notes:

Step 1 was conducted using HBTU as the coupling reagent, DIEA and DMAP as bases, and DMF as the solvent at 80° C. Step 2 was conducted with TFA/DCM. HPLC Prep Purification Method: (C18 column; gradient: 0-90% MeCN in water containing 0.1% ammonium hydroxide over 15 minutes); the product was isolated by lyophilization.

$^{53}$Notes:

Step 1 was conducted using HBTU as the coupling reagent, DIEA and DMAP as bases, and DMF as the solvent at 80° C. Step 2 was conducted with TFA/DCM. HPLC Prep Purification Method: (C18 column; gradient: 0-90% MeCN in water containing 0.1% ammonium hydroxide over 15 minutes); the product was isolated by lyophilization.

$^{54}$Notes:

Step 1 was conducted using HBTU as the coupling reagent, DIEA and DMAP as bases, and DMF as the solvent at 80° C. Step 2 was conducted with TFA/DCM. HPLC Prep Purification Method: (C18 column; gradient: 0-90% MeCN in water containing 0.1% ammonium hydroxide over 15 minutes); the product was isolated by lyophilization.

$^{55}$Notes:

Step 1 was conducted using HBTU as the coupling reagent, DIEA and DMAP as bases, and DMF as the solvent at 80° C. Step 2 was conducted with TFA/DCM. HPLC Prep Purification Method: (C18 column; gradient: 0-90% MeCN in water containing 0.1% ammonium hydroxide over 15 minutes); the product was isolated by lyophilization.

$^{56}$HPLC Prep Purification Method: Column, X Bridge C18; 19 * 150 mm, 5 μm; mobile phase: A: water (modified with 10 mM NH$_4$HCO$_3$ and 0.05% ammonia) and B: CH$_3$CN; Gradient: 15% to 30% B in 8 min; Flow rate: 20 mL/min.

$^{57}$Notes:

TFA/DCM was used for Step 2. HPLC Prep Purification Method: SHIMADZU LC-20AD, LC parameters: Pump Mode: Binary gradient, Start Conc. of Pump B: 30.0%, End Conc. of Pump B: 55.0%, Total Flow: 20 mL/min, Time: 7 min, Phase A: Water (10 mmol/L NH$_4$HCO$_3$), Phase B: MeCN-HPLC, Column Name: SunFire Prep C18 OBD Column, Length: 150 mm. Internal Diameter: 19 mm, Particle Size: 5 μm, Aperture Size: 130 Å, Column Temp: 25° C., PDA Model: SPD-M20A, Wavelength: from 190 nm to 500 nm.

$^{58}$Notes:

TFA/DCM was used for Step 2. HPLC Prep Purification Method: Waters, LC parameters: Pump Mode: Binary gradient, Start Conc. of Pump B: 25.0%, End Conc. of Pump B: 35.0% Total Flow: 20 mL/min, Time: 10 min, Phase A: Water (10 mmol/L NH4HCO3 + 0.05% NH3H2O), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

$^{59}$Notes:

TFA/DCM was used for Step 2. HPLC Prep Purification Method: Waters, LC parameters: Pump Mode: Binary gradient, Start Conc. of Pump B: 25.0%, End Conc. of Pump B: 30.0% Total Flow: 15 mL/min, Time: 11 min, Phase A: Water (10 mmol/L NH$_4$HCO$_3$ + 0.05% NH$_3$H$_2$O), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from $^{60}$Notes:

TFA/DCM was used for Step 2. HPLC Prep Purification Method: SHIMADZU LC-20AD, LC parameters: Pump Mode: Binary gradient, Start Conc. of Pump B: 25.0%, End Conc. of Pump B: 68.0% Total Flow: 20 mL/min, Time: 7 min, Phase A: Water (10 mmol/L NH$_4$HCO$_3$), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

$^{61}$Notes:

Step 1 was conducted at RT. TFA/DCM was used for Step 2. HPLC Prep Purification Method: SHIMADZU LC-20AD, LC parameters: Pump Mode: Binary gradient, Start Conc. of Pump B: 10.0%, End Conc. of Pump B: 70.0%, Total Flow: 20 mL/min, Time: 8 min, Phase A: Water (10 mmol/L NH$_4$HCO$_3$), Phase B: MeCN-HPLC, Column Name: XBridge BEH C18 OBD Prep Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

$^{62}$Notes:

TFA/DCM was used for Step 2. HPLC Prep Purification Method: SHIMADZU LC-20AD, LC parameters: Pump Mode: Binary gradient, Start Conc. of Pump B: 58.0%, End Conc. of Pump B: 78.0% Total Flow: 20 mL/min, Time: 8 min, Phase A: Water (10 mmol/L NH$_4$HCO$_3$ + 0.05% NH$_3$•H$_2$O). Phase B: MeCN-HPLC, Column Name: XBridge Prep C18 OBD Column, Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm.

$^{63}$Notes:

HCl gas in dioxane was used in Step 2. Isolation Method: The title compound was isolated by concentrating the reaction mixture from Step 2 in vacuo then triturating the resulting solid with diethyl ether/MeOH (10:1).

Example 82 (I-73)

3-Amino-N-(3-(difluoromethoxy)-4-(piperazin-1-yl) phenethyl)-6-methylthieno[2,3-b]pyridine-2-carboxamide (formate salt)

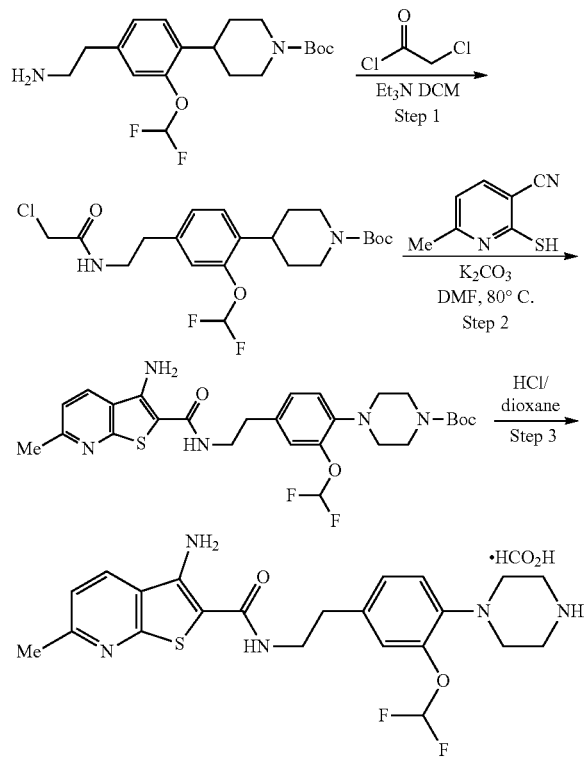

Example 82 (I-73)

Step 1. tert-Butyl 4-(4-(2-2-chloroacetamido)ethyl)-2-(difluoromethoxy)phenyl)piperazine-1-carboxylate Into a 50-mL round-bottom flask was added tert-butyl 4-[4-(2-aminoethyl)-2-(difluoromethoxy)phenyl]piperazine-1-carboxylate (0.210 g, 0.57 mmol), triethylamine (0.172 g, 0.237 mL, 1.70 mmol) and dichloromethane (10 mL) followed by a solution of 2-chloroacetyl chloride (0.069 g, 0.61 mmol) in dichloromethane (2 mL). The resulting solution was stirred for 1 h at RT and then concentrated in vacuo. The resulting crude product was purified by FCC eluting with ethyl acetate/petroleum ether (1:1) to afford tert-butyl 4-(4-(2-(2-chloroacetamido)ethyl)-2-(difluoromethoxy)phenyl)piperazine-1-carboxylate as a white solid (220 mg, 87%). LCMS (ESI, m/z): 448 [M+H]+.

Step 2. tert-Butyl 4-(4-(2-(3-amino-6-methylthieno[2,3-b]pyridine-2-carboxamido)ethyl)-2-(difluoromethoxy)phenyl)piperazine-1-carboxylate Into a 50-mL round-bottom flask, purged and maintained under an inert atmosphere of nitrogen, was added tert-butyl 4-(4-(2-(2-chloroacetamido)ethyl)-2-(difluoromethoxy)phenyl)piperazine-1-carboxylate (0.220 g, 0.49 mmol), 2-mercapto-6-methylnicotinonitrile (0.110 g, 0.73 mmol), potassium carbonate (0.204 g, 1.48 mmol), and DMF (4 mL). The reaction mixture was stirred overnight at 80° C. and then quenched with water (20 mL) and extracted with ethyl acetate (3×50 mL). The combined organic layers were dried over sodium sulfate, filtered, and concentrated in vacuo. The crude product was purified by FCC eluting with ethyl acetate/petroleum ether (1:1) to afford tert-butyl 4-(4-(2-(3-amino-6-methylthieno[2,3-b]pyridine-2-carboxamido) ethyl)-2-(difluoromethoxy)phenyl)piperazine-1-carboxylate as a red solid (300 mg, 99%). LCMS (ESI, m/z): 562 [M+H]+.

Step 3. 3-Amino-N-(3-(difluoromethoxy)-4-(piperazin-1-yl)phenethyl)-6-methylthieno[2,3-b]pyridine-2-carboxamide (formate salt)

Into a 50-mL round-bottom flask was added tert-butyl 4-(4-(2-(3-amino-6-methylthieno[2,3-b]pyridine-2-carboxamido)ethyl)-2-(difluoromethoxy)phenyl)piperazine-1-carboxylate (0.290 g, 0.52 mmol) and 4 N hydrogen chloride in 1,4-dioxane (20 mL). The reaction mixture was stirred for 2 h at RT and then concentrated in vacuo to provide a crude product that was purified by Prep-HPLC under the following conditions (waters-2767): Column: SunFire™ Prep C18, 5 μm, 19×150 mm; mobile phase, A: water (containing 0.1% formic acid) and B: $CH_3CN$ (20% to 25% over 3 min); UV Detector: 220 nm. This afforded the title compound as a light yellow solid (4 mg, 1%). LCMS (ESI, m/z): 462 [M+H]+; $^1$H-NMR (300 MHz, DMSO-$d_6$) δ ppm 8.36-8.21 (m, 2H), 7.77-7.69 (m, 1H), 7.31-7.29 (m, 1H), 7.12-6.78 (m, 5H), 3.40-3.37 (m, 2H), 2.89 (s, 8H), 2.80-2.77 (m, 2H), 2.62 (s, 3H).

Example 83 (I-74)

3-Amino-6-methyl-N-(3-methyl-4-(piperazin-1-yl) phenethyl)thieno[2,3-b]pyridine-2-carboxamide

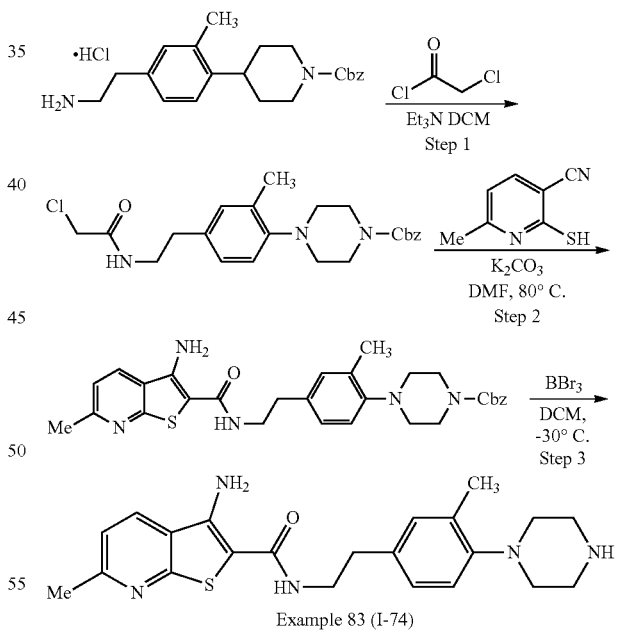

Example 83 (I-74)

Step 1. Benzyl 4-(4-(2-(2-chloroacetamido)ethyl)-2-methylphenyl)piperazine-1-carboxylate Into a 50-mL round-bottom flask was added benzyl 4-[4-(2-aminoethyl)-2-methylphenyl]piperazine-1-carboxylate hydrochloride (0.372 g, 0.94 mmol), $Et_3N$ (0.291 g, 0.401 mL, 2.88 mmol), and dichloromethane (20 mL). This was followed by the dropwise addition of a solution of 2-chloroacetyl chloride (0.128 g, 0.090 mL, 1.13 mmol) in dichloromethane (5 mL) at 0° C. with stirring. The resulting solution was stirred for 2 h at 0° C. and then concentrated in vacuo to a crude product that was purified by FCC eluting with ethyl acetate/petroleum ether (1:3) to afford benzyl 4-(4-(2-(2-chloroacetamido)ethyl)-2-methylphenyl)piperazine-1-carboxylate as a white solid (272 mg, 67%). LCMS (ESI, m/z): 430 [M+H]⁺.

Step 2. Benzyl 4-(4-(2-(3-amino-6-methylthieno[2,3-b]pyridine-2-carboxamido)ethyl)-2-methylphenyl)piperazine-1-carboxylate Into a 50-mL round-bottom flask was added benzyl 4-(4-(2-(2-chloroacetamido)ethyl) -2-methylphenyl)piperazine-1-carboxylate (0.27 g, 0.63 mmol), 2-mercapto-6-methylnicotinonitrile (0.114 g, 0.76 mmol), potassium carbonate (0.261 g, 1.89 mmol) and DMF (4 mL). The reaction mixture was heated and stirred overnight at 80° C. and then concentrated in vacuo. The resulting crude product was purified by FCC eluting with ethyl acetate/petroleum ether (1:1) to afford benzyl 4-(4-(2-(3-amino-6-methylthieno[2,3-b]pyridine-2-carboxamido)ethyl)-2-methylphenyl)piperazine-1-carboxylate as an orange oil (212 mg, 62%). LCMS (ESI, m/z): 544 [M+H]⁺.

Step 3. 3-Amino-6-methyl-N-(3-methyl-4-(piperazin-1-yl)phenethyl)thieno[2,3-b]pyridine-2-carboxamide Into a 50-mL round-bottom flask was added benzyl 4-(4-(2-(3-amino-6-methylthieno[2,3-b]pyridine-2-carboxamido)ethyl)-2-methylphenyl)piperazine-1-carboxylate (0.200 g, 0.37 mmol) and dichloromethane (1 mL). The resulting mixture was cooled to −30° C. and then a solution of BBr₃ in DCM was added dropwise (1 M; 2 mL). The resulting solution was stirred for 30 min at −30° C. and then concentrated in vacuo to provide a crude product that was purified by Prep-HPLC using the following conditions (waters-2767): Column, SunFire™ C18, 5 μm, 19*150 mm; mobile phase, A: water (containing 0.05% ammonia) and B: CH₃CN (18% to 25% over 8 min); UV Detector: 254 nm. This afforded the title compound as a light yellow solid (6.5 mg, 4%). LCMS (ESI, m/z): 410 [M+H]⁺; ¹H-NMR (300 MHz, DMSO-d₆) δ ppm 8.30 (d, J =8.4 Hz, 1H), 7.79-7.62 (m, 1H), 7.31 (d, J=8.0 Hz, 1H), 7.12 (br s, 2H), 7.03-6.88 (m, 3H), 3.41-3.33 (m, 2H), 2.88-2.79 (m, 4H), 2.75-2.66 (m, 6H), 2.58 (s, 3H), 2.22 (s, 3H).

The Examples in Table 15 below were synthesized according to the procedures outlined above for Examples 82 (I-73) and 83 (I-74), using the appropriate synthetic precursors. Additional detail around the synthetic methods as well as HPLC purification conditions appears below each example. Method A (Acid promoted amine deprotection) or Method B (BBr3 promoted amine deprotection) was used in Step 3.

TABLE 15

| Example (Cmpd no.) | Structure | MS (ESI, m/z) [M + H] | ¹H NMR |
|---|---|---|---|
| 84-1¹ (I-75) | | 450 | (300 MHz, DMSO-d₆) δ ppm 8.29 (d, J = 8.1 Hz, 1H), 7.67 (t, J = 5.4 Hz, 1H), 7.30 (d, J = 8.1 Hz, 1H), 7.06-7.11 (m, 4H), 6.86 (d, J = 8.7 Hz, 2H), 3.32 (m, 2H), 3.05-3.09 (m, 4H), 2.69-2.74 (m, 3H), 2.58 (s, 3H), 2.35-2.38 (m, 4H), 2.01-1.96 (m, 2H), 1.75-1.88 (m, 2H), 1.64-1.69 (m, 2H) |
| 84-2² (I-76) | | 430 | (300 MHz, DMSO-d₆) δ ppm 8.29 (d, J = 8.3 Hz, 1H), 7.81-7.64 (m, 1H), 7.30 (d, J = 8.3 Hz, 1H), 7.22-7.01 (m, 3H), 6.96-6.77 (m, 2H), 3.42-3.33 (m, 2H), 3.06-2.97 (m, 4H), 2.88-2.74 (m, 6H), 2.57 (s, 3H), 2.46-2.41 (m, 1H) |
| 84-3³ (I-77) | | 430 | (300 MHz, DMSO-d₆) δ 8.30 (d, J = 8.1 Hz, 1H), 7.73 (t, J = 5.4 Hz, 1H), 7.26-7.32 (m, 2H), 7.04-7.13 (m, 4H), 3.34-3.42 (m, 2H), 2.78-2.83 (m, 8H), 2.74-2.76 (m, 2H), 2.58 (s, 3H), 2.38 (br s, 1H) |

TABLE 15-continued

| Example (Cmpd no.) | Structure | MS (ESI, m/z) [M + H] | ¹H NMR |
|---|---|---|---|
| 84-4[4] (I-78) | 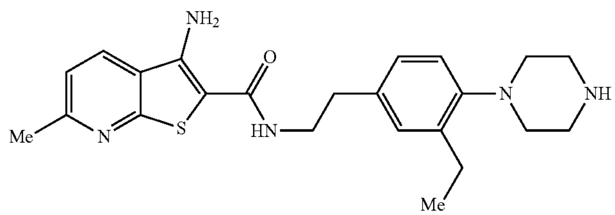 [SMILES: CCc1cc(CCNC(=O)c2sc3nc(C)ccc3c2N)ccc1N1CCNCC1] | 424 | (300 MHz, CD$_3$OD) δ ppm 8.27 (d, J = 8.4 Hz, 1H), 7.36 (d, J = 8.4 Hz, 1H), 7.19 (s, 1H), 7.14 (s, 2H), 3.60-3.50 (m, 2H), 3.45-3.32 (m, 4H), 3.12-3.09 (m, 4H), 2.89-2.84 (m, 2H), 2.76-2.71 (m, 2H), 2.68 (s, 3H), 1.23 (t, J = 8.4 Hz, 3H) |
| 84-5[5] (I-79) | 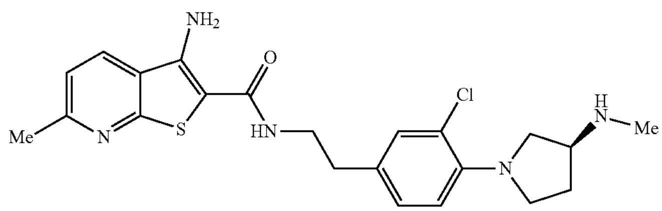 [SMILES: CN[C@H]1CCN(c2ccc(CCNC(=O)c3sc4nc(C)ccc4c3N)cc2Cl)C1] | 444 | (300 MHz, DMSO-d$_6$) δ ppm 8.29 (d, J = 9 Hz, 1H), 7.71-7.70 (m, 1H), 7.30 (d, J = 9 Hz, 1H), 7.16-6.86 (m, 4H), 6.87 (d, J = 6 Hz, 1H), 3.49-3.02 (m, 6H), 2.79-2.70 (m, 2H), 2.58 (s, 3H), 2.27 (s, 3H), 2.04-1.96 (m, 2H), 1.71-1.66 (m, 1H) |
| 84-6[6] (I-80) | 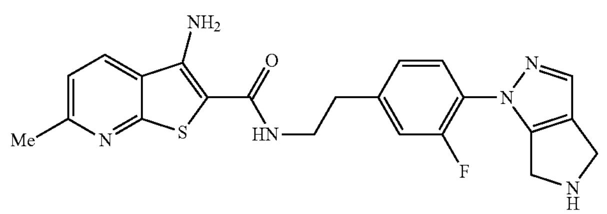 [SMILES: Cc1ccc2c(N)c(C(=O)NCCc3ccc(-n4ncc5c4CNC5)c(F)c3)sc2n1] | 437 | (300 MHz, DMSO-d$_6$) δ ppm 10.22 (br s, 2H), 8.31 (d, J = 8.4 Hz, 1H), 7.81-7.73 (m, 1H), 7.68 (s, 1H), 7.65-7.58 (m, 1H), 7.50-7.19 (m, 4H), 4.49 (br s, 2H), 4.33 (br s, 2H), 3.52-3.45 (m, 2H), 2.94-2.90 (m, 2H), 2.73 (s, 3H) |
| 84-7[7] (I-81) | 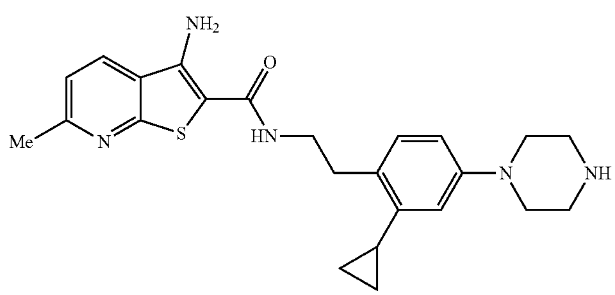 [SMILES: Cc1ccc2c(N)c(C(=O)NCCc3ccc(N4CCNCC4)cc3C3CC3)sc2n1] | 436 | (300 MHz, DMSO-d$_6$) δ ppm 8.30 (d, J = 8.3 Hz, 1H), 7.83-7.71 (m, 1H), 7.30 (d, J = 8.3 Hz, 1H), 7.13 (s, 2H), 6.98 (d, J = 8.3 Hz, 1H), 6.72-6.58 (m, 1H), 6.47-6.37 (m, 1H), 3.39-3.35 (m, 2H), 3.01-2.78 (m, 10H), 2.58 (s, 3H), 2.10-2.00 (m, 1H), 0.96-0.86 (m, 2H), 0.67-0.60 (m, 2H). |
| 84-8[8] (I-82) | 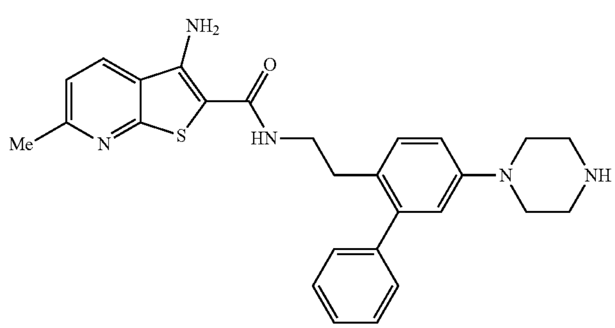 [SMILES: Cc1ccc2c(N)c(C(=O)NCCc3ccc(N4CCNCC4)cc3-c3ccccc3)sc2n1] | 472 | (300 MHz, DMSO-d$_6$) δ ppm 8.28 (d, J = 8.3 Hz, 1H), 7.73-7.59 (m, 1H), 7.48-7.03 (m, 9H), 6.97-6.83 (m, 1H), 6.71-6.59 (m, 1H), 3.28-3.21 (m, 2H), 3.09-2.99 (m, 4H), 2.87-2.78 (m, 4H), 2.69-2.61 (m, 2H), 2.56 (s, 3H) |
| 84-9[9] (I-83) | 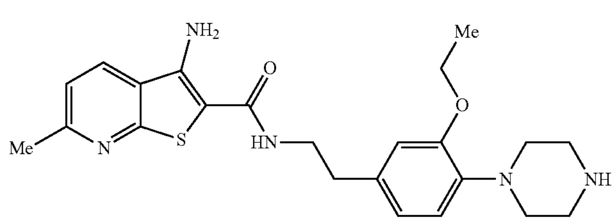 | 440 | (300 MHz, DMSO-d$_6$) δ ppm 8.70 (br s, 2H), 8.30 (d, J = 8.2 Hz, 1H), 7.77-7.59 (m, 1H), 7.31 (d, J = 8.3 Hz, 1H), 6.88-6.70 (m, 3H), 4.05-3.95 (m, 2H), 3.46-3.34 (m, 2H), 3.31-3.09 (m, 8H), 2.87-2.70 (m, 2H), 2.58 (s, 3H), 1.38-1.26 (m, 3H) |

TABLE 15-continued

| Example (Cmpd no.) | Structure | MS (ESI, m/z) [M + H] | 1H NMR |
|---|---|---|---|
| 84-10[10] (I-84) | 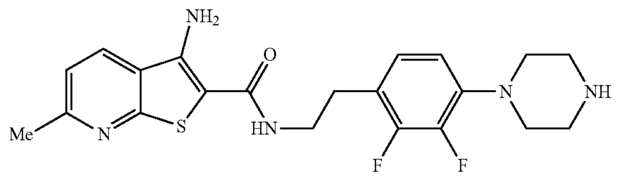 [SMILES: Cc1ccc2c(N)c(C(=O)NCCc3ccc(N4CCNCC4)c(F)c3F)sc2n1] | 432 | (300 MHz, DMSO-d6) δ ppm 8.29 (d, J = 8.1 Hz, 1H), 7.80-7.74 (m, 1H), 7.30 (d, J = 8.1 Hz, 1H), 7.12 (br s, 2H), 7.03-6.95 (m, 1H), 6.80-6.74 (m, 1H), 3.40-3.38 (m, 2H), 2.91-2.90 (m, 4H), 2.84-2.82 (m, 6H), 2.68 (s, 3H) |
| 84-11[11] (I-85) | 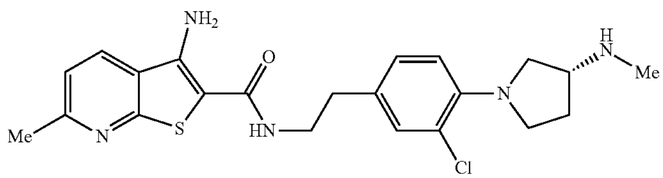 [SMILES: CN[C@@H]1CCN(c2ccc(CCNC(=O)c3sc4nc(C)ccc4c3N)cc2Cl)C1] | 444 | (300 MHz, DMSO-d6) δ ppm 8.32-8.25 (m, 1H), 7.70 (br s, 1H), 7.30 (d, J = 9 Hz, 1H), 7.16-6.86 (m, 4H), 6.87 (d, J = 6 Hz, 1H), 3.49-3.06 (m, 7H), 2.79-2.70 (m, 2H), 2.58 (s, 3H), 2.27 (s, 3H), 2.04-1.96 (m, 1H), 1.71-1.66 (m, 1H) |
| 84-12 (I-86) | 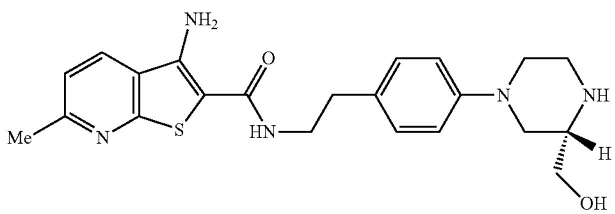 [SMILES: Cc1ccc2c(N)c(C(=O)NCCc3ccc(N4CCN[C@H](CO)C4)cc3)sc2n1] | 426 | (300 MHz, CD3OD) δ ppm 8.19 (d, J = 6 Hz, 1H), 7.30 (d, J = 9 Hz, 1H), 7.17 (d, J = 9 Hz, 2H), 6.94 (d, J = 6 Hz, 2H), 3.62-3.50 (m, 7H), 3.27-2.94 (m, 3H), 2.85-2.70 (m, 3H), 2.64 (s, 3H), 2.55-2.45 (m, 1H) |
| 84-13[12] (I-87) | 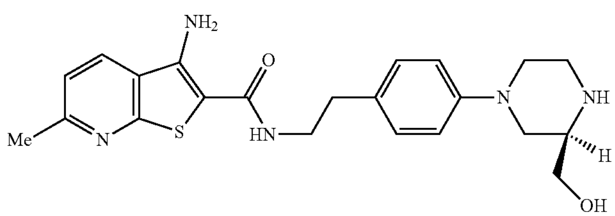 [SMILES: Cc1ccc2c(N)c(C(=O)NCCc3ccc(N4CCN[C@@H](CO)C4)cc3)sc2n1] | 426 | (300 MHz, CD3OD) δ ppm 8.19 (d, J = 6 Hz, 1H), 7.30 (d, J = 9 Hz, 1H), 7.17 (d, J = 9 Hz, 2H), 6.94 (d, J = 6 Hz, 2H), 3.62-3.50 (m, 7H), 3.27-2.94 (m, 3H), 2.85-2.70 (m, 3H), 2.64 (s, 3H), 2.55-2.45 (m, 1H) |
| 84-14[13] (I-88) | 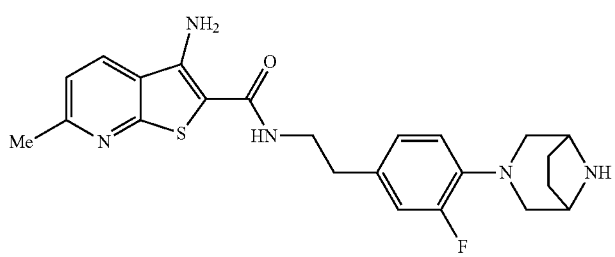 [SMILES: Cc1ccc2c(N)c(C(=O)NCCc3ccc(N4CC5CCC(C4)N5)c(F)c3)sc2n1] | 440 | (300 MHz, CD3OD) δ ppm 8.56 (brs, 1H), 8.21 (d, J = 8.4 Hz, 1H), 7.32 (d, J = 8.1 Hz, 1H), 7.08-6.90 (m, 3H), 3.98-3.80 (br s, 2H), 3.57-3.50 (m, 2H), 3.30-3.22 (m, 2H),), 3.07 (d, J = 11.7 Hz, 2H), 2.90-2.80 (m, 2H), 2.66 (s, 3H), 2.20-2.15 (m, 2H), 2.00-1.90 (m, 2H) |
| 84-15[14] (I-89) | 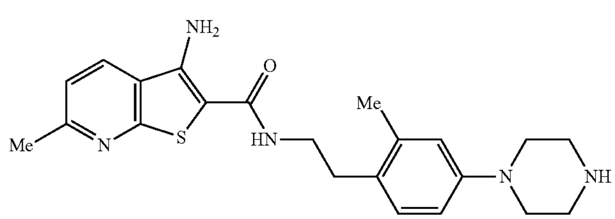 [SMILES: Cc1ccc2c(N)c(C(=O)NCCc3ccc(N4CCNCC4)cc3C)sc2n1] | 410 | (300 MHz, DMSO-d6) δ ppm 8.30 (d, J = 8.4 Hz, 1H), 7.74 (m, 1H), 7.30 (d, J = 8.2 Hz, 1H), 7.13 (br s, 2H), 6.98 (d, J = 8.4 Hz, 1H), 6.78-6.61 (m, 2H), 3.30-3.25 (m, 2H), 3.03-2.92 (m, 4H), 2.85-2.78 (m, 4H), 2.73-2.66 (m, 2H), 2.58 (s, 3H), 2.28 (s, 3H) |

TABLE 15-continued

| Example (Cmpd no.) | Structure | MS (ESI, m/z) [M + H] | ¹H NMR |
|---|---|---|---|
| 84-16[15] (I-90) | (structure: 3-amino-6-methyl-thieno[2,3-b]pyridine-2-carboxamide linked via NH-CH2CH2- to tetrahydroisoquinoline) | 367 | (300 MHz, DMSO-d$_6$) δ ppm 8.29 (d, J = 8.4 Hz, 1H), 7.73-7.70 (m, 1H), 7.30 (d, J = 8.4 Hz, 1H), 7.12 (br s, 2H), 7.00-6.92 (m, 2H), 6.85 (s, 1H), 3.79 (s, 2H), 3.32-3.29 (m, 2H), 2.92-2.84 (m, 2H), 2.78-2.69 (m, 2H), 2.66-2.55 (m, 5H) |

[1] Notes: Step 3 was not necessary. Prep HPLC Purification Method: Column, X Bridge C18, 19*150 mm, 5 μm; mobile phase; A: water (containing 10 mM NH$_4$HCO$_3$ + 0.05% ammonium hydroxide) and B: CH$_3$CN (50% to 65% over 8 min); UV Detector: 254 nm.
[2] Notes: Method B was used for Step 3. Prep HPLC Purification Method: (waters-2767): Column: X Bridge C18 19*150 mm, 5 μm; mobile phase, A: water (containing 10 mM NH$_4$HCO$_3$ + 0.5% ammonium hydroxide) and B: CH$_3$CN (40% to 50% over 5 min); UV Detector: 254 nm.
[3] Notes: Method A was used for Step 3. Isolation Method: The reaction mixture was concentrated in vacuo to the crude product with was taken up into water (20 mL). The pH of the solution was adjusted to approximately 8 with aqueous ammonia (1 M). The solid product was collected by filtration, washed with of water (2 × 10 mL) and dried in vacuo.
[4] Notes: Method A (TFA/DCM) was used for Step 3. Prep HPLC Purification Method: (Waters 2767): Column: X Bridge C18, 19*150 mm, 5 μm; mobile phase, A: water (containing 10 mm NH$_4$HCO$_3$ + 0.05% ammonium hydroxide) and B: CH$_3$CN (20% to 60% over 8 min); UV Detector: 254 nm.
[5] Notes: NaOMe was used as the base in Step 2. Method A (HCl/dioxane) was used for Step 3. The solid product was isolated directly after Step 3 by pH adjustment to 7-8 with aqueous sodium bicarbonate.
[6] Notes: Method B (at −30° C.) was used for Step 3. Prep HPLC Purification Method: Column, X Bridge C18, 19*150 mm, 5 μm; mobile phase, A: water (containing 10 mM NH$_4$HCO$_3$ + 0.05% ammonium hydroxide) and B: CH$_3$CN (5% to 50% over 8 min); UV Detector: 254 nm.
[7] Notes: Method B (at 0° C.) was used for Step 3. Prep HPLC Purification Method: (waters-2767): Column; X Bridge C18, 19*150 mm, 5 μm; mobile phase; A: water (containing 10 mM NH$_4$CO$_3$ + 0.05% ammonium hydroxide) and B: CH$_3$CN (25% to 45% over 5 min); UV Detector: 254 nm.
[8] Notes: Method B (at 0° C.) was used for Step 3. Prep HPLC Purification Method: (waters-2767): Column: X Bridge C18, 19*150 mm, 5 μm; mobile phase; A: water (containing 10 mM NH$_4$CO$_3$ + 0.05% ammonium hydroxide) and B: CH$_3$CN (25% to 45% over 5 min); UV Detector: 254 nm.
[9] Notes: Method B was used for Step 3. Prep HPLC Purification Method: (waters2767): Column, SunFire Prep C18 5 μm 19 × 150 mm; mobile phase, A: water (containing 0.05% TFA) and B: CH$_3$CN (20% up to 35% CH$_3$CN over 8 min); UV Detector: 254 nm.
[10] Notes: NaOMe was used as the base in Step 2. Method A (TFA/DCM) was used in Step 3. Prep HPLC Purification Method: (waters 2767): Column: SunFire Prep C18 5 μm 19*150 mm; mobile phase, A: water (containing 0.1% formic acid) and B: CH$_3$CN (10% to 35% over 8 min); Flow rate: 15 mL/min; UV Detector: 254 nm. The purified product was then dissolved in small amount of MeOH and passed through a pre-packed cartridge (agilent, PL-HCO3 MP SPE 100 mg/6 mL) to remove formic acid.
[11] Notes: Method A (HCl/dioxane) was used in Step 3. Prep HPLC Purification Method: (Waters-3767): Column, Xbridge RP18, 5 μm, 19*100 mm; mobile phase, A: water (containing 0.03% ammonium hydroxide) and B: CH$_3$CN (45% to 60% over 5 min); UV Detector: 254 nm.
[12] Notes: Method A (HCl/dioxane) was used in Step 3. Purification and isolation method: Prep HPLC: (Waters-2767): Column, XBridge RP18, 5 μm, 19* 100 mm; mobile phase, A: water (containing 0.03% ammonium hydroxide) and B: CH$_3$CN (45% to 60% over 5 min); UV Detector: 254 nm. Chiral HPLC: SHIMADZU LC-09, LC parameters: Pump Mode: Binary gradient, Start Conc. of Pump B: 50.0%, Total Flow: 1 mL/min, Phase A: Hex (0.1% DEA), Phase B: EtOH, Column Name: DAICEL CHIRALPAK AS-H, Length: 50 mm, Internal Diameter: 4.6 mm, Particle Size: 3 um, Column Temp: 25° C., PDA Model: SPD-M20A, Wavelength: 190 nm to 500 nm.
[13] Notes: DIEA was used in step 1 instead of TEA. Step 2 was conducted at 60° C. Method A (TFA/DCM) was used in Step 3. Purification and isolation method: Prep HPLC: (waters 2767): Column, X Bridge C18, 19*150 m, 5 μm; mobile phase, A: water (containing 10 mM NH$_4$HCO$_3$ + 0.05% ammonium hydroxide) and B: CH$_3$CN (65% to 75% over 8 min); Flow rate: 20 mL/min; UV Detector: 254 nm.
[14] Notes: DIEA was used in step 1 instead of TEA. NaOMe in THF at 50° C. was used in Step 2. Method A (HCl/dioxane) was used in Step 3. Prep HPLC Purification Method: Column, X Bridge C18 19 × 150 mm, 5 μm; mobile phase, A: water (10 mM NH$_4$HCO$_3$ and 0.05% ammonium hydroxide) B: CH$_3$CN (30% to 50% over 8 min); Flow rate: 20 mL/min; UV Detector: 254 nm.
[15] Notes: NaOMe in DMF at 50° C. was used in Step 2. Method B (at RT) was used in Step 3. Prep HPLC Purification Method: (Waters I): Column, Xbridge Prep C18 OBD column, 5 μm, 19*150 mm; mobile phase, A: water (containing 0.03% NH$_4$OH) and B: CH$_3$CN (16% to 34% over 10 min); UV Detector: 220 & 254 nm.

Examples 85-A (I-91) and 85-B (I-92): cis-3-Amino-6-methyl-N-(3-(4-(piperazin-1-yl)phenyl)cyclobutyl)thieno [2,3-b]pyridine-2-carboxamide (formate salt) and trans-3-amino -6-methyl-N-(3-(4-(piperazin-1-yl)phenyl)cyclobutyl)thieno[2,3-b]pyridine-2-carboxamide -continued

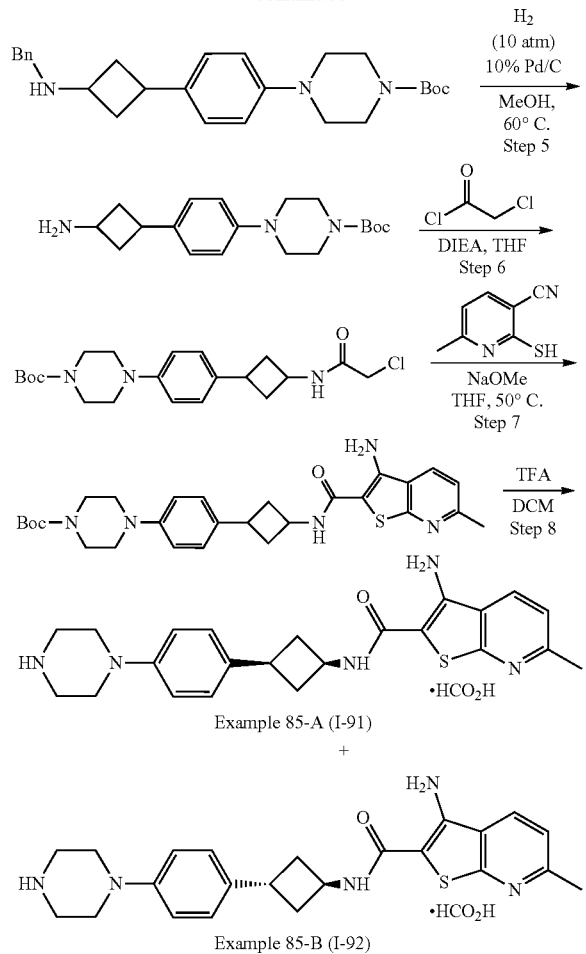

Example 85-A (I-91)

+

Example 85-B (I-92)

Step 1. 3-(4-Bromophenyl)-2,2-dichlorocyclobutan-1-one

Into a 100-mL round-bottom flask was added 1-bromo-4-ethenylbenzene (0.920 g, 5.03 mmol) and ether (30 mL) followed by the dropwise addition of POCl₃ (0.51 mL) with stirring. Trichloroacetyl chloride (1.84 g, 10.12 mmol) and Zn—Cu (0.980 g, 15.1 mmol) were then added portion-wise and the reaction mixture was stirred for 2 h at 40° C. The reaction was cooled to RT and allowed to stir for an additional 16 h. The solids were removed by filtration and the filtrate was washed with brine (50 mL), dried over anhydrous sodium sulfate, filtered, and concentrated in vacuo to afford 3-(4-bromophenyl)-2,2-dichlorocyclobutan-1-one as a white solid (400 mg, 27%). LCMS (ESI, m/z): 293, 295 [M+H]⁺.

Step 2. 3-(4-Bromophenyl)cyclobutan-1-one

Into a 500-mL round-bottom flask was added 3-(4-bromophenyl)-2,2-dichlorocyclobutan-1-one (13.9 g, 47.4 mmol), zinc (12.6 g, 190 mmol), and acetic acid (200 mL). The reaction mixture was stirred for 2 h at RT and then heated to 120° C. and stirred for an additional 6 h. The reaction mixture was filtered, and the filtrate was diluted with H₂O (200 mL) and extracted with dichloromethane (3×200 mL). The combined organic layers were washed with 5% aqueous sodium bicarbonate (200 mL), dried over sodium sulfate, filtered, and concentrated in vacuo. The crude product was purified by FCC eluting with ethyl acetate/petroleum ether (1:2) to afford 3-(4-bromophenyl)cyclobutan-1-one as a light yellow solid (7.8 g, 73%). LCMS (ESI, m/z): 225, 227 [M+H]⁺.

Step 3. N-benzyl-3-(4-bromophenyl)cyclobutan-1-amine

Into a 250-mL round-bottom flask was added 3-(4-bromophenyl)cyclobutan-1-one (3.00 g, 13.3 mmol) and benzylamine (1.40 g, 13.1 mmol) followed by the addition of a solution of Ti(Oi-Pr)₄ (15.0 g, 16.0 mmol, 52.8 mmol) in ethanol (120 mL) at 50° C. The resulting solution was stirred for 6 h at 50° C. and then cooled to RT. NaBH₃CN (1.20 g, 19.1 mmol) was added and the reaction mixture was allowed to stir for an additional 12 h. The reaction mixture was concentrated in vacuo and the crude product was purified by FCC eluting with ethyl acetate/petroleum ether (1:4) to afford N-benzyl-3-(4-bromophenyl) cyclobutan-1-amine as a yellow liquid (2.2 g, 52%). LCMS (ESI, m/z): 316, 318 [M+H]⁺.

Step 4. tert-Butyl 4-(4-(3-(benzylamino)cyclobutyl)phenyl)piperazine-1-carboxylate Into a 25-mL round-bottom flask was added N-benzyl-3-(4-bromophenyl)cyclobutan -1-amine (0.100 g, 0.31 mmol), tert-butyl piperazine-1-carboxylate (0.059 g, 0.32 mmol), Pd(dppf)Cl₂ (0.023 g, 0.03 mmol), SPhos (0.013 g, 0.03 mmol), and Cs₂CO₃ (0.300 g, 0.95 mmol) followed by toluene (8 mL). Nitrogen was bubbled through the reaction mixture for 5 minutes and then the reaction mixture was stirred for 12 h at 100° C. After cooling to RT, the reaction mixture was concentrated in vacuo and the crude product was purified by FCC eluting with ethyl acetate/petroleum ether (0 to 100%) to afford tert-butyl 4-(4-(3-(benzylamino) cyclobutyl)phenyl) piperazine-1-carboxylate as a yellow solid (58 mg, 44%). LCMS (ESI, m/z): 422 [M+H]⁺.

Step 5. tert-Butyl 4-(4-(3-aminocyclobutyl)phenyl)piperazine-1-carboxylate

Into a 250-mL pressure reactor under an atmosphere of nitrogen was added a solution of tert-butyl 4-(4-(3-(benzylamino)cyclobutyl)phenyl)piperazine-1-carboxylate (1.10 g, 2.61 mmol) in methanol (100 mL) followed by the addition of 10% palladium on carbon (0.027 g, 0.25 mmol). The reaction vessel was pressurized with hydrogen (10 atm) and the resulting mixture was stirred for 12 h at 60° C. The reaction was vented to nitrogen, the solids were removed by filtration through a pad of Celite and the resulting filtrate was concentrated in vacuo to afford tert-butyl 4(4-(3-aminocyclobutyl)phenyl) piperazine-1-carboxylate as a gray solid (800 mg, 93%). LCMS (ESI, m/z): 332 [M+H]⁺.

Step 6. tert-Butyl 4-(4-(3-(2-chloroacetamido)cyclobutyl) phenyl)piperazine-1-carboxylate Into a 25-mL round-bottom flask was added tert-butyl 4-(4-(3-aminocyclobutyl)phenyl)piperazine-1-carboxylate (0.400 g, 1.21 mmol) followed by tetrahydrofuran (5 mL), 2-Chloroacetyl chloride (0.136 g, 1.20 mmol), and DIEA (0.310 g, 0.418 mL, 2.40 mmol). The resulting solution was stirred for 2 h at RT and then concentrated in vacuo. The resulting crude product was purified by FCC eluting with ethyl acetate/petroleum ether (1:1). This afforded the title compound as a gray solid (240 mg, 49%). LCMS (ESI, m/z): 408 [M+H]⁺.

Step 7. tert-Butyl 4-(4-(3-(3-amino-6-methylthieno[2,3-b]pyridine-2-carboxamido) cyclobutyl)phenyl)piperazine-1-carboxylate Into a 25-mL round-bottom flask was added tert-butyl 4-(4-(3-(2-chloroacetamido)cyclobutyl)phenyl)piperazine-1-carboxylate (0.085 mg, 0.21 mmol) followed by THF (5 mL). 2-mercapto-6-methylnicotinonitrile (0.047 g, 0.31 mmol,) was added followed by sodium methoxide (0.034 g, 0.63 mmol). The resulting solution was stirred for 14 h at 50° C. and then concentrated in vacuo. The crude product was purified by FCC eluting with ethyl acetate/petroleum ether (1:1) to afford tert-butyl 4-(4-(3-(3-amino-6-methylthieno[2,3-b]pyridine-2-carboxamido)cyclobutyl)phenyl)piperazine-1-carboxylate as a yellow solid (45 mg, 41%). LCMS (ESI, m/z): 522 [M+H]+.

Step 8. cis-3-Amino-6-methyl-N-(3-(4-(piperazin-1-yl)phenyl)cyclobutyl)thieno[2,3-b]pyridine-2-carboxamide (formate salt) and trans-3-amino-6-methyl-N-(3-(4-(piperazin-1-yl)phenyl)cyclobutyl)thieno [2,3-b]pyridine-2-carboxamide (formate salt)

Into a 25-mL round-bottom flask was added tert-butyl 4-(4-(3-(3-amino-6-methylthieno[2,3-b]pyridine-2-carboxamido)cyclobutyl)phenyl)piperazine-1-carboxylate (0.050 g, 0.05 mmol) followed by dichloromethane (5 mL) and TFA (0.5 mL). The resulting solution was stirred for 1 h at RT and then concentrated in vacuo. The crude product was diluted with DMF (2 mL) and then purified by Prep-HPLC using the following conditions (WATERS 2767): Column, Column: X Bridge C18, 19*150 mm, 5 μm; mobile phase, mobile phase, A: water (containing 0.1% FA)and B: $CH_3CN$; Detector, 254 nm, UV wavelength: 254 nm to afford cis-3-amino-6-methyl-N-(3-(4-(piperazin-1-yl)phenyl)cyclobutyl)thieno[2,3-b]pyridine-2-carboxamide (formate salt) (Example 85-A (I-91), 12.3 mg, 30%) as a light yellow solid, and 12 mg of the cis/trans isomer mixture. The cis/trans isomer mixture (12 mg) was purified further by Chiral -Prep-HPLC using the following conditions (SHIMADZU LC-20AD): Column, DAICEL CHIRANCEL OJ-3; mobile phase, A: Ethanol (containing 0.1% DEA) and B: Methanol; UV Detector: 190 nm to 500 nm to afford trans-3-amino-6-methyl-N-(3-(4-(piperazin-1-yl)phenyl)cyclobutyl)thieno[2,3-b]pyridine-2-carboxamide (Example 85-B (I-92), 2.2 mg, 5%) as a light yellow solid.

Example 85-A (I-91)

LCMS (ESI, m/z): 422 [M+H]+; $^1$H NMR (300 MHz, $CD_3OD$) δ ppm 8.20 (d, J=8.4 Hz, 1H), 7.25-7.30 (m, 3H), 7.98-6.04 (m, 2H), 4.40-4.52 (m, 1H), 3.393.22 (m, 8H), 3.20-3.10 (m, 1H), 2.65-2.77 (m, 2H), 2.63 (s, 3H), 2.20-2.26 (m, 2H).

Example 85-B (I-92)

LCMS (ESI, m/z): 422 [M+H]+; $^1$H NMR (300 MHz, $CD_3OD$) δ ppm 8.24 (d, J=8.4 Hz, 1H), 7.30-7.35 (m, 3H), 7.02-7.05 (m, 2H), 4.60-4.71 (m, 1H) , 3.49-3.63 (m, 1H), 3.40 (br s, 8H), 2.67 (s, 3H), 2.63-2.42 (m, 4H).

Examples 86-1A (I-93) and 86-1B (1-94)

3-Amino-N-(4-((3aS,6aS)-hexahydropyrrolo[3,2-b]pyrrol-1(2H)-yl)phenethyl)-6-methylthieno[2,3-b]pyridine-2-carboxamide (hydrochloride salt) (stereochemical configuration assumed) and 3-Amino-N-(4-((3aR,6aR)-hexahydropyrrolo[3,2-b]pyrrol-1(2H)-yl)phenethyl)-6-methylthieno[2,3-b]pyridine-2-carboxamide (hydrochloride salt) (stereochemical configuration assumed)

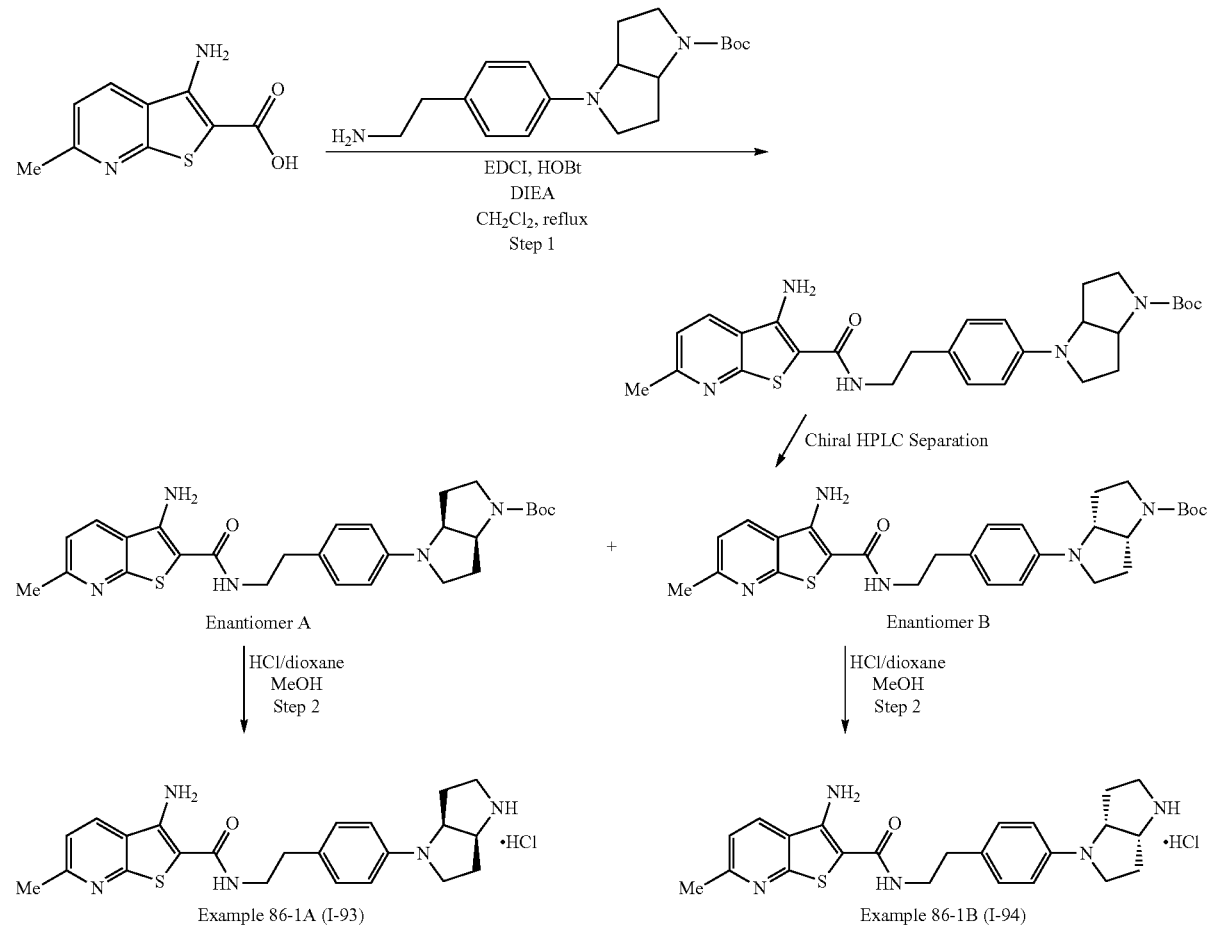

229

Step 1. tert-Butyl (3aS,6aS)-4-(4-(2-(3-amino-6-methylthieno[2,3-b]pyridine-2-carboxamido)ethyl)phenyl)hexahydropyrrolo[3,2-b] pyrrole-1(2H)-carboxylate (stereochemical configuration assumed) and tert-Butyl (3aR,6aR)-4-(4-(2-(3-amino-6-methylthieno[2,3-b]pyridine-2-carboxamido)ethyl)phenyl)hexahydropyrrolo [3,2-b]pyrrole-1(2H)-carboxylate (stereochemical configuration assumed)

Into a 25-mL round-bottom flask was added tert-butyl 4-[4-(2-aminoethyl)phenyl]-octahydropyrrolo[3,2-b]pyrrole-1-carboxylate (0.300 g, 0.91 mmol), 3-amino-6-methylthieno [2,3-b]pyridine-2-carboxylic acid (0.188 g, 0.90 mmol), HOBt (0.146 g, 1.08 mmol), EDCI (0.208 g, 1.09 mmol), and dichloromethane (5 mL) followed by the addition of DIEA (0.350 mg, 0.472 mL, 2.71 mmol). The resulting solution was stirred for 2 h at reflux and then cooled and washed with water (2×10 mL). The organic layer was concentrated in vacuo to provide a crude product that was further purified by Prep-HPLC using the following conditions (Waters I): Column, Xbridge phenyl column, 5 μm, 19*150 mm; mobile phase, A: water (0.05% NH$_4$OH+ 10 mM NH$_4$HCO$_3$) and B: CH$_3$CN (52% to 57% over 7 min); UV Detector: 254 nm. This afforded the title compounds as a mixture of cis stereoisomers (light yellow solid, 150 mg, 32%. The stereoisomers were then separated by Chiral-Prep-HPLC using the following conditions (SHIMADZU LC-20AD): LC parameters: Pump Mode: Binary gradient, Start Conc. of Pump B: 50.0%, Total Flow: 1 mL/min, Column, DAICEL CHIRALCEL OD-3; mobile phase, Phase A: n -Hexane (0.1% DEA), Phase B: Ethanol ; Length: 50 mm, Internal Diameter: 4.6 mm, Particle Size: 3.0 μm Column Temp.: 25° C., PDA Model: SPD-M20A, Wavelength: 190 nm to 500 nm. This resulted in the following: Step 1, Enantiomer A: 1$^{st}$ eluting peak: (retention time=2.45 min, 40 mg, yellow solid). LCMS (ESI, m/z): 522 [M+H]$^+$. Step 1, Enantiomer B: 2$^{nd}$ eluting peak: (retention time=4.34 min, 50 mg, yellow solid). LCMS (ESI, m/z): 522 [M+H]$^+$.

Step 2.

Example 86-1A (I-93)

3-Amino-N-(4-((3aS,6aS)-hexahydropyrrolo[3,2-b]pyrrol -1(2H)-yl)phenethyl)-6-methylthieno[2,3-b]pyridine-2-carboxamide (hydrochloride salt) (stereochemical configuration assumed)

Into a 25-mL round-bottom flask was added tert-butyl (3aS,6aS (assumed))-4-(4-(2-(3-amino-6-methylthieno[2,3-b]pyridine-2-carboxamido)ethyl)phenyl)hexahydropyrrolo [3,2-b] pyrrole-1(2H)-carboxylate (40 mg, 0.08 mmol) and methanol (2 mL) followed by 4 N HCl/dioxane (2 mL) and the resulting solution was stirred for 2 h at RT. The reaction mixture was concentrated in vacuo to remove some of the solvent and the resulting solids were collected by filtration, washed with ether (2×10 mL), and dried in vacuo to afford the title compound as a yellow solid (5.6 mg, 16%). LCMS (ESI, m/z): 422 [M+H]$^+$; $^1$H-NMR (300 MHz, DMSO-d$_6$) δ ppm 9.56 (br s, 1H), 9.30 (br s, 1H), 8.34 (d, J=8.3 Hz, 1H), 7.83-7.60 (m, 1H), 7.32 (d, J=8.3 Hz, 1H), 7.08 (d, J =8.4 Hz, 2H), 6.60 (d, J=8.5 Hz, 2H), 4.32 (br s, 2H), 3.58-3.41 (m, 1H), 3.41-3.13 (m, 4H), 3.06 (br s, 1H), 2.78-2.64 (m, 2H), 2.55 (s, 3H), 2.31-2.16 (m, 2H), 2.16-2.05 (m, 1H), 1.94-1.82 (m, 1H).

Step 2.

Example 86-1B (I-94)

3-Amino-N-(4-((3aR,6aR)-hexahydropyrrolo[3,2-b]pyrrol -1(2H)-yl)phenethyl)-6-methylthieno[2,3-b]pyridine-2-carboxamide (hydrochloride salt) (stereochemical configuration assumed)

The same synthetic procedure described to prepare Example 86-1A (I-93) was applied to Enantiomer B to afford the title compound as a yellow solid (17 mg, 39%). LCMS (ESI, m/z): 422 [M+H]$^+$; $^1$H-NMR (300 MHz, DMSO-d$_6$) δ ppm 9.51 (br s, 1H), 9.26 (br s, 1H), 8.33 (d, J=8.1 Hz, 1H), 7.72-7.68 (m, 1H), 7.32 (d, J=8.4 Hz, 1H), 7.08 (d, J=8.4 Hz, 2H), 6.60 (d, J=8.5 Hz, 2H), 4.32 (br s, 2H), 3.52-3.44 (m, 1H), 3.44-3.23 (m, 4H), 3.06 (br s, 1H), 2.73-2.68 (m, 2H), 2.51 (s, 3H), 2.31-2.06 (m, 3H), 1.94-1.87 (m, 1H).

The Examples in Table 16 below were synthesized according to the procedures outlined above for Examples 86-1A (I-93) and 86-1B (I-94), using the appropriate synthetic precursors. Additional detail around the synthetic methods as well as Chiral HPLC (after Step 1) and Prep HPLC purification conditions appear below the examples.

TABLE 16

| Example (Cmpd no.) | Structure | MS (ESI, m/z) [M + H] | $^1$H NMR |
|---|---|---|---|
| 86-2A[1] (I-95) | (structure shown) | 458 | (300 MHz, DMSO-d$_6$) δ ppm 9.25 (br s, 1H), 8.90 (br s, 1H), 8.28 (d, J = 10.5 Hz, 1H), 7.71 (t, J = 5.7 Hz, 1H), 7.30 (d, J = 3.6 Hz, 1H), 7.13-7.05 (m, 1H), 6.71 (dd, J = 7.5 Hz, 1H), 4.24 (br s, 1H), 3.75-3.68 (m, 1H), 3.30-3.27 (m, 4H), 3.22-3.16 (m, 3H), 3.07-3.04 (m, 1H), 2.78-2.73 (m, 2H), 2.57 (s, 3H), 2.19-2.12 (m, 1H), 1.88-1.83 (m, 1H) |

TABLE 16-continued

| Example (Cmpd no.) | Structure | MS (ESI, m/z) [M + H] | ¹H NMR |
|---|---|---|---|
| 86-2B[1] (I-96) | 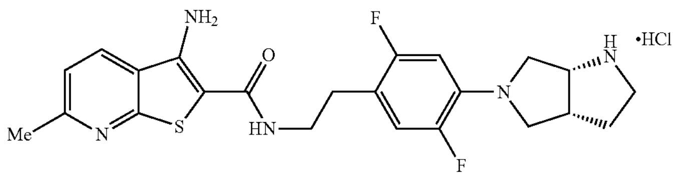 [SMILES: Cc1ccc2c(N)c(C(=O)NCCc3cc(F)c(N4C[C@H]5CCN[C@H]5C4)cc3F)sc2n1 ; Cl] | 458 | (300 MHz, DMSO-d$_6$) δ ppm 9.25 (br s, 1H), 8.90 (br s, 1H), 8.30 (d, J = 8.10 Hz, 1H), 7.71 (t, J = 5.4 Hz, 1H), 7.34-7.29 (m, 1H), 7.17-7.00 (m, 2H), 6.71 (dd, J = 7.5 Hz, 1H), 4.24 (br s, 1H), 4.15-4.01 (m, 1H), 3.42-3.33 (m, 4H), 3.19-3.13 (m, 3H), 3.06-3.03 (m, 1H), 2.78-2.73 (m, 2H), 2.50 (s, 3H), 2.18-2.11 (m, 1H), 1.88-1.84 (m, 1H) |
| 86-3A[2] (I-97) | 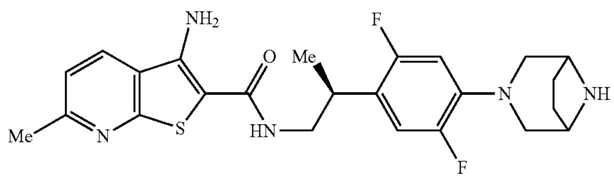 [SMILES: Cc1ccc2c(N)c(C(=O)NC[C@@H](C)c3cc(F)c(N4CC5CCC(C4)N5)cc3F)sc2n1] | 472 | (300 MHz, CD$_3$OD) δ 8.18 (d, J = 8.4 Hz, 1H), 7.29 (d, J = 8.4 Hz, 1H), 6.97-7.03 (m, 1H), 6.60-6.67 (m, 1H), 3.42-3.54 (m, 5H), 3.20-3.24 (m, 2H), 2.88-2.92 (m, 2H), 2.64 (s, 3H), 1.98-2.01 (m, 2H), 1.86-1.91 (m, 2H), 0.88-0.91 (m, 3H) |
| 86-3B[2] (I-98) | 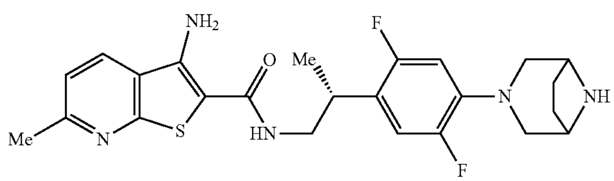 [SMILES: Cc1ccc2c(N)c(C(=O)NC[C@H](C)c3cc(F)c(N4CC5CCC(C4)N5)cc3F)sc2n1] | 472 | (300 MHz, CD$_3$OD) δ 8.17 (d, J = 8.1 Hz, 1H), 7.29 (d, J = 8.4 Hz, 1H), 6.96-7.03 (m, 1H), 6.59-6.66 (m, 1H), 3.43-3.54 (m, 5H), 3.19-3.23 (m, 2H), 2.88-2.92 (m, 2H), 2.63 (s, 3H), 1.96-2.04 (m, 2H), 1.82-1.91 (m, 2H), 1.25-1.28 (m, 3H). |
| 86-4A[3] (I-99) | 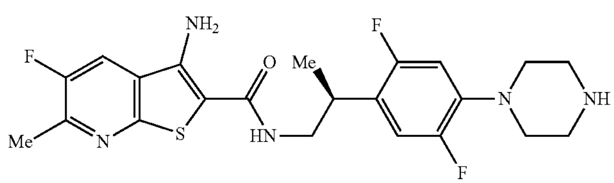 [SMILES: Cc1nc2sc(C(=O)NC[C@@H](C)c3cc(F)c(N4CCNCC4)cc3F)c(N)c2cc1F] | 464 | (300 MHz, CD$_3$OD) δ 8.01 (d, J = 9.9 Hz, 1H), 6.98-7.10 (m, 1H), 6.65-6.73 (m, 1H), 3.33-3.56 (m, 3H), 2.93-3.08 (m, 8H), 2.60 (d, J = 3.0 Hz, 3H), 1.27 (d, J = 6.6 Hz, 3H). |
| 86-4B[3] (I-100) | 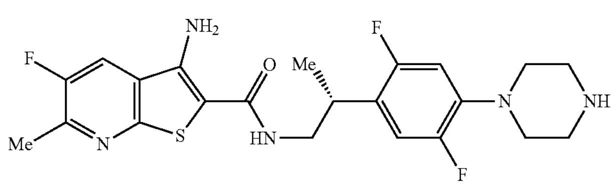 [SMILES: Cc1nc2sc(C(=O)NC[C@H](C)c3cc(F)c(N4CCNCC4)cc3F)c(N)c2cc1F] | 464 | (300 MHz, CD$_3$OD) δ 8.01 (d, J = 9.9 Hz, 1H), 6.98-7.10 (m, 1H), 6.65-6.73 (m, 1H), 3.33-3.56 (m, 3H), 2.93-3.08 (m, 8H), 2.60 (d, J = 3.0 Hz, 3H), 1.27 (d, J = 6.6 Hz, 3H) |
| 86-5A[4] (I-101) | 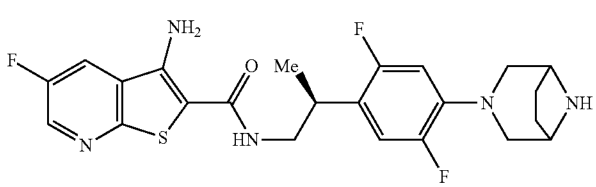 [SMILES: C[C@H](CNC(=O)c1sc2ncc(F)cc2c1N)c1cc(F)c(N2CC3CCC(C2)N3)cc1F] | 476 | (400 MHz, CD$_3$OD) δ 8.54 (s, 1H), 8.10-8.12 (m, 1H), 6.97-7.02 (m, 1H), 6.60-6.65 (m, 1H), 3.52-3.56 (m, 2H), 3.33-3.50 (m, 3H), 3.20-3.30 (m, 2H), 2.88-2.91 (m, 2H), 1.96-2.03 (m, 2H), 1.84-1.86 (m, 2H), 1.25-1.28 (m, 3H) |

TABLE 16-continued

| Example (Cmpd no.) | Structure | MS (ESI, m/z) [M + H] | 1H NMR |
|---|---|---|---|
| 86-5B[4] (I-102) | 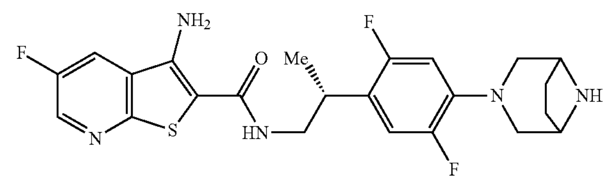 [SMILES: C[C@@H](CNC(=O)c1sc2ncc(F)cc2c1N)c1cc(F)c(N2CC3CCC(C2)N3)cc1F] | 476 | (400 MHz, CD₃OD) δ 8.54-8.55 (m, 1H), 8.10-8.12 (m, 1H), 6.97-7.02 (m, 1H), 6.60-6.65 (m, 1H), 3.52-3.56 (m, 2H), 3.33-3.50 (m, 3H), 3.20-3.30 (m, 2H), 2.88-2.91 (m, 2H), 1.96-2.03 (m, 2H), 1.84-1.86 (m, 2H), 1.25-1.28 (m, 3H) |
| 86-6A[5] (I-103) | 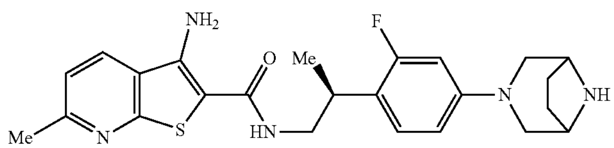 [SMILES: Cc1ccc2c(N)c(C(=O)NC[C@@H](C)c3ccc(N4CC5CCC(C4)N5)cc3F)sc2n1] | 454 | (400 MHz, CD₃OD) δ 8.19 (d, J = 8.4 Hz, 1H), 7.31 (d, J = 8.0 Hz, 1H), 7.11-7.23 (m, 1H), 6.57-6.75 (m, 1H), 6.43-6.62 (m, 1H), 3.58-3.62 (m, 2H), 3.39-3.59 (m, 5H), 2.82-2.90 (m, 2H), 2.65 (s, 3H), 1.82-1.89 (m, 4H), 1.28 (t, J = 6.8 Hz, 3H) |
| 86-6B[5] (I-104) | 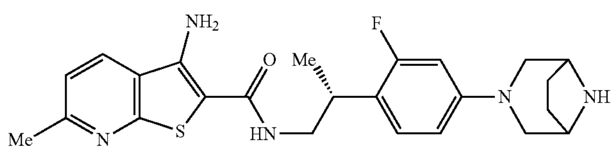 [SMILES: Cc1ccc2c(N)c(C(=O)NC[C@H](C)c3ccc(N4CC5CCC(C4)N5)cc3F)sc2n1] | 454 | (400 MHz, CD₃OD) δ 8.19 (d, J = 8.4 Hz, 1H), 7.23-7.42 (m, 1H), 7.11-7.18 (m, 1H), 6.58-6.73 (m, 1H), 6.42-6.56 (m, 1H), 3.60-3.67 (m, 2H), 3.40-3.59 (m, 5H), 2.85-2.93 (m, 2H), 2.65 (s, 3H), 1.86-1.92 (m, 4H), 1.28 (t, J = 6.80 Hz, 3H) |
| 86-7A[6] (I-105) | 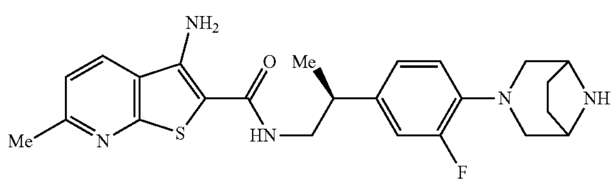 [SMILES: Cc1ccc2c(N)c(C(=O)NC[C@@H](C)c3ccc(N4CC5CCC(C4)N5)c(F)c3)sc2n1] | 454 | (400 MHz, CD₃OD) δ 8.18 (d, J = 8.0 Hz, 1H), 7.29 (d, J = 8.0 Hz, 1H), 6.86-7.02 (m, 3H), 3.63-3.69 (m, 2H), 3.33-3.48 (m, 5H), 3.22 (d, J = 11.2 Hz, 2H), 2.94-3.10 (m, 3H), 2.02-2.08 (m, 2H), 1.85-1.91 (m, 2H), 1.26 (d, J = 7.2 Hz, 3H) |
| 86-7B[6] (I-106) | 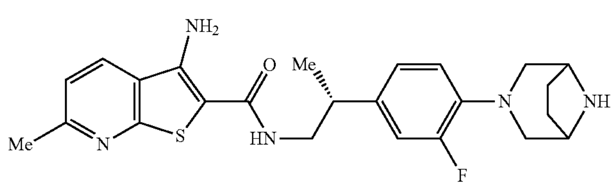 [SMILES: Cc1ccc2c(N)c(C(=O)NC[C@H](C)c3ccc(N4CC5CCC(C4)N5)c(F)c3)sc2n1] | 454 | (400 MHz, CD₃OD) δ 8.18 (d, J = 8.4 Hz, 1H), 7.29 (d, J = 8.4 Hz, 1H), 6.85-7.02 (m, 3H), 3.65 (s, 2H), 3.33-3.48 (m, 2H), 3.17-3.25 (m, 2H), 2.93-3.09 (m, 3H), 2.63 (s, 3H), 1.96-2.06 (m, 2H), 1.80-1.88 (m, 2H), 1.26 (d, J = 7.2 Hz, 3H) |

TABLE 16-continued

| Example (Cmpd no.) | Structure | MS (ESI, m/z) [M + H] | 1H NMR |
|---|---|---|---|
| 86-8A[7] (I-107) | 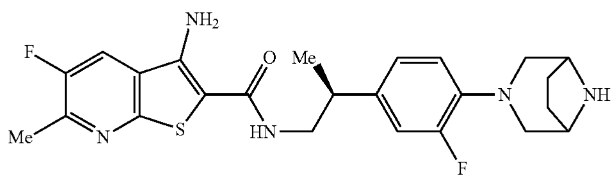 [SMILES: Cc1nc2sc(C(=O)NC[C@@H](C)c3ccc(N4CC5CCC(C4)N5)c(F)c3)c(N)c2cc1F] | 472 | (300 MHz, CD3OD) δ 7.97 (d, J = 9.9 Hz, 1H), 6.77-6.97 (m, 3H), 3.31-3.56 (m, 4H), 3.08-3.13 (m, 2H), 2.90-2.99 (m, 1H), 2.82-2.92 (m, 2H), 2.55 (d, J = 3.0 Hz, 3H), 1.85-2.04 (m, 2H), 1.70-1.78 (m, 2H), 1.22 (d, J = 7.2 Hz, 3H) |
| 86-8B[7] (I-108) | 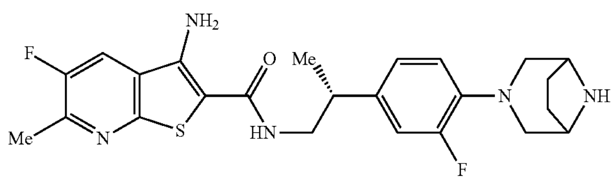 [SMILES: Cc1nc2sc(C(=O)NC[C@H](C)c3ccc(N4CC5CCC(C4)N5)c(F)c3)c(N)c2cc1F] | 472 | (300 MHz, CD3OD) δ 7.97 (d, J = 9.9 Hz, 1H), 6.77-6.97 (m, 3H), 3.31-3.56 (m, 4H), 3.08-3.13 (m, 2H), 2.90-2.99 (m, 1H), 2.82-2.92 (m, 2H), 2.55 (d, J = 3.0 Hz, 3H), 1.85-2.04 (m, 2H), 1.70-1.78 (m, 2H), 1.22 (d, J = 7.2 Hz, 3H) |
| 86-9A[8] (I-109) | 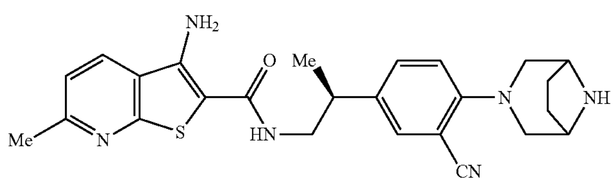 [SMILES: Cc1ccc2c(N)c(C(=O)NC[C@@H](C)c3ccc(N4CC5CCC(C4)N5)c(C#N)c3)sc2n1] | 461 | (400 MHz, CD3OD) δ 8.18 (d, J = 8.0 Hz, 1H), 7.43-7.65 (m, 2H), 7.23-7.45 (m, 1H), 7.07 (d, J = 8.8 Hz, 1H), 3.55-3.60 (m, 2H), 3.32-3.54 (m, 2H), 3.25-3.41 (m, 2H), 3.03-3.09 (m, 1H), 2.96-3.05 (m, 2H), 2.63 (s, 3H), 2.18 (d, J = 7.6 Hz, 2H), 1.79-1.95 (m, 2H), 1.28 (d, J = 6.8 Hz, 3H) |
| 86-9B[8] (I-110) | 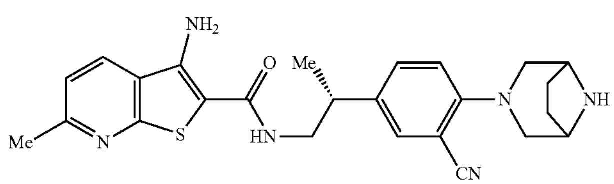 [SMILES: Cc1ccc2c(N)c(C(=O)NC[C@H](C)c3ccc(N4CC5CCC(C4)N5)c(C#N)c3)sc2n1] | 461 | (400 MHz, CD3OD) δ 8.18 (d, J = 8.4 Hz, 1H), 7.43-7.55 (m, 2H), 7.29 (d, J = 8.4 Hz, 1H), 7.06 (d, J = 8.8 Hz, 1H), 3.50-3.58 (m, 2H), 3.35-3.50 (m, 2H), 3.29-3.32 (m, 2H), 3.05-3.09 (m, 1H), 2.95-3.03 (m, 2H), 2.63 (s, 3H), 2.10-2.19 (m, 2H), 1.81-1.88 (m, 2H), 1.28 (d, J = 7.2 Hz, 3H) |
| 86-10A[9] (I-111) | 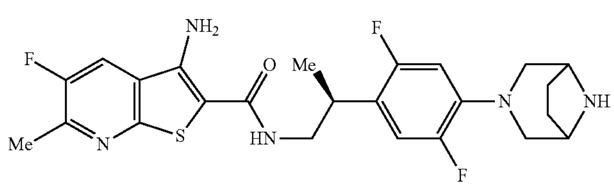 [SMILES: Cc1nc2sc(C(=O)NC[C@@H](C)c3cc(F)c(N4CC5CCC(C4)N5)cc3F)c(N)c2cc1F] | 490 | (400 MHz, CD3OD) δ 8.02 (d, J = 9.9 Hz, 1H), 6.97-7.02 (m, 1H), 6.61-6.66 (m, 1H), 3.51-3.60 (m, 2H), 3.33-3.53 (m, 3H), 3.19-3.28 (m, 2H), 2.85-2.92 (m, 2H), 2.59 (s, 3H), 1.98-2.06 (m, 2H), 1.80-1.87 (s, 2H), 1.21-1.29 (m, 3H) |

TABLE 16-continued

| Example (Cmpd no.) | Structure | MS (ESI, m/z) [M + H] | ¹H NMR |
|---|---|---|---|
| 86-10B[9] (I-112) | 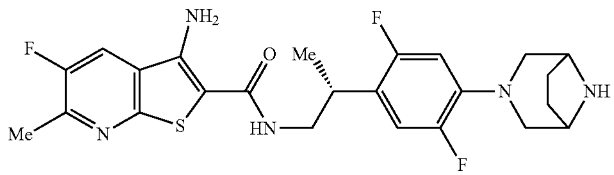 [SMILES: Cc1nc2sc(C(=O)NC[C@H](C)c3cc(F)c(N4CC5CCC(C4)N5)cc3F)c(N)c2cc1F] | 490 | (400 MHz, CD₃OD) δ 8.02 (d, J = 9.9 Hz, 1H), 6.97-7.02 (m, 1H), 6.61-6.66 (m, 1H), 3.51-3.60 (m, 2H), 3.33-3.53 (m, 3H), 3.19-3.28 (m, 2H), 2.85-2.92 (m, 2H), 2.59 (s, 3H), 1.98-2.06 (m, 2H), 1.80-1.87 (s, 2H), 1.21-1.29 (m, 3H) |
| 86-11A[10] (I-202) | ·HCl | 410 | (300 MHz, DMSO + D₂O) δ 8.31 (d, J = 8.4 Hz, 1H), 7.33 (d, J = 8.1, 1H), 7.16-7.13 (m, 2H), 6.95-6.92 (m, 2H), 3.35-3.30 (m, 10H), 2.97-2.89 (m, 1H), 2.58 (s, 3H), 1.16 (d, J = 6.9 Hz, 3H) |
| 86-11B[10] (I-203) | ·HCl | 410 | (300 MHz, DMSO + D₂O) δ 8.11 (d, J = 8.4, Hz, 1H), 7.18-7.23 (m, 3H), 7.02-6.99 (m, 2H), 3.34-3.23 (m, 10H), 2.97-2.89 (m, 1H), 2.53 (s, 3H), 1.17 (d, J = 6.9 Hz, 3H) |
| 86-12A (I-207)[11] | 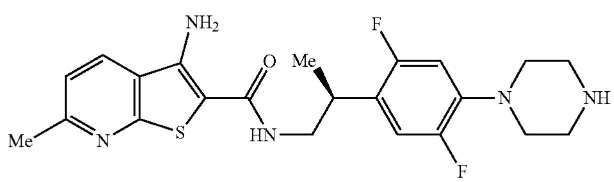 [SMILES: Cc1ccc2c(N)c(C(=O)NC[C@@H](C)c3cc(F)c(N4CCNCC4)cc3F)sc2n1] | 446 | (400 MHz, CD₃OD) δ 8.19 (d, J = 8.0 Hz, 1H), 7.30 (d, J = 8.4 Hz, 1H), 7.02-7.10 (m, 1H), 6.72-6.78 (m, 1H), 3.34-3.58 (m, 3H), 2.98-3.13 (m, 8H), 2.65 (s, 3H), 1.29 (d, J = 6.8 Hz, 3H) |
| 86-12B (I-208)[11] | 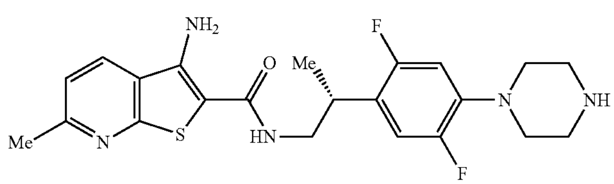 [SMILES: Cc1ccc2c(N)c(C(=O)NC[C@H](C)c3cc(F)c(N4CCNCC4)cc3F)sc2n1] | 446 | (400 MHz, CD₃OD) δ 8.19 (d, J = 8.4 Hz, 1H), 7.31 (d, J = 8.4 Hz, 1H), 7.03-7.08 (m, 1H), 6.72-6.78 (m, 1H), 3.36-3.55 (m, 3H), 2.97-3.05 (m, 8H), 2.65 (s, 3H), 1.29 (d, J = 7.2 Hz, 3H) |

[1]Notes: Step 2 was conducted with 4 N HCl/dioxane. Chiral HPLC conditions for Step 1: SHIMADZU LC-20AD, LC parameters: Pump Mode: Binary gradient, Start Conc. of Pump B: 50.0%, Total Flow: 1.0 mL/min, Phase A: n-Hexane (containing 0.1% DEA), Phase B: Ethanol, Column Name: DAICEL CHIRALPAK OD-3, Length: 50 mm, Internal Diameter: 4.6 mm, Particle Size: 3 μm, Column Temp: 25° C., PDA Model: SPD-M20A, UV Wavelength: from 190 nm to 500 nm. This afforded the title compounds as follows: Step 1, Enantiomer A: 1ˢᵗ eluting peak (retention time = 1.94 min, 30 mg, 40%) as a yellow solid. LCMS (ES, m/z): 558 [M + H]⁺. Step 1, Enantiomer B: 2ⁿᵈ eluting peak (retention time = 3.56 min, 30 mg, 40%) as a yellow solid. LCMS (ES, m/z): 558 [M + H]⁺. Examples 86-2A (I-95) and 86-2B (I-96) were isolated as their HCl salts by direct filtration and washing with diethyl ether.
[2]Notes: Step 2 was conducted with TFA/DCM. Chiral HPLC conditions for Step 1: SHIMADZU LC-20AD, LC parameters: Pump Mode: Binary gradient, Start Conc. of Pump B: 100.0%, Total Flow: 20 mL/min, Phase A: MTBE, Phase B: Methanol, Column Name: (R,R)-WHELK-O1-Kromasil, Length: 25 mm, Internal Diameter: 5 cm, Particle Size: 5 um, Column Temp: 20° C., PDA Model: SPD-M20A, Wavelength: from 190 nm to 500 nm. Step 1, Enantiomer A: 1ˢᵗ eluting peak (retention time = 15.2 min, 40 mg, 12%) as a white solid. LCMS (ESI, m/z): 572 [M + H]⁺. Step 1, Enantiomer B: 2ⁿᵈ eluting peak (retention time = 22.3 min, 40 mg, 12%) as a white solid. LCMS (ESI, m/z): 572 [M + H]⁺. Prep HPLC Purification Method for Step 2: SHIMADZU LC-20AD, LC parameters: Pump Mode: Binary gradient, Start Conc. of Pump B: 20.0%, End Conc. of Pump B: 50.0% Total Flow: 20 mL/min, Time: 8 min, Phase A: Water (10 mmol/L NH₄HCO₃), Phase B: MeCN-HPLC, Column Name: XBridge Prep C18 OBD Column, Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm.
[3]Notes: Step 2 was conducted with TFA/DCM. Chiral HPLC conditions for Step 1: SHIMADZU LC-20AD, LC parameters: Pump Mode: Binary gradient, Start Conc. of Pump B: 35%, Total Flow: 20 mL/min, Phase A: Hexane-HPLC, Phase B: EtOH-HPLC, Column Name: DAICEL CHIRALPAK IC, Length: 250 mm, Internal Diameter: 20 mm, Particle Size: 5 um, Column Temp: 20° C., PDA Model: SPD-M20A, Wavelength: from 190 nm to 500 nm. Step 1, Enantiomer A: 1ˢᵗ eluting peak (retention time = 9.20 min, 40 mg, 21%) as a yellow solid. LCMS (ESI, m/z): 564 [M + H]⁺. Step 1, Enantiomer B: 2ⁿᵈ eluting peak (retention time = 11.3 min, 40 mg, 21%) as a yellow solid. LCMS (ESI, m/z): 564 [M + H]⁺. Prep HPLC Method for Step 2: SHIMADZU LC-20AD, LC parameters: Pump Mode: Binary gradient, Start Conc. of Pump B: 5.0%, End Conc. of Pump B: 77.0%, Total Flow: 20 mL/min, Time: 7 min, Phase A: Water (10 mmol/L NH₄HCO₃), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm TABLE 16-continued

| Example (Cmpd no.) | Structure | MS (ESI, m/z) [M + H] | 1H NMR |
|---|---|---|---|

[4]Notes: Step 1 was conducted at RT. Step 2 was conducted with TFA/DCM. Chiral HPLC conditions for Step 1: SHIMADZU LC-20AD, LC parameters: Pump Mode: Binary gradient, Start Conc. of Pump B: 50.0%, Total Flow: 20 mL/min, Phase A: Hexane (0.1% DEA), Phase B: Ethanol-HPLC, Column Name: (R,R)-WHELK-O1-Kromasil, Length: 250 mm, Internal Diameter: 50 mm, Particle Size: 5 um, Column Temp: 20° C., PDA Model: SPD-M20A, Wavelength: from 190 nm to 500 nm. Step 1, Enantiomer A: 1st eluting peak (retention time = 6.3 min, 45 mg, 15%) as a white solid. LCMS (ESI, m/z): 576 [M + H]+. Step 1, Enantiomer B: 2nd eluting peak (retention time = 8.3 min, 45 mg, 15%) as a white solid. LCMS (ESI, m/z): 576 [M + H]+. Prep HPLC Method for Step 2: SHIMADZU LC-20AD, LC parameters: Pump Mode: Binary gradient, Start Conc. of Pump B: 35.0%, End Conc. of Pump B: 45.0% Total Flow: 20 mL/min, Time: 8 min, Phase A: Water (10 mmol/L NH4HCO3), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

[5]Notes: Step 2 was conducted with TFA/DCM. Chiral HPLC conditions for Step 1: SHIMADZU LC-20AD, LC parameters: Pump Mode: Binary gradient, Start Conc. of Pump B: 50%, Total Flow: 15 mL/min, Phase A: Hexane (0.1% DEA), Phase B: EtOH-HPLC, Column Name: DACEL CHIRALPAK AD-H SFC, Length: 25 cm, Internal Diameter: 5 cm, Particle Size: 5 μm, Column Temp: 20° C., PDA Model: SPD-M20A, Wavelength: from 190 nm to 500 nm. Step 1, Enantiomer A: 1st eluting peak (retention time = 11.2 min, 40 mg, 53%) as a yellow solid. LCMS (ESI, m/z): 554 [M + H]+. Step 1, Enantiomer B: 2nd eluting peak (retention time = 14.0 min, 30 mg, 40%) as a yellow solid. LCMS (ESI, m/z): 554 [M + H]+. Prep HPLC Method for Step 2: SHIMADZU LC-20AD, LC parameters: Pump Mode: Binary gradient, Start Conc. of Pump B: 12.0%, End Conc. of Pump B: 42.0% Total Flow: 20 mL/min, Time: 7 min, Phase A: Water (10 mmol/L NH4HCO3), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

[6]Notes: Step 1 was conducted at RT. Step 2 was conducted with TFA/DCM. Chiral HPLC conditions for Step 1: SHIMADZU LC-20AD, LC parameters: Pump Mode: Binary gradient, Start Conc. of Pump B: 30.0%, Total Flow: 20 mL/min, Phase A Hexane (0.1% DEA), Phase B: Ethanol-HPLC, Column Name: DAICEL CHIRALPAK AD-H-SL001, Length: 250 mm, Internal Diameter: 20 mm, Particle Size: 5 μm, Column Temp: 20° C., PDA Model: SPD-M20A, Wavelength: from 190 nm to 500 nm. Step 1, Enantiomer A: 1st eluting peak (retention time = 11.2 min, 40 mg, 22%) as a yellow oil. LCMS (ESI m/z): 554 [M + H]+. Step 1, Enantiomer B: 2nd eluting peak (retention time = 14.8 min, 30 mg, 16%) as a yellow oil. LCMS (ESI, m/z): 554 [M + H]+. Prep HPLC Method for Step 2: SHIMADZU LC-20AD, LC parameters: Pump Mode: Binary gradient, Start Conc. of Pump B: 25.0%, End Conc. of Pump B: 65.0% Total Flow: 20 mL/min, Time: 7 min, Phase A: Water (10 mmol/L NH4HCO3), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

[7]Notes: Step 2 was conducted with TFA/DCM. Chiral HPLC conditions for Step 1: SHIMADZU LC-20AD, LC parameters: Pump Mode: Binary gradient, Start Conc. of Pump B: 30.0%, Total Flow: 20 mL/min, Phase A Hexane (0.1% DEA), Phase B: IPA-HPLC, Column Name: DAICEL CHIRALPAK-AD-H-SL001, Length: 250 mm, Internal Diameter: 20 mm, Particle Size: 5 μm, Column Temp: 20° C., PDA Model: SPD-M20A, Wavelength: from 190 nm to 500 nm. Step 1, Enantiomer A: 1st eluting peak (retention time = 8.2 min, 40 mg, 21%) as a yellow solid. LCMS (ESI m/z): 572 [M + H]+. Step 1, Enantiomer B: 2nd eluting peak (retention time = 12.0 min, 40 mg, 21%) as a yellow solid. LCMS (ESI, m/z): 572 [M + H]+. Prep HPLC Method for Step 2: SHIMADZU LC-20AD, LC parameters: Pump Mode: Binary gradient, Start Conc. of Pump B: 5.0%, End Conc. of Pump B: 69.0% Total Flow: 20 mL/min, Time: 8 min, Phase A: Water (10 mmol/L NH4HCO3), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

[8]Notes: Step 2 was conducted with TFA/DCM. Chiral HPLC conditions for Step 1: SHIMADZU LC-20AD, LC parameters: Pump Mode: Binary gradient, Start Conc. of Pump B: 50.0%, Total Flow: 20 mL/min, Phase A: Hexane-HPLC, Phase B: IPA-HPLC, Column Name: Repaired DAICEL CHIRALPAK IA, Length: 250 mm, Internal Diameter: 21.2 mm, Particle Size: 5 μm, Column Temp: 20° C., PDA Model: SPD-M20A, Wavelength: from 190 nm to 500 nm. Step 1, Enantiomer A: 1st eluting peak (retention time = 11.8 min, 30 mg, 25%) as a yellow oil. LCMS (ESI, m/z): 561 [M + H]+. Step 1, Enantiomer B: 2nd eluting peak (retention time = 15.6 min, 30 mg, 25%) as a yellow oil. LCMS (ESI, m/z): 561 [M + H]+. Prep HPLC Method for Step 2: SHIMADZU LC-20AD, LC parameters: Pump Mode: Binary gradient, Start Conc. of Pump B: 35.0%, End Conc. of Pump B: 52.0% Total Flow: 20 mL/min, Time: 7 min, Phase A: Water (10 mmol/L NH4HCO3), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

[9]Notes: Step 2 was conducted with TFA/DCM. Chiral HPLC conditions for Step 1: SHIMADZU LC-20AD, LC parameters: Pump Mode: Binary gradient, Start Conc. of Pump B: 30%, Total Flow: 20 mL/min, Phase A: Hexane (0.1% DEA), Phase B: EtOH-HPLC, Column Name: (R,R)-WHELK-O1-Kromasil, Length: 25 cm, Internal Diameter: 5 cm, Particle Size: 5 um, Column Temp: 20° C., PDA Model: SPD-M20A, Wavelength: from 190 nm to 500 nm. Step 1, Enantiomer A: 1st eluting peak (retention time = 13.3 min, 60 mg, 80%) as a yellow oil. LCMS (ESI, m/z): 590 [M + H]+. Step 1, Enantiomer B: 2nd eluting peak (retention time = 15.6 min, 50 mg, 67%) as a yellow oil. LCMS (ESI, m/z): 590 [M + H]+. Prep HPLC Method for Step 2: SHIMADZU LC-20AD, LC parameters: Pump Mode: Binary gradient, Start Conc. of Pump B: 18.0%, End Conc. of Pump B: 38.0% Total Flow: 20 mL/min, Time: 8 min, Phase A: Water (10 mmol/L NH4HCO3), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm.

[10]Notes: HATU with DIEA in DMF was used for Step 1. Step 2 was conducted with TFA/DCM. Chiral HPLC conditions for Step 1: SHIMADZU LC-20AD, LC parameters: Pump Mode: Binary gradient, Start Conc. of Pump B: 10.0%, Total Flow: 1.0 mL/min, Phase A: ACN (0.1% DEA), Phase B: Methanol, Column Name: DAICEL CHIRALPAK AD-3, Length: 50 mm, Internal Diameter: 4.6 mm, Particle Size: 3 μm, Column Temp: 25° C., PDA Model: SPD-M20A, Wavelength: from 190 nm to 500 nm. Step 1, Enantiomer A: 1st eluting peak (retention time = 1.5 min, 50 mg, 77%) as a yellow solid. LCMS (ESI, m/z): 510 [M + H]+. Step 1, Enantiomer B: 2nd eluting peak (retention time = 2.3 min, 51 mg, 78%) as a yellow solid. LCMS (ESI, m/z): 510 [M + H]+. Isolation method: The title compounds were isolated directly after Step 2 by trituration with diethyl ether and collection by vacuum filtration.

[11]Notes: Step 2 was conducted with TFA/DCM. Chiral HPLC conditions for Step 1: Prep STC350-1, LC parameters: Pump Mode: Binary gradient, Start Conc. of Pump B: 50%, Total Flow: 150 mL/min, Phase A: CO2, Phase B: Methanol, Column Name: DAICEL CHIRALPAK AD-H, Length: 250 mm, Internal Diameter: 50 mm, Particle Size: 5 μm, Column Temp: 20° C., PDA Model: UV, Wavelength: 270 nm, Step 1, Enantiomer A: 1st eluting peak (retention time = 6.8 min, 300 mg, 65%) as a yellow oil. LCMS (ESI, m/z): 546 [M + H]+. Step 1, Enantiomer B: 2nd eluting peak (retention time = 12.6 min, 300 mg, 65%) as a yellow solid. LCMS (ESI, m/z): 546 [M + H]+. HPLC Purification conditions: Waters, LC parameters: Pump Mode: Binary gradient, Start Conc. of Pump B: 18.0%, End Conc. of Pump B: 38.0% Total Flow: 20 mL/min, Time: 8 min, Phase A: Water (10 mmol/L NH4HCO3), Phase B: MeCN-HPLC, Column Name: XBridge Prep C18 OBD Column, Length: 150 mm, Internal Diameter: 19 mm, Particle Size: 5 um, Aperture Size: 130 Å, Column Temp: 25° C., PDA Model: SPD-M20A, Wavelength: from 190 nm to 500 nm.

Example 87 (I-113)

3-Amino-N-(2,5-difluoro-4-(piperidin-4-yl)phenethyl)-6-methylthieno[2,3-b]pyridine-2-carboxamide

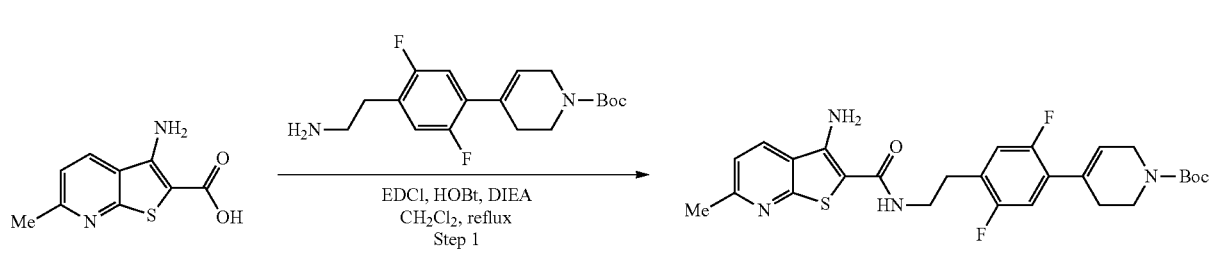

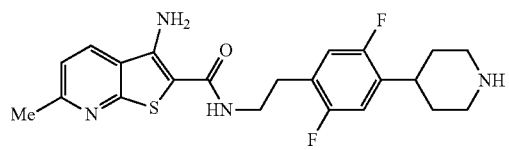

Example 87 (I-113)

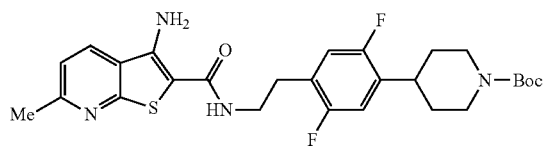

-continued

TFA/DCM
Step 3

Step 1. tert-Butyl 4-(4-(2-(3-amino-6-methylthieno[2,3-b]pyridine-2-carboxamido)ethyl)-2,5-difluorophenyl)-3,6-dihydropyridine-1(2H)-carboxylate Into a 100-mL round-bottom flask was added tert-butyl 4-[4-(2-aminoethyl)-2,5-difluorophenyl]-1,2,3,6-tetrahydropyridine-1-carboxylate (0.20 g, 0.59 mmol), 3-amino-6-methylthieno[2,3-b]pyridine-2-carboxylic acid (0.148 g, 0.710 mmol), dichloromethane (10 mL), HOBt (0.120 g, 0.78 mmol), DIEA (0.300 g, 2.3 mmol), and EDCI (0.171 g, 0.89 mmol). The resulting solution was stirred overnight at 40° C. and then cooled and concentrated in vacuo to provide a crude product that was purified via silica gel chromatography and eluted with dichloromethane/methanol (20:1) to afford tert-butyl 4-(4-(2-(3-amino-6-methylthieno[2,3-b]pyridine-2-carboxamido)ethyl)-2,5-difluorophenyl)-3,6-dihydropyridine-1(2H)-carboxylate as yellow oil (70 mg, 22%). LCMS (ES, m/z): 529 [M+H]+.

Step 2. tert-Butyl 4-(4-(2-(3-amino-6-methylthieno[2,3-b]pyridine-2-carboxamido)ethyl)-2,5-difluorophenyl)piperidine-1-carboxylate Into a 50-mL round-bottom flask that was purged and maintained under an atmosphere of nitrogen was added tert-butyl 4-(4-(2-(3-amino-6-methylthieno[2,3-b]pyridine-2-carboxamido)ethyl)-2,5-difluorophenyl)-3,6-dihydropyridine-1(2H)-carboxylate (0.070 g, 0.13 mmol), methanol (10 mL), 20% Pd(OH)$_2$/C (0.010 g, 0.21 mmol). The resulting mixture was sparged with hydrogen (balloon) and then stirred overnight at 40° C. under hydrogen (balloon). The solids were removed by filtration over Celite, and the filtrate was concentrated in vacuo to afford tert-butyl 4-(4-(2-(3-amino-6-methylthieno[2,3-b]pyridine-2-carboxamido)ethyl)-2,5-difluorophenyl)piperidine-1-carboxylate as a brown solid (60 mg, 85%). LCMS (ESI, m/z): 531 [M+H]+.

Step 3. 3-Amino-N-(2,5-difluoro-4-(piperidin-4-yl)phenethyl)-6-methylthieno[2,3-b]pyridine-2-carboxamide Into a 50-mL round-bottom flask was added tert-butyl 4-(4-(2-(3-amino-6-methylthieno[2,3-b]pyridine-2-carboxamido)ethyl)-2,5-difluorophenyl)piperidine-1-carboxylate (0.060 g, 0.11 mmol) and dichloromethane (4 mL). Trifluoroacetic acid (0.7 mL) was added and the resulting solution was stirred for 3 h at RT. The reaction mixture was concentrated in vacuo to provide a crude product that was purified by Prep-HPLC using the following conditions: Column, X Bridge C18, 19*150 mm, 5 um; mobile phase, A: water (containing 0.1% formic acid) and B: CH$_3$CN (20% to 60% over 3 min; and then 60% to 80% over 8 min); UV Detector: 254 nm. The purified product was then dissolved in small amount of MeOH and passed through a pre-packed cartridge (agilent, PL-HCO$_3$ MP SPE 100 mg/6 mL) to remove formic acid to afford the title compound as a light yellow solid (10.4 mg, 21%). LCMS (ESI, m/z): 431 [M+H]+. $^1$H-NMR (300 MHz, CD$_3$OD) δ ppm 8.20 (d, J=8.4 Hz, 1H), 7.31 (d, J=8.4 Hz, 1H), 7.01-6.96 (m, 2H), 3.61-3.51 (m, 2H), 3.27-3.11 (m, 2H), 3.08-2.74 (m, 5H), 2.65 (s, 3H), 1.90-1.60 (m, 4H).

Example 88 (I-114)

3-Amino-6-cyclopropyl-N-(4-(piperazin-1-yl)phenethyl)thieno[2,3-b]pyridine-2-carboxamide

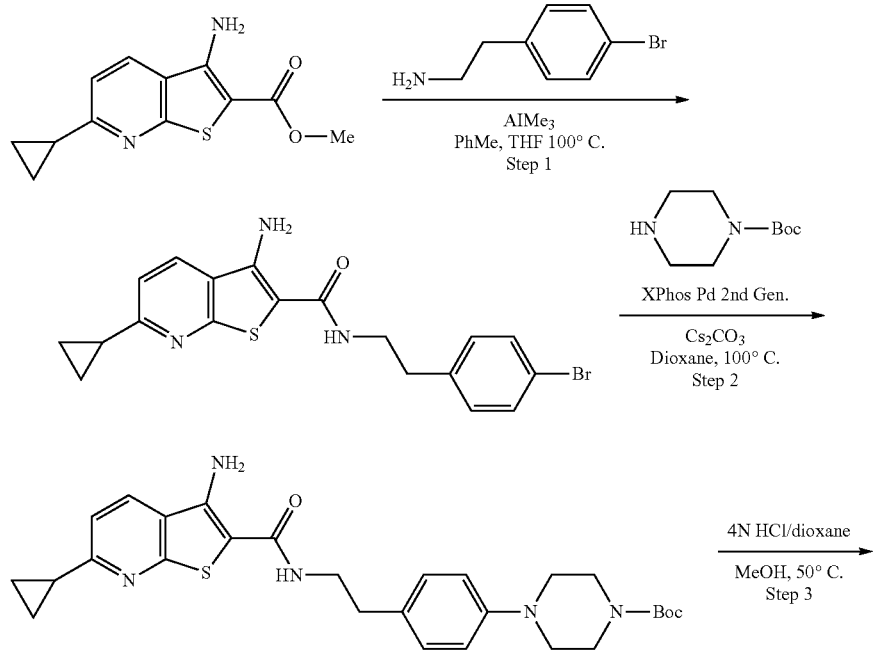

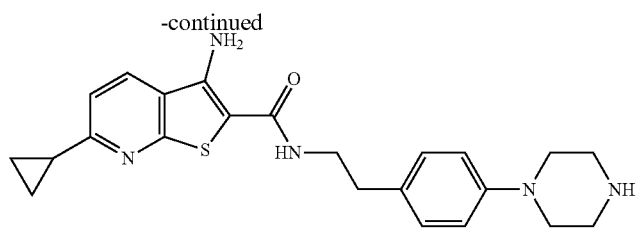

Example 88 (I-114)

Step 1. 3-Amino-N-(4-bromophenethyl)-6-cyclopropylthieno[2,3-b]pyridine-2-carboxamide Into an 8 mL reaction vial was added methyl 3-amino-6-cyclopropylthieno[2,3-b]pyridine-2-carboxylate (0.100 g, 0.403 mmol) and 2-(4-bromophenyl)ethanamine (0.121 g, 0.604 mmol) followed by a mixture of toluene/THF (10:1; 2.2 mL). A solution of trimethylaluminum (2 M in toluene; 0.604 mL, 1.21 mmol) was added and the reaction mixture was heated to 80° C. overnight. The reaction was quenched with a saturated solution of NaHCO$_3$ (2 mL), heated at 50° C. for 30 minutes, and then extracted with ethyl acetate (2×3 mL). The combined organic layers were washed with brine (3 mL), dried over anhydrous sodium sulfate, filtered, and concentrated in vacuo to provide a crude product that was suspended in ethyl acetate (2 mL) and sonicated for 15 minutes. The resulting white precipitate was filtered, washed with ethyl acetate (3 mL), and dried in vacuo overnight to afford 3-amino-N-(4-bromophenethyl)-6-cyclopropylthieno[2,3-b]pyridine-2-carboxamide (139 mg, 83% yield). LCMS (ESI, m/z): 416 [M+H]$^+$.

Step 2. tert-Butyl 4-(4-(2-(3-amino-6-cyclopropylthieno[2,3-b]pyridine-2-carboxamido) ethyl)phenyl)piperazine-1-carboxylate Into a 2 mL reaction vial was added 3-amino-N-(4-bromophenethyl)-6-cyclopropylthieno[2,3-b]pyridine-2-carboxamide (0.013 g, 0.030 mmol), tert-butyl piperazine-1-carboxylate (0.011 g, 0.060 mmol), cesium carbonate (0.039 g, 0.12 mmol), XPhos Precatalyst 2nd Generation (0.006 g, 7.50 µmol, and dioxane (0.4 mL). The vial was flushed with nitrogen, sealed and heated overnight at 100° C. on a heater shaker. The reaction mixture was diluted with ethyl acetate (0.5 mL) and washed with saturated aqueous NaHCO$_3$ solution (0.5 mL). The organic layer was concentrated under a stream of nitrogen to afford crude tert-butyl 4-(4-(2-(3-amino-6-cyclopropylthieno[2,3-b]pyridine-2-carboxamido)ethyl)phenyl)piperazine-1-carboxylate. The material was used without further purification.

Step 3. 3-Amino-6-cyclopropyl-N-(4-(piperazin-1-yl)phenethyl)thieno[2,3-b]pyridine-2-carboxamide Crude tert-butyl 4-(4-(2-(3-amino-6-cyclopropylthieno[2,3-b]pyridine-2-carboxamido)ethyl)phenyl)piperazine-1-carboxylate was taken up into MeOH/dioxane (1:1; 300 µL) and 4 N HCl in dioxane (100 µL). The reaction was heated for 1 hour at 50° C., concentrated to a crude material that was dissolved in methanol (1 mL) and purified via SCX (500 mg) column chromatography. The impurities were eluted with methanol (3 mL) and the product was then eluted with a mixture of hexanes/EtOAc/Et$_3$N (10:1:0.5; 3 mL). The crude product was purified by mass triggered preparatory HPLC to afford the title compound (0.5 mg, 4% yield). LCMS (ESI, m/z): 422 [M+H]$^+$.

Example 89 (I-115)

3,6-Diamino-5-fluoro-N-(4-(piperazin-1-yl)phenethyl)thieno[2,3-b]pyridine-2-carboxamide

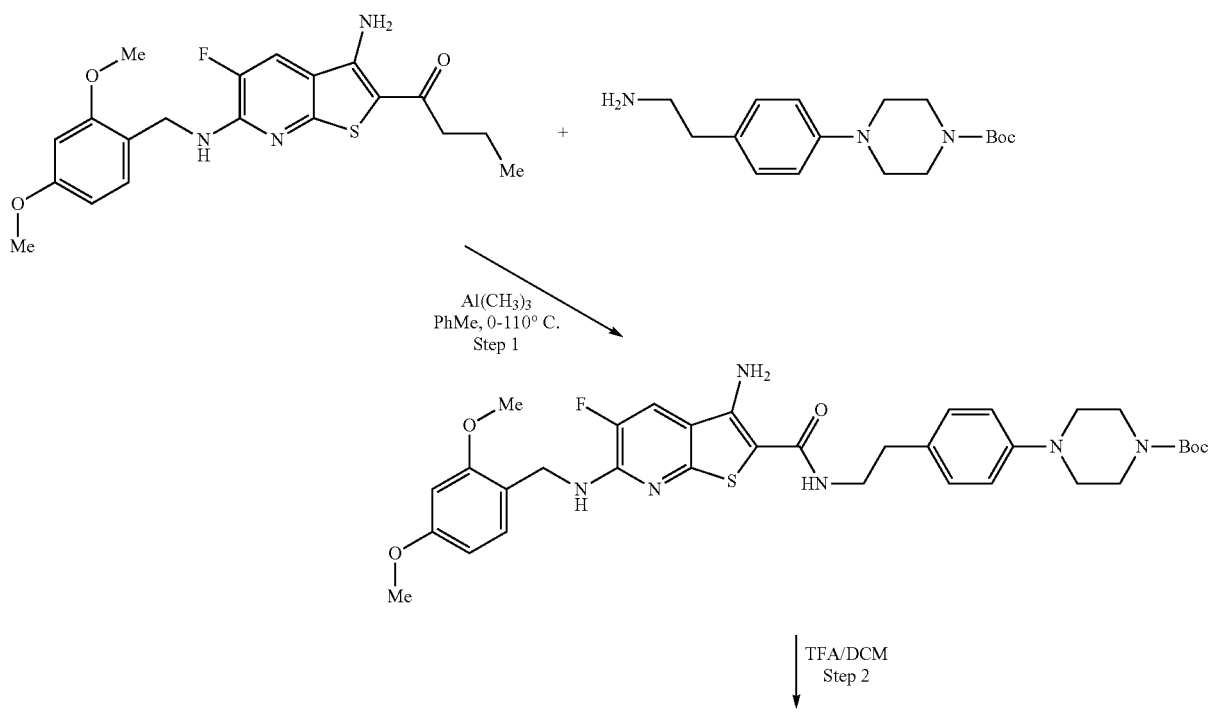

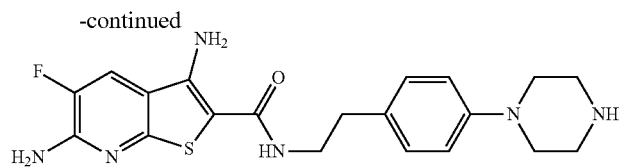

Example 89 (I-115)

Step 1. tert-Butyl 4-(4-(2-(3-amino-6-((2,4-dimethoxybenzyl)amino)-5-fluorothieno[2,3-b]pyridine-2-carboxamido)ethyl)phenyl)piperazine-1-carboxylate Into a 100-mL 3-necked round-bottom flask, purged and maintained under an inert atmosphere of nitrogen, was added ethyl 3-amino-6-[[(2,4-dimethoxyphenyl)methyl]amino]-5-fluorothieno[2,3-b]pyridine-2-carboxylate (0.300 g, 0.74 mmol), tert-butyl 4-(4-(2-aminoethyl)phenyl)piperazine-1-carboxylate (0.271 g, 0.89 mmol), and toluene (20 mL). The reaction mixture was cooled to 0° C. and a solution of trimethylaluminum in heptane (1 M, 11.1 mL, 11.1 mmol) was added dropwise with stirring. The resulting solution was stirred overnight at 110° C. and then cooled and quenched by addition of MeOH (50 mL). The solids were removed by filtration and the filtrate was concentrated in vacuo. The resulting crude product was purified by FCC eluting with ethyl acetate/petroleum ether (1:2) to afford tert-butyl 4-(4-(2-(3-amino-6-((2,4-dimethoxybenzyl)amino)-5-fluorothieno[2,3-b]pyridine-2-carboxamido)ethyl) phenyl)piperazine-1-carboxylate as a yellow oil (120 mg, 24%). LCMS (ESI, m/z): 665 [M+H]$^+$.

Step 2. 3,6-Diamino-5-fluoro-N-(4-(piperazin-1-yl)phenethyl)thieno[2,3-b]pyridine-2-carboxamide Into a 25-mL round-bottom flask was added tert-butyl 4-(4-(2-(3-amino-6-((2,4-dimethoxybenzyl)amino)-5-fluorothieno[2,3-b]pyridine-2-carboxamido)ethyl)phenyl)piperazine -1-carboxylate (0.100 g, 0.15 mmol) and dichloromethane (5 mL) followed by trifluoroacetic acid (3 mL) and the resulting solution was stirred for 2 h at RT. The reaction mixture was then concentrated in vacuo to provide a crude product that was purified by Prep-HPLC using the following conditions (Waters I): Column, Xbridge Prep C18 OBD column, 5 μm, 19*150 mm; mobile phase, A: water (containing 10 mM NH$_3$HCO$_3$+0.05% NH$_4$OH) and B: CH$_3$CN (10% to 45% over 5 min and then 45% to 75% over 5 min); UV Detector: 254 nm. This afforded the title compound as a white solid (28 mg, 45%). LCMS (ESI, m/z): 415 [M+H]$^+$; $^1$H-NMR (300 MHz, DMSO-d$_6$) δ ppm 7.96 (d, J=11.8 Hz, 1H), 7.43-7.33 (m, 1H), 7.09-7.01 (m, 2H), 7.00-6.70 (m, 6H), 3.33-3.26 (m, 2H), 3.07-2.94 (m, 4H), 2.92-2.77 (m, 4H), 2.74-2.60 (m, 2H).

Example 90-1 (I-116)

3-Amino-N-(4-(5,6-dihydroimidazo[1,2-a]pyrazin-7(8H)-yl)phenethyl)-6-methylthieno[2,3-b]pyridine-2-carboxamide

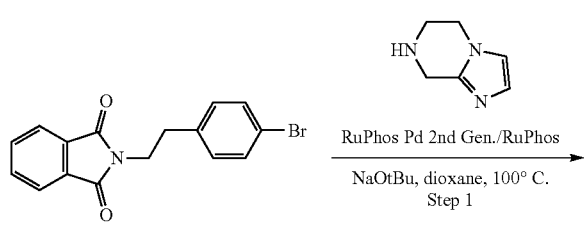

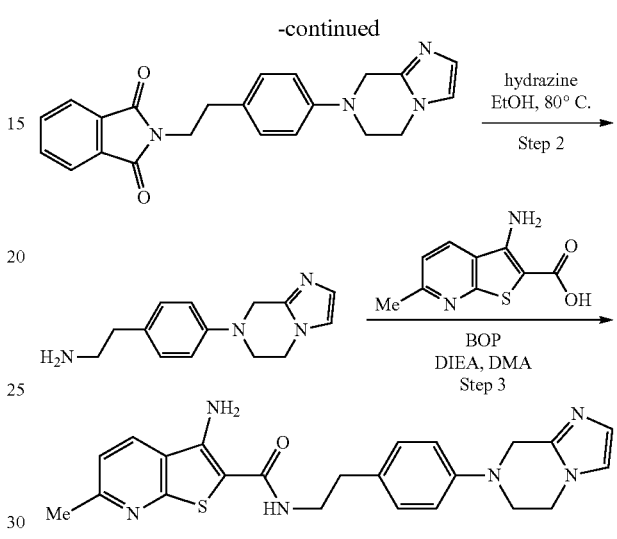

Example 90-1 (I-116)

Step 1. 2-(4-(5,6-Dihydroimidazo[1,2-a]pyrazin-7(8H)-yl)phenethyl)isoindoline-1,3-dione To a solution of 2-(4-bromophenethyl)isoindoline-1,3-dione (prepared according to the procedure described in Francis et al.: Journal of Medicinal Chemistry (1991), 34(8), 2570-2579; 0.2 M in anhydrous 1,4-dioxane; 150 μL, 30 μmol), was added 5,6,7,8-tetrahydroimidazo[1,2-a]pyrazine (0.2 M in anhydrous 1,4-dioxane; 180 μL, 36 μmol), RuPhos solution (0.02 M in anhydrous 1,4-dioxane/EtOAc; 75 μL, 1.5 μmol), RuPhos-Pd 2$^{nd}$ generation catalyst (0.02 M in anhydrous 1,4-dioxane, 75 μL, 1.5 μmol) and sodium tert-butoxide (2 M in THF; 150 μL, 300 μmol). The resulting mixture was heated at 100° C. overnight. The reaction mixture was cooled to RT and used directly in Step 2 without further workup or isolation.

Step 2. 2-(4-(5,6-Dihydroimidazo[1,2-a]pyrazin-7(8H)-yl)phenyl)ethan-1-amine

To the reaction mixture from Step 1 was added hydrazine solution (2 M in ethanol, 150 μL, 300 μmol). The resulting mixture was heated to 80° C. overnight, brine (0.5 mL) was added, and the resulting mixture was extracted with ethyl acetate (2×0.5 mL). The combined organic layers were concentrated in vacuo to provide a crude product that was carried on without further purification.

Step 3. 3-Amino-N-(4-(5,6-dihydroimidazo[1,2-a]pyrazin-7(8H)-yl)phenethyl)-6-methylthieno[2,3-b]pyridine-2-carboxamide The crude product from Step 2 was dissolved in a solution of 10% DIEA in DMA (250 μL). 3-Amino-6-methylthieno[2,3-b]pyridine-2-carboxylic acid (0.2 M in DMA with 5% DIEA; 150 μL, 30 μmol) and ((1H-benzo[d][1,2,3]triazol-1-yl)oxy)tris(dimethylamino) phosphonium hexafluorophosphate(V) solution (BOP reagent, 0.2 M in acetonitrile, 180 μL, 36 μmol) were then added and the resulting mixture was placed on shaker at RT for 2 h. Brine (0.5 mL) was added and the mixture was extracted with ethyl acetate (2×0.5 mL). The combined organic layers were concentrated in vacuo to provide a crude product that was purified by HPLC: Waters Autopurification MS-directed HPLC prep fraction collection using the following conditions: Column: Waters XBridge OBD C18, 5 μm, 19×50 mm; flow rate 20 ml/min; mobile phase, A: water with 0.1% ammonium hydroxide and B: methanol with 0.1% ammonium hydroxide using the following gradient: 0 to 2 mins (15% B), 2 to 6 mins (15-100% B); Detector ZQ Mass Detector in electrospray ionization mode. This afforded the title compound (5 mg, 37%). LCMS (ESI m/z): 433 [M+H]$^+$.

The Examples in Table 17 below were synthesized according to the procedures outlined above for Example 90-1 (I-116), using the appropriate synthetic precursors.

TABLE 17

| Example (Cmpd no.) | Structure | MS (ESI, m/z) [M + H] |
|---|---|---|
| 90-2 (I-117) | 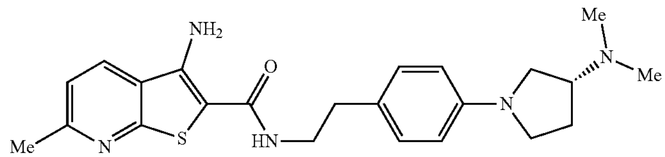 [SMILES: Cc1ccc2c(N)c(C(=O)NCCc3ccc(N4CC[C@@H](N(C)C)C4)cc3)sc2n1] | 424 |
| 90-3 (I-118) | 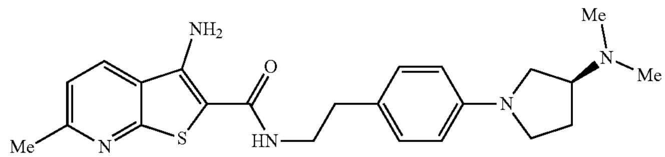 [SMILES: Cc1ccc2c(N)c(C(=O)NCCc3ccc(N4CC[C@H](N(C)C)C4)cc3)sc2n1] | 424 |
| 90-4 (I-119) | 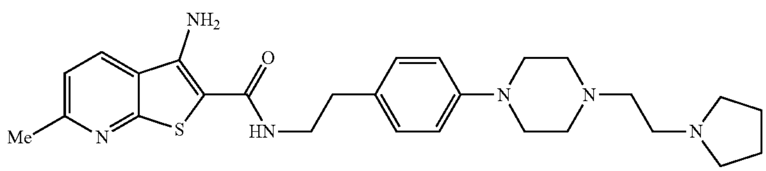 [SMILES: Cc1ccc2c(N)c(C(=O)NCCc3ccc(N4CCN(CCN5CCCC5)CC4)cc3)sc2n1] | 493 |
| 90-5 (I-120) | 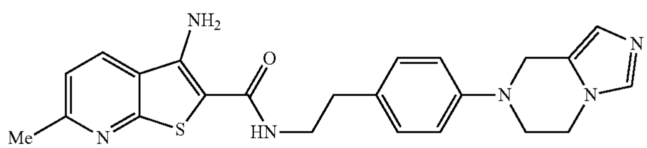 [SMILES: Cc1ccc2c(N)c(C(=O)NCCc3ccc(N4CCn5cncc5C4)cc3)sc2n1] | 433 |

Example 91-1 (I-121)

(S)-3-amino-6-methyl-N-(4-(3-methylpiperazin-1-yl)phenethyl)thieno[2,3-b]pyridine-2-carboxamide

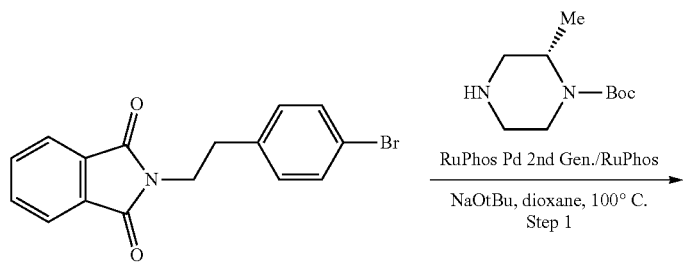

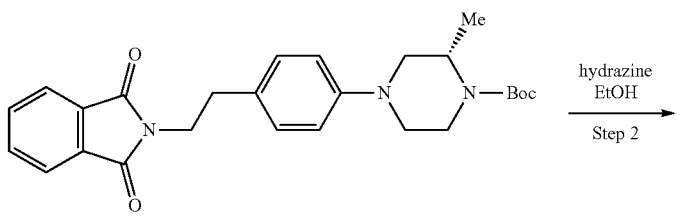

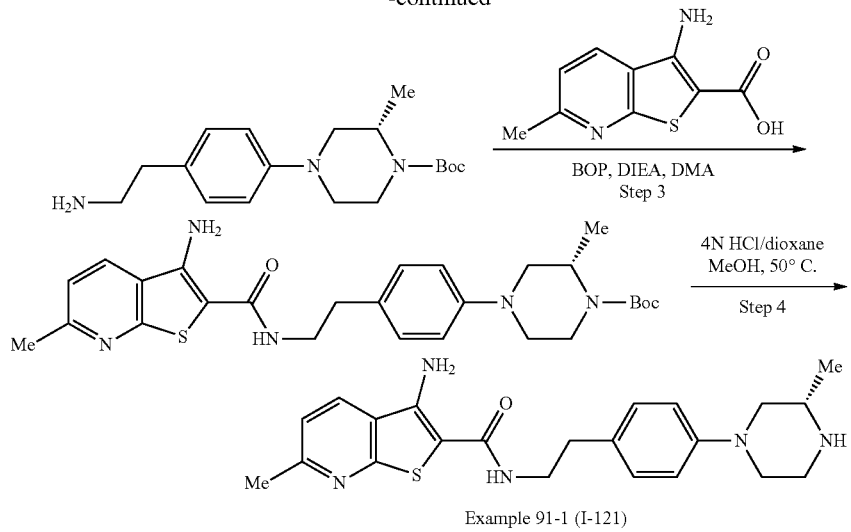

Steps 1-3. These steps were carried out as described above for Example 90-1 (I-116) using the appropriate synthetic precursors.

Step 4. (S)-3-amino-6-methyl-N-(4-(3-methylpiperazin-1-yl)phenethyl)thieno[2,3-b]pyridine-2-carboxamide The crude product obtained as described above from Step 3 was dissolved in methanol (0.4 mL) and 4 N HCl in dioxane solution (75 μL, 300 μmol) was added. The resulting mixture was heated to 50° C. for 1 h and then concentrated in vacuo. The crude product was purified by HPLC: Water Autopurification MS-directed HPLC prep fraction collection using the following conditions Column, Waters XBridge OBD C18, 5 μm, 19×50 mm; flow rate 20 ml/min; mobile phase, A: water with 0.1% ammonium hydroxide and B: methanol with 0.1% ammonium hydroxide using the following gradient: 0 to 2 mins (15% B), 2 to 6 mins (15-100% B); Detector ZQ Mass Detector in electrospray ionization mode. This afforded the title compound (6 mg, 46%). LCMS (ESI m/z): 410 [M+H]$^+$.

The Examples in Table 18 below were synthesized according to the procedures outlined above for Example 91-1 (I-121), using the appropriate synthetic precursors.

TABLE 18

| Example (Cmpd no.) | Structure | MS (ESI, m/z) [M + H] |
|---|---|---|
| 91-2 (I-122) | 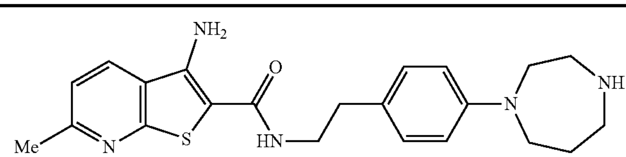 | 411 |
| 91-3 (I-123) | 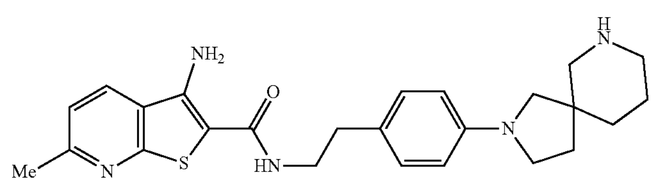 [SMILES: Cc1ccc2c(N)c(C(=O)NCCc3ccc(N4CCC5(CCCNC5)C4)cc3)sc2n1] | 451 |
| 91-4 (I-124) | 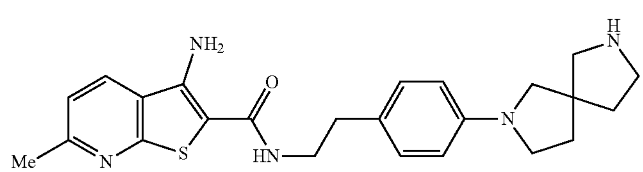 [SMILES: Cc1ccc2c(N)c(C(=O)NCCc3ccc(N4CCC5(CCNC5)C4)cc3)sc2n1] | 437 |
| 91-5 (I-125) | 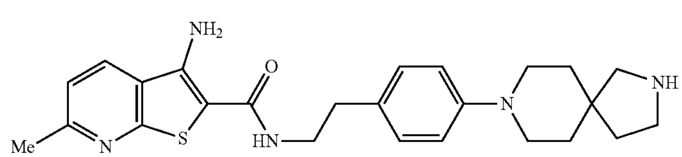 [SMILES: Cc1ccc2c(N)c(C(=O)NCCc3ccc(N4CCC5(CCNC5)CC4)cc3)sc2n1] | 451 |

TABLE 18-continued

| Example (Cmpd no.) | Structure | MS (ESI, m/z) [M + H] |
|---|---|---|
| 91-6 (I-126) | 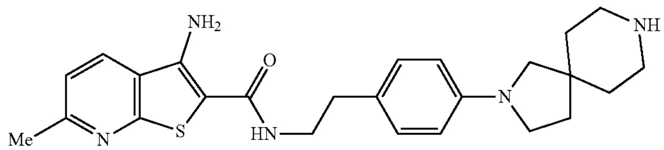 [SMILES: Cc1ccc2c(N)c(C(=O)NCCc3ccc(N4CCC5(CCNCC5)C4)cc3)sc2n1] | 451 |
| 91-7 (I-127) | 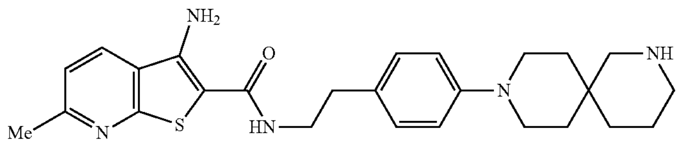 [SMILES: Cc1ccc2c(N)c(C(=O)NCCc3ccc(N4CCC5(CCCNC5)CC4)cc3)sc2n1] | 465 |
| 91-8 (I-128) | 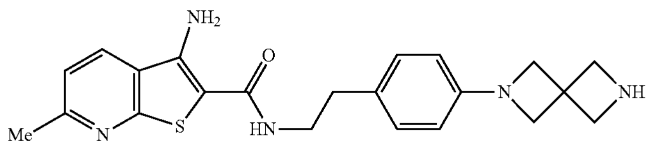 [SMILES: Cc1ccc2c(N)c(C(=O)NCCc3ccc(N4CC5(CNC5)C4)cc3)sc2n1] | 409 |
| 91-9 (I-129) | 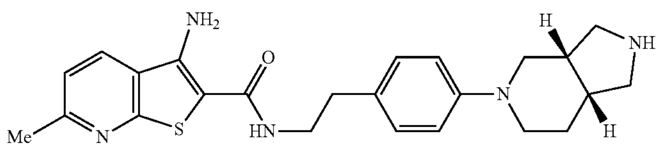 [SMILES: Cc1ccc2c(N)c(C(=O)NCCc3ccc(N4CC[C@H]5CNC[C@H]5C4)cc3)sc2n1] | 437 |
| 91-10 (I-130) | 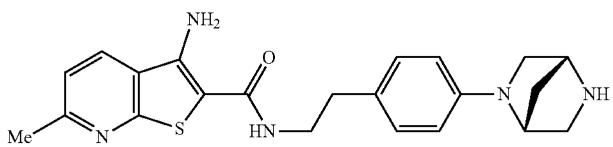 [SMILES: Cc1ccc2c(N)c(C(=O)NCCc3ccc(N4C[C@H]5C[C@@H]4CN5)cc3)sc2n1] | 409 |
| 91-11 (I-131) | 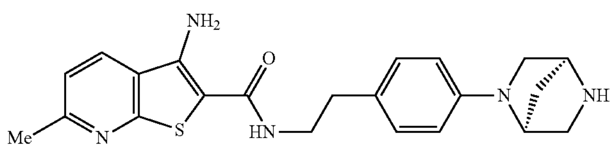 [SMILES: Cc1ccc2c(N)c(C(=O)NCCc3ccc(N4C[C@@H]5C[C@H]4CN5)cc3)sc2n1] | 409 |
| 91-12 (I-132) | 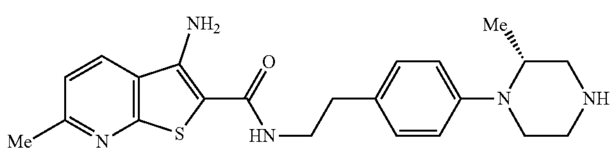 [SMILES: Cc1ccc2c(N)c(C(=O)NCCc3ccc(N4CCNC[C@H]4C)cc3)sc2n1] | 411 |
| 91-13 (I-133) | 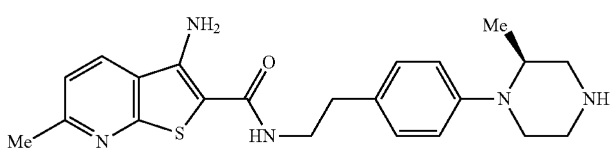 [SMILES: Cc1ccc2c(N)c(C(=O)NCCc3ccc(N4CCNC[C@@H]4C)cc3)sc2n1] | 411 |
| 91-14 (I-134) | 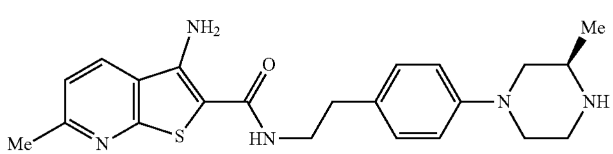 [SMILES: Cc1ccc2c(N)c(C(=O)NCCc3ccc(N4CCN[C@H](C)C4)cc3)sc2n1] | 411 |
| 91-15 (I-135) | 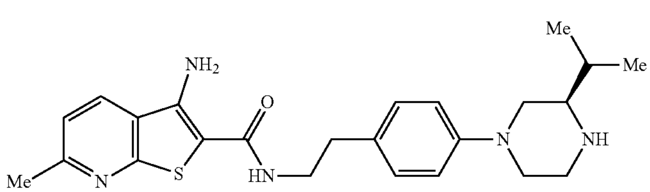 [SMILES: Cc1ccc2c(N)c(C(=O)NCCc3ccc(N4CCN[C@H](C(C)C)C4)cc3)sc2n1] | 439 |

TABLE 18-continued

| Example (Cmpd no.) | Structure | MS (ESI, m/z) [M + H] |
|---|---|---|
| 91-16 (I-136) | 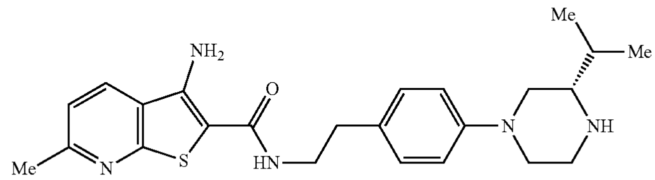 [SMILES: Cc1ccc2c(N)c(C(=O)NCCc3ccc(N4CCN[C@@H](C(C)C)C4)cc3)sc2n1] | 439 |
| 91-17 (I-137) | 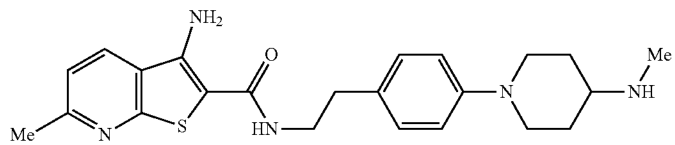 [SMILES: CNC1CCN(c2ccc(CCNC(=O)c3sc4nc(C)ccc4c3N)cc2)CC1] | 425 |
| 91-18 (I-138) | 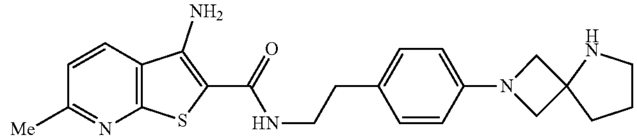 [SMILES: Cc1ccc2c(N)c(C(=O)NCCc3ccc(N4CC5(CCCN5)C4)cc3)sc2n1] | 423 |
| 91-19 (I-139) | 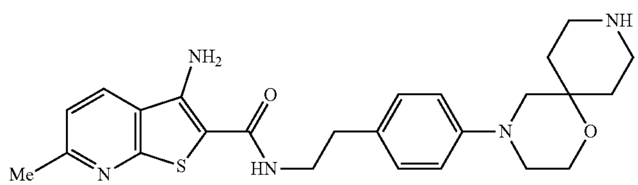 | 467 |
| 91-20 (I-140) | 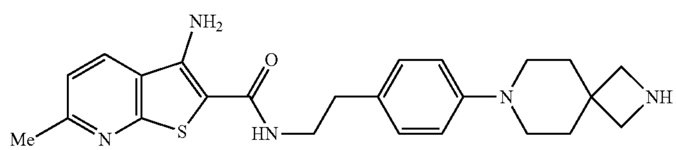 [SMILES: Cc1ccc2c(N)c(C(=O)NCCc3ccc(N4CCC5(CC4)CNC5)cc3)sc2n1] | 437 |
| 91-21 (I-141) | 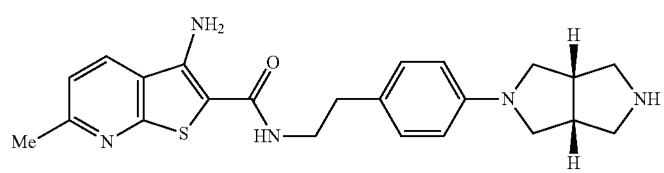 [SMILES: Cc1ccc2c(N)c(C(=O)NCCc3ccc(N4C[C@H]5CNC[C@H]5C4)cc3)sc2n1] | 423 |
| 91-22 (I-142) | 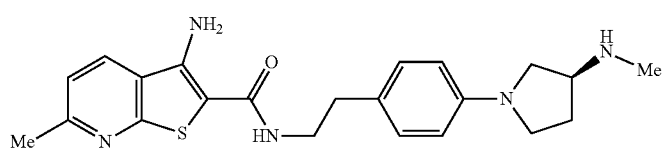 [SMILES: CN[C@H]1CCN(c2ccc(CCNC(=O)c3sc4nc(C)ccc4c3N)cc2)C1] | 411 |
| 91-23 (I-143) | 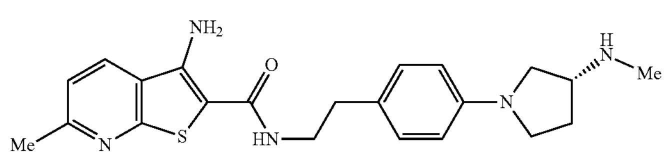 [SMILES: CN[C@@H]1CCN(c2ccc(CCNC(=O)c3sc4nc(C)ccc4c3N)cc2)C1] | 411 |
| 91-24 (I-144) | 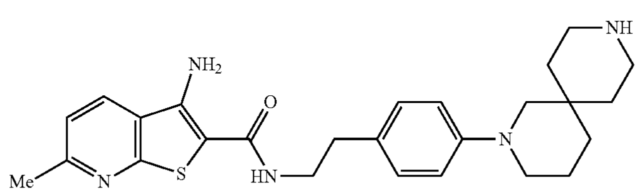 [SMILES: Cc1ccc2c(N)c(C(=O)NCCc3ccc(N4CCCC5(CCNCC5)C4)cc3)sc2n1] | 465 |

TABLE 18-continued

| Example (Cmpd no.) | Structure | MS (ESI, m/z) [M + H] |
|---|---|---|
| 91-25 (I-145) | 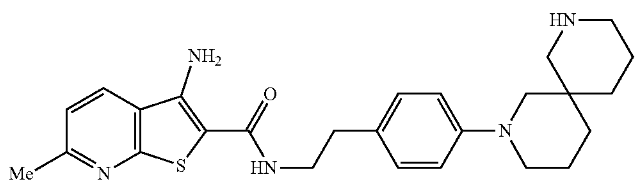 [SMILES: Cc1ccc2c(N)c(C(=O)NCCc3ccc(N4CCCC5(CCCNC5)C4)cc3)sc2n1] | 465 |
| 91-26 (I-146) | 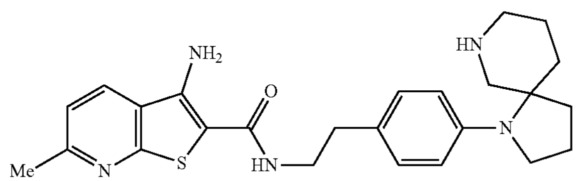 [SMILES: Cc1ccc2c(N)c(C(=O)NCCc3ccc(N4CCCC45CCCNC5)cc3)sc2n1] | 451 |
| 91-27 (I-147) | 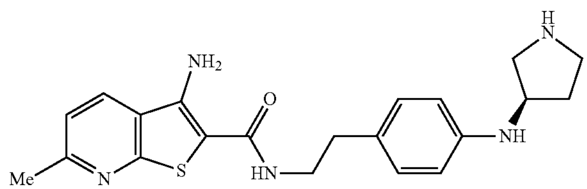 [SMILES: Cc1ccc2c(N)c(C(=O)NCCc3ccc(N[C@@H]4CCNC4)cc3)sc2n1] | 397 |
| 91-28 (I-148) | 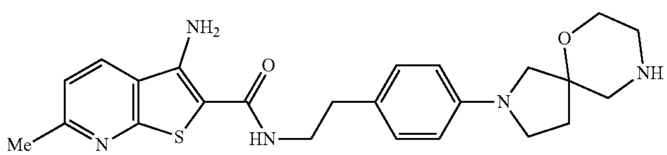 [SMILES: Cc1ccc2c(N)c(C(=O)NCCc3ccc(N4CCC5(CNCCO5)C4)cc3)sc2n1] | 453 |
| 91-29 (I-149) | 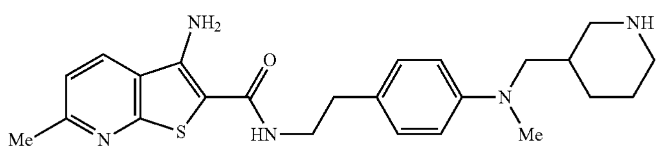 [SMILES: Cc1ccc2c(N)c(C(=O)NCCc3ccc(N(C)CC4CCCNC4)cc3)sc2n1] | 439 |
| 91-30 (I-150) | 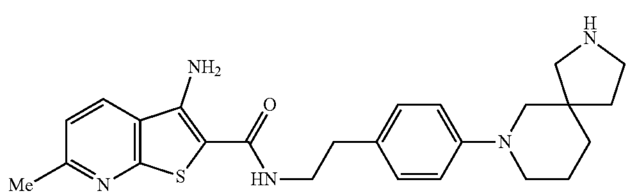 [SMILES: Cc1ccc2c(N)c(C(=O)NCCc3ccc(N4CCCC5(CCNC5)C4)cc3)sc2n1] | 451 |
| 91-31 (I-151) | 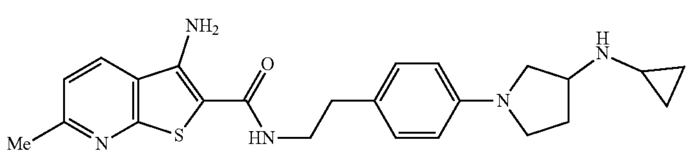 [SMILES: Cc1ccc2c(N)c(C(=O)NCCc3ccc(N4CCC(NC5CC5)C4)cc3)sc2n1] | 437 |
| 91-32[1] (I-216) | 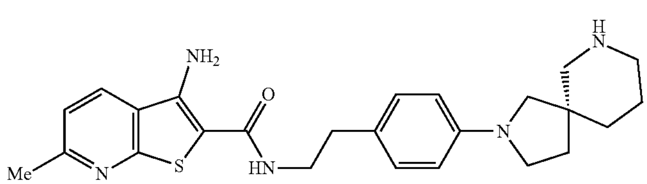 | 451 |

TABLE 18-continued

| Example (Cmpd no.) | Structure | MS (ESI, m/z) [M + H] |
|---|---|---|
| 91-33[1] (I-217) | 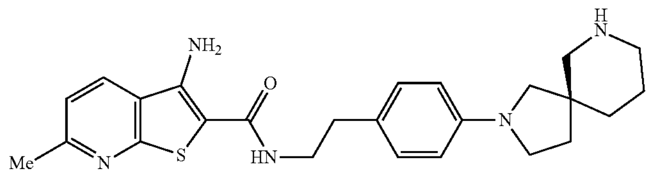 [SMILES: Cc1ccc2c(N)c(C(=O)NCCc3ccc(N4CC[C@@]5(CCCNC5)C4)cc3)sc2n1] | 451 |

[1]Notes:
The enantiomers of Example 91-3 (I-123) were further separated at the Boc protected intermediate (Step 3 product). by chiral HPLC using tlte following conditions: (SHIMADZU LC-20AD): LC parameters: Pump Mode: Binary gradient. Start Conc, of Pump B: 25.0%, Total Flow: 20 mL/min, Phase A: Hexane-HPLC, Phase B: Ethanol-HPLC, Column Name: CHIRALPAK IG, Length: 250 mm, Internal Diameter: 20 mm, Particle Size: 5 μm, Column Temp. 20° C., PDA Model: SPD-M20A, Wavelength: from 190 nm to 500 nm, This afforded the enantiomers as follows: 1st eluting peak (retention time = 5.04 min, 40 mg, 50%) as a light yellow solid. LCMS (ES, m/z): 550 [M + H]+. 2nd eluting peak (retention time = 6.18 min, 38 mg, 47%) as a light yellow solid. LCMS (ES, m/z): 550 [M + H]+. Step 4 for each enantiomer was conducted with TFA in DCM at room temperature, followed by treatment with ammonia in MeOH to afford Examples 91-32 (I-216) and 91-33 (I-217) from the 1st and 2nd eluting peaks, respectively.
Examples 91-32 (I-216): LCMS (ES, m/z): 450 [M + H]+. 1H-NMR (300 MHz, Methanol-d4) δ ppm 8.17 (d, J = 8.4 Hz, 1H), 7.29 (d, J = 8.4 Hz, 6H), 7.08 (d, J = 8.7 Hz, 2H), 6.53 (d, J = 8.4 Hz, 2H), 3.46 (t, J = 6.6 Hz, 2H), 3.34-3.36 (m, 1H), 3.23-3.26 (m, 2H), 3.04-3.07 (m, 1H), 2.73-2.85 (m, 6H), 2.63 (s, 3H), 1.64-1.95 (m, 6H).
Examples 91-33 (I-217): LCMS (ES, m/z): 450 [M + H]+. 1H-NMR (300 MHz, Methanol-d4) δ ppm 8.18 (d, J = 8.4 Hz, 1H), 7.29 (d, J = 8.4 Hz, 6H), 7.08 (d, J = 8.4 Hz, 2H), 6.53 (d, J = 8.7 Hz, 2H), 3.47 (t, J = 7.2 Hz, 2H), 3.34-3.36 (m, 1H), 3.23-3.26 (m, 2H), 3.05-3.08 (m, 1H), 2.73-2.90 (m, 6H), 2.63 (s, 3H), 1.67-2.00 (m, 6H).

Example 92-1 (I-152)

3-Amino-N-(3-(1-(difluoromethyl)-1H-pyrazol-4-yl)-4-(piperazin-1-yl)phenethyl)-6-methylthieno[2,3-b]pyridine-2-carboxamide

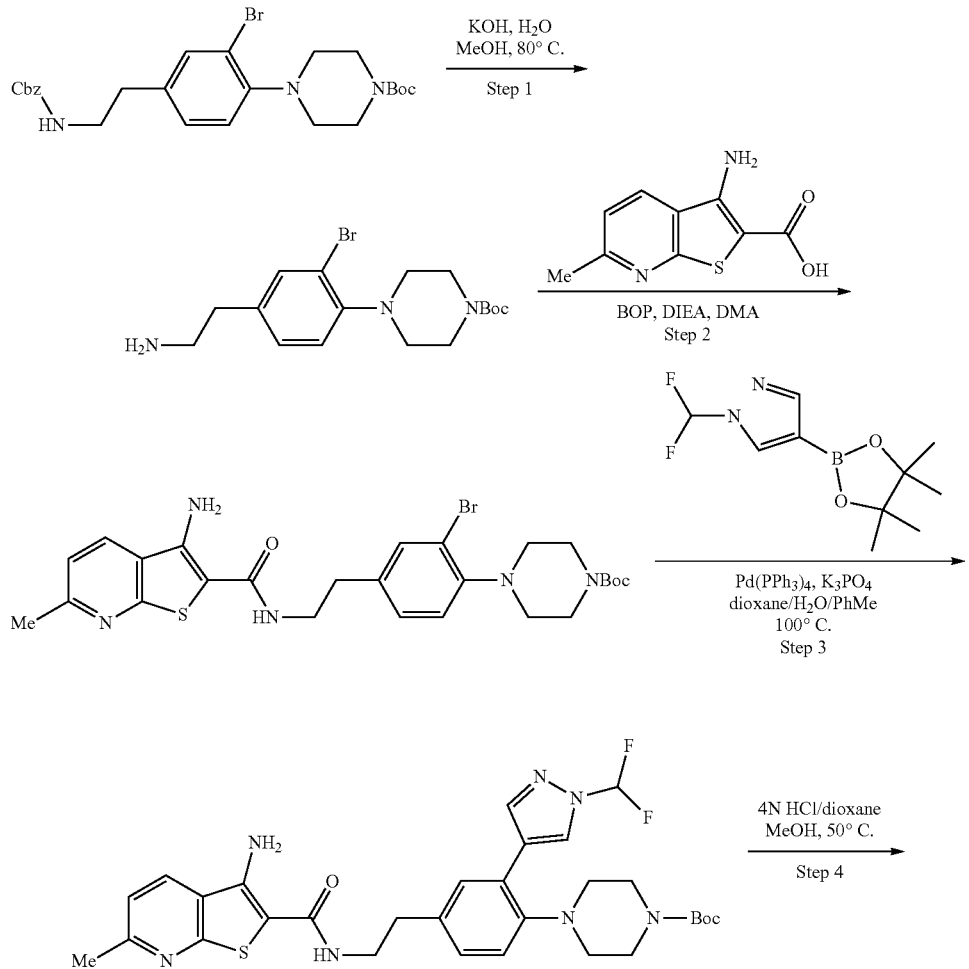

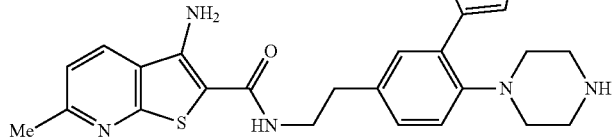

Example 92-1 (I-152)

Step 1. tert-Butyl 4-(4-(2-aminoethyl)-2-bromophenyl)piperazine-1-carboxylate

Into a 250-mL round-bottom flask was added tert-butyl 4-[4-(2-[[(benzyloxy)carbonyl]amino]ethyl)-2-bromophenyl]piperazine-1-carboxylate (3.00 g, 5.79 mmol), methanol (80 mL), and aqueous potassium hydroxide solution (40%; 40 mL). The resulting solution was stirred for 8 h at 80° C. in an oil bath. The reaction was cooled to RT, and then was concentrated in vacuo to remove most of the organic solvent. The resulting mixture was taken up into water (50 mL), and extracted with dichloromethane (3×30 mL). The combined organic layers were washed with brine (30 mL), dried over anhydrous sodium sulfate, filtered, and concentrated in vacuo to afford tert-butyl 4-(4-(2-aminoethyl)-2-bromophenyl)piperazine- 1-carboxylate (1.08 g) as a yellow oil. LCMS (ESI, m/z): 384, 386 [M+H]$^+$.

Step 2: tert-Butyl 4-(4-(2-(3-amino-6-methylthieno[2,3-b]pyridine-2-carboxamido)ethyl)-2-bromophenyl)piperazine-1-carboxylate To a solution of 3-amino-6-methylthieno[2,3-b]pyridine-2-carboxylic acid (0.416 g, 2 mmol) in DMF with 5% DIEA (10 mL) was added tert-butyl 4-(4-(2-aminoethyl)-2-bromophenyl)piperazine-1-carboxylate (0.769 g, 2.00 mmol), followed by BOP (1.06 g, 2.4 mmol). The resulting mixture was stirred at RT for 2 h and then poured into a well-stirred ice-water mixture (25 mL). The resulting precipitate was collected by vacuum filtration, washed with water, and dried to afford tert-butyl 4-(4-(2-(3-amino-6-methylthieno[2,3-b]pyridine-2-carboxamido)ethyl)-2-bromophenyl)piperazine-1-carboxylate (0.9 g, 78% yield). The material was used without further purification.

Step 3. tert-Butyl 4-(4-(2-(3-amino-6-methylthieno[2,3-b]pyridine-2-carboxamido)ethyl)-2-(1-(difluoromethyl)-1H-pyrazol-4-yl)phenyl)piperazine-1-carboxylate To a solution of tert-butyl 4-(4-(2-(3-amino-6-methylthieno[2,3-b][2,3-b]pyridine-2-carboxamido)ethyl)-2-bromophenyl)piperazine-1-carboxylate in 1,4-dioxane (0.2 M in 1,4-dioxane; 150 µL, 0.02 mmol) was added 1-(difluoromethyl)-4-(4,4,5,5-tetramethyl-1,3,2-dioxaborolan-2-yl)-1H-pyrazole (0.2 M in 1,4-dioxane; 225 µL, 0.45 mmol) and potassium phosphate tribasic solution (1 M aqueous; 150 µL, 0.15 mmol). The mixture was sparged with nitrogen and then tetrakis(triphenylphosphine)palladium(0) (0.02 M in toluene, 75 µL, 1.5 µmol) was added. The resulting mixture was placed in a shaker in a glove box under an atmosphere of nitrogen atmosphere and heated at 80° C. overnight. After being cooled to RT, the mixture was diluted with brine (0.4 mL) and EtOAc (0.5 mL). The organic layer was separated and the aqueous layer was extracted again with EtOAc (0.6 mL). The combined organic layers were concentrated in vacuo and the material was used without further purification.

Step 4. 3-Amino-N-(3-(1-(difluoromethyl)-1H-pyrazol-4-yl)-4-(piperazin-1-yl)phenethyl)-6-methylthieno[2,3-b]pyridine-2-carboxamide The crude product from Step 3 was re-dissolved in methanol (200 µL) and 4 N HCl/dioxane (75 L, 0.3 mmol) was added. The mixture was placed on a shaker at 50° C. for 1 hour. The reaction mixture was concentrated in vacuo and the crude product was purified by HPLC using the following conditions: Waters Autopurification MS-directed HPLC prep fraction collection using the following conditions Column, Waters XBridge OBD C18, 5 µm, 19×50 mm; flow rate 20 ml/min; mobile phase, A: water with 0.1% ammonium hydroxide and B: methanol with 0.1% ammonium hydroxide running the following gradient 0 to 2 mins (15% B), 2 to 6 mins (15-100% B); Detector ZQ Mass Detector in electrospray ionization mode. This afforded the title compound (2 mg, 12%). LCMS (ESI, m/z): 512 [M+H]$^+$.

The Examples in Table 19 below were synthesized according to the procedures outlined above for Example 92-1 (I-152), using the appropriate synthetic precursors.

TABLE 19

| Example (Cmpd no.) | Structure | MS (ESI, m/z) [M + H] |
|---|---|---|
| 92-2 (I-153) | 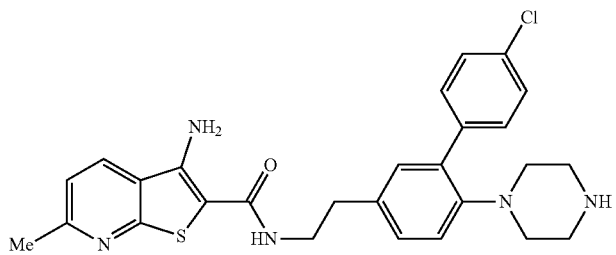 | 507 |

TABLE 19-continued
| Example (Cmpd no.) | Structure | MS (ESI, m/z) [M + H] |
|---|---|---|
| 92-3 (I-154) | 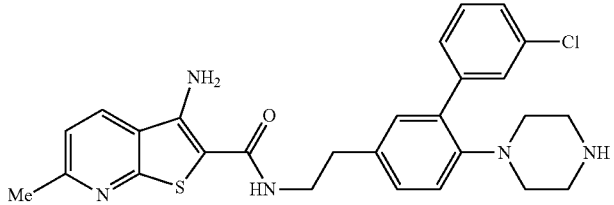 [SMILES: Cc1ccc2c(N)c(C(=O)NCCc3ccc(N4CCNCC4)c(-c4cccc(Cl)c4)c3)sc2n1] | 507 |
| 92-4 (I-155) | 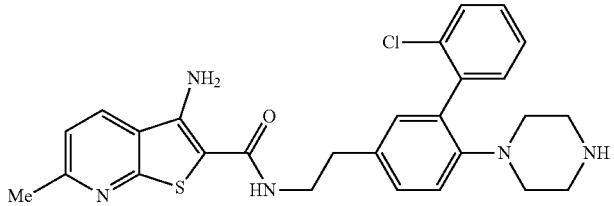 [SMILES: Cc1ccc2c(N)c(C(=O)NCCc3ccc(N4CCNCC4)c(-c4ccccc4Cl)c3)sc2n1] | 507 |
| 92-5 (I-156) | 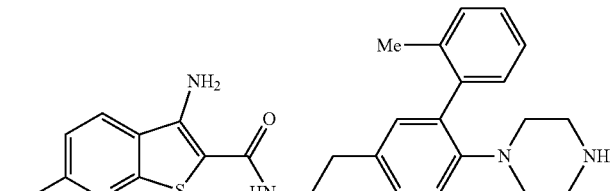 | 487 |
| 92-6 (I-157) | 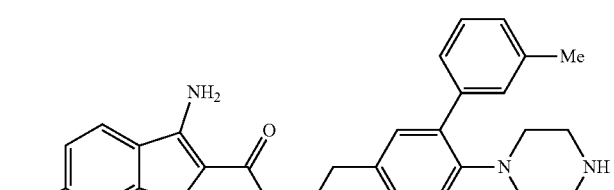 | 487 |
| 92-7 (I-158) | 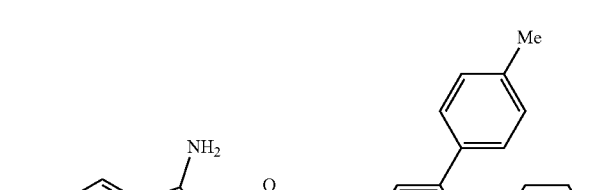 | 487 |
| 92-8 (I-159) | 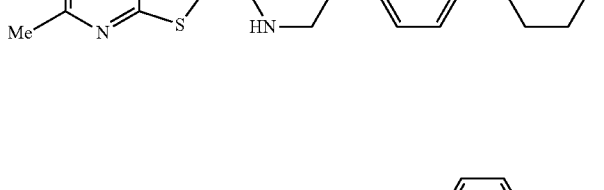 | 491 |

TABLE 19-continued

| Example (Cmpd no.) | Structure | MS (ESI, m/z) [M + H] |
|---|---|---|
| 92-9 (I-160) | 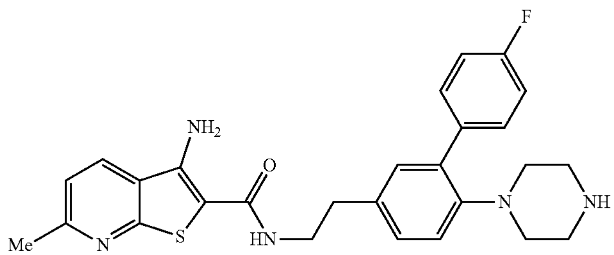 [SMILES: Cc1ccc2c(N)c(C(=O)NCCc3ccc(N4CCNCC4)c(-c4ccc(F)cc4)c3)sc2n1] | 491 |
| 92-10 (I-161) | 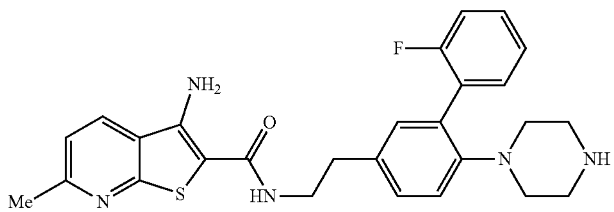 [SMILES: Cc1ccc2c(N)c(C(=O)NCCc3ccc(N4CCNCC4)c(-c4ccccc4F)c3)sc2n1] | 491 |
| 92-11 (I-162) | 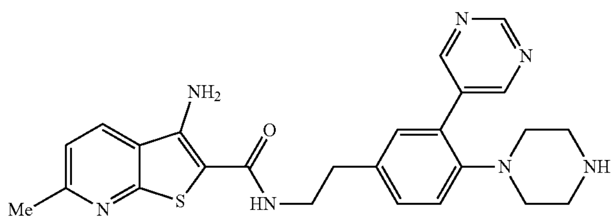 [SMILES: Cc1ccc2c(N)c(C(=O)NCCc3ccc(N4CCNCC4)c(-c4cncnc4)c3)sc2n1] | 475 |
| 92-12 (I-163) | 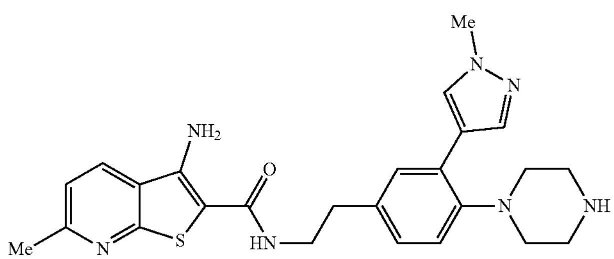 [SMILES: Cc1ccc2c(N)c(C(=O)NCCc3ccc(N4CCNCC4)c(-c4cnn(C)c4)c3)sc2n1] | 477 |
| 92-13 (I-164) | 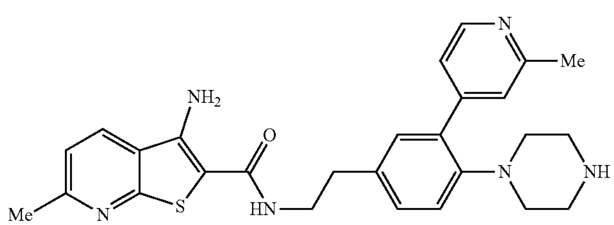 [SMILES: Cc1cc(-c2cc(CCNC(=O)c3sc4nc(C)ccc4c3N)ccc2N2CCNCC2)ccn1] | 488 |
| 92-14 (I-165) | 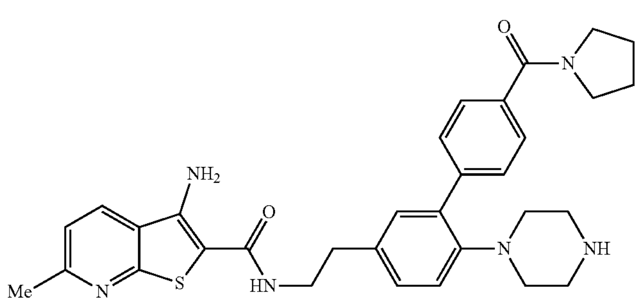 [SMILES: Cc1ccc2c(N)c(C(=O)NCCc3ccc(N4CCNCC4)c(-c4ccc(C(=O)N5CCCC5)cc4)c3)sc2n1] | 570 |

TABLE 19-continued
| Example (Cmpd no.) | Structure | MS (ESI, m/z) [M + H] |
|---|---|---|
| 92-15 (I-166) | 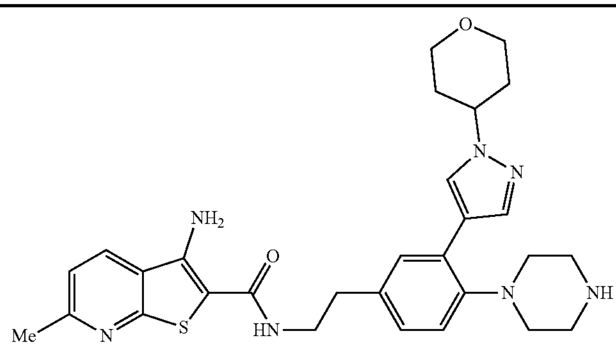 | 547 |
| 92-16 (I-167) | 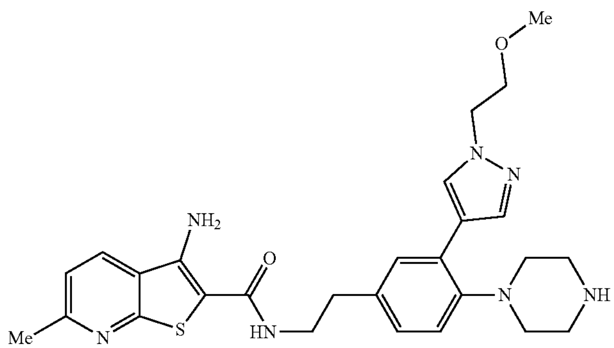 [SMILES: COCCn1cc(-c2cc(CCNC(=O)c3sc4nc(C)ccc4c3N)ccc2N2CCNCC2)cn1] | 521 |
Example 93 (I-168)
3-Amino-6-methyl-N-(4-(piperazin-1-yl)-3-(pyridin-2-yl)phenethyl) thieno[2,3-b]pyridine-2-carboxamide
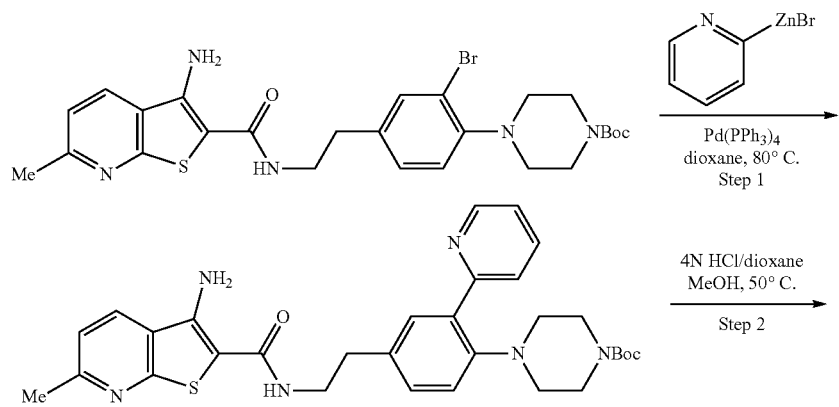
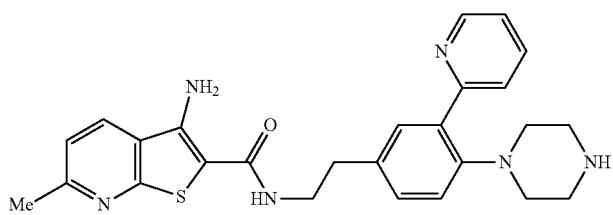
Example 93 (I-168)

Step 1. tert-Butyl 4-(4-(2-(3-amino-6-methylthieno [2,3-b]pyridine-2-carboxamido)ethyl)-2-(pyridin-2-yl)phenyl)piperazine-1-carboxylate To a solution of tert-butyl 4-(4-(2-(3-amino-6-methylthieno[2,3-b]pyridine-2-carboxamido)ethyl)-2-bromophenyl) piperazine-1-carboxylate in dioxane (0.2 M; 100 μL, 20 μmol) was added a solution of pyridin-2-ylzinc (II) bromide (0.5 M THF, 200 μL, 100 μmol) and tetrakis(triphenylphosphine)palladium (0) (0.02 M toluene, 50 μL, 1 μmol). The resulting mixture was heated to 80° C. overnight. After being cooled to RT, brine (0.5 ml) was added and the resulting mixture was extracted with EtOAc (2×0.5 mL). The combined organic layers were concentrated in vacuo to afford crude tert-butyl 4-(4-(2-(3-amino-6-methylthieno[2, 3-b]pyridine -2-carboxamido)ethyl)-2-(pyridin-2-yl)phenyl)piperazine-1-carboxylate. The material was used without further purification.

Step 2. 3-Amino-6-methyl-N-(4-(piperazin-1-yl)-3-(pyridin-2-yl)phenethyl)thieno[2,3-b]pyridine-2-carboxamide The crude product from Step 1 was dissolved in methanol (400 μL), and 4 N HCl in dioxane (50 μL, 200 μmol) was added. The resulting mixture was heated to 50° C. for 1 h and then cooled and concentrated in vacuo to provide a crude product that was purified by HPLC: Waters Autopurification MS-directed HPLC prep fraction collection using the following conditions Column, Waters XBridge OBD C18, 5 μm, 19×50 mm; flow rate 20 ml/min; mobile phase, A: water with 0.1% ammonium hydroxide and B: methanol with 0.1% ammonium hydroxide (B) eluting with the following gradient: 0 to 2 mins (15% B), 2 to 6 mins (15-100% B); Detector ZQ Mass Detector in electrospray ionization mode. This afforded the title compound (3.7 mg, 39%). LCMS (ESI, m/z): 473 [M+H]$^+$.

Example 94-1 (I-169)

3-Amino-N-(3-fluoro-4-(piperidin-4-yl)phenethyl)-6-methylthieno [2,3-b]pyridine-2-carboxamide

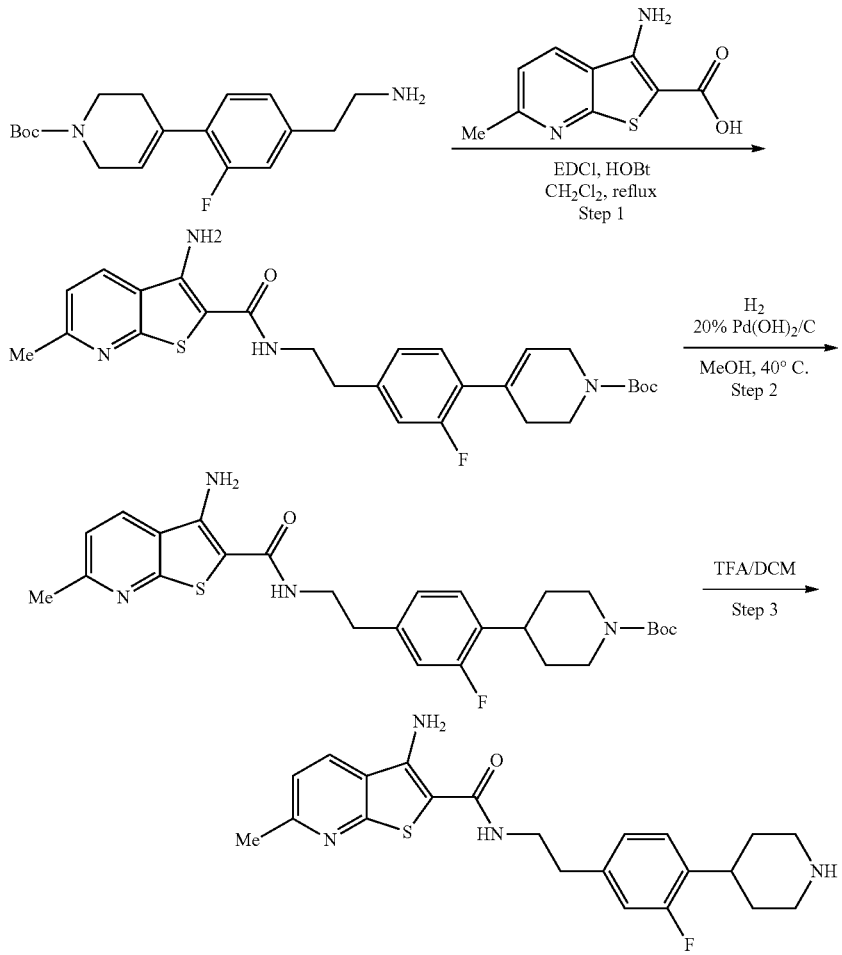

Example 94-1 (I-169)

Step 1. tert-Butyl 4-(4-(2-(3-amino-6-methylthieno[2,3-b]pyridine-2-carboxamido)ethyl)-2-fluorophenyl)-3,6-dihydropyridine-1(2H)-carboxylate.

Into a 100-mL round-bottom flask was added tert-butyl 4-[4-(2-aminoethyl)-2-fluorophenyl]-1,2,3,6-tetrahydropyridine-1-carboxylate (0.20 g, 0.62 mmol), dichloromethane (10 mL), 3-amino-6-methylthieno[2,3-b]pyridine-2-carboxylic acid (0.192 g, 0.92 mmol), HOBt (0.127 g, 0.940 mmol), and EDCI (0.18 g, 0.94 mmol). The resulting solution was stirred overnight at 40° C. The solids were removed by filtration, and the filtrate was concentrated in vacuo to provide a crude product that was purified via silica gel chromatography and eluted with dichloromethane/methanol (20:1) to afford tert-butyl 4-(4-(2-(3-amino-6-methylthieno[2,3-b]pyridine-2-carboxamido)ethyl)-2-fluorophenyl)-3,6-dihydropyridine-1(2H)-carboxylate as a light yellow oil (88 mg, 28%). LCMS (ES, m/z): 511 [M+H]+.

Step 2. tert-Butyl 4-(4-(2-(3-amino-6-methylthieno[2,3-b]pyridine-2-carboxamido)ethyl)-2-fluorophenyl)piperidine-1-carboxylate Into a 50-mL round-bottom flask purged and maintained with nitrogen was added tert-butyl 4-(4-(2-(3-amino-6-methylthieno[2,3-b]pyridine-2-carboxamido)ethyl)-2-fluorophenyl)-3,6-dihydropyridine-1(2H)-carboxylate (0.088 g, 0.17 mmol), 20% Pd(OH)$_2$/C (20 mg), and methanol (5 mL). The reaction mixture was sparged with H$_2$, and the reaction mixture was stirred overnight at 40° C. The reaction was vented to nitrogen and the solids were removed by filtration over Celite. The filtrate was concentrated in vacuo to afford tert-butyl 4-(4-(2-(3-amino-6-methylthieno[2,3-b]pyridine-2-carboxamido)ethyl)-2-fluorophenyl)piperidine-1-carboxylate as a black oil (70 mg, 79%). LCMS (ESI, m/z): 513 [M+H]+.

Step 3. 3-Amino-N-(3-fluoro-4-(piperidin-4-yl)phenethyl)-6-methylthieno[2,3-b]pyridine-2-carboxamide Into a 50-mL round-bottom flask was added tert-butyl 4-(4-(2-(3-amino-6-methylthieno[2,3-b]pyridine-2-carboxamido)ethyl)-2-fluorophenyl)piperidine-1-carboxylate (0.070 g, 0.14 mmol) and dichloromethane (3 mL). Trifluoroacetic acid (0.6 mL) was added and the resulting solution was stirred for 2 h at RT. The reaction mixture was concentrated in vacuo and the crude product was diluted with methanol (5 mL). The pH of the solution was adjusted to approximately 8 with ammonium hydroxide and the crude product was then purified by Prep-HPLC using the following conditions: Column: SunFire Prep C18 5 µm 19*150 mm; mobile phase, A: water (containing 0.05% ammonium hydroxide) and B: CH$_3$CN (20% to 40% over 8 min); UV Detector: 254 nm. This afforded the title compound as a light yellow oil (7.6 mg, 13%). LCMS (ESI, m/z): 413 [M+H] +; $^1$H-NMR (300 MHz, CD$_3$OD) δ ppm 8.21 (d, J=8.1 Hz, 1H), 7.32 (d, J=8.1 Hz, 1H), 7.23 (m, 1H), 7.07-6.98 (m, 2H), 3.55-3.50 (m, 2H), 3.30-3.20 (m, 2H), 3.11-2.98 (m, 1H), 2.94-2.78 (m, 4H), 2.65 (s, 3H), 1.91-1.69 (m, 4H).

The Example in Table 20 below was synthesized according to the procedures outlined above for Example 94-1 (I-169), using the appropriate synthetic precursors. Additional detail around the synthetic methods as well as HPLC purification conditions appears below the example.

TABLE 20

| Example (Cmpd no.) | Structure | MS (ESI, m/z) [M + H] | $^1$H NMR |
|---|---|---|---|
| 94-2 (I-170) | 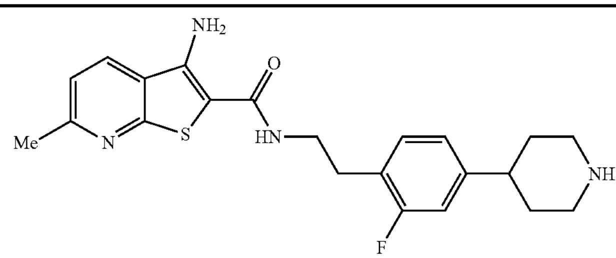 | 413 | (300 MHz, CD$_3$OD) δ ppm 8.20 (d, J = 8.1 Hz, 1H), 7.40-7.22 (m, 2H), 7.05-6.90 (m, 2H), 3.60-3.50 (m, 2H), 3.30-3.20 (m, 2H), 2.98-2.61 (m, 5H), 2.60 (s, 3H), 1.98-1.80 (m, 2H), 1.80-1.60 (m, 2H) |

HPLC Purification Method: Column, SunFire C18, 30* 150 mm, 5 µm; mobile phase, A: water (containing 0.05% ammonium hydroxide) and B: CH$_3$CN (22% to 48% over 6 min); UV Detector: 283 nm.

Examples 95-A (I-171) and 95-B (I-172)

N-(4-(8-azabicyclo[3.2.1]octan-3-yl)phenethyl)-3-amino-6-methylthieno[2,3-b]pyridine-2-carboxamide (Diastereomers A and B)

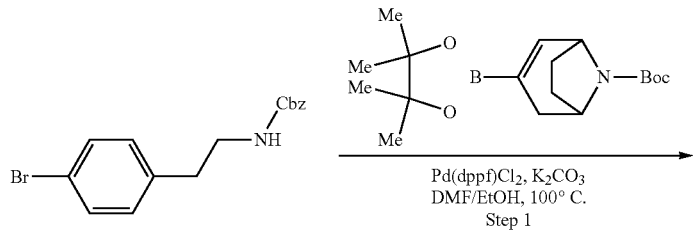

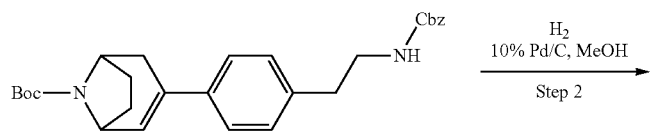

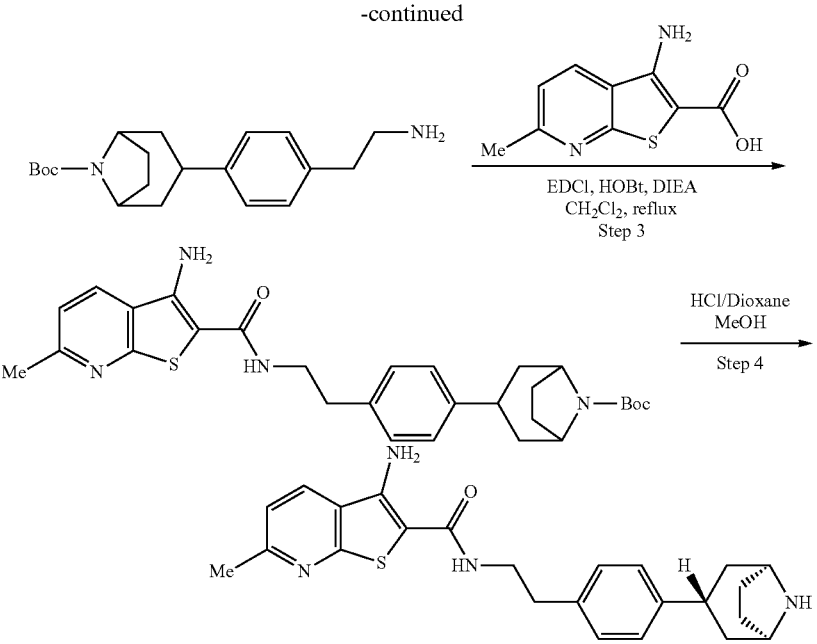

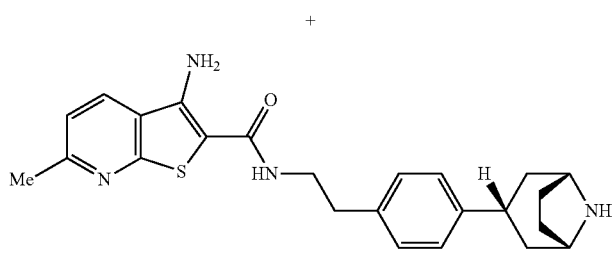

Example 95-A (I-171): Diastereomer A

+

Example 95-B (I-172): Diastereomer B

Step 1. tert-Butyl 3-(4-(2-(((benzyloxy)carbonyl)amino) ethyl)phenyl)-8-azabicyclo[3.2.1]oct -2-ene-8-carboxylate Into a 50-mL 3-necked round-bottom flask, purged and maintained with nitrogen, was added benzyl N-[2-(4-bromophenyl)ethyl]carbamate (0.500 g, 1.50 mmol), tert-butyl 3-(4,4,5,5-tetramethyl-1,3,2-dioxaborolan-2-yl)-8-azabicyclo[3.2.1]oct-2-ene-8-carboxylate (0.553 g, 1.64 mmol), potassium carbonate (0.622 g, 4.50 mmol), Pd(dppf)Cl$_2$·CH$_2$Cl$_2$ (0.243 g, 0.30 mmol), DMF (8 mL), and ethanol (2 mL). The reaction mixture was stirred for 2 h at 100° C. and then cooled to RT and diluted with water (10 mL). The resulting solution was extracted with ethyl acetate (3×30 mL) and the combined organic layers were washed with brine (10 mL), dried over anhydrous sodium sulfate, filtered, and concentrated in vacuo. The resulting crude product was purified by FCC eluting with ethyl acetate/petroleum ether (1:5) to afford tert-butyl 3-(4-(2-(((benzyloxy)carbonyl) amino) ethyl)phenyl)-8-azabicyclo[3.2.1]oct-2-ene-8-carboxylate as a yellow oil (340 mg, 49%). LCMS (ESI, m/z): 463 [M+H]$^+$.

Step 2. tert-Butyl 3-(4-(2-aminoethyl)phenyl)-8-azabicyclo[3.2.1]octane-8-carboxylate (cisltrans mixture)

Into a 50-mL round-bottom flask, purged and maintained with nitrogen, was added tert -butyl 3-(4-(2-(((benzyloxy) carbonyl)amino)ethyl)phenyl)-8-azabicyclo[3.2.1]oct-2-ene-8-carboxylate (0.33 g, 0.71 mmol), 10% palladium on carbon (100 mg), and methanol (10 mL). The reaction mixture was sparged with H$_2$ and the reaction was stirred for 2 h at RT. The reaction was vented to nitrogen and the solids were removed by filtration over Celite. The filtrate was concentrated in vacuo to afford a cis/trans mixture of tert-butyl 3-(4-(2-aminoethyl)phenyl)-8-azabicyclo[3.2.1]octane-8-carboxylate as a yellow solid (220 mg, 94%). LCMS (ESI, m/z): 331 [M+H]$^+$.

Step 3. tert-Butyl 3-(4-(2-(3-amino-6-methylthieno[2,3-b]pyridine-2-carboxamido)ethyl) phenyl)-8-azabicyclo [3.2.1]octane-8-carboxylate (cis/trans mixture)

Into a 50-mL round-bottom flask was added tert-butyl 3-(4-(2-aminoethyl)phenyl)-8-azabicyclo[3.2.1]octane-8-carboxylate (0.150 g, 0.45 mmol), dichloromethane (5 mL), 3-amino -6-methylthieno[2,3-b]pyridine-2-carboxylic acid (0.095 g, 0.46 mmol), EDCI (0.105 g, 0.55 mmol), HOBT (0.074 g, 0.55 mmol), and DIEA (0.176 g, 0.237 mL, 1.36 mmol). The resulting solution was stirred for 2 h at room temperature and then concentrated in vacuo to provide a crude product that was purified by Prep-HPLC using the following conditions : Column, SunFire Prep C18 5 μm 19*150 um; mobile phase, Water (it contains 0.05% TFA) and CH$_3$CN; Detector, 254 nm. This afforded a cis/trans mixture of tert-butyl 3-(4-(2-(3-amino-6-methylthieno[2,3-b]pyridine-2-carboxamido)ethyl)phenyl)-8-azabicyclo [3.2.1]octane-8-carboxylate as a yellow solid (85 mg, 36%). LCMS (ES, m/z): 521 [M+H]$^+$.

Step 4. N-(4-(8-azabicyclo[3.2.1]octan-3-yl)phenethyl)-3-amino-6-methylthieno[2,3-b]pyridine-2-carboxamide (Diastereomers A and B)

Into a 25-mL round-bottom flask was added tert-butyl 3-(4-(2-(3-amino-6-methylthieno[2,3-b]pyridine-2-carboxamido)ethyl)phenyl)-8-azabicyclo[3.2.1]octane-8-carboxylate (0.030 g, 0.06 mmol) and methanol (1 mL) followed by 4 N Hydrogen chloride/dioxane (2 mL) and the resulting solution was stirred for 2 h at RT. The reaction mixture was concentrated in vacuo to provide a crude product that was purified by Chiral-Prep-HPLC using the following conditions: Column, DAICEL CHIRALPAK AD-3; mobile phase, A: ethanol (containing 0.1% DEA) and B: methanol; UV Detector: 254 nm. This afforded the title compounds as follows: 7.5 mg (31%) of N-(4-(8-azabicyclo[3.2.1]octan-3-yl)phenethyl)-3-amino-6-methylthieno[2,3-b]pyridine-2-carboxamide (Diastereomer A, assumed cis, first eluting isomer, RT=2.03) as an off-white solid and 4.5 mg (19%) of N-(4-(8-azabicyclo[3.2.1]octan-3-yl)phenethyl)-3-amino-6-methylthieno[2,3-b]pyridine-2-carboxamide (Diastereomer B, assumed trans, second eluting isomer, RT=4.41) as an off-white solid.

Example 95-A (I-171), Diastereomer A

LCMS (ESI, m/z): 421 [M+H]$^+$; $^1$H-NMR (300 MHz, Acetone-d$_6$) δ ppm 8.24 (d, J=8.0 Hz, 1H), 7.30 (d, J=8.2 Hz, 1H), 7.20 (s, 4H), 3.64-3.48 (m, 4H), 2.94-2.86 (m, 2H), 2.61 (s, 3H), 2.10 (s, 2H), 1.84-1.76 (m, 4H), 1.75-1.72 (m, 1H), 1.71-1.64 (m, 2H).

Example 95-B (I-172), Diastereomer B

LCMS (ESI, m/z): 421 [M+H]$^+$; $^1$H-NMR (300 MHz, CD$_3$OD) δ ppm 8.21 (d, J=8.3 Hz, 1H), 7.36-7.20 (m, 5H), 3.68 (br s, 2H), 3.57-3.49 (m, 2H), 3.04-2.98 (m, 1H), 2.91-2.86 (m, 2H), 2.66 (s, 3H), 2.38-2.25 (m, 2H), 1.96-1.65 (m, 6H).

Example 96-1 (I-173)

4-(2-(3-Amino-6-methylthieno[2,3-b]pyridine-2-carboxamido)ethyl) benzoic acid

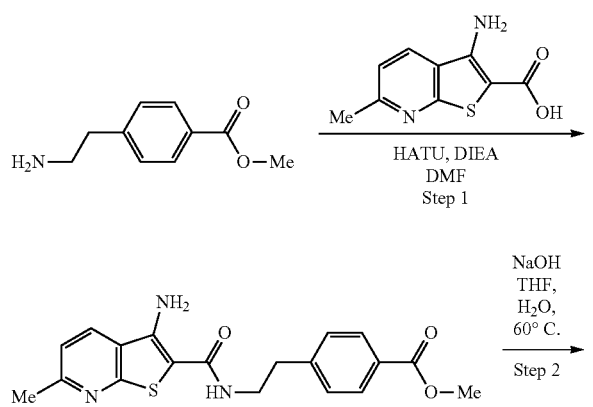

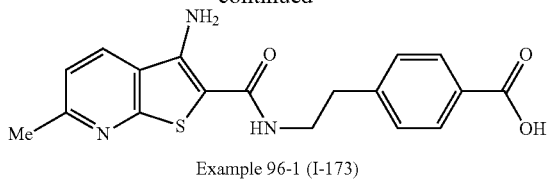

Example 96-1 (I-173)

Step 1. Methyl 4-(2-(3-amino-6-methylthieno[2,3-b]pyridine-2-carboxamido)ethyl)benzoate Into a 100-mL round-bottom flask was added 3-amino-6-methylthieno[2,3-b][2,3-b]pyridine-2-carboxylic acid (0.581 g, 2.79 mmol), DMF (8 mL), HATU (1.59 g, 6.61 mmol), methyl 4-(2-aminoethyl)benzoate (0.500 g, 2.79 mmol), and DIEA (1.08 g, 8.36 mmol). The reaction mixture was stirred for 2 h at room temperature and then extracted with ethyl acetate (3×20 mL). The combined organic layers were dried over sodium sulfate, filtered, and concentrated in vacuo to provide a crude product that was purified via silica gel chromatography and eluted with ethyl acetate/petroleum ether (1:1) to afford methyl 4-(2-(3-amino-6-methylthieno[2,3-b]pyridine-2-carboxamido)ethyl)benzoate as a yellow solid (520 mg, 50%). LCMS (ESI, m/z): 370 [M+H]$^+$.

Step 2. 4-(2-(3-Amino-6-methylthieno[2,3-b]pyridine-2-carboxamido)ethyl)benzoic acid Into a 50-mL round-bottom flask was added methyl 4-(2-(3-amino-6-methylthieno[2,3-b]pyridine-2-carboxamido)ethyl)benzoate (0.500 g, 1.35 mmol), sodium hydroxide (0.271 g, 6.78 mmol) in), THF (3 mL) and water (2 mL). The resulting solution was stirred for 4 h at 60° C. The pH of the solution was adjusted to approximately 2 with aqueous HCl (1 M) and the resulting precipitate was collected by filtration and dried in vacuo. The crude product was purified by Prep -HPLC using the following conditions (waters 2767): Column, XBridge RP18 19×150 mm, 5 µm; mobile phase, A: Water (containing 10 mM NH$_4$HCO$_3$+ 0.05% ammonium hydroxide) and B: MeCN (8% to 15% over 8 min.); Flow rate: 20 mL/min; UV Detector: 254 nm. This afforded the title compound as a light yellow solid (11.9 mg, 2%). LCMS (ESI, m/z): 356 [M+H]$^+$; $^1$H NMR (300 MHz, DMSO-d$_6$) δ ppm 8.29 (d, J=8.4 Hz, 1H), 7.84 (d, J=8.1 Hz, 2H), 7.77-7.73 (m, 1H), 7.32-7.28 (m, 3H), 7.12 (br s, 2H), 3.46-3.39 (m, 2H), 2.97-2.86 (m, 2H), 2.57 (s, 3H).

The Examples in Table 21 below were synthesized according to the procedures outlined above for Example 96-1 (I-173), using the appropriate synthetic precursors. Additional detail around the synthetic methods as well as HPLC purification conditions appears below each example.

TABLE 21

| Example (Cmpd no.) | Structure | MS (ESI, m/z) [M + H] | $^1$H NMR |
|---|---|---|---|
| 96-2[1] (I-174) | 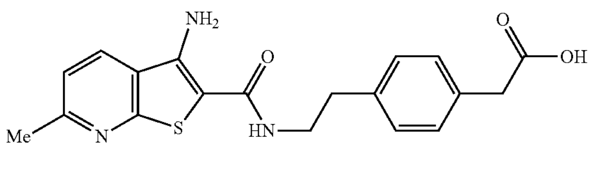 [SMILES: Cc1ccc2c(N)c(C(=O)NCCc3ccc(CC(=O)O)cc3)sc2n1] | 370 | (300 MHz, DMSO-$d_6$) δ ppm 8.29 (d, J = 8.4 Hz, 1H), 7.76-7.72 (m, 1H), 7.41 (d, J = 7.2 Hz, 1H), 7.31-7.13 (m, 6H), 3.41-3.36 (m, 4H), 2.89-2.73 (m, 2H), 2.57 (s, 3H) |
| 96-3[2] (I-175) | ·HCl | 356 | (300 MHz, CD$_3$OD) δ ppm 8.72 (d, J = 8.4 Hz, 1H), 7.95 (s, 1H), 7.89 (d, J = 7.8 Hz, 1H), 7.70 (d, J = 8.4 Hz, 1H), 7.54-7.52 (m, 1H), 7.45-7.40 (m, 1H), 3.63-3.58 (m, 2H), 3.02-2.97 (m, 2H), 2.85 (s, 3H) |
| 96-4A[3] (I-176) | 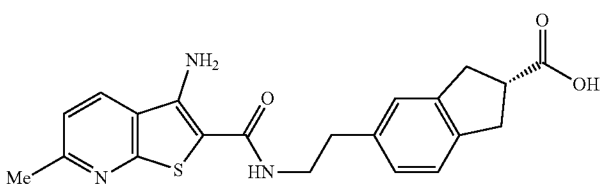 [SMILES: Cc1ccc2c(N)c(C(=O)NCCc3ccc4c(c3)C[C@H](C(=O)O)C4)sc2n1] | 396 | (300 MHz, DMSO) δ ppm 8.29 (d, J = 8.1 Hz, 1H), 7.76-7.72 (m, 1H), 7.30 (d, J = 8.1 Hz, 1H), 7.20-6.97 (m, 5H), 3.33 (s, 2H), 3.17-3.03 (m, 4H), 2.79-2.72 (m, 2H), 2.57 (s, 3H), 2.54-2.49 (m, 1H) |
| 96-4B[3] (I-177) | 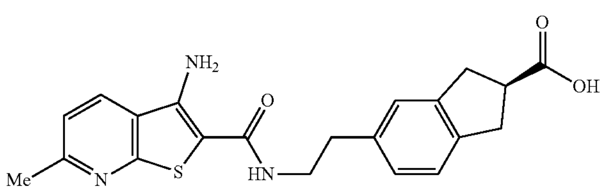 [SMILES: Cc1ccc2c(N)c(C(=O)NCCc3ccc4c(c3)C[C@@H](C(=O)O)C4)sc2n1] | 396 | (300 MHz, DMSO) δ ppm 8.29 (d, J = 8.1 Hz, 1H), 7.76-7.74 (m, 1H), 7.30 (d, J = 8.1 Hz, 1H), 7.13-6.97 (m, 5H), 3.33 (s, 2H), 3.09-3.04 (m, 4H), 2.78-2.74 (m, 2H), 2.57 (s, 3H), 2.54-2.49 (m, 1H) |
| 96-5[4] (I-178) | ·HCl | 370 | (300 MHz, CD$_3$OD) δ ppm 8.19 (d, J = 8.1 Hz, 1H), 7.32-7.14 (m, 5H), 3.59-3.52 (m, 4H), 2.92-2.87 (m, 2H), 2.65 (s, 3H) |

[1]Notes:

Dioxane was used instead of THF and the reaction temp was 100° C., HPLC Purification Method: (Water-I): Column. X Bridge Prep C18 5 μm 19* 150 mm; mobile phase. A: water (containing 0.05% TFA) and B: CH$_3$CN (40% to 50% over 6 min); UV Detector: 254 nm.

[2]Notes:

MeOH was used instead of THF. HPLC Purification Method: Column. SunFire Prep C18 5 μm 19* 150 mm; mobile phase, A: water (containing 0.1% formic acid) and B: CH$_3$CN (40% to 45% over 8 min); UV Detector: 254 nm. After lyophilization, the crude product was dissolved in 4N HCl/dioxane (2 mL) and stirred for 30 min. Diethyl ether (5 mL) was added, and the resulting solids were collected by filtration and dried in vacuo.

[3]Notes:

Step 1 was conducted at RT. Purification and isolation method: Prep HPLC: Column: Waters XBridge RP18 19* 150 mm, 5 μm; mobile phase, A: water (containing 0.05% ammonium hydroxide) and B: CH$_3$CN (45% to 49% over 4 min); UV Detector: 254 nm. Chiral HPLC: Column: DAICEL CHIRALPAK IA-3 20 × 250 mm, 5 μm; mobile phase, A: Hexanes and B: Ethanol (containing 0.1% TFA + 0.05% DBA) (A:B 50/50); UV Detector: 310 nm.

[4]Notes:

Step 1 was conducted with NaOH/MeOH at RT. HPLC Purification Method: Column, SunFire Prep C18, 5 μm, 19* 150 mm; mobile phase, A: water (containing 0.1% formic acid) and B: CH$_3$CN (35% to 50% over 8 min); UV Detector: 254 nm. The purified product was then redissolved in 4N HCl/dioxane (2 mL) and stirred for 1 hour. Diethyl ether (5 mL) was added and the solid product was collected by filtration.

Example 97 (I-179)

3-Amino-N-(3-chloro-4-(piperazin-1-yl)phenethyl)-6-(difluoromethyl) thieno[2,3-b]pyridine-2-carboxamide

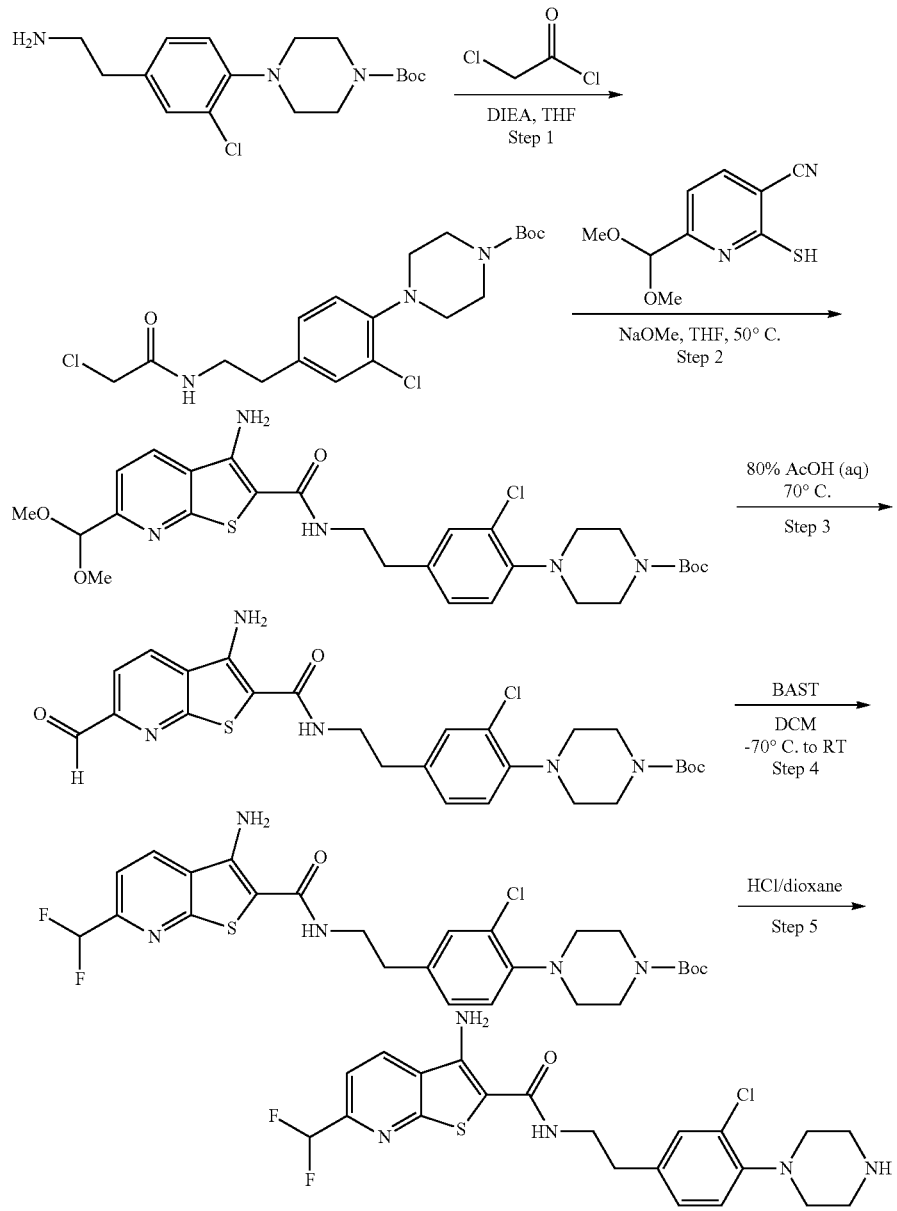

Example 97 (I-179)

Step 1. tert-Butyl 4-(2-chloro-4-(2-(2-chloroacetamido)ethyl)phenyl)piperazine-1-carboxylate Into a 100-mL round-bottom flask, purged and maintained under an inert atmosphere of nitrogen, was added tert-butyl 4-[4-(2-aminoethyl)-2-chlorophenyl]piperazine-1-carboxylate (0.456 g, 1.34 mmol), tetrahydrofuran (6 mL), and DIEA (0.348 g, 0.469 mL, 2.69 mmol) followed by the dropwise addition of 2-chloroacetyl chloride (182 mg, 1.61 mmol). The resulting solution was stirred for 3 h at RT. The reaction mixture was concentrated in vacuo to provide a crude product that was purified by FCC eluting with petroleum ether/ethyl acetate (1:1) to afford tert-butyl 4-(2-chloro-4-(2-(2-chloroacetamido)ethyl)phenyl)piperazine-1-carboxylate as a yellow oil (200 mg, 36%). LCMS (ESI, m/z) 416 [M+H]$^+$.

Step 2. tert-Butyl 4-(4-(2-(3-amino-6-(dimethoxymethyl)thieno[2,3-b]pyridine-2-carboxamido)ethyl)-2-chlorophenyl)piperazine-1-carboxylate Into a 50-mL round-bottom flask that purged and maintained under an inert atmosphere of nitrogen was added tert-butyl 4-(2-chloro-4-(2-(2-chloroacetamido)ethyl) phenyl)piperazine-1-carboxylate (0.200 g, 0.48 mmol), 6-(dimethoxymethyl)-2-sulfanylpyridine-3-carbonitrile (0.123 g, 0.59 mmol), NaOMe (0.130 g, 2.41 mmol), and tetrahydrofuran (2 mL). The reaction mixture was stirred overnight at 50° C. and then cooled and concentrated in vacuo to provide a crude product that was purified by FCC eluting with petroleum ether/ethyl acetate (1:3) to afford tert-butyl 4(4-(2-(3-amino-6-(dimethoxymethyl)thieno[2,3-b]pyridine-2-carboxamido)ethyl)-2-chlorophenyl)piperazine-1-carboxylate as a yellow oil (315 mg). The material was used without further purification. LCMS (ESI, m/z) 590 [M+H]$^+$.

Step 3. tert-Butyl 4-(4-(2-(3-amino-6-formylthieno[2,3-b]pyridine-2-carboxamido)ethyl)-2-chlorophenyl)piperazine-1-carboxylate Into a 50-mL round-bottom flask was added tert-butyl 4-(4-(2-(3-amino-6-(dimethoxymethyl)thieno[2,3-b]pyridine-2-carboxamido)ethyl)-2-chlorophenyl)piperazine-1-carboxylate (0.40 g, 0.68 mmol) and aqueous AcOH (80%; 6 mL). The resulting solution was stirred for 2 h at 70° C. and then cooled to RT and concentrated in vacuo to provide a crude product that was dissolved in DCM (5 mL). The pH of the solution was adjusted to approximately 7 with saturated aqueous sodium bicarbonate. The solids were removed by filtration and the filtrate was extracted with DCM (20 mL) and washed with brine (2×10 ml). The organic layer was dried over anhydrous sodium sulfate, filtered, and concentrated in vacuo to afford tert-butyl 4-(4-(2-(3-amino-6-formylthieno[2,3-b]pyridine-2-carboxamido)ethyl)-2-chlorophenyl) piperazine-1-carboxylate as a yellow solid (30 mg, 8%). LCMS (ESI, m/z) 544 [M+H]$^+$.

Step 4. tert-Butyl 4-(4-(2-(3-amino-6-(difluoromethyl)thieno[2,3-b]pyridine-2-carboxamido)ethyl)-2-chlorophenyl)piperazine-1-carboxylate Into a 50-mL round-bottom flask, purged and maintained under an inert atmosphere of nitrogen, was added tert-butyl 4-(4-(2-(3-amino-6-formylthieno[2,3-b]pyridine-2-carboxamido)ethyl)-2-chlorophenyl)piperazine-1-carboxylate (0.080 g, 0.15 mmol) and dichloromethane (4 mL). The resulting mixture was cooled to −70° C. and then a solution of BAST (0.325 g, 1.47 mmol) in dichloromethane (1 mL) was added dropwise. The resulting solution was warmed and stirred overnight at RT. The reaction mixture was then cooled to −70° C., quenched with methanol (2 mL), and concentrated in vacuo to provide a crude product that was purified by FCC eluting with petroleum ether/ethyl acetate (1:1) to afford tert-butyl 4-(4-(2-(3-amino-6-(difluoromethyl)thieno[2,3-b]pyridine-2-carboxamido)ethyl)-2-chlorophenyl) piperazine-1-carboxylate as a yellow oil (40 mg, 48%). LCMS (ESI, m/z) 566 [M+H]$^+$.

Step 5. 3-Amino-N-(3-chloro-4-(piperazin-1-yl)phenethyl)-6-(difluoromethyl)thieno[2,3-b]pyridine-2-carboxamide Into a 50-mL round-bottom flask was added tert-butyl 4-(4-(2-(3-amino-6-(difluoromethyl)thieno[2,3-b]pyridine-2-carboxamido)ethyl)-2-chlorophenyl)piperazine-1-carboxylate (0.020 g, 0.04 mmol) and 4 N hydrogen chloride/dioxane (3 mL). The solution was stirred for 2 h at RT and then concentrated in vacuo to provide a crude product that was purified by Prep-HPLC using the following conditions: Column, X Bridge C18, 19*150 mm, 5 µm; mobile phase, A: water (containing 10 mM NH$_4$HCO$_3$+0.05% ammonium hydroxide) and B: MeCN (15% to 45% over 4 min and then 45% to 80% over 8 min); Flow rate: 15 ml/min; UV Detector: 254 nm. This afforded the title compound as a yellow solid (3.0 mg, 18%). LCMS (ESI, m/z) 466 [M+H]$^+$; $^1$H NMR (300 MHz, CD$_3$OD) δ ppm 8.47 (d, J=8.7 Hz, 1H), 7.70 (d, J=8.1 Hz, 1H), 7.36-7.32 (m, 1H), 7.24-7.11 (m, 1H), 7.10-7.06 (m, 1H), 6.82 (t, J=55.2 Hz, 1H), 3.57-3.52 (m, 2H), 3.25-3.20 (m, 4H), 3.17-3.15 (m, 4H), 2.90-2.85 (m, 2H).

Examples 98-A (I-180) and 98-B (I-181)

(R)-3-amino-6-methyl-N-(4-(pyrrolidin-3-yl)phenethyl)thieno[2,3-b]pyridine-2-carboxamide (stereochemical configuration assumed) and (S)-3-amino-6-methyl-N-(4-(pyrrolidin-3-yl)phenethyl)thieno[2,3-b]pyridine-2-carboxamide (stereochemical configuration assumed)

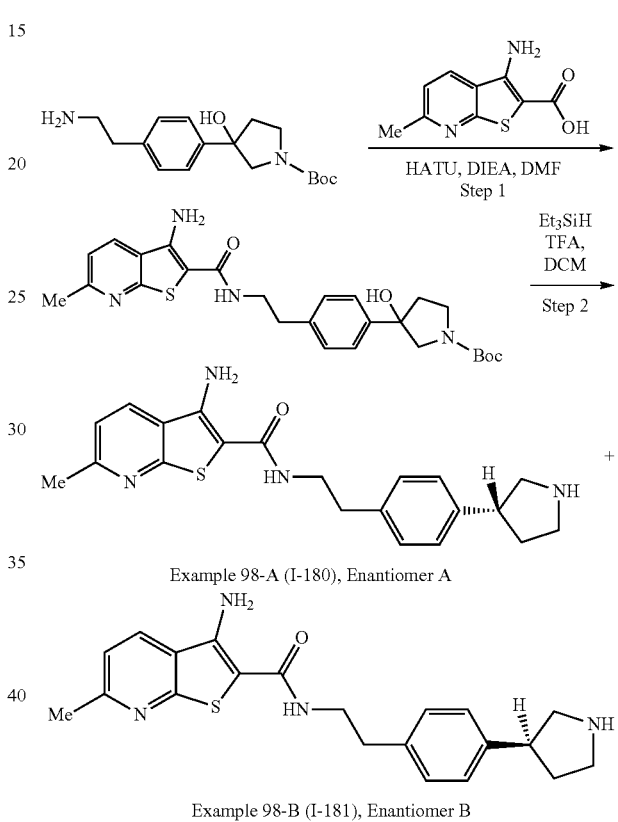

Example 98-A (I-180), Enantiomer A

Example 98-B (I-181), Enantiomer B

Step 1. Racemic tert-butyl 3-(4-(2-(3-amino-6-methylthieno[2,3-b]pyridine-2-carboxamido) ethyl)phenyl)-3-hydroxypyrrolidine-1-carboxylate Into a 100-mL round-bottom flask was added tert-butyl 3-[4-(2-aminoethyl)phenyl]-3-hydroxypyrrolidine-1-carboxylate (3.00 g, 9.79 mmol), 3-amino-6-methylthieno[2,3-b]pyridine -2-carboxylic acid (1.63 g, 7.83 mmol), HATU (3.73 g, 9.81 mmol), DIEA (3.79 g, 5.11 mL, 29.33 mmol), and DMF (30 mL). The resulting solution was stirred for 4 h at RT and then water (100-mL) was added. The resulting solution was extracted with ethyl acetate (3×50-mL) and the combined organic layers were concentrated in vacuo to provide a crude product that was purified via silica gel chromatography and eluted with ethyl acetate/petroleum ether (1:1) to afford racemic tert-butyl 3-(4-(2-(3-amino-6-methylthieno[2,3-b]pyridine-2-carboxamido)ethyl) phenyl)-3-hydroxypyrrolidine-1-carboxylate as a yellow solid (280 mg, 6%). LCMS (ESI, m/z): 497 [M+H]$^+$.

Step 2. Enantiomer A: (R)-3-amino-6-methyl-N-(4-(pyrrolidin-3-yl)phenethyl)thieno[2,3-b]pyridine-2-carboxamide (stereochemical configuration assumed), and Enantiomer B: (S)-3-amino-6-methyl-N-(4-(pyrrolidin-3-yl)phenethyl)thieno[2,3-b]pyridine-2-carboxamide (stereochemical configuration assumed)

Into a 50-mL round-bottom flask was added racemic tert-butyl 3-(4-(2-(3-amino-6-methylthieno[2,3-b]pyridine-2-carboxamido)ethyl)phenyl)-3-hydroxyl)yrrolidine-1-carboxylate (0.200 g, 0.40 mmol), Et₃SiH (0.935 g, 8.06 mmol), and dichloromethane (20 mL). The resulting solution was stirred for 1 h at RT. TFA (0.459 g, 0.308 mL, 4.03 mmol) was added and the resulting solution was stirred for 4 h at RT. The reaction mixture was then concentrated in vacuo to provide a crude product that was purified by Prep-HPLC using the following conditions (waters 2767): Column, X Bridge C18, 19*150 mm, 5 µm; mobile phase, A: water (containing 10 mM NH₄HCO₃+0.05% ammonium hydroxide) and B: CH₃CN (15% to 30% over 3 min, and then 30% to 75% over 8 min); Flow rate: 20 mL/min; UV Detector: 254 nm. 80 mg of pure product was obtained as a mixture of stereoisomers. The mixture was then purified by Chiral-Prep-HPLC using the following conditions (SHIMADZU LC-20AD): Column, DAICEL CHIRALPAK AD-3; mobile phase, Phase A: Acetonitrile (0.1% DEA) Phase B: Ethanol; UV Detector: 190 nm to 500 nm. This afforded the title compounds as follows:

Enantiomer A: 8.8 mg (6%) as a yellow solid (retention time=2.38 min). LCMS (ESI, m/z): 381 [M+H]⁺; ¹H NMR (300 MHz, CD₃OD) δ ppm 8.19 (d, J=8.4 Hz, 1H), 7.32 (d, J=8.1 Hz, 5H), 7.26-7.22 (m, 4H), 3.62-3.39 (m, 5H), 3.26-3.11 (m, 1H), 3.01-2.83 (m, 3H), 2.65 (s, 3H), 2.41-2.28 (m, 1H), 2.05-1.89 (m, 1H).

Enantiomer B: 2.8 mg (2%) as a yellow oil (retention time=3.04 min). LCMS (ESI, m/z): 381 [M+H]⁺; ¹H NMR (300 MHz, CD₃OD) δ ppm 8.20 (d, J=8.1 Hz, 1H), 7.42-7.12 (m, 5H), 3.62-3.32 (m, 5H), 3.26-3.11 (m, 1H), 3.01-2.83 (m, 3H), 2.65 (s, 3H), 2.41-2.28 (m, 1H), 2.08-1.92 (m, 1H).

Example 99 (I-182)

3-Amino-N-(3-hydroxy-4-(piperazin-1-yl)phenethyl)-6-methylthieno [2,3-b]pyridine-2-carboxamide Step 1. tert-butyl 4-(4-(2-(3-amino-6-methylthieno[2,3-b]pyridine-2-carboxamido)ethyl)-2-hydroxyphenyl)piperazine-1-carboxylate To a solution of tert-butyl 4-(4-(2-(3-amino-6-methylthieno[2,3-b]pyridine-2-carboxamido)ethyl)-2-bromophenyl)piperazine-1-carboxylate (0.2 M in 1,4-dioxane, 150 µL, 0.03 mmol) was added aqueous cesium hydroxide (2 M; 300 µL, 0.6 mmol), di-tert-butyl(2',4',6'-triisopropyl-3,6-dimethoxy-[1,1'-biphenyl]-2-yl)phosphine (tBuBrettPhos, 0.02 M in 1,4-dioxane, 240 µL, 4.80 µmol) and tris(dibenzylideneacetone)dipalladium(0) (0.02 M in 1,4-dioxane, 30 µL, 0.6 µmol). The resulting mixture was heated to 80° C. overnight. After being cooled to RT, brine (0.5 mL) was added and the mixture was extracted with ethyl acetate (2×0.5 mL). The combined organic layers were concentrated in vacuo to afford crude tert-butyl 4-(4-(2-(3-amino-6-methylthieno[2,3-b]pyridine-2-carboxamido)ethyl)-2-hydroxyphenyl)piperazine-1-carboxylate which was used in the next step without further purification.

Step 2. 3-Amino-N-(3-hydroxy-4-(piperazin-1-yl)phenethyl)-6-methylthieno[2,3-b]pyridine -2-carboxamide The crude product from Step 1 was dissolved in methanol (0.4 mL) and then 4 N HCl in dioxane (75 µL, 0.3 mmol) was added. The resulting mixture was heated to 50° C. for 1 h and then concentrated in vacuo to provide a crude product that was purified by HPLC (Waters Autopurification MS-directed HPLC prep fraction collection using the following conditions: Column:Waters XBridge OBD C18, 5 µm, 19×50 mm; flow rate 20 mL/min; mobile phase, A: water with 0.1% ammonium hydroxide and B: methanol with 0.1% ammonium hydroxide running the following gradient 0 to 2 mins (15% B), 2 to 6 mins (15-100% B); Detector ZQ Mass Detector in electrospray ionization mode) to afford 3-amino-N-(3-hydroxy-4-(piperazin-1-yl)phenethyl)-6-methylthieno[2,3-b]pyridine-2-carboxamide (1.8 mg, 15%). LCMS (ESI m/z): 412 [M+H]⁺.

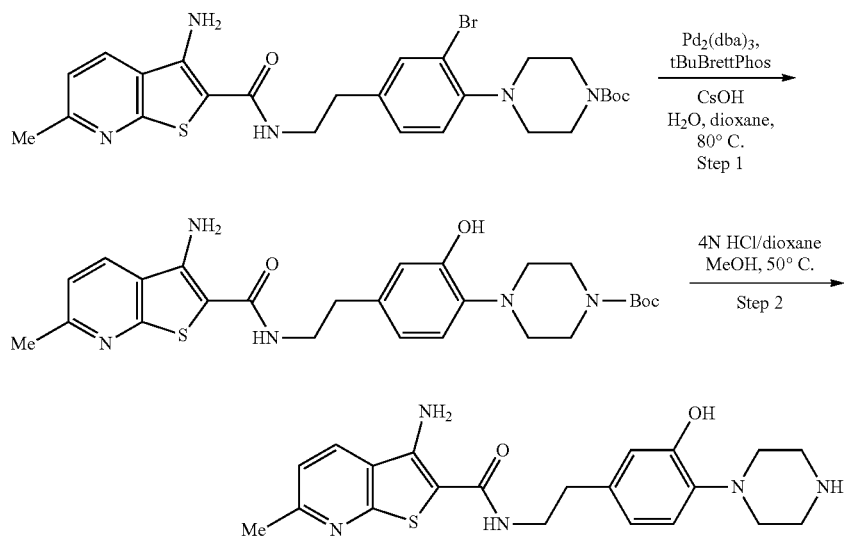

Example 99 (I-182)

Example 100-1 (I-183)

3,6-Diamino-4-methyl-N-(4-(piperazin-1-yl)phenethyl)thieno[2,3-b]pyridine-2-carboxamide

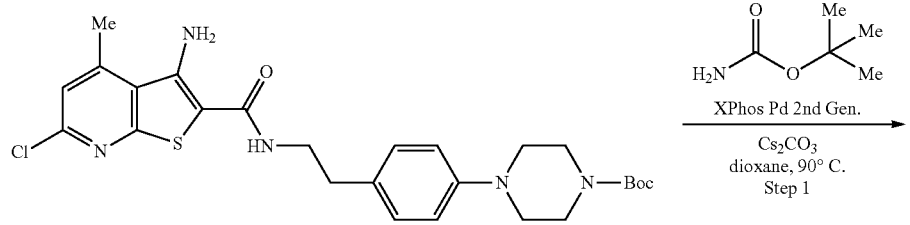

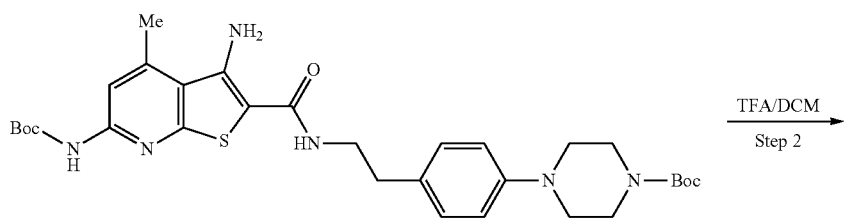

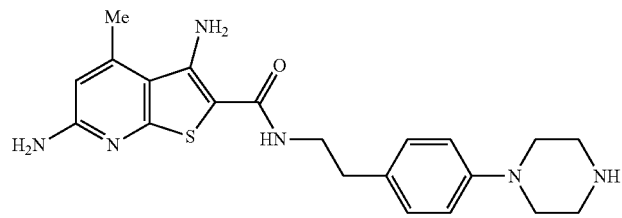

Example 100-1 (I-183)

Step 1. tert-Butyl 4-(4-(2-(3-amino-6-((tert-butoxycarbonyl)amino)-4-methylthieno[2,3-b]pyridine-2-carboxamido)ethyl)phenyl)piperazine-1-carboxylate To a suspension of tert-butyl 4-(4-(2-(3-amino-6-chloro-4-methylthieno[2,3-b]pyridine-2-carboxamido)ethyl)phenyl)piperazine-1-carboxylate (100.0 mg, 0.189 mmol), tert-butyl carbamate (110 mg, 0.943 mmol), and cesium carbonate (307 mg, 0.943 mmol) in 1,4-dioxane (1 ml) was added XPhos Pd $2^{nd}$ generation precatalyst (37.1 mg, 0.047 mmol). Nitrogen was bubbled through the reaction mixture for 2 minutes and then the reaction was heated to 90° C. overnight. The reaction was cooled to RT and the crude product was purified by FCC eluting with 20-40% EtOAc in hexanes. The resulting product was dissolved in 1:1 MeOH/water (2 mL) and purified by RP HPLC (C18 column; gradient: 0-90% MeCN in water containing 0.1% ammonium hydroxide over 15 minutes). Lyophilization afforded the title compound as a light yellow solid (24 mg, 20.8%). LCMS (ESI, m/z): 611 [M+H]$^+$.

Step 2. 3,6-Diamino-4-methyl-N-(4-(piperazin-1-yl)phenethyl)thieno[2,3-b]pyridine-2-carboxamide Trifluoroacetic acid (100 µl, 1.535 mmol) was slowly added to a solution of tert-butyl 4-(4-(2-(3-amino-6-((tert-butoxycarbonyl)amino)-4-methylthieno[2,3-b]pyridine-2-carboxamido)ethyl)phenyl)piperazine-1-carboxylate (20.0 mg, 0.033 mmol) in dichloromethane (1.0 ml). The reaction was stirred at RT for 2 hours and then concentrated in vacuo to provide a crude product that was dissolved in MeOH (1 mL) and purified by RP HPLC (C18 column; gradient: 0-90% MeCN in water containing 0.1% ammonium hydroxide over 15 minutes). Lyophilization afforded the title compound as a white powder (3.1 mg, 49%). LCMS (ESI, m/z):411 [M+H]$^+$; $^1$H NMR (300 MHz, DMSO-d$_6$) δ ppm 7.33 (m, 1H), 7.05 (d, J=8.5 Hz, 2H), 6.84 (d, J=8.8 Hz, 2H), 6.64 (s, 2H), 6.44 (s, 2H), 6.19 (s, 1H), 3.34 (m, 2H), 2.98 (m, 4H), 2.82 (m, 4H), 2.70 (m, 2H), 2.54 (s, 3H).

The Examples in Table 22 below were synthesized according to the procedures outlined above for Example 100-1 (I-183), using the appropriate synthetic precursors. Additional detail around the synthetic methods as well as HPLC purification conditions appears the table below.

TABLE 22

| Example (Cmpd no.) | Structure | MS (ESI, m/z) [M + H] | $^1$H NMR |
|---|---|---|---|
| 100-2[1] (I-184) | 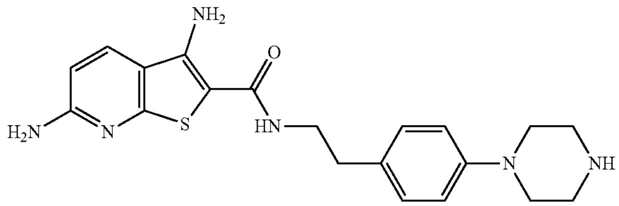 [SMILES: Nc1ccc2c(N)c(C(=O)NCCc3ccc(N4CCNCC4)cc3)sc2n1] | 397 | (300 MHz, DMSO-$d_6$) δ ppm 7.91 (d, J = 8.8 Hz, 1H), 7.31 (m, 1H), 7.05 (d, J = 8.5 Hz, 2H), 6.94 (s, 2H), 6.84 (d, J = 8.8 Hz, 2H), 6.55 (s, 2H), 6.45 (d, J = 8.8 Hz, 1H), 3.32 (m, 2H), 2.98 (m, 4H), 2.81 (m, 4H), 2.70 (m, 2H) |
| 100-3[2] (I-185) | 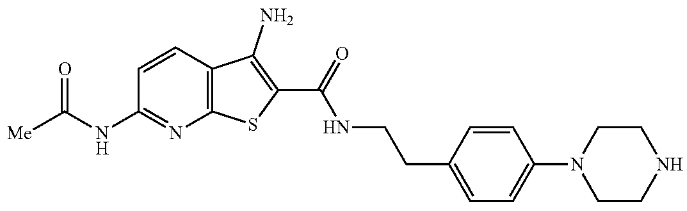 [SMILES: CC(=O)Nc1ccc2c(N)c(C(=O)NCCc3ccc(N4CCNCC4)cc3)sc2n1] | 440 | (300 MHz, DMSCMs) δ ppm 8.36 (d, J = 8.2 Hz, 1H), 8.33 (s, 1H), 8.12 (d, J = 8.2 Hz, 1H), 7.67 (m, 1H), 7.14 (s, 2H), 7.07 (d, J = 8.5 Hz, 2H), 6.85 (d, J = 8.5 Hz, 2H), 3.37 (m, 2H), 3.02 (m, 4H), 2.85 (m, 4H), 2.70 (m, 2H), 2.12 (s, 3H) |

[1] Prep HPLC Purification Method: (C18 column; gradient: 0-90% MeCN in water containing 0.1% ammonium hydroxide over 15 minutes).
[2] Prep HPLC Purification Method: HPLC (C18 column; gradient: 0-90% MeCN in water containing 0.1% formic acid over 8 minutes)

Example 101-1 (I-186)

3-Amino-6-(dimethylamino)-N-(4-(piperazin-1-yl) phenethyl)thieno [2,3-b]pyridine-2-carboxamide

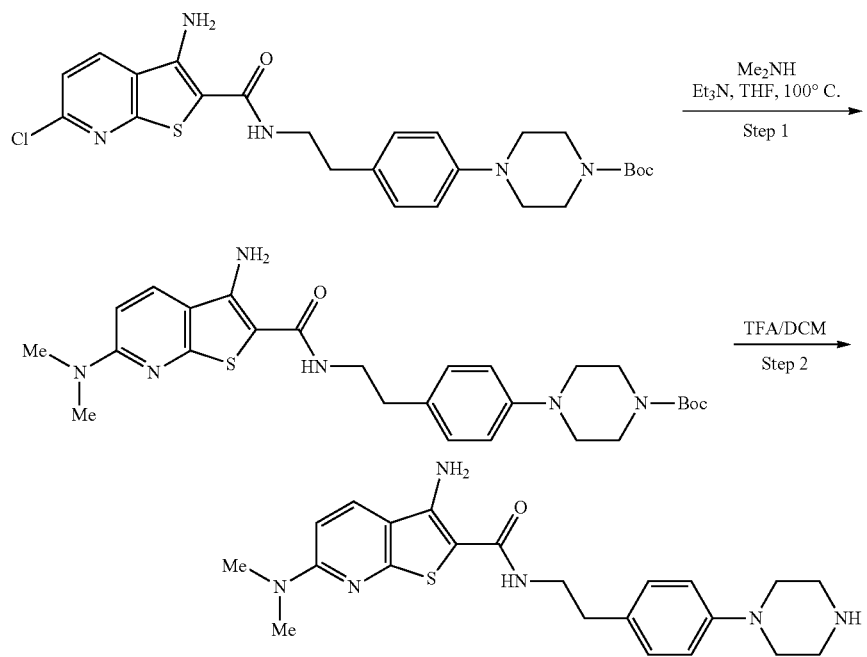

Example 101-1 (I-186)

Step 1. tert-Butyl 4-(4-(2-(3-amino-6-(dimethylamino) thieno[2,3-b]pyridine-2-carboxamido) ethyl)phenyl)piperazine-1-carboxylate To a solution of tert-butyl 4-(4-(2-(3-amino-6-chlorothieno[2,3-b]pyridine-2-carboxamido)ethyl)phenyl)piperazine-1-carboxylate (0.030 g, 0.058 mmol), and dimethylamine (2.0 M in THF, 1.0 mL, 2.0 mmol) was added DIEA (0.030 mL, 0.174 mmol). The reaction mixture was heated in a sealed tube at 100° C. overnight and then cooled and concentrated in vacuo to provide a crude product that was purified by FCC eluting with 50-70% EtOAc in hexanes to afford tert-butyl 4-(4-(2-(3-amino-6-(dimethylamino)thieno [2,3-b]pyridine-2-carboxamido)ethyl)phenyl)piperazine-1-carboxylate as a light yellow solid (18.9 mg, 62%). LCMS (ESI, m/z): 525 [M+H]$^+$.

Step 2. 3-Amino-6-(dimethylamino)-N-(4-(piperazin-1-yl)phenethyl)thieno[2,3-b]pyridine-2-carboxamide Trifluoroacetic acid (1.00 mL, 15.3 mmol) was slowly added to a solution of tert-butyl 4-(4-(2-(3-amino-6-(dimethylamino)thieno[2,3-b]pyridine-2-carboxamido)ethyl) phenyl) piperazine-1-carboxylate (0.018 g, 0.034 mmol) in dichloromethane (2.0 ml). The reaction was stirred at RT for 2 hours and then concentrated in vacuo to provide a crude product that was then dissolved in DMSO (1 mL) and purified by RP HPLC (C18 column; gradient: 0-90% MeCN in water containing 0.1% ammonium hydroxide over 15 minutes). Lyophilization afforded the title compound as a white powder (13 mg, 87%). LCMS (ESI, m/z): 425 [M+H]$^+$; $^1$H NMR (300 MHz, DMSO-d$_6$) δ ppm 8.05 (d, J=9.1 Hz, 1H), 7.30 (m, 1H), 7.06 (d, J=8.5 Hz, 2H), 6.99 (s, 2H), 6.84 (d, J=8.5 Hz, 2H), 6.74 (d, J=9.1 Hz, 1H), 3.30 (m, 2H), 3.10 (s, 6H), 2.99 (m, 4H), 2.82 (m, 4H), 2.68 (m, 2H).

The Examples in Table 23 below were synthesized according to the procedures outlined above for Example 101-1 (I-186), using the appropriate synthetic precursors. Additional detail around the synthetic methods as well as HPLC purification conditions appears in the table below.

TABLE 23

| Example (Cmpd no.) | Structure | MS (ESI, m/z) [M + H] | $^1$H NMR |
|---|---|---|---|
| 101-2[1] (I-187) | 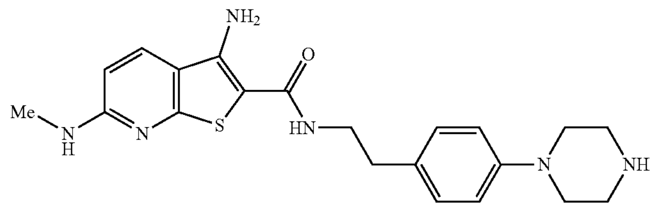 [SMILES: CNc1ccc2c(N)c(C(=O)NCCc3ccc(N4CCNCC4)cc3)sc2n1] | 411 | (300 MHz, DMSO-d6) δ ppm 7.90 (d, J = 9.1 Hz, 1H), 7.28 (m, 1H), 7.12 (m, 1H), 7.05 (d, J = 8.8 Hz, 2H), 6.94 (s, 2H), 6.84 (d, J = 8.8 Hz, 2H), 6.47 (d, J = 9.1 Hz, 1H), 3.34 (m, 2H), 2.98 (m, 4H), 2.81 (m, 7H), 2.68 (m, 2H). |
| 101-3[1] (I-188) | 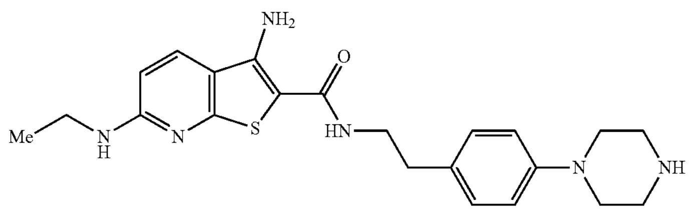 | 425 | (300 MHz, CD$_3$OD) δ ppm 7.78 (d, J = 8.8 Hz, 1H), 7.17 (d, J = 8.5 Hz, 2H), 6.94 (d, J = 8.8 Hz, 2H), 6.48 (d, J = 9.1 Hz, 1H), 3.43 (m, 4H), 3.18 (m, 4H), 3.08 (m, 4H), 2.80 (m, 2H), 1.24 (t, J = 7.2 Hz, 3H). |
| 101-4[1] (I-189) | 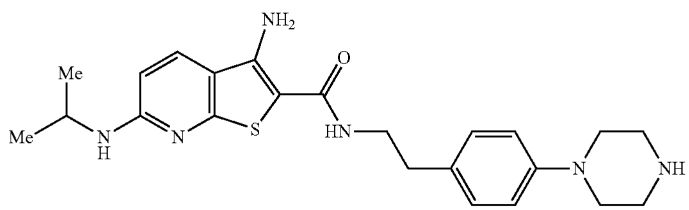 [SMILES: CCNc1ccc2c(N)c(C(=O)NCCc3ccc(N4CCNCC4)cc3)sc2n1] | 439 | (300 MHz, CD$_3$OD) δ ppm 7.76 (d, J = 9.1 Hz, 1H), 7.16 (d, J = 8.5 Hz, 2H), 6.94 (d, J = 8.5 Hz, 2H), 6.45 (d, J = 9.1 Hz, 1H), 4.12 (m, 1H), 3.47 (m, 2H), 3.13 (m, 4H), 3.03 (m, 4H), 2.78 (m, 2H), 1.22 (d, J = 6.4 Hz, 6H). |

[1]Prep HPLC Purification Method: (C18 column; gradient: 0-90% MeCN in water containing 0.1% ammonium hydroxide over 15 minutes)
[2]Notes:
Step 1 was conducted with propan-2-amine as solvent in a sealed pressure tube. Prep HPLC Purification Method: (C18 column: gradient: 0-90% MeCN in water containing 0.1% ammonium hydroxide over 15 minutes).

Example 102-1 (I-190)

3-Amino-6-methoxy-N-(4-(piperazin-1-yl)phenethyl)thieno[2,3-b]pyridine-2-carboxamide

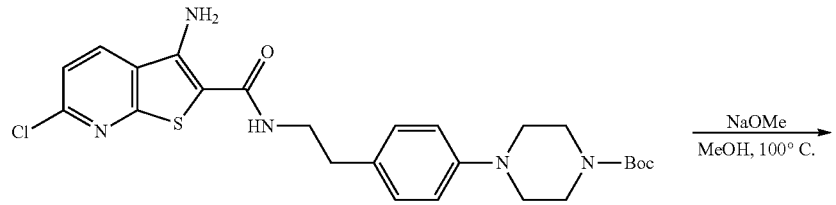

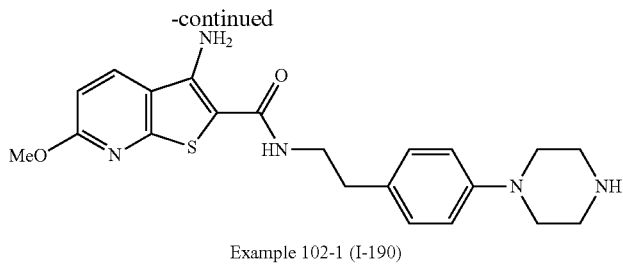

Example 102-1 (I-190)

To a solution of tert-butyl 4-(4-(2-(3-amino-6-chlorothieno[2,3-b]pyridine-2-carboxamido)ethyl)phenyl)piperazine-1-carboxylate (0.050 g, 0.097 mmol) in MeOH (1.0 mL) was added sodium methoxide (25 wt % in MeOH; 0.250 g, 1.157 mmol). The reaction mixture was heated to 100° C. in a sealed tube overnight and then cooled to RT and concentrated in vacuo to afford the crude product. The crude product was dissolved in DMSO (1 mL) and was purified by RP HPLC (C18 column; gradient: 0-90% MeCN in water containing 0.1% ammonium hydroxide over 15 minutes). Lyophilization afforded the title compound as a white powder (15 mg, 37%). LCMS (ESI, m/z): 412 [M+H]$^+$; $^1$H NMR (300 MHz, DMSO-d$_6$) δ ppm 8.30 (d, J=8.8 Hz, 1H), 7.59 (m, 1H), 7.11 (s, 2H), 7.06 (d, J=8.8 Hz, 2H), 6.85 (m, 3H), 3.93, (s, 3H), 3.34 (m, 2H), 2.98 (m, 4H), 2.81 (m, 4H), 2.70 (m, 2H).

The Examples in Table 24 below were synthesized according to the procedures outlined above for Example 102-1 (I-190), using the appropriate synthetic precursors. Additional detail around the synthetic methods as well as HPLC purification conditions appears below each example.

TABLE 24

| Example (Cmpd no.) | Structure | MS (ESI, m/z) [M + H] | $^1$H NMR |
|---|---|---|---|
| 102-2[1] (I-191) | 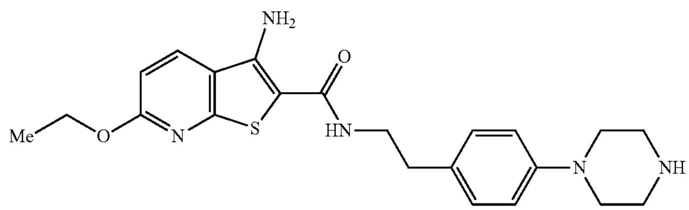 [SMILES: CCOc1ccc2c(N)c(C(=O)NCCc3ccc(N4CCNCC4)cc3)sc2n1] | 426 | (300 MHz, CD3OD) δ ppm 8.10 (d, J = 8.8 Hz, 1H), 7.17 (d, J = 8.8 Hz, 2H), 6.94 (d, J = 8.8 Hz, 2H), 6.75 (d, J = 8.8 Hz, 1H), 4.40 (q, J = 6.7 Hz, 2H), 3.47 (m, 2H), 3.16 (m, 4H), 3.07 (m, 4H), 2.80 (m, 2H), 1.40 (t, J = 7.0 Hz, 3H) |
| 102-3[2] (I-192) | 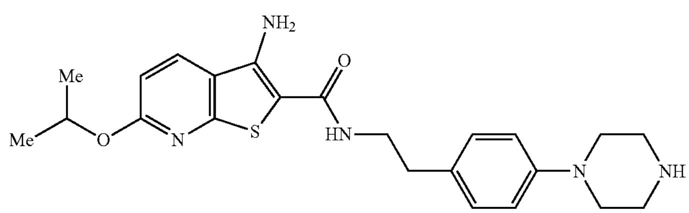 [SMILES: CC(C)Oc1ccc2c(N)c(C(=O)NCCc3ccc(N4CCNCC4)cc3)sc2n1] | 440 | (300 MHz, CD$_3$OD) δ ppm 8.06 (d, J = 8.8Hz, 1H), 7.16 (d, J = 8.5 Hz, 2H), 6.94 (d, J = 8.5 Hz, 2H), 6.69 (d, J = 8.8 Hz, 1H), 5.35 (m, 1H), 3.47 (m, 2H), 3.10 (m, 4H), 2.98 (m, 4H), 2.78 (m, 2H), 1.36 (d, J = 6.4 Hz, 6H) |

[1]Prep TLC Purification Method: 5 ×10 cm silica gel plates. Plates were developed using 30% EtOAc in MeOH and eluted 5 additional times to achieve the desired separation. The bands of desired product were collected, washed, and filtered using DCM.
[2]Notes:
iPrOH/NaH in THF at 100° C. (sealed pressure tube) was used Prep HPLC Purification Method: (C18 column; gradient: 0-90% MeCN in water containing 0.1% NH$_4$OH over 15 min).

Example 103 (I-193)

3-Amino-6-(difluoromethoxy)-N-(4-(piperazin-1-yl) phenethyl) thieno [2,3-b]pyridine-2-carboxamide

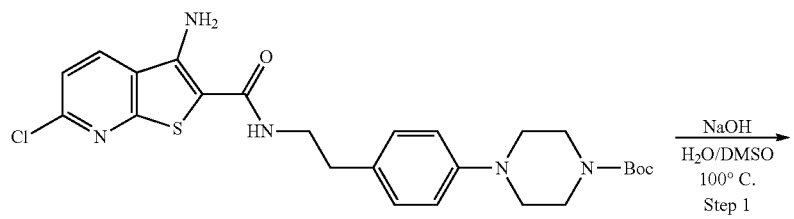

Step 1

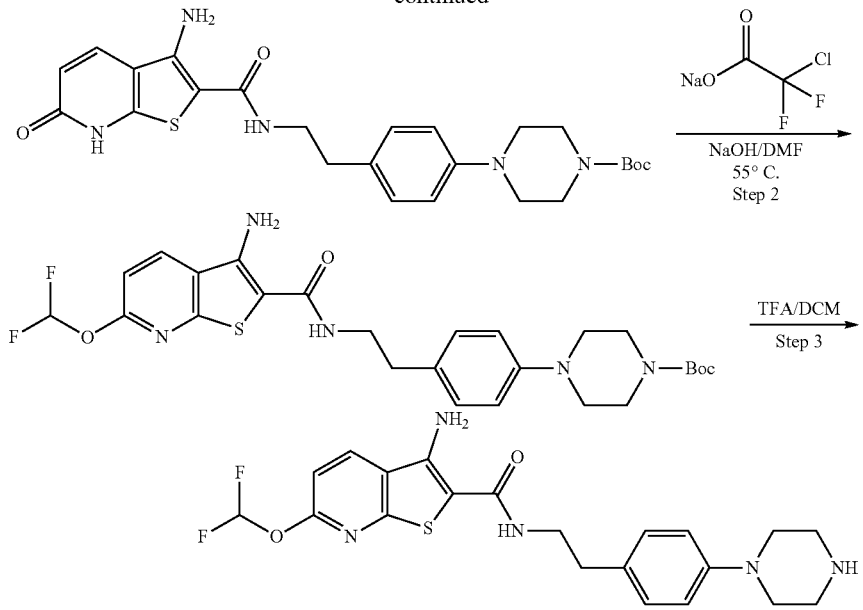

Example 103 (I-193)

Step 1. tert-Butyl 4-(4-(2-(3-amino-6-oxo-6,7-dihydrothieno[2,3-b]pyridine-2-carboxamido) ethyl)phenyl)piperazine-1-carboxylate To a solution of tert-butyl 4-(4-(2-(3-amino-6-chlorothieno[2,3-b]pyridine-2-carboxamido)ethyl)phenyl)piperazine-1-carboxylate (0.050 g, 0.097 mmol) in DMSO (1.0 ml) and water (1.0 ml) was added sodium hydroxide (0.039 g, 0.969 mmol). The reaction mixture was heated to 100° C. overnight and then cooled to RT, diluted with brine (10 mL), and extracted with EtOAc (2×25 mL). The combined organic layers were washed with brine (10 mL), dried over sodium sulfate, filtered, and concentrated in vacuo to provide a crude product that was purified by FCC eluting with 60-80% EtOAc in hexanes to afford tert-butyl 4-(4-(2-(3-amino-6-oxo-6,7-dihydrothieno[2,3-b]pyridine-2-carboxamido)ethyl)pheny Dpiperazine-1-carboxylate as a light red solid (19 mg, 39%). LCMS (ESI, m/z): 498 [M+H]$^+$.

Step 2. tert-Butyl 4-(4-(2-(3-amino-6-(difluoromethoxy)thieno[2,3-b]pyridine-2-carboxamido)ethyl)phenyl)piperazine-1-carboxylate Sodium hydroxide (0.003 g, 0.066 mmol) was added to a solution of tert-butyl 4-(4-(2-(3 -amino-6-oxo-6,7-dihydrothieno[2,3-b]pyridine-2-carboxamido)ethyl)phenyl)piperazine-1-carboxylate (30 mg, 0.060 mmol) and sodium 2-chloro-2,2-difluoroacetate (18.38 mg, 0.121 mmol) in DMF (0.5 ml). The reaction mixture was heated to 55° C. overnight, and then cooled and quenched with water (5 mL). The reaction was extracted with EtOAc (2×10 mL). The combined organic layers were washed with saturated sodium bicarbonate (aq, 10 mL) and brine (10 mL), dried over sodium sulfate, filtered, and concentrated in vacuo to provide a crude product that was purified by FCC eluting with 50-70% EtOAc in hexanes to afford tert-butyl 4-(4-(2-(3-amino-6-(difluoromethoxy)thieno[2,3-b]pyridine-2-carboxamido)ethyl)phenyl) piperazine-1-carboxylate as a white solid (18 mg, 54%). LCMS (ESI, m/z): 548 [M+H]$^+$.

Step 3. 3-Amino-6-(difluoromethoxy)-N-(4-(piperazin-1-yl)phenethyl)thieno[2,3-b]pyridine-2-carboxamide TFA (0.5 mL, 7.67 mmol) was slowly added to a solution of tert-butyl 4-(4-(2-(3-amino-6-(difluoromethoxy)thieno[2,3-b]pyridine-2-carboxamido)ethyl)phenyl)piperazine-1-carboxylate (15.0 mg, 0.027 mmol) in dichloromethane (1.0 ml). The reaction was stirred at RT for 2 hours and then concentrated in vacuo to provide a crude product that was dissolved in DMSO (1 mL) and was purified by RP HPLC (C18 column; gradient: 0-90% MeCN in water containing 0.1% ammonium hydroxide over 15 minutes). Lyophilization afforded the title compound as a white powder (8.7 mg, 71%). LCMS (ESI, m/z): 448 [M+H]$^+$; $^1$H NMR (300 MHz, DMSO-d$_6$) δ ppm 8.52 (d, J=8.8 Hz, 1H), 7.80 (s, 1H), 7.76 (m, 1H), 7.20 (s, 2H), 7.13 (d, J=8.8 Hz, 1H), 7.05 (d, J=8.5 Hz, 2H), 6.84 (d, J=8.5 Hz, 2H), 3.34 (m, 2H), 2.98 (m, 4H), 2.81 (m, 4H), 2.73 (m, 2H).

Example 104-1 (I-194)

3-Amino-6-(methylamino)-N-(4-(1-methylpiperidin-4-yl)phenethyl)thieno[2,3-b]pyridine-2-carboxamide

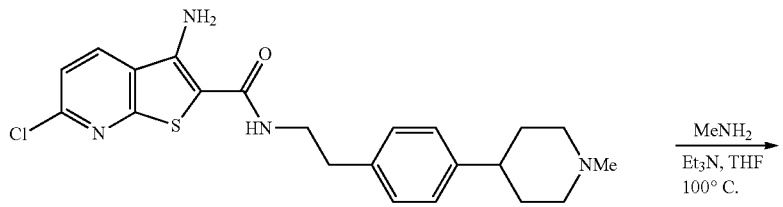

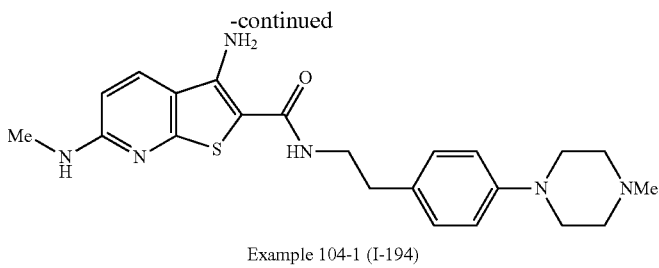

Example 104-1 (I-194)

To a solution of 3-amino-6-chloro-N-(4-(1-methylpiperidin-4-yl)phenethyl)thieno[2,3-b]pyridine-2-carboxamide (0.100 g, 0.233 mmol) and methanamine (2.0M in THF; 2.0 mL, 4.00 mmol) was added DIEA (0.122 mL, 0.699 mmol). The reaction mixture was heated to 100° C. overnight in a sealed tube and then cooled and concentrated in vacuo to provide a crude product that was purified by FCC eluting with 60-80% EtOAc in hexanes to afford 3-amino-6-(methylamino)-N-(4-(1-methylpiperidin-4-yl)phenethyl)thieno[2,3-b]pyridine-2-carboxamide as a light yellow solid (10.4 mg, 11%). LCMS (ESI, m/z): 510 [M+H]+; 1H NMR (300 MHz, DMSO -d6) δ ppm 7.90 (d, J=8.8 Hz, 1H), 7.32 (m, 1H), 7.15 (m, 5H), 6.94 (s, 2H), 6.48 (d, J=8.8 Hz, 1H), 3.33 (m, 3H), 2.83 (m, 5H), 2.73 (m, 2H), 2.18 (s, 3H), 1.95 (m, 2H), 1.69 (m, 4 H).

The Examples in Table 25 below were synthesized according to the procedures outlined above for Example 104-1 (I-194), using the appropriate synthetic precursors. Additional detail around the synthetic methods as well as HPLC purification conditions appears below each example.

TABLE 25

| Example (Cmpd no.) | Structure | MS (ESI, m/z) [M + H] | 1H NMR |
|---|---|---|---|
| 104-2[1] (I-195) | 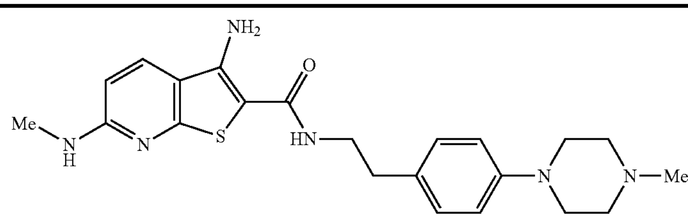 | 425 | (300 MHz, DMSO-d6) δ ppm 7.90 (d, J = 8.8 Hz, 1H), 7.27 (m, 1H), 7.10 (m, 1H), 7.05 (d, J = 8.5 Hz, 2H), 6.93 (s, 2H), 6.86 (d, J = 8.5 Hz, 2H), 6.47 (d, J = 8.8 Hz, 1H), 3.31 (m, 2H), 3.07 (m, 4H), 2.82 (d, J = 4.7 Hz, 3H), 2.68 (m, 2H), 2.42 (m, 4H), 2.21 (s, 3H) |
| 104-3[2] (I-196) | 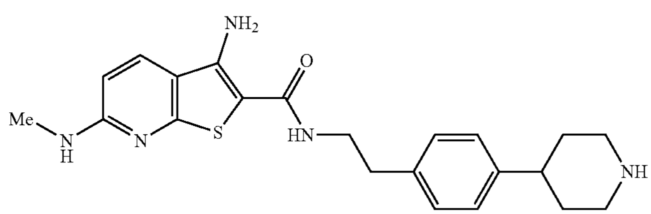 | 410 | (300 MHz, CD3OD) δ ppm 7.80 (d, J = 8.8 Hz, 1H), 7.20 (m, 4H), 6.49 (d, J = 8.8 Hz, 1H), 4.92 (m, 2H), 4.52 (m, 1H), 3.47 (m, 2H), 2.93 (m, 5H), 2.87 (m, 2H), 1.93 (m, 2 H), 1.79 (m, 2H) |

[1]Note:
Boc deprotection was not necessary. Prep HPLC Purification Method: (C18 column; gradient: 0-90% MeCN in water containing 0.1% NH4OH over 15 min).

[2]Notes:
TFA/DCM was used to deprotect the Boc-protected piperidine. Prep HPLC Purification Method: (C18 column; gradient: 0-90% MeCN in water containing 0.1% NH4OH over 15 min)

Example 105 (I-197)

3-Amino-5-cyclopropyl-6-methyl-N-(4-(piperazin-1-yl)phenethyl)thieno[2,3-b]pyridine-2-carboxamide (hydrochloride salt)

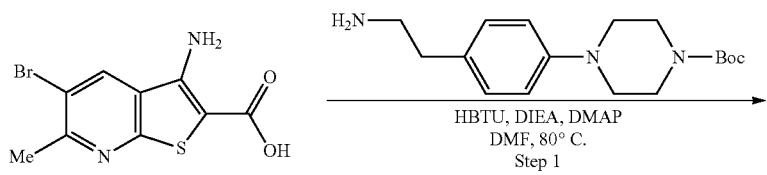

HBTU, DIEA, DMAP
DMF, 80° C.
Step 1

-continued

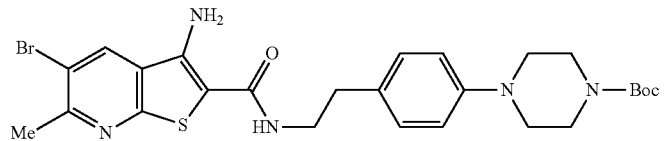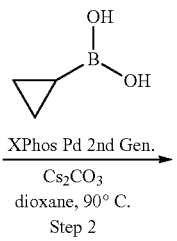

XPhos Pd 2nd Gen.
Cs₂CO₃
dioxane, 90° C.
Step 2

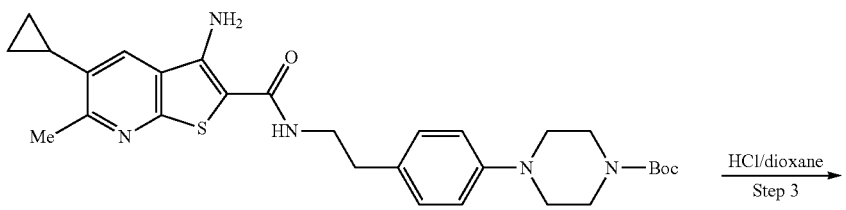

HCl/dioxane
Step 3

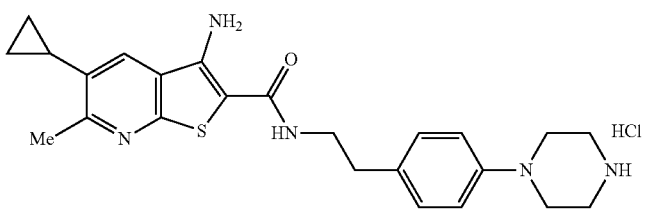

Example 105 (I-197)

Step 1. tert-Butyl 4-(4-(2-(3-amino-5-bromo-6-methylthieno[2,3-b]pyridine-2-carboxamido) ethyl)phenyl)piperazine-1-carboxylate To a solution of 3-amino-5-bromo-6-methylthieno[2,3-b]pyridine-2-carboxylic acid (0.400 g, 1.39 mmol), tert-butyl 4-(4-(2-aminoethyl)phenyl)piperazine-1-carboxylate (0.425 g, 1.393 mmol), DMAP (0.017 g, 0.139 mmol), and HBTU (0.634 g, 1.672 mmol) in DMF (10.0 ml) was added DIEA (0.728 ml, 4.18 mmol). The reaction was stirred at 80° C. overnight and then cooled to RT. Water (10 mL) was added, and a light orange precipitate formed. The precipitate was collected via filtration, washed sequentially with saturated aqueous ammonium chloride (10 mL), aqueous sodium bicarbonate (10 mL), water (10 mL), and ether (10 mL). The precipitate was collected, suspended, and slightly sonicated in EtOAc (10 mL). The suspended solid was then collected by filtration and dried in vacuo to afford tert-butyl 4-(4-(2-(3-amino-5-bromo-6-methylthieno[2,3-b]pyridine-2-carboxamido)ethyl)phenyl)piperazine-1-carboxylate as a light grey powder that was carried on without further purification (88%). LCMS (ES, m/z): 575 [M+H]⁺.

Step 2. tert-Butyl 4-(4-(2-(3-amino-5-cyclopropyl-6-methylthieno[2,3-b]pyridine-2-carboxamido)ethyl)phenyl)piperazine-1-carboxylate To a suspension of tert-butyl 4-(4-(2-(3-amino-5-bromo-6-methylthieno[2,3-b]pyridine-2-carboxamido)ethyl)phenyl)piperazine-1-carboxylate (0.050 g, 0.087 mmol), cyclopropylboronic acid (0.007 g, 0.087 mmol), and cesium carbonate (0.142 g, 0.435 mmol) in 1,4-dioxane (1 ml) was added XPhos Pd 2$^{nd}$ generation precatalyst (0.017 g, 0.022 mmol). The reaction mixture was sparged with nitrogen for 2 minutes and then the reaction was heated to 90° C. overnight. The reaction mixture was cooled and concentrated in vacuo to provide a crude product that was purified by FCC eluting with 40-60% EtOAc in hexanes to afford tert-butyl 4-(4-(2-(3-amino-5-cyclopropyl-6-methylthieno[2,3-b]pyridine-2-carboxamido)ethyl)phenyl) piperazine-1-carboxylate as a light yellow solid (32 mg, 68%). LCMS (ESI, m/z): 536 [M+H]⁺.

Step 3. 3-Amino-5-cyclopropyl-6-methyl-N-(4-(piperazin-1-yl)phenethyl)thieno[2,3-b]pyridine-2-carboxamide (hydrochloride salt)

To a solution of tert-butyl 4-(4-(2-(3-amino-5-cyclopropyl-6-methylthieno[2,3-b]pyridine-2-carboxamido)ethyl)phenyl)piperazine-1-carboxylate (0.030 g, 0.056 mmol) in dioxane (1.0 ml) was added 4 N HCl in dioxane (0.50-mL, 2.0 mmol) at RT. The reaction solution was stirred for 2 hours resulting in a precipitate. The reaction mixture was diluted with ether (2 mL) and the precipitate was collected by vacuum filtration. The precipitate was further washed with ether (1 mL), collected, and dried in vacuo to afford the title compound as a light orange solid (9.1 mg, 34%). LCMS (ESI, m/z): 436 [M+H]⁺; ¹H NMR (300 MHz, DMSO-d₆) δ ppm 8.05 (s, 1H), 7.68 (m, 1H), 7.10 (s, 2H), 7.04 (d, J=8.5 Hz, 2H), 6.86 (d, J=8.5 Hz, 2H), 3.35 (m, 2H), 2.91 (m, 4H), 2.73 (m, 4H), 2.67 (m, 5H), 2.04 (m, 1H), 1.01 (m, 2H), 0.98 (m, 2H).

Example 106 (I-198)

3,5-Diamino-6-methyl-N-(4-(piperazin-1-yl)phenethyl)thieno[2,3-b]pyridine-2-carboxamide

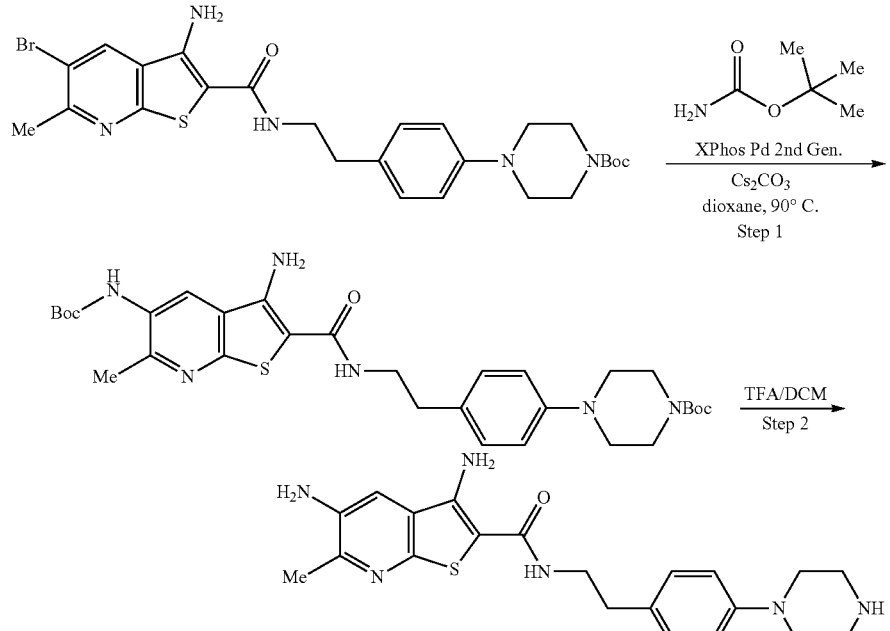

Example 106 (I-198)

Step 1. tert-Butyl 4-(4-(2-(3-amino-5-((tert-butoxycarbonyl)amino)-6-methylthieno[2,3-b]pyridine-2-carboxamido)ethyl)phenyl)piperazine-1-carboxylate To a suspension of tert-butyl 4-(4-(2-(3-amino-5-bromo-6-methylthieno[2,3-b]pyridine-2-carboxamido)ethyl)phenyl)piperazine-1-carboxylate (0.050 g, 0.087 mmol), tert-butyl carbamate (0.051 g, 0.44 mmol), and cesium carbonate (0.142 g, 0.435 mmol) in 1,4-dioxane (1 ml) was added XPhos Pd $2^{nd}$ generation precatalyst (0.017 g, 0.022 mmol). The reaction mixture was sparged with nitrogen for 2 minutes and then heated at 90° C. overnight. The reaction mixture was cooled and concentrated in vacuo to provide a crude product that was purified by FCC eluting with 40-60% EtOAc in hexanes to afford tert-butyl 4-(4-(2-(3-amino-5-((tert -butoxycarbonyl)amino)-6-methylthieno[2,3-b]pyridine-2-carboxamido)ethyl)phenyl)piperazine -1-carboxylate as a light yellow solid (39 mg, 78%). LCMS (ES, m/z): 611 [M+H]⁺.

Step 2. 3,5-Diamino-6-methyl-N-(4-(piperazin-1-yl) phenethyl)thieno[2,3-b]pyridine-2-carboxamide To a solution of tert-butyl 4-(4-(2-(3-amino-5-((tert-butoxycarbonyl)amino)-6-methylthieno [2,3-b]pyridine-2-carboxamido)ethyl)phenyl)piperazine-1-carboxylate (0.035 g, 0.057 mmol) in DCM (2.0 ml) was added trifluoroacetic acid (0.50-mL, 7.67 mmol) at RT. The reaction solution was stirred for 2 hours and then concentrated in vacuo to provide a crude product that was dissolved in 1:1 DMSO/water (2 mL) and purified by RP HPLC (C18 column; gradient: 0-90% MeCN in water containing 0.1% ammonium hydroxide over 15 minutes). Lyophilization afforded the title compound as a white powder (15 mg, 65%). LCMS (ESI, m/z): 411 [M+H]⁺; ¹H NMR (300 MHz, DMSO-d₆) δ ppm 7.52 (m, 1H), 7.38 (s, 1H), 7.05 (d, J=8.5 Hz, 2H), 6.90 (s, 2H), 6.84 (d, J=8.5 Hz, 2H), 5.16 (s, 2H), 3.29 (m, 2H), 2.98 (m, 4H), 2.82 (m, 4H), 2.69 (m, 2H), 2.39 (s, 3H).

Example 107 (I-199)

3-Amino-N-(2,5-difluoro-4-(3-(methylamino)azetidin-1-yl)phenethyl) -6-methylthieno[2,3-b]pyridine-2-carboxamide

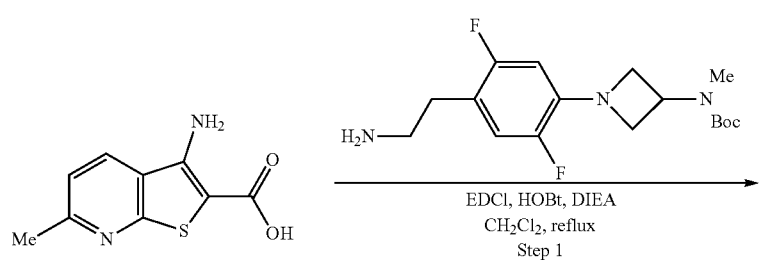

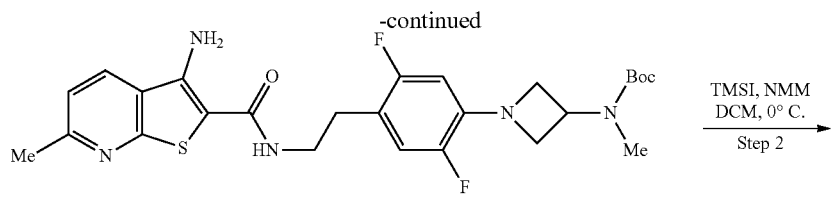

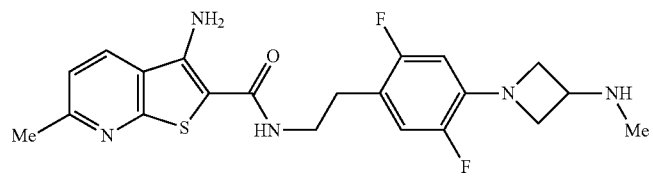

Example 107 (I-199)

Step 1. tert-Butyl (1-(4-(2-(3-amino-6-methylthieno[2,3-b]pyridine-2-carboxamido)ethyl) -2,5-difluorophenyl)azetidin-3-yl)(methyl)carbamate Into a 25-mL round-bottom flask was added 3-amino-6-methylthieno[2,3-b]pyridine -2-carboxylic acid (0.11 g, 0.53 mmol), tert-butyl N-[1-[4-(2-aminoethyl)-2,5-difluorophenyl]azetidin-3-yl]-N-methylcarbamate (0.18 g, 0.53 mmol), HOBt (0.086 g, 0.63 mmol), EDCI (0.120 g, 0.63 mmol), DIEA (0.205 g, 1.58 mmol), and dichloromethane (10 mL). The resulting solution was stirred for 2 h at 40° C. and then cooled and concentrated in vacuo to provide a crude product that was purified by Prep-HPLC using the following conditions (Waters I): LC parameters: Pump Mode: Binary gradient, Start Conc. of Pump B: 15.0%, End Conc. of Pump B: 70.0% Total Flow: 20 mL/min, Time: 8 min, Phase A: Water (0.1% FA), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm. This afforded tert-butyl (1-(4-(2-(3-amino-6-methylthieno[2,3-b]pyridine-2-carboxamido)ethyl)-2,5-difluorophenyl) azetidin-3-yl)(methyl)carbamate as a yellow solid (60 mg, 21%). LCMS (ESI, m/z): 532 [M+H]$^+$.

Step 2. 3-Amino-N-(2,5-difluoro-4-(3-(methylamino)azetidin-1-yl)phenethyl)-6-methylthieno[2,3-b]pyridine-2-carboxamide Into a 50-mL round-bottom flask was added tert-butyl (1-(4-(2-(3-amino-6-methylthieno[2,3-b]pyridine-2-carboxamido)ethyl)-2,5-difluorophenyl)azetidin-3-yl)(methyl) carbamate (0.060 g, 0.11 mmol), N-methyl morpholine (0.034 g, 0.037 mL, 0.34 mmol), and dichloromethane (10 mL) followed by the dropwise addition of trimethylsilyl iodide (0.045 g, 0.032 mL, 0.23 mmol) with stirring at 0° C. The resulting solution was stirred for 1 h at 0° C. and then concentrated in vacuo to provide a crude product that was purified by Prep-HPLC using the following conditions (SHIMADZU LC-20AD): LC parameters: Pump Mode: Binary gradient, Start Conc. of Pump B: 25.0%, End Conc. of Pump B: 38.0% Total Flow: 20 mL/min, Time: 8 min, Phase A: Water (10 mmol/L NH$_4$HCO$_3$), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm. This afforded 3-Amino-N-(2,5-difluoro-4-(3-(methylamino)azetidin-1-yl)phenethyl)-6-methylthieno[2,3-b]pyridine-2-carboxamide as a white solid (15 mg, 30%). LCMS (ESI, m/z): 432 [M+H]$^+$. $^1$H NMR (400 MHz, CD$_3$OD) δ ppm: δ 8.18 (d, J=8.0 Hz, 1H), 7.29 (d, J=8.4 Hz, 1H), 6.87-6.92 (m, 1H), 6.24-6.29 (m, 1H), 4.13-4.15 (m, 2H), 3.57-3.64 (m, 3H), 3.46-3.49 (m, 2H), 2.78-2.81 (m, 2H), 2.63 (s, 3H), 2.33 (s, 3H).

Example 108-1 (I-200)

(R)-3-amino-N-(4-(3-(ethylamino)pyrrolidin-1-yl) phenethyl)-6-methylthieno[2,3-b]pyridine-2-carboxamide

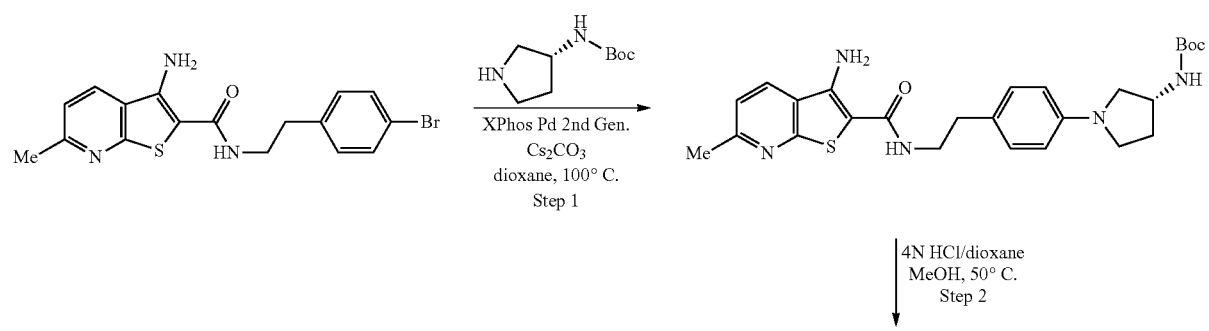

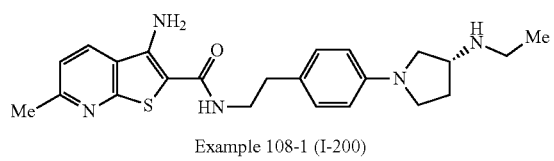

Example 108-1 (I-200)

-continued

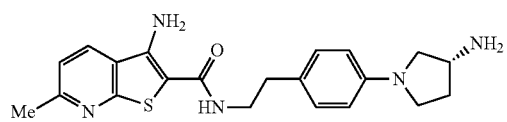

Step 1. tert-Butyl (R)-(1-(4-(2-(3-amino-6-methylthieno[2,3-b]pyridine-2-carboxamido)ethyl)phenyl)pyrrolidin-3-yl)carbamate To a solution of 3-amino-N-(4-bromophenethyl)-6-methylthieno[2,3-b]pyridine-2-carboxamide (0.55 g, 1.4 mmol) in anhydrous 1,4-dioxane (10 mL) was added (R)-tert-butyl pyrrolidin-3-ylcarbamate (0.39 g, 2.1 mmol), XPhos Pd-G2 precatalyst (0.055 g, 0.07 mmol) and cesium carbonate (1.8 g, 5.6 mmol). The resulting mixture was heated under an atmosphere of nitrogen at 100° C. overnight. After being cooled to RT, the reaction mixture was partitioned between brine and ethyl acetate. The layers were separated and the aqueous layer was extracted with EtOAc again. The combined organic layers were dried over anhydrous sodium sulfate, filtered, and concentrated in vacuo. The crude product was purified by Prep-TLC (50% EtOAc in hexanes) to afford tert-butyl (R)-(1-(4-(2-(3-amino-6-methylthieno[2,3-b]pyridine-2-carboxamido)ethyl)phenyl)pyrrolidin-3-yl)carbamate (98 mg, 14%).

Step 2. (R)-3-amino-N-(4-(3-aminopyrrolidin-1-yl)phenethyl)-6-methylthieno[2,3-b]pyridine-2-carboxamide To a solution of tert-butyl (R)-(1-(4-(2-(3-amino-6-methylthieno[2,3-b]pyridine-2-carboxamido)ethyl)phenyl)pyrrolidin-3-yl)carbamate (0.098 g, 0.20 mmol) in methanol (2 mL) was added 4 N HCl/dioxane solution (0.5 mL, 2 mmol). The resulting mixture was heated to 50 ° C. for 1 h, cooled to RT, and concentrated in vacuo. The crude product was used without further purification. LCMS (ESI, m/z): 396 [M+H]+.

Step 3. (R)-3-amino-N-(4-(3-(ethylamino)pyrrolidin-1-yl)phenethyl)-6-methylthieno[2,3-b] pyridine-2-carboxamide To a solution of crude (R)-3-amino-N-(4-(3-aminopyrrolidin-1-yl)phenethyl)-6-methylthieno [2,3-b]pyridine-2-carboxamide from Step 2 above (0.2 M in 5% DIEA/DCM, 100 µL, 0.02 mmol) was added acetaldehyde (0.2 M in 10% HOAc/DCM, 120 µL, 0.024 mmol). The mixture was placed on a shaker for 30 min and then a sodium triacetoxyborohydride solution (0.2 M in DCM, 200 µL, 0.04 mmol) was added. The mixture was placed on shaker at RT overnight. The reaction mixture was partitioned between 0.5 mL of 1 N NaOH in brine and 0.7 mL of ethyl acetate. The organic layer was separated and the aqueous layer was extracted again with EtOAc (0.7 mL). The combined organic layers were concentrated in vacuo to provide a crude product that was purified by HPLC using the following method: Waters Autopurification MS-directed HPLC prep fraction collection using the following conditions Column, Waters XBridge OBD C18, 5 µm, 19×50 mm; flow rate 20 mL/min; mobile phase, A: water with 0.1% ammonium hydroxide and B: methanol with 0.1% ammonium hydroxide running the following gradient 0 to 2 mins (15% B), 2 to 6 mins (15-100% B); Detector ZQ Mass Detector in electrospray ionization mode. This afforded the title compound (5 mg, 54%). LCMS (ESI, m/z): 424 [M+H]+.

The Example in Table 26 below was synthesized according to the procedures outlined above for Example 108-1 (I-200), using the appropriate synthetic precursors.

TABLE 26

| Example (Cmpd no.) | Structure | MS (ESI, m/z) [M + H] |
|---|---|---|
| 108-2 (I-201) | 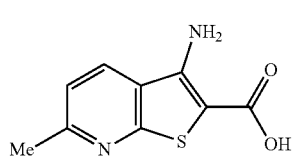 | 438 |

Example 109-1 (I-209)

(R)-3-amino-N-(2,5-difluoro-4-(3-methylpiperazin-1-yl)phenethyl) -6-methylthieno[2,3-b]pyridine-2-carboxamide

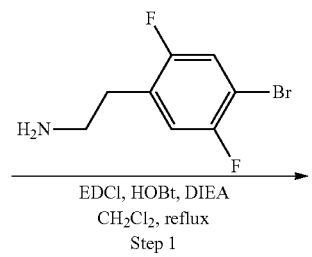

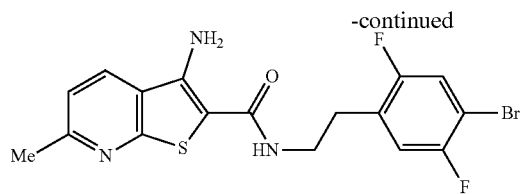 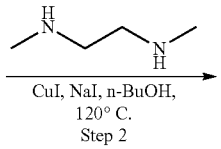

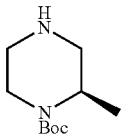

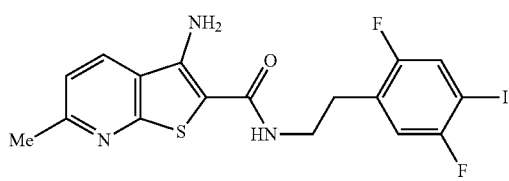

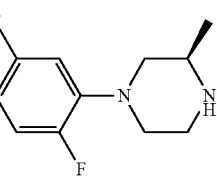

Example 109-1 (I-209)

Step 1. 3-amino-N-(4-bromo-2,5-difluorophenethyl)-6-methylthieno[2,3-b]pyridine-2-carboxamide Into a 50-mL round-bottom flask, was placed a solution of 2-(4-bromo-2,5-difluorophenyl)ethan-1-amine (930 mg, 3.94 mmol) in dichloromethane (100 mL), 3-amino-6-methylthieno[2,3-b]pyridine-2-carboxylic acid (820 mg, 3.94 mmol), EDCI (908 mg, 4.74 mmol), HOBT (638 mg, 4.72 mmol), and DIEA (1.53 g, 11.8 mmol). The resulting solution was stirred overnight at RT. The reaction was then quenched by the addition of 50 mL of water. The resulting solution was extracted with 3×50 mL of dichloromethane and the organic layers combined. The resulting mixture was washed with brine. The mixture was dried over anhydrous sodium sulfate, filtered, and concentrated under vacuum. The crude product was purified via silica gel column chromatography and eluted with ethyl acetate/petroleum ether (1:1) to afford 3-amino-N-(4-bromo-2,5-difluorophenethyl)-6-methylthieno[2,3-b]pyridine-2-carboxamide (780 mg, 46%) as a light yellow solid. LCMS (ESI, m/z): 428 [M+H]$^+$.

Step 2. 3-amino-N-(2,5-difluoro-4-iodophenethyl)-6-methylthieno[2,3-b]pyridine-2-carboxamide Into reaction vial were added sodium iodide (0.030 g, 0.2 mmol), copper(I) iodide (1.9 mg, 0.01 mmol), 3-amino-N-(4-bromo-2,5-difluorophenethyl)-6-methylthieno[2,3-b]pyridine-2-carboxamide (0.043 mg, 0.1 mmol), 700 uL n-BuOH and 0.2 M solution of N1,N2-dimethylethane-1,2-diamine (0.200 mL, 0.04 mmol) in n-BuOH. The reaction mixture was degassed with nitrogen, sealed and heated at 120° C. overnight. The reaction was allowed to cool down and worked-up with 10% aqueous ammonia and ethyl acetate. The organic layer was washed with brine, dried over anhydrous Na$_2$SO$_4$, filtered, and concentrated in vacuo to afford 3-amino-N-(2,5-difluoro-4-iodophenethyl)-6-methylthieno[2,3-91]pyridine-2-carboxamide (38 mg, 69%). LCMS (ESI, m/z): 474 [M+H]$^+$.

Step 3. (R)-3-amino-N-(2,5-difluoro-4-(3-methylpiperazin-1-yl)phenethyl)-6-methylthieno[2,3-b]pyridine-2-carboxamide The reaction vial was charged with 3-amino-N-(2,5-difluoro-4-iodophenethyl)-6-methylthieno[2,3-b]pyridine-2-carboxamide (15 mg, 0.032 mmol), (R)-tert-butyl 2-methylpiperazine-1-carboxylate (15.87 mg, 0.079 mmol), cesium carbonate (51.6 mg, 0.158 mmol), t-BuXPhos pre-catalyst G4 (5.12 mg, 6.34 µmol) and 300 µL DMF/Dioxane (2:1) mixture. The reaction vial was flushed with nitrogen, sealed and stirred at 92° C. for 4 hours. The reaction mixture was allowed to cool down, diluted with 1 mL Ethyl Acetate and filtered through SiliaPrepMB DMT 200 mg SPE cartridge to remove palladium catalyst. The cartridge was washed with 2 mL EA and volatiles were evaporated. The residue was dissolved in 1 mL methanol and loaded on 500 mg SCX SPE cartridge. The impurities were eluted with 3 mL methanol and the product was eluted with 3 mL 2M NH$_3$ in methanol. Volatiles were evaporated and the resulting crude material was used directly without further purification. The material was dissolved in 100 µL MeOH and 100 µL Dioxane and 4N HCl (79 µl, 0.317 mmol) in Dioxane was added. The reaction was heated at 50° C. for 30 min, cooled to RT and then concentrated. The residue was azeotroped with toluene, dissolved in 500 µL DMSO and purified by prep HPLC to afford (R)-3-amino-N-(2,5-difluoro-4-(3-methylpiperazin-1-yl)phenethyl)-6-methylthieno[2,3-b]pyridine-2-carboxamide (0.5 mg, 3.54%). LCMS (ESI, m/z): 446 [M+H]$^+$.

The Example in Table 27 below was synthesized according to the procedures outlined above for Example 109-1 (I-209), using the appropriate synthetic precursors.

TABLE 27
| Example (Cmpd no.) | Structure | MS (ESI, m/z) [M + H] |
|---|---|---|
| 109-2 (I-210) | 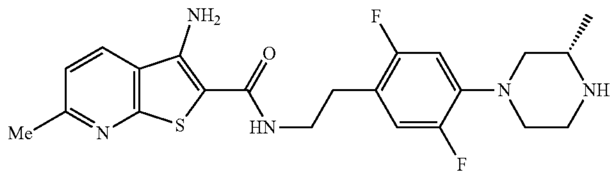 [SMILES: Cc1ccc2c(N)c(C(=O)NCCc3cc(F)c(N4CCN[C@@H](C)C4)cc3F)sc2n1] | 446 |
Examples 110-A (I-211) and 110-B (I-212)
3-Amino-N-(2,5-difluoro-4-((3S,4R)-3-fluoro-4-(methylamino)pyrrolidin-1-yl)phenethyl)-6-methyl-thieno[2,3-b]pyridine-2-carboxamide and 3-Amino-N-(2,5-difluoro-4-3R,4S)-3-fluoro-4-(methylamino)pyrrolidin-1-yl)phenethyl)-6-methylthieno[2,3-b]pyridine-2-carboxamide
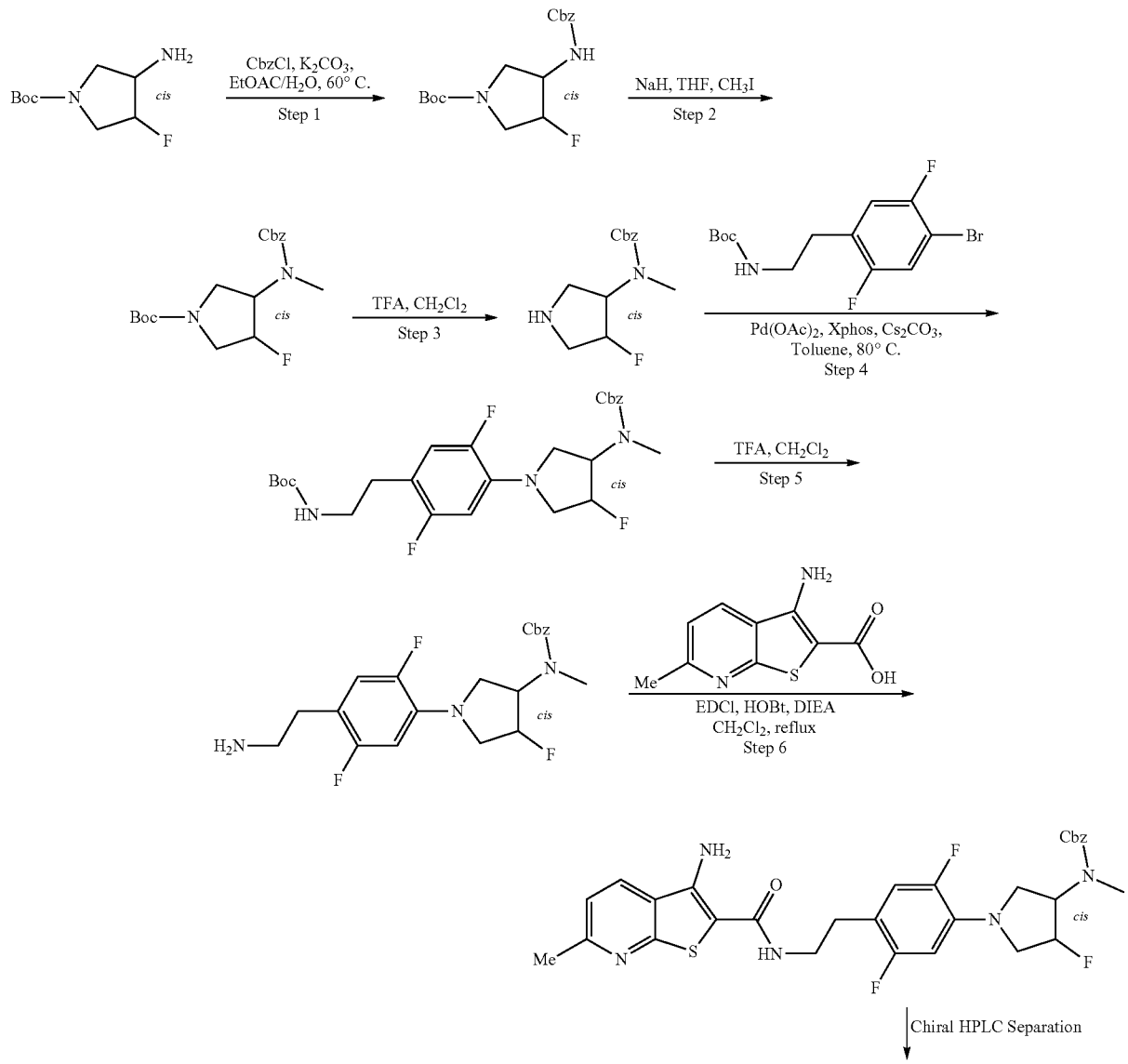

-continued

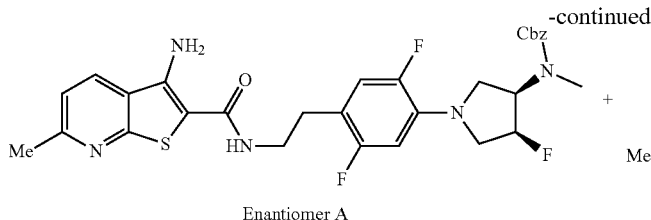

Enantiomer A

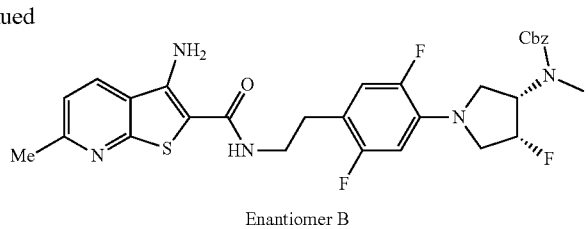

Enantiomer B

| BBr₃, CH₂Cl₂, -30° C.
Step 7

| BBr₃, CH₂Cl₂, -30° C.
Step 7

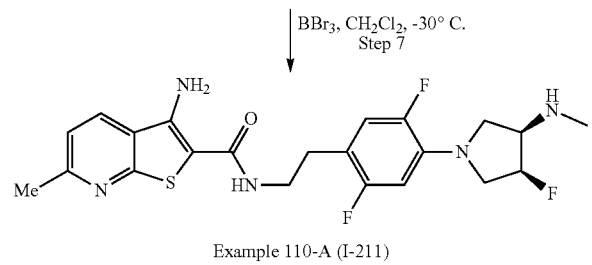

Example 110-A (I-211)

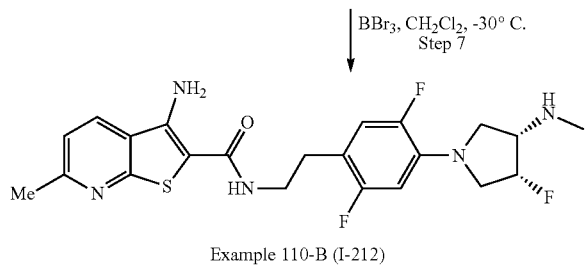

Example 110-B (I-212)

Step 1. cis-tert-Butyl-3-[[(benzyloxy)carbonyl]amino]-4-fluoropyrrolidine-1-carboxylate Into a 100-mL round-bottom flask, was placed cis tert-butyl-3-amino-4-fluoropyrrolidine-1-carboxylate (1.0 g, 4.9 mmol), potassium carbonate (2.0 g, 14.7 mmol), benzyl chloroformate (835 mg, 4.9 mmol), ethyl acetate (15 mL) and water (15 mL). The resulting solution was stirred for 4 h at 60° C. in an oil bath. The resulting solution was cooled to room temperature and extracted with 3×10 mL of ethyl acetate, washed with 30 mL of brine, dried over anhydrous sodium sulfate, filtered, and concentrated under vacuum to afford cis-tert-butyl-3-[[(benzyloxy)carbonyl]amino]-4-fluoropyrrolidine-1-carboxylate as a yellow oil (1.5 g crude). LCMS (ESI, m/z): 339 [M+H]⁺.

Step 2. cis tert-Butyl 3-(((benzyloxy)carbonyl)(methyl) amino)-4-fluoropyrrolidine-1-carboxylate Into a 50-mL round-bottom flask purged and maintained with an inert atmosphere of nitrogen, was placed cis-tert-butyl-3-[[(benzyloxy)carbonyl]amino]-4-fluoropyrrolidine-1-carboxylate (1.5 g, 4.43 mmol) and THF (20 mL). This was followed by the addition of sodium hydride (2.66 g, 6.65 mmol, 60% dispersion in oil) at 0° C. The mixture was stirred for 20 min at 0° C. To this was added CH₃I (944 mg, 6.65 mmol). The resulting solution was stirred for 14 h at room temperature. The resulting mixture was diluted with 20 mL of water, extracted with 3×15 mL of ethyl acetate, dried over anhydrous sodium sulfate, filtered, and concentrated under vacuum. The crude product was purified via silica gel column chromatography and eluted with ethyl acetate/petroleum ether (1:10) to afford cis tert-butyl 3-(((benzyloxy)carbonyl)(methyl)amino)-4-fluoropyrrolidine-1-carboxylate as a light yellow oil (1.2 g, 77%). LCMS (ESI, m/z): 353 [M+H]⁺.

Step 3. cis Benzyl (4-fluoropyrrolidin-3-yl)(methyl)carbamate

Into a 50-mL round-bottom flask, was placed cis tert-butyl 3-(((benzyloxy)carbonyl)(methyl)amino)-4-fluoropyrrolidine-1-carboxylate (600 mg, 1.70 mmol), dichloromethane (15 mL) and TFA (3 mL). The resulting solution was stirred for 2 h at room temperature. The pH value of the solution was adjusted to 8 with ammonia. The resulting mixture was extracted with 3×100 mL of ethyl acetate, washed with 100 mL of brine, dried over anhydrous sodium sulfate, filtered, and concentrated under vacuum to afford cis benzyl (4-fluoropyrrolidin -3-yl)(methyl)carbamate as a brown solid (420 mg crude). LCMS (ESI, m/z): 253 [M+H]⁺.

Step 4. cis Benzyl (1-(4-(2-((tert-butoxycarbonyl)amino) ethyl)-2,5-difluorophenyl)-4-fluoropyrrolidin-3-yl)(methyl) carbamate Into a 50-mL round-bottom flask purged and maintained with an inert atmosphere of nitrogen, was placed cis benzyl (4-fluoropyrrolidin-3-yl)(methyl)carbamate (360.0 mg, 1.43 mmol), tert-butyl (4-bromo-2,5-difluorophenethyl)carbamate (479.7 mg, 1.43 mmol), Pd(OAc)₂ (32.0 mg, 0.14 mmol), XPhos (68.0 mg, 0.14 mmol), Cs₂CO₃ (228 mg, 0.70 mmol) and toluene (10 mL). The resulting solution was stirred for 6 h at 80° C. in an oil bath, and then cooled to room temperature and diluted with 20 mL of water. The resulting mixture was extracted with 3×20 mL of ethyl acetate, washed with 50 mL of brine, dried over anhydrous sodium sulfate, filtered, and concentrated under vacuum. The crude product was purified via silica gel column chromatography and eluted with ethyl acetate/petroleum ether (1:10) to afford cis benzyl (1-(4-(2-((tert -butoxycarbonyl)amino)ethyl)-2,5-difluorophenyl)-4-fluoropyrrolidin-3-yl)(methyl)carbamate as a yellow solid (580 mg, 80%). LCMS (ESI, m/z): 508 [M+H]⁺.

Step 5 cis Benzyl (1-(4-(2-aminoethyl)-2,5-difluorophenyl)-4-fluoropyrrolidin-3-yl)(methyl)carbamate Into a 100-mL round-bottom flask was placed cis benzyl (1-(4-(2-((tert -butoxycarbonyl)amino)ethyl)-2,5-difluorophenyl)-4-fluoropyrrolidin-3-yl)(methyl)carbamate (560 mg, 1.10 mmol) and dichloromethane (25 mL). This was followed by the addition of trifluoroacetic acid (5 mL) at 0° C. The resulting solution was stirred for 2 h at room temperature. The pH value of the solution was adjusted to 8 with ammonia. The resulting mixture was extracted with 3×20 mL of dichloromethane, dried over anhydrous sodium sulfate, filtered, and concentrated under vacuum to afford cis benzyl (1-(4-(2-aminoethyl)-2,5-difluorophenyl)-4-fluoropyrrolidin-3-yl)(methyl)carbamate as a brown solid (380 mg, crude). LCMS (ESI, m/z): 408 [M+H]⁺.

Step 6. Benzyl ((3R,4S)-1-(4-(2-(3-amino-6-methylthieno[2,3-b]pyridine-2-carboxamido)ethyl)-2,5-difluorophenyl)-4-fluoropyrrolidin-3-yl)(methyl)carbamate and Benzyl ((3S,4R)-1-(4-(2-(3-amino-6-methylthieno[2,3-b]pyridine-2-carboxamido)ethyl)-2,5-difluorophenyl)-4-fluoropyrrolidin-3-yl)(methyl)carbamate Into a 25-mL round-bottom flask was placed cis benzyl (1-(4-(2-aminoethyl)-2,5-difluorophenyl)-4-fluoropyrrolidin-3-yl)(methyl)carbamate (210.0 mg, 0.52 mmol), 3-amino-6-methylthieno[2,3-b]pyridine-2-carboxylic acid (107.6 mg, 0.52 mmol), EDCI (129.8 mg, 0.68 mmol), HOBT (83.8 mg, 0.62 mmol), DIEA (133.6 mg, 1.04 mmol) and DMF (5 mL). The resulting solution was stirred for 14 h at 40° C. The resulting mixture was diluted with 10 mL of water and extracted with 3×10 mL of ethyl acetate. The organic layers were combined, dried over anhydrous sodium sulfate, filtered. and concentrated under vacuum. The crude product was purified via silica gel column chromatography and eluted with ethyl acetate/petroleum ether (1:1). The racemate (270 mg) was separated by Chiral-Prep-HPLC using the following conditions (SHIMADZU LC-20AD): LC parameters: Pump Mode: Binary gradient, Start Conc. of Pump B: 30.0%, Total Flow: 20 mL/min, Phase A Hexanes, Phase B: Ethanol, Column Name: CHIRALCEL OJ-H, Length: 25 mm, Internal Diameter: 2 mm, Particle Size: 5 μm, Column Temp: 20° C., PDA Model: SPD-M20A, Wavelength: from 190 nm to 500 nm. This resulted in the following: Step 6, Enantiomer A: 1$^{st}$ eluting peak (retention time=11.6 min, 50 mg, 12% yield, yellow solid) assigned as benzyl ((3R,4S)-1-(4-(2-(3-amino-6-methylthieno[2,3-b]pyridine-2-carboxamido)ethyl)-2,5-difluorophenyl)-4-fluoropyrrolidin-3-yl)(methyl)carbamate. LCMS (ESI, m/z): 598 [M+H]$^+$; and Step 6, Enantiomer B: 2$^{nd}$ eluting peak (retention time=13.1 min, 45 mg, 11% yield, yellow solid) assigned as benzyl ((3S,4R)-1-(4-(2-(3-amino-6-methylthieno[2,3-b]pyridine-2-carboxamido)ethyl)-2,5-difluorophenyl)-4-fluoropyrrolidin-3-yl)(methyl)carbamate. LCMS (ESI, m/z): 598 [M+H]$^+$.

Step 7. 3-Amino-N-(2,5-difluoro-4-((3S,4R)-3-fluoro-4-(methylamino)pyrrolidin-1-yl)phenethyl)-6-methylthieno[2,3-b]pyridine-2-carboxamide Into a 25-mL round-bottom flask was placed benzyl ((3R,4S)-1-(4-(2-(3-amino-6-methylthieno[2,3-b]pyridine-2-carboxamido)ethyl)-2,5-difluorophenyl)-4-fluoropyrrolidin-3-yl)(methyl)carbamate (Step 6, Enantiomer A) (40 mg, 0.07 mmol) and dichloromethane (2 mL). Then a solution of BBr$_3$ in dichloromethane (1M) (2.1 mL, 2.10 mmol) was added at −30° C. The resulting solution was stirred for 1 h at −30° C. in a liquid nitrogen bath, and then concentrated under vacuum. The pH value of the solution was adjusted to 8 with ammonia. The resulting mixture was extracted with 3×10 mL of ethyl acetate. The organic layers combined, washed with 10 mL of brine, dried over anhydrous sodium sulfate, filtered, and concentrated under vacuum. The residue was purified by Prep-HPLC using the following conditions (SHIMADZU LC-20AD): LC parameters: Pump Mode: Binary gradient, Start Conc. of Pump B: 20.0%, End Conc. of Pump B: 22.0%, Total Flow: 20 mL/min, Time: 17 min, Phase A: Water (0.05% TFA), Phase B: MeCN -HPLC, Column Name: XBridge BEH C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm. This afforded 3-amino-N-(2,5-difluoro-4-((3S,4R)-3-fluoro -4-(methylamino)pyrrolidin-1-yl)phenethyl)-6-methylthieno [2,3-b]pyridine-2-carboxamide as a light yellow solid (2.4 mg, 8%). LCMS (ESI, m/z): 464 [M+H]$^+$, $^1$H-NMR (300 MHz, Methanol -d$_4$) δ ppm 8.15 (d, J=8.1 Hz, 1H), 7.26 (d, J=8.4 Hz, 1H), 6.79-6.96 (m, 1H), 6.26-6.48 (m, 1H), 5.11-5.31 (m, 1H), 3.71-3.90 (m, 1H), 3.46-3.67 (m, 4H), 3.16-3.44 (m, 2H), 2.77 (t, J=7.2 Hz, 2H), 2.60 (s, 3H), 2.46 (s, 3H).

Step 7. 3-Amino-N-(2,5-difluoro-4-((3R,4S)-3-fluoro-4-(methylamino)pyrrolidin-1-yl)phenethyl)-6-methylthieno[2,3-b]pyridine-2-carboxamide The same synthetic procedure described to prepare 3-amino-N-(2,5-difluoro-4-((3S,4R)-3-fluoro-4-(methylamino)pyrrolidin-1-yl)phenethyl)-6-methylthieno[2,3-b]pyridine-2-carboxamide was applied to Step 6, Enantiomer B except using the following Prep-HPLC conditions (SHIMADZU LC-20AD): LC parameters: Pump Mode: Binary gradient, Start Conc. of Pump B: 31.0%, End Conc. of Pump B: 53.0% Total Flow: 20 mL/min, Time: 7 min, Phase A: Water (10 mmol NH$_4$HCO$_3$), Phase B: MeCN-HPLC, Column Name: XBridge BEH C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm. This afforded 3-amino-N-(2,5-difluoro-4-((3R,4S)-3-fluoro-4-(methylamino)pyrrolidin-1-yl)phenethyl)-6-methylthieno[2,3-b]pyridine-2-carboxamide as a yellow solid (2.3 mg, 10%). LCMS (ESI, m/z): 464 [M+H]$^+$, $^1$H-NMR (300 MHz, Methanol-d$_4$) δ ppm 8.15 (d, J=8.4 Hz, 1H), 7.26 (d, J=8.4 Hz, 1H), 6.79-6.96 (m, 1H), 6.26-6.48 (m, 1H), 5.11-5.30 (m, 1H), 3.72-3.92 (m,1H), 3.44-3.66 (m, 4H), 3.16-3.39 (m, 2H), 2.77 (t, J=7.2 Hz, 2H), 2.60 (s, 3H), 2.46 (s, 3H).

Examples 111-A (I-213) and 111-B (I-214)

3-Amino-N-(2,5-difluoro-4-((3R,4R)-3-fluoro-4-(methylamino)pyrrolidin-1-yl)phenethyl)-6-methyl-thieno[2,3-b]pyridine-2-carboxamide and 3-Amino-N-(2,5-difluoro-4-((3S,4S)-3-fluoro-4-(methylamino)pyrrolidin-1-yl)phenethyl)-6-methylthieno[2,3-b]pyridine-2-carboxamide

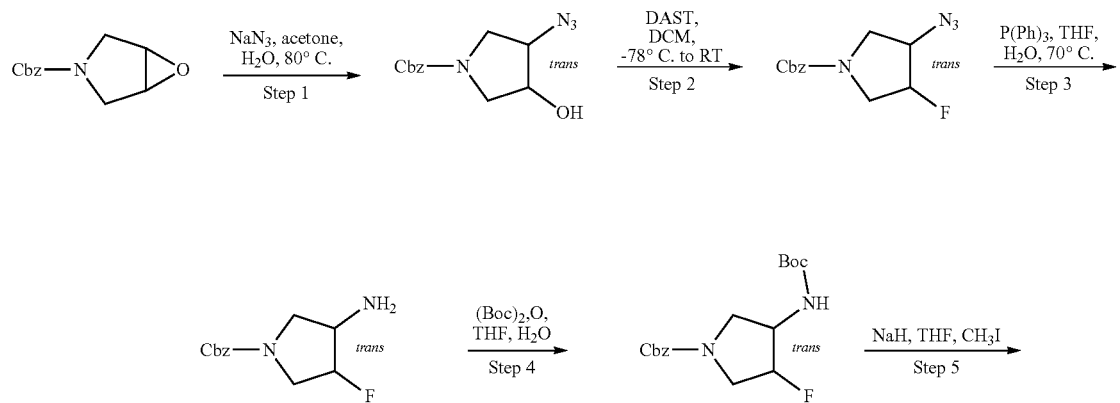

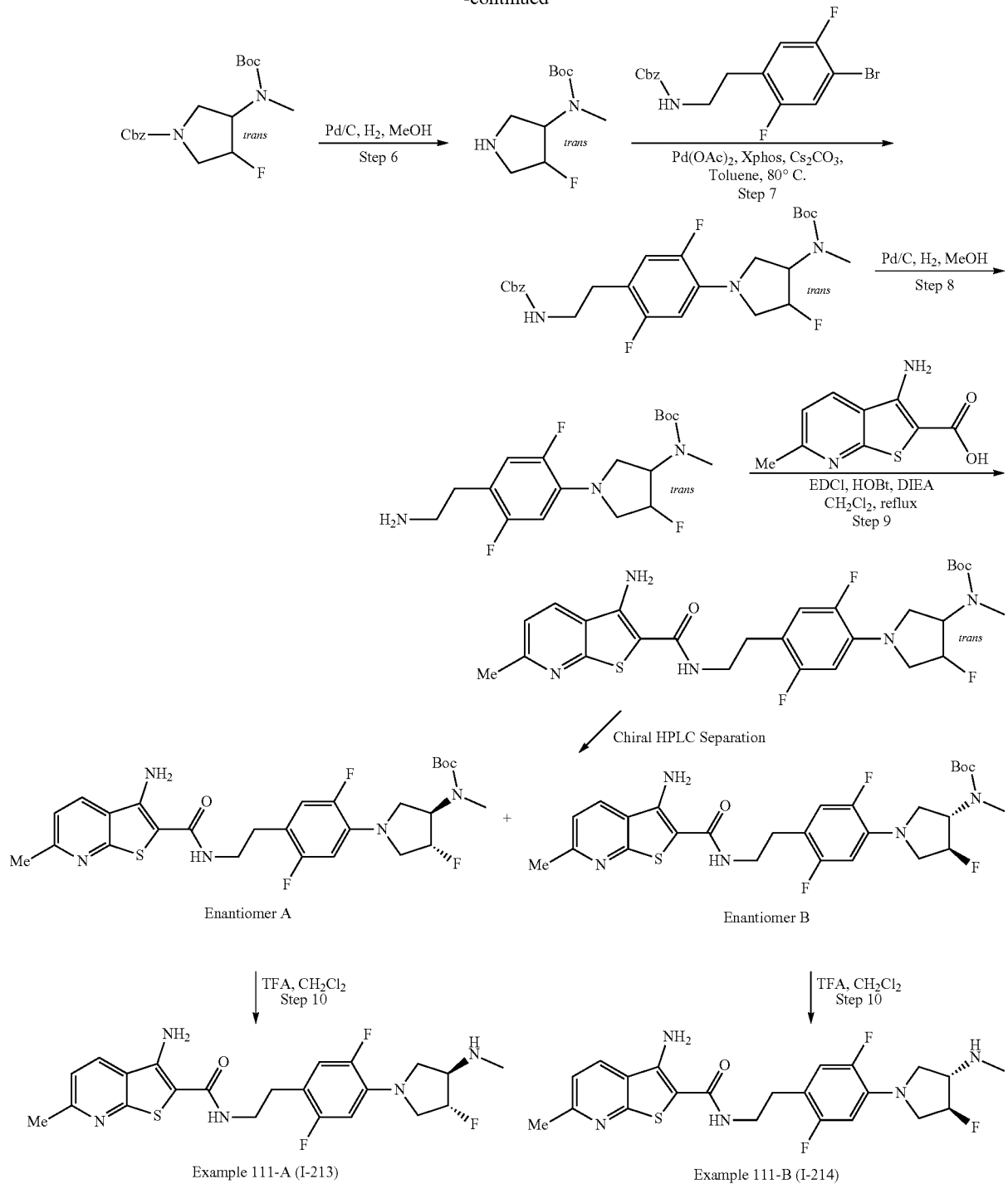

Step 1. trans Benzyl 3-azido-4-hydroxypyrrolidine-1-carboxylate

Into a 500-mL round-bottom flask, was placed benzyl 6-oxa-3-azabicyclo[3.1.0]hexane-3-carboxylate (10.0 g, 45.6 mmol), acetone (80 mL), water (20 mL) and $NaN_3$ (6.0 g, 92.3 mmol). The resulting solution was stirred for 18 h at 80° C. The reaction mixture was cooled to room temperature, and then quenched by the addition of sat. aq. sodium carbonate solution (50 mL). The resulting mixture was extracted with 3×200 mL ethyl acetate, washed with 200 mL of brine, dried over anhydrous sodium sulfate, filtered, and concentrated under vacuum. The crude product was purified via silica gel column chromatography and eluted with ethyl acetate/petroleum ether (2:3) to afford trans benzyl 3-azido-4-hydroxyl)yrrolidine-1-carboxylate as a yellow oil (10 g, 84%). LCMS (ESI, m/z): 263 [M+H]$^+$.

Step 2. trans Benzyl 3-azido-4-fluoropyrrolidine-1-carboxylate

Into a 500-mL 3-necked round-bottom flask was placed trans benzyl 3-azido-4-hydroxypyrrolidine-1-carboxylate (5.0 g, 19.06 mmol) and dichloromethane (150 mL). Then DAST (9.6 g, 59.29 mmol) was added at −78° C. The resulting solution was stirred for 1 h at −78° C. in a liquid nitrogen bath. The resulting solution was allowed to react, with stirring, for an additional 14 h at room temperature. The reaction was then quenched by the addition of methanol (50 mL). The resulting mixture was concentrated under vacuum. The crude product was purified via silica gel column chromatography and eluted with ethyl acetate/petroleum ether (1:10) to afford trans benzyl 3-azido-4-fluoropyrrolidine-1-carboxylate as yellow oil (1.8 g, 36%). LCMS (ESI, m/z): 265 [M+H]$^+$.

Step 3. trans Benzyl 3-amino-4-fluoropyrrolidine-1-carboxylate

Into a 25-mL round-bottom flask purged and maintained with an inert atmosphere of nitrogen, was placed trans benzyl 3-azido-4-fluoropyrrolidine-1-carboxylate (300 mg, 1.14 mmol), PPh$_3$ (890 mg, 3.40 mmol), tetrahydrofuran (5 mL) and water (1 mL). The resulting solution was stirred for 2 h at 70° C. in an oil bath under an atmosphere of nitrogen. The resulting mixture was concentrated under vacuum and the residue diluted with EtOAc (100 mL) and washed with sat. aq. citric acid solution (2×100 mL). The combined aqueous extracts were washed with EtOAc (3×50 mL). The pH of the aqueous phase was adjusted to 8 with sat. aq. K$_2$CO$_3$ solution. The resulting mixture was extracted with DCM (4×100 mL). The combined organic extracts were washed with brine (100 mL), dried over Na$_2$SO$_4$, filtered, and concentrated under vacuum to afford trans benzyl 3-amino-4-fluoropyaolidine-1-carboxylate as colorless oil (216 mg, crude). LCMS (ESI, m/z): 239 [M+H]$^+$.

Step 4. trans Benzyl 3-((tert-butoxycarbonyl)amino)-4-fluoropyrrolidine-1-carboxylate Into a 25-mL round-bottom flask, was placed trans benzyl 3-amino-4-fluoropyrrolidine-1-carboxylate (216 mg, 0.91 mmol), di-tert-butyl dicarbonate (218 mg, 1.00 mmol), water (1 mL) and THF (5 mL). The resulting solution was stirred for 14 h at room temperature. The reaction was then quenched by the addition of 30 mL of water. The resulting solution was extracted with 3×15 mL of ethyl acetate. The organic layers were combined, dried over anhydrous sodium sulfate, filtered, and concentrated under vacuum. The crude product was purified via silica gel column chromatography and eluted with ethyl acetate/petroleum ether (1:8) to afford trans benzyl 3-((tert-butoxycarbonyl)amino)-4-fluoropyrrolidine-1-carboxylate as a colorless oil (260 mg, 85%). LCMS (ESI, m/z): 339 [M+H]$^+$.

Step 5. trans Benzyl 3-((tert-butoxycarbonyl)(methyl)amino)-4-fluoropyrrolidine-1-carboxylate Into a 50-mL round-bottom flask purged and maintained with an inert atmosphere of nitrogen, was placed trans benzyl 3-((tert-butoxycarbonyl)amino)-4-fluoropyrrolidine-1-carboxylate (2.00 g, 5.91 mmol), THF (20 mL), sodium hydride (591.1 mg, 14.78 mmol, 60% dispersion in oil) and CH$_3$I (1.25 g, 8.87 mmol). The resulting solution was stirred for 4 h at room temperature under an atmosphere of nitrogen, and then poured into 20 mL of water/ice. The resulting mixture was extracted with 3×20 mL of dichloromethane, dried over anhydrous sodium sulfate, filtered, and concentrated under vacuum. The crude product was purified via silica gel column chromatography and eluted with ethyl acetate/petroleum ether (1:5) to afford trans benzyl -3-((tert-butoxycarbonyl)(methyl)amino)-4-fluoropyrrolidine-1-carboxylate as yellow oil (1.3 g, 62%). LCMS (ESI, m/z): 353 [M+H]$^+$.

Step 6. trans tert-Butyl (4-fluoropyrrolidin-3-yl)(methyl)carbamate

Into a 50-mL round-bottom flask fitted with a hydrogen balloon was placed trans benzyl-3-((tert-butoxycarbonyl)(methyDamino)-4-fluoropyrrolidine-1-carboxylate (1.3 g, 3.69 mmol), 10% palladium on carbon (200 mg) and methanol (20 mL). The resulting solution was stirred for 2 h at room temperature under hydrogen. The solids were filtered out. The filtrate was concentrated under vacuum to afford trans tert-butyl (4-fluoropyrrolidin-3-yl)(methyl)carbamate as colorless oil (850 mg crude). LCMS (ESI, m/z): 219 [M+H]$^+$.

Step 7. trans tert-Butyl (1-(4-(2-(((benzyloxy)carbonyl)amino)ethyl)-2,5-difluorophenyl)-4-fluoropyrrolidin-3-yl)(methyl)carbamate Into a 50-mL round-bottom flask purged and maintained with an inert atmosphere of nitrogen, was placed trans tert-butyl (4-fluoropyrrolidin-3-yl)(methyl)carbamate (450.0 mg, 2.06 mmol), benzyl (4-bromo-2,5-difluorophenethyl)carbamate (763.2 mg, 2.06 mmol), Pd(OAc)$_2$ (46.3 mg, 0.21 mmol), XPhos (98.3 mg, 0.21 mmol), Cs$_2$CO$_3$ (2.02 g, 6.18 mmol) and toluene (20 mL). The resulting solution was stirred for 4 h at 80° C. in an oil bath under an atmosphere of nitrogen. The resulting mixture was cooled to room temperature and quenched by the addition of 20 mL of water. The resulting solution was extracted with 3×20 mL of dichloromethane, washed with 20 mL of brine, dried over anhydrous sodium sulfate, filtered, and concentrated under vacuum. The crude product was purified via silica gel column chromatography and eluted with ethyl acetate/petroleum ether (1:6) to afford trans tert-butyl (1-(4-(2-(((benzyloxy)carbonyl)amino)ethyl)-2,5-difluorophenyl)-4-fluoropyrrolidin-3-yl)(methyl)carbamate as a yellow oil (480 mg, 46%). LCMS (ESI, m/z): 508 [M+H]$^+$.

Step 8. trans tert-Butyl (1-(4-(2-aminoethyl)-2,5-difluorophenyl)-4-fluoropyrrolidin-3-yl)(methyl)carbamate Into a 50-mL round-bottom flask fitted with a hydrogen balloon, was placed trans tert -butyl (1-(4-(2-(((benzyloxy)carbonyl)amino)ethyl)-2,5-difluorophenyl)-4-fluoropyrrolidin-3-yl)(methyl)carbamate (480 mg, 0.95 mmol), 10% palladium on carbon (100 mg) and methanol (20 mL). The resulting solution was stirred for 2 h at room temperature under hydrogen. The solids were filtered out. The filtrate was concentrated under vacuum to afford trans tert-butyl (1-(4-(2-aminoethyl)-2,5-difluorophenyl)-4-fluoropyrrolidin-3-yl)(methyl)carbamate as a brown oil (290 mg crude). LCMS (ESI, m/z): 374 [M+H]$^+$.

Step 9. tert-Butyl ((3R,4R)-1-(4-(2-(3-amino-6-methylthieno[2,3-b]pyridine-2-carboxamido)ethyl)-2,5-difluorophenyl)-4-fluoropyrrolidin-3-yl)(methyl)carbamate and tert-Butyl ((3S,4S)-1-(4-(2-(3-amino-6-methylthieno[2,3-b]pyridine-2-carboxamido)ethyl) -2,5-difluorophenyl)-4-fluoropyrrolidin-3-yl)(methyl)carbamate Into a 50-mL round-bottom flask, was placed trans tert-butyl (1-(4-(2-aminoethyl)-2,5-difluorophenyl)-4-fluoropyrrolidin-3-yl)(methyl)carbamate (280 mg, 0.75 mmol), dichloromethane (5 mL), 3-amino-6-methylthieno[2,3-b]pyridine-2-carboxylic acid (156 mg, 0.75 mmol), EDCI (187 mg, 0.97 mmol), HOBt (122 mg, 0.90 mmol) and DIEA (194 mg, 1.50 mmol). The resulting solution was stirred for 2 h at 40° C. in an oil bath, and then quenched by the addition of 10 mL of water. The resulting solution was extracted with 3×10 mL of ethyl acetate. The organic layers were combined, dried over anhydrous sodium sulfate, filtered, and concentrated under vacuum. The crude product was purified via silica gel column chromatography and eluted with ethyl acetate/petroleum ether (1:1). The racemate (260 mg) was separated by Chiral-Prep -HPLC using the following conditions (SHIMADZU LC-20AD): LC parameters: Pump Mode: Binary gradient, Start Conc. of Pump B: 30.0%, Total Flow: 20 mL/min, Phase A: Hexanes-HPLC, Phase B: Ethanol-HPLC, Column Name: CHIRALCEL OJ-H, Length: 250 mm, Internal Diameter: 20 mm, Particle Size: 5μm, Column Temp: 20° C., PDA Model: SPD-M20A, Wavelength: from 190 nm to 500 nm. This resulted in the following: Step 9, Enantiomer A: 1$^{st}$ eluting peak (retention time=8.19 min, 50 mg, 12% yield, yellow solid) assigned as tert-butyl ((3R,4R)-1-(4-(2-(3-amino-6-methylthieno[2,3-b]pyridine-2-carboxamido)ethyl)-2,5-difluorophenyl)-4-fluoropyrrolidin-3-yl)(methyl)carbamate. LCMS (ESI, m/z): 564 [M+H]$^+$; and Step 9, Enantiomer B: 2nd eluting peak (retention time=11.8 min, 45 mg, 11% yield, yellow solid) assigned as tert-butyl ((3S,4S)-1-(4-(2-(3-amino-6-methylthieno[2,3-b]pyridine-2-carboxamido)ethyl)-2,5-difluorophenyl)-4-fluoropyrrolidin-3-yl)(methyl)carbamate. LCMS (ESI, m/z): 564 [M+H]$^+$;

Step 10. 3-Amino-N-(2,5-difluoro-4-((3R,4R)-3-fluoro-4-(methylamino)pyrrolidin-1-yl)phenethyl)-6-methylthieno[2,3-b]pyridine-2-carboxamide Into a 10-mL round-bottom flask, was placed tert-butyl ((3R,4R)-1-(4-(2-(3-amino-6-methylthieno[2,3-b]pyridine-2-carboxamido)ethyl)-2,5-difluorophenyl)-4-fluoropyrrolidin-3-yl)(methyl)carbamate (Step 9, Enantiomer A) (30 mg, 0.05 mmol), dichloromethane (2 mL) and TFA (0.5 mL). The resulting solution was stirred for 1 h at room temperature. The resulting mixture was concentrated under vacuum and the residue was diluted with 3 mL of water. The pH value of the solution was adjusted to 8 with ammonia. The resulting mixture was extracted with 3×10 mL ethyl acetate. The organic layers were combined, washed with 10 mL of brine, dried over anhydrous sodium sulfate, filtered, and concentrated under vacuum. The residue was purified by Prep-HPLC using the following conditions (SHIMADZU LC-20AD): LC parameters: Pump Mode: Binary gradient, Start Conc. of Pump B: 40.0%, End Conc. of Pump B: 43.0% Total Flow: 20 mL/min, Time: 8 min, Phase A: Water (10 mmol/L NH$_4$HCO$_3$), Phase B: MeCN-HPLC, Column Name: XBridge Prep C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm. This afforded 3-amino-N-(2,5-difluoro-4-((3R,4R)-3-fluoro -4-(methylamino)pyrrolidin-1-yl)phenethyl)-6-methylthieno [2,3-b] pyridine-2-carboxamide as an off-white solid (6.5 mg, 26%). LCMS (ESI, m/z): 464 [M+H]$^+$. $^1$H-NMR (300 MHz, Methanol-d$_4$) δ ppm 8.15 (d, J=8.4 Hz, 1H), 7.26 (d, J=8.4 Hz, 1H), 6.95-6.91 (m, 1H), 6.48-6.42 (m, 1H), 5.12-4.94 (m, 1H), 3.92-3.61 (m, 2H), 3.61-3.32 (m, 4H), 3.28-3.16 (m, 1H), 2.78 (t, J=7.2 Hz, 2H), 2.60 (s, 3H), 2.42 (s, 3H).

Step 10. 3-Amino-N-(2,5-difluoro-4-((3S,4S)-3-fluoro-4-(methylamino)pyrrolidin-1-yl)phenethyl)-6-methylthieno[2,3-b]pyridine-2-carboxamide The same synthetic procedure described to prepare 3-amino-N-(2,5-difluoro-4-((3R,4R)-3-fluoro-4-(methylamino)pyrrolidin-1-yl)phenethyl)-6-methylthieno[2,3-b]pyridine-2-carboxamide was applied to Step 9, Enantiomer B except using the following Prep-HPLC conditions (SHIMADZU LC-20AD): LC parameters: Pump Mode: Binary gradient, Start Conc. of Pump B: 30.0%, End Conc. of Pump B: 36.0% Total Flow: 20 mL/min, Time: 8 min, Phase A: Water (10 mmol NH$_4$HCO$_3$), Phase B: MeCN-HPLC, Column Name: XBridge BEH C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm. This afforded 3-amino-N-(2,5-difluoro-4-(3S,4S)-3-fluoro-4-(methylamino)pyrrolidin-1-yl)phenethyl)-6-methylthieno [2,3-b]pyridine-2-carboxamide as an off-white solid (1.7 mg, 7%). LCMS (ESI, m/z): 464 [M+H]$^+$, $^1$H-NMR (300 MHz, Methanol-d$_4$) δ ppm 8.15 (d, J=8.4 Hz, 1H), 7.27 (d, J=8.4 Hz, 1H), 6.95-6.88 (m, 1H), 6.48-6.42 (m, 1H), 5.19-4.90 (m, 1H), 3.88 -3.62 (m, 2H), 3.60-3.29 (m, 4H), 3.18-3.15 (m, 1H), 2.78 (t, J=7.2 Hz, 2H), 2.60 (s, 3H), 2.41 (s, 3H).

Example 112 (I-215)

3-Amino-N-(2-(5-chloro-6-(piperazin-1-yl)pyridin-3-yl)ethyl)-6-methylthieno[2,3-b]pyridine-2-carboxamide

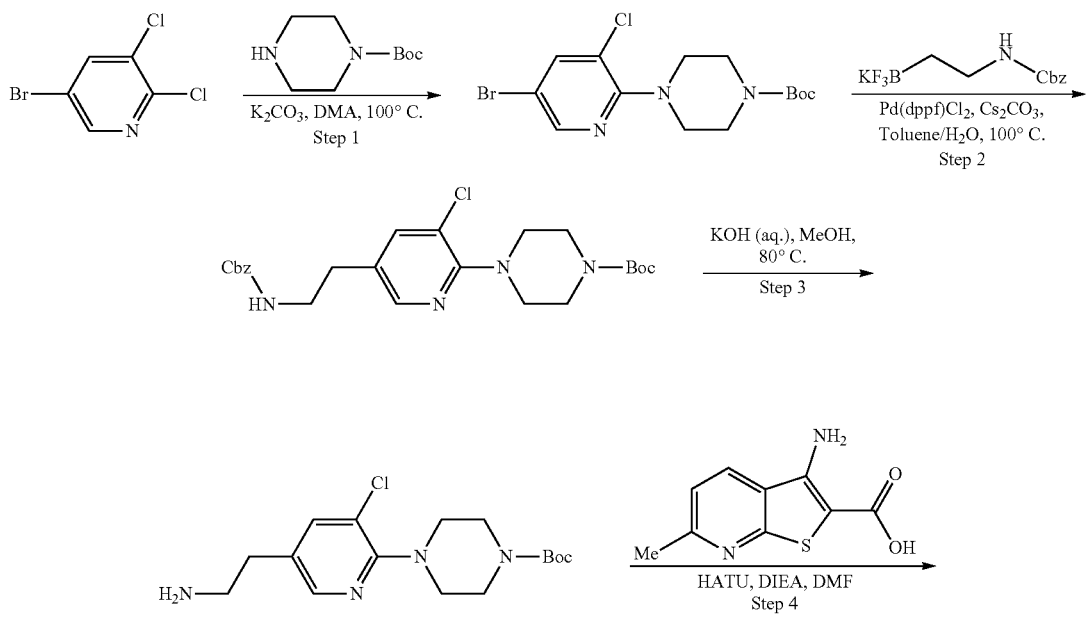

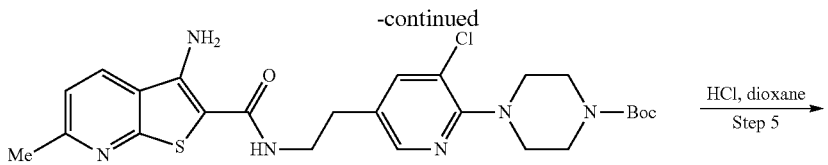

-continued

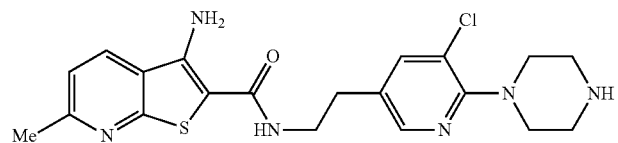

Step 1. tert-Butyl 4-(5-bromo-3-chloropyridin-2-yl)piperazine-1-carboxylate

Into a 250-mL round-bottom flask, was placed 5-bromo-2,3-dichloropyridine (5.0 g, 22.04 mmol), DMA (50 mL), potassium carbonate (9.16 g, 66.28 mmol), and tert-butyl piperazine -1-carboxylate (4.53 g, 24.32 mmol). The resulting solution was stirred overnight at 100° C. in an oil bath. The resulting solution was quenched with 200 mL of water and extracted with 3×250 mL of ethyl acetate. The organic layers were combined, washed with 3×750 mL of brine, and concentrated under vacuum. The crude product was purified via silica gel column chromatography and eluted with ethyl acetate/petroleum ether (1/1) to afford tert-butyl 4-(5-bromo-3-chloropyridin-2-yl)piperazine-1-carboxylate as colorless oil (3.2 g, 39%). LCMS (ESI, m/z): 376, 378 $[M+H]^+$.

Step 2. tert-Butyl 4-(5-(2-(((benzyloxy)carbonyl)amino)ethyl)-3-chloropyridin-2-yl)piperazine-1-carboxylate Into a 50-mL round-bottom flask purged and maintained with an inert atmosphere of nitrogen, was placed tert-butyl 4-(5-bromo-3-chloropyridin-2-yl)piperazine-1-carboxylate (1.5 g, 3.98 mmol), toluene/water (15 mL/5 mL), $Cs_2CO_3$ (3.1 g, 9.51 mmol), $Pd(dppf)Cl_2$ (300 mg, 0.41 mmol), and potassium (2-(benzyloxycarbonylamino)ethyl) trifluoroborate (1.63 g, 5.72 mmol). The resulting solution was stirred overnight at 100° C. in an oil bath. The resulting mixture was cooled to room temperature and concentrated under vacuum. The crude product was purified via silica gel column chromatography and eluted with ethyl acetate/petroleum ether (1/1) to afford tert-butyl 4-(5-(2-(((benzyloxy)carbonyl)amino)ethyl)-3-chloropyridin-2-yl)piperazine-1-carboxylate as colorless oil (800 mg, 42%). LCMS (ESI, m/z): 475 $[M+H]^+$.

Step 3. tert-Butyl 4-(5-(2-aminoethyl)-3-chloropyridin-2-yl)piperazine-1-carboxylate Into a 50-mL round-bottom flask, was placed tert-butyl 4-(5-(2-(((benzyloxy)carbonyl)amino)ethyl)-3-chloropyridin-2-yl)piperazine-1-carboxylate (300 mg, 0.63 mmol) and a solution of potassium hydroxide (40% aq.)/methanol (6 mL/6 mL). The resulting solution was stirred for 4 h at 80° C. in an oil bath. The resulting mixture was concentrated under vacuum and diluted with 5 mL of water. The resulting solution was extracted with 3×5 mL of dichloromethane. The organic layers were combined and concentrated under vacuum to afford tert-butyl 4-(5-(2-aminoethyl)-3-chloropyridin-2-yl)piperazine-1-carboxylate as a yellow solid (200 mg crude). LCMS (ESI, m/z): 341 $[M+H]^+$.

Step 4. tert-Butyl 4-(5-(2-(3-amino-6-methylthieno[2,3-b]pyridine-2-carboxamido)ethyl)-3-chloropyridin-2-yl)piperazine-1-carboxylate Into a 50-mL round-bottom flask, was placed tert-butyl 4-(5-(2-aminoethyl)-3-chloropyridin-2-yl-piperazine-1-carboxylate (100 mg, 0.29 mmol), DMF (3 mL), DIEA (129 mg, 1.00 mmol), HATU (123 mg, 0.32 mmol), and 3-amino-6-methylthieno[2,3-b]pyridine-2-carboxylic acid (62 mg, 0.30 mmol). The resulting solution was stirred for 2 h at room temperature. The resulting solution was diluted with 9 mL of water and extracted with 3×12 mL of ethyl acetate. The organic layers were combined, washed with 3×36 mL of brine, and concentrated under vacuum. The crude product was purified via silica gel column chromatography and eluted with ethyl acetate/petroleum ether (1/1) to afford tert-butyl 4-(5-(2-(3-amino-6-methylthieno[2,3-b]pyridine-2-carboxamido)ethyl)-3-chloropyridin-2-yl)piperazine-1-carboxylate as a yellow solid (60 mg, 39%). LCMS (ESI, m/z): 531 $[M+H]^+$.

Step 5. 3-Amino-N-(2-(5-chloro-6-(piperazin-1-yl)pyridin-3-yl)ethyl)-6-methylthieno[2,3-b]pyridine-2-carboxamide Into a 50-mL round-bottom flask, was placed tert-butyl 4-(5-(2-(3-amino-6-methylthieno[2,3-b]pyridine-2-carboxamido)ethyl)-3-chloropyridin-2-yl)piperazine-1-carboxylate (60 mg, 0.11 mmol) and HCl/dioxane (4M, 5 mL). The resulting solution was stirred for 2 h at room temperature. The resulting mixture was concentrated under vacuum. The crude product was purified by Prep-HPLC using the following conditions: Column: X Bridge C18, 19×150 mm, 5 μm; Mobile Phases: water (10 mM $NH_4HCO_3$ and 0.05% ammonia) and $CH_3CN$; Gradient: 20% to 60% in 8 min; Flow rate: 15 mL/min; Detector, 254 nm. This afforded 3-amino -N-(2-(5-chloro-6-(piperazin-1-yl)pyridin-3-yl)ethyl)-6-methylthieno[2,3-b]pyridine-2-carboxamide as a light yellow solid (11.7 mg, 24%). LCMS (ESI, m/z): 431 $[M+H]^+$. $^1$H-NMR (300 MHz, DMSO-$d_6$) δ ppm 8.30 (d, J=8.4 Hz, 1H), 8.07 (s, 1H), 7.80-7.69 (m, 2H), 7.31 (d, J=8.4 Hz, 1H), 7.12 (br s, 2H), 3.45-3.39 (m, 2H), 3.15-3.13 (m, 4H), 2.89-2.70 (m, 6H), 2.58 (s, 3H).

Examples 113-A (I-218) and 113-B (I-219)
(S)-N-(4-((5-oxa-2-azaspiro[3.4]octan-7-yl)oxy)phenethyl)-3-amino-6-methylthieno[2,3-b]pyridine-2-carboxamide and (R)-N-(4-((5-oxa-2-azaspiro[3.4]octan-7-yl)oxy)phenethyl)-3-amino-6-methylthieno[2,3-b]pyridine-2-carboxamide
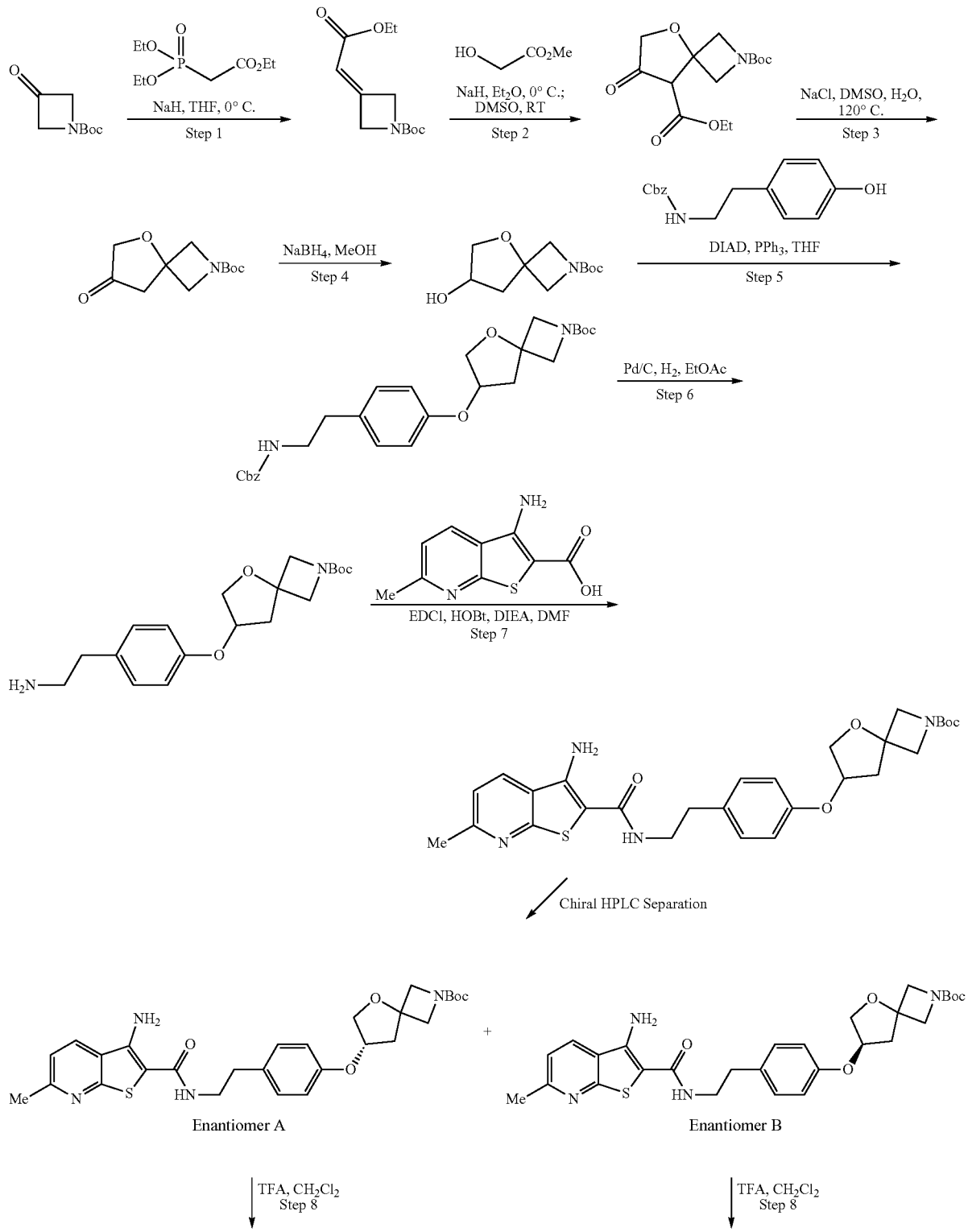

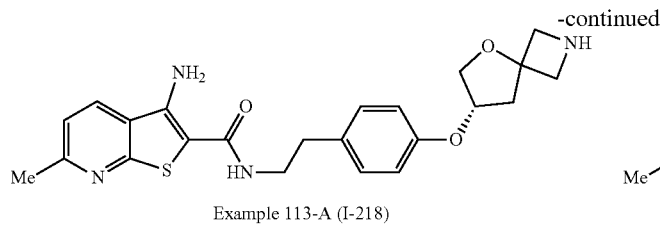

Example 113-A (I-218)

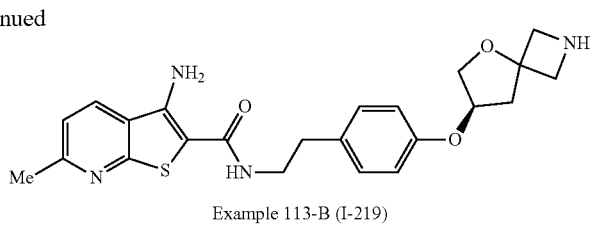

Example 113-B (I-219)

Step 1. tert-Butyl 3-(2-ethoxy-2-oxoethylidene)azetidine-1-carboxylate

Into a 2-L round-bottom flask, was placed a solution of ethyl 2-(diethoxyphosphoryl)acetate (262 g, 1.17 mol) in THF. This was followed by the addition of NaH (46.6 g, 1.17 mol, 60% dispersion in oil) at 0° C. over 1.5 h. After stirring for 30 min at RT, a solution of tert-butyl 3-oxoazetidine-1-carboxylate (100 g, 584 mmol) in THF (1.2 L) was added at 0° C. over 30 min. The resulting mixture was stirred for 40 min at RT. The reaction was then quenched by the addition of 50 mL of $H_2O$ and extracted with 3×500 mL of EtOAc. The combined organic layers was dried over anhydrous $Na_2SO_4$, filtered, and concentrated under vacuum. The crude product was purified via silica gel column chromatography and eluted with EtOAc/petroleum ether (1:5) to afford tert-butyl 3-(2-ethoxy-2-oxoethylidene)azetidine-1-carboxylate as yellow oil (130 g, 92%). LCMS (ESI, m/z): 186 [M+H-tBu]$^+$.

Step 2. 2-(tert-Butyl) 8-ethyl 7-oxo-5-oxa-2-azaspiro[3.4]octane-2,8-dicarboxylate Into a 2-L round-bottom flask purged and maintained with an inert atmosphere of $N_2$ (g), was placed a solution of NaH (8 g, 200 mmol, 60% dispersion in oil) in ether (1 L). This was followed by the addition of methyl 2-hydroxyacetate (18 g, 200 mmol) dropwise with stirring at 0° C. over 30 min. After stirred for 30 min, the ether was removed in vacuo and to this was added a solution of tert-butyl 3-(2-ethoxy-2-oxoethylidene)azetidine-1-carboxylate (40 g, 166 mmol) in DMSO (1 L) dropwise with stirring at RT over 30 min. The resulting solution was stirred overnight at RT. The pH value of the solution was adjusted to 4-5 with 1N HCl and extracted with 3×1 L of ether. The organic phase washed with 3×500 mL of $H_2O$ and dried over anhydrous $Na_2SO_4$, filtered, and concentrated under vacuum to afford 2-(tert-butyl) 8-ethyl 7-oxo-5-oxa-2-azaspiro[3.4]octane-2,8-dicarboxylate as yellow oil (46 g, 83%). LCMS (ESI, m/z): 300 [M+H]$^+$.

Step 3. tert-Butyl 7-oxo-5-oxa-2-azaspiro[3.4]octane-2-carboxylate

Into a 2-L 3-necked round-bottom flask purged and maintained with an inert atmosphere of $N_2$ (g), was placed a solution of 2-tert-butyl 8-ethyl 7-oxo-5-oxa-2-azaspiro[3.4]octane-2,8-dicarboxylate (46 g, 138 mmol) and NaCl (16.7 g, 286 mmol) in DMSO/$H_2O$ (450 mL/45 mL). The resulting solution was stirred for 2 h at 120° C. in an oil bath. The reaction was then quenched by the addition of 40 mL of brine. The resulting solution was extracted with 5×1 L of ether. The combined organic layers was dried over anhydrous $Na_2SO_4$, filtered, and concentrated under vacuum. The crude product was purified via silica gel column chromatography and eluted with EtOAc/petroleum ether (1:5) to afford tert-butyl 7-oxo-5-oxa-2-azaspiro[3.4]octane-2-carboxylate as a yellow solid (21.8 g, 69%). LCMS (ESI, m/z): 228 [M+H]$^+$.

Step 4. tert-Butyl 7-hydroxy-5-oxa-2-azaspiro [3.4]octane-2-carboxylate

Into a 250-mL round-bottom flask, was placed tert-butyl 7-oxo-5-oxa-2-azaspiro[3.4]octane-2-carboxylate (2 g, 8.80 mmol) and MeOH (15 mL). This was followed by the addition of $NaBH_4$ (1 g, 27.16 mmol) in portions. The resulting solution was stirred overnight at room temperature. The reaction was then quenched by the addition of 5 mL of water. The MeOH was removed under vacuum. The resulting solution was extracted with 3×10 mL of EtOAc. The combined organic layers were dried over anhydrous $Na_2SO_4$, filtered, and concentrated under vacuum to afford tert-butyl 7-hydroxy-5-oxa-2-azaspiro[3.4]octane-2-carboxylate as a green liquid (2.01 g crude). LCMS (ESI, m/z): 230 [M+H]$^+$.

Step 5. tert-Butyl 7-(4-(2-(((benzyloxy)carbonyl)amino)ethyl)phenoxy)-5-oxa-2-azaspiro[3.4]octane-2-carboxylate Into a 25-mL round-bottom flask was purged and maintained with an inert atmosphere of nitrogen, was placed benzyl (4-hydroxyphenethyl)carbamate (325 mg, 1.20 mmol), THF (6 mL), tert-butyl 7-hydroxy-5-oxa-2-azaspiro [3.4]octane-2-carboxylate (413 mg, 1.80 mmol) and triphenylphosphine (472 mg, 1.80 mmol). This was followed by the addition of diisopropyl azodicarboxylate (DIAD) (364 mg, 1.80 mmol) dropwise with stirring at 0° C. The resulting solution was stirred for overnight at room temperature. The resulting mixture was poured into 20 mL of water and the resulting mixture was extracted with 3×40 mL of ethyl acetate. The organic layers were combined, dried over anhydrous sodium sulfate, filtered, and concentrated under vacuum. The residue was purified by silica gel column chromatography and eluting with ethyl acetate/petroleum ether (2:1) to afford tert-butyl 7-(4-(2-(((benzyloxy)carbonyl)amino)ethyl)phenoxy)-5-oxa-2-azaspiro[3.4]octane-2-carboxylate as a white solid (410 mg , 71%). LCMS (ESI, m/z): 483 [M+H]$^+$.

Step 6. tert-Butyl 7-(4-(2-aminoethyl)phenoxy)-5-oxa-2-azaspiro[3.4]octane-2-carboxylate Into a 25-mL round-bottom flask equipped with hydrogen balloon, was placed tert -butyl 7-(4-(2-(((benzyloxy)carbonyl)amino)ethyl)phenoxy)-5-oxa-2-azaspiro[3.4]octane-2-carboxylate (410 mg, 0.85 mmol), methanol (12 mL) and 10% Pd/C (60 mg). The resulting mixture was stirred for 3 h at room temperature under hydrogen. The solids were filtered out and the filtrate was concentrated under vacuum to afford tert-butyl 7-(4-(2-aminoethyl)phenoxy)-5-oxa-2-azaspiro[3.4]octane-2-carboxylate as colorless oil (244 mg, crude). LCMS (ESI, m/z): 349 [M+H]$^+$.

Step 7. tert-Butyl (S)-7-(4-(2-(3-amino-6-methylthieno[2,3-b]pyridine-2-carboxamido)ethyl)phenoxy)-5-oxa-2-azaspiro[3.4]octane-2-carboxylate and tert-Butyl (R) -7-(4-(2-(3-amino-6-methylthieno[2,3-b]pyridine-2-carboxamido)ethyl)phenoxy)-5-oxa-2-azaspiro[3.4]octane-2-carboxylate Into a 25-mL round-bottom flask, was placed tert-butyl 7-(4-(2-aminoethyl)phenoxy)-5-oxa-2-azaspiro[3.4]octane-2-carboxylate (132 mg, 0.38 mmol), DMF (4 mL), 3-amino-6-methylthieno[2,3-b]pyridine-2-carboxylic acid (79 mg, 0.38 mmol), DIEA (155 mg, 1.20 mmol), EDCI (150 mg, 0.78 mmol) and HOBt (133 mg, 0.98 mmol). The resulting solution was stirred for overnight at room temperature. The resulting solution was poured into 30 mL of water and the mixture was extracted with 3×20 mL of ethyl acetate. The organic layers were combined, washed with 3×20 mL of brine, dried over anhydrous sodium sulfate, filtered, and concentrated under vacuum. The residue was purified by silica gel column chromatography and eluted with ethyl acetate/petroleum ether (3:1) to afford tert-butyl 7-(4-(2-(3-amino-6-methylthieno[2,3-b]pyridine -2-carboxamido) ethyl)phenoxy)-5-oxa-2-azaspiro[3.4]octane-2-carboxylate as a light brown solid (110 mg, 54%). The racemate was separated by Chiral-Prep-HPLC using the following conditions (SHIMADZU LC-20AD): LC parameters: Pump Mode: Binary gradient, Start Conc. of Pump B: 50.0%, Total Flow: 20 mL/min, Phase A: Hex-HPLC, Phase B: EtOH-HPLC, Column Name: CHIRALPAK IF, Length: 25 mm, Internal Diameter: 2 cm, Particle Size: 5 μm, Column Temp: 20° C., PDA Model: SPD-M20A, Wavelength: from 190 nm to 500 nm. This resulted in the following: Step 7, Enantiomer A: $1^{st}$ eluting peak (retention time=14.4 min, 40 mg, 20% yield, white solid) assigned as tert-butyl (S)-7-(4-(2-(3-amino-6-methylthieno[2,3-b]pyridine-2-carboxamido) ethyl)phenoxy)-5-oxa-2-azaspiro[3.4]octane-2-carboxylate. LCMS (ESI, m/z): 539 [M+H]$^+$; and Step 7, Enantiomer B: $2^{nd}$ eluting peak (retention time=19.3 min, 39 mg, 19% yield, white solid) assigned as tert-butyl (R)-7-(4-(2-(3-amino-6-methylthieno[2,3-b]pyridine-2-carboxamido) ethyl)phenoxy)-5-oxa-2-azaspiro[3.4]octane-2-carboxylate. LCMS (ESI, m/z): 539 [M+H]$^+$.

Step 8. (S)-N-(4-((5-oxa-2-azaspiro[3.4]octan-7-yl)oxy) phenethyl)-3-amino-6-methylthieno[2,3-b]pyridine-2-carboxamide Into a 8-mL vial, was placed tert-butyl (S)-7-(4-(2-(3-amino-6-methylthieno[2,3-b]pyridine-2-carboxamido) ethyl)phenoxy)-5-oxa-2-azaspiro[3.4]octane-2-carboxylate (Step 7, Enantiomer A) (45 mg, 0.08 mmol), dichloromethane (2.1 mL) and trifluoroacetic acid (0.7 mL). The mixture was stirred for 1 h at room temperature. The solvent was evaporated under vacuum and then the residue was dissolved in methanol (1 mL). This was followed by the addition of a solution of NH$_3$ in MeOH (7M, 5 mL) dropwise with stirring. The resulting solution was stirred for 0.5 h at room temperature, and then concentrated under vacuum. The crude product was purified by Prep-HPLC using the following conditions (SHIMADZU LC-20AD): LC parameters: Pump Mode: Binary gradient, Start Conc. of Pump B: 25.0%, End Conc. of Pump B: 45.0% Total Flow: 20 mL/min, Time: 7 min, Phase A: Water (0.1% formic acid), Phase B: MeCN-HPLC, Column Name: XBridge Prep C18 OBD Column, Length: 250 mm, Internal Diameter: 19 mm, Particle Size: 5 μm, Aperture Size: 100 Å, Column Temp: 25° C., PDA Model: SPD-M20A, Wavelength: from 190 nm to 500 nm. This afforded (S)-N-(4-((5-oxa-2-azaspiro[3.4]octan-7-yl)oxy)phenethyl)-3-amino-6-methylthieno[2,3-b]pyridine-2-carboxamide as a green solid (16 mg, 44%). LCMS (ESI, m/z): 439 [M+H]$^+$. $^1$H-NMR (300 MHz, DMSO-d$_6$) δ ppm 8.36 (s, 1H), 8.31 (d, J=8.1 Hz, 1H), 7.72 (t, J=5.4 Hz, 1H), 7.31 (d, J=8.4 Hz, 1H), 7.17-7.12 (m, 4H), 6.84 (m, J=8.4 Hz 2H), 5.01-5.03 (m, 1H), 3.98-4.03 (m, 1H), 3.72-3.91 (m, 5H), 3.42-3.35 (m, 2H), 2.78-2.73 (m, 2H), 2.58 (s, 3H), 2.45-2.27 (m, 2H).

Step 8. (R)-N-(4-((5-oxa-2-azaspiro[3.4]octan-7-yl)oxy) phenethyl)-3-amino-6-methylthieno[2,3-b]pyridine-2-carboxamide The same synthetic procedure described to prepare (S)-N-(4-((5-oxa-2-azaspiro[3.4]octan-7-yl)oxy)phenethyl)-3-amino-6-methylthieno[2 ,3-b]pyridine-2-carboxamide was applied to Step 7, Enantiomer B to afford (R)-N-(4-((5-oxa-2-azaspiro[3.4]octan-7-yl)oxy)phenethyl)-3-amino-6-methylthieno[2,3-b]pyridine-2-carboxamide as a green solid (18.8 mg, 51%). LCMS (ESI, m/z): 439 [M+H]$^+$. $^1$H-NMR (300 MHz, DMSO-d$_6$) δ ppm 8.34 (s, 1H), 8.29 (d, J=8.4 Hz, 1H), 7.70 (t, J=5.7 Hz, 1H), 7.30 (d, J=8.4 Hz, 1H), 7.17-7.12 (m, 4H), 6.84 (d, J=8.7 Hz, 2H), 5.01-5.03 (m, 1H), 3.98-4.03 (m, 1H), 3.67-3.89 (m, 5H), 3.42-3.35 (m, 2H), 2.78-2.73 (m, 2H), 2.58 (s, 3H), 2.43-2.29 (m, 2H).

Example 114 (I-220)

3-Amino-6-cyano-N-(2,5-difluoro-4-(piperazin-1-yl) phenethyl)thieno[2,3-b]pyridine-2-carboxamide

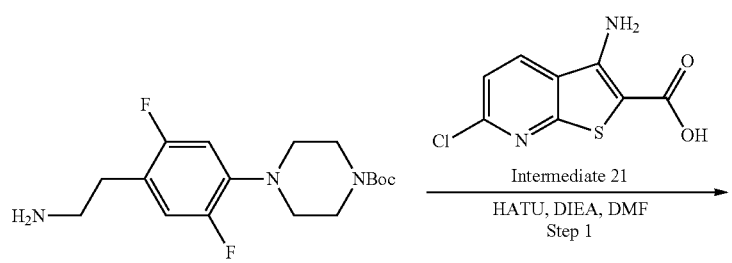

Intermediate 49

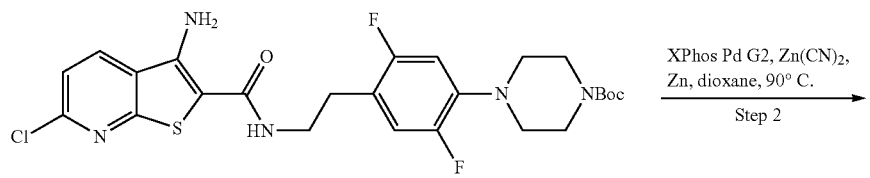

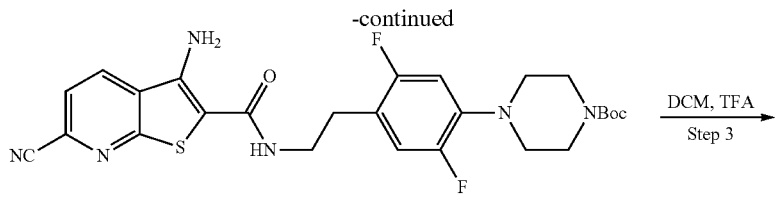

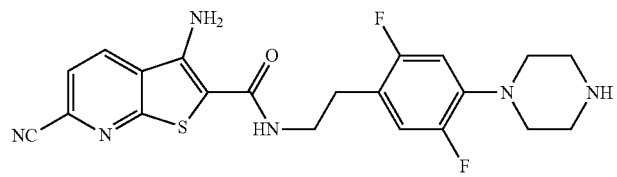

Step 1. tert-Butyl 4-(4-(2-(3-amino-6-chlorothieno[2,3-b]pyridine-2-carboxamido)ethyl)-2,5-difluorophenyl)piperazine-1-carboxylate Into a 50-mL round-bottom flask, was placed a solution of 3-amino-6-chlorothieno[2,3-b]pyridine-2-carboxylic acid (Intermediate 21) (300 mg, 1.31 mmol) in DMF (3 mL), HATU (608 mg, 1.60 mmol), DIEA (255 mg, 1.97 mmol) and tert-butyl 4-(4-(2-aminoethyl)-2,5-difluorophenyl)piperazine-1-carboxylate (Intermediate 49) (403 mg, 1.18 mmol). The resulting solution was stirred for 1 h at room temperature. The reaction was then quenched by the addition of 10 mL of water. The resulting mixture was extracted with 3×10 mL of ethyl acetate. The organic layers were combined, washed with 30 mL of brine, dried over anhydrous sodium sulfate, filtered, and concentrated under vacuum. The residue was purified by silica gel chromatography and eluted with ethyl acetate/petroleum ether (1:1) to afford tert-butyl 4-(4-(2-(3-amino-6-chlorothieno[2,3-b]pyridine-2-carboxamido)ethyl)-2,5-difluorophenyl)piperazine-1-carboxylate as a yellow solid (300 mg, 41%). LCMS (ESI, m/z): 552, 554 [M+H]$^+$.

Step 2. tert-Butyl 4-(4-(2-(3-amino-6-cyanothieno[2,3-b]pyridine-2-carboxamido)ethyl)-2,5-difluorophenyl)piperazine-1-carboxylate Into a 50-mL round-bottom flask purged and maintained with an inert atmosphere of nitrogen, was placed tert-butyl 4-(4-(2-(3-amino-6-chlorothieno[2,3-b]pyridine-2-carboxamido)ethyl)-2,5-difluorophenyl)piperazine-1-carboxylate (240 mg, 0.43 mmol), Zn(CN)$_2$ (80 mg, 0.68 mmol), Zn (6 mg, 0.09 mmol), 2nd Generation XPhos Precatalyst (XPhos Pd G2) (36 mg, 0.046 mmol) and dioxane (4 mL). The resulting solution was stirred overnight at 90° C. under an atmosphere of nitrogen. The resulting mixture was cool to room temperature. The reaction was then quenched by the addition of 20 mL of water. The resulting solution was extracted with 3 ×20 mL of ethyl acetate. The organic layers were combined, dried over anhydrous sodium sulfate, filtered, and concentrated under vacuum. The residue was purified by silica gel chromatography and eluted with ethyl acetate/petroleum ether (1:1) to afford tert-butyl 4-(4-(2-(3-amino-6-cyanothieno[2,3-b]pyridine-2-carboxamido)ethyl)-2,5-difluorophenyl)piperazine-1-carboxylate as a yellow solid (150 mg, 64%). LCMS (ESI, m/z): 543 [M+H]$^+$.

Step 3. 3-Amino-6-cyano-N-(2,5-difluoro-4-(piperazin-1-yl)phenethyl)thieno[2,3-b]pyridine-2-carboxamide Into a 50-mL round-bottom flask, was placed tert-butyl 4-(4-(2-(3-amino-6-cyanothieno [2,3-b]pyridine-2-carboxamido)ethyl)-2,5-difluorophenyl)piperazine-1-carboxylate (60 mg, 0.11 mmol), DCM (1 mL) and TFA (0.5 mL). The resulting solution was stirred for 0.5 h at room temperature and concentrated under vacuum. The pH value of the residue was adjusted to 8 with a solution of NH$_3$ in MeOH (7M). The resulting mixture was extracted with 3×10 mL ethyl acetate. The organic layers were combined, washed with 10 mL of brine, dried over anhydrous sodium sulfate, filtered, and concentrated under vacuum. The residue was purified by Prep-HPLC using the following conditions (SHIMADZU LC-20AD): LC parameters: Pump Mode: Binary gradient, Start Conc. of Pump B: 25.0%, End Conc. of Pump B: 80.0% Total Flow: 15 mL/min, Time: 9 min, Phase A: Water (10 mM NH$_4$HCO$_3$), Phase B: MeCN-HPLC, Column Name: XBridge BEH C18 OBD Column, Length: 150 mm, Internal Diameter: 19 mm, Particle Size: 5 μm, Aperture Size: 130 Å, Column Temp: 25° C., PDA Model: SPD-M20A, Wavelength: from 190 nm to 500 nm. This afforded 3-amino-6-cyano-N-(2,5-difluoro-4-(piperazin-1-yl)phenethyl)thieno[2,3-b]pyridine-2-carboxamide as a yellow solid (2.9 mg, 6%). LCMS (ESI, m/z): 443 [M+H]$^+$. $^1$H-NMR (300 MHz, Methanol-d$_4$) δ ppm 8.47 (d, J=8.4 Hz, 1H), 7.83 (d, J =8.1 Hz, 1H), 7.04-6.97 (m, 1H), 6.79-6.73 (m, 1H), 3.57-3.52 (m, 2H), 3.13-2.92 (m, 8H), 2.90-2.85 (m, 2H).

Examples 115-A (I-221) and 115-B (I-222)
(S)-3-Amino-6-(1-hydroxyethyl)-N-(4-(piperazin-1-yl)phenethyl)thieno[2,3-b]pyridine-2-carboxamide and (R)-3-Amino-6-(1-hydroxyethyl)-N-(4-(piperazin-1-yl)phenethyl)thieno[2,3-b]pyridine-2-carboxamide
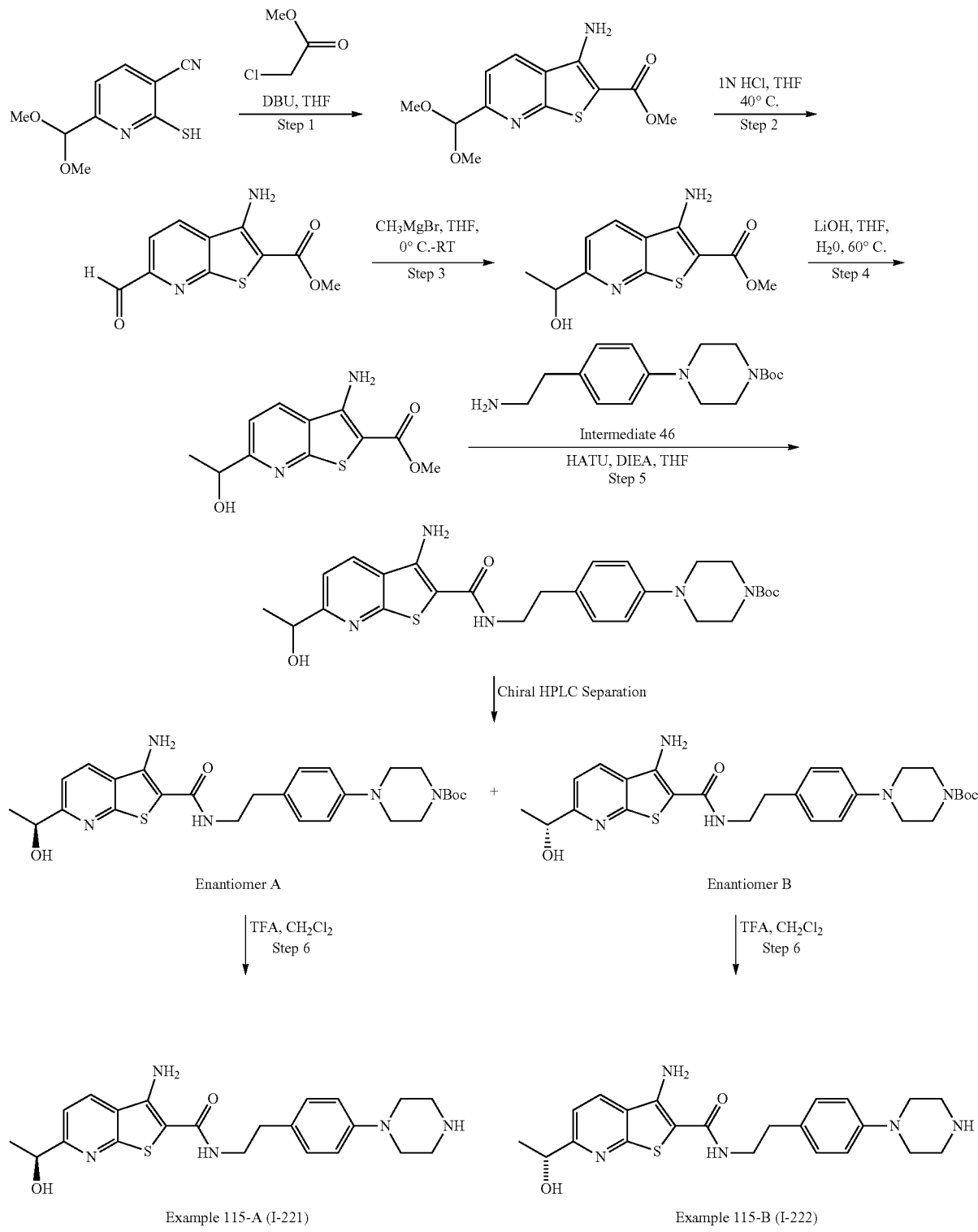

Step 1. Methyl 3-amino-6-(dimethoxymethyl)thieno[2,3-b]pyridine-2-carboxylate

Into a 50-mL 3-necked round-bottom flask purged and maintained with an inert atmosphere of nitrogen, was placed 6-(dimethoxymethyl)-2-sulfanylpyridine-3-carbonitrile (500 mg, 2.38 mmol), THF (10 mL), methyl 2-chloroacetate (310 mg, 2.86 mmol), and DBU (1.09 g, 7.16 mmol). The resulting solution was stirred overnight at room temperature. The resulting mixture was concentrated under vacuum. The residue was purified by silica gel chromatography and eluted with ethyl acetate/petroleum ether (3:7) to afford methyl 3-amino-6-(dimethoxymethyl)thieno[2,3-b]pyridine-2-carboxylate as a yellow solid (852 mg, crude). LCMS (ESI, m/z): 283[M+H]$^+$.

Step 2. Methyl 3-amino-6-formylthieno[2,3-b]pyridine-2-carboxylate

Into a 100-mL round-bottom flask, was placed methyl 3-amino-6-(dimethoxymethyl)thieno[2,3-b]pyridine-2-carboxylate (842.5 mg, 2.98 mmol), THF (10 mL), and aq. HCl (1N, 30 mL). The resulting solution was stirred overnight at 40° C. The resulting mixture was concentrated under vacuum. The resulting solution was extracted with 2×200 mL of ethyl acetate. The organic layers were combined and washed with 50 mL of sat. aq. sodium bicarbonate solution and 50 mL of brine. The organic phase was dried over anhydrous sodium sulfate, filtered, and concentrated under vacuum to afford methyl 3-amino-6-formylthieno[2,3-b]pyridine-2-carboxylate as a yellow solid (870 mg, crude). $^1$H-NMR (300 MHz, CDCl$_3$) δ ppm 10.17 (s, 1H), 8.13-8.11 (m, 1H), 8.00-7.97 (m, 1H), 3.96 (s, 3H).

Step 3. Methyl 3-amino-6-(1-hydroxyethyl)thieno[2,3-b]pyridine-2-carboxylate

Into a 100-mL round-bottom flask purged and maintained with an inert atmosphere of nitrogen, was placed methyl 3-amino-6-formylthieno[2,3-b]pyridine-2-carboxylate (870 mg, 3.68 mmol), THF (20 mL). This was followed by the addition of CH$_3$MgBr (3M in diethyl ether) (12 mL) dropwise with stirring at 0° C. in 1 hr. The resulting solution was stirred overnight at room temperature. The reaction was then quenched by the addition of 20 mL of methanol. The resulting mixture was concentrated under vacuum. The residue was purified by silica gel chromatography and eluted with dichloromethane/ethyl acetate (1:1) to afford methyl 3-amino-6-(1-hydroxyethyl)thieno[2,3-b]pyridine-2-carboxylate as a yellow solid (300 mg, 32%). $^1$H-NMR (300 MHz, CDCl$_3$) δ ppm 7.93 (d, J=8.4 Hz, 1H), 7.29 (d, J=8.4 Hz, 1H), 5.05-4.98 (m, 1H), 3.91 (s, 3H), 1.58-1.55 (m, 3H).

Step 4. 3-Amino-6-(1-hydroxyethyl)thieno[2,3-b]pyridine-2-carboxylic acid

Into a 50-mL round-bottom flask, was placed methyl 3-amino-6-(1-hydroxyethyl)thieno[2,3-b]pyridine-2-carboxylate (350 mg, 1.39 mmol), THF (10 mL), water (3 mL), and LiOH (100 mg, 4.18 mmol). The resulting solution was stirred overnight at 60° C. The reaction mixture was cooled to room temperature and concentrated under vacuum. The pH value of the solution was adjusted to 3 with 1N HCl. The solids were collected by filtration to afford 3-amino-6-(1-hydroxyethyl)thieno[2,3-b]pyridine-2-carboxylic acid as a yellow solid (40 mg, 12%). LCMS (ESI, m/z): 239 [M+H]$^+$.

Step 5. tert-Butyl (S)-4-(4-(2-(3-amino-6-(1-hydroxyethyl)thieno[2,3-b]pyridine-2-carboxamido)ethyl)phenyl)piperazine-1-carboxylate and tert-Butyl (R)-4-(4-(2-(3-amino-6-(1-hydroxyethyl)thieno[2,3-b]pyridine-2-carboxamido)ethyl)phenyl)piperazine-1-carboxylate Into a 8-mL round-bottom flask purged and maintained with an inert atmosphere of nitrogen, was placed 3-amino-6-(1-hydroxyethyl)thieno[2,3-b]pyridine-2-carboxylic acid (28.4 mg, 0.12 mmol), tert-butyl 4-(4-(2-aminoethyl)phenyl)piperazine-1-carboxylate (43.7 mg, 0.14 mmol), HATU (68.4 mg, 0.18 mmol), DIEA (31 mg, 0.24 mmol), and THF (2 mL). The resulting solution was stirred overnight at room temperature. The resulting mixture was concentrated under vacuum. The crude product was purified by Prep-TLC with ethyl acetate to afford tert-butyl 4-(4-(2-(3-amino-6-(1-hydroxyethyl)thieno[2,3-b]pyridine-2-carboxamido)ethyl) phenyl)piperazine-1-carboxylate as a solid (20 mg, 32%). The racemate was separated by Chiral-Prep-HPLC using the following conditions (SHIMADZU LC-20AD): LC Parameters: Pump Mode, Binary gradient, start conc. of pump B, 40.0%; Total Flow:1 mL/min; Phase A: n-Hexanes, Phase B: Isopropanol; Column Name: DAICEL CHIRAL PAK AD-3; Length: 50 mm; Internal Diameter: 4.6 mm; Particle size: 3 μm; Column Temp.: 25° C.; PDA Model: SPD-M20A; Wavelength: from 190 nm to 500 nm. This resulted in the following: Step 5, Enantiomer A: 1$^{st}$ eluting peak (retention time =4.0 min, 60 mg, 50% yield, yellow solid) assigned as tert-butyl (S)-4-(4-(2-(3-amino-6-(1-hydroxyethyl)thieno[2,3-b]pyridine-2-carboxamido)ethyl)phenyl)piperazine-1-carboxylate. LCMS (ESI, m/z): 526 [M+H]$^+$; and Step 5, Enantiomer B: 2$^{nd}$ eluting peak (retention time=5.2 min, 50 mg, 50% yield, yellow solid) assigned as tert-butyl (R)-4-(4-(2-(3-amino-6-(1-hydroxyethyl)thieno[2,3-b]pyridine-2-carboxamido)ethyl)phenyl)piperazine-1-carboxylate. LCMS (ESI, m/z): 526 [M+H]$^+$.

Step 6. (S)-3-Amino-6-(1-hydroxyethyl)-N-(4-(piperazin-1-yl)phenethyl)thieno[2,3-b]pyridine-2-carboxamide Into a 50-mL round-bottom flask, was placed tert-butyl (S)-4-(4-(2-(3-amino-6-(1-hydroxyethyl)thieno[2,3-b]pyridine-2-carboxamido)ethyl)phenyl)piperazine-1-carboxylate (Step 5, Enantiomer A) (22 mg, 0.04 mmol), dichloromethane (2 mL), and TFA (0.4 mL). The resulting solution was stirred for 1 h at room temperature, and then concentrated under vacuum. The crude product was purified by Prep-HPLC using the following conditions: Column: X Bridge C18, 19×150 mm, 5 μm; mobile phase: water (10 mM NH$_4$HCO$_3$, 0.05% ammonia) and CH$_3$CN; Gradient: 35% to 45% in 8 min; Flow rate:15 mL/min; Detector: 254 nm. This afforded (S)-3-amino-6-(1-hydroxyethyl)-N-(4-(piperazin-1-yl)phenethyl)thieno[2,3-b]pyridine-2-carboxamide as a yellow solid (9 mg, 51%). LCMS (ESI, m/z): 426 [M+H]$^+$. $^1$H-NMR (300 MHz, Methanol-d$_4$) δ ppm 8.30 (d, J=8.1 Hz, 1H), 7.57 (d, J=8.4 Hz, 1H), 7.20-7.17 (m, 2H), 6.96-6.93 (m, 2H), 4.97-4.91 (m, 1H), 3.59-3.51 (m, 2H), 3.17-3.12 (m, 4H), 3.08-2.93 (m, 4H), 2.89-2.80 (m, 2H), 1.53 (d, J=6.6 Hz, 3H).

Step 6. (R)-3-Amino-6-(1-hydroxyethyl)-N-(4-(piperazin-1-yl)phenethyl)thieno[2,3-b]pyridine-2-carboxamide The same synthetic procedure described to prepare (S)-3-amino-6-(1-hydroxyethyl)-N -(4-(piperazin-1-yl)phenethyl)thieno[2,3-b]pyridine-2-carboxamide was applied to Step 5, Enantiomer B to afford (R)-3-amino-6-(1-hydroxyethyl)-N-(4-(piperazin-1-yl)phenethyl)thieno[2,3-b]pyridine-2-carboxamide as a yellow solid (9 mg, 51%). LCMS (ESI, m/z): 426 [M+H]$^+$. $^1$H-NMR (300 MHz, Methanol-d$_4$) δ ppm 8.30 (d, J=8.4 Hz, 1H), 7.57 (d, J =8.4 Hz, 1H), 7.19-7.12 (m, 2H), 6.96-6.93 (m, 2H), 5.00-4.91(m, 1H), 3.54-3.49 (m, 2H), 3.13-3.11 (m, 4H), 3.10-2.93 (m, 4H), 2.85-2.80 (m, 2H), 1.53 (d, J=6.6 Hz, 3H).

Example 116 (I-223)

3-Amino-7-hydroxy-N-(4-(piperazin-1-yl)phen-ethyl)-6,7-dihydro-5H-cyclopenta[b]thieno[3,2-e]pyridine-2-carboxamide

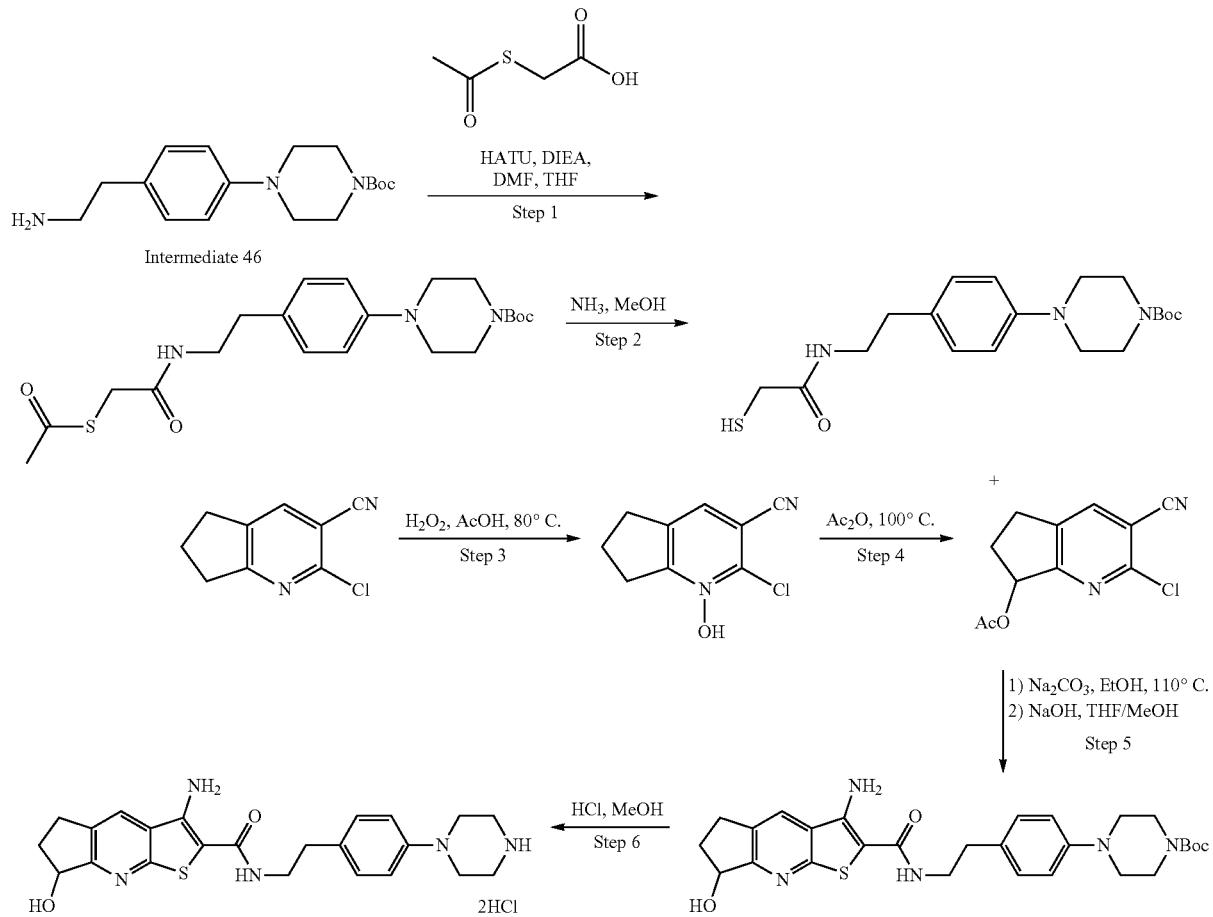

Step 1. tert-Butyl 4-(4-(2-(2-(acetylthio)acetamido)ethyl)phenyl)piperazine-1-carboxylate A mixture of HATU (1.62 g, 4.26 mmol), DIEA (1.72 mL, 9.82 mmol), tert-butyl 4-(4-(2-aminoethyl)phenyl)piperazine-1-carboxylate (1 g, 3.27 mmol), and 2-(acetylthio)acetic acid (0.338 mL, 3.27 mmol) in THF (20 mL) and DMF (40 mL) was stirred at RT overnight, and then concentrated under vacuum. The residue was taken up in EtOAc, and then washed with water and brine. The organic phase was dried and concentrated. The crude product was purified by silica gel chromatography and eluted with 10 to 100% EtOAc/Hexanes to afford tert-butyl 4-(4-(2-(2-(acetylthio)acetamido)ethyl)phenyl)piperazine-1-carboxylate (700 mg, 50.7%). LCMS (ESI, m/z): 220 [M+H]$^+$. $^1$H-NMR (300 MHz, CDCl$_3$) δ ppm 7.08 (d, J=8.2 Hz, 2H), 6.87 (d, J=8.2 Hz, 2H), 6.14 (br s, 1H), 3.56 (m, 4H), 3.48 (s, 2H), 3.41-3.47 (m, 2H), 3.09 (m, 4H), 2.80 (d, J =0.9 Hz, 2H), 2.71 (m, 2H), 2.35 (s, 3H), 1.48 (s, 9H).

Step 2. tert-Butyl 4-(4-(2-(2-mercaptoacetamido)ethyl)phenyl)piperazine-1-carboxylate A solution of tert-butyl 4-(4-(2-(2-(acetylthio)acetamido)ethyl)phenyl)piperazine-1-carboxylate (620 mg, 1.47 mmol) in MeOH (20 mL) was bubbled with N$_2$ for 15 min, and then ammonia (7N, 10 mL, 70 mmol) was added. The mixture was stirred under N$_2$ gas for 2 h. The reaction mixture was concentrated under vacuum. The residue was taken up in sat. aq. NH$_4$Cl solution, extracted with EtOAc, dried and concentrated to afford tert-butyl 4-(4-(2-(2-mercaptoacetamido)ethyl)phenyl) piperazine-1-carboxylate (354 mg, 63.4%). LCMS (ESI, m/z): 380 [M+H]$^+$. $^1$H-NMR (300 MHz, CDCl$_3$) δ ppm 6.98-7.12 (d, J=8.5 Hz, 2H), 6.80 (d, J=8.5 Hz, 2H), 6.48 (m, 1H), 3.39-3.63 (m, 6H), 3.28 (s, 2H), 2.97-3.10 (m, 4H), 2.66-2.83 (m,2H), 1.41 (s, 9H).

Step 3. 2-Chloro-1-(λ$^1$-oxidanyl)-6,7-dihydro-5H-1λ$^4$-cyclopenta[b]pyridine-3-carbonitrile To a stirred solution of 2-chloro-6,7-dihydro-5H-cyclopenta[b]pyridine-3-carbonitrile (600 mg, 3.36 mmol)) in acetic acid (10 mL) was added H$_2$O$_2$ (1.54 mL, 15.12 mmol). The resultant mixture was heated at 80° C. for 16 h. The reaction mixture was then allowed to cool to room temperature and concentrated in vacuo. The residue was taken up in water (100 mL). The slightly acidic solution was neutralized by the careful addition of potassium carbonate (~1.0 g) and then extracted with chloroform (3×30 mL). The combined organic extracts were washed with water (3×15 mL), dried over anhydrous magnesium sulfate, filtered, and concentrated in vacuo to afford crude 2-chloro-1-($\lambda^1$-oxidanyl)-6,7-dihydro-5H-1$\lambda^4$-cyclopenta[b]pyridine-3-carbonitrile as a white crystalline solid.

Step 4. 2-Chloro-3-cyano-6,7-dihydro-5H-cyclopenta[b]pyridin-7-yl acetate

The crude 2-chloro-1-($\lambda^1$-oxidanyl)-6,7-dihydro-5H-1$\lambda^4$-cyclopenta[b]pyridine-3-carbonitrile from above was taken up in acetic anhydride (25 mL) and the resultant suspension was stirred at room temperature for 1 h and then heated at 100° C. for 4 h. The reaction mixture was then allowed to cool to room temperature and was concentrated in vacuo. The crude product was purified by silica gel chromatography and eluted with hexanes/diethyl ether (1:1) to afford 2-chloro-3-cyano-6,7-dihydro-5H-cyclopenta[b]pyridin-7-yl acetate (500 mg, 63% yield over 2 steps). LCMS (ESI, m/z): 238 [M+H]$^+$. $^1$H-NMR (300 MHz, CDCl$_3$) δ ppm 8.05 (s, 1H), 6.11 (dd, J=7.3, 3.5 Hz, 1H), 3.24 (dd, J=8.8, 6.7 Hz, 1H), 3.08 (br dd, J=8.9, 4.8 Hz, 1H), 2.48-2.72 (m, 1H), 2.27 (m,1H), 2.08 (s 3H).

Step 5. tert-Butyl 4-(4-(2-(3-amino-7-hydroxy-6,7-dihydro-5H-cyclopenta[b]thieno[3,2-e]pyridine-2-carboxamido)ethyl)phenyl)piperazine-1-carboxylatelate A mixture of Na$_2$CO$_3$ (134 mg, 1.27 mmol), 2-chloro-3-cyano-6,7-dihydro-5H-cyclopenta[b]pyridin-7-yl acetate (100 mg, 0.423 mmol), and tert-butyl 4-(4-(2-(2-mercaptoacetamido)ethyl)phenyl)piperazine-1-carboxylate (160 mg, 0.423 mmol) in ethanol (2 mL) was stirred at 110° C. (oil bath temperature) in a sealed tube. The reaction mixture was then cooled to RT and diluted with 15 mL of water. The resulting mixture was filtered, and the solid was purified by silica gel chromatography and eluted with 0 to 10% MeOH/DCM to afford tert-butyl 4-(4-(2-(7-acetoxy-3-amino-6,7-dihydro-5H-cyclopenta[b]thieno[3,2-e]pyridine-2-carboxamido)ethyl)phenyl)piperazine-1-carboxylate (77 mg, 31.4%). To a solution of tert-butyl 4-(4-(2-(7-acetoxy-3-amino-6,7-dihydro-5H-cyclopenta[b]thieno[3,2-e]pyridine-2-carboxamido)ethyl)phenyl)piperazine-1-carboxylate (77 mg, 0.133 mmol) in 10 mL of MeOH and 10 mL of THF was added 10 mL of 1N NaOH. The mixture was stirred at RT overnight, and then concentrated in vacuo. The residue was taken up in EtOAc, washed with brine, dried, filtered, and concentrated. The crude product was purified by silica gel chromatography and eluted with 20 to 100% EtOAc/Hexanes to afford tert-butyl 4-(4-(2-(3-amino-7-hydroxy-6,7-dihydro-5H-cyclopenta[b]thieno[3,2-e]pyridine-2-carboxamido)ethyl)phenyl)piperazine-1-carboxylate (37 mg, 51.7%). LCMS (ESI, m/z): 538 [M+H]$^+$. $^1$H-NMR (300 MHz, CDCl$_3$) δ ppm 7.77 (s, 1H), 7.15 (d, J=8.5 Hz, 2H), 6.89 (d, J=8.5 Hz, 2H), 6.01 (br s, 2H), 5.54-5.68 (m, 1H), 5.22-5.37 (m, 1H), 3.52-3.73 (m, 6H), 3.10 (br s, 4H), 2.76-2.99 (m, 4H), 2.58-2.74 (m, 1H), 1.48 (s, 9H).

Step 6. 3-Amino-7-hydroxy-N-(4-(piperazin-1-yl)phenethyl)-6,7-dihydro-5H-cyclopenta[b]thieno[3,2-e]pyridine-2-carboxamide hydrochloride salt To a solution of tert-butyl 4-(4-(2-(3-amino-7-hydroxy-6,7-dihydro-5H-cyclopenta[b]thieno[3,2-e]pyridine-2carboxamido)ethyl)phenyl)piperazine-1-carboxylate (37 mg, 0.069 mmol) in methanol (10 mL) was added 2N HCl (0.052 mL, 0.206 mmol) at RT. The mixture was stirred at RT overnight and concentrated. The residue was taken up in diethyl ether, filtered, and the solids dried to afford 3-amino-7-hydroxy-N-(4-(piperazin-1-yl)phenethyl)-6,7-dihydro-5H-cyclopenta[b]thieno [3,2-e]pyridine-2-carboxamide as the hydrochloride salt (29.2 mg). LCMS (ESI, m/z): 438 [M+H]$^+$. $^1$H-NMR (300 MHz, DMSO-d$_6$) δ ppm 9.07 (br s, 2H), 8.20 (s, 1H), 7.67 (br t, J=5.3 Hz, 1H), 7.06 (br d, J=8.5 Hz, 2H), 6.87 (br d, J=8.5 Hz, 2H), 4.95 (m, 1H), 3.56-3.71 (m, 1H), 3.30 (m, 2H), 3.11 (m, 4H), 2.85-3.05 (m, 2H), 2.56-2.84 (m, 3H), 2.21-2.39 (m, 2H), 1.83 (m, 2H).

Example 117

Biochemical Assay: Ubiquitin-Rhodamine 110 Assay for USP28 Activity

The assay was performed in a final volume of 20 μL in assay buffer containing 20 mM Tris-HCl (pH 8.0, (1M Tris-HCl, pH 8.0 solution; Corning 46-031-CM)), 2 mM CaCl$_2$ (1M Calcium Chloride solution; Sigma #21114) 2 mM BME (2-Mercaptoethanol; Sigma 63689-25ML -F), 0.01% Prionex (0.22 μM filtered, Sigma #G-0411), and 0.01% Triton X-100. Stock compound solutions were stored at −20° C. as 10 mM in DMSO. Up to 1 month prior to the assay, 2 mM test compounds were pre-dispensed into assay plates (Black, low volume; Corning #3820) and frozen at −20° C. Prestamped assay plates were allowed to come to room temperature on the day of the assay. For the screen, 100 nL of 2 mM was pre-dispensed for a final screening concentration of 10 μM (DMSO$_{(fc)}$=0.5%). Enzyme (USP28, construct USP28 (USP28-5(1-1077)-TEV-6*His; LifeSensors) concentration and incubation times were optimized for the maximal signal-to -background while maintaining initial velocity conditions at a fixed substrate concentration. The final concentration of the enzyme in the assay was 400 pM. Final substrate (Ub-Rh110; Ubiquitin -Rhodamine 110, R&D Systems #U-555) concentration was 25 nM with [Ub-Rh110]<<Km. 10 μL of 2× enzyme was added to assay plates (pre-stamped with compound) either simultaneously with 2×Ub-Rh110 or preincubated with USP28 40 minutes prior to the addition of 10 μL of 2×Ub -Rh110 to compound plates. Plates were incubated stacked for 90 minutes at room temperature before fluorescence was read on the Envision (Excitation at 485 nm and Emission at 535 nm; Perkin Elmer) or on the PheraSTAR (Excitation at 485 nm and Emission at 535 nm; BMG Labtech).

For follow-up studies, the assay was performed in a final volume of 15 μL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 μM filtered, Sigma, G7516-25G), and 0.01% Triton X-100 (Sigma, T9284-10L). Nanoliter quantities of either an 8-point or 10-point, 3-fold serial dilution in DMSO was pre-dispensed into assay plates (Perkin Elmer, ProxiPlate-384 F Plus) for a final test concentration of either 25 μM to 11 nM or 25 μM to 1.3 nM, respectively. Enzyme USP28, construct USP28 (USP28-5 (1-1077)-TEV-6*His; LifeSensors) concentration and incubation times were optimized for the maximal signal-to -background while maintaining initial velocity conditions at a fixed substrate concentration. The final concentration of the enzyme in the assay was 75 pM. Final substrate (Ub-Rh110; Ubiquitin -Rhodamine 110, R&D Systems #U-555) concentration was 25 nM with [Ub-Rh110]<<Km. 5 μL of 2× enzyme was added to assay plates (pre-stamped with compound) preincubated with USP28 for 30 minutes and then 5 μL of 2× Ub-Rh110 was added to assay plates. Plates were incubated stacked for 20 min at room temperature before 5 μL of stop solution was added (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

Example 118

Biochemical Assay: Ubiquitin-Rhodamine 110 Assay for USP25 Activity

The assay was performed in a final volume of 9 μL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 μM filtered, Sigma, G7516-25G), and 0.01% Triton X-100 (Sigma, T9284-10L). Nanoliter quantities of 10-point, 3-fold serial dilution in DMSO was pre-dispensed into 1536 assay plates (Corning, #3724BC) for a final test concentration of 25 μM to 1.3 nM, top to lowest dose, respectively. Enzyme USP25, construct USP25-His6, (Boston Biochem E-546). Concentration and incubation times were optimized for the maximal signal-to-background while maintaining initial velocity conditions at a fixed substrate concentration. The final concentration of the enzyme in the assay was 75 pM. Final substrate (Ub -Rh110; Ubiquitin-Rhodamine 110, R&D Systems #U-555) concentration was 25 nM with [Ub -Rh110]<<Km. 3 μL of 2× enzyme was added to assay plates (pre-stamped with compound) preincubated with USP25 for 30 minutes and then 3 μL of 2× Ub-Rh110 was added to assay plates. Plates were incubated for 45 minutes at room temperature before addition of 3 μL of stop solution (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

For both the USP28 and USP25 assay formats, data were reported as percent inhibition compared with control wells based on the following equation: % inh=1-((FLU-Ave$_{Low}$)/(Ave$_{High}$-Ave$_{Low}$)) where FLU=measured Fluorescence, Ave$_{Low}$=average Fluorescence of no enzyme control (n=16), and Ave$_{High}$=average Fluorescence of DMSO control (n=16). IC$_{50}$ values were determined by curve fitting of the standard 4 parameter logistic fitting algorithm included in the Activity Base software package: IDBS XE Designer Model205. Data is fitted using the Levenburg Marquardt algorithm.

Table 28: USP28 and USP25 activities of compounds of the disclosure in USP28 and USP25 assays. ++++ indicates an IC$_{50}$ of less than about 0.2 μM, +++ indicates an IC$_{50}$ between about 0.2 μM and about 2 μM, ++ indicates an IC$_{50}$ between about 2 μM and about 10 μM, and + indicates an IC$_{50}$ between about 10 μM and about 25 μM. ND indicates that the data has not been determined.

TABLE 28

USP28 and USP25 Assays

| Compound No. | USP28 IC$_{50}$ | USP25 IC$_{50}$ |
|---|---|---|
| I-1 | +++ | +++ |
| I-2 | ++++ | ++++ |
| I-3 | +++ | ND |
| I-4 | ++++ | ND |
| I-5 | +++ | +++ |
| I-6 | ++++ | +++ |
| I-7 | +++ | ++++ |
| I-8 | ++++ | ND |
| I-9 | +++ | ND |
| I-10 | ++ | +++ |
| I-11 | +++ | +++ |
| I-12 | ++++ | +++ |
| I-13 | ++++ | +++ |
| I-14 | ++++ | ++++ |
| I-15 | ++++ | +++ |
| I-16 | ++++ | +++ |
| I-17 | +++ | ++ |
| I-18 | ++++ | ++++ |
| I-19 | ++++ | ++++ |
| I-20 | +++ | +++ |
| I-21 | ++++ | ++++ |
| I-22 | ++++ | +++ |
| I-23 | +++ | ++ |
| I-24 | ++ | + |
| I-25 | +++ | ++ |
| I-26 | +++ | ++ |
| I-27 | ++ | + |
| I-28 | ++ | ++ |
| I-29 | ++ | ++ |
| I-30 | ++ | + |
| I-31 | ++ | ++ |
| I-32 | ++ | ND |
| I-33 | ++ | ++ |
| I-34 | ++++ | +++ |
| I-35 | ++++ | ND |
| I-36 | ++++ | +++ |
| I-37 | ++++ | +++ |
| I-38 | +++ | ++ |
| I-39 | ++ | ND |
| I-40 | +++ | ++ |
| I-41 | ++++ | +++ |
| I-42 | +++ | ND |
| I-43 | +++ | ++ |
| I-44 | ++++ | ++++ |
| I-45 | ++++ | ND |
| I-46 | +++ | ND |
| I-47 | ++++ | ++++ |
| I-48 | ++++ | ++++ |
| I-49 | ++++ | ND |
| I-50 | +++ | ND |
| I-51 | ++++ | ND |
| I-52 | ++++ | +++ |
| I-53 | ++++ | ++++ |
| I-54 | ++++ | +++ |
| I-55 | ++++ | ND |
| I-56 | +++ | +++ |
| I-57 | +++ | ND |
| I-58 | ++++ | +++ |
| I-59 | +++ | +++ |
| I-60 | +++ | +++ |
| I-61 | +++ | ++ |
| I-62 | ++++ | ++++ |
| I-63 | ++++ | +++ |
| I-64 | ++++ | ++++ |
| I-65 | ++++ | ++++ |
| I-66 | ++++ | ND |
| I-67 | ++++ | ++++ |
| I-68 | +++ | ++ |
| I-69 | ++++ | +++ |
| I-70 | ++++ | +++ |
| I-71 | +++ | +++ |
| I-72 | ++++ | +++ |
| I-73 | +++ | +++ |
| I-74 | ++++ | ND |
| I-75 | +++ | +++ |
| I-76 | ++++ | +++ |
| I-77 | +++ | +++ |
| I-78 | ++++ | +++ |
| I-79 | +++ | +++ |
| I-80 | ++ | ND |
| I-81 | ++++ | ++++ |
| I-82 | ++++ | ++++ |
| I-83 | +++ | +++ |
| I-84 | +++ | +++ |
| I-85 | +++ | +++ |
| I-86 | +++ | +++ |
| I-87 | ++++ | +++ |

TABLE 28-continued

USP28 and USP25 Assays

| Compound No. | USP28 $IC_{50}$ | USP25 $IC_{50}$ |
|---|---|---|
| I-88 | ++++ | +++ |
| I-89 | ++++ | +++ |
| I-90 | +++ | +++ |
| I-91 | +++ | +++ |
| I-92 | +++ | +++ |
| I-93 | ++++ | ++++ |
| I-94 | +++ | +++ |
| I-95 | ++++ | +++ |
| I-96 | ++++ | +++ |
| I-97 | +++ | ++ |
| I-98 | ++++ | +++ |
| I-99 | ++ | ++ |
| I-100 | +++ | ++ |
| I-101 | ++ | ++ |
| I-102 | ++ | ++ |
| I-103 | +++ | +++ |
| I-104 | +++ | +++ |
| I-105 | +++ | +++ |
| I-106 | +++ | ++ |
| I-107 | +++ | + |
| I-108 | +++ | +++ |
| I-109 | +++ | ++ |
| I-110 | +++ | ++ |
| I-111 | ++++ | +++ |
| I-112 | +++ | ++ |
| I-113 | ++++ | ND |
| I-114 | ++++ | ND |
| I-115 | ++++ | +++ |
| I-116 | +++ | +++ |
| I-117 | +++ | ND |
| I-118 | +++ | ND |
| I-119 | ++ | ND |
| I-120 | ++++ | ND |
| I-121 | +++ | +++ |
| I-122 | +++ | +++ |
| I-123 | ++++ | +++ |
| I-124 | +++ | ++ |
| I-125 | +++ | ND |
| I-126 | +++ | ++ |
| I-127 | +++ | +++ |
| I-128 | +++ | ++ |
| I-129 | +++ | ND |
| I-130 | ++++ | ++++ |
| I-131 | ++++ | +++ |
| I-132 | ++++ | ++++ |
| I-133 | ++++ | ND |
| I-134 | ++++ | +++ |
| I-135 | ++++ | +++ |
| I-136 | +++ | +++ |
| I-137 | +++ | ND |
| I-138 | ++++ | +++ |
| I-139 | +++ | ND |
| I-140 | ++++ | +++ |
| I-141 | +++ | +++ |
| I-142 | +++ | +++ |
| I-143 | +++ | ND |
| I-144 | ++++ | +++ |
| I-145 | +++ | +++ |
| I-146 | ++++ | +++ |
| I-147 | ++++ | ND |
| I-148 | +++ | ++ |
| I-149 | +++ | +++ |
| I-150 | +++ | +++ |
| I-151 | +++ | +++ |
| I-152 | ++ | + |
| I-153 | +++ | ++ |
| I-154 | ++ | ++ |
| I-155 | +++ | +++ |
| I-156 | +++ | ++ |
| I-157 | + | ++ |
| I-158 | ++ | ++ |
| I-159 | +++ | ++ |
| I-160 | ++ | ++ |
| I-161 | +++ | ++ |
| I-162 | +++ | +++ |
| I-163 | +++ | ++ |
| I-164 | ++ | + |
| I-165 | +++ | + |
| I-166 | ++ | + |
| I-167 | ++ | ++ |
| I-168 | ++ | + |
| I-169 | ++++ | +++ |
| I-170 | ++++ | +++ |
| I-171 | +++ | +++ |
| I-172 | ++++ | ++++ |
| I-173 | +++ | +++ |
| I-174 | +++ | ++ |
| I-175 | ++ | ++ |
| I-176 | +++ | +++ |
| I-177 | +++ | +++ |
| I-178 | ++ | ++ |
| I-179 | ++ | ++ |
| I-180 | ++++ | +++ |
| I-181 | ++++ | +++ |
| I-182 | +++ | ++ |
| I-183 | +++ | +++ |
| I-184 | +++ | +++ |
| I-185 | ++ | ND |
| I-186 | ++ | + |
| I-187 | +++ | ND |
| I-188 | ++++ | +++ |
| I-189 | +++ | ++ |
| I-190 | +++ | +++ |
| I-191 | +++ | ++ |
| I-192 | +++ | ++ |
| I-193 | ++++ | +++ |
| I-194 | ++++ | +++ |
| I-195 | ++++ | +++ |
| I-196 | +++ | +++ |
| I-197 | ++ | + |
| I-198 | ++ | + |
| I-199 | +++ | +++ |
| I-200 | +++ | +++ |
| I-201 | +++ | +++ |
| I-202 | +++ | ND |
| I-203 | +++ | ++ |
| I-204 | +++ | ++++ |
| I-205 | ++++ | +++ |
| I-206 | ++++ | ++++ |
| I-207 | +++ | ND |
| I-208 | +++ | ++ |
| I-209 | + | ND |
| I-210 | +++ | ++ |
| I-211 | +++ | ++ |
| I-212 | +++ | +++ |
| I-213 | +++ | +++ |
| I-214 | +++ | ++ |
| I-215 | +++ | ++ |
| I-216 | +++ | +++ |
| I-217 | +++ | +++ |
| I-218 | +++ | +++ |
| I-219 | +++ | +++ |
| I-220 | ++ | ++ |
| I-221 | + | + |
| I-222 | +++ | +++ |
| I-223 | ++ | +++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula (I):

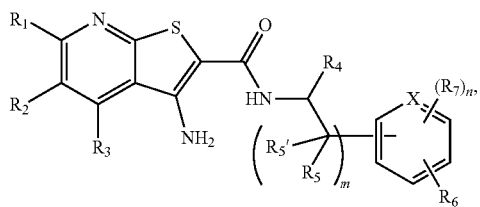

or a pharmaceutically acceptable salt, hydrate, solvate, prodrug, stereoisomer, and tautomer thereof,
wherein:
X is N or $CR_7$;
$R_1$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —CN, or —$NR_9R_{10}$;
$R_2$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{11}R_{12}$;
$R_3$ is H, $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, or —$NR_{13}R_{14}$;
wherein at least one of $R_1$, $R_2$, or $R_3$ is not H;
or $R_1$ and $R_2$ together form a $(C_4-C_8)$ cycloalkyl optionally substituted with one or more $R_{15}$;
or $R_2$ and $R_3$ together form a $(C_4-C_8)$ cycloalkyl optionally substituted with one or more $R_{15}$;
$R_4$ is H, $(C_1-C_6)$ alkyl, or $(C_1-C_6)$ haloalkyl;
$R_5$ is H, $(C_1-C_6)$ alkyl, halogen, or $(C_1-C_6)$ haloalkyl;
$R_{5'}$ is H, $(C_1-C_6)$ alkyl, halogen, or $(C_1-C_6)$ haloalkyl; or
$R_4$ and $R_5$ together with the carbon atoms to which they are attached form a $(C_3-C_8)$ cycloalkyl ring;
$R_6$ is —$(C_0-C_3)$ alkylene-C(O)OH, —$(C_0-C_3)$ alkylene-heterocycloalkyl, —O-heterocycloalkyl, —$(C_0-C_3)$ alkylene-aryl, —$(C_0-C_3)$ alkylene-heteroaryl or —$N(R_8)$-$(C_0-C_3)$ alkylene-heterocycloalkyl, wherein the heterocycloalkyl, aryl and heteroaryl are optionally substituted with one or more $R_{16}$;
each $R_7$ is independently at each occurrence H, $(C_1-C_6)$ alkyl, $(C_1-C_6)$ alkoxy, $(C_1-C_6)$ haloalkyl, $(C_1-C_6)$ haloalkoxy, halogen, —OH, —CN, $(C_3-C_8)$ cycloalkyl, heterocycloalkyl, aryl, or heteroaryl, wherein the alkyl is optionally substituted with one or more $(C_1-C_6)$ alkoxy or —OH, and wherein the cycloalkyl, heterocycloalkyl, aryl, and heteroaryl are optionally substituted with one or more $R_{17}$; or
$R_6$ and $R_7$ together when on adjacent atoms form a $(C_4-C_8)$ cycloalkyl ring optionally substituted with one or more $R_{18}$; or $R_6$ and $R_7$ together when on adjacent atoms form a heterocycloalkyl ring optionally substituted with one or more $R_{18}$; $R_6$ and $R_7$ together when on adjacent atoms form an aryl ring optionally substituted with one or more $R_{18}$; or $R_6$ and $R_7$ together when on adjacent atoms form a heteroaryl ring optionally substituted with one or more $R_{18}$; or
two $R_7$ together when on adjacent atoms form a $(C_4-C_8)$ cycloalkyl ring; or two $R_7$ together when on adjacent atoms form a heterocycloalkyl ring; two $R_7$ together when on adjacent atoms form an aryl ring; or two $R_7$ together when on adjacent atoms form a heteroaryl ring;

$R_8$ is H or $(C_1-C_6)$ alkyl;
each $R_9$, $R_{10}$, $R_{11}$, $R_{12}$, $R_{13}$, and $R_{14}$ is independently H, $(C_1-C_6)$ alkyl, or —$C(O)(C_1-C_6)$ alkyl;
each $R_{15}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or —OH;
each $R_{16}$ is independently at each occurrence $(C_1-C_6)$ alkyl, $(C_1-C_6)$ alkoxy, $(C_1-C_6)$ haloalkyl, $(C_1-C_6)$ haloalkoxy, $(C_1-C_6)$ hydroxyalkyl, halogen, $(C_3-C_8)$ cycloalkyl, —$C(O)NR_{21}R_{22}$, —$S(O)_2(C_1-C_6)$ alkyl, —OH, or —$NR_{19}R_{20}$, wherein the alkyl is optionally substituted with one or more substituents independently selected from $(C_1-C_6)$ alkoxy, OH, and heterocycloalkyl; or
two $R_{16}$ together when attached to the same carbon can form —C=(O) when $R_6$ is —$(C_0-C_3)$ alkylene-heterocycloalkyl, —O-heterocycloalkyl, or —$N(R_8)$-$(C_0-C_3)$ alkylene-heterocycloalkyl; or two $R_{16}$ together when attached to the same atom form a $(C_3-C_8)$ spirocycloalkyl optionally substituted with one or more $R_{23}$ when $R_6$ is —$(C_0-C_3)$ alkylene-heterocycloalkyl, —O-heterocycloalkyl, or —$N(R_8)$-$(C_0-C_3)$ alkylene-heterocycloalkyl; or two $R_{16}$ together when attached to the same atom form a $(C_3-C_8)$ spiroheterocycloalkyl optionally substituted with one or more $R_{23}$ when $R_6$ is —$(C_0-C_3)$ alkylene-heterocycloalkyl, —O-heterocycloalkyl, or —$N(R_8)$-$(C_0-C_3)$ alkylene-heterocycloalkyl; or two $R_{16}$ together when on adjacent atoms form a heterocycloalkyl ring optionally substituted with one or more $R_{23}$; or two $R_{16}$ together when on adjacent atoms form a heteroaryl ring optionally substituted with one or more $R_{23}$; or two $R_{16}$ together with the atoms to which they are attached can form a bridged heterocycloalkyl ring optionally substituted with one or more $R_{23}$ when $R_6$ is —$(C_0-C_3)$ alkylene-heterocycloalkyl, —O-heterocycloalkyl, or —$N(R_8)$-$(C_0-C_3)$ alkylene-heterocycloalkyl;
each $R_{17}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, cycloalkyl, heterocycloalkyl, or —C(O)-heterocycloalkyl, wherein the alkyl is optionally substituted with one or more substituents independently selected from $(C_1-C_6)$ alkoxy and —OH;
each $R_{18}$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, —CN, —C(O)OH, or —$C(O)O(C_1-C_6)$ alkyl;
each $R_{19}$ and $R_{20}$ is independently H, $(C_1-C_6)$ alkyl, $(C_3-C_8)$ cycloalkyl, —$CH_2C(O)NH_2$, —$S(O)_2(C_1-C_6)$ alkyl, —$S(O)_2(C_6-C_{10})$ aryl or —$C(O)(C_1-C_6)$ alkyl;
each $R_{21}$ and $R_{22}$ is independently H or $(C_1-C_6)$ alkyl;
each $R_{23}$ is independently at each occurrence $(C_1-C_6)$ alkyl, $(C_1-C_6)$ alkoxy, $(C_1-C_6)$ haloalkyl, $(C_1-C_6)$ haloalkoxy, or halogen; or
two $R_{23}$ together when attached to the same carbon form —C=(O);
m is 1 or 2; and
n is 0, 1, 2, or 3.
2. The compound of claim 1, wherein $R_1$ is $(C_1-C_6)$ alkyl, $R_2$ is H or $(C_1-C_6)$ alkyl, or $R_1$ and $R_2$ together form a $(C_4-C_8)$ cycloalkyl optionally substituted with one or more $R_{15}$; and $R_3$ is H.

3. The compound of claim 1, having the structure of Formula (Id):

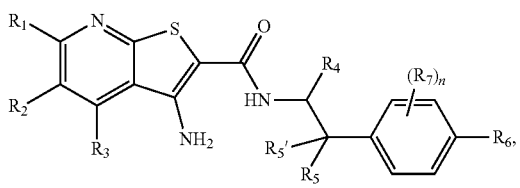

(Id)

or a pharmaceutically acceptable salt, hydrate, solvate, prodrug, stereoisomer, and tautomer thereof.

4. The compound of claim 1, wherein $R_4$, $R_5$, and $R_{5'}$ are each independently chosen from H or $(C_1-C_6)$ alkyl.

5. The compound of claim 1, wherein $R_4$ and $R_5$ are each independently chosen from H or $CH_3$, and $R_{5'}$ is H.

6. The compound of claim 1, wherein $R_6$ is —$(C_0-C_3)$ alkylene-heterocycloalkyl, wherein the heterocycloalkyl is optionally substituted with one or more $R_{17}$.

7. The compound of claim 1, wherein X is CH.

8. The compound of claim 3, wherein $R_1$ is $(C_1-C_6)$ alkyl, $R_2$ is H or $(C_1-C_6)$ alkyl, or $R_1$ and $R_2$ together form a $(C_4-C_8)$ cycloalkyl optionally substituted with one or more $R_{15}$; $R_3$ is H; $R_4$, $R_5$, and $R_{5'}$ are each independently chosen from H or $(C_1-C_6)$ alkyl; and $R_6$ is —$(C_0-C_3)$ alkylene-heterocycloalkyl, wherein the heterocycloalkyl is optionally substituted with one or more $R_{17}$.

9. The compound of claim 8, wherein $R_1$ is $CH_3$, $R_2$ is H; $R_3$ is H; $R_4$, $R_5$, and $R_{5'}$ are each independently chosen from H or $CH_3$; and $R_6$ is —$(C_0-C_3)$ alkylene-heterocycloalkyl, wherein the heterocycloalkyl is optionally substituted with one or more $R_{17}$.

10. The compound of claim 9, wherein $R_4$, $R_5$, and $R_{5'}$ are each H.

11. The compound of claim 9, wherein $R_6$ is piperazinyl ring.

12. The compound of claim 3, wherein $R_1$ and $R_2$ together form a $(C_4-C_8)$ cycloalkyl optionally substituted with one or more $R_{15}$, wherein $R_{15}$ is independently at each occurrence $(C_1-C_6)$ alkyl, halogen, or —OH; $R_3$ is H; $R_4$, $R_5$, and $R_{5'}$ are each independently chosen from H or $(C_1-C_6)$ alkyl; and $R_6$ is —$(C_0)$ alkylene-heterocycloalkyl.

13. The compound of claim 12, wherein $R_1$ and $R_2$ together form a $(C_5)$ cycloalkyl substituted with one $R_{15}$ that is —OH; and $R_4$, $R_5$, and $R_{5'}$ are each H.

14. The compound of claim 1, selected from:

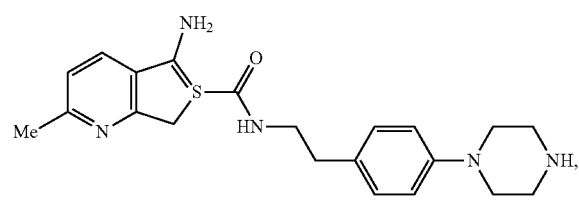

I-1

3-Amino-6-methyl-N-(4-(piperazin-1-yl)phenethyl)thieno[2,3-b]pyridine-2-carboxamide -continued

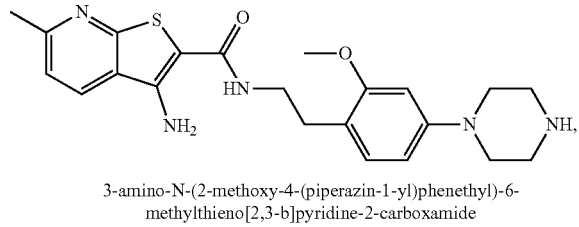

I-2

3-amino-N-(2-methoxy-4-(piperazin-1-yl)phenethyl)-6-methylthieno[2,3-b]pyridine-2-carboxamide

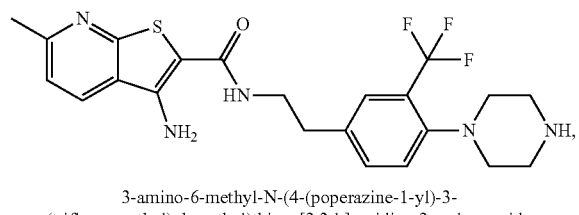

I-3

3-amino-6-methyl-N-(4-(poperazine-1-yl)-3-(trifluoromethyl)phenethyl)thieno[2,3-b]pyridine-2-carboxamide

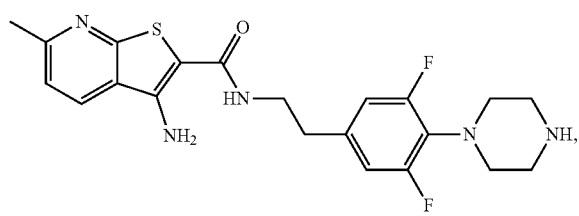

I-4

3-amino-N-(3,5-difluoro-4-(piperazin-1-yl)phenethyl)-6-methylthieno[2,3-b]pyridine-2-carboxamide

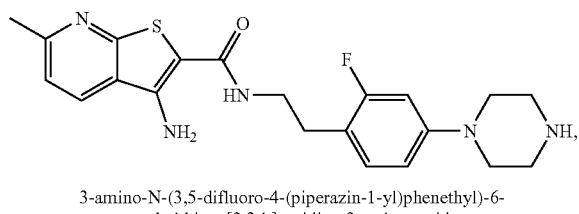

I-5

3-amino-N-(3,5-difluoro-4-(piperazin-1-yl)phenethyl)-6-methylthieno[2,3-b]pyridine-2-carboxamide

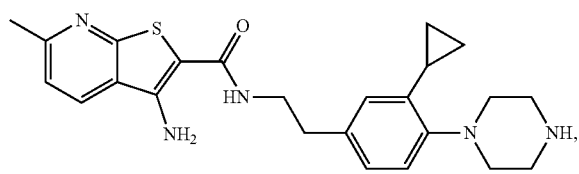

I-6

3-amino-N-(3-cyclopropyl-4-(piperazin-1-yl)phenethyl)-6-methylthieno[2,3-b]pyridine-2-carboxamide

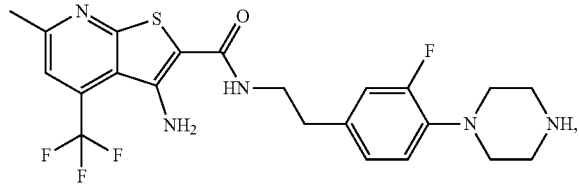

I-7

3-amino-N-(3-fluoro-4-(piperazin-1-yl)phenethyl)-6-methyl-4-(trifluoromethyl)thieno[2,3-b]pyridine-2-carboxamide

I-8

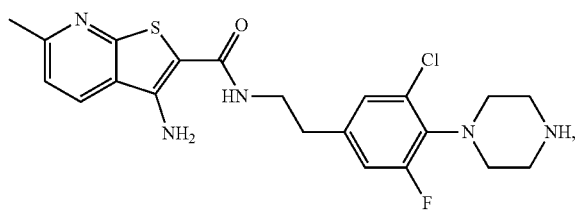

3-amino-N-(3-chloro-5-fluoro-4-(piperazin-1-yl)phenethyl)-6-methylthieno[2,3-b]pyridine-2-carboxamide

I-9

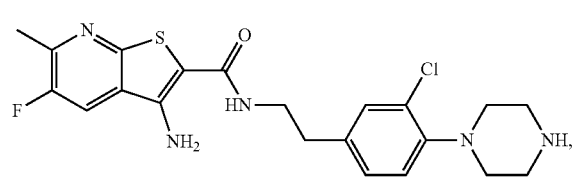

3-amino-N-(3-chloro-4-(piperazin-1-yl)phenethyl)-5-fluoro-6-methylthieno[2,3-b]pyridine-2-carboxamide

I-10

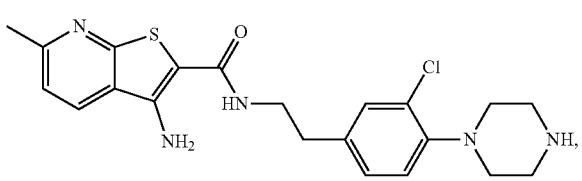

3-Amino-N-(3-fluoro-4-(piperazin-1-yl)phenethyl)-6-methylthieno[2,3-b]pyridine-2-carboxamide

I-11

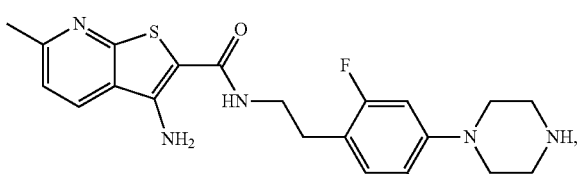

3-Amino-N-(2,5difluoro-4-(piperazin-1-yl)phenethyl)-6-methylthieno[2,3-b]pyridine-2-carboxamide

I-12

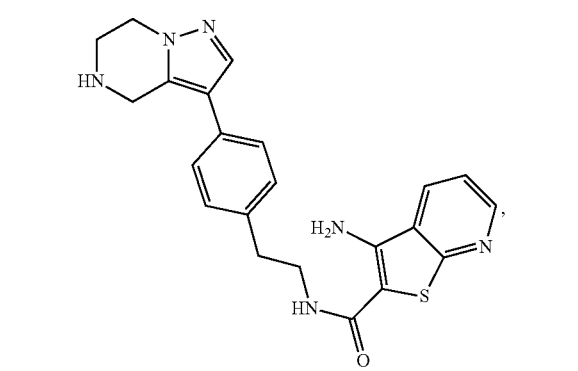

3-amino-6-methyl-N-(4-(4,5,6,7-tetrahydropyrazolo[1,5-a]pyrazin-3-yl)phenethyl)thieno[2,3-b]pyridine-2-carboxamide

I-13

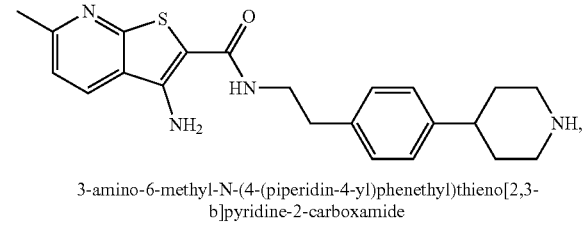

3-amino-6-methyl-N-(4-(piperidin-4-yl)phenethyl)thieno[2,3-b]pyridine-2-carboxamide

I-14

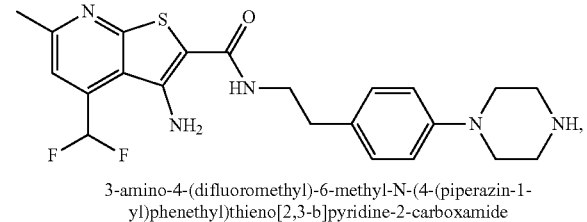

3-amino-4-(difluoromethyl)-6-methyl-N-(4-(piperazin-1-yl)phenethyl)thieno[2,3-b]pyridine-2-carboxamide

I-15

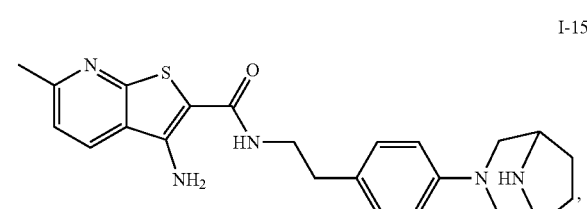

N-(4-(3,8-diazabicyclo[3.2.1]octan-3-yl)phenethyl)-3-amino-6-methylthieno[2,3-b]pyridine-2-carboxamide

I-16

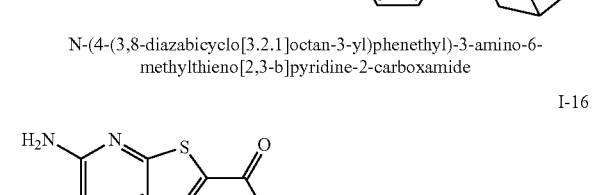

3,6-diamino-4-(difluoromethyl)-N-(4-(piperazin-1-yl)phenethyl)thieno[2,3-b]pyridine-2-carboxamide

I-17

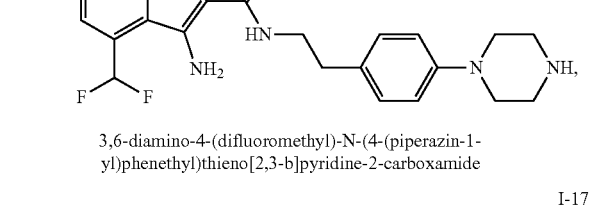

3,6-diamino-N-(3-chloro-4-(piperazin-1-yl)phenethyl)-4-methylthieno[2,3-b]pyridine-2-carboxamide

I-18

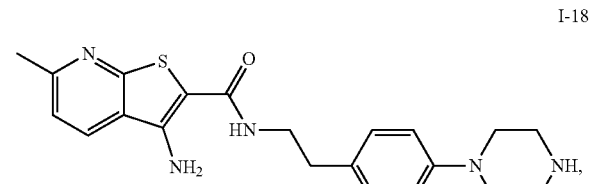

3-amino-6-methyl-N-(2-(7-(piperazin-1-yl)-2,3-dihydro-1H-inden-4-yl)ethyl)thieno[2,3-b]pyridine-2-carboxamide

I-19

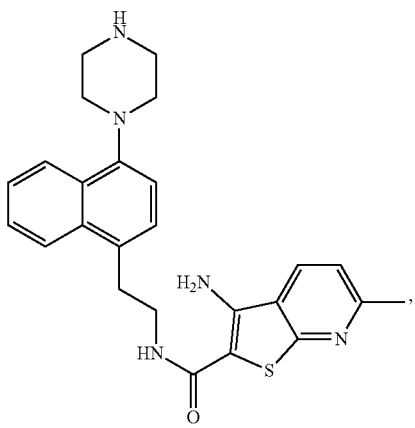

3-amino-6-methyl-N-(2-(4-(piperazin-1-yl)naphthalen-1-yl)ethyl)thieno[2,3-b]pyridine-2-carboxamide

I-20

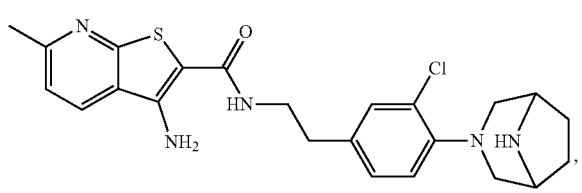

N-(4-(3,8-diazabicyclo[3.2.1]octan-3-yl)-3-chlorophenethyl)-3-amino-6-methylthieno[2,3-b]pyridine-2-carboxamide

I-21

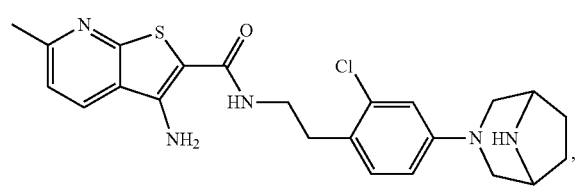

N-(4-(3,8-diazabicyclo[3.2.1]octan-3-yl)-2-chlorophenethyl)-3-amino-6-methylthieno[2,3-b]pyridine-2-carboxamide

I-22

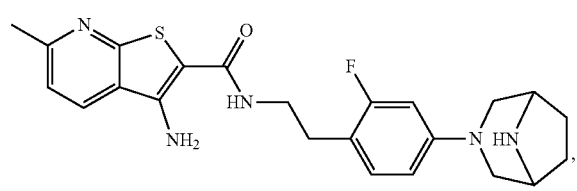

N-(4-(3,8-diazabicyclo[3.2.1]octan-3-yl)-2-fluorophenethyl)-3-amino-6-methylthieno[2,3-b]pyridine-2-carboxamide

I-23

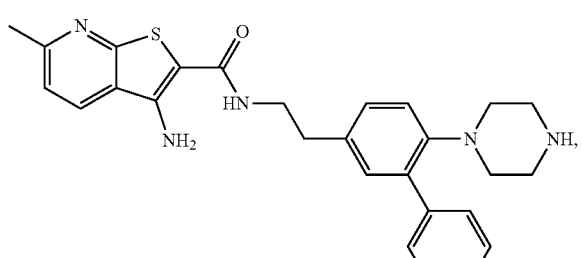

3-amino-6-methyl-N-(2-(6-(piperazin-1-yl)-[1,1'-biphenyl]-3-yl)ethyl)thieno[2,3-b]pyridine-2-carboxamide

I-24

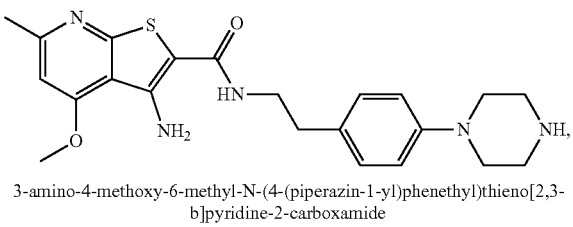

3-amino-4-methoxy-6-methyl-N-(4-(piperazin-1-yl)phenethyl)thieno[2,3-b]pyridine-2-carboxamide

I-25

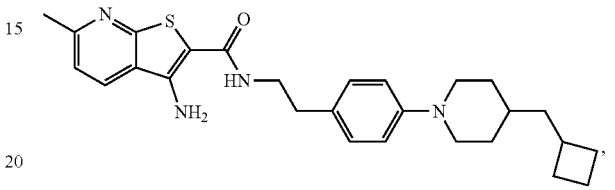

3-amino-6-methyl-N-(4-(4-(oxetan-2-ylmethyl)piperazin-1-yl)phenethyl)thieno[2,3-b]pyridine-2-carboxamide

I-26

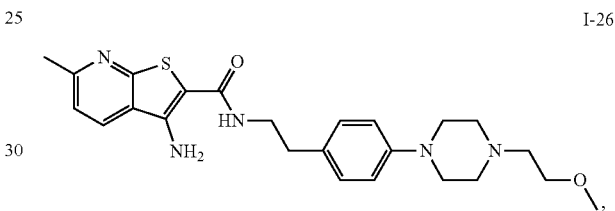

3-amino-N-(4-(4-(2-methoxyethyl)piperazin-1-yl)phenethyl)-6-methylthieno[2,3-b]pyridine-2-carboxamide

I-27

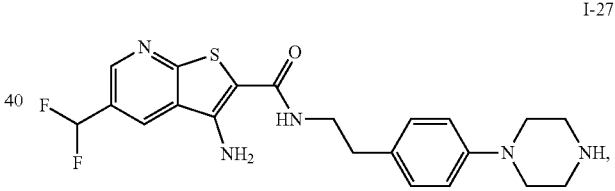

3-amino-5-(difluoromethyl)-N-(4-piperazin-1-yl)phenethyl)thieno[2,3-b]pyridine-2-carboxamide

I-28

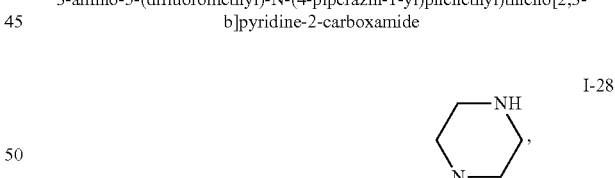

1-amino-N-(4-(piperazin-1-yl)phenethyl)-7,8-dihydro-6H-cyclopenta[d]thieno[2,3-b]pyridine-2-carboxamide -continued

I-29

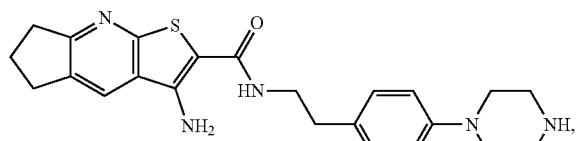

3-amino-N-(4-(piperazin-1-yl)phenethyl)-6,7-dihydro-5H-cyclopenta[b]thieno[3,2-e]pyridine-2-carboxamide

I-30

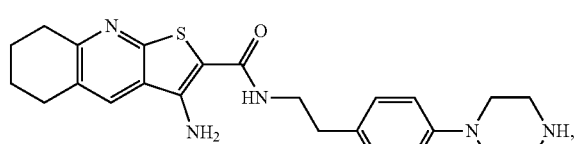

3-amino-N-(4-(piperazin-1-yl)phenethyl)-5,6,7,8-tetrahydrothieno[2,3-b]quionoline-pyridine-2-carboxamide

I-31

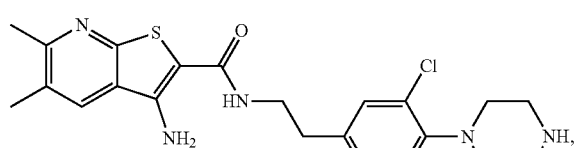

3-amino-N-(3-chloro-4-(piperazin-1-yl)phenethyl)-5,6-dimethylthieno[2,3-b]pyridine-2-carboxamide

I-32

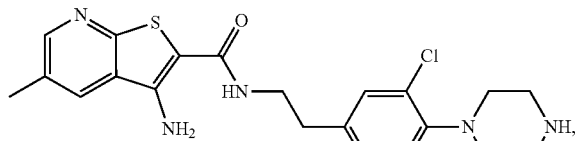

3-amino-N-(3-chloro-4-(piperazin-1-yl)phenethyl)-5-methylthieno[2,3-b]pyridine-2-carboxamide

I-33

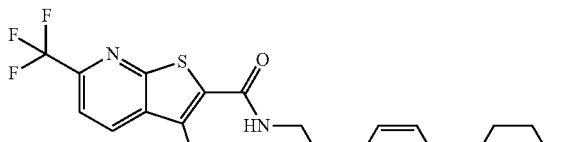

3-amino-N-(4-(piperazin-1-yl)phenethyl)-6-trifluoromethyl)thieno[2,3-b]pyridine-2-carboxamide

I-34

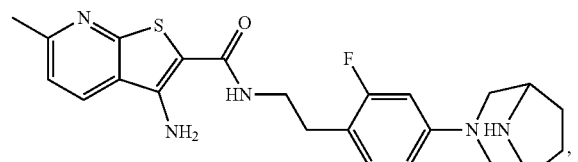

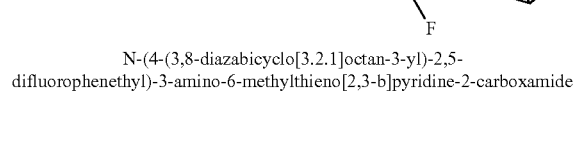

N-(4-(3,8-diazabicyclo[3.2.1]octan-3-yl)-2,5-difluorophenethyl)-3-amino-6-methylthieno[2,3-b]pyridine-2-carboxamide -continued

I-35

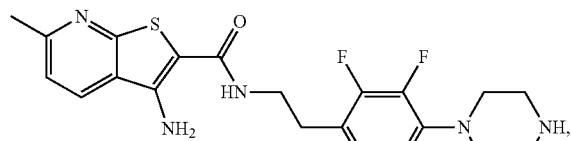

3-amino-6-methyl-N-(2,3,5-trifluoro-4-(piperazin-1-yl)phenethyl)thieno[2,3-b]pyridine-2-carboxamide

I-36

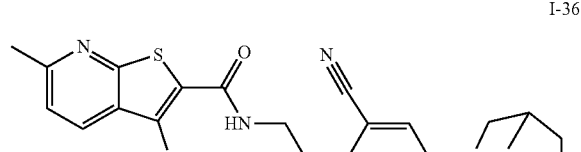

N-(4-(3,8-diazabicyclo[3.2.1]octan-3-yl)-2-cyanophenethyl)-3-amino-6-methylthieno[2,3-b]pyridine-2-carboxamide

I-37

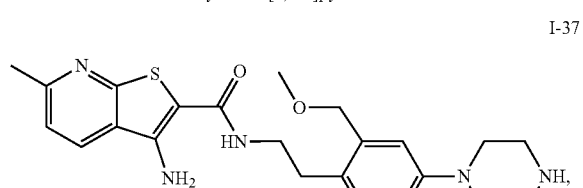

3-amino-N-(2-(methoxymethyl-4-(piperzain-1-yl)phenethyl-6-methylthieno[2,3-b]pyridine-2-carboxamide

I-38

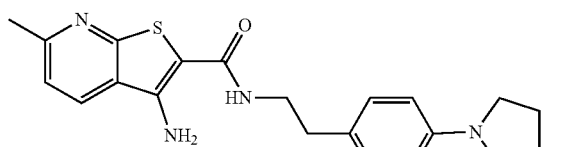

3-amino-N-(4-(5,6-dihydropyrrolo[3,4-c]pyrazol-1(4H)-yl)phenethyl-6-methylthieno[2,3-b]pyridine-2-carboxamide

I-39

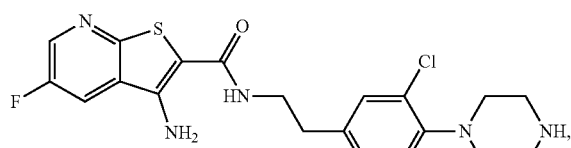

3-amino-N-(3-chloro-4-(piperazin-1-yl)phenethyl)-5-fluorothieno[2,3-b]pyridine-2-carboxamide

I-40

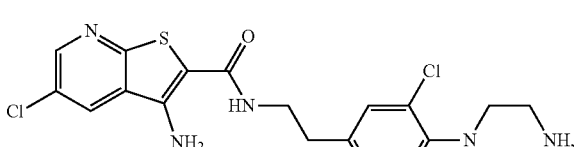

3-amino-5-chloro-N-(3-chloro-4-(piperazin-1-yl)phenethyl)thieno[2,3-b]pyridine-2-carboxamide

I-41

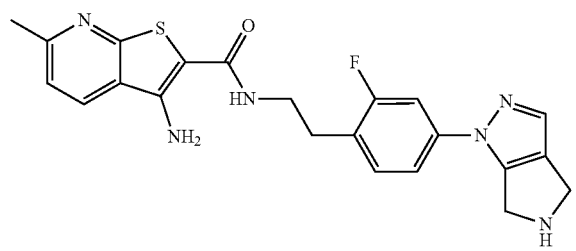

3-amino-N-(4-(5,6-dihydropyrrolo[3,4-c]pyrazol-1(4H-yl)-2-fluorophenethyl)-6-methylthieno[2,3-b]pyridine-2-carboxamide

I-42

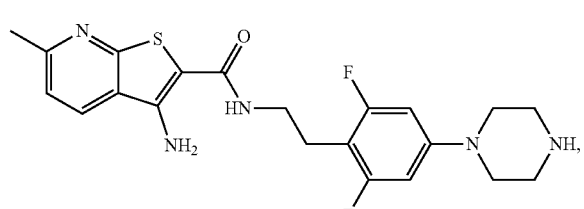

3-amino-N-(2,6-difluoro-4-(piperazin-1-yl)phenethyl)-6-methylthieno[2,3-b]pyridine-2-carboxamide

I-43

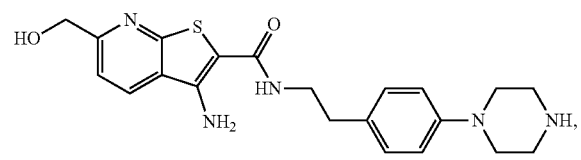

3-amino-6-(hydroxymethyl)-N-(4-(piperazin-1-yl)phenethyl)thieno[2,3-b]pyridine-2-carboxamide

I-44

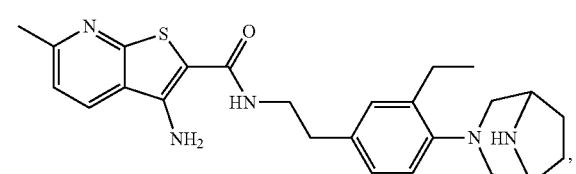

N-(4-(3,8-diazabicyclo[3.2.1]octan-3-yl)-3-ethylphenethyl)-3-amino-6-methylthieno[2,3-b]pyridine-2-carboxamide

I-45

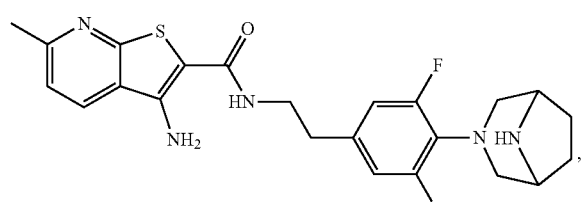

N-(4-(3,8-diazabicyclo[3.2.1]octan-3-yl)-3,5-difluorophenethyl)3-amino-6-methylthieno[2,3-b]pyridine-2-carboxamide

I-46

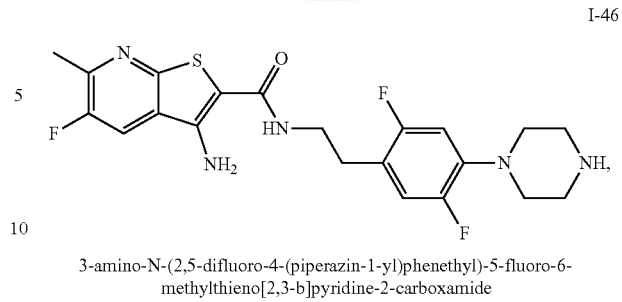

3-amino-N-(2,5-difluoro-4-(piperazin-1-yl)phenethyl)-5-fluoro-6-methylthieno[2,3-b]pyridine-2-carboxamide

I-47

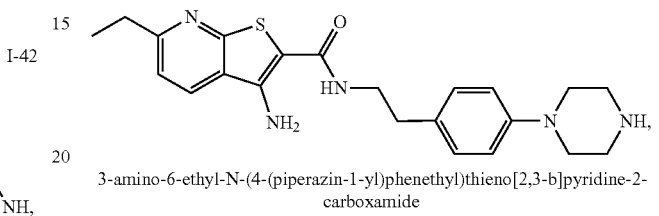

3-amino-6-ethyl-N-(4-(piperazin-1-yl)phenethyl)thieno[2,3-b]pyridine-2-carboxamide

I-48

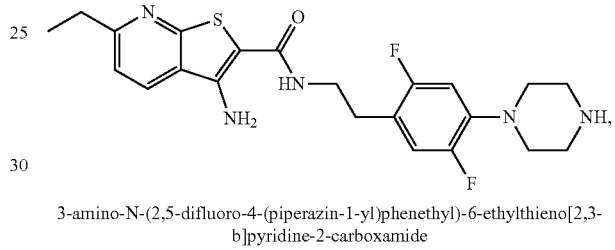

3-amino-N-(2,5-difluoro-4-(piperazin-1-yl)phenethyl)-6-ethylthieno[2,3-b]pyridine-2-carboxamide

I-49

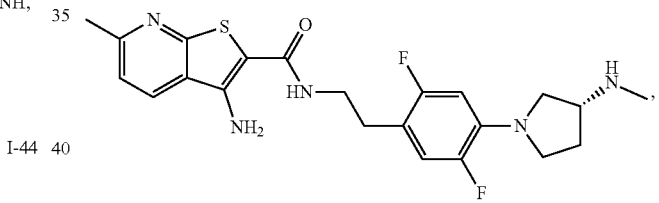

(R)-3-amino-N-(2,5-difluoro-4-(3-(methylamino)pyrrolidin-1-yl)phenethyl-6-methylthieno[2,3-b]pyridine-2-carboxamide

I-50

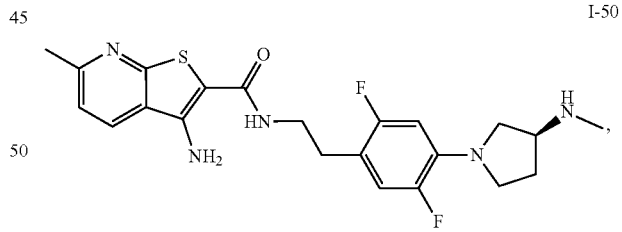

(S)-3-amino-N-(2,5-difluoro-4-(3-(methylamino)pyrrolidin-1-yl)phenethyl-6-methylthieno[2,3-b]pyridine-2-carboxamide

I-51

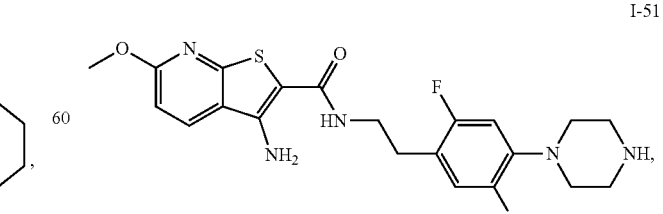

3-amino-N-(2,5-difluoro-4-(ppiperazin-1-yl)phenethyl-6-methoxythieno[2,3-b]pyridine-2-carboxamide

I-52

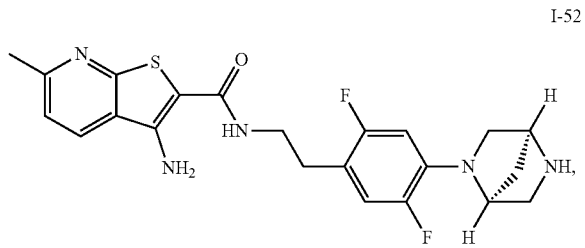

N-(4-((1S,4S)-2,5-diazabicyclo[2.2.1]heptan-2-yl)-2,5-difluorophenethyl-3-amino-6-methylthieno[2,3-b]pyridine-2-carboxamide

I-53

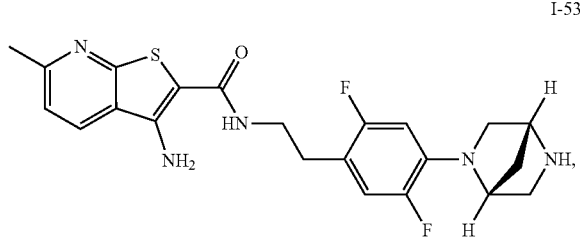

N-(4-((1R,4R)-2,5-diazabicyclo[2.2.1]heptan-2-yl)-2,5-difluorophenethyl-3-amino-6-methylthieno[2,3-b]pyridine-2-carboxamide

I-54

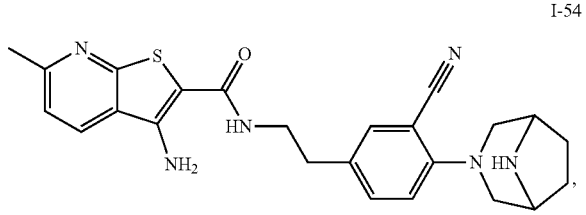

N-(4-(3,8-diazabicyclo[3.2.1]octan-3-yl)-3-cyanophenethyl)-3-amino-6-methylthieno[2,3-b]pyridine-2-carboxamide

I-55

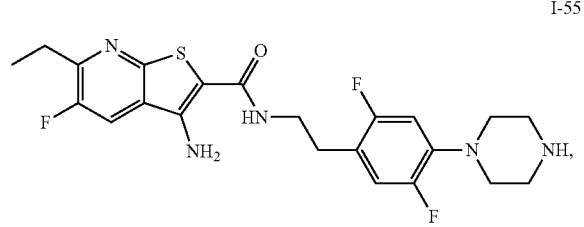

3-amino-N-(2,5-difluoro-4-(piperazin-1-yl)phenethyl)-6-ethyl-5-fluorothieno[2,3-b]pyridine-2-carboxamide

I-56

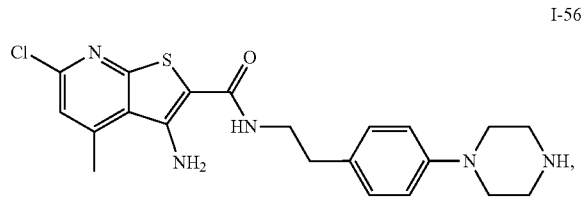

3-amino-6-chloro-4-methyl-N-(4-(piperazin-1-yl)phenethyl)thieno[2,3-b]pyridine-2-carboxamide

I-57

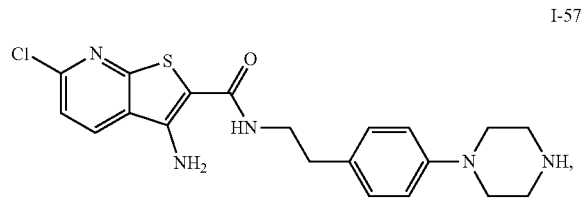

3-amino-6-chloro-N-(4(piperazin-1-yl)phenethyl)thieno[2,3-b]pyridine-2-carboxamide

I-58

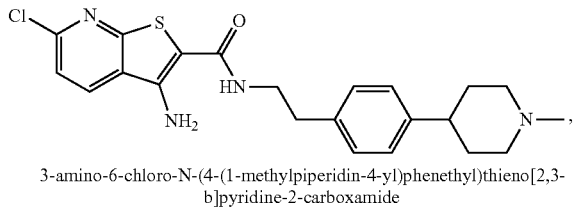

3-amino-6-chloro-N-(4-(1-methylpiperidin-4-yl)phenethyl)thieno[2,3-b]pyridine-2-carboxamide

I-59

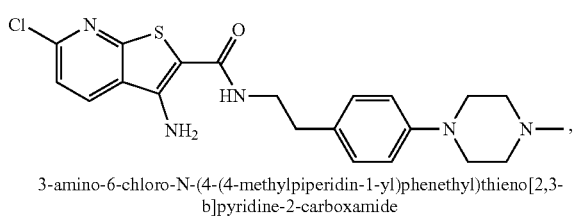

3-amino-6-chloro-N-(4-(4-methylpiperidin-1-yl)phenethyl)thieno[2,3-b]pyridine-2-carboxamide

I-60

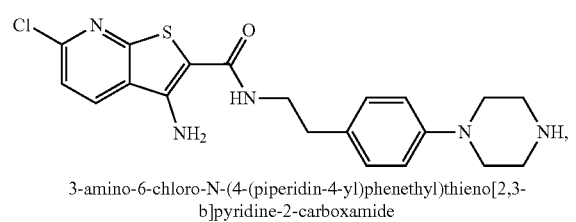

3-amino-6-chloro-N-(4-(piperidin-4-yl)phenethyl)thieno[2,3-b]pyridine-2-carboxamide

I-61

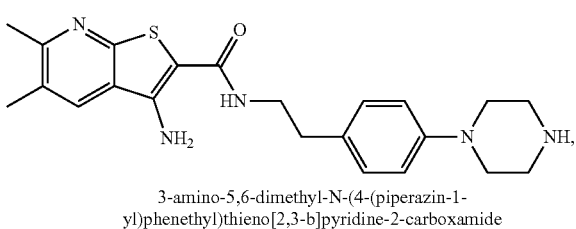

3-amino-5,6-dimethyl-N-(4-(piperazin-1-yl)phenethyl)thieno[2,3-b]pyridine-2-carboxamide

I-62

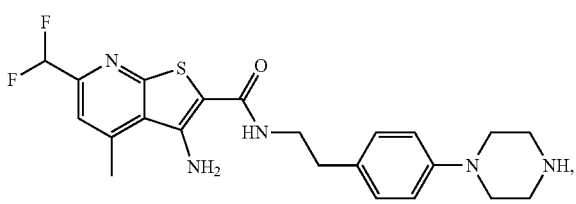

3-amino-6-(difluoromethyl)-4-methyl-N-(4-(piperazin-1-yl)phenethyl)thieno[2,3-b]pyridine-2-carboxamide

I-63

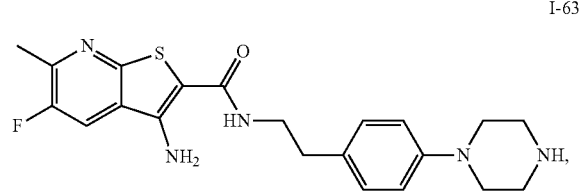

3-amino-5-fluoro-6-methyl-N-(4-(piperazin-1-yl)phenethyl)thieno[2,3-b]pyridine-2-carboxamide

I-64

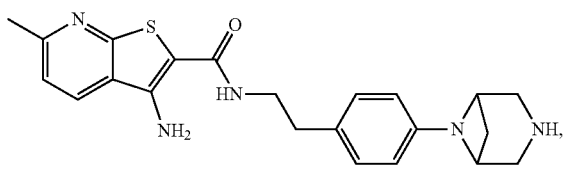

N-(4-(3,6-diazabicyclo[3.1.1]heptan-6-yl)phenethyl)3-amino-6-methylthieno[2,3-b]pyridine-2-carboxamide

I-65

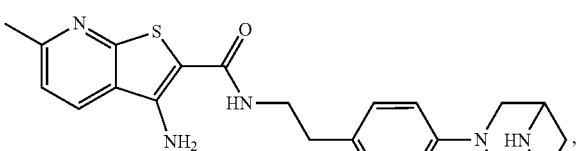

N-(4-(3,6-diazabicyclo[3.1.1]heptan-3-yl)phenethyl)3-amino-6-methylthieno[2,3-b]pyridine-2-carboxamide

I-66

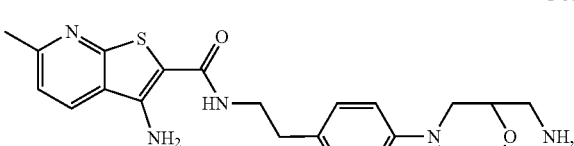

N-(4-(9-oxa-3,7-diazabicyclo[3.1.1]nonan-3-yl)phenethyl)3-amino-6-methylthieno[2,3-b]pyridine-2-carboxamide

I-67

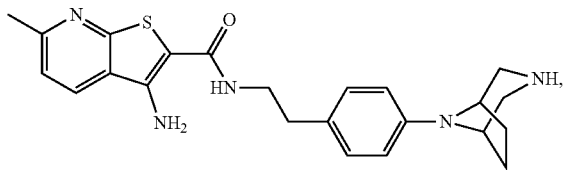

N-(4-(3,8-diazabicyclo[3.2.1]octan-8-yl)phenethyl)-3-amino-6-methylthieno[2,3-b]pyridine-2-carboxamide

I-68

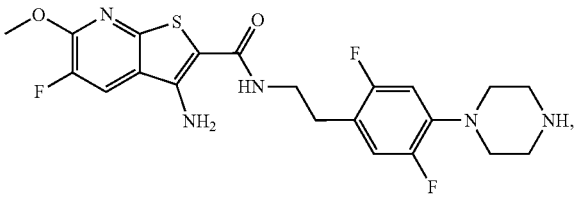

3-amino-N-(2,5-difluoro-4-(piperazin-1-yl)phenethyl-5-fluoro-6-methylthieno[2,3-b]pyridine-2-carboxamide

I-69

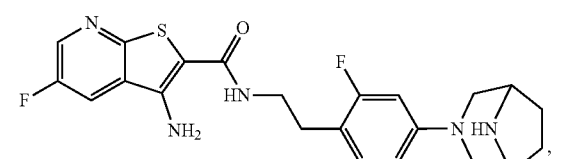

N-(4-(3,8-diazabicyclo[3.2.1]octan-3-yl)-2,5-difluorophenethyl)-3-amino-5-fluorothieno[2,3-b]pyridine-2-carboxamide

I-70

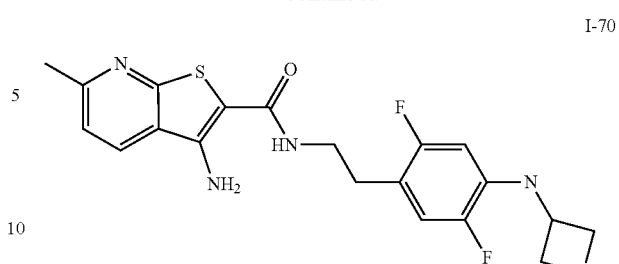

3-amino-N-(4-(azetidin-3-ylamino)-2,5-difluorophenethyl)-6-methylthieno[2,3-b]pyridine-2-carboxamide

I-71

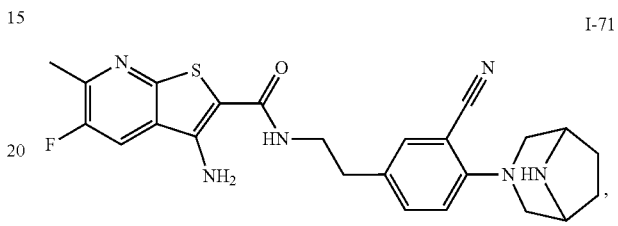

N-(4-(3,8-diazabicyclo[3.2.1]octan-3-yl)-3-cyanophenethyl)-3-amino-5-fluoro-6-methylthieno[2,3-b]pyridine-2-carboxamide

I-72

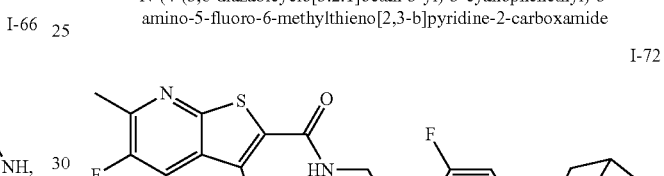

N-(4-(3,8-diazabicyclo[3.2.1]octan-3-yl)-2,5-difluorophenethyl-3-amino-5-fluoro-6-methylthieno[2,3-b]pyridine-2-carboxamide

I-73

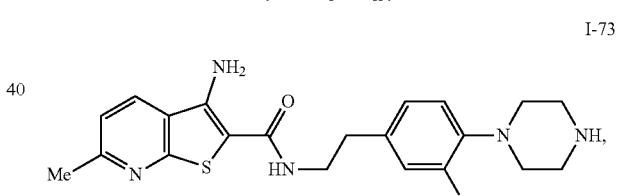

3-Amino-N-(3-(difluoromethoxy)-4-(piperazin-1-yl)phenethyl)-6-methylthieno[2,3-b]pyridine-2-carboxamide

I-74

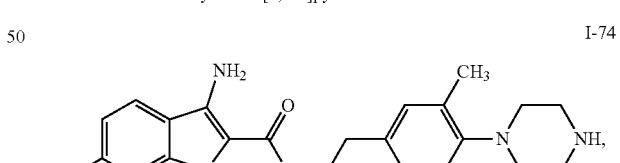

3-Amino-6-methyl-N-(3-methyl-4-(piperazin-1-yl)phenethyl)thieno[2,3-b]pyridine-2-carboxamide

I-75

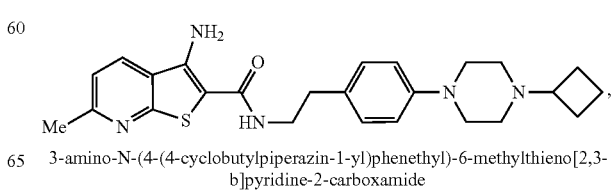

3-amino-N-(4-(4-cyclobutylpiperazin-1-yl)phenethyl)-6-methylthieno[2,3-b]pyridine-2-carboxamide

I-76

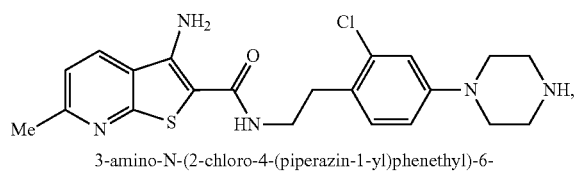

3-amino-N-(2-chloro-4-(piperazin-1-yl)phenethyl)-6-methylthieno[2,3-b]pyridine-2-carboxamide

I-77

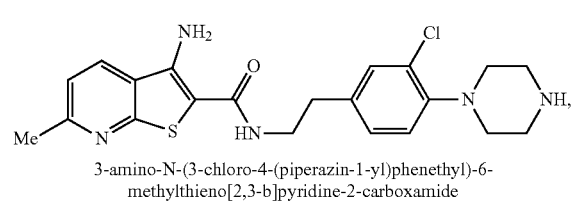

3-amino-N-(3-chloro-4-(piperazin-1-yl)phenethyl)-6-methylthieno[2,3-b]pyridine-2-carboxamide

I-78

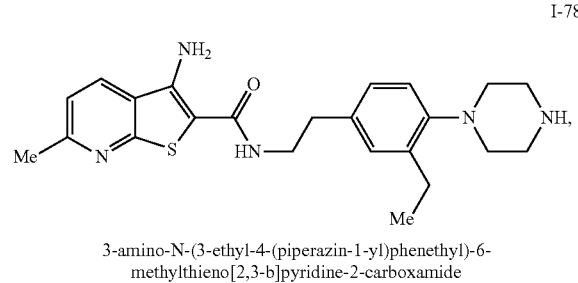

3-amino-N-(3-ethyl-4-(piperazin-1-yl)phenethyl)-6-methylthieno[2,3-b]pyridine-2-carboxamide

I-79

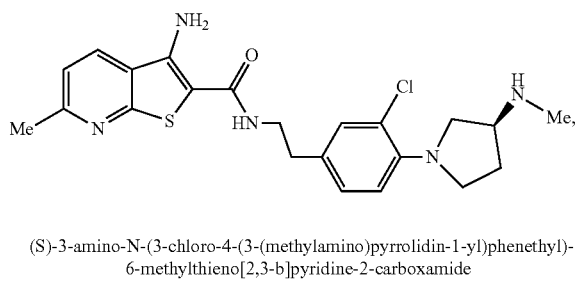

(S)-3-amino-N-(3-chloro-4-(3-(methylamino)pyrrolidin-1-yl)phenethyl)-6-methylthieno[2,3-b]pyridine-2-carboxamide

I-80

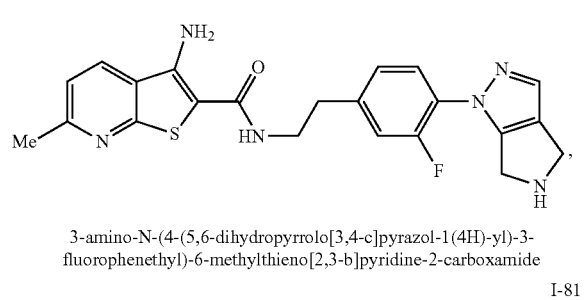

3-amino-N-(4-(5,6-dihydropyrrolo[3,4-c]pyrazol-1(4H)-yl)-3-fluorophenethyl)-6-methylthieno[2,3-b]pyridine-2-carboxamide

I-81

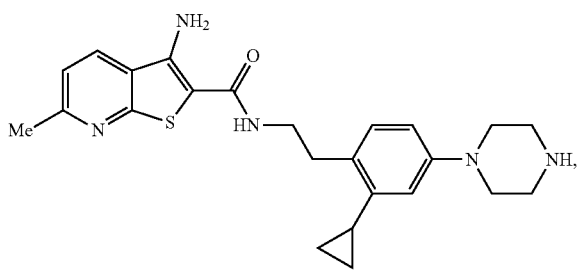

3-amino-N-(2-cyclopropyl-4-(piperazin-1-yl)phenethyl)-6-methylthieno[2,3-b]pyridine-2-carboxamide

I-82

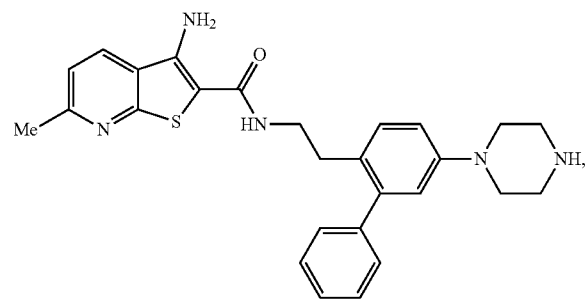

3-amino-6-methyl-N-(2-(5-(piperazin-1-yl)-[1,1'-biphenyl]-2-yl)ethyl)thieno[2,3-b]pyridine-2-carboxamide

I-83

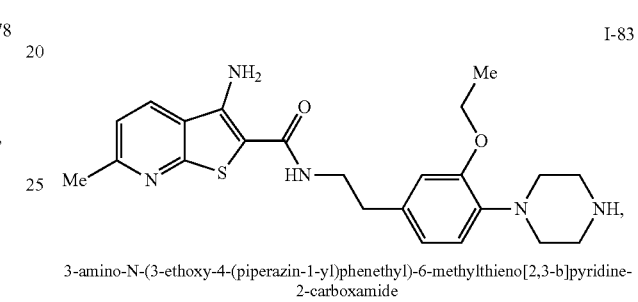

3-amino-N-(3-ethoxy-4-(piperazin-1-yl)phenethyl)-6-methylthieno[2,3-b]pyridine-2-carboxamide

I-84

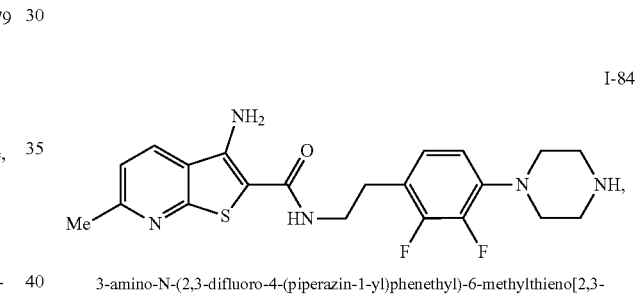

3-amino-N-(2,3-difluoro-4-(piperazin-1-yl)phenethyl)-6-methylthieno[2,3-b]pyridine-2-carboxamide

I-85

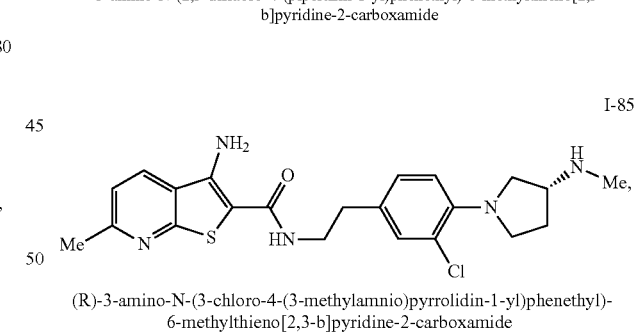

(R)-3-amino-N-(3-chloro-4-(3-methylamnio)pyrrolidin-1-yl)phenethyl)-6-methylthieno[2,3-b]pyridine-2-carboxamide

I-86

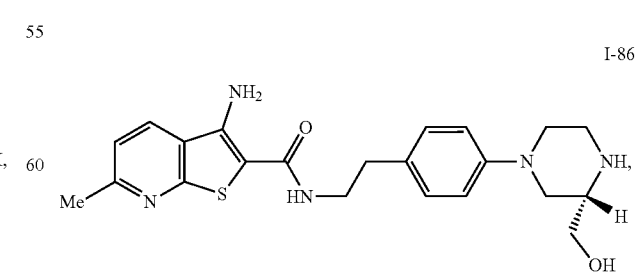

(S)-3-amino-N-(4-(3-hydroxymethyl)piperazin-1-yl)phenethyl)-6-methylthieno[2,3-b]pyridine-2-carboxamide

I-87

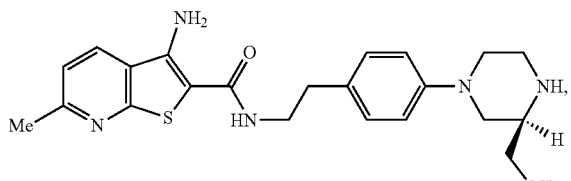

(R)-3-amino-N-(4-(3-hydroxymethyl)piperazin-1-yl)phenethyl)-6-methylthieno[2,3-b]pyridine-2-carboxamide

I-88

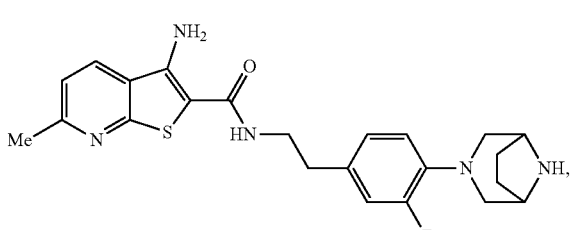

N-(3,8-diazabicyclo[3.2.1]octan-3-yl)-3-fluorophenethyl)-3-amino-6-methylthieno[2,3-b]pyridine-2-carboxamide

I-89

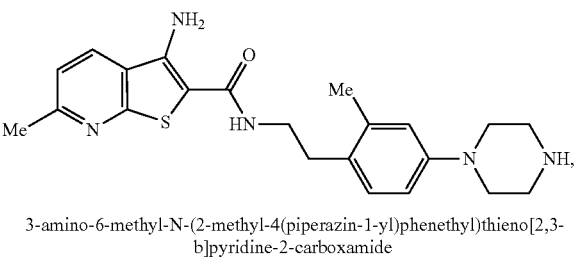

3-amino-6-methyl-N-(2-methyl-4(piperazin-1-yl)phenethyl)thieno[2,3-b]pyridine-2-carboxamide

I-90

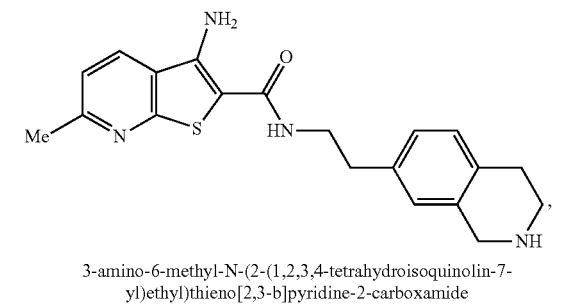

3-amino-6-methyl-N-(2-(1,2,3,4-tetrahydroisoquinolin-7-yl)ethyl)thieno[2,3-b]pyridine-2-carboxamide

I-91

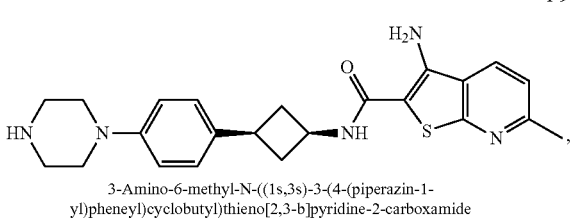

3-Amino-6-methyl-N-((1s,3s)-3-(4-(piperazin-1-yl)pheneyl)cyclobutyl)thieno[2,3-b]pyridine-2-carboxamide

I-92

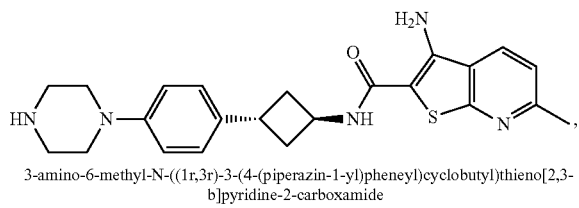

3-amino-6-methyl-N-((1r,3r)-3-(4-(piperazin-1-yl)pheneyl)cyclobutyl)thieno[2,3-b]pyridine-2-carboxamide

I-93

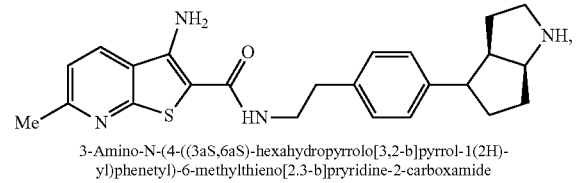

3-Amino-N-(4-((3aS,6aS)-hexahydropyrrolo[3,2-b]pyrrol-1(2H)-yl)phenetyl)-6-methylthieno[2.3-b]pryridine-2-carboxamide

I-94

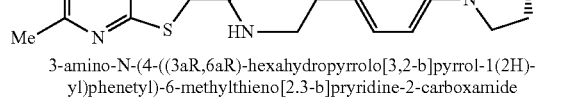

3-amino-N-(4-((3aR,6aR)-hexahydropyrrolo[3,2-b]pyrrol-1(2H)-yl)phenetyl)-6-methylthieno[2.3-b]pryridine-2-carboxamide

I-95

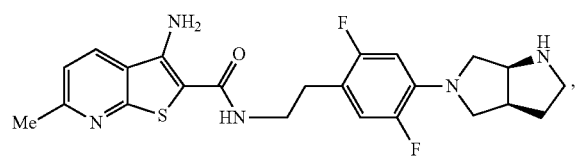

3-amino-N-(2,5-difluoro-4-((3aS,6aS)-hexahydropyrrolo[3,4-b]pyrrol-5(1H)-yl)phenethyl)-6-methylthieno[2.3-b]pryridine-2-carboxamide

I-96

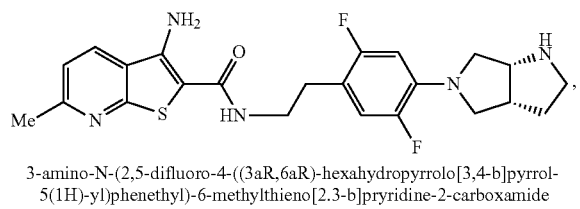

3-amino-N-(2,5-difluoro-4-((3aR,6aR)-hexahydropyrrolo[3,4-b]pyrrol-5(1H)-yl)phenethyl)-6-methylthieno[2.3-b]pryridine-2-carboxamide

I-97

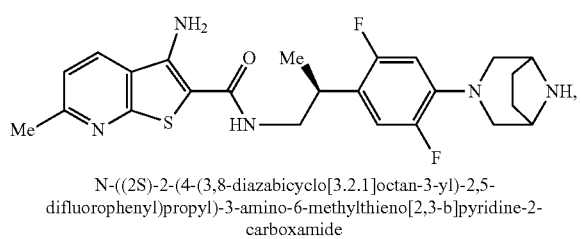

N-((2S)-2-(4-(3,8-diazabicyclo[3.2.1]octan-3-yl)-2,5-difluorophenyl)propyl)-3-amino-6-methylthieno[2,3-b]pyridine-2-carboxamide

I-98

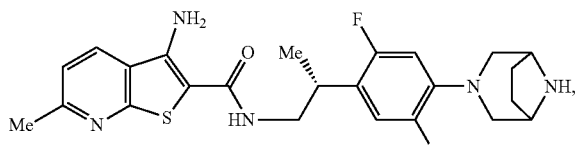

N-((2R)-2-(4-(3,8-diazabicyclo[3.2.1]octan-3-yl)-2,5-difluorophenyl)propyl)-3-amino-6-methylthieno[2,3-b]pyridine-2-carboxamide

I-99

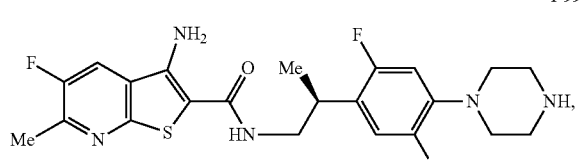

(S)-3-amino-N-(2-(2,5-difluoro-4-(piperazin-1-yl)pheneyl)propyl)-5-fluoro-6-methylthieno[2,3-b]pyridine-2-carboxamide

I-100

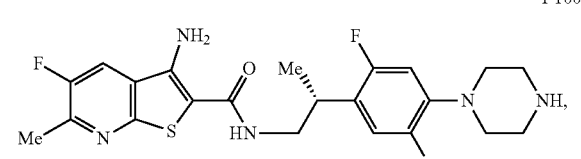

(R)-3-amino-N-(2-(2,5-difluoro-4-(piperazin-1-yl)pheneyl)propyl)-5-fluoro-6-methylthieno[2,3-b]pyridine-2-carboxamide

I-101

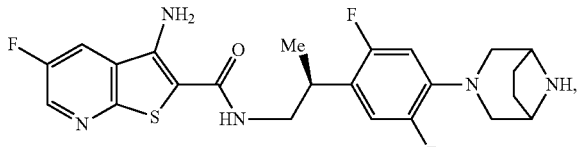

N-((2S)-2-(4-(3,8-diazabicyclo[3.2.1]octan-3-yl)-2,5-difluorophenyl)propyl)-3-amino-5-fluorothieno[2,3-b]pyridine-2-carboxamide

I-102

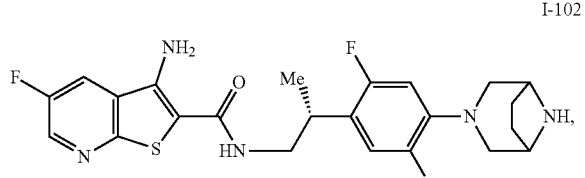

N-((2R)-2-(4-(3,8-diazabicyclo[3.2.1]octan-3-yl)-2,5-difluorophenyl)propyl)-3-amino-5-fluorothieno[2,3-b]pyridine-2-carboxamide

I-103

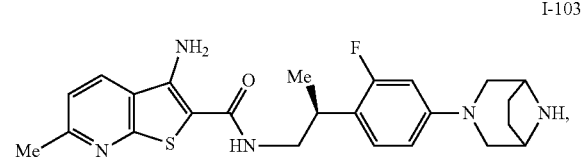

N-((2S)-2-(4-(3,8-diazabicyclo[3.2.1]octan-3-yl)-2-fluorophenyl)propyl)-3-amino-6-methylthieno[2,3-b]pyridine-2-carboxamide

I-104

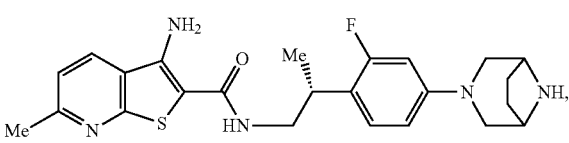

N-((2R)-2-(4-(3,8-diazabicyclo[3.2.1]octan-3-yl)-2-fluorophenyl)propyl)-3-amino-6-methylthieno[2,3-b]pyridine-2-carboxamide

I-105

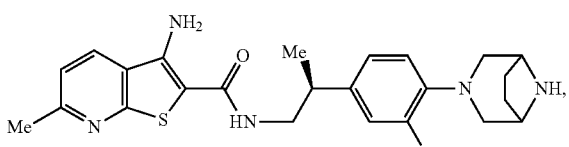

N-((2S)-2-(4-(3,8-diazabicyclo[3.2.1]octan-3-yl)-3-fluorophenyl)propyl)-3-amino-6-methylthieno[2,3-b]pyridine-2-carboxamide

I-106

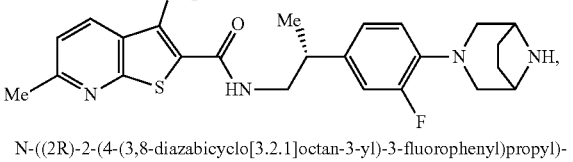

N-((2R)-2-(4-(3,8-diazabicyclo[3.2.1]octan-3-yl)-3-fluorophenyl)propyl)-3-amino-6-methylthieno[2,3-b]pyridine-2-carboxamide

I-107

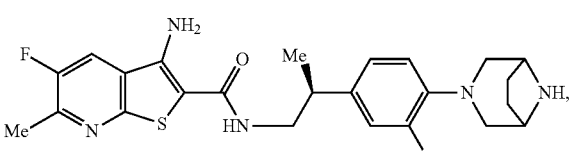

N-((2S)-2-(4-(3,8-diazabicyclo[3.2.1]octan-3-yl)-3-fluorophenyl)propyl)-3-amino-5-fluoro-6-methylthieno[2,3-b]pyridine-2-carboxamide

I-108

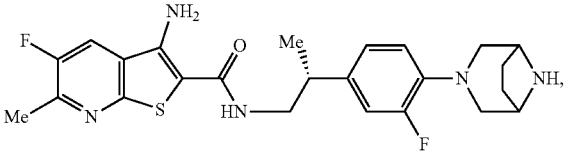

N-((2R)-2-(4-(3,8-diazabicyclo[3.2.1]octan-3-yl)-3-fluorophenyl)propyl)-3-amino-5-fluoro-6-methylthieno[2,3-b]pyridine-2-carboxamide

I-109

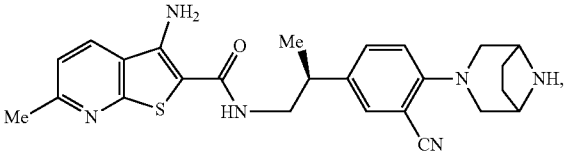

N-((2S)-2-(4-(3,8-diazabicyclo[3.2.1]octan-3-yl)-3-cyanophenyl)propyl)-3-amino-6-methylthieno[2,3-b]pyridine-2-carboxamide -continued

I-110

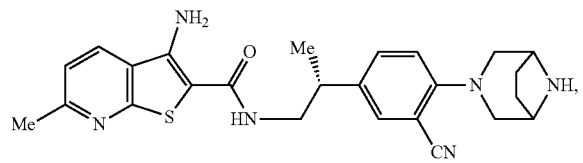

N-((2R)-2-(4-(3,8-diazabicyclo[3.2.1]octan-3-yl)-3-cyanophenyl)propyl)-
3-amino-6-methylthieno[2,3-b]pyridine-2-carboxamide

I-111

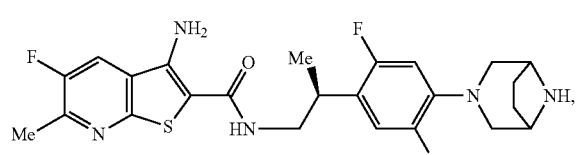

N-((2S)-2-(4-(3,8-diazabicyclo[3.2.1]octan-3-yl)-2,5-
difluorophenyl)propyl)-3-amino-5-fluoro-6-methylthieno[2,3-
b]pyridine-2-carboxamide

I-112

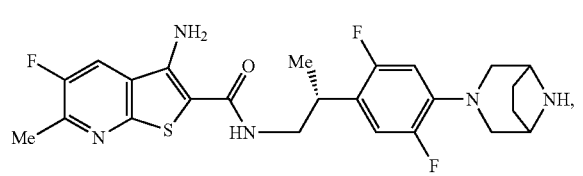

N-((2R)-2-(4-(3,8-diazabicyclo[3.2.1]octan-3-yl)-2,5-
difluorophenyl)propyl)-3-amino-5-fluoro-6-methylthieno[2,3-
b]pyridine-2-carboxamide

I-113

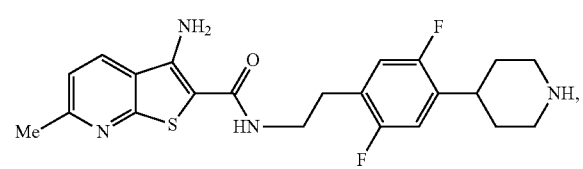

3-amino-N-(2,5-difluoro-4-(piperidin-4-yl)phenethyl)-6-methylthieno[2,3-
b]pyridine-2-carboxamide

I-114

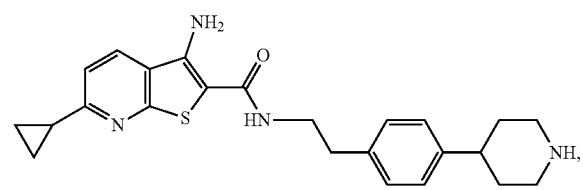

3-amino-6-cyclopropyl-N-(4-(piperazin-1-yl)phenethyl)thieno[2,3-
b]pyridine-2-carboxamide

I-115

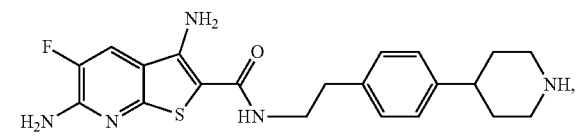

3,6-diamino-5-fluoro-N-(4-(piperazin-1-yl)phenethyl)thieno[2,3-
b]pyridine-2-carboxamide -continued

I-116

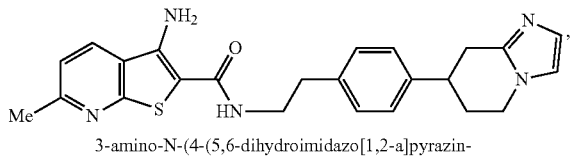

3-amino-N-(4-(5,6-dihydroimidazo[1,2-a]pyrazin-
7(8H)-yl)phenethyl)-6-methylthieno[2,3-b]pyridine-2-carboxamide

I-117

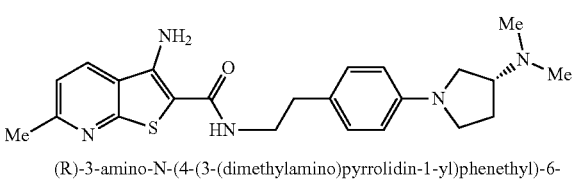

(R)-3-amino-N-(4-(3-(dimethylamino)pyrrolidin-1-yl)phenethyl)-6-
methylthieno[2,3-b]pyridine-2-carboxamide

I-118

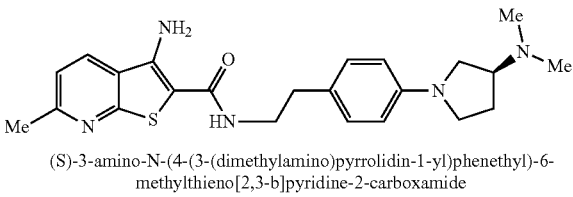

(S)-3-amino-N-(4-(3-(dimethylamino)pyrrolidin-1-yl)phenethyl)-6-
methylthieno[2,3-b]pyridine-2-carboxamide

I-119

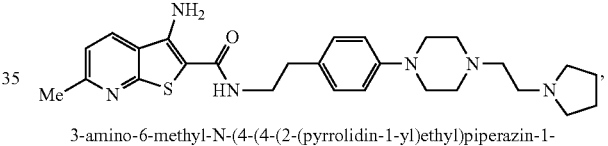

3-amino-6-methyl-N-(4-(4-(2-(pyrrolidin-1-yl)ethyl)piperazin-1-
yl)phenethyl)thieno[2,3-b]pyridine-2-carboxamide

I-120

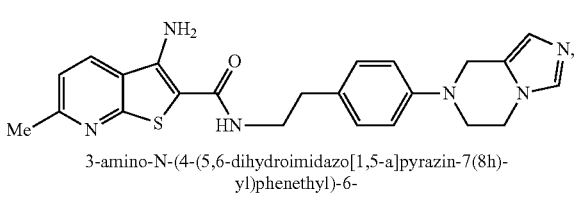

3-amino-N-(4-(5,6-dihydroimidazo[1,5-a]pyrazin-7(8h)-
yl)phenethyl)-6-
methylthieno[2,3-b]pyridine-2-carboxamide

I-121

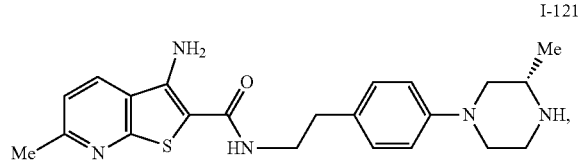

(S)-3-amino-6-methyl-N-(4-(3-methylpiperazin-1-
y)phenethyl)thieno[2,3-
b]pyridine-2-carboxamide

I-122

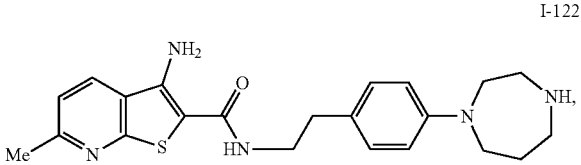

N-(4-(1,4-diazpan-1-yl)phenethyl)-3-amino-6-methylthieno[2,3-
b]pyridine-2-carboxamide

I-123

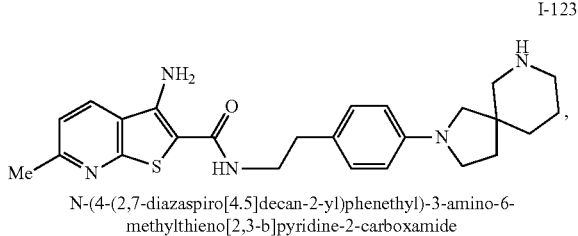

N-(4-(2,7-diazaspiro[4.5]decan-2-yl)phenethyl)-3-amino-6-methylthieno[2,3-b]pyridine-2-carboxamide

I-124

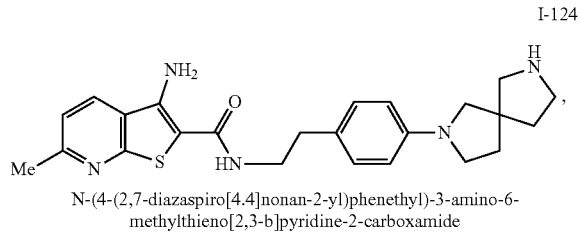

N-(4-(2,7-diazaspiro[4.4]nonan-2-yl)phenethyl)-3-amino-6-methylthieno[2,3-b]pyridine-2-carboxamide

I-125

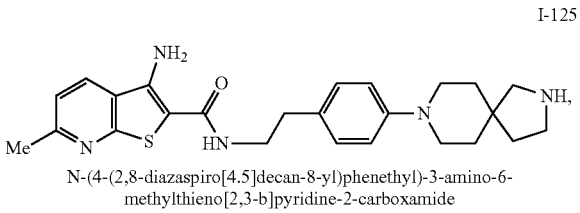

N-(4-(2,8-diazaspiro[4.5]decan-8-yl)phenethyl)-3-amino-6-methylthieno[2,3-b]pyridine-2-carboxamide

I-126

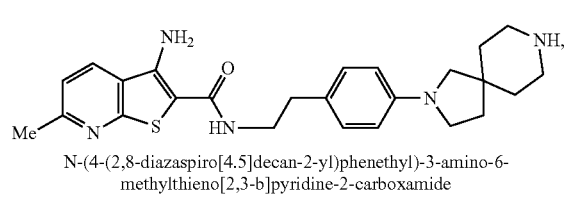

N-(4-(2,8-diazaspiro[4.5]decan-2-yl)phenethyl)-3-amino-6-methylthieno[2,3-b]pyridine-2-carboxamide

I-127

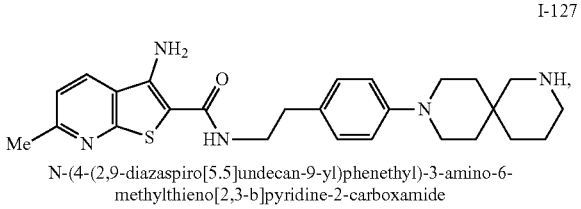

N-(4-(2,9-diazaspiro[5.5]undecan-9-yl)phenethyl)-3-amino-6-methylthieno[2,3-b]pyridine-2-carboxamide

I-128

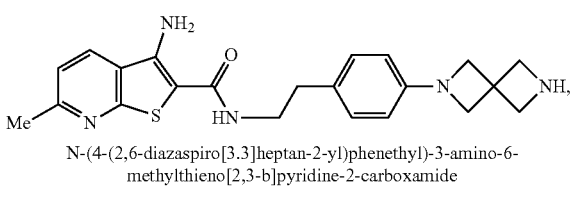

N-(4-(2,6-diazaspiro[3.3]heptan-2-yl)phenethyl)-3-amino-6-methylthieno[2,3-b]pyridine-2-carboxamide

I-129

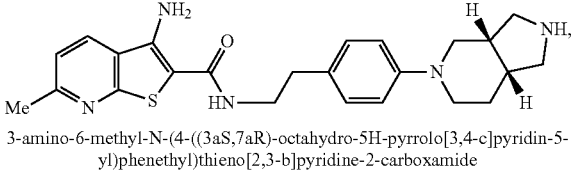

3-amino-6-methyl-N-(4-((3aS,7aR)-octahydro-5H-pyrrolo[3,4-c]pyridin-5-yl)phenethyl)thieno[2,3-b]pyridine-2-carboxamide

I-130

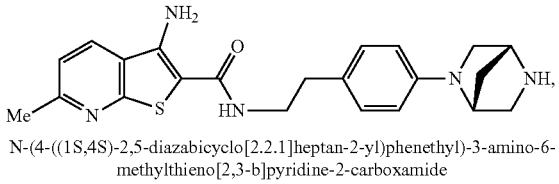

N-(4-((1S,4S)-2,5-diazabicyclo[2.2.1]heptan-2-yl)phenethyl)-3-amino-6-methylthieno[2,3-b]pyridine-2-carboxamide

I-131

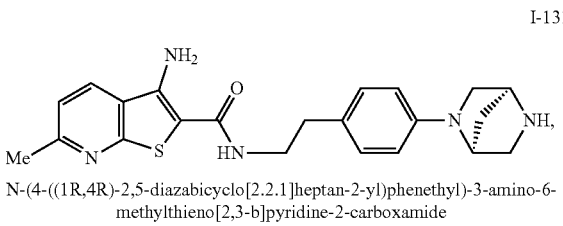

N-(4-((1R,4R)-2,5-diazabicyclo[2.2.1]heptan-2-yl)phenethyl)-3-amino-6-methylthieno[2,3-b]pyridine-2-carboxamide

I-132

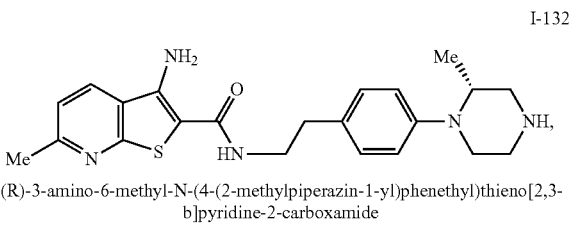

(R)-3-amino-6-methyl-N-(4-(2-methylpiperazin-1-yl)phenethyl)thieno[2,3-b]pyridine-2-carboxamide

I-133

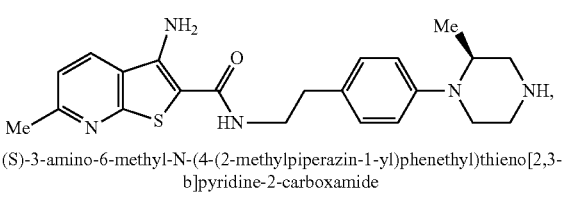

(S)-3-amino-6-methyl-N-(4-(2-methylpiperazin-1-yl)phenethyl)thieno[2,3-b]pyridine-2-carboxamide

I-134

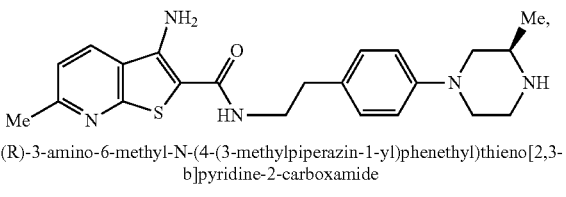

(R)-3-amino-6-methyl-N-(4-(3-methylpiperazin-1-yl)phenethyl)thieno[2,3-b]pyridine-2-carboxamide

I-135

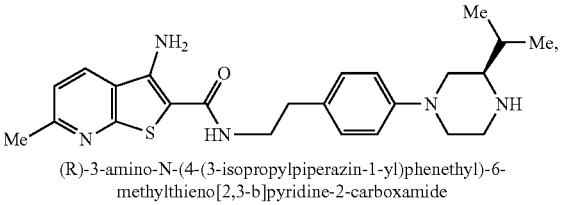

(R)-3-amino-N-(4-(3-isopropylpiperazin-1-yl)phenethyl)-6-methylthieno[2,3-b]pyridine-2-carboxamide

I-136

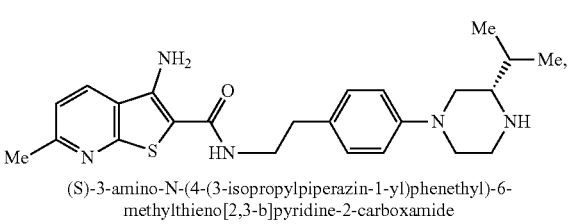

(S)-3-amino-N-(4-(3-isopropylpiperazin-1-yl)phenethyl)-6-methylthieno[2,3-b]pyridine-2-carboxamide

I-137

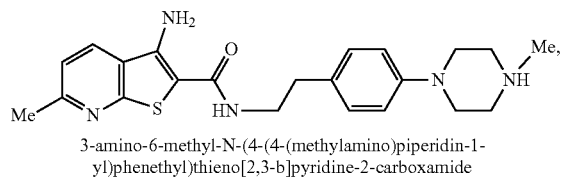

3-amino-6-methyl-N-(4-(4-(methylamino)piperidin-1-yl)phenethyl)thieno[2,3-b]pyridine-2-carboxamide

I-138

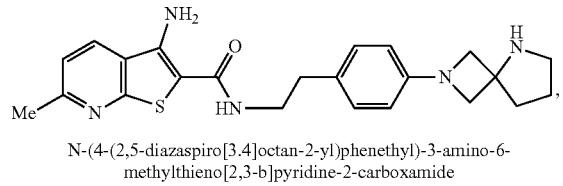

N-(4-(2,5-diazaspiro[3.4]octan-2-yl)phenethyl)-3-amino-6-methylthieno[2,3-b]pyridine-2-carboxamide

I-139

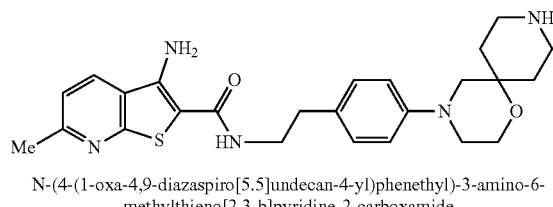

N-(4-(1-oxa-4,9-diazaspiro[5.5]undecan-4-yl)phenethyl)-3-amino-6-methylthieno[2,3-b]pyridine-2-carboxamide

I-140

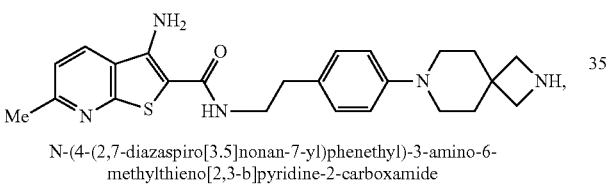

N-(4-(2,7-diazaspiro[3.5]nonan-7-yl)phenethyl)-3-amino-6-methylthieno[2,3-b]pyridine-2-carboxamide

I-141

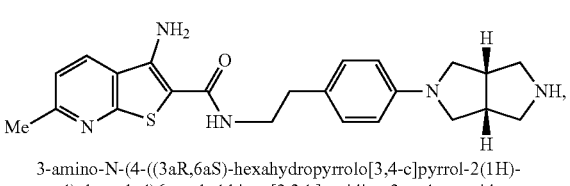

3-amino-N-(4-((3aR,6aS)-hexahydropyrrolo[3,4-c]pyrrol-2(1H)-yl)phenethyl)6-methylthieno[2,3-b]pyridine-2-carboxamide

I-142

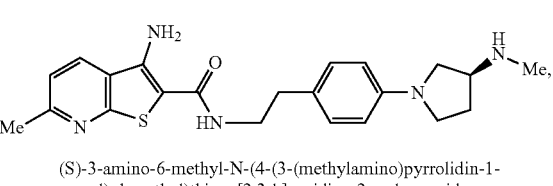

(S)-3-amino-6-methyl-N-(4-(3-(methylamino)pyrrolidin-1-yl)phenethyl)thieno[2,3-b]pyridine-2-carboxamide

I-143

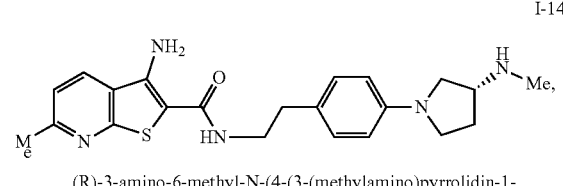

(R)-3-amino-6-methyl-N-(4-(3-(methylamino)pyrrolidin-1-yl)phenethyl)thieno[2,3-b]pyridine-2-carboxamide

I-144

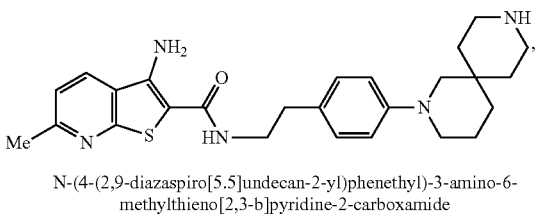

N-(4-(2,9-diazaspiro[5.5]undecan-2-yl)phenethyl)-3-amino-6-methylthieno[2,3-b]pyridine-2-carboxamide

I-145

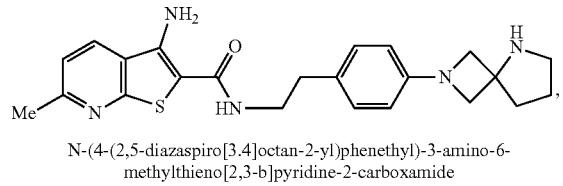

N-(4-(2,8-diazaspiro[5.5]undecan-2-yl)phenethyl)-3-amino-6-methylthieno[2,3-b]pyridine-2-carboxamide

I-146

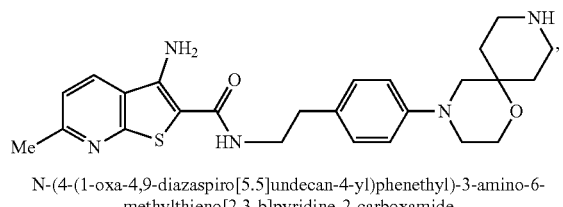

N-(4-(1,7-diazaspiro[4.5]decan-1-yl)phenethyl)-3-amino-6-methylthieno[2,3-b]pyridine-2-carboxamide

I-147

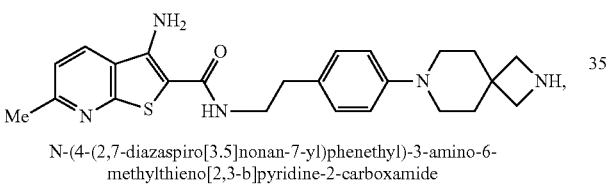

(R)-3-amino-6-methyl-N-(4-(pyrrolidin-3-ylamino)phenethyl)thieno[2,3-b]pyridine-2-carboxamide

I-148

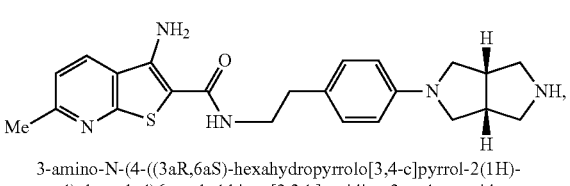

N-(4-(6-oxa-2,9-diazaspiro[4.5]decan-2-yl)phenethyl)-3-amino-6-methylthieno[2,3-b]pyridine-2-carboxamide

I-149

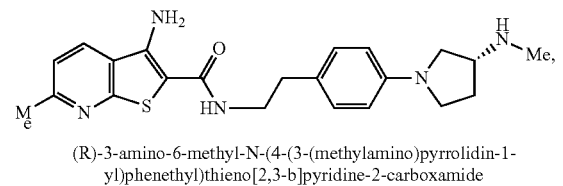

3-amino-6-methyl-N-4(4-(methyl(piperidin-3-ylmethyl)amino)phenethyl)thieno[2,3-b]pyridine-2-carboxamide

I-150

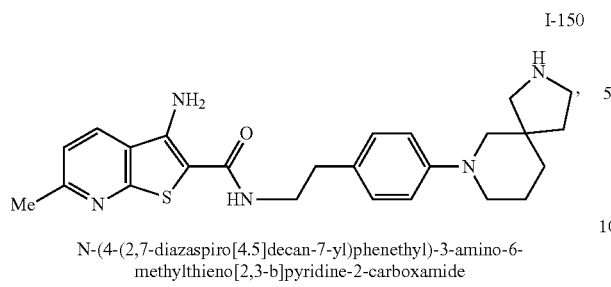

N-(4-(2,7-diazaspiro[4.5]decan-7-yl)phenethyl)-3-amino-6-
methylthieno[2,3-b]pyridine-2-carboxamide

I-151

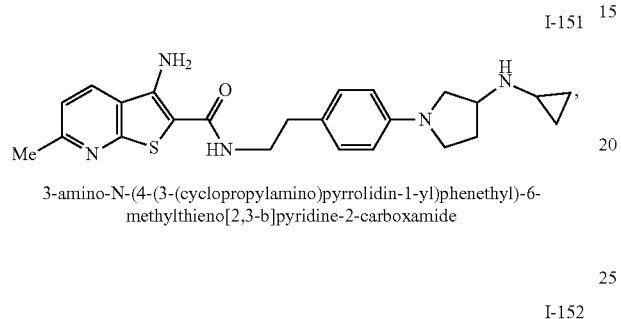

3-amino-N-(4-(3-(cyclopropylamino)pyrrolidin-1-yl)phenethyl)-6-
methylthieno[2,3-b]pyridine-2-carboxamide

I-152

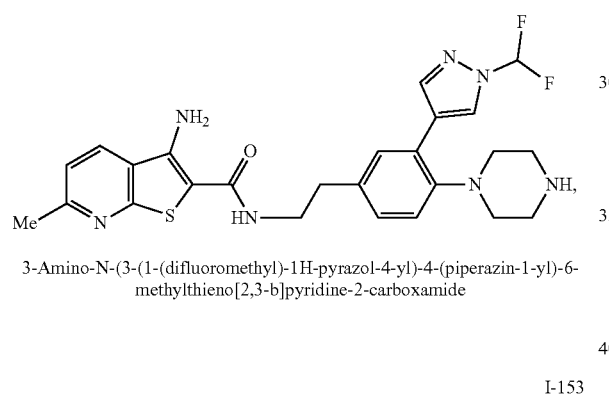

3-Amino-N-(3-(1-(difluoromethyl)-1H-pyrazol-4-yl)-4-(piperazin-1-yl)-6-
methylthieno[2,3-b]pyridine-2-carboxamide

I-153

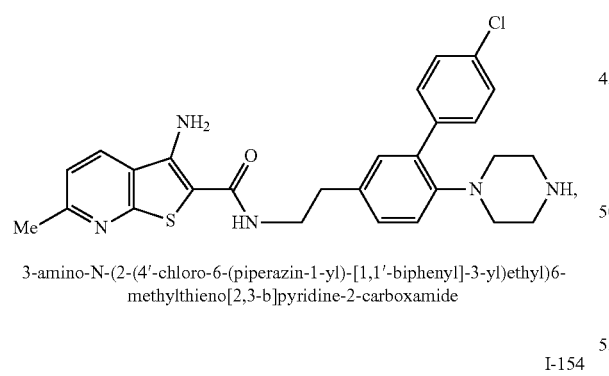

3-amino-N-(2-(4'-chloro-6-(piperazin-1-yl)-[1,1'-biphenyl]-3-yl)ethyl)6-
methylthieno[2,3-b]pyridine-2-carboxamide

I-154

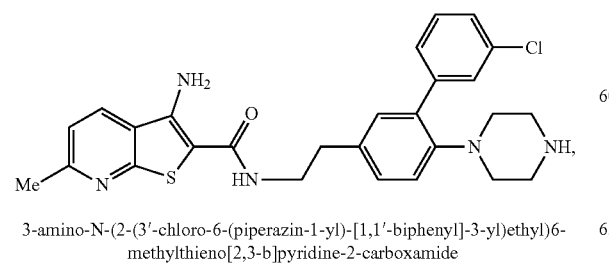

3-amino-N-(2-(3'-chloro-6-(piperazin-1-yl)-[1,1'-biphenyl]-3-yl)ethyl)6-
methylthieno[2,3-b]pyridine-2-carboxamide

I-155

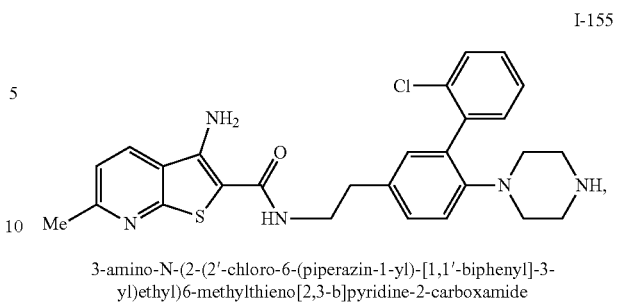

3-amino-N-(2-(2'-chloro-6-(piperazin-1-yl)-[1,1'-biphenyl]-3-
yl)ethyl)6-methylthieno[2,3-b]pyridine-2-carboxamide

I-156

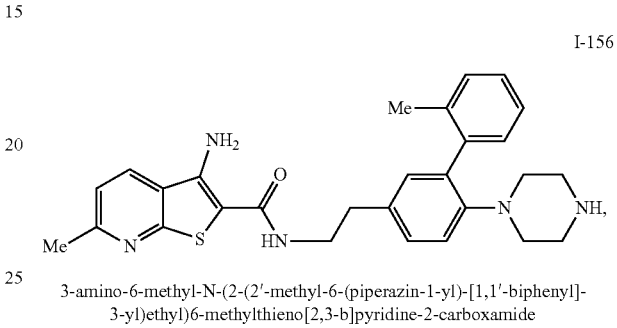

3-amino-6-methyl-N-(2-(2'-methyl-6-(piperazin-1-yl)-[1,1'-biphenyl]-
3-yl)ethyl)6-methylthieno[2,3-b]pyridine-2-carboxamide

I-157

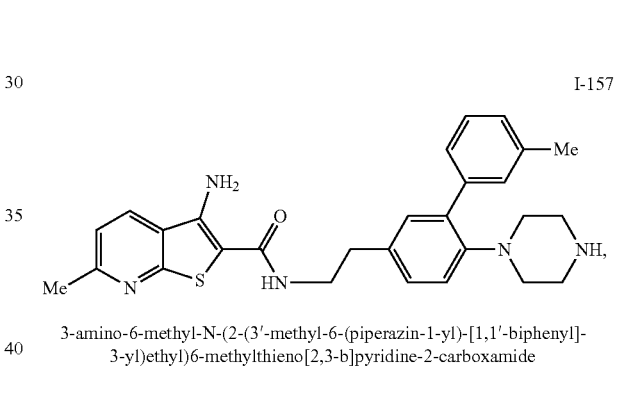

3-amino-6-methyl-N-(2-(3'-methyl-6-(piperazin-1-yl)-[1,1'-biphenyl]-
3-yl)ethyl)6-methylthieno[2,3-b]pyridine-2-carboxamide

I-158

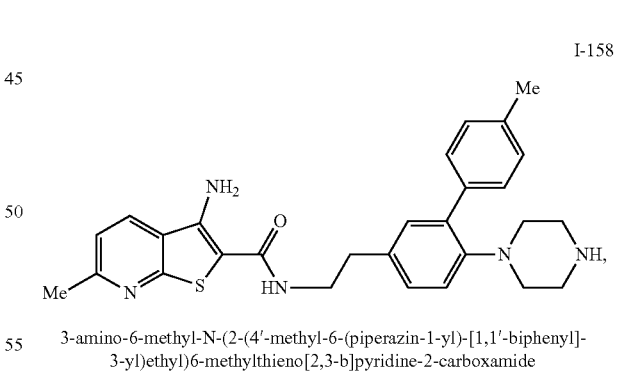

3-amino-6-methyl-N-(2-(4'-methyl-6-(piperazin-1-yl)-[1,1'-biphenyl]-
3-yl)ethyl)6-methylthieno[2,3-b]pyridine-2-carboxamide

I-159

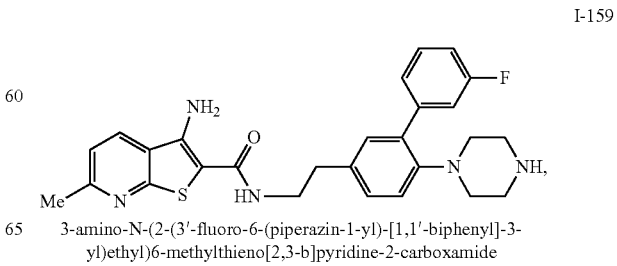

3-amino-N-(2-(3'-fluoro-6-(piperazin-1-yl)-[1,1'-biphenyl]-3-
yl)ethyl)6-methylthieno[2,3-b]pyridine-2-carboxamide -continued

I-160

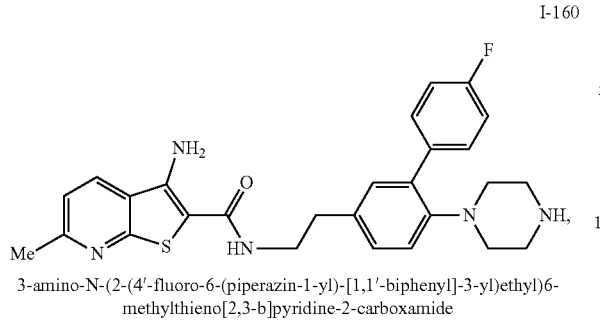

3-amino-N-(2-(4'-fluoro-6-(piperazin-1-yl)-[1,1'-biphenyl]-3-yl)ethyl)6-methylthieno[2,3-b]pyridine-2-carboxamide

I-161

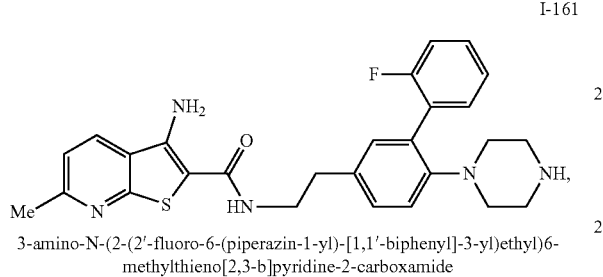

3-amino-N-(2-(2'-fluoro-6-(piperazin-1-yl)-[1,1'-biphenyl]-3-yl)ethyl)6-methylthieno[2,3-b]pyridine-2-carboxamide

I-162

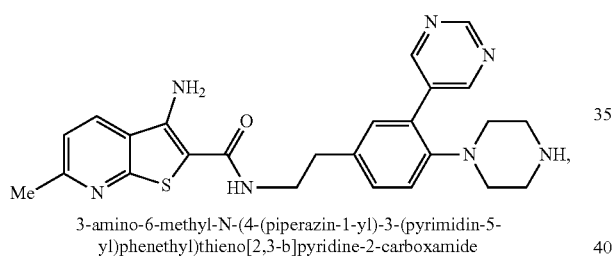

3-amino-6-methyl-N-(4-(piperazin-1-yl)-3-(pyrimidin-5-yl)phenethyl)thieno[2,3-b]pyridine-2-carboxamide

I-163

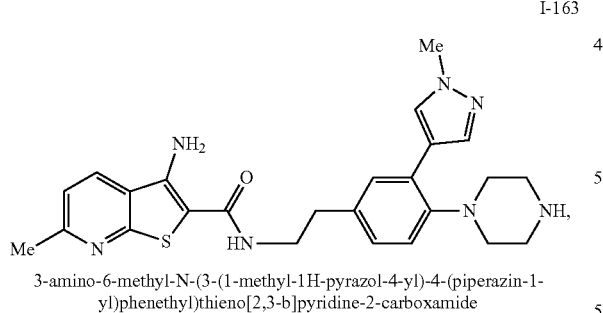

3-amino-6-methyl-N-(3-(1-methyl-1H-pyrazol-4-yl)-4-(piperazin-1-yl)phenethyl)thieno[2,3-b]pyridine-2-carboxamide

I-164

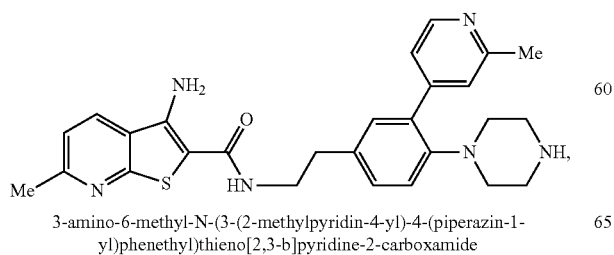

3-amino-6-methyl-N-(3-(2-methylpyridin-4-yl)-4-(piperazin-1-yl)phenethyl)thieno[2,3-b]pyridine-2-carboxamide -continued

I-165

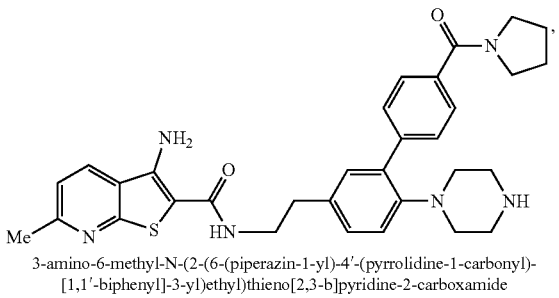

3-amino-6-methyl-N-(2-(6-(piperazin-1-yl)-4'-(pyrrolidine-1-carbonyl)-[1,1'-biphenyl]-3-yl)ethyl)thieno[2,3-b]pyridine-2-carboxamide

I-166

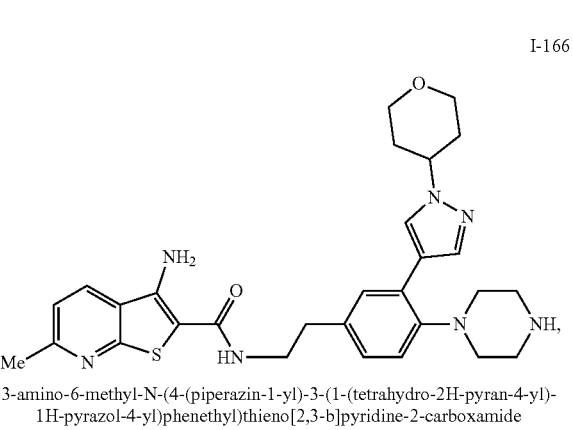

3-amino-6-methyl-N-(4-(piperazin-1-yl)-3-(1-(tetrahydro-2H-pyran-4-yl)-1H-pyrazol-4-yl)phenethyl)thieno[2,3-b]pyridine-2-carboxamide

I-167

3-amino-N-(3-(1-(2-methoxyethyl)-1H-pyrazol-4-yl)-4-(piperazin-1-yl)phenethyl)-6-methylthieno[2,3-b]pyridine-2-carboxamide

I-168

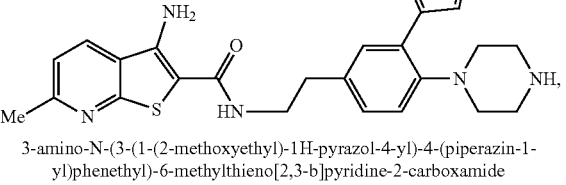

3-Amino-6-methyl-N-(4-piperazin-1-yl)-3-(pyridin-2-yl)phenethyl)thieno[2,3-b]pyridine-2-carboxamide

I-169

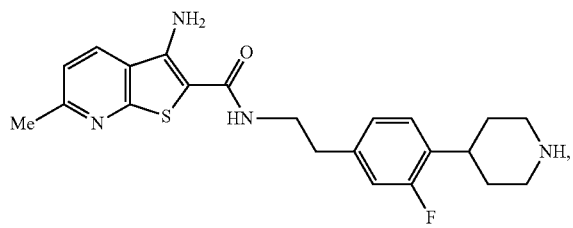

3-Amino-N-(3-fluoro-4-(piperidin-4-yl)phenethyl)-6-methylthieno[2,3-b]pyridine-2-carboxamide

I-170

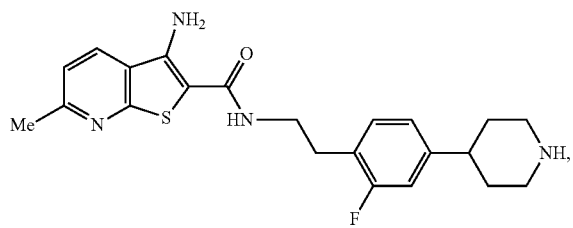

3-amino-N-(2-fluoro-4-(piperidin-4-yl)phenethyl)-6-methylthieno[2,3-b]pyridine-2-carboxamide

I-171

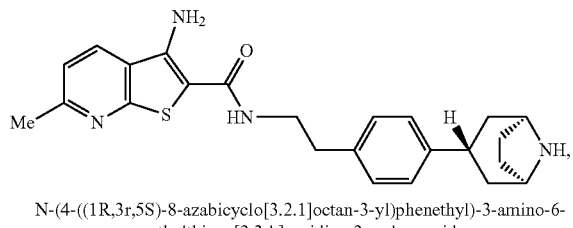

N-(4-((1R,3r,5S)-8-azabicyclo[3.2.1]octan-3-yl)phenethyl)-3-amino-6-methylthieno[2,3-b]pyridine-2-carboxamide

I-172

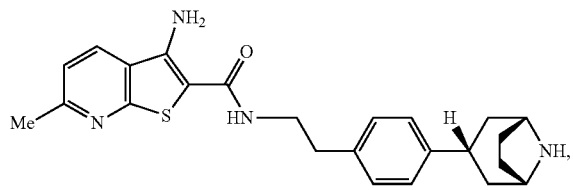

N-(4-((1R,3s,5S)-8-azabicyclo[3.2.1]octan-3-yl)phenethyl)-3-amino-6-methylthieno[2,3-b]pyridine-2-carboxamide

I-173

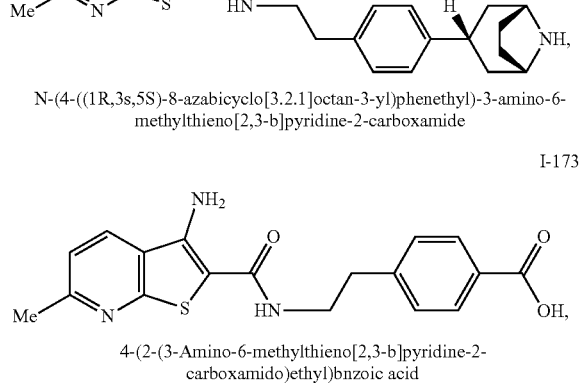

4-(2-(3-Amino-6-methylthieno[2,3-b]pyridine-2-carboxamido)ethyl)bnzoic acid

I-174

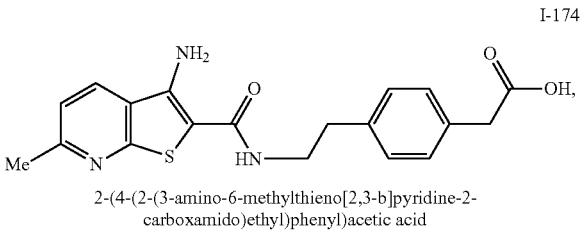

2-(4-(2-(3-amino-6-methylthieno[2,3-b]pyridine-2-carboxamido)ethyl)phenyl)acetic acid

I-175

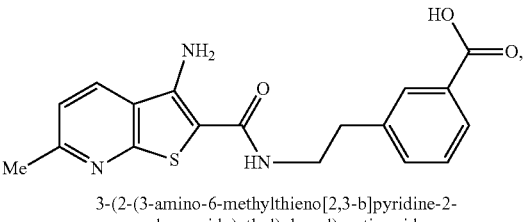

3-(2-(3-amino-6-methylthieno[2,3-b]pyridine-2-carboxamido)ethyl)phenyl)acetic acid

I-176

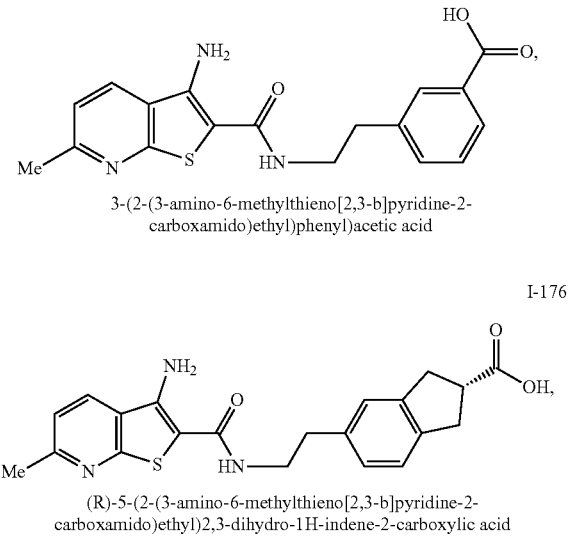

(R)-5-(2-(3-amino-6-methylthieno[2,3-b]pyridine-2-carboxamido)ethyl)2,3-dihydro-1H-indene-2-carboxylic acid

I-177

(S)-5-(2-(3-amino-6-methylthieno[2,3-b]pyridine-2-carboxamido)ethyl)2,3-dihydro-1H-indene-2-carboxylic acid

I-178

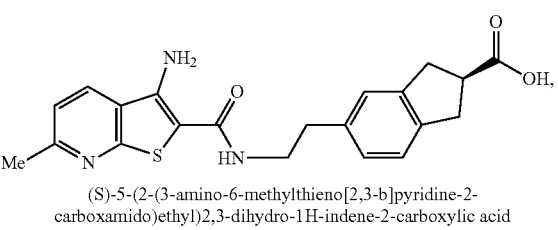

2-(3-(2-(3-amino-6-methylthieno[2,3-b]pyridine-2-carboxamido)ethyl)phenyl)acetic acid

I-179

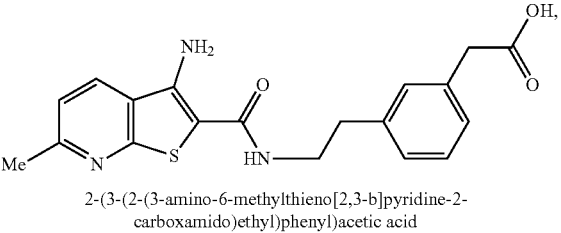

3-Amino-N-(3-chloro-4-(piperazin-1-yl)phenethyl)-6-difluoromentyl)thieno[2,3-b]pyridine-2-carboxamide

I-180

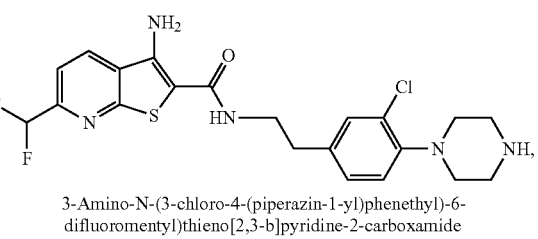

(R)-3-amino-6-methyl-N-(4-(pyrrolidin-3-yl)phenethyl)thieno[2,3-b]pyridine-2-carboxamide

I-181

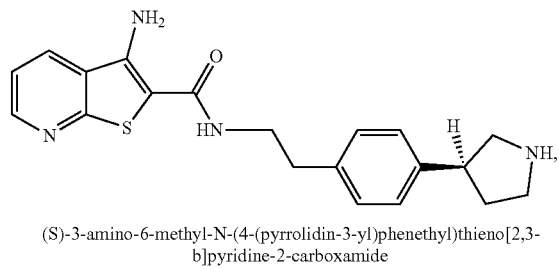

(S)-3-amino-6-methyl-N-(4-(pyrrolidin-3-yl)phenethyl)thieno[2,3-b]pyridine-2-carboxamide

I-182

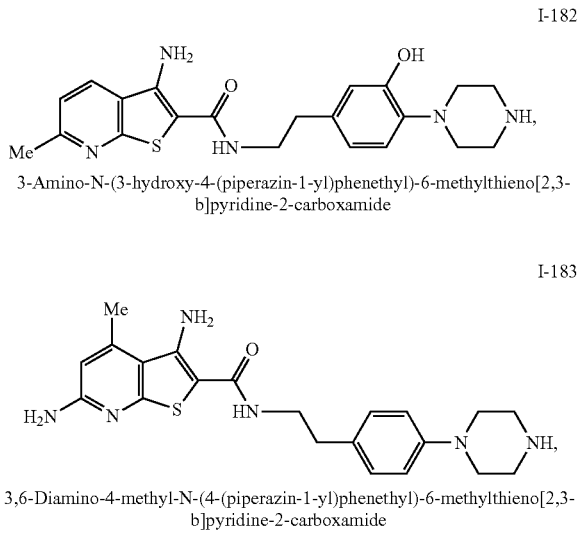

3-Amino-N-(3-hydroxy-4-(piperazin-1-yl)phenethyl)-6-methylthieno[2,3-b]pyridine-2-carboxamide

I-183

3,6-Diamino-4-methyl-N-(4-(piperazin-1-yl)phenethyl)-6-methylthieno[2,3-b]pyridine-2-carboxamide

I-184

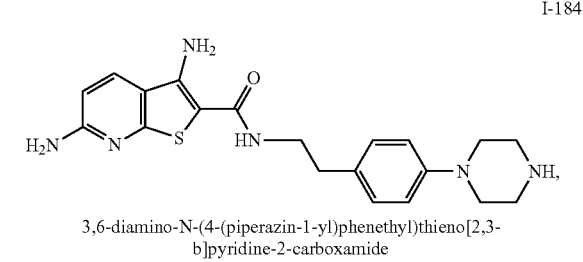

3,6-diamino-N-(4-(piperazin-1-yl)phenethyl)thieno[2,3-b]pyridine-2-carboxamide

I-185

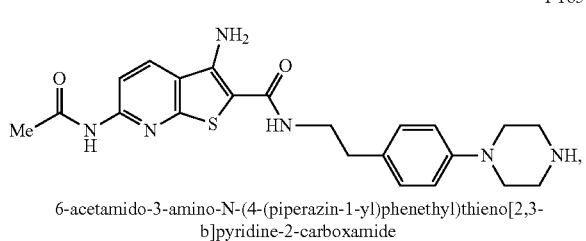

6-acetamido-3-amino-N-(4-(piperazin-1-yl)phenethyl)thieno[2,3-b]pyridine-2-carboxamide

I-186

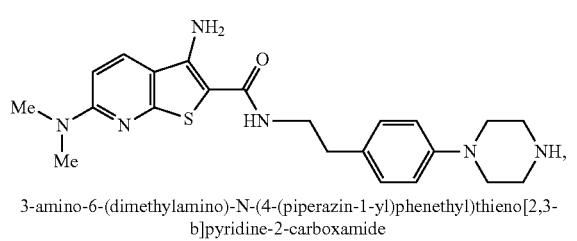

3-amino-6-(dimethylamino)-N-(4-(piperazin-1-yl)phenethyl)thieno[2,3-b]pyridine-2-carboxamide

I-187

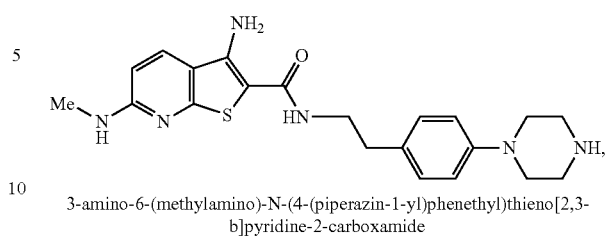

3-amino-6-(methylamino)-N-(4-(piperazin-1-yl)phenethyl)thieno[2,3-b]pyridine-2-carboxamide

I-188

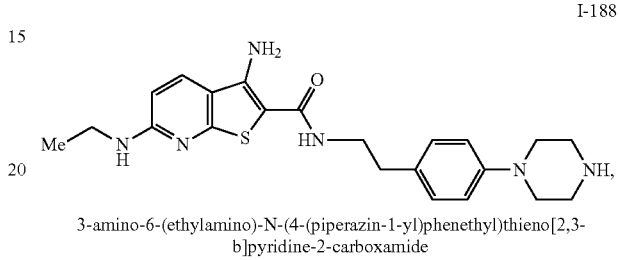

3-amino-6-(ethylamino)-N-(4-(piperazin-1-yl)phenethyl)thieno[2,3-b]pyridine-2-carboxamide

I-189

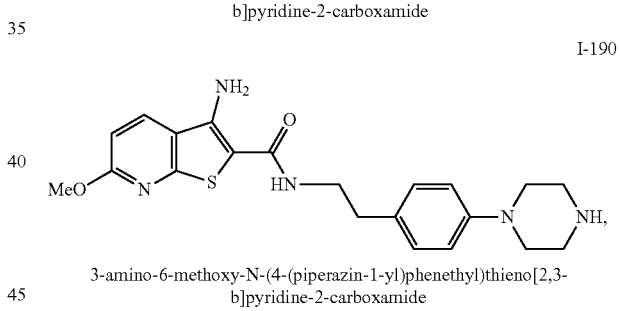

3-amino-6-(isopropylamino)-N-(4-(piperazin-1-yl)phenethyl)thieno[2,3-b]pyridine-2-carboxamide

I-190

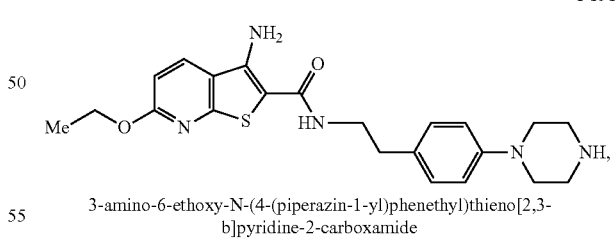

3-amino-6-methoxy-N-(4-(piperazin-1-yl)phenethyl)thieno[2,3-b]pyridine-2-carboxamide

I-191

3-amino-6-ethoxy-N-(4-(piperazin-1-yl)phenethyl)thieno[2,3-b]pyridine-2-carboxamide

I-192

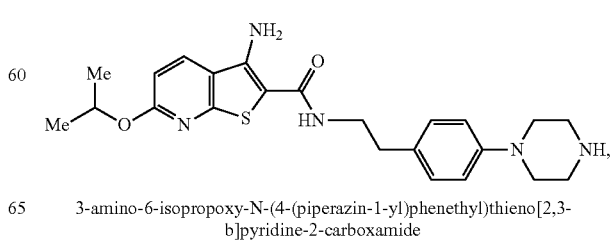

3-amino-6-isopropoxy-N-(4-(piperazin-1-yl)phenethyl)thieno[2,3-b]pyridine-2-carboxamide

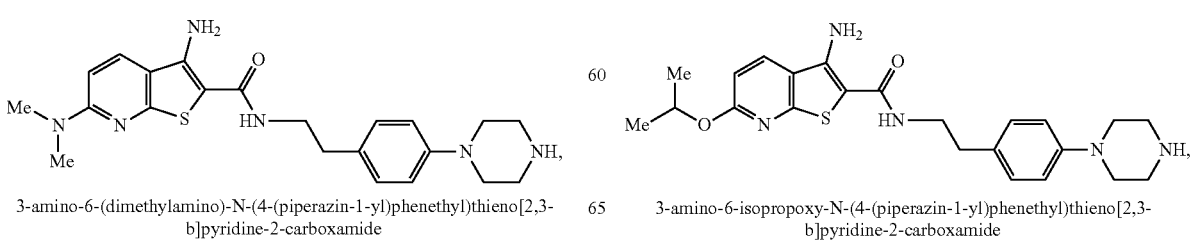

I-193

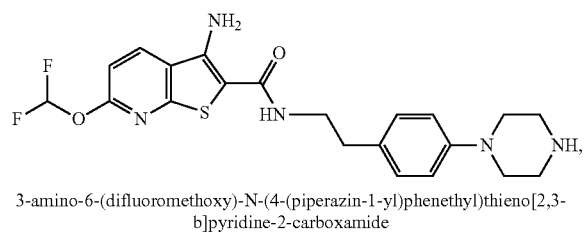

3-amino-6-(difluoromethoxy)-N-(4-(piperazin-1-yl)phenethyl)thieno[2,3-b]pyridine-2-carboxamide

I-194

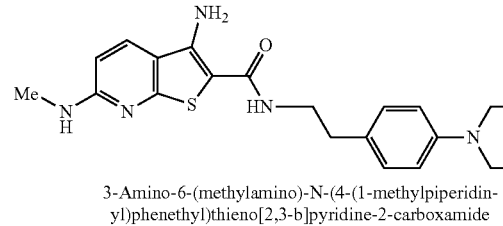

3-Amino-6-(methylamino)-N-(4-(1-methylpiperidin-yl)phenethyl)thieno[2,3-b]pyridine-2-carboxamide

I-195

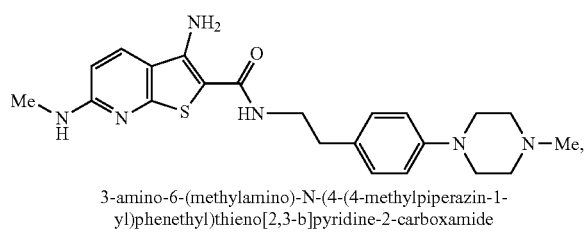

3-amino-6-(methylamino)-N-(4-(4-methylpiperazin-1-yl)phenethyl)thieno[2,3-b]pyridine-2-carboxamide

I-196

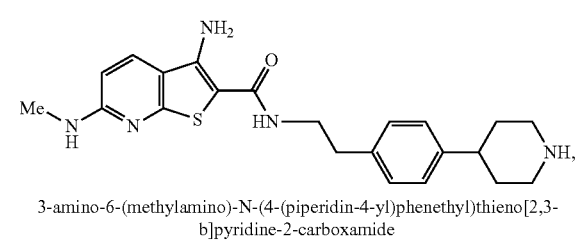

3-amino-6-(methylamino)-N-(4-(piperidin-4-yl)phenethyl)thieno[2,3-b]pyridine-2-carboxamide

I-197

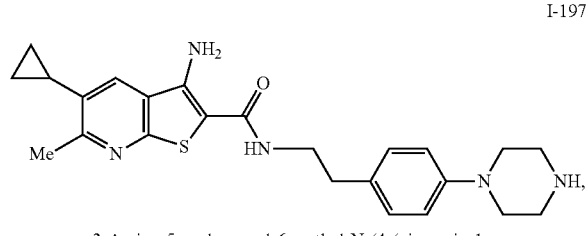

3-Amino-5-cyclopropyl-6-methyl-N-(4-(piperazin-1-yl)phenethyl)thieno[2,3-b]pyridine-2-carboxamide

I-198

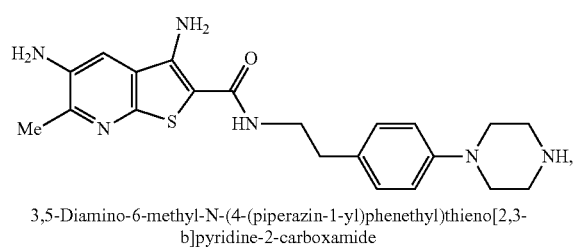

3,5-Diamino-6-methyl-N-(4-(piperazin-1-yl)phenethyl)thieno[2,3-b]pyridine-2-carboxamide

I-199

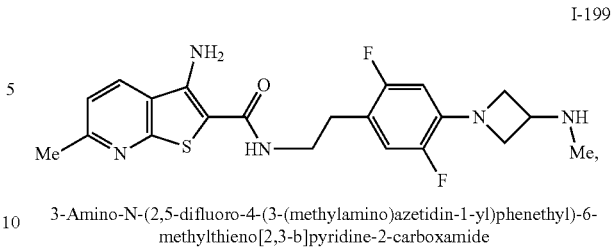

3-Amino-N-(2,5-difluoro-4-(3-(methylamino)azetidin-1-yl)phenethyl)-6-methylthieno[2,3-b]pyridine-2-carboxamide

I-200

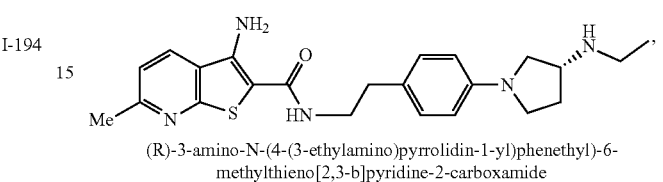

(R)-3-amino-N-(4-(3-ethylamino)pyrrolidin-1-yl)phenethyl)-6-methylthieno[2,3-b]pyridine-2-carboxamide

I-201

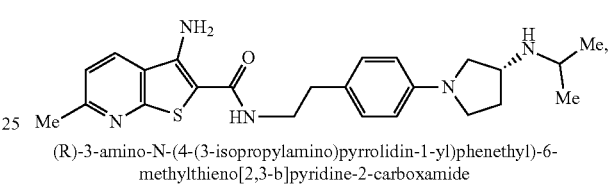

(R)-3-amino-N-(4-(3-isopropylamino)pyrrolidin-1-yl)phenethyl)-6-methylthieno[2,3-b]pyridine-2-carboxamide

I-202

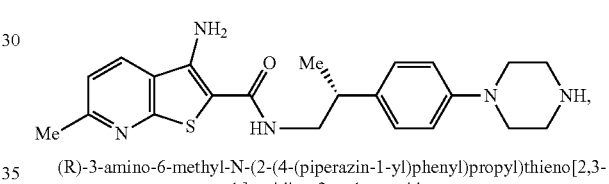

(R)-3-amino-6-methyl-N-(2-(4-(piperazin-1-yl)phenyl)propyl)thieno[2,3-b]pyridine-2-carboxamide

I-203

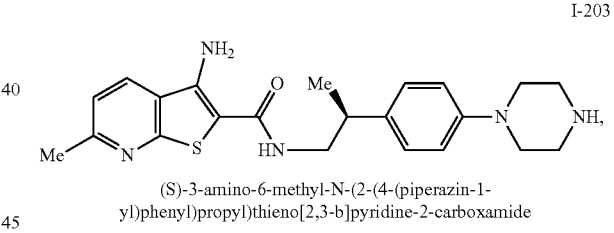

(S)-3-amino-6-methyl-N-(2-(4-(piperazin-1-yl)phenyl)propyl)thieno[2,3-b]pyridine-2-carboxamide

I-204

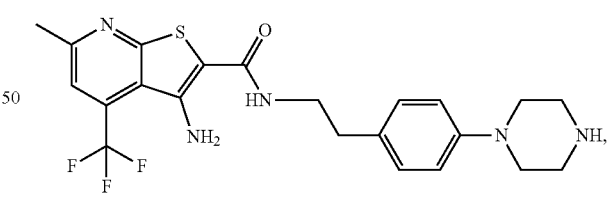

3-amino-6-methyl-N-(4-(piperazin-1-yl)phenethyl)-4-(trifluoromethyl)thieno[2,3-b]pyridine-2-carboxamide

I-205

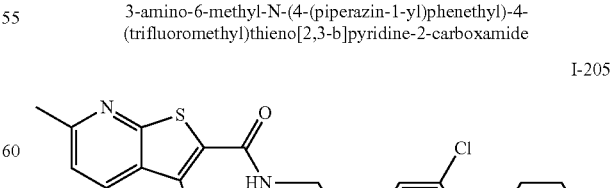

3-amino-N-(3-chloro-4-(piperidin-4-yl)phenethyl)-6-methylthieno[2,3-b]pyridine-2-carboxamide

I-206

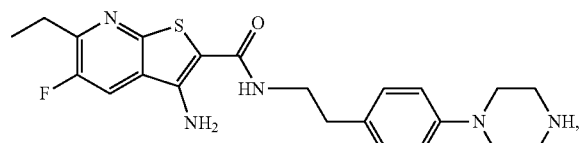

3-amino-6-ethyl-5-fluoro-N-(4-(piperazin-1-yl)phenethyl)thieno[2,3-b]pyridine-2-carboxamide

I-207

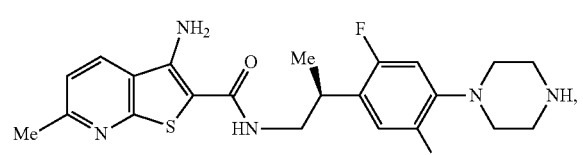

(S)-3-amino-N-(2-(2,5-difluoro-4-(piperazin-1-yl)pheneyl)propyl)6-methylthieno[2,3-b]pyridine-2-carboxamide

I-208

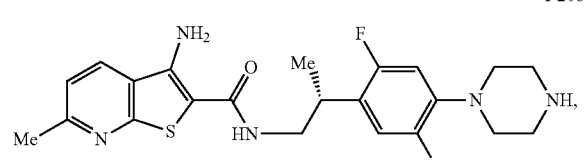

(R)-3-amino-N-(2-(2,5-difluoro-4-(piperazin-1-yl)pheneyl)propyl)6-methylthieno[2,3-b]pyridine-2-carboxamide

I-209

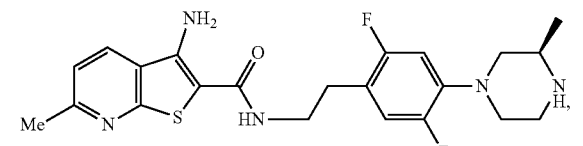

(R)-3-amino-N-(2,5-difluoro-4-(3-methylpiperazin-1-yl)phenethyl)6-methylthieno[2,3-b]pyridine-2-carboxamide

I-210

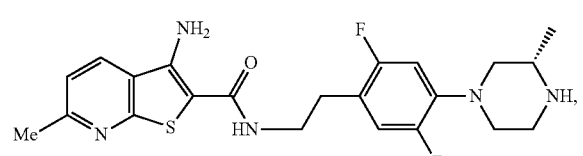

(S)-3-amino-N-(2,5-difluoro-4-(3-methylpiperazin-1-yl)phenethyl)6-methylthieno[2,3-b]pyridine-2-carboxamide

I-211

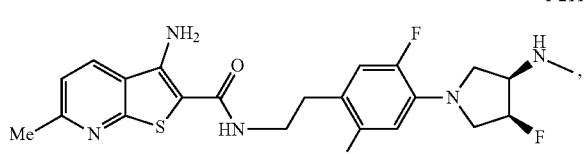

3-Amino-N-(2,5-difluoro-4-((3S,4R)-3-fluoro-4-(methylamino)pyrrolidin-1-yl)phenethyl)-6-methylthieno[2,3-b]pyridine-2-carboxamide

I-212

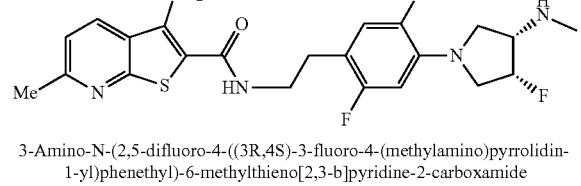

3-Amino-N-(2,5-difluoro-4-((3R,4S)-3-fluoro-4-(methylamino)pyrrolidin-1-yl)phenethyl)-6-methylthieno[2,3-b]pyridine-2-carboxamide

I-213

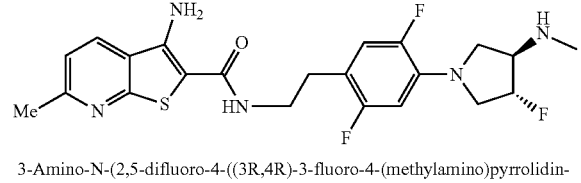

3-Amino-N-(2,5-difluoro-4-((3R,4R)-3-fluoro-4-(methylamino)pyrrolidin-1-yl)phenethyl)-6-methylthieno[2,3-b]pyridine-2-carboxamide

I-214

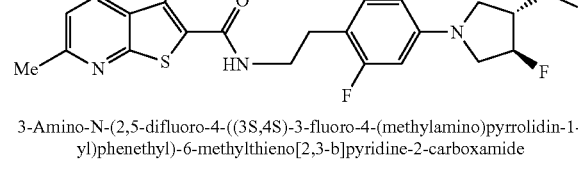

3-Amino-N-(2,5-difluoro-4-((3S,4S)-3-fluoro-4-(methylamino)pyrrolidin-1-yl)phenethyl)-6-methylthieno[2,3-b]pyridine-2-carboxamide

I-215

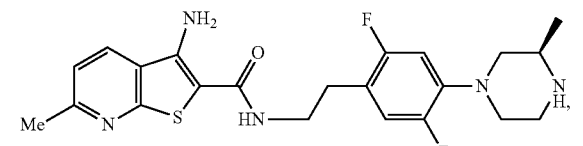

3-Amino-N-(2-(5-chloro-6-(piperazin-1-yl)pyridin-3-yl)ethyl)-6-methylthieno[2,3-b]pyridine-2-carboxamide

I-216

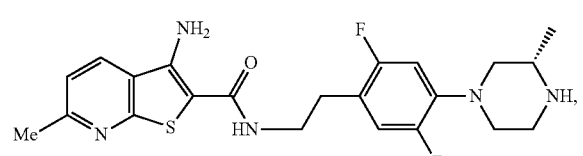

(S)-N-(4-(2,7-diazaspiro[4.5]decan-2-yl)phenethyl)-3-amino-6-methylthieno[2,3-b]pyridine-2-carboxamide

I-217

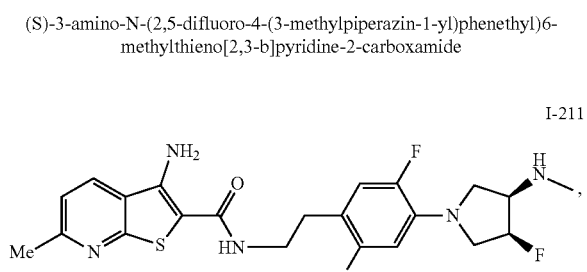

(R)-N-(4-(2,7-diazaspiro[4.5]decan-2-yl)phenethyl)-3-amino-6-methylthieno[2,3-b]pyridine-2-carboxamide

I-218

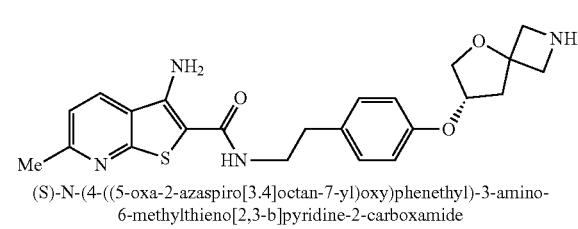

(S)-N-(4-((5-oxa-2-azaspiro[3.4]octan-7-yl)oxy)phenethyl)-3-amino-6-methylthieno[2,3-b]pyridine-2-carboxamide -continued

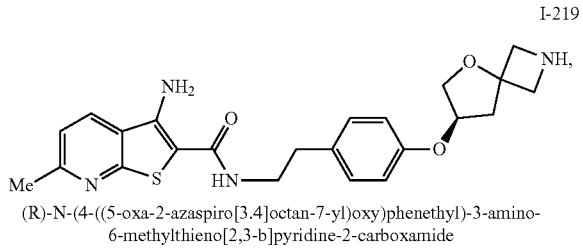

(R)-N-(4-((5-oxa-2-azaspiro[3.4]octan-7-yl)oxy)phenethyl)-3-amino-6-methylthieno[2,3-b]pyridine-2-carboxamide

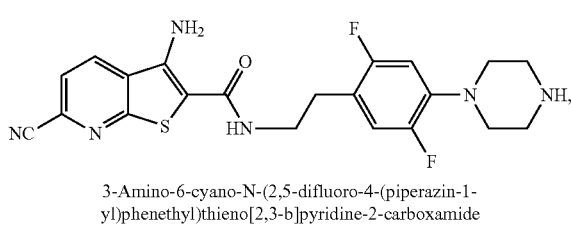

3-Amino-6-cyano-N-(2,5-difluoro-4-(piperazin-1-yl)phenethyl)thieno[2,3-b]pyridine-2-carboxamide

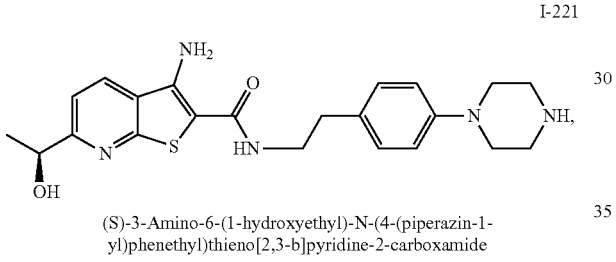

(S)-3-Amino-6-(1-hydroxyethyl)-N-(4-(piperazin-1-yl)phenethyl)thieno[2,3-b]pyridine-2-carboxamide

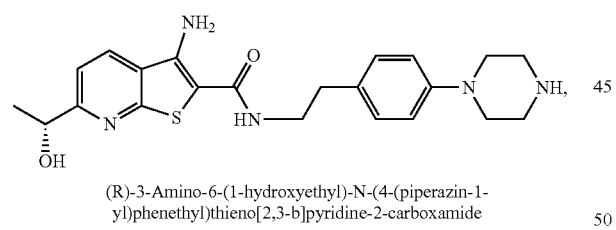

(R)-3-Amino-6-(1-hydroxyethyl)-N-(4-(piperazin-1-yl)phenethyl)thieno[2,3-b]pyridine-2-carboxamide

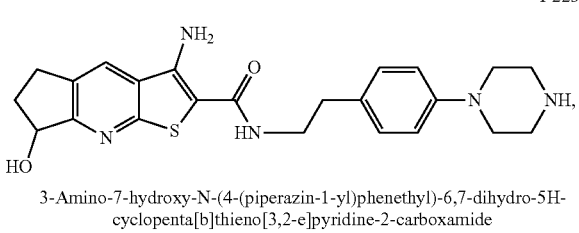

3-Amino-7-hydroxy-N-(4-(piperazin-1-yl)phenethyl)-6,7-dihydro-5H-cyclopenta[b]thieno[3,2-e]pyridine-2-carboxamide or a pharmaceutically acceptable salt, hydrate, solvate, prodrug, stereoisomer, and tautomer thereof.

15. The compound of claim 1, selected from

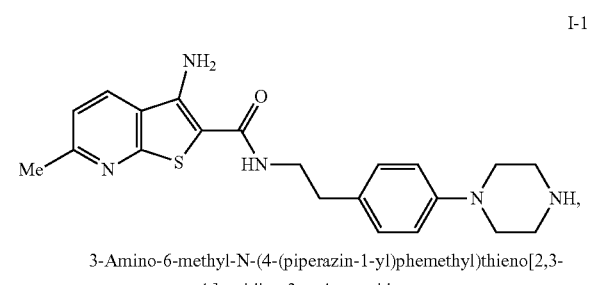

3-Amino-6-methyl-N-(4-(piperazin-1-yl)phemethyl)thieno[2,3-b]pyridine-2-carboxamide

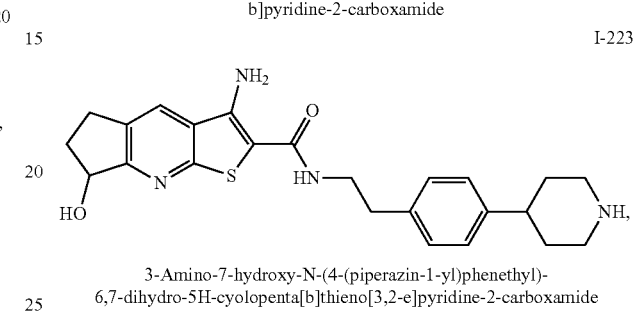

3-Amino-7-hydroxy-N-(4-(piperazin-1-yl)phenethyl)-6,7-dihydro-5H-cyolopenta[b]thieno[3,2-e]pyridine-2-carboxamide or a pharmaceutically acceptable salt, hydrate, solvate, prodrug, stereoisomer, and tautomer thereof.

16. A compound of Formula (I):

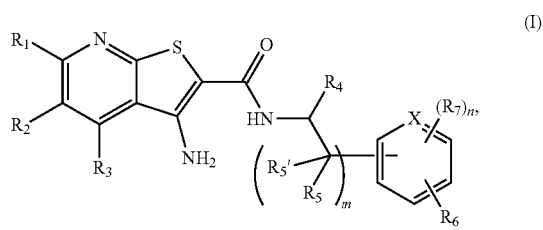

or a pharmaceutically acceptable salt, hydrate, solvate, prodrug, stereoisomer, and tautomer thereof,
wherein:
X is $CR_7$;
$R_1$ is H, or ($C_1$-$C_6$) alkyl;
$R_2$ is H, or ($C_1$-$C_6$) alkyl;
$R_3$ is H, or ($C_1$-$C_6$) alkyl;
wherein at least one of $R_1$, $R_2$, or $R_3$ is not H;
or $R_1$ and $R_2$ together form a ($C_4$-$C_8$) cycloalkyl optionally substituted with one or more $R_{15}$;
$R_4$, $R_5$, and $R_{5'}$ are each H;
$R_6$ is a —($C_0$-$C_3$) alkylene-heterocycloalkyl, wherein the heterocycloalkyl is optionally substituted with one or more $R_{16}$;
each $R_7$ is independently at each occurrence H or halogen;
each $R_{15}$ is independently at each occurrence ($C_1$-$C_6$) alkyl, halogen, or —OH;
each $R_{16}$ is independently at each occurrence ($C_1$-$C_6$) alkyl, or halogen;
m is 1; and
n is 0, 1, 2, or 3.

17. The compound of claim 16, wherein $R_1$ is a ($C_1$-$C_6$) alkyl; $R_2$ is H; $R_3$ is H; and $R_6$ is a —($C_0$) alkylene-heterocycloalkyl.

18. The compound of claim 16, wherein $R_1$ and $R_2$ together form a ($C_5$) cycloalkyl substituted with one $R_{15}$; $R_3$ is H; $R_6$ is a —($C_0$) alkylene-heterocycloalkyl; and $R_{15}$ is —OH.

19. A composition comprising a compound of claim 14, and a pharmaceutically acceptable carrier.

20. A composition comprising a pharmaceutically acceptable carrier and a compound selected from

I-1

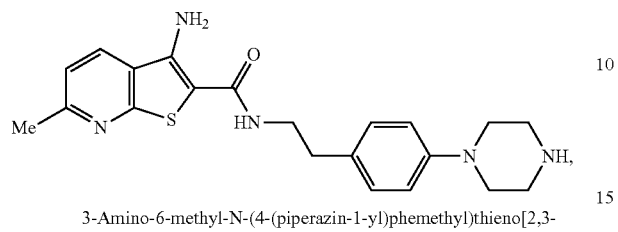

3-Amino-6-methyl-N-(4-(piperazin-1-yl)phemethyl)thieno[2,3-b]pyridine-2-carboxamide

I-223

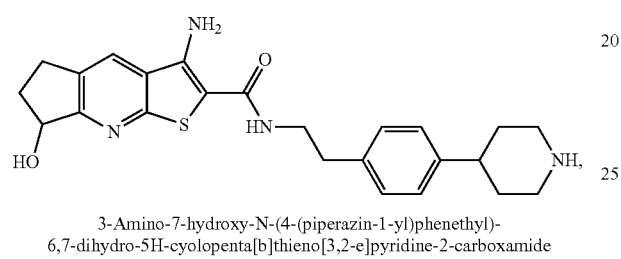

3-Amino-7-hydroxy-N-(4-(piperazin-1-yl)phenethyl)-6,7-dihydro-5H-cyolopenta[b]thieno[3,2-e]pyridine-2-carboxamide or a pharmaceutically acceptable salt, hydrate, solvate, prodrug, stereoisomer, and tautomer thereof.

* * * * *